(12) United States Patent
Challita-Eid et al.

(10) Patent No.: US 7,510,840 B1
(45) Date of Patent: Mar. 31, 2009

(54) METHOD OF INHIBITING GROWTH OR SURVIVAL OF A CELL BY PROVIDING AN ANTI-108P5H8 ANTIBODY

(75) Inventors: Pia M. Challita-Eid, Encino, CA (US); Mary Faris, Los Angeles, CA (US); Daniel E. H. Afar, Brisbane, CA (US); Rene S. Hubert, Los Angeles, CA (US); Steve Chappell Mitchell, Gurnee, IL (US); Elana Levin, Los Angeles, CA (US); Karen Jane Meyrick Morrison, Santa Monica, CA (US); Arthur B. Raitano, Los Angeles, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 1178 days.

(21) Appl. No.: 10/280,711

(22) Filed: Oct. 25, 2002

Related U.S. Application Data

(63) Continuation of application No. 10/024,652, filed on Dec. 17, 2001.

(60) Provisional application No. 60/256,210, filed on Dec. 15, 2000.

(51) Int. Cl.
*G01N 33/53* (2006.01)
*G01N 33/574* (2006.01)
*C07K 16/00* (2006.01)
*A61K 39/395* (2006.01)

(52) U.S. Cl. ............. 435/7.1; 530/387.1; 530/387.3; 530/388.1; 530/387.9; 530/391.3; 530/391.7; 514/2; 514/12; 424/130.1; 424/139.1

(58) Field of Classification Search ............. 530/387.1, 530/387.3, 387.9, 388.1, 391.3, 391.7, 350; 514/2, 12; 424/130.1, 135.1, 141.1, 178.1; 435/4, 375
See application file for complete search history.

(56) References Cited

U.S. PATENT DOCUMENTS 5,869,045 A 2/1999 Hellstrom et al.

FOREIGN PATENT DOCUMENTS

| EP | 1033401 A2 | 9/2000 |
|---|---|---|
| WO | WO 9733602 | 9/1997 |
| WO | WO0055174 A1 | 9/2000 |
| WO | WO0159063 A2 | 8/2001 |
| WO | WO0160860 A2 | 8/2001 |
| WO | WO0210449 A2 | 2/2002 |
| WO | WO0218632 A2 | 3/2002 |
| WO | WO 0224718 | 3/2002 |
| WO | WO0224718 A1 | 3/2002 |
| WO | WO0230268 A2 | 4/2002 |
| WO | WO02/055700 A2 | 7/2002 |
| WO | WO2002060953 | 8/2002 |
| WO | WO03050236 | 6/2003 |

OTHER PUBLICATIONS

Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Murgia et al. Cloning, expression, and vesicular localization of zinc transporter Dri 27/ZnT4 in intestinal tissue and cells. Am J Physiol 277 (Gastroinst Liver Physiol 40): G1231-G1239, 1999.*
Moore, G. Genetically engineered antibodies. Clin Chem 35(9): 1849-1853, 1989.*
Dillman et al. Monoclonal antibodies in the treatment of malignancy: basic concepts and recent developments. Cancer Invest 19(8): 833-841, 2001.*
Skolnick et al. From genes to protein structure and function: novel applications of computational approaches in the genomic era. Trends in Biotech 18(1): 34-39, 2000.*
Bork et al. Go hunting in sequence databases but watch out for the traps. Trends in Genetics. 12(10): 425-427, 1996.*
Wells, J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Daniel et al. Virology 202:540-549, 1994.*
Haynes et al. Proteome analysis: biological assay or data archive. Electrophoresis 19: 1862-1871, 1998.*
Hu et al. Analysis of genomic and proteomic data using advanced literature mining. J. Proteome Res 2: 405-412, 2003.*
Chen et al. Discordant protein and mRNA expression in lung adenocarcinomas. Molec Cellular Proteomics 1: 304-313, 2002.*
Huang et al., Nature Genetics (1997) 17(3):292-297.
Hwang et al., Seminars in Oncology (1999) 26(2):192-201.
Southwood et al., Journal of Immunology (1998) 160(7):3363-3373.
Campbell et al., Theriogenology (1997) 47:63-72.
Kaufman et al., Blood (1999) 9:3178-3184.
Wang et al. Nucleic Acids Res. (1999) 27(23):4609-4618.

* cited by examiner

*Primary Examiner*—Bridget E Bunner
(74) *Attorney, Agent, or Firm*—Morrison & Foerster LLP

(57) ABSTRACT

A novel gene (designated 108P5H8) and its encoded protein, and variants thereof, are described wherein 108P5H8 exhibits tissue specific expression in normal adult tissue, and is aberrantly expressed in the cancers listed in Table I. Consequently, 108P5H8 provides a diagnostic, prognostic, prophylactic and/or therapeutic target for cancer. The 108P5H8 gene or fragment thereof, or its encoded protein, or variants thereof, or a fragment thereof, can be used to elicit a humoral or cellular immune response; antibodies or T cells reactive with 191P1E1B can be used in active or passive immunization.

7 Claims, 44 Drawing Sheets

Figure 1:

```
  1 GATCCAGATT TCTCTGCACA CTGGACTTCG TAGAGTAAGT GTGGTAGACA AAGAGACTAC
 61 ACTGCACAAC CACCAGTGAA TATCATTGCT AAGAAGACTT TGGGTCGTGT TTCTCAGCCA
121 CTCTCACAGC TTTTGTAGAC TTATTTGATT TTGAAACAAG CAGTTAGCTA AATCTATTTT
181 CCTTTTATGC ATATATGTTA ATTGGCTCAA CTTAATATGG TGTTCTTACA GAATATGAGC
241 CCATTTGAAA TAAGGTTTTA GGCAATTTTG CTGTTGGCTC TGATTTGTAT ATAGCAAATT
301 TAAAGGTACA GAGTGTTTCC TAGATAGAAG ATTAGTTCAT TTGGTTCATT TTGTCTTTGA
361 AGCAAGCCAA GCTCATGAGC CAGTTGGTTA TTTGTCATAA ATGAACACCC ATCACTATAT
421 GCTATGTTGA GGGGAGGCAA GGCTGATC
```

Figure 2A-1

```
   1 gccggcctccagcagcgggcgcggcgggcgcgagcacgaccccactctcctgcggccgcg
  61 ggtggagcagcgcgagcccgcctcgctgagccggccggggggggggagatgagttgcggc
 121 cccgcggcagcgccccaggatggggagggacgcgcggcactgccctcgagaactggcgct
 181 ccggtgaagtaggcgccgccggccgtccgcctcccccaagccgttccgcaccgcggccgc
   1                    M   A   G   S   G   A   W   K   R   L   K   S   M   L   R   K
 241 tcagcctctgccATGGCCGGCTCTGGCGCGTGGAAGCGCCTCAAATCTATGCTAAGGAAG
  17  D   D   A   P   L   F   L   N   D   T   S   A   F   D   F   S   D   E   A   G
 301 GATGATGCGCCGCTGTTTTTAAATGACACCAGCGCCTTTGACTTCTCGGATGAGGCGGGG
  37  D   E   G   L   S   R   F   N   K   L   R   V   V   V   A   D   D   G   S   E
 361 GACGAGGGGCTTTCTCGGTTCAACAAACTTCGAGTTGTGGTGGCCGATGACGGTTCCGAA
  57  A   P   E   R   P   V   N   G   A   H   P   T   L   Q   A   D   D   D   S   L
 421 GCCCCGGAAAGGCCTGTTAACGGGGCGCACCCGACCCTCCAGGCCGACGATGATTCCTTA
  77  L   D   Q   D   L   P   L   T   N   S   Q   L   S   L   K   V   D   S   C   D
 481 CTGGACCAAGACTTACCTTTGACCAACAGTCAGCTGAGTTTGAAGGTGGACTCCTGTGAC
  97  N   C   S   K   Q   R   E   I   L   K   Q   R   K   V   K   A   R   L   T   I
 541 AACTGCAGCAAACAGAGAGAGATACTGAAGCAGAGAAAGGTGAAAGCCAGGTTGACCATT
 117  A   A   V   L   Y   L   L   F   M   I   G   E   L   V   G   G   Y   I   A   N
 601 GCTGCCGTTCTGTACTTGCTTTTCATGATTGGAGAACTTGTAGGTGGATACATTGCAAAT
 137  S   L   A   I   M   T   D   A   L   H   M   L   T   D   L   S   A   I   I   L
 661 AGCCTAGCAATCATGACAGATGCACTTCATATGTTAACTGACCTAAGCGCCATCATACTC
 157  T   L   L   A   L   W   L   S   S   K   S   P   T   K   R   F   T   F   G   F
 721 ACCCTGCTTGCTTTGTGGCTATCATCAAAATCACCAACCAAAAGATTCACCTTTGGATTT
 177  H   R   L   E   V   L   S   A   M   I   S   V   L   L   V   Y   I   L   M   G
 781 CATCGCTTAGAGGTTTTGTCAGCTATGATTAGTGTGCTGTTGGTGTATATACTTATGGGA
 197  F   L   L   Y   E   A   V   Q   R   T   I   H   M   N   Y   E   I   N   G   D
 841 TTCCTCTTATATGAAGCTGTGCAAAGAACTATCCATATGAACTATGAAATAAATGGAGAT
 217  I   M   L   I   T   A   A   V   G   V   A   V   N   V   I   M   G   F   L   L
 901 ATAATGCTCATCACCGCAGCTGTTGGAGTTGCAGTTAATGTAATAATGGGGTTTCTGTTG
 237  N   Q   S   G   H   R   H   S   H   S   H   S   L   P   S   N   S   P   T   R
 961 AACCAGTCTGGTCACCGTCACTCCCATTCCCACTCCCTGCCTTCAAATTCCCCTACCAGA
 257  G   S   G   C   E   R   N   H   G   Q   D   S   L   A   V   R   A   A   F   V
1021 GGTTCTGGGTGTGAACGTAACCATGGGCAGGATAGCCTGGCAGTGAGAGCTGCATTTGTA
 277  H   A   L   G   D   L   V   Q   S   V   G   V   L   I   A   A   Y   I   I   R
1081 CATGCTTTGGGAGATTTGGTACAGAGTGTTGGTGTGCTAATAGCTGCATACATCATACGA
 297  F   K   P   E   Y   K   I   A   D   P   I   C   T   Y   V   F   S   L   L   V
1141 TTCAAGCCAGAATACAAGATTGCTGACCCCATCTGTACATACGTATTTTCATTACTTGTG
```

Figure 2A-2

```
 317 A  F  T  T  F  R  I  I  W  D  T  V  V  I  I  L  E  G  V  P
1201 GCTTTTACAACATTTCGAATCATATGGGATACAGTAGTTATAATACTAGAAGGTGTGCCA
 337 S  H  L  N  V  D  Y  I  K  E  A  L  M  K  I  E  D  V  Y  S
1261 AGCCATTTGAATGTAGACTATATCAAAGAAGCCTTGATGAAAATAGAAGATGTATATTCA
 357 V  E  D  L  N  I  W  S  L  T  S  G  K  S  T  A  I  V  H  I
1321 GTCGAAGATTTAAATATCTGGTCTCTCACTTCAGGAAAATCTACTGCCATAGTTCACATA
 377 Q  L  I  P  G  S  S  S  K  W  E  E  V  Q  S  K  A  N  H  L
1381 CAGCTAATTCCTGGAAGTTCATCTAAATGGGAGGAAGTACAGTCCAAAGCAAACCATTTA
 397 L  L  N  T  F  G  M  Y  R  C  T  I  Q  L  Q  S  Y  R  Q  E
1441 TTATTGAACACATTTGGCATGTATAGATGTACTATTCAGCTTCAGAGTTACAGGCAAGAA
 417 V  D  R  T  C  A  N  C  Q  S  S  P  *
1501 GTGGACAGAACTTGTGCAAATTGTCAGAGTTCTAGTCCCTAAtttatgtatttgggaa
1561 ctcctgccttatttatcctgcagtcacagacttgagagcaataaatgcaaacctaaatga
1621 gaaaatggaatccctgacagctgtgtccgtatcaagcatcagtctctcaaacagttgccc
1681 cagcctgacagtgctagtctctgtttaatggtaaaaggagactttgccataatttttcaga
1741 tgaagatgtttcccaaacactgtttacagaatgagatgtgactctacagatacctcatag
1801 aagacaatccaagatcatacttcattaacttgacagagtacgtgtcttaaaggaagcatc
1861 aagaattcaatatttgcatttaaaaatacttttaaggccatttatattaagccagtgc
1921 tggaaaactgaatttttttattatgtataataatctcgacacccagcttctggaattgc
1981 tgctttcttttacagaaattactacccaacagatttcaggaagtactagtagttatccc
2041 aaaagtggaataagcatgtattcctaagtgtttcagaaatgttttatttcacacataagt
2101 cttaatgttattgttatgattatactttataaacaaccttttccagatgctacagggttt
2161 tgaatctcaaagttaacattttcattatttgtaatcttagaaccaaatctttatttatt
2221 gtggtcactgttattaaatgatttaggaaatactttcaatattattctgaatggctgaag
2281 ttagtcttaaactcaaattactatatgatgatttaaaacaaataaaagagcgaggatgg
2341 ggaaaaaaaaaaaaaaaaaaaaaa
```

Figure 2B-1

```
  1 M   A   G   S   G   A   W   K   R   L   K   S   M   L   R   K   D   D   A   P
  1 ATGGCCGGCTCTGGCGCGTGGAAGCGCCTCAAATCTATGCTAAGGAAGGATGATGCGCCG
 21 L   F   L   N   D   T   S   A   F   D   F   S   D   E   A   G   D   E   G   L
 61 CTGTTTTTAAATGACACCAGCGCCTTTGACTTCTCGGATGAGGCGGGGGACGAGGGGCTT
 41 S   R   F   N   K   L   R   V   V   V   A   D   D   G   S   E   A   P   E   R
121 TCTCGGTTCAACAAACTTCGAGTTGTGGTGGCCGATGACGGTTCCGAAGCCCCGGAAAGG
 61 P   V   N   G   A   H   P   T   L   Q   A   D   D   D   S   L   L   D   Q   D
181 CCTGTTAACGGGGCGCACCCGACCCTCCAGGCCGACGATGATTCCTTACTGGACCAAGAC
 81 L   P   L   T   N   S   Q   L   S   L   K   V   D   S   C   D   N   C   S   K
241 TTACCTTTGACCAACAGTCAGCTGAGTTTGAAGGTGGACTCCTGTGACAACTGCAGCAAA
101 Q   R   E   I   L   K   Q   R   K   V   K   A   R   L   T   I   A   A   V   L
301 CAGAGAGAGATACTGAAGCAGAGAAAGGTGAAAGCCAGGTTGACCATTGCTGCCGTTCTG
121 Y   L   L   F   M   I   G   E   L   V   G   G   Y   I   A   N   S   L   A   I
361 TACTTGCTTTTCATGATTGGAGAACTTGTAGGTGGATACATTGCAAATAGCCTAGCAATC
141 M   T   D   A   L   H   M   L   T   D   L   S   A   I   I   L   T   L   L   A
421 ATGACAGATGCACTTCATATGTTAACTGACCTAAGCGCCATCATACTCACCCTGCTTGCT
161 L   W   L   S   S   K   S   P   T   K   R   F   T   F   G   F   H   R   L   E
481 TTGTGGCTATCATCAAAATCACCAACCAAAAGATTCACCTTTGGATTTCATCGCTTAGAG
181 V   L   S   A   M   I   S   V   L   L   V   Y   I   L   M   G   F   L   L   Y
541 GTTTTGTCAGCTATGATTAGTGTGCTGTTGGTGTATATACTTATGGGATTCCTCTTATAT
201 E   A   V   Q   R   T   I   H   M   N   Y   E   I   N   G   D   I   M   L   I
601 GAAGCTGTGCAAAGAACTATCCATATGAACTATGAAATAAATGGAGATATAATGCTCATC
221 T   A   A   V   G   V   A   V   N   V   I   M   G   F   L   L   N   Q   S   G
661 ACCGCAGCTGTTGGAGTTGCAGTTAATGTAATAATGGGGTTTCTGTTGAACCAGTCTGGT
241 H   R   H   S   H   S   H   S   L   P   S   N   S   P   T   R   G   S   G   C
721 CACCGTCACTCCCATTCCCACTCCCTGCCTTCAAATTCCCCTACCAGAGGTTCTGGGTGT
261 E   R   N   H   G   Q   D   S   L   A   V   R   A   A   F   V   H   A   L   G
781 GAACGTAACCATGGGCAGGATAGCCTGGCAGTGAGAGCTGCATTTGTACATGCTTTGGGA
281 D   L   V   Q   S   V   G   V   L   I   A   A   Y   I   I   R   F   K   P   E
841 GATTTGGTACAGAGTGTTGGTGTGCTAATAGCTGCATACATCATACGATTCAAGCCAGAA
301 Y   K   I   A   D   P   I   C   T   Y   V   F   S   L   L   V   A   F   T   T
901 TACAAGATTGCTGATCCCATCTGTACATACGTATTTTCATTACTTGTGGCTTTTACAACA
321 F   R   I   I   W   D   T   V   V   I   I   L   E   G   V   P   S   H   L   N
961 TTTCGAATCATATGGGATACAGTAGTTATAATACTAGAAGGTGTGCCAAGCCATTTGAAT
341 V   D   Y   I   K   E   A   L   M   K   I   E   D   V   Y   S   V   E   D   L
```

Figure 2B-2

```
1021 GTAGACTATATCAAAGAAGCCTTGATGAAAATAGAAGATGTATATTCAGTCGAAGATTTA
 361 N   I   W   S   L   T   S   G   K   S   T   A   I   V   H   I   Q   L   I   P
1081 AATATCTGGTCTCTCACTTCAGGAAAATCTACTGCCATAGTTCACATACAGCTAATTCCT
 381 G   S   S   S   K   W   E   E   V   Q   S   K   A   N   H   L   L   L   N   T
1141 GGAAGTTCATCTAAATGGGAGGAAGTACAGTCCAAAGCAAACCATTTATTATTGAACACA
 401 F   G   M   Y   R   C   T   I   Q   L   Q   S   Y   R   Q   E   V   D   R   T
1201 TTTGGCATGTATAGATGTACTATTCAGCTTCAGAGTTACAGGCAAGAAGTGGACAGAACT
 421 C   A   N   C   Q   S   S   S   P   *
1261 TGTGCAAATTGTCAGAGTTCTAGTCCCTAAttttatgtatttgggactcctgccttat
1321 ttatcctgcagtcacagacttgagagcaataaatgcaaacctaaatgagaaaatggaatc
1381 cctgacagctgtgtccgtatcaagcatcagtctctcaaacagttgccccagcctgacagt
1441 gctagtctctgtttaatggtaaaaggagactttgccataatttcagatgaagatgtttc
1501 ccaaacactgtttacagaatgagatgtgactctacagatacctcatag
```

Figure 2C-1

```
  1 M   A   G   S   G   A   W   K   R   L   K   S   M   L   R   K   D   D   A   P
  1 ATGGCCGGCTCTGGCGCGTGGAAGCGCCTCAAATCTATGCTAAGGAAGGATGATGCGCCG
 21 L   F   L   N   D   T   S   A   F   E   F   S   D   E   A   G   D   E   G   L
 61 CTGTTTTTAAATGACACCAGCGCCTTTGAGTTCTCGGATGAGGCGGGGGACGAGGGGCTT
 41 S   R   F   N   K   L   R   V   V   V   A   D   D   G   S   E   A   P   E   R
121 TCTCGGTTCAACAAACTTCGAGTTGTGGTGGCCGATGACGGTTCCGAAGCCCCGGAAAGG
 61 P   V   N   G   A   H   P   T   L   Q   A   D   D   D   S   L   L   D   Q   D
181 CCTGTTAACGGGGCGCACCCGACCCTCCAGGCCGACGATGATTCCTTACTGGACCAAGAC
 81 L   P   L   T   N   S   Q   L   S   L   K   V   D   S   C   D   N   C   S   K
241 TTACCTTTGACCAACAGTCAGCTGAGTTTGAAGGTGGACTCCTGTGACAACTGCAGCAAA
101 Q   R   E   I   L   K   Q   R   K   V   K   A   R   L   T   I   A   A   V   L
301 CAGAGAGAGATACTGAAGCAGAGAAAGGTGAAAGCCAGGTTGACCATTGCTGCCGTTCTG
121 Y   L   L   F   M   I   G   E   L   V   G   G   Y   I   A   N   S   L   A   I
361 TACTTGCTTTTCATGATTGGAGAACTTGTAGGTGGATACATTGCAAATAGCCTAGCAATC
141 M   T   D   A   L   H   M   L   T   D   L   S   A   I   I   L   T   L   L   A
421 ATGACAGATGCACTTCATATGTTAACTGACCTAAGCGCCATCATACTCACCCTGCTTGCT
161 L   W   L   S   S   K   S   P   T   K   R   F   T   F   G   F   H   R   L   E
481 TTGTGGCTATCATCAAAATCACCAACCAAAAGATTCACCTTTGGATTTCATCGCTTAGAG
181 V   L   S   A   M   I   S   V   L   L   V   Y   I   L   M   G   F   L   L   Y
541 GTTTTGTCAGCTATGATTAGTGTGCTGTTGGTGTATATACTTATGGGATTCCTCTTATAT
201 E   A   V   Q   R   T   I   H   M   N   Y   E   I   N   G   D   I   M   L   I
601 GAAGCTGTGCAAAGAACTATCCATATGAACTATGAAATAAATGGAGATATAATGCTCATC
221 T   A   A   V   G   V   A   V   N   V   I   M   G   F   L   L   N   Q   S   G
661 ACCGCAGCTGTTGGAGTTGCAGTTAATGTAATAATGGGGTTTCTGTTGAACCAGTCTGGT
241 H   R   H   S   H   S   H   S   L   P   S   N   S   P   T   R   G   S   G   C
721 CACCGTCACTCCCATTCCCACTCCCTGCCTTCAAATTCCCCTACCAGAGGTTCTGGGTGT
261 E   R   N   H   G   Q   D   S   L   A   V   R   A   A   F   V   H   A   L   G
781 GAACGTAACCATGGGCAGGATAGCCTGGCAGTGAGAGCTGCATTTGTACATGCTTTGGGA
281 D   L   V   Q   S   V   G   V   L   I   A   A   Y   I   I   R   F   K   P   E
841 GATCTGGTACAGAGTGTTGGTGTGCTAATAGCTGCATACATCATACGATTCAAGCCAGAA
301 Y   K   I   A   D   P   I   C   T   Y   V   F   S   L   L   V   A   F   T   T
901 TACAAGATTGCTGACCCCATCTGTACATACGTATTTTCATTACTTGTGGCTTTTACAACA
321 F   R   I   I   W   D   T   V   V   I   I   L   E   G   V   P   S   H   L   N
961 TTTCGAATCATATGGGATACAGTAGTTATAATACTAGAAGGTGTGCCAAGCCATTTGAAT
```

Figure 2C-2

```
 341 V  D  Y  I  K  E  A  L  M  K  I  E  D  V  Y  S  V  E  D  L
1021 GTAGACTATATCAAAGAAGCCTTGATGAAAATAGAAGATGTATATTCAGTCGAAGATTTA

361 N  I  W  S  L  T  S  G  K  S  T  A  I  V  H  I  Q  L  I  P
1081 AATATCTGGTCTCTCACTTCAGGAAAATCTACTGCCATAGTTCACATACAGCTAATTCCT

381 G  S  S  S  K  W  E  E  V  Q  S  K  A  N  H  L  L  N  T
1141 GGAAGTTCATCTAAATGGGAGGAAGTACAGTCCAAAGCAAACCATTTATTATTGAACACA

401 F  G  M  Y  R  C  T  I  Q  L  Q  S  Y  R  Q  E  V  D  R  T
1201 TTTGGCATGTATAGATGTACTATTCAGCTTCAGAGTTACAGGCAAGAAGTGGACAGAACT

421 C  A  N  C  Q  S  S  S  P  *
1261 TGTGCAAATTGTCAGAGTTCTAGTCCCTAAttttatgtattgttttagcattgctgaatt
1321 cactttatttatcctgcagtcacagacttgagagcaataaatgcaaacctaaatgagaaa
1381 atggaatccctgacagctgtgtccgtatcaagcatcagtctctcaaacagttgccccagc
1441 ctgacagtgctagtctctgtttaatggtaaaaggagactttgccataattttcagatgaa
1501 gatgtttcccaaacactgtttacagaatgagatgtgactcctacagatacctcatag
```

Figure 3A

```
  1 MAGSGAWKRL KSMLRKDDAP LFLNDTSAFD FSDEAGDEGL SRFNKLRVVV ADDGSEAPER
 61 PVNGAHPTLQ ADDDSLLDQD LPLTNSQLSL KVDSCDNCSK QREILKQRKV KARLTIAAVL
121 YLLFMIGELV GGYIANSLAI MTDALHMLTD LSAIILTLLA LWLSSKSPTK RFTFGFHRLE
181 VLSAMISVLL VYILMGFLLY EAVQRTIHMN YEINGDIMLI TAAVGVAVNV IMGFLLNQSG
241 HRHSHSHSLP SNSPTRGSGC ERNHGQDSLA VRAAFVHALG DLVQSVGVLI AAYIIRFKPE
301 YKIADPICTY VFSLLVAFTT FRIIWDTVVI ILEGVPSHLN VDYIKEALMK IEDVYSVEDL
361 NIWSLTSGKS TAIVHIQLIP GSSSKWEEVQ SKANHLLLNT FGMYRCTIQL QSYRQEVDRT
421 CANCQSSSP*
```

Figure 3B

```
  1 MAGSGAWKRL KSMLRKDDAP LFLNDTSAFE FSDEAGDEGL SRFNKLRVVV ADDGSEAPER
 61 PVNGAHPTLQ ADDDSLLDQD LPLTNSQLSL KVDSCDNCSK QREILKQRKV KARLTIAAVL
121 YLLFMIGELV GGYIANSLAI MTDALHMLTD LSAIILTLLA LWLSSKSPTK RFTFGFHRLE
181 VLSAMISVLL VYILMGFLLY EAVQRTIHMN YEINGDIMLI TAAVGVAVNV IMGFLLNQSG
241 HRHSHSHSLP SNSPTRGSGC ERNHGQDSLA VRAAFVHALG DLVQSVGVLI AAYIIRFKPE
301 YKIADPICTY VFSLLVAFTT FRIIWDTVVI ILEGVPSHLN VDYIKEALMK IEDVYSVEDL
361 NIWSLTSGKS TAIVHIQLIP GSSSKWEEVQ SKANHLLLNT FGMYRCTIQL QSYRQEVDRT
421 CANCQSSSP*
```

Figure 4A-1

```
        1              15 16              30 31              45 46              60 61              75 76
  v.1  GCCGGGCCTCCAGCAG  CGGGCGCGGCGGGCG   CGAGCACGACCCCAC   TCTCCTGCGGCCGCG   GGTGGAGCAGGCGA
  v.2  ----------------  ---------------   ---------------   ---------------   --------------
  v.3  ----------------  ---------------   ---------------   ---------------   --------------

91             105 106            120 121            135 136            150 151            165 166
  v.1  CCGGCCGGGGCGGG    GAGATGAGTTGCGGC   CCCGCGGCAGCGCCC   CAGGATGGGGAGGGA   CGCGCGGCACTGCCC
  v.2  --------------    ---------------   ---------------   ---------------   ---------------
  v.3  --------------    ---------------   ---------------   ---------------   ---------------

181            195 196            210 211            225 226            240 241            255 256
  v.1  CCGGTGAAGTAGGCG   CCGCCGGCCGTCCGC   CTCCCCCAAGCCGTT   CCGCACCGGGGCCGC   TCAGCCTCTGCCATG
  v.2  ---------------   ---------------   ---------------   --------------- ----ATG
  v.3  ---------------   ---------------   ---------------   --------------- --------ATG 271            285 286            300 301            315 316            330 331            345 346
  v.1  GCCGGCTCTGGCGCG
  v.2  GCCGGCTCTGGCGCG
  v.3  GCCGGCTCTGGCGCG
       360
```

(Partial alignment — v.1 extends further with sequence TCGAGAACTGGGCT at position 180 and GCCCGCCTCGCTGAG at position 90)

Figure 4A-2

```
v.1 TGGAAGCGCCTCAAA TCTATGCTAAGGAAG GATGATGCGCCGCTG TTTTTAAATGACACC AGCGCCTTTGACTTC
    TCGGATGAGGCGGGG
v.2 TGGAAGCGCCTCAAA TCTATGCTAAGGAAG GATGATGCGCCGCTG TTTTTAAATGACACC AGCGCCTTTGACTTC
    TCGGATGAGGCGGGG
v.3 TGGAAGCGCCTCAAA TCTATGCTAAGGAAG GATGATGCGCCGCTG TTTTTAAATGACACC AGCGCCTTTGAGTTC
    TCGGATGAGGCGGGG 361             375 376             390 391             405 406             420 421             435 436
450
v.1 GACGAGGGGCTTTCT CGGTTCAACAAACTT CGAGTTGTGGTGGCC GATGACGGTTCCGAA GCCCCGGAAAGGCCT
    GTTAACGGGGCGCAC
v.2 GACGAGGGGCTTTCT CGGTTCAACAAACTT CGAGTTGTGGTGGCC GATGACGGTTCCGAA GCCCCGGAAAGGCCT
    GTTAACGGGGCGCAC
v.3 GACGAGGGGCTTTCT CGGTTCAACAAACTT CGAGTTGTGGTGGCC GATGACGGTTCCGAA GCCCCGGAAAGGCCT
    GTTAACGGGGCGCAC 451             465 466             480 481             495 496             510 511             525 526
540
v.1 CCGACCCCTCCAGGCC GACGATGATTCCTTA CTGGACCAAGACTTA CCTTTGACCAACAGT CAGCTGAGTTTGAAG
    GTGGACTCCTGTGAC
v.2 CCGACCCCTCCAGGCC GACGATGATTCCTTA CTGGACCAAGACTTA CCTTTGACCAACAGT CAGCTGAGTTTGAAG
    GTGGACTCCTGTGAC
v.3 CCGACCCCTCCAGGCC GACGATGATTCCTTA CTGGACCAAGACTTA CCTTTGACCAACAGT CAGCTGAGTTTGAAG
    GTGGACTCCTGTGAC 541             555 556             570 571             585 586             600 601             615 616
630
v.1 AACTGCAGCAAACAG AGAGAGATACTGAAG CAGAGAAAGGTGAAA GCCAGGTTGACCATT GCTGCCGTTCTGTAC
    TTGCTTTTCATGATT
```

Figure 4A-3

```
     631            645 646                            660 661                            675 676                            690 691                            705 706
v.2 AACTGCAGCAAACAG AGAGAGATACTGAAG CAGAGAAAGGTGAAA GCCAGGTTGACCATT GCTGCCGTTCTGTAC
    TTGCTTTTCATGATT
v.3 AACTGCAGCAAACAG AGAGAGATACTGAAG CAGAGAAAGGTGAAA GCCAGGTTGACCATT GCTGCCGTTCTGTAC
    TTGCTTTTCATGATT 720            735 736                            750 751                            765 766                            780 781                            795 796
v.1 GGAGAACTTGTAGGT GGATACATTGCAAAT AGCCTAGCAATCATG ACAGATGCACTTCAT ATGTTAACTGACCTA
    AGCGCCATCATACTC
v.2 GGAGAACTTGTAGGT GGATACATTGCAAAT AGCCTAGCAATCATG ACAGATGCACTTCAT ATGTTAACTGACCTA
    AGCGCCATCATACTC
v.3 GGAGAACTTGTAGGT GGATACATTGCAAAT AGCCTAGCAATCATG ACAGATGCACTTCAT ATGTTAACTGACCTA
    AGCGCCATCATACTC 810            825 826                            840 841                            855 856                            870 871                            885 886
v.1 ACCCTGCTTGCTTTG TGGCTATCATCAAAA TCACCAACCAAAAGA TTCACCTTTGGATTT CATCGCTTAGAGGTT
    TTGTCAGCTATGATT
v.2 ACCCTGCTTGCTTTG TGGCTATCATCAAAA TCACCAACCAAAAGA TTCACCTTTGGATTT CATCGCTTAGAGGTT
    TTGTCAGCTATGATT
v.3 ACCCTGCTTGCTTTG TGGCTATCATCAAAA TCACCAACCAAAAGA TTCACCTTTGGATTT CATCGCTTAGAGGTT
    TTGTCAGCTATGATT 900
v.1 AGTGTGCTGTTGGTG TATATACTTATGGGA TTCCTCTTATATGAA GCTGTGCAAAGAACT ATCCATATGAACTAT
    GAAATAAATGGAGAT
v.2 AGTGTGCTGTTGGTG TATATACTTATGGGA TTCCTCTTATATGAA GCTGTGCAAAGAACT ATCCATATGAACTAT
    GAAATAAATGGAGAT
v.3 AGTGTGCTGTTGGTG TATATACTTATGGGA TTCCTCTTATATGAA GCTGTGCAAAGAACT ATCCATATGAACTAT
    GAAATAAATGGAGAT
```

Figure 4A-4

```
             901       915 916       930 931       945 946       960 961       975 976
   v.1 ATAATGCTCATCACC GCAGCTGTGTGGAGTT GCAGTTAATGTAATA ATGGGGTTTCTGTTG AACCAGTCTGGTCAC
CGTCACTCCCATTCC
   v.2 ATAATGCTCATCACC GCAGCTGTGTGGAGTT GCAGTTAATGTAATA ATGGGGTTTCTGTTG AACCAGTCTGGTCAC
CGTCACTCCCATTCC
   v.3 ATAATGCTCATCACC GCAGCTGTGTGGAGTT GCAGTTAATGTAATA ATGGGGTTTCTGTTG AACCAGTCTGGTCAC
CGTCACTCCCATTCC 991      1005 1006     1020 1021     1035 1036     1050 1051     1065
   v.1 CACTCCCTGCCTTCA AATTCCCCTACCAGA GGTTCTGGGTGTGAA CGTAACCATGGGCAG GATAGCCTGGCAGTG
AGAGCTGCATTTGTA
   v.2 CACTCCCTGCCTTCA AATTCCCCTACCAGA GGTTCTGGGTGTGAA CGTAACCATGGGCAG GATAGCCTGGCAGTG
AGAGCTGCATTTGTA
   v.3 CACTCCCTGCCTTCA AATTCCCCTACCAGA GGTTCTGGGTGTGAA CGTAACCATGGGCAG GATAGCCTGGCAGTG
AGAGCTGCATTTGTA 1081     1095 1096     1110 1111     1125 1126     1140 1141     1155
   v.1 CATGCTTTGGGAGAT TTGGTACAGAGTGTT GGTGTGCTAATAGCT GCATACATCATACGA TTCAAGCCAGAATAC
AAGATTGCTGACCCC
   v.2 CATGCTTTGGGAGAT TTGGTACAGAGTGTT GGTGTGCTAATAGCT GCATACATCATACGA TTCAAGCCAGAATAC
AAGATTGCTGACCCC
   v.3 CATGCTTTGGGAGAT CTGGTACAGAGTGTT GGTGTGCTAATAGCT GCATACATCATACGA TTCAAGCCAGAATAC
AAGATTGCTGACCCC 1171     1185 1186     1200 1201     1215 1216     1230 1231     1245
```

Figure 4A-5

```
v.1 ATCTGTACATACGTA TTTTCATTACTTGTG GCTTTTACAACATTT CGAATCATATGGGAT ACAGTAGTTATAATA

CTAGAAGGTGTGCCA
v.2 ATCTGTACATACGTA TTTTCATTACTTGTG GCTTTTACAACATTT CGAATCATATGGGAT ACAGTAGTTATAATA
    CTAGAAGGTGTGCCA
v.3 ATCTGTACATACGTA TTTTCATTACTTGTG GCTTTTACAACATTT CGAATCATATGGGAT ACAGTAGTTATAATA
    CTAGAAGGTGTGCCA
    1261            1275 1276       1290 1291       1305 1306       1320 1321   1335
    1336
v.1 AGCCATTTGAATGTA GACTATATCAAAGAA GCCCTTGATGAAAATA CAGCTAATTCCTGGA AGTTCATCTAAATGG
    ATCTGGTCTCTCACT
v.2 AGCCATTTGAATGTA GACTATATCAAAGAA GCCCTTGATGAAAATA CAGCTAATTCCTGGA AGTTCATCTAAATGG
    ATCTGGTCTCTCACT
v.3 AGCCATTTGAATGTA GACTATATCAAAGAA GCCCTTGATGAAAATA CAGCTAATTCCTGGA AGTTCATCTAAATGG
    ATCTGGTCTCTCACT
    1351            1365 1366       1380 1381       1395 1396       1410 1411   1425
    1426
v.1 TCAGGAAAATCTACT GCCATAGTTCACATA CAGCTAATTCCTGGA AGTTCATCTAAATGG GAGGAAGTACAGTCC
    AAAGCAAACCATTTA
v.2 TCAGGAAAATCTACT GCCATAGTTCACATA CAGCTAATTCCTGGA AGTTCATCTAAATGG GAGGAAGTACAGTCC
    AAAGCAAACCATTTA
v.3 TCAGGAAAATCTACT GCCATAGTTCACATA CAGCTAATTCCTGGA AGTTCATCTAAATGG GAGGAAGTACAGTCC
    AAAGCAAACCATTTA
    1441            1455 1456       1470 1471       1485 1486       1500 1501   1515
    1516
v.1 TTATTGAACACATTT GGCATGTATAGATGT ACTATTCAGCTTCAG AGTTACAGGCAAGAA GTGGACAGAACTTGT
    GCAAATTGTCAGAGT
v.2 TTATTGAACACATTT GGCATGTATAGATGT ACTATTCAGCTTCAG AGTTACAGGCAAGAA GTGGACAGAACTTGT
    GCAAATTGTCAGAGT
```

Figure 4A-6

```
v.3  TTATTGAACACATTT GGCATGTATAGATGT ACTATTCAGCTTCAG AGTTACAGGCAAGAA GTGGACAGAACTGT
     GCAAATTGTCAGAGT 1531            1545 1546                       1560 1561                       1575 1576                      1590 1591                      1605
     v.1 TCTAGTCCCTAATTT TATGTATT  TTGGG AACTGCTG      C CTTATTTATCCTGCA GTCACAGACTTGAGA
     1606                   1620
     GCAATAAATGCAAAC
     v.2 TCTAGTCCCTAATTT TATGTATT  TTGGG GACTGCTG      C CTTATTTATCCTGCA GTCACAGACTTGAGA
     GCAATAAATGCAAAC
     v.3 TCTAGTCCCTAATTT TATGTATTGTTTAG  CATTGCTGAATTCAC TTTATTTATCCTGCA GTCACAGACTTGAGA
     GCAATAAATGCAAAC 1621           1635 1636                       1650 1651                       1665 1666                       1680 1681                      1695
     v.1 CTAAAATGAGAAAATG GAATCCCTGACAGCT GTGTCCGTATCAAGC ATCAGTCTCTCAAAC AGTTGCCCCAGCCTG
     1696                   1710
     ACAGTGCTAGTCTCT
     v.2 CTAAAATGAGAAAATG GAATCCCTGACAGCT GTGTCCGTATCAAGC ATCAGTCTCTCAAAC AGTTGCCCCAGCCTG
     ACAGTGCTAGTCTCT
     v.3 CTAAAATGAGAAAATG GAATCCCTGACAGCT GTGTCCGTATCAAGC ATCAGTCTCTCAAAC AGTTGCCCCAGCCTG
     ACAGTGCTAGTCTCT 1711           1725 1726                       1740 1741                      1755 1756                       1770 1771                       1785
     v.1 GTTTAATGGTAAAAG GAGACTTTGCCATAA TTTTCAGATGAAGAT GTTTCCCAAACACTG TTTACAGAATGAGAT
     1786                   1800
     GTGACTCTACAGAT
     v.2 GTTTAATGGTAAAAG GAGACTTTGCCATAA TTTTCAGATGAAGAT GTTTCCCAAACACTG TTTACAGAATGAGAT
     GTGACTCTACAGAT
     v.3 GTTTAATGGTAAAAG GAGACTTTGCCATAA TTTTCAGATGAAGAT GTTTCCCAAACACTG TTTACAGAATGAGAT
     GTGACTCTACAGAT
```

Figure 4A-7

```
      1801       1815 1816                      1830 1831                      1845 1846                      1860 1861                      1875
1876       1890
      v.1 ACCTCATAGAAGACA ATCCAAGATCATACT TCATTAACTTGACAG AGTACGTGTCTTAAA GGAAGCATCAAGAAT
TCAATATTTGCATTT
      v.2 ACCTCATAG----- --------------- --------------- --------------- ---------------
---------------
      v.3 ACCTCATAG----- --------------- --------------- --------------- ---------------
---------------

1891       1905 1906                      1920 1921                      1935 1936                      1950 1951                      1965
1966       1980
      v.1 AAAAATACTTTTTAA GGCCATTTTATATTA AGCCAGTGCTGGAAA ACTGAATTTTTTTA TTATGTATAATAATC
TCGACACCCAGCTTC
      v.2 --------------- --------------- --------------- --------------- ---------------
---------------
      v.3 --------------- --------------- --------------- --------------- ---------------
---------------

1981       1995 1996                      2010 2011                      2025 2026                      2040 2041                      2055
2056       2070
      v.1 TGGAATTGCTGCTTT CTTTTTTACAGAAATT ACTACCCCAACAGATT TCAGGAAGTACTAGT AGTTATCCCAAAAGT
GGAATAAGCATGTAT
      v.2 --------------- --------------- --------------- --------------- ---------------
---------------
      v.3 --------------- --------------- --------------- --------------- ---------------
---------------

2071       2085 2086                      2100 2101                      2115 2116                      2130 2131                      2145
2146       2160
      v.1 TCCTAAGTGTTTCAG AAATGTTTTATTTCA CACATAAGTCTTAAT GTTATTGTTATGATT ATACTTTATAAACAA
CCTTTTCCAGATGCT
```

Figure 4A-8

```
       2161         2175 2176              2190 2191                   2205 2206              2220 2221              2235 2236
  v.1 ACAGGGTTTTGAATC TCAAAGTTAACATTT TTCATTATTGTAAT CTTAGAACCAAATCT TTATTTATTGTGGTC
2250 ACTGTTATTAAATGA
  v.2 ---------------
  v.3 ---------------

2251         2265 2266              2280 2281                   2295 2296              2310 2311              2325
  v.1 TTTAGGAAATACTTT CAATATTATTCTGAA TGGCTGAAGTTAGTC TTAAACTCAAATTAC TATATGATGATTTAA
2326 AACAAAATAAAGAG
  v.2 --------------
  v.3 --------------

2341         2355 2356      2370
  v.1 CGAGGATGGGGAAAA AAAAAAAAAAAAAA AAA   2364
  v.2 ---------------  --------------  ---  1548
  v.3 ---------------  --------------  ---  1557
```

Figure 4B-1

```
          1              15 16             30 31             45 46             60 61             75
   v.1 MAGSGAWKRLKSMLR KDDAPLFLNDTSAFD FSDEAGDEGLSRFNK LRVVVADDGSEAPER PVNGAHPTLQADDDS
   v.2 MAGSGAWKRLKSMLR KDDAPLFLNDTSAFD FSDEAGDEGLSRFNK LRVVVADDGSEAPER PVNGAHPTLQADDDS
   v.3 MAGSGAWKRLKSMLR KDDAPLFLNDTSAFE FSDEAGDEGLSRFNK LRVVVADDGSEAPER PVNGAHPTLQADDDS 76              90
     LLDQDLPLTNSQLSL
     LLDQDLPLTNSQLSL
     LLDQDLPLTNSQLSL 91             105 106           120 121           135 136           150 151           165
   v.1 KVDSCDNCSKQREIL KQRKVKARLTIAAVL YLLFMIGELVGGYIA NSLAIMTDALHMLTD LSAIILTLLALWLSS
   v.2 KVDSCDNCSKQREIL KQRKVKARLTIAAVL YLLFMIGELVGGYIA NSLAIMTDALHMLTD LSAIILTLLALWLSS
   v.3 KVDSCDNCSKQREIL KQRKVKARLTIAAVL YLLFMIGELVGGYIA NSLAIMTDALHMLTD LSAIILTLLALWLSS 166             180
     KSPTKRFTFGFHRLE
     KSPTKRFTFGFHRLE
     KSPTKRFTFGFHRLE 181             195 196           210 211           225 226           240 241           255
   v.1 VLSAMISVLLVYILM GFLLYEAVQRTIHMN YEINGDIMLITAAVG VAVNVIMGFLLNQSG HRHSHSHSLPSNSPT
   v.2 VLSAMISVLLVYILM GFLLYEAVQRTIHMN YEINGDIMLITAAVG VAVNVIMGFLLNQSG HRHSHSHSLPSNSPT
   v.3 VLSAMISVLLVYILM GFLLYEAVQRTIHMN YEINGDIMLITAAVG VAVNVIMGFLLNQSG HRHSHSHSLPSNSPT 256             270 271           285 286           300 301           315 316           330 331           345
     RGSGCERNHGQDSLA
     RGSGCERNHGQDSLA
     RGSGCERNHGQDSLA 346             360
```

Figure 4B-2 v.1 VRAAFVHALGDLVQS VGVLIAAYIIRFKPE YKIADPICTYVFSLL VAFTTFRIIWDTVVI ILEGVPSHLNVDYIK
EALMKIEDVYSVEDL
v.2 VRAAFVHALGDLVQS VGVLIAAYIIRFKPE YKIADPICTYVFSLL VAFTTFRIIWDTVVI ILEGVPSHLNVDYIK
EALMKIEDVYSVEDL
v.3 VRAAFVHALGDLVQS VGVLIAAYIIRFKPE YKIADPICTYVFSLL VAFTTFRIIWDTVVI ILEGVPSHLNVDYIK
EALMKIEDVYSVEDL

```
         361           375 376           390 391           405 406          420 421
v.1 NIWSLTSGKSTAIVH IQLIPGSSSKWEEVQ SKANHLLLNTFGMYR CTIQLQSYRQEVDRT CANCQSSSP    429
v.2 NIWSLTSGKSTAIVH IQLIPGSSSKWEEVQ SKANHLLLNTFGMYR CTIQLQSYRQEVDRT CANCQSSSP    429
v.3 NIWSLTSGKSTAIVH IQLIPGSSSKWEEVQ SKANHLLLNTFGMYR CTIQLQSYRQEVDRT CANCQSSSP    429
```

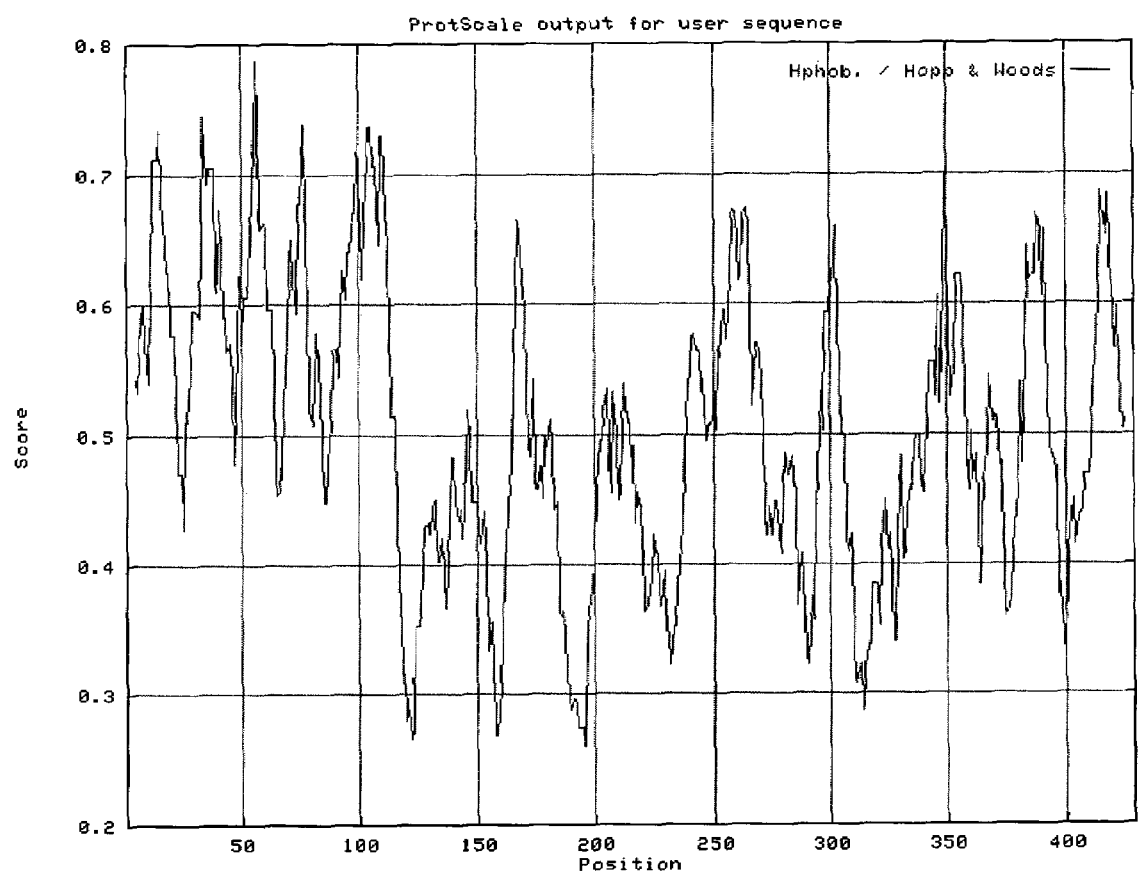
Figure 5: 108P5H8 Hydrophilicity profile
(Hopp T.P., Woods K.R., 1981. Proc. Natl. Acad. Sci. U.S.A. 78:3824-3828)

Figure 6: 108P5H8 Hydropathicity Profile
(Kyte J., Doolittle R.F., 1982. J. Mol. Biol. 157:105-132)
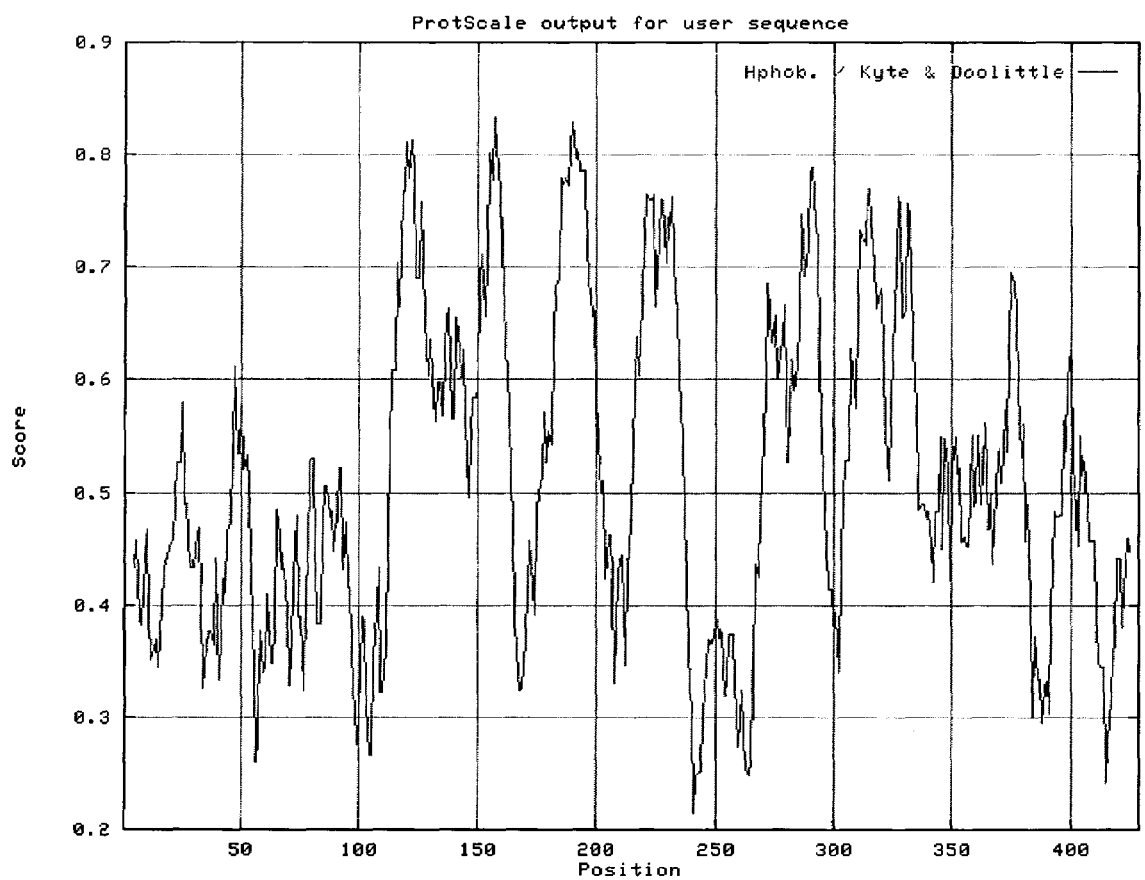

Figure 7: 108P5H8 % Accessible Residues Profile
(Janin J., 1979. Nature 277:491-492)
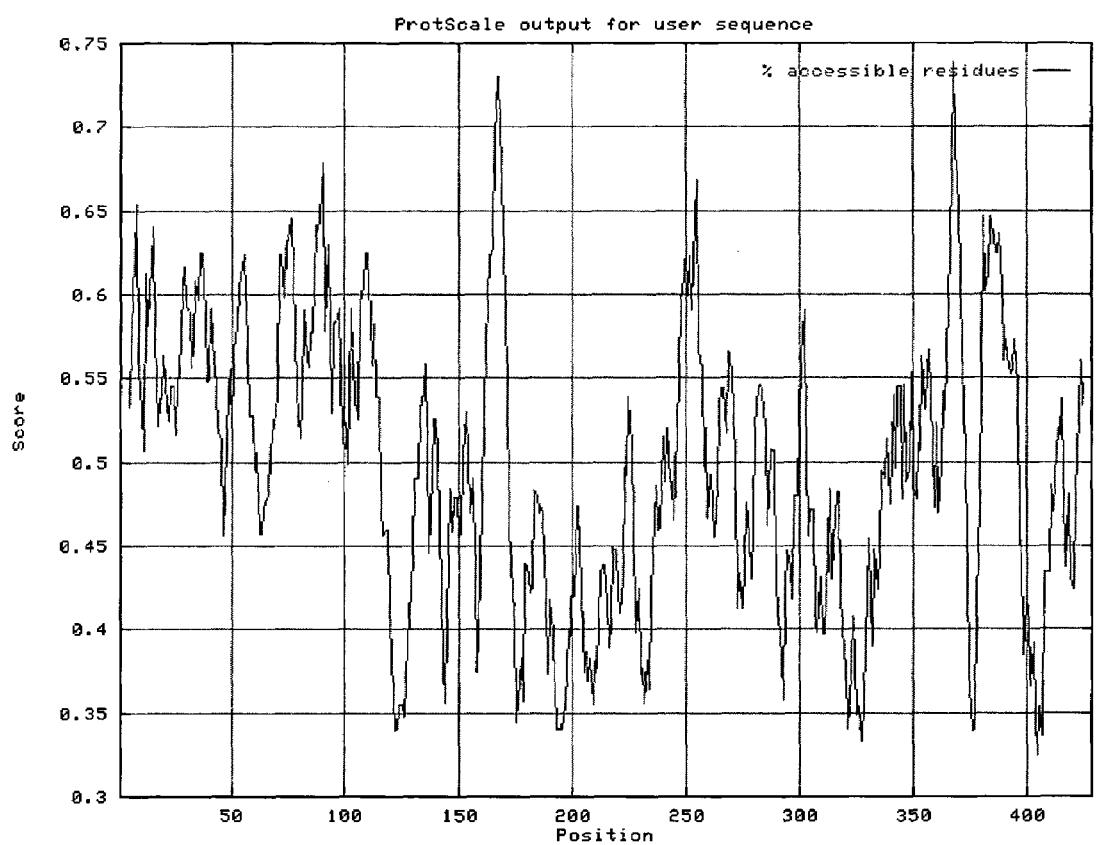

Figure 8: 108P5H8 Average Flexibility Profile
(Bhaskaran R., Ponnuswamy P.K., 1988.
Int. J. Pept. Protein Res. 32:242-255)
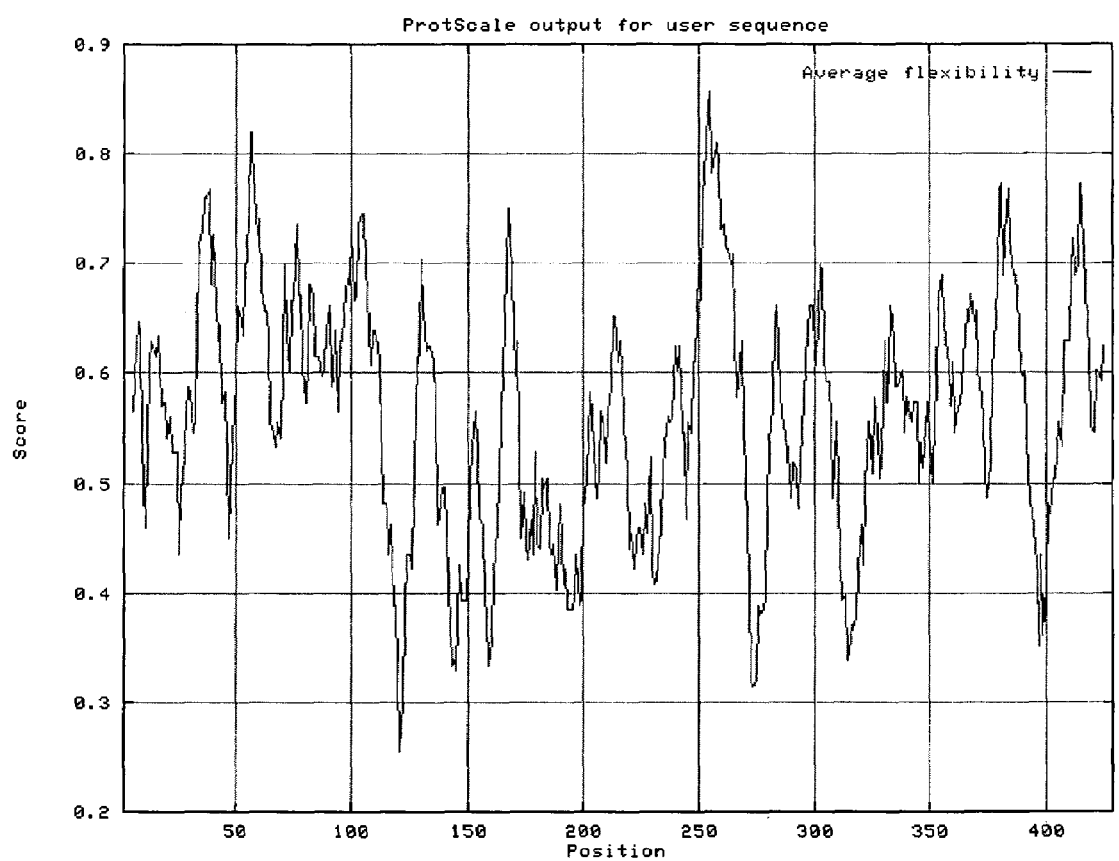

Figure 9: 108P5H8 Beta-turn Profile
(Deleage, G., Roux B. 1987. Protein Engineering 1:289-294)
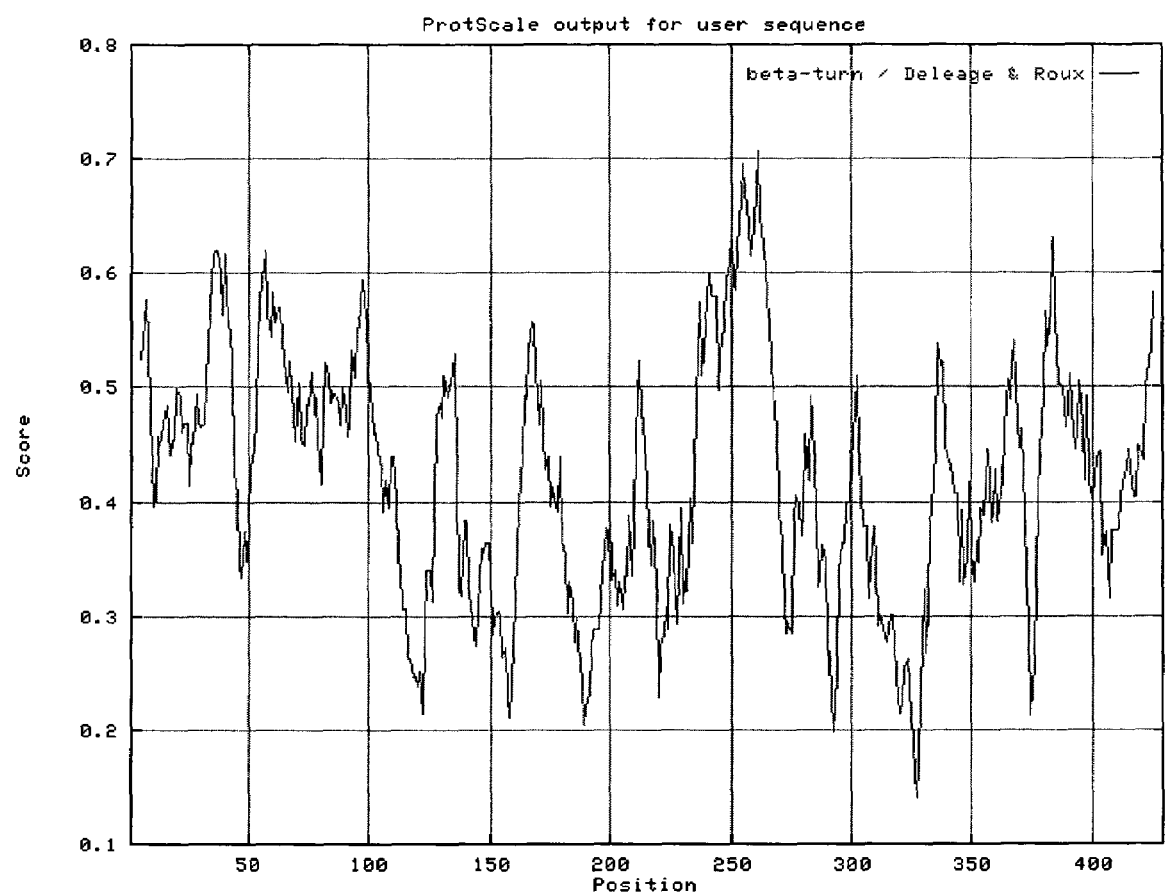

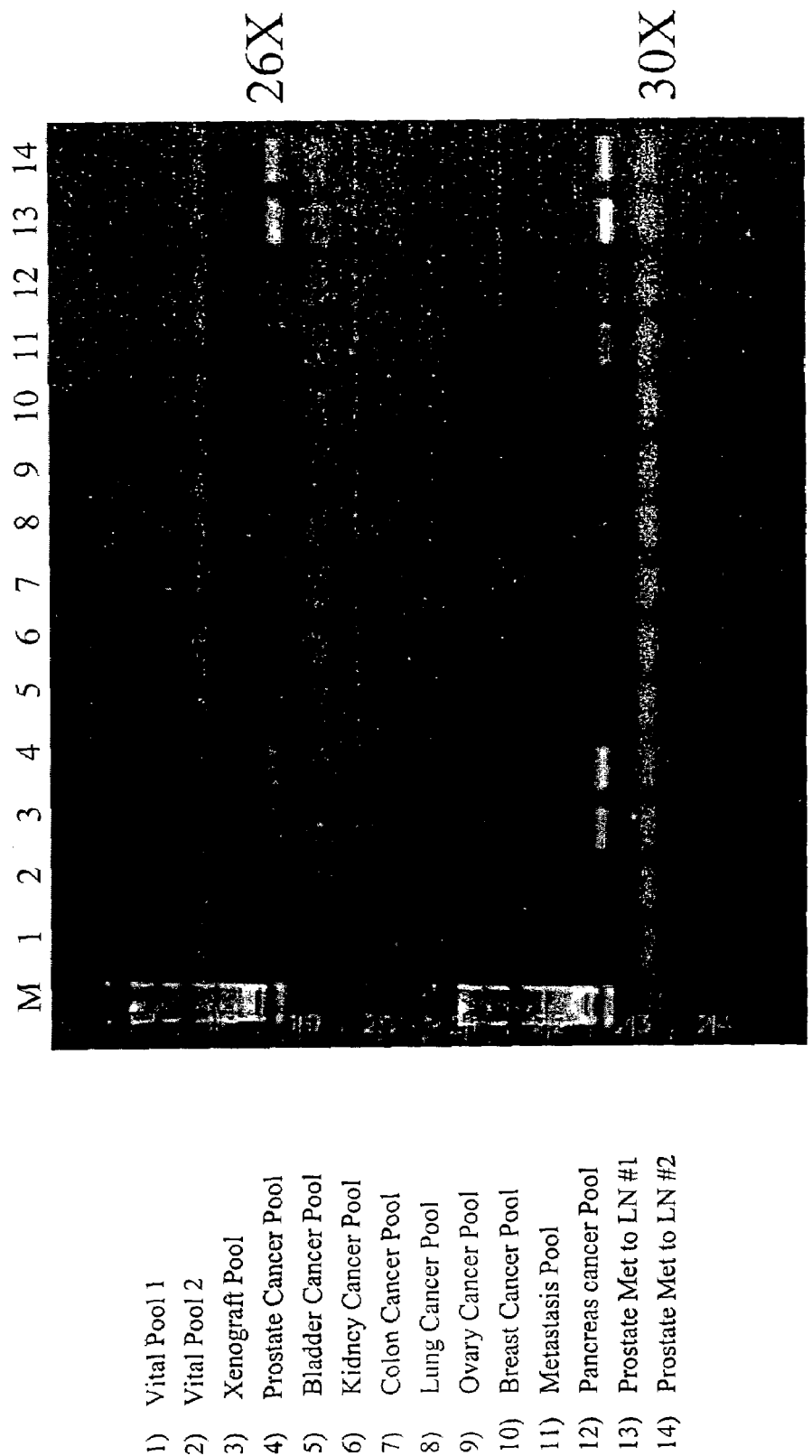
Figure 10 Expression of 108P5H8 by RT-PCR
1) Vital Pool 1
2) Vital Pool 2
3) Xenograft Pool
4) Prostate Cancer Pool
5) Bladder Cancer Pool
6) Kidney Cancer Pool
7) Colon Cancer Pool
8) Lung Cancer Pool
9) Ovary Cancer Pool
10) Breast Cancer Pool
11) Metastasis Pool
12) Pancreas cancer Pool
13) Prostate Met to LN #1
14) Prostate Met to LN #2

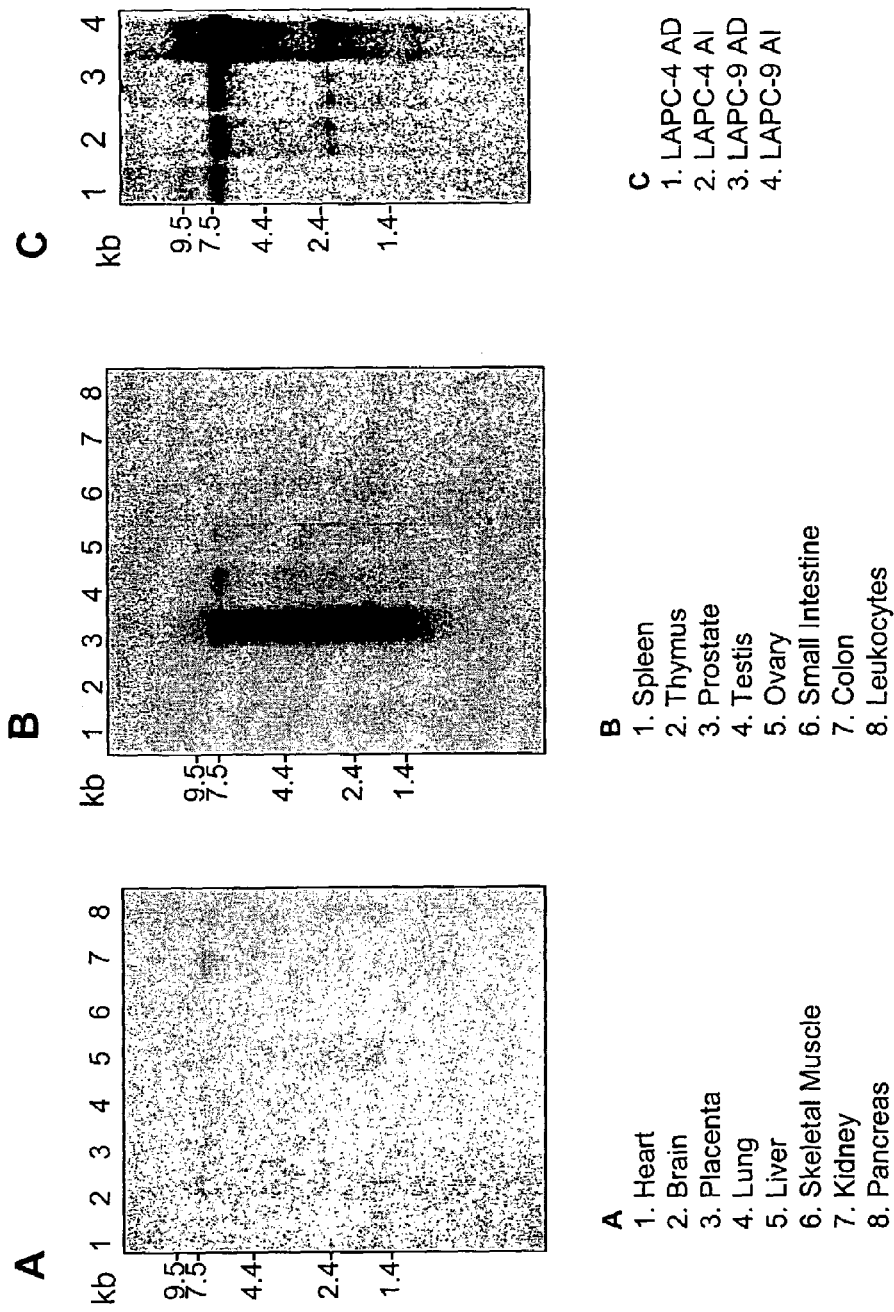
Figure 11 Expression of 108P5H8 in Prostate Cancer Xenografts and restricted normal tissues

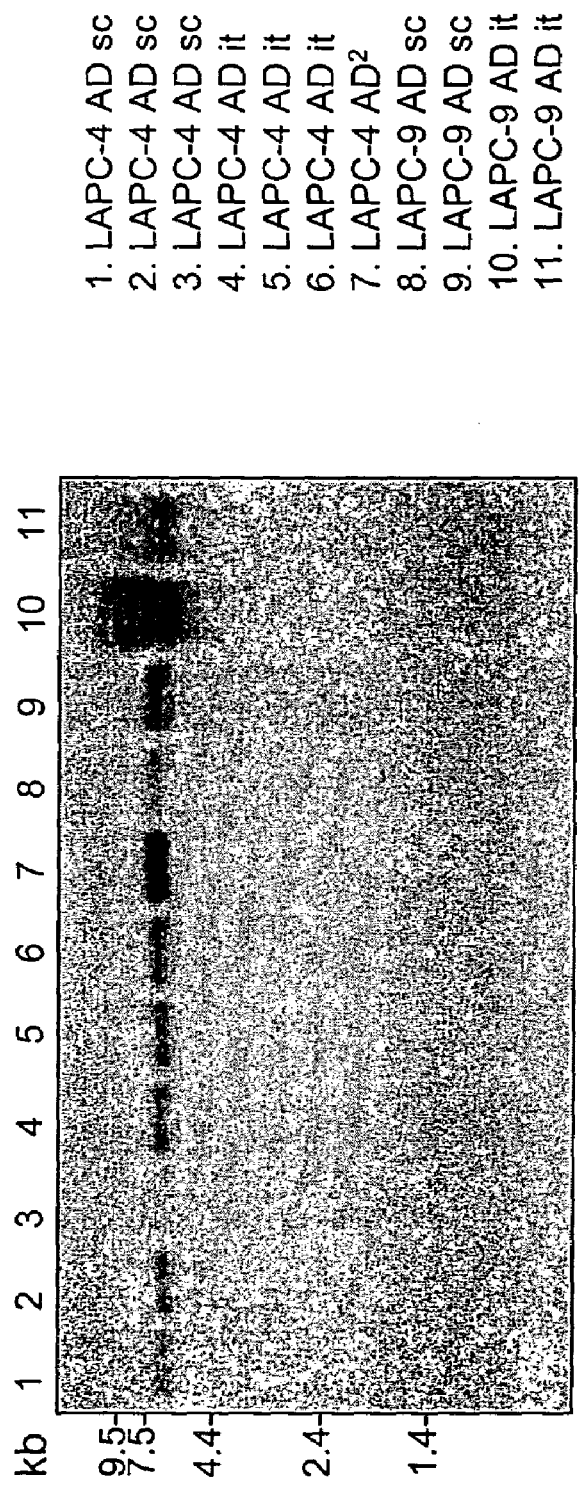
Figure 12  Expression of 108P5H8 in prostate cancer xenografts

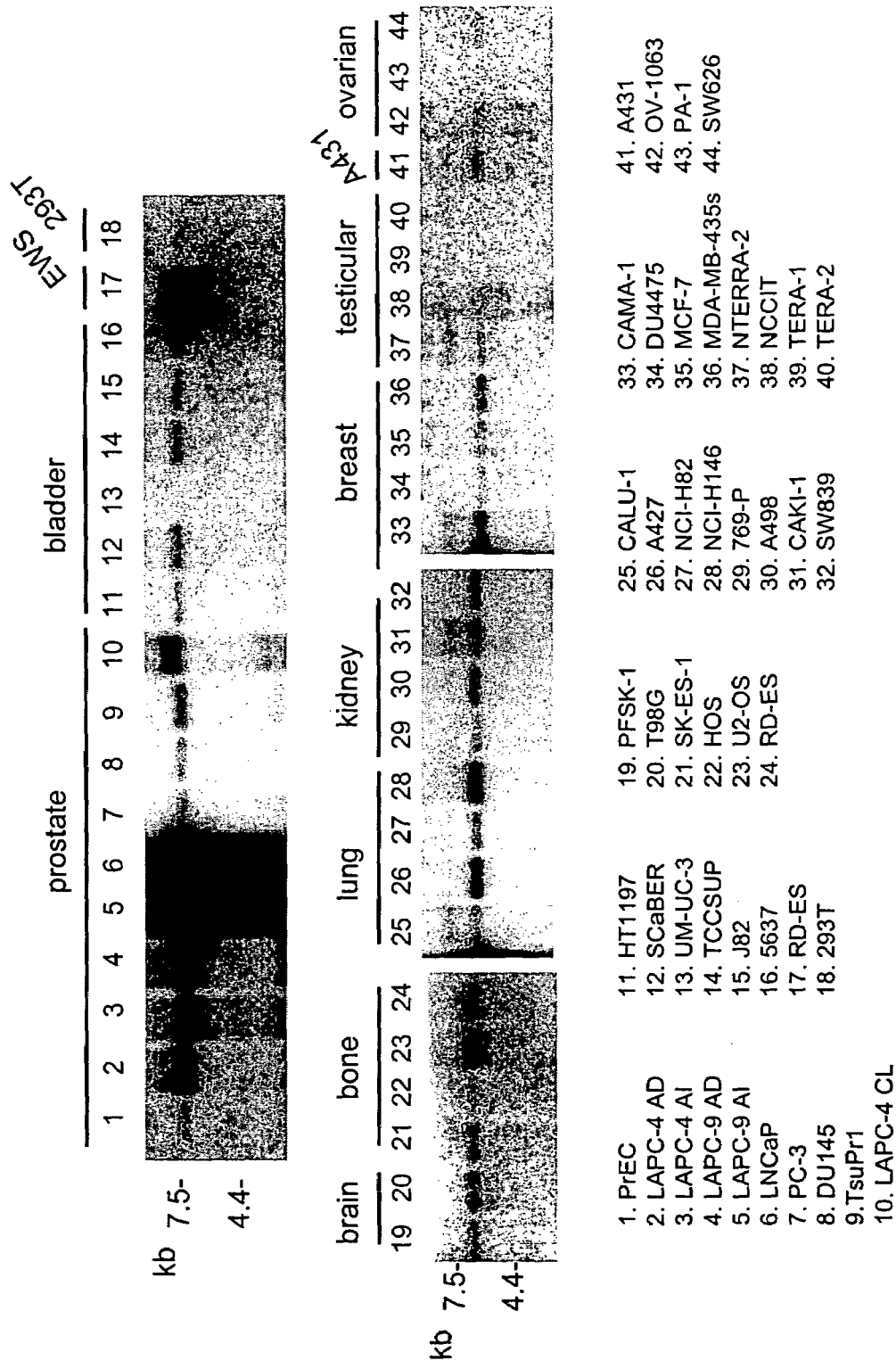
Figure 13 Expression of 108P5H8/ZnT4 in prostate and multiple cancer cell lines

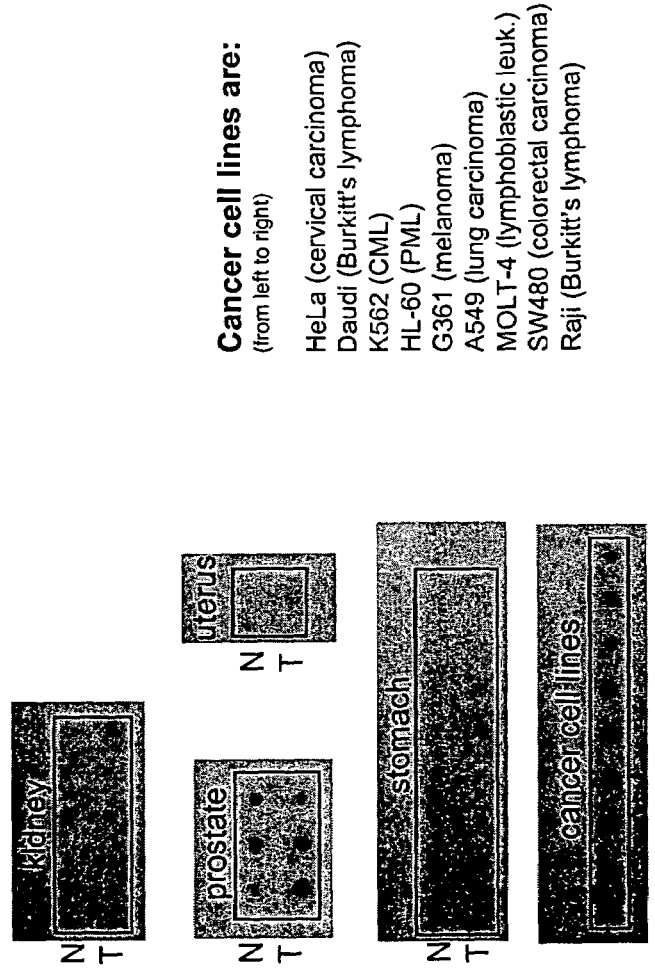
Figure 14 Expression of 108P5H8 in Human Cancers

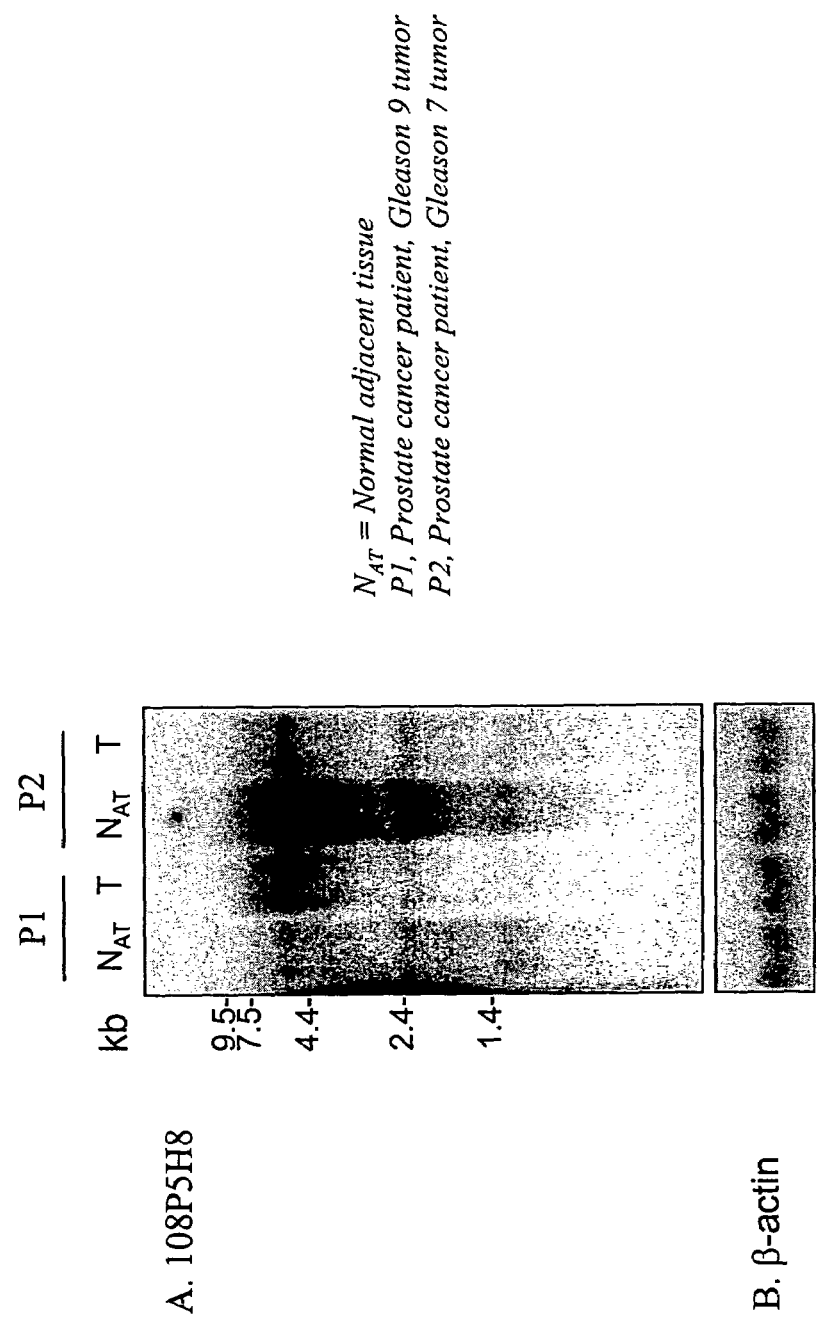
Figure 15  Expression of 108P5H8 in prostate cancer patients samples

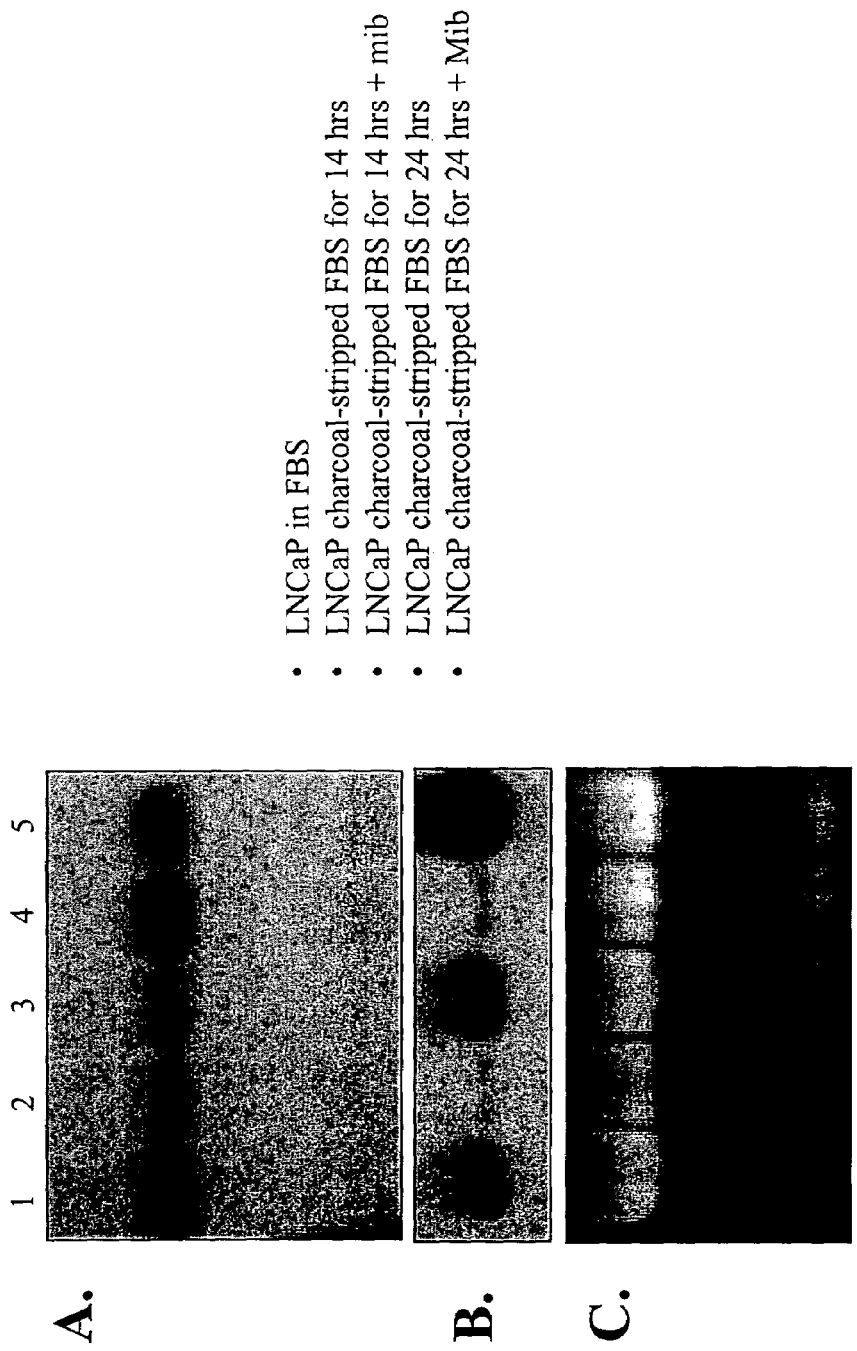
Figure 16 108P5H8 is not Androgen-Regulated

Figure 17 Expression of 108P5H8 in Prostate Cancer Metastasis Specimens
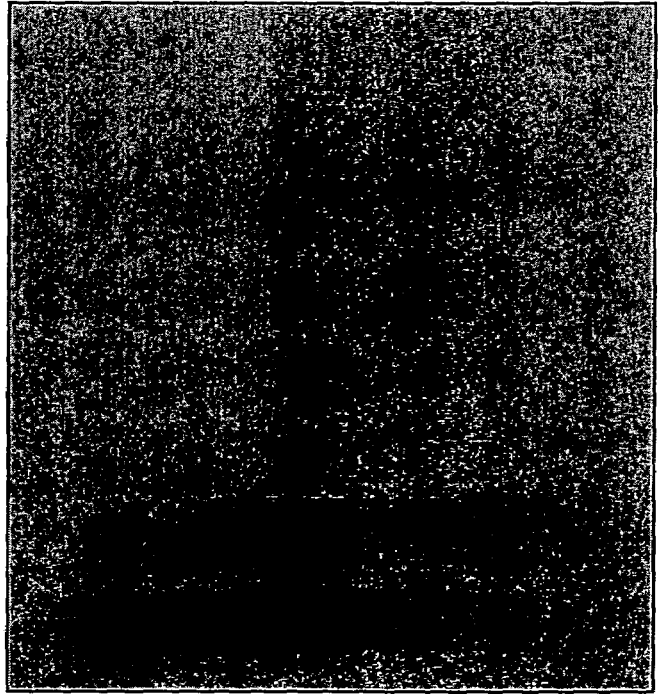
Met1 = Prostate cancer metastasis to lymph node from patient 1
Met2 = Prostate cancer metastasis to lymph node from patient 2
NB = normal bladder
NK = normal kidney
NL = normal lung
NBr = normal breast
NO = normal ovary
NPa = normal pancreas

Figure 18

```
         10        20        30        40        50        60        70
         |         |         |         |         |         |         |
MAGSGAWKRLKSMLRKDDAPLFLNDTSAFDFSDEAGDEGLSRFNKLRVVVADDGSEAPERPVNGAHPTLQ
ccchhhhhhhhhhcccccccccceeecccccchhhhhcccceeeeeccccccccccccccccccccc
ADDDSLLDQDLPLTNSQLSLKVDSCDNCSKQREILKQRKVKARITIAAVLYLLFMIGELVGGYIANSLAI
ccccccccccccccccccccccccceeeeccccccccchhhhhhhhhhhhhhhhhhhhhhchhhhhhh
MTDALHMLTDLSAIILTLLALWLSSKSPTKRFTFGFHRLEVLSAMISVLLVYILMGFLLYEAVQRTIHMN
hhhhhhhhhhhhhhhhhhhhhhhccccccceeechhhhhhhhhhhhhhhhhhhhhhhhhhhhhhhec
YEINGDIMLITAAVGVAVNVIMGFLLNQSGHRHSHSHSLPSNSPTRGSSGCERNHGQDSLAVRAAFVHALG
ccccchhhhhhhhhhhhhhhhhhheecccccccccccccccccccccccccchhhhhhhhhhhhhhh
DLVQSVGVLIAAYIIRFKPEYKIADPICTYVFSLLVAFTTFRIIWDTVVIILEGVPSHLNVDYIKEALMK
hhhhhhhhhhhhheeecccccccchhhhhhhhhhhcchheeeeecccccchcccchhhhhhhhhhhh
IEDVYSVEDLNIWSLTSGKSTAIVHIQLIPGSSSKWEEVQSKANHLLLNTFGMYRCTIQLQSYRQEVDRT
hhchhehcccceeeecccccccchhhhhhhhhhhhhhccchheeeeeccccchhhhhc
CANCQSSSP
ccccccccc c: random coil   (38.46%)
e: extended strand (11.66%)
h: alpha helix    (49.88%)
```

Figure 20: Androgen-independent expression of 108P5H8 in prostate cancer cells
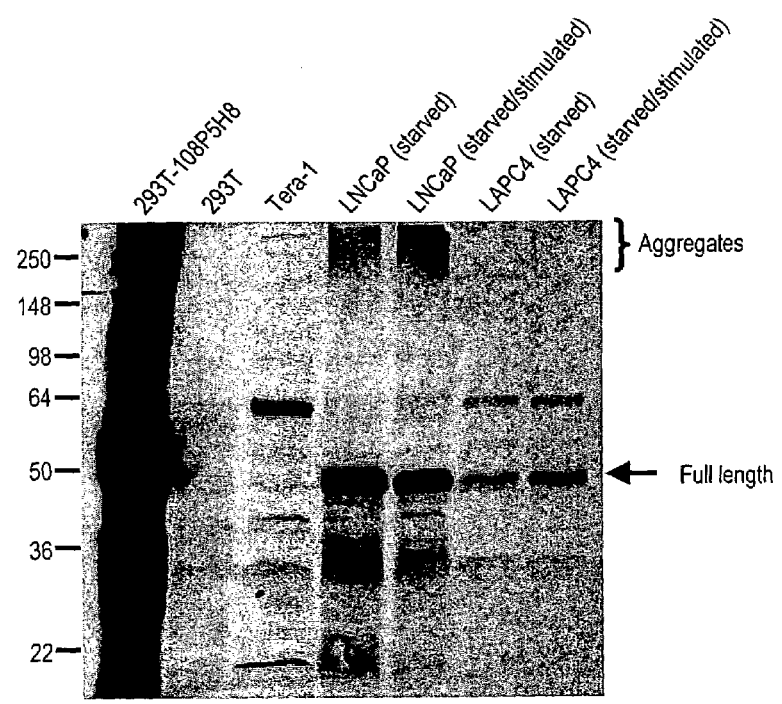

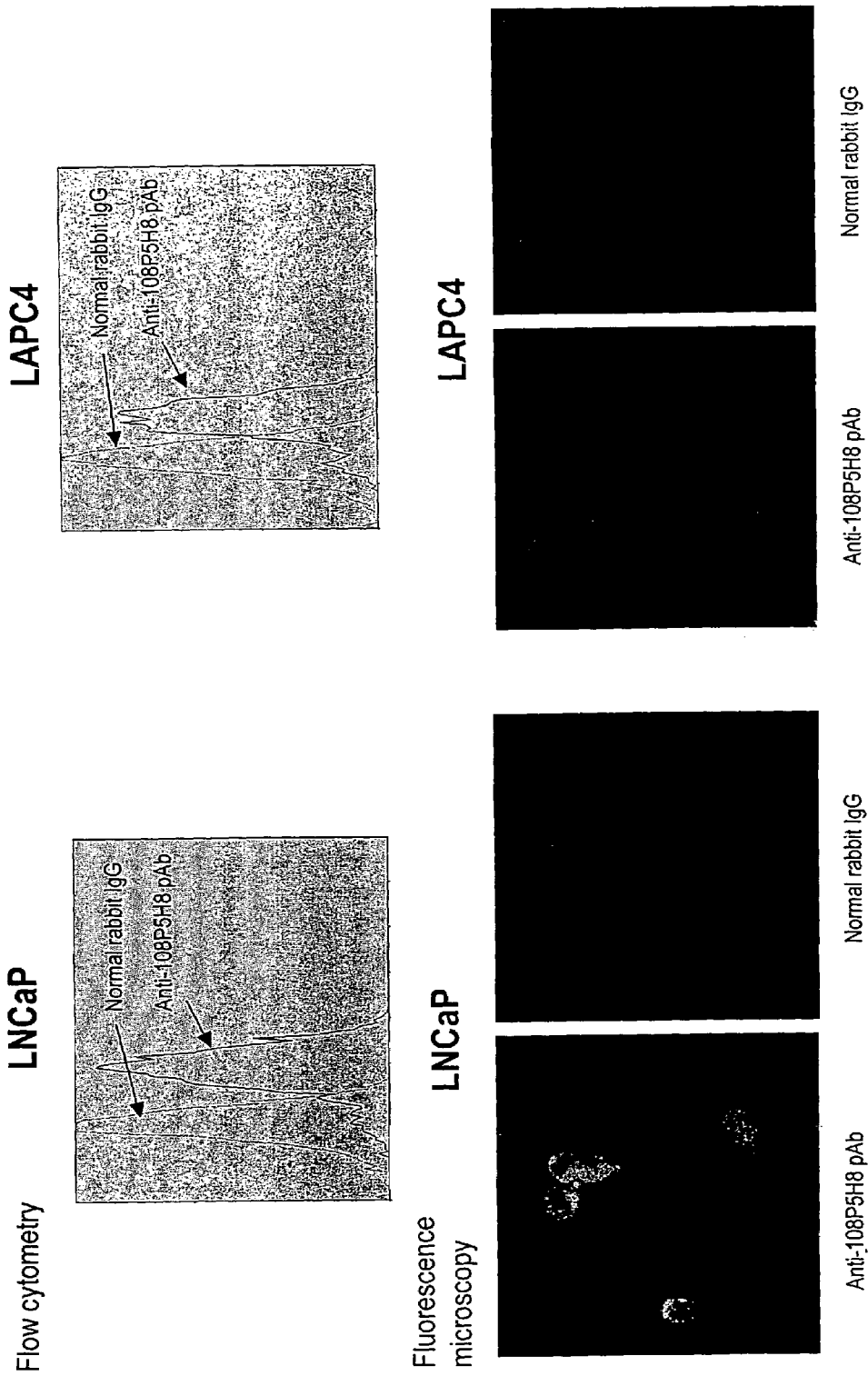
Figure 21: Surface expression of 108P5H8 in prostate cancer cells

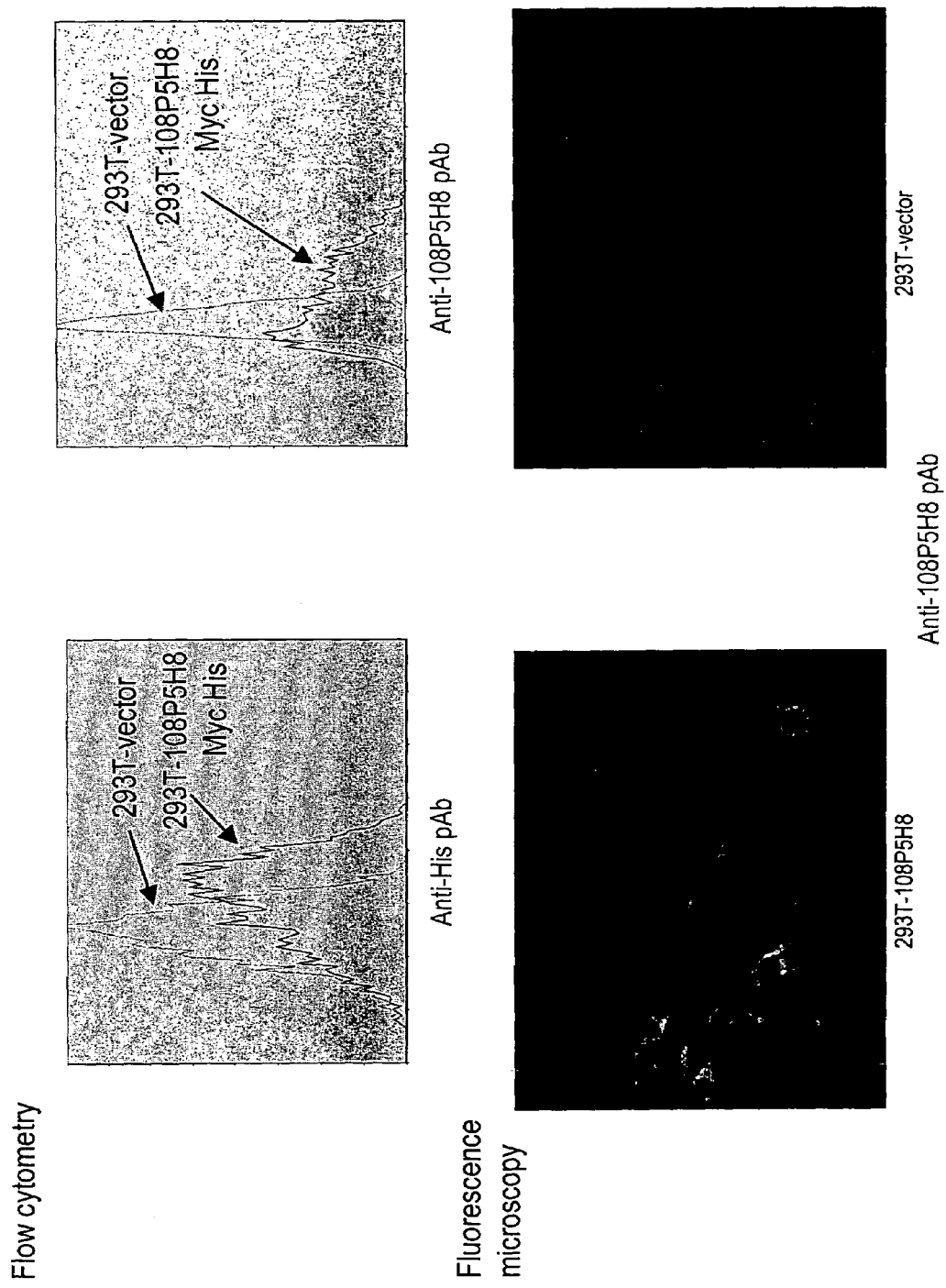
Figure 22: Surface expression of 108P5H8 in 293T cells

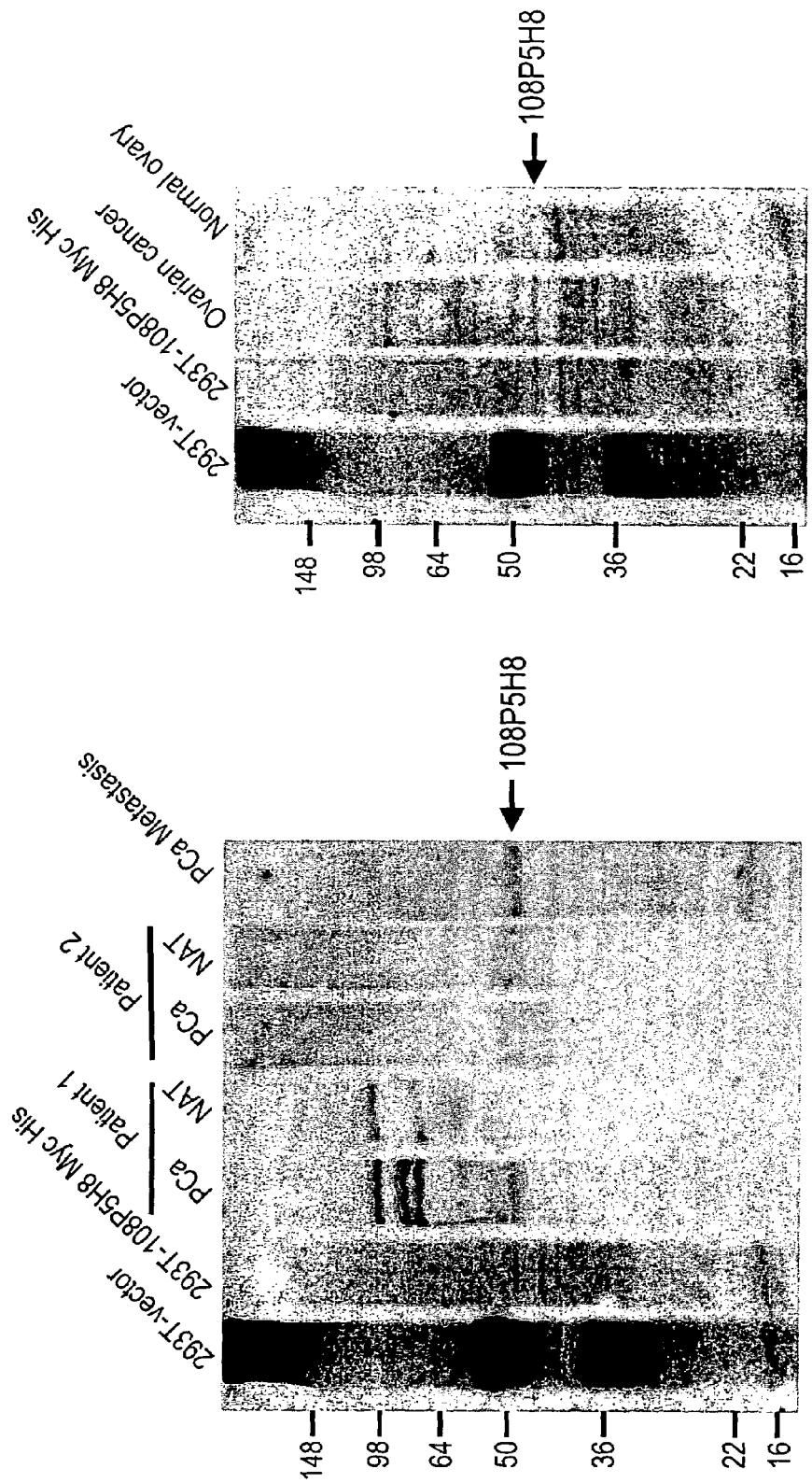
Figure 23: Expression of 108P5H8 in prostate and ovarian cancer patient specimens

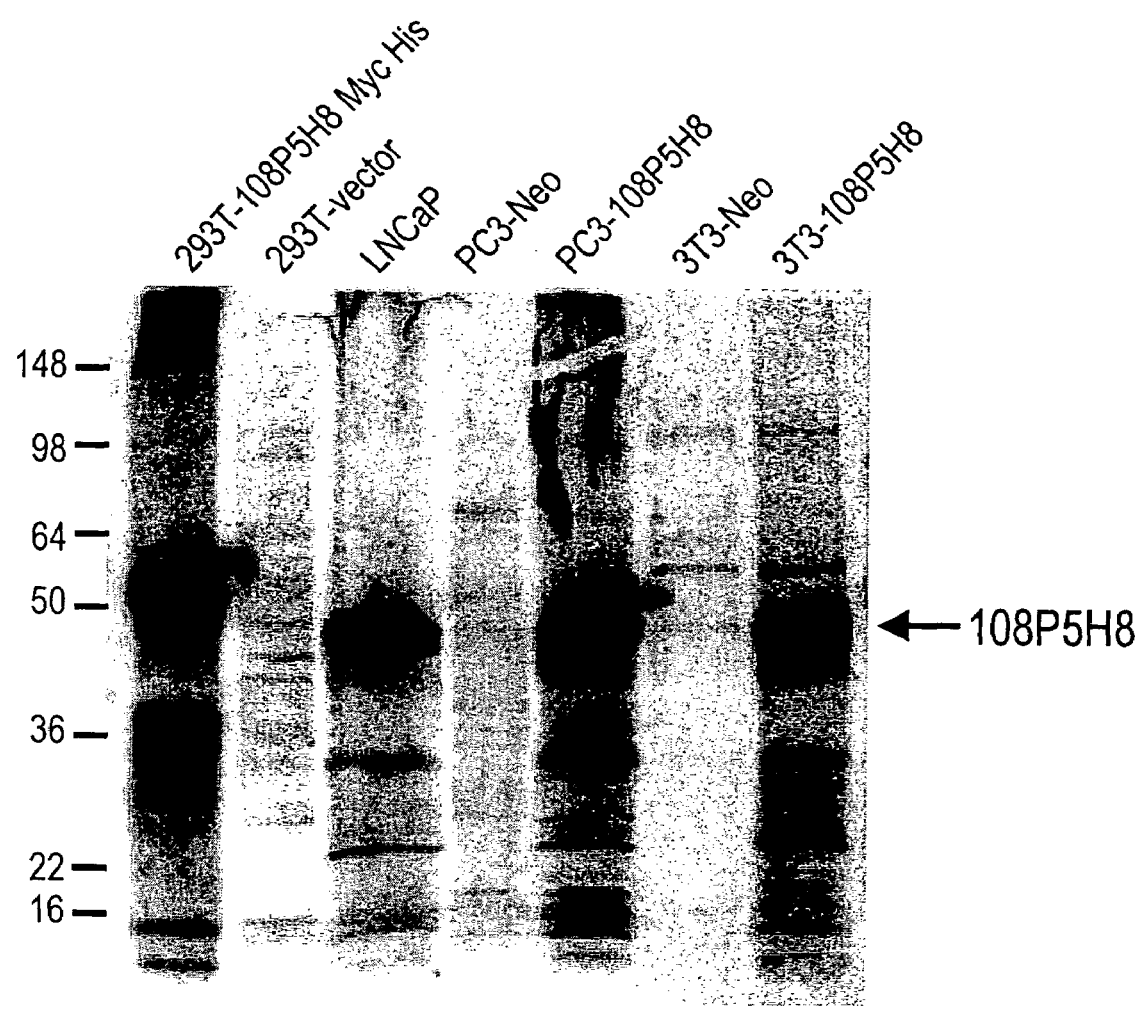
Figure 24: Expression of 108P5H8 in engineered cell lines

Figure 25 A
A-Alignment of 108P5H8 with the human zinc transporter 4, i.e. gi 11432533

Identities = 429/429 (100%), Positives = 429/429 (100%)

```
108P5:   1  MAGSGAWKRLKSMLRKDDAPLFLNDTSAFDFSDEAGDEGLSRFNKLRVVVADDGSEAPER   60
            MAGSGAWKRLKSMLRKDDAPLFLNDTSAFDFSDEAGDEGLSRFNKLRVVVADDGSEAPER
Sbjct:   1  MAGSGAWKRLKSMLRKDDAPLFLNDTSAFDFSDEAGDEGLSRFNKLRVVVADDGSEAPER   60

108P5:  61  PVNGAHPTLQADDDSLLDQDLPLTNSQLSLKVDSCDNCSKQREILKQRKVKARLTIAAVL  120
            PVNGAHPTLQADDDSLLDQDLPLTNSQLSLKVDSCDNCSKQREILKQRKVKARLTIAAVL
Sbjct:  61  PVNGAHPTLQADDDSLLDQDLPLTNSQLSLKVDSCDNCSKQREILKQRKVKARLTIAAVL  120

108P5: 121  YLLFMIGELVGGYIANSLAIMTDALHMLTDLSAIILTLLALWLSSKSPTKRFTFGFHRLE  180
            YLLFMIGELVGGYIANSLAIMTDALHMLTDLSAIILTLLALWLSSKSPTKRFTFGFHRLE
Sbjct: 121  YLLFMIGELVGGYIANSLAIMTDALHMLTDLSAIILTLLALWLSSKSPTKRFTFGFHRLE  180

108P5: 181  VLSAMISVLLVYILMGFLLYEAVQRTIHMNYEINGDIMLITAAVGVAVNVIMGFLLNQSG  240
            VLSAMISVLLVYILMGFLLYEAVQRTIHMNYEINGDIMLITAAVGVAVNVIMGFLLNQSG
Sbjct: 181  VLSAMISVLLVYILMGFLLYEAVQRTIHMNYEINGDIMLITAAVGVAVNVIMGFLLNQSG  240

108P5: 241  HRHSHSHSLPSNSPTRGSGCERNHGQDSLAVRAAFVHALGDLVQSVGVLIAAYIIRFKPE  300
            HRHSHSHSLPSNSPTRGSGCERNHGQDSLAVRAAFVHALGDLVQSVGVLIAAYIIRFKPE
Sbjct: 241  HRHSHSHSLPSNSPTRGSGCERNHGQDSLAVRAAFVHALGDLVQSVGVLIAAYIIRFKPE  300

108P5: 301  YKIADPICTYVFSLLVAFTTFRIIWDTVVIILEGVPSHLNVDYIKEALMKIEDVYSVEDL  360
            YKIADPICTYVFSLLVAFTTFRIIWDTVVIILEGVPSHLNVDYIKEALMKIEDVYSVEDL
Sbjct: 301  YKIADPICTYVFSLLVAFTTFRIIWDTVVIILEGVPSHLNVDYIKEALMKIEDVYSVEDL  360

108P5: 361  NIWSLTSGKSTAIVHIQLIPGSSSKWEEVQSKANHLLLNTFGMYRCTIQLQSYRQEVDRT  420
            NIWSLTSGKSTAIVHIQLIPGSSSKWEEVQSKANHLLLNTFGMYRCTIQLQSYRQEVDRT
Sbjct: 361  NIWSLTSGKSTAIVHIQLIPGSSSKWEEVQSKANHLLLNTFGMYRCTIQLQSYRQEVDRT  420

108P5: 421  CANCQSSSP  429
            CANCQSSSP
Sbjct: 421  CANCQSSSP  429
```

B-Alignment of 108P5H8 with the human zinc transporter ZNT4, i.e. gi 8134840

Identities = 428/429 (99%), Positives = 429/429 (99%)

```
108P5:   1  MAGSGAWKRLKSMLRKDDAPLFLNDTSAFDFSDEAGDEGLSRFNKLRVVVADDGSEAPER   60
            MAGSGAWKRLKSMLRKDDAPLFLNDTSAF+FSDEAGDEGLSRFNKLRVVVADDGSEAPER
Sbjct:   1  MAGSGAWKRLKSMLRKDDAPLFLNDTSAFEFSDEAGDEGLSRFNKLRVVVADDGSEAPER   60

108P5:  61  PVNGAHPTLQADDDSLLDQDLPLTNSQLSLKVDSCDNCSKQREILKQRKVKARLTIAAVL  120
            PVNGAHPTLQADDDSLLDQDLPLTNSQLSLKVDSCDNCSKQREILKQRKVKARLTIAAVL
Sbjct:  61  PVNGAHPTLQADDDSLLDQDLPLTNSQLSLKVDSCDNCSKQREILKQRKVKARLTIAAVL  120

108P5: 121  YLLFMIGELVGGYIANSLAIMTDALHMLTDLSAIILTLLALWLSSKSPTKRFTFGFHRLE  180
            YLLFMIGELVGGYIANSLAIMTDALHMLTDLSAIILTLLALWLSSKSPTKRFTFGFHRLE
Sbjct: 121  YLLFMIGELVGGYIANSLAIMTDALHMLTDLSAIILTLLALWLSSKSPTKRFTFGFHRLE  180

108P5: 181  VLSAMISVLLVYILMGFLLYEAVQRTIHMNYEINGDIMLITAAVGVAVNVIMGFLLNQSG  240
            VLSAMISVLLVYILMGFLLYEAVQRTIHMNYEINGDIMLITAAVGVAVNVIMGFLLNQSG
Sbjct: 181  VLSAMISVLLVYILMGFLLYEAVQRTIHMNYEINGDIMLITAAVGVAVNVIMGFLLNQSG  240

108P5: 241  HRHSHSHSLPSNSPTRGSGCERNHGQDSLAVRAAFVHALGDLVQSVGVLIAAYIIRFKPE  300
            HRHSHSHSLPSNSPTRGSGCERNHGQDSLAVRAAFVHALGDLVQSVGVLIAAYIIRFKPE
Sbjct: 241  HRHSHSHSLPSNSPTRGSGCERNHGQDSLAVRAAFVHALGDLVQSVGVLIAAYIIRFKPE  300

108P5: 301  YKIADPICTYVFSLLVAFTTFRIIWDTVVIILEGVPSHLNVDYIKEALMKIEDVYSVEDL  360
```

Figure 25 B

```
              YKIADPICTYVFSLLVAFTTFRIIWDTVVIILEGVPSHLNVDYIKEALMKIEDVYSVEDL
Sbjct:  301   YKIADPICTYVFSLLVAFTTFRIIWDTVVIILEGVPSHLNVDYIKEALMKIEDVYSVEDL  360

108P5:  361   NIWSLTSGKSTAIVHIQLIPGSSSKWEEVQSKANHLLLNTFGMYRCTIQLQSYRQEVDRT  420
              NIWSLTSGKSTAIVHIQLIPGSSSKWEEVQSKANHLLLNTFGMYRCTIQLQSYRQEVDRT
Sbjct:  361   NIWSLTSGKSTAIVHIQLIPGSSSKWEEVQSKANHLLLNTFGMYRCTIQLQSYRQEVDRT  420

108P5:  421   CANCQSSSP  429
              CANCQSSSP
Sbjct:  421   CANCQSSSP  429
```

C-Alignment of 108P5H8 with the rat zinc transporter ZNT-4, i.e. gi 8134837

Identities = 387/430 (90%), Positives = 407/430 (94%), Gaps = 3/430 (0%)

```
108P5:    1   MAGSGAWKRLKSMLRKDDAPLFLNDTSAFDFSDEAGDEGLSRFNKLRVVVADDGSEAPER   60
              MAG GAWKRLKS+LRKDDAPLFLNDTSAFDF DE  DEGLSRFNKLRVVVADD SEAPER
Sbjct:    1   MAGPGAWKRLKSLLRKDDAPLFLNDTSAFDFLDEVSDEGLSRFNKLRVVVADDDSEAPER   60

108P5:   61   PVNGAHPTLQADDDSLLDQDLPLTNSQLSLKVDSCDNCSKQREILKQRKVKARLTIAAVL  120
              PVNGAHP LQADDDSLLDQ+LPLTNSQLSLK+D CDNCSK+RE+LKQRKVK RLTIAAVL
Sbjct:   61   PVNGAHPALQADDDSLLDQELPLTNSQLSLKMDPCDNCSKRRELLKQRKVKTRLTIAAVL  120

108P5:  121   YLLFMIGELVGGYIANSLAIMTDALHMLTDLSAIILTLLALWLSSKSPTKRFTFGFHRLE  180
              YLLFMIGELVGGY+ANSLAIMTDALHMLTDLSAIILTLLALWLSSKSPT+RFTFGFHRLE
Sbjct:  121   YLLFMIGELVGGYMANSLAIMTDALHMLTDLSAIILTLLALWLSSKSPTRRFTFGFHRLE  180

108P5:  181   VLSAMISVLLVYILMGFLLYEAVQRTIHMNYEINGDIMLITAAVGVAVNVIMGFLLNQ--  238
              VLSAMISV+LVY+LMGFLLYEA+QRTIHMNYEINGD+MLITAAVGVAVNVIMGFLLNQ
Sbjct:  181   VLSAMISVMLVYVLMGFLLYEAMQRTIHMNYEINGDVMLITAAVGVAVNVIMGFLLNQSG  240

108P5:  239   SGHRHSHSHSLPSNSPTRGSGCERNHGQDSLAVRAAFVHALGDLVQSVGVLIAAYIIRFK  298
                H H+HSHSLPSNSP+  S     +HGQDSLAVRAAFVHALGDLVQSVGVLIAAYIIRFK
Sbjct:  241   HHHSHAHSHSLPSNSPSMVSS-GHSHGQDSLAVRAAFVHALGDLVQSVGVLIAAYIIRFK  299

108P5:  299   PEYKIADPICTYVFSLLVAFTTFRIIWDTVVIILEGVPSHLNVDYIKEALMKIEDVYSVE  358
              PEYKIADPICTY+FSLLVAFTT RIIWDTVVIILEGVPSHLNVDYIKE+LMKIEDVYSVE
Sbjct:  300   PEYKIADPICTYIFSLLVAFTTLRIIWDTVVIILEGVPSHLNVDYIKESLMKIEDVYSVE  359

108P5:  359   DLNIWSLTSGKSTAIVHIQLIPGSSSKWEEVQSKANHLLLNTFGMYRCTIQLQSYRQEVD  418
              DLNIWSLTSGK+TAIVH+QLIPGSSSKWEEVQSKA HLLLNTFGMY+CT+QLQSYRQE
Sbjct:  360   DLNIWSLTSGKATAIVHMQLIPGSSSKWEEVQSKAKHLLLNTFGMYKCTVQLQSYRQEAT  419

108P5:  419   RTCANCQSSS  428
              RTCANCQSSS
Sbjct:  420   RTCANCQSSS  429
```

*There are three insertions in variant 3: GT, AATTCAC and C at 1553, 1566 and 1784, respectively; numbering is relevant to variant 1.

METHOD OF INHIBITING GROWTH OR SURVIVAL OF A CELL BY PROVIDING AN ANTI-108P5H8 ANTIBODY

RELATED APPLICATIONS

This application claims priority from provisional application U.S. Ser. No. 60/256,210 filed 15 Dec. 2000, the contents of which are incorporated herein by reference.

SUBMISSION ON COMPACT DISK

The contents of the following submission on compact discs are incorporated herein by reference in its entirety: A compact disc copy of the Sequence Listing (COPY 1) (file name: 511582002500, date recorded: 2 Jun. 2002, size: 434 KB); a duplicate compact disc copy of Sequence Listing (COPY 2) (file name: 511582002500, date recorded: 2 Jun. 2002, size: 434 KB); a computer readable form copy of the Sequence Listing (CRF COPY) (file name: 511582002500, date recorded: 2 Jun. 2002, size: 434 KB).

FIELD OF THE INVENTION

The invention described herein relates to a gene and its encoded protein, termed 108P5H8, expressed in certain cancers such as those listed in Table I, and to diagnostic, prognostic, prophylactic and/or therapeutic methods and compositions useful in the management of cancers that express 108P5H8.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease— second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 September 2 (9): 1445-51), STEAP (Hubert, et al., Proc Natl Acad Sci USA. 1999 Dec. 7; 96(25): 14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and 8 per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer.

Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF THE INVENTION

The present invention relates to a gene, designated 108P5H8, that has now been found to be over-expressed in the cancer(s) listed in Table I. Northern blot expression analysis of 108P5H8 gene expression in normal tissues shows a restricted expression pattern in adult tissues. The nucleotide (FIG. 2) and amino acid (FIG. 2, and FIG. 3) sequences of 108P5H8 are provided. The tissue-related profile of 108P5H8 in normal adult tissues, combined with the over-expression observed in the tumors listed in Table I, shows that 108P5H8 is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 108P5H8 genes, mRNAs, and/or coding sequences, preferably in isolated form, including polynucleotides encoding 108P5H8-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 108P5H8-related protein, as well as the peptides/proteins themselves; DNA, RNA, DNA/RNA hybrids, and related molecules, polynucleotides or oligonucleotides complementary or having at least a 90% homology to the 108P5H8 genes or mRNA sequences or parts thereof, and polynucleotides or oligonucleotides that hybridize to the 108P5H8 genes, mRNAs, or to 108P5H8-encoding polynucleotides. Also provided are means for isolating cDNAs and the genes encoding 108P5H8. Recombinant DNA molecules containing 108P5H8 polynucleotides, cells transformed or transduced with such molecules, and host-vector systems for the expression of 108P5H8 gene products are also provided. The invention further provides antibodies that bind to 108P5H8 proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 108P5H8 polynucleotides and proteins in various biological samples, as well as methods for identifying cells that express 108P5H8. A typical embodiment of this invention provides methods for monitoring 108P5H8 gene products in a tissue or hematology sample having or suspected of having some form of growth dysregulation such as cancer.

The invention further provides various immunogenic or therapeutic compositions and strategies for treating cancers that express 108P5H8 such as cancers of tissues listed in Table I, including therapies aimed at inhibiting the transcription, translation, processing or function of 108P5H8 as well as cancer vaccines. In one aspect, the invention provides compositions, and methods comprising them, for treating a cancer that expresses 108P5H8 in a human subject wherein the composition comprises a carrier suitable for human use and a human unit dose of one or more than one agent that inhibits the production or function of 108P5H8. Preferably, the carrier is a uniquely human carrier. In another aspect of the invention, the agent is a moiety that is immunoreactive with 108P5H8 protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to 108P5H8 and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 108P5H8 as described above. The one or more than one nucleic acid molecule may also be, or encodes, a molecule that inhibits production of 108P5H8. Non-limiting examples of such molecules include, but are not limited to, those complementary to a nucleotide sequence essential for production of 108P5H8 (e.g. antisense sequences or molecules that form a triple helix with a nucleotide double helix essential for 108P5H8 production) or a ribozyme effective to lyse 108P5H8 mRNA.

BRIEF DESCRIPTION OF THE FIGURES

FIG. 1. The 108P5H8 sequence of 448 nucleotides (SEQ ID NO: 2568).

FIG. 2. The cDNA (SEQ ID. NO.: 2569) and amino acid sequence (SEQ ID. NO.: 2570) of 108P5H8 v.1 is shown in 2A-1, 2A-2, 2B-1, 2B-2, 2C-1, 2C-2. The start methionine is underlined. The open reading frame extends from nucleic acid 253-1542 including the stop codon. The nucleic acid (SEQ ID. NO.: 2571) and amino acid sequence of 108P5H8 variant 2 (SEQ ID. NO.: 2572) is shown in FIG. 2B, the codon for the start methionine is underlined. The open reading frame for variant 2 extends from nucleic acid 1 to 1290 including the stop codon. The nucleic acid (SEQ ID. NO.: 2573) and amino acid sequence of 108P5H8 variant 3 (SEQ ID. NO.: 2574) is shown in FIG. 2C, the codon for the start methionine is underlined. The open reading frame for variant 3 extends from nucleic acid 1-1290 including the stop codon.

FIG. 3. Amino acid sequence of 108P5H8 variant 1 and of 108P5H8 variant 2 (SEQ ID. NO.: 2572) is shown in FIG. 3A. The proteins encoded by the variant 1 and variant 2 nucleic acid sequences are identical and each have 429 amino acids. The amino acid sequence of 108P5H8 variant 3 (SEQ ID. NO.: 2574) is shown in FIG. 3B, the 108P5H8 v.3 protein has 429 amino acids.

FIG. 4. FIGS. 4A-1 to 4A-8 shows nucleotide sequence alignments of 108P5H8 variants 1-3 and FIGS. 4B-1 to 4B-2 shows amino acid alignments of 108P5H8 variant 1 (SEQ ID. NO.: 2570), variant 2 (SEQ ID. NO.: 2572) and variant 3 (SEQ ID. NO.: 2574).

FIG. 5. Hydrophilicity amino acid profile of 108P5H8 determined by computer algorithm sequence analysis using the method of Hopp and Woods (Hopp T. P., Woods K. R., 1981. Proc. Natl. Acad. Sci. U.S.A. 78:3824-3828) accessed on the Protscale website through the ExPasy molecular biology server.

FIG. 6. Hydropathicity amino acid profile of 108P5H8 determined by computer algorithm sequence analysis using the method of Kyte and Doolittle (Kyte J., Doolittle R. F., 1982. J. Mol. Biol. 157:105-132) accessed on the ProtScale website through the ExPasy molecular biology server.

FIG. 7. Percent accessible residues amino acid profile of 108P5H8 determined by computer algorithm sequence analysis using the method of Janin (Janin J., 1979 Nature 277:491-492) accessed on the ProtScale website through the ExPasy molecular biology server.

FIG. 8. Average flexibility amino acid profile of 108P5H8 determined by computer algorithm sequence analysis using the method of Bhaskaran and Ponnuswamy (Bhaskaran R., and Ponnuswamy P. K., 1988. Int. J. Pept. Protein Res. 32:242-255) accessed on the ProtScale website through the ExPasy molecular biology server.

FIG. 9. Beta-turn amino acid profile of 108P5H8 determined by computer algorithm sequence analysis using the method of Deleage and Roux (Deleage, G., Roux B. 1987 Protein Engineering 1:289-294) accessed on the ProtScale website through the ExPasy molecular biology server.

FIG. 10. Expression of 108P5H8 by RT-PCR. First strand cDNA was prepared from vital pool 1 (VP1: liver, lung and kidney), vital pool 2 (VP2, pancreas, colon and stomach), prostate xenograft pool (LAPC-4AD, LAPC-4AI, LAPC-9AD, LAPC-9AI), normal thymus, prostate cancer pool, bladder cancer pool, kidney cancer pool, colon cancer pool, lung cancer pool, ovary cancer pool, breast cancer pool, metastasis cancer pool, pancreas cancer pool, and from prostate cancer metastasis to lymph node from 2 different patients. Normalization was performed by PCR using primers to actin and GAPDH. Semi-quantitative PCR using primers to 108P5H8 was performed at 26 and 30 cycles of amplification. Strong expression of 108P5H8 was observed in prostate cancer xenograft pool, prostate cancer pool and in the 2 different prostate cancer metastasis samples. Lower expression was detected in bladder cancer pool, kidney cancer pool, colon cancer pool, lung cancer pool, ovary cancer pool, breast cancer pool, metastasis pool, pancreas cancer pool, VP1 and VP2.

FIG. 11. Expression of 108P5H8 in normal human tissues and in prostate cancer xenografts. (A and B) Two multiple tissue Northern blots, with 2 mg of mRNA/lane, were probed with 108P5H8 sequence. Size standards in kilobases (kb) are indicated on the side. The results show strong expression of an approximately 7 kb 108P5H8 transcript in prostate and lower expression in other tissues. (C) RNA was extracted from normal prostate, and from prostate cancer xenografts, LAPC4AD, LAPC-4AI, LAPC-9AD, and LAPC-9AI. Northern blot with 10 mg of total RNA/lane was probed with 108P5H8 sequence. Size standards in kilobases (kb) are indicated on the side. The results show expression of 108P5H8 in all 4 xenografts and in normal prostate.

FIG. 12. Expression of 108P5H8 in prostate cancer xenografts. RNA was extracted from prostate cancer xenografts, LAPC-4AD, and LAPC-9AD, injected either subcutaneously (sc) or intra-tibially (it) within the mouse bone. LAPC4 was also grown within a human bone implant in SCID mice (LAPC4 AD2). Northern blots with 10 µg of total RNA/lane were probed with the 108P5H8 SSH fragment. Size standards in kilobases (kb) are indicated on the side. Results show expression of 108P5H8 in all prostate cancer xenograft tissues tested.

FIG. 13. Expression of 108P5H8 in human cancer cell lines. RNA was extracted from a panel of human cancer cell lines. Northern blots with 10 mg of total RNA/lane were probed with the 108P5H8 SSH fragment. Size standards in kilobases (kb) are indicated on the side. Results show that 108P5H8 is expressed in all cell lines tested such as prostate, bladder, brain, lung, kidney, breast, testis and ovary cancer cell lines.

FIG. 14. Expression of 108P5H8 in patient cancer specimens and cancer cell lines. Expression of 108P5H8 was assayed in a panel of human cancers (T) and their respective matched normal tissues (N) on RNA dot blots. 108P5H8 expression was seen in prostate, kidney, uterus and stomach cancers. The expression detected in some normal adjacent tissues (isolated from diseased tissues), but not in normal tissues (isolated from healthy donors), may indicate that these tissues are not fully normal and that 108P5H8 may be expressed in early stage tumors. 108P5H8 was also expressed in all 9 human cancer cell lines tested.

FIG. 15. Expression of 108P5H8 in prostate cancer patient specimens. RNA was extracted from prostate tumors (T) and matched normal adjacent tissue (NAT) isolated from prostate cancer patients. Northern blots with 10 mg of total RNA/lane were probed with 108P5H8 sequence. Size standards in kilobases (kb) are indicated on the side. The results show expression of 108P5H8 in the two prostate tumors and in the normal matched tissues.

FIG. 16. 108P5H8 is not Androgen-Regulated. LNCaP cells were grown in charcoal-stripped medium and stimulated with the synthetic androgen mibolerone, for either 14 or 24 hours. Northern blots with 10 mg of total RNA/lane were probed with either the 108P5H8 sequence (A), or with the androgen-regulated gene PSA (B). A picture of the ethidium-bromide staining of the RNA gel is also presented (C). Results show expression of 108P5H8 is not regulated by androgen. The experimental samples were confirmed by testing for the expression of the androgen-regulated prostate cancer gene PSA (B). This experiment shows that, as expected, PSA levels go down in presence of charcoal-stripped serum, and expression is induced at 14 and 24 hours in presence of the synthetic androgen.

FIG. 17. Expression of 108P5H8 in cancer metastasis patient specimens. RNA was extracted from prostate cancer metastasis to lymph node obtained from two different patient, as well as from normal bladder (NB), normal kidney (NK), normal lung (NL), normal breast (NBr), normal ovary (NO), and normal pancreas (NPa). Northern blots with 10 mg of total RNA/lane were probed with 108P5H8 sequence. Size standards in kilobases (kb) are indicated on the side. The results show expression of 108P5H8 in both cancer metastasis samples but not in normal tissues.

FIG. 18. Secondary structure and transmembrane prediction for 108P5H8 (SEQ ID. NO.: 2570). The secondary structure of 108P5H8 protein was predicted using the HNN— Hierarchical Neural Network method (Guermeur, 1997), accessed from the ExPasy molecular biology server. This method predicts the presence and location of alpha helices, extended strands, and random coils from the primary protein sequence. The percent of the protein in a given secondary structure is also given.

FIG. 20. Androgen-independent expression of 108P5H8 in prostate cancer cells. Western analysis of the indicated cell lysates were carried out with a 1:2000 dilution of an anti-108P5H8 polyclonal antibody derived from immunization of a rabbit with a GST-fusion protein encoding amino acids 1-112 of 108P5H8. 108P5H8 specific bands were developed by incubation with an anti-rabbit HRP-conjugated secondary antibody and visualized by enhanced chemiluminescence and exposure to autoradiography film. Indicated with an arrow is the full length 108P5H8 protein. 293T cells overexpressing Myc His-tagged 108P5H8 serves as a positive control FIG. 21. Surface expression of 108P5H8 in prostate cancer cells. LNCaP and LAPC4 cells were subjected to flow cytometric and fluorescence microscopic analysis of 108P5H8 expression using an anti-108P5H8 polyclonal antibody or control rabbit IgG. Fluorescence was monitored following incubation with an FITC-conjugated anti-rabbit IgG secondary antibody FIG. 22. Surface expression of 108P5H8 in 293T cells. 293T cells were transfected with either empty control vector or with pCDNA 3.1 encoding the 108P5H8 cDNA and subjected to flow cytometry and fluorescence microscopy using an anti-108P5H8 polyclonal antibody (1:100 dilution). Fluorescence was monitored following incubation with an FITC-conjugated anti-rabbit IgG secondary antibody. 293T-108P5H8 cells exhibited strong surface fluorescence.

FIG. 23. Expression of 108P5H8 in prostate and ovarian cancer patient specimens. Lysates from tumor (PCa) and normal adjacent tissue (NAT) from 2 prostate cancer patients and from a prostate cancer metastasis and tumor and normal adjacent tissue from an ovarian cancer patient were subjected to Western analysis using anti-108P5H8 polyclonal antibody as described in FIG. 20. Indicated with an arrow is a 48 kD band representing full length 108P5H8. 108P5H8 protein was present in the tumor tissue from the 2 prostate cancer patients and the metastasis sample and in the normal adjacent tissue of 1 of the patients. 108P5H8 was also expressed in the ovarian cancer sample but not in normal ovary. Low expression is seen in RNA positive 293T cells and strong expression in the overexpressed 293T-108P5H8 cells.

FIG. 24. Expression of 108P5H8 in engineered cell lines. PC3 human prostate cancer cells and NIH3T3 murine fibroblasts were engineered to stably express 108P5H8 through infection with retrovirus harboring the 108P5H8 cDNA. Stable lines were generated by G418 selection for neomycin resistance. 108P5H8 expression was verified by Western blot analysis with anti-108P5H8 polyclonal antibody as described in FIG. 20, using the respective cell lines expressing only the neomycin resistance gene as negative controls.

FIG. 25. FIGS. 25A and 25B show 108P5H8 protein variants show homology to human zinc transporter 4.

FIG. 28.

DETAILED DESCRIPTION OF THE INVENTION

Outline of Sections

Figure 19:
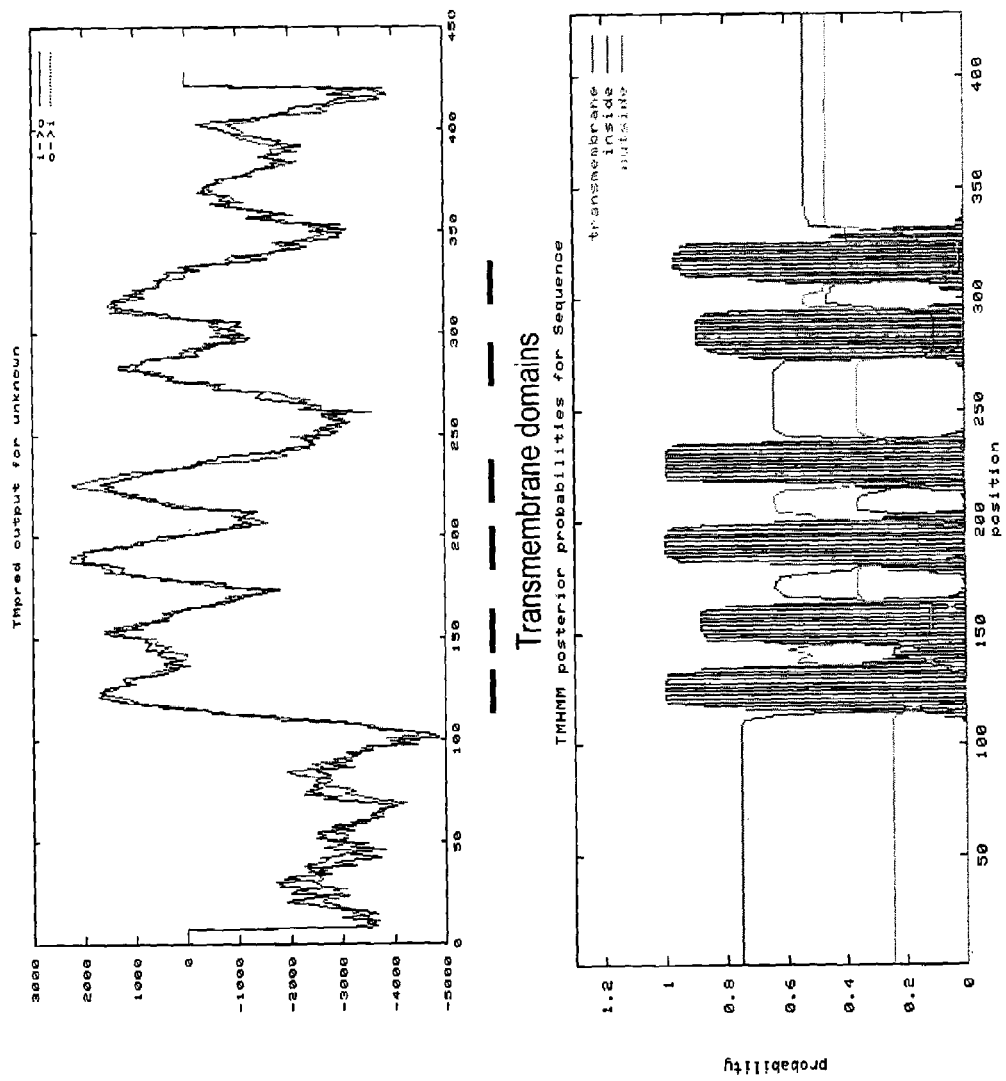
FIG. 19. Transmembrane prediction for 108P5H8. A. Schematic representation of the probability of existence of transmembrane regions and orientation of 108P5H8 based on the TMpred algorithm of Hofmann and Stoffel which utilizes TMBASE (K. Hofmann, W. Stoffel. TMBASE—A database of membrane spanning protein segments Biol. Chem. Hoppe-Seyler 374:166, 1993). B. Schematic representation of the probability of the existence of transmembrane regions and the extracellular and intracellular orientation of 108P5H8 based on the TMHMM algorithm of Sonnhammer, von Heijne, and Krogh (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998). The TMpred and TMHMM algorithms are accessed from the ExPasy molecular biology server. The results of the transmembrane prediction programs presented in A and B depict 108P5H8 as containing 6 transmembrane domains.

I.) Definitions
II.) 108P5H8 Polynucleotides
II.A.) Uses of 108P5H8 Polynucleotides
II.A.1.) Monitoring of Genetic Abnormalities
II.A.2.) Antisense Embodiments
II.A.3.) Primers and Primer Pairs
II.A.4.) Isolation of 108P5H8-Encoding Nucleic Acid Molecules
II.A.5.) Recombinant Nucleic Acid Molecules and Host-Vector Systems
III.) 108P5H8-related Proteins
III.A.) Motif-bearing Protein Embodiments
III.B.) Expression of 108P5H8-related Proteins
III.C.) Modifications of 108P5H8-related Proteins
III.D.) Uses of 108P5H8-related Proteins
IV.) 108P5H8 Antibodies
V.) 108P5H8 Cellular Immune Responses
VI.) 108P5H8 Transgenic Animals
VII.) Methods for the Detection of 108P5H8
VIII.) Methods for Monitoring the Status of 108P5H8-related Genes and Their Products
IX.) Identification of Molecules That Interact With 108P5H8
X.) Therapeutic Methods and Compositions
X.A.) Anti-Cancer Vaccines
X.B.) 108P5H8 as a Target for Antibody-Based Therapy
X.C.) 108P5H8 as a Target for Cellular Immune Responses
X.C.1. Minigene Vaccines
X.C.2. Combinations of CTL Peptides with Helper Peptides
X.C.3. Combinations of CTL Peptides with T Cell Priming Agents
X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of 108P5H8.
XII.) Inhibition of 108P5H8 Protein Function
XII.A.) Inhibition of 108P5H8 With Intracellular Antibodies
XII.B.) Inhibition of 108P5H8 with Recombinant Proteins
XII.C.) Inhibition of 108P5H8 Transcription or Translation
XII.D.) General Considerations for Therapeutic Strategies
XIII.) KITS

I.) DEFINITIONS

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 108P5H8 (either by removing the underlying glycosylation site or by deleting the glycosylation by chemical and/or enzymatic means), and/or adding one or more glycosylation sites that are not present in the native sequence 108P5H8. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 108P5H8-related protein). For example an analog of a 108P5H8 protein can be specifically bound by an antibody or T cell that specifically binds to 108P5H8.

The term "antibody" is used in the broadest sense. Therefore an "antibody" can be naturally occurring or man-made such as monoclonal antibodies produced by conventional hybridoma technology. Anti-108P5H8 antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-108P5H8 antibodies and clones thereof (including agonist, antagonist and neutralizing antibodies) and anti-108P5H8 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alphasarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu. Antibodies may also be conjugated to an anti-cancer pro-drug activating enzyme capable of converting the pro-drug to its active form.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/ 100 μg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 108P5H8 genes or that encode polypeptides other than 108P5H8 gene product or fragments thereof. A skilled artisan can readily employ nucleic acid isolation procedures to obtain an isolated 108P5H8 polynucleotide. A protein is said to be "isolated," for example, when physical, mechanical or chemical methods are employed to remove the 108P5H8 proteins from cellular constituents that are normally associated with the protein. A skilled artisan can readily employ standard purification methods to obtain an isolated 108P5H8 protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage T×N×M+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of an 108P5H8-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. In another embodiment, for example, the primary anchor residues of a peptide that will bind an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

A "recombinant" DNA or RNA molecule is a DNA or RNA molecule that has been subjected to molecular manipulation in vitro.

Non-limiting examples of small molecules include compounds that bind or interact with 108P5H8, ligands including hormones, neuropeptides, chemokines, odorants, phospholipids, and functional equivalents thereof that bind and preferably inhibit 108P5H8 protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 108P5H8 protein; are not found in naturally occurring metabolic pathways; and/or are more soluble in aqueous than non-aqueous solutions "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 108P5H8 protein shown in FIG. 2 or FIG. 3. An analog is an example of a variant protein. Splice isoforms and single nucleotides polymorphisms (SNPs) are further examples of variants.

The "108P5H8-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 108P5H8 proteins or fragments thereof, as well as fusion proteins of a 108P5H8 protein and a heterologous polypeptide are also included. Such 108P5H8 proteins are collectively referred to as the 108P5H8-related proteins, the proteins of the invention, or 108P5H8. The term "108P5H8-related protein" refers to a polypeptide fragment or an 108P5H8 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100 or more than 100 amino acids.

II.) 108P5H8 POLYNUCLEOTIDES

One aspect of the invention provides polynucleotides corresponding or complementary to all or part of an 108P5H8 gene, mRNA, and/or coding sequence, preferably in isolated form, including polynucleotides encoding an 108P5H8-related protein and fragments thereof, DNA, RNA, DNA/RNA hybrid, and related molecules, polynucleotides or oligonucleotides complementary to an 108P5H8 gene or mRNA sequence or a part thereof, and polynucleotides or oligonucleotides that hybridize to an 108P5H8 gene, mRNA, or to an 108P5H8 encoding polynucleotide (collectively, "108P5H8 polynucleotides"). In all instances when referred to in this section, T can also be U in FIG. 2.

Embodiments of a 108P5H8 polynucleotide include: a 108P5H8 polynucleotide having the sequence shown in FIG. 2, the nucleotide sequence of 108P5H8 as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 108P5H8 nucleotides comprise, without limitation:

(I) a polynucleotide comprising, consisting essentially of, or consisting of a sequence as shown in FIG. 2 (SEQ ID Nos.: 2569, 2571, & 2573), wherein T can also be U;

(II) a polynucleotide comprising, consisting essentially of, or consisting of the sequence as shown in FIG. 2A (SEQ ID NO.: 2569), from nucleotide residue number 253 through nucleotide residue number 1542, wherein T can also be U;

(III) a polynucleotide comprising, consisting essentially of, or consisting of the sequence as shown in FIG. 2B (SEQ ID NO.: 2571), from nucleotide residue number 1 through nucleotide residue number 1290, wherein T can also be U;

(IV) a polynucleotide comprising, consisting essentially of, or consisting of the sequence as shown in FIG. 2C (SEQ ID NO.: 2573), from nucleotide residue number 1 through nucleotide residue number 1290, wherein T can also be U;

(V) a polynucleotide that encodes an 108P5H8-related protein that is at least 90% homologous to an entire amino acid sequence shown in FIGS. 2A-C (SEQ ID Nos.: 2570, 2572, & 2574);

(VI) a polynucleotide that encodes an 108P5H8-related protein that is at least 90% identical to an entire amino acid sequence shown in FIGS. 2A-C (SEQ ID Nos.: 2570, 2572, & 2574);

(VII) a polynucleotide that encodes at least one peptide set forth in Tables V-XVIII, XXII, and XXIII;

(VIII) a polynucleotide that encodes a peptide region of at least 5 amino acids of a peptide of FIG. 3A or 3B in any whole number increment up to 429 that includes an amino acid position having a value greater than 0.5 in the Hydrophilicity profile of FIG. 5;

(IX) a polynucleotide that encodes a peptide region of at least 5 amino acids of a peptide of FIG. 3A or 3B in any whole number increment up to 429 that includes an amino acid position having a value less than 0.5 in the Hydropathicity profile of FIG. 6;

(X) a polynucleotide that encodes a peptide region of at least 5 amino acids of a peptide of FIG. 3A or 3B in any whole number increment up to 429 that includes an amino acid position having a value greater than 0.5 in the Percent Accessible Residues profile of FIG. 7;

(XI) a polynucleotide that encodes a peptide region of at least 5 amino acids of a peptide of FIG. 3A or 3B in any whole number increment up to 429 that includes an amino acid position having a value greater than 0.5 in the Average Flexibility profile on FIG. 8;

(XII) a polynucleotide that encodes a peptide region of at least 5 amino acids of a peptide of FIG. 3A or 3B in any whole number increment up to 429 that includes an amino acid position having a value greater than 0.5 in the Beta-turn profile of FIG. 9;

(XIII) a polynucleotide that encodes a 108P5H8-related protein whose sequence is encoded by the cDNAs contained in the plasmid designated p108P5H8-C deposited with American Type Culture Collection as Accession No. PTA-2198;

(XIV) a polynucleotide that is fully complementary to a polynucleotide of any one of (I)-(XIII);

(XV) a polynucleotide that selectively hybridizes under stringent conditions to a polynucleotide of (I)-(XIV);

(XVI) a peptide that is encoded by any of (I)-(XIII); and, (XLII) a polynucleotide of any of (I)-(XV) or peptide of (XVI) together with a pharmaceutical excipient and/or in a human unit dose form.

As used herein, a range is understood to specifically disclose all whole unit positions thereof.

Typical embodiments of the invention disclosed herein include 108P5H8 polynucleotides that encode specific portions of 108P5H8 mRNA sequences (and those which are complementary to such sequences) such as those that encode the proteins and/or fragments thereof, for example:

4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 250, 275, 300, 325, 350, 375, 400, 425, or 429 contiguous amino acids of variants 1, 2 or 3.

For example, representative embodiments of the invention disclosed herein include: polynucleotides and their encoded peptides themselves encoding about amino acid 1 to about amino acid 10 of the 108P5H8 protein shown in FIG. 2 or FIG. 3, polynucleotides encoding about amino acid 10 to about amino acid 20 of the 108P5H8 protein shown in FIG. 2, or FIG. 3, polynucleotides encoding about amino acid 20 to about amino acid 30 of the 108P5H8 protein shown in FIG. 2 or FIG. 3, polynucleotides encoding about amino acid 30 to about amino acid 40 of the 108P5H8 protein shown in FIG. 2 or FIG. 3, polynucleotides encoding about amino acid 40 to about amino acid 50 of the 108P5H8 protein shown in FIG. 2 or FIG. 3, polynucleotides encoding about amino acid 50 to about amino acid 60 of the 108P5H8 protein shown in FIG. 2 or FIG. 3, polynucleotides encoding about amino acid 60 to about amino acid 70 of the 108P5H8 protein shown in FIG. 2 or FIG. 3, polynucleotides encoding about amino acid 70 to about amino acid 80 of the 108P5H8 protein shown in FIG. 2 or FIG. 3, polynucleotides encoding about amino acid 80 to about amino acid 90 of the 108P5H8 protein shown in FIG. 2 or FIG. 3, polynucleotides encoding about amino acid 90 to about amino acid 100 of the 108P5H8 protein shown in FIG. 2 or FIG. 3, in increments of about 10 amino acids, ending at the carboxyl terminal amino acid set forth in FIG. 2 or FIG. 3. Accordingly polynucleotides encoding portions of the amino acid sequence (of about 10 amino acids), of amino acids 100 through the carboxyl terminal amino acid of the 108P5H8 protein are embodiments of the invention. Wherein it is understood that each particular amino acid position discloses that position plus or minus five amino acid residues.

Polynucleotides encoding relatively long portions of a 108P5H8 protein are also within the scope of the invention. For example, polynucleotides encoding from about amino acid 1 (or 20 or 30 or 40 etc.) to about amino acid 20, (or 30, or 40 or 50 etc.) of the 108P5H8 protein shown in FIG. 2 or FIG. 3 can be generated by a variety of techniques well known in the art. These polynucleotide fragments can include any portion of the 108P5H8 sequence as shown in FIG. 2.

Additional illustrative embodiments of the invention disclosed herein include 108P5H8 polynucleotide fragments encoding one or more of the biological motifs contained within a 108P5H8 protein sequence, including one or more of the motif-bearing subsequences of a 108P5H8 protein set forth in Tables V-XVIII, XXII, and XXIII. In another embodiment, typical polynucleotide fragments of the invention encode one or more of the regions of 108P5H8 that exhibit homology to a known molecule. In another embodiment of the invention, typical polynucleotide fragments can encode one or more of the 108P5H8 N-glycosylation sites, cAMP and cGMP-dependent protein kinase phosphorylation sites, casein kinase II phosphorylation sites or N-myristoylation site and amidation sites.

II.A.) Uses of 108P5H8 Polynucleotides

II.A.1.) Monitoring of Genetic Abnormalities

The polynucleotides of the preceding paragraphs have a number of different specific uses. The human 108P5H8 gene maps to the chromosomal location set forth in Example 3. For example, because the 108P5H8 gene maps to this chromosome, polynucleotides that encode different regions of the 108P5H8 proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al, P.N.A.S. 85(23): 9158-9162 (1988)). Thus, polynucleotides encoding specific regions of the 108P5H8 proteins provide new tools that can be used to delineate, with greater precision than previously possible, cytogenetic abnormalities in the chromosomal region that encodes 108P5H8 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 108P5H8 was shown to be highly expressed in bladder and other cancers, 108P5H8 polynucleotides are used in methods assessing the status of 108P5H8 gene products in normal versus cancerous tissues. Typically, polynucleotides that encode specific regions of the 108P5H8 proteins are used to assess the presence of perturbations (such as deletions, insertions, point mutations, or alterations resulting in a loss of an antigen etc.) in specific regions of the 108P5H8 gene, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 108P5H8. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 108P5H8 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 108P5H8. See for example, Jack Cohen, Oligodeoxynucleotides, Antisense Inhibitors of Gene Expression, CRC Press, 1989; and Synthesis 1:1-5 (1988). The 108P5H8 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. Soc. 112:1253-1254 (1990). Additional 108P5H8 antisense oligonucleotides of the present invention include morpholino antisense oligonucleotides known in the art (see, e.g., Partridge et al., 1996, Antisense & Nucleic Acid Drug Development 6: 169-175).

The 108P5H8 antisense oligonucleotides of the present invention typically can be RNA or DNA that is complementary to and stably hybridizes with the first 100 5' codons or last 100 3' codons of a 108P5H8 genomic sequence or the corresponding mRNA. Absolute complementarity is not required, although high degrees of complementarity are preferred. Use of an oligonucleotide complementary to this region allows for the selective hybridization to 108P5H8 mRNA and not to mRNA specifying other regulatory subunits of protein kinase. In one embodiment, 108P5H8 antisense oligonucleotides of the present invention are 15 to 30-mer fragments of the antisense DNA molecule that have a sequence that hybridizes to 108P5H8 mRNA. Optionally, 108P5H8 antisense oligonucleotide is a 30-mer oligonucleotide that is complementary to a region in the first 10 5' codons or last 10 3' codons of 108P5H8. Alternatively, the antisense molecules are modified to employ ribozymes in the inhibition of 108P5H8 expression, see, e.g., L. A. Couture & D. T. Stinchcomb; Trends Genet. 12: 510-515 (1996).

II.A.3.) Primers and Primer Pairs

Further specific embodiments of this nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 108P5H8 polynucleotide in a sample and as a means for detecting a cell expressing a 108P5H8 protein.

Examples of such probes include polypeptides comprising all or part of the human 108P5H8 cDNA sequence shown in FIG. 2. Examples of primer pairs capable of specifically amplifying 108P5H8 mRNAs are also described in the Examples. As will be understood by the skilled artisan, a great many different primers and probes can be prepared based on the sequences provided herein and used effectively to amplify and/or detect a 108P5H8 mRNA.

The 108P5H8 polynucleotides of the invention are useful for a variety of purposes, including but not limited to their use as probes and primers for the amplification and/or detection of the 108P5H8 gene(s), mRNA(s), or fragments thereof; as reagents for the diagnosis and/or prognosis of prostate cancer and other cancers; as coding sequences capable of directing the expression of 108P5H8 polypeptides; as tools for modulating or inhibiting the expression of the 108P5H8 gene(s) and/or translation of the 108P5H8 transcript(s); and as therapeutic agents.

The present invention includes the use of any probe as described herein to identify and isolate a 108P5H8 or 108P5H8 related nucleic acid sequence from a naturally occurring source, such as humans or other mammals, as well as the isolated nucleic acid sequence per se, which would comprise all or most of the sequences found in the probe used.

II.A.4.) Isolation of 108P5H8-Encoding Nucleic Acid Molecules

The 108P5H8 cDNA sequences described herein enable the isolation of other polynucleotides encoding 108P5H8 gene product(s), as well as the isolation of polynucleotides encoding 108P5H8 gene product homologs, alternatively spliced isoforms, allelic variants, and mutant forms of a 108P5H8 gene product as well as polynucleotides that encode analogs of 108P5H8-related proteins. Various molecular cloning methods that can be employed to isolate full length cDNAs encoding an 108P5H8 gene are well known (see, for example, Sambrook, J. et al, Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 108P5H8 gene cDNAs can be identified by probing with a labeled 108P5H8 cDNA or a fragment thereof. For example, in one embodiment, a 108P5H8 cDNA (e.g., FIG. 2) or a portion thereof can be synthesized and used as a probe to retrieve overlapping and full-length cDNAs corresponding to a 108P5H8 gene. A 108P5H8 gene itself can be isolated by screening genomic DNA libraries, bacterial artificial chromosome libraries (BACs), yeast artificial chromosome libraries (YACs), and the like, with 108P5H8 DNA probes or primers.

II.A.5.) Recombinant Nucleic Acid Molecules and Host-Vector Systems

The invention also provides recombinant DNA or RNA molecules containing an 108P5H8 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 108P5H8 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 108P5H8 or a fragment, analog or homolog thereof can be used to generate 108P5H8 proteins or fragments thereof using any number of host-vector systems routinely used and widely known in the art.

A wide range of host-vector systems suitable for the expression of 108P5H8 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 108P5H8 can be expressed in several prostate cancer and non-prostate cell lines, including for example 293, 293T, rat-1, NIH 3T3 and TsuPr1. The host-vector systems of the invention are useful for the production of a 108P5H8 protein or fragment thereof. Such host-vector systems can be employed to study the functional properties of 108P5H8 and 108P5H8 mutations or analogs.

Recombinant human 108P5H8 protein or an analog or homolog or fragment thereof can be produced by mammalian cells transfected with a construct encoding a 108P5H8-related nucleotide. For example, 293T cells can be transfected with an expression plasmid encoding 108P5H8 or fragment, analog or homolog thereof, a 108P5H8-related protein is expressed in the 293T cells, and the recombinant 108P5H8 protein is isolated using standard purification methods (e.g., affinity purification using anti-108P5H8 antibodies). In another embodiment, a 108P5H8 coding sequence is subcloned into the retroviral vector pSRαMSVtkneo and used to infect various mammalian cell lines, such as NIH 3T3, TsuPr1, 293 and rat-1 in order to establish 108P5H8 expressing cell lines. Various other expression systems well known in the art can also be employed. Expression constructs encoding a leader peptide joined in frame to a 108P5H8 coding sequence can be used for the generation of a secreted form of recombinant 108P5H8 protein.

As discussed herein, redundancy in the genetic code permits variation in 108P5H8 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 108P5H8-RELATED PROTEINS

Another aspect of the present invention provides 108P5H8-related proteins. Specific embodiments of 108P5H8 proteins comprise a polypeptide having all or part of the amino acid sequence of human 108P5H8 as shown in FIG. 2 or FIG. 3. Alternatively, embodiments of 108P5H8 proteins comprise variant, homolog or analog polypeptides that have alterations in the amino acid sequence of 108P5H8 shown in FIG. 2 or FIG. 3.

In general, naturally occurring allelic variants of human 108P5H8 share a high degree of structural identity and homology (e.g., 90% or more homology). Typically, allelic variants of a 108P5H8 protein contain conservative amino acid substitutions within the 108P5H8 sequences described herein or contain a substitution of an amino acid from a corresponding position in a homologue of 108P5H8. One class of 108P5H8 allelic variants are proteins that share a high degree of homology with at least a small region of a particular 108P5H8 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein.

Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" $2^{nd}$ ED. Lubert Stryer ed (Stanford University); Henikoff et al., PNAS 1992 Vol 89 10915-10919; Lei et al., J Biol Chem 1995 May 19; 270(20): 11882-6).

Embodiments of the invention disclosed herein include a wide variety of art-accepted variants or analogs of 108P5H8 proteins such as polypeptides having amino acid insertions, deletions and substitutions. 108P5H8 variants can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., Gene, 34:315 (1985)), restriction selection mutagenesis (Wells et al., *Philos. Trans. R. Soc. London SerA*, 317:415 (1986)) or other known techniques can be performed on the cloned DNA to produce the 108P5H8 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, 108P5H8 variants, analogs or homologs, have the distinguishing attribute of having at least one epitope that is "cross reactive" with a 108P5H8 protein having an amino acid sequence of FIG. 3. As used in this sentence, "cross reactive" means that an antibody or T cell that specifically binds to an 108P5H8 variant also specifically binds to a 108P5H8 protein having an amino acid sequence set forth in FIG. 3. A polypeptide ceases to be a variant of a protein shown in FIG. 3, when it no longer contains any epitope capable of being recognized by an antibody or T cell that specifically binds to the starting 108P5H8 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165(12): 6949-6955; Hebbes et al., Mol Immunol (1989) 26(9):865-73; Schwartz et al., J Immunol (1985) 135(4):2598-608.

Other classes of 108P5H8-related protein variants share 70%, 75%, 80%, 85% or 90% or more similarity with an amino acid sequence of FIG. 3, or a fragment thereof. Another specific class of 108P5H8 protein variants or analogs comprise one or more of the 108P5H8 biological motifs described herein or presently known in the art. Thus, encompassed by the present invention are analogs of 108P5H8 fragments (nucleic or amino acid) that have altered functional (e.g. immunogenic) properties relative, to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a 108P5H8 protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a 108P5H8 protein shown in FIG. 2 or FIG. 3.

Moreover, representative embodiments of the invention disclosed herein include polypeptides consisting of about amino acid 1 to about amino acid 10 of a 108P5H8 protein shown in FIG. 2 or FIG. 3, polypeptides consisting of about amino acid 10 to about amino acid 20 of a 108P5H8 protein shown in FIG. 2 or FIG. 3, polypeptides consisting of about amino acid 20 to about amino acid 30 of a 108P5H8 protein shown in FIG. 2 or FIG. 3, polypeptides consisting of about amino acid 30 to about amino acid 40 of a 108P5H8 protein shown in FIG. 2 or FIG. 3, polypeptides consisting of about amino acid 40 to about amino acid 50 of a 108P5H8 protein shown in FIG. 2 or FIG. 3, polypeptides consisting of about amino acid 50 to about amino acid 60 of a 108P5H8 protein shown in FIG. 2 or FIG. 3, polypeptides consisting of about amino acid 60 to about amino acid 70 of a 108P5H8 protein shown in FIG. 2 or FIG. 3, polypeptides consisting of about amino acid 70 to about amino acid 80 of a 108P5H8 protein shown in FIG. 2 or FIG. 3, polypeptides consisting of about amino acid 80 to about amino acid 90 of a 108P5H8 protein shown in FIG. 2 or FIG. 3, polypeptides consisting of about amino acid 90 to about amino acid 100 of a 108P5H8 protein shown in FIG. 2 or FIG. 3, etc. throughout the entirety of a 108P5H8 amino acid sequence. Moreover, polypeptides consisting of about amino acid 1 (or 20 or 30 or 40 etc.) to about amino acid 20, (or 130, or 140 or 150 etc.) of a 108P5H8 protein shown in FIG. 2 or FIG. 3 are embodiments of the invention. It is to be appreciated that the starting and stopping positions in this paragraph refer to the specified position as well as that position plus or minus 5 residues.

108P5H8-related proteins are generated using standard peptide synthesis technology or using chemical cleavage methods well known in the art. Alternatively, recombinant methods can be used to generate nucleic acid molecules that encode a 108P5H8-related protein. In one embodiment, nucleic acid molecules provide a means to generate defined fragments of a 108P5H8 protein (or variants, homologs or analogs thereof).

III.A.) Motif-Bearing Protein Embodiments

Additional illustrative embodiments of the invention disclosed herein include 108P5H8 polypeptides comprising the amino acid residues of one or more of the biological motifs contained within a 108P5H8 polypeptide sequence set forth in FIG. 2 or FIG. 3. Various motifs are known in the art, and a protein can be evaluated for the presence of such motifs by a number of publicly available Internet sites (see, e.g., Epimatrix™ and Epimer™, Brown University; and BIMAS).

Motif bearing subsequences of all 108P5H8 variant proteins are set forth and identified in Table XIX.

Table XX sets forth several frequently occurring motifs based on pfam searches. The columns of Table XX list (1) motif name abbreviation, (2) percent identity found amongst the different member of the motif family, (3) motif name or description and (4) most common function; location information is included if the motif is relevant for location.

In another embodiment, proteins of the invention comprise one or more of the immunoreactive epitopes identified in accordance with art-accepted methods, such as the peptides set forth in Tables V-XVIII, XXII, and XXIII. CTL epitopes can be determined using specific algorithms to identify peptides within an 108P5H8 protein that are capable of optimally binding to specified HLA alleles (e.g., Table IV; Epimatrix™ and Epimer™, Brown University, and BIMAS.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, one can substitute out a deleterious residue in favor of any other residue, such as a preferred residue as defined in Table IV; substitute a less-preferred residue with a preferred residue as defined in Table IV; or substitute an originally-occurring preferred residue with another preferred residue as defined in Table IV. Substitutions can occur at primary anchor positions or at other positions in a peptide; see, e.g., Table IV.

A variety of references reflect the art regarding the identification and generation of epitopes in a protein of interest as well as analogs thereof. See, for example, WO 9733602 to Chesnut et al; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al., Immunol. Res. 1998 18(2): 79-92.

Related embodiments of the inventions include polypeptides comprising combinations of the different motifs set forth in Table XIX, and/or, one or more of the predicted CTL epitopes of Tables V-XVIII, Table XXII, Table XXIII, and/or, one or more of the T cell binding motifs known in the art. Preferred embodiments contain no insertions, deletions or substitutions either within the motifs or the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

108P5H8-related proteins are embodied in many forms, preferably in isolated form. A purified 108P5H8 protein molecule will be substantially free of other proteins or molecules that impair the binding of 108P5H8 to antibody, T cell or other ligand. The nature and degree of isolation and purification will depend on the intended use. Embodiments of a 108P5H8-related proteins include purified 108P5H8-related proteins and functional, soluble 108P5H8-related proteins. In one embodiment, a functional, soluble 108P5H8 protein or fragment thereof retains the ability to be bound by antibody, T cell or other ligand.

The invention also provides 108P5H8 proteins comprising biologically active fragments of a 108P5H8 amino acid sequence shown in FIG. 2 or FIG. 3. Such proteins exhibit properties of the starting 108P5H8 protein, such as the ability to elicit the generation of antibodies that specifically bind an epitope associated with the starting 108P5H8 protein; to be bound by such antibodies; to elicit the activation of HTL or CTL; and/or, to be recognized by HTL or CTL that also specifically bind to the starting protein.

108P5H8-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments that contain such structures are particularly useful in generating subunit-specific anti-108P5H8 antibodies, or T cells or in identifying cellular factors that bind to 108P5H8.

CTL epitopes can be determined using specific algorithms to identify peptides within an 108P5H8 protein that are capable of optimally binding to specified HLA alleles (e.g., by using the SYFPEITHI site at World Wide Web; the listings in Table IV(A)-(E); Epimatrix™ and Epimer™, Brown University and BIMAS. Illustrating this, peptide epitopes from 108P5H8 that are presented in the context of human MHC class I molecules HLA-A1, A2, A3, A11, A24, B7 and B35 were predicted (Tables V-XVIII, XXII, and XXIII). Specifically, the complete amino acid sequence of the 108P5H8 protein and relevant portions of other variants, i.e., for HLA Class I predictions 9 flanking residues on either side of a point mutation, and for HLA Class II predictions 14 flanking residues on either side of a point mutation, were entered into the HLA Peptide Motif Search algorithm found in the Bioinformatics and Molecular Analysis Section (BIMAS) web site listed above; for HLA Class II the site SYFPEITHI was used.

The HLA peptide motif search algorithm was developed by Dr. Ken Parker based on binding of specific peptide sequences in the groove of HLA Class I molecules, in particular HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for class I HLA-A2, the epitopes preferably contain a leucine (L)

or methionine (M) at position 2 and a valine (V) or leucine (L) at the C-terminus (see, e.g., Parker et al., J. Immunol. 149: 3580-7 (1992)). Selected results of 108P5H8 predicted binding peptides are shown in Tables V-XVIII, XXII, and XXIII herein. In Tables V-XVIII, the top 50 ranking candidates, 9-mers and 10-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/, or BIMAS, bimas.dcrt.nih.gov/) are to be "applied" to a 108P5H8 protein in accordance with the invention. As used in this context "applied" means that a 108P5H8 protein is evaluated, e.g., visually or by computer-based patterns finding methods, as appreciated by those of skill in the relevant art. Every subsequence of a 108P5H8 protein of 8, 9, 10, or 11 amino acid residues that bears an HLA Class I motif, or a subsequence of 9 or more amino acid residues that bear an HLA Class II motif are within the scope of the invention.

III.B.) Expression of 108P5H8-Related Proteins

In an embodiment described in the examples that follow, 108P5H8 can be conveniently expressed in cells (such as 293T cells) transfected with a commercially available expression vector such as a CMV-driven expression vector encoding 108P5H8 with a C-terminal 6xHis and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 108P5H8 protein in transfected cells. The secreted HIS-tagged 108P5H8 in the culture media can be purified, e.g., using a nickel column using standard techniques.

III.C.) Modifications of 108P5H8-Related Proteins

Modifications of 108P5H8-related proteins such as covalent modifications are included within the scope of this invention. One type of covalent modification includes reacting targeted amino acid residues of a 108P5H8 polypeptide with an organic derivatizing agent that is capable of reacting with selected side chains or the N- or C-terminal residues of a 108P5H8 protein. Another type of covalent modification of a 108P5H8 polypeptide included within the scope of this invention comprises altering the native glycosylation pattern of a protein of the invention. Another type of covalent modification of 108P5H8 comprises linking a 108P5H8 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The 108P5H8-related proteins of the present invention can also be modified to form a chimeric molecule comprising 108P5H8 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 108P5H8 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 108P5H8. A chimeric molecule can comprise a fusion of a 108P5H8-related protein with a polyhistidine epitope tag, which provides an epitope to which immobilized nickel can selectively bind, with cytokines or with growth factors. The epitope tag is generally placed at the amino- or carboxyl-terminus of a 108P5H8 protein. In an alternative embodiment, the chimeric molecule can comprise a fusion of a 108P5H8-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 108P5H8 polypeptide in place of at least one variable region within an Ig molecule. In a preferred embodiment, the immunoglobulin fusion includes the hinge, CH2 and CH3, or the hinge, CH1, CH2 and CH3 regions of an IgGI molecule. For the production of immunoglobulin fusions see, e.g., U.S. Pat. No. 5,428, 130 issued Jun. 27, 1995.

III.D.) Uses of 108P5H8-Related Proteins

The proteins of the invention have a number of different specific uses. As 108P5H8 is highly expressed in prostate and other cancers, 108P5H8-related proteins are used in methods that assess the status of 108P5H8 gene products in normal versus cancerous tissues, thereby elucidating the malignant phenotype. Typically, polypeptides from specific regions of a 108P5H8 protein are used to assess the presence of perturbations (such as deletions, insertions, point mutations etc.) in those regions (such as regions containing one or more motifs). Exemplary assays utilize antibodies or T cells targeting 108P5H8-related proteins comprising the amino acid residues of one or more of the biological motifs contained within a 108P5H8 polypeptide sequence in order to evaluate the characteristics of this region in normal versus cancerous tissues or to elicit an immune response to the epitope. Alternatively, 108P5H8-related proteins that contain the amino acid residues of one or more of the biological motifs in a 108P5H8 protein are used to screen for factors that interact with that region of 108P5H8.

108P5H8 protein fragments/subsequences are particularly useful in generating and characterizing domain-specific antibodies (e.g., antibodies recognizing an extracellular or intracellular epitope of an 108P5H8 protein), for identifying agents or cellular factors that bind to 108P5H8 or a particular structural domain thereof, and in various therapeutic and diagnostic contexts, including but not limited to diagnostic assays, cancer vaccines and methods of preparing such vaccines.

Proteins encoded by the 108P5H8 genes, or by analogs, homologs or fragments thereof, have a variety of uses, including but not limited to generating antibodies and in methods for identifying ligands and other agents and cellular constituents that bind to an 108P5H8 gene product. Antibodies raised against an 108P5H8 protein or fragment thereof are useful in diagnostic and prognostic assays, and imaging methodologies in the management of human cancers characterized by expression of 108P5H8 protein, such as those listed in Table I. Such antibodies can be expressed intracellularly and used in methods of treating patients with such cancers. 108P5H8-related nucleic acids or proteins are also used in generating HTL or CTL responses.

Various immunological assays useful for the detection of 108P5H8 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 108P5H8-expressing cells (e.g., in radioscintigraphic imaging methods). 108P5H8 proteins are also particularly useful in generating cancer vaccines, as further described herein.

IV.) 108P5H8 ANTIBODIES

Another aspect of the invention provides antibodies that bind to 108P5H8-related proteins. Preferred antibodies specifically bind to a 108P5H8-related protein and do not bind (or bind weakly) to peptides or proteins that are not 108P5H8-related proteins. For example, antibodies that bind 108P5H8 can bind 108P5H8-related proteins such as the homologs or analogs thereof.

108P5H8 antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 108P5H8 is also expressed or overexpressed in these other cancers. Moreover, intracellularly expressed antibodies (e.g., single chain antibodies) are therapeutically useful in treating cancers in which the expression of 108P5H8 is involved, such as advanced or metastatic prostate cancers.

The invention also provides various immunological assays useful for the detection and quantification of 108P5H8 and mutant 108P5H8-related proteins. Such assays can comprise one or more 108P5H8 antibodies capable of recognizing and binding a 108P5H8-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 108P5H8 are also provided by the invention, including but not limited to radioscintigraphic imaging methods using labeled 108P5H8 antibodies. Such assays are clinically useful in the detection, monitoring, and prognosis of 108P5H8 expressing cancers such as prostate cancer.

108P5H8 antibodies are also used in methods for purifying a 108P5H8-related protein and for isolating 108P5H8 homologues and related molecules. For example, a method of purifying a 108P5H8-related protein comprises incubating an 108P5H8 antibody, which has been coupled to a solid matrix, with a lysate or other solution containing a 108P5H8-related protein under conditions that permit the 108P5H8 antibody to bind to the 108P5H8-related protein; washing the solid matrix to eliminate impurities; and eluting the 108P5H8-related protein from the coupled antibody. Other uses of 108P5H8 antibodies in accordance with the invention include generating anti-idiotypic antibodies that mimic a 108P5H8 protein.

Various methods for the preparation of antibodies are well known in the art. For example, antibodies can be prepared by immunizing a suitable mammalian host using a 108P5H8-related protein, peptide, or fragment, in isolated or immuno-conjugated form (Antibodies: A Laboratory Manual, CSH Press, Eds., Harlow, and Lane (1988); Harlow, Antibodies, Cold Spring Harbor Press, NY (1989)). In addition, fusion proteins of 108P5H8 can also be used, such as a 108P5H8 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 108P5H8-related protein is synthesized and used as an immunogen.

In addition, naked DNA immunization techniques known in the art are used (with or without purified 108P5H8-related protein or 108P5H8 expressing cells) to generate an immune response to the encoded immunogen (for review, see Donnelly et al., 1997, Ann. Rev. Immunol. 15: 617-648).

The amino acid sequence of a 108P5H8 protein as shown in FIG. 2 or FIG. 3 can be analyzed to select specific regions of the 108P5H8 protein for generating antibodies. For example, hydrophobicity and hydrophilicity analyses of a 108P5H8 amino acid sequence are used to identify hydrophilic regions in the 108P5H8 structure. Regions of a 108P5H8 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Thus, each region identified by any of these programs or methods is within the scope of the present invention. Methods for the generation of 108P5H8 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 108P5H8 immunogen is often conducted by injection over a suitable time period and with use of a suitable adjuvant, as is understood in the art. During the immunization schedule, titers of antibodies can be taken to determine adequacy of antibody formation.

108P5H8 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 108P5H8-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 108P5H8 protein can also be produced in the context of chimeric or complementarity determining region (CDR) grafted antibodies of multiple species origin. Humanized or human 108P5H8 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et at., 1988, Science 239: 1534-1536). See also, Carter et al., 1993, Proc. Natl. Acad. Sci. USA 89: 4285 and Sims et al, 1993, J. Immunol. 151: 2296.

Methods for producing fully human monoclonal antibodies include phage display and tansgenic methods (for review, see Vaughan et al., 1998, Nature Biotechnology 16: 535-539). Fully human 108P5H8 monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 108P5H8 monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. Nos. 6,162,963 issued 19 Dec. 2000; 6,150,584 issued 12 Nov. 2000; and, 6,114,598 issued 5 Sep. 2000). This method avoids the in vitro manipulation required with phage display technology and efficiently produces high affinity authentic human antibodies.

Reactivity of 108P5H8 antibodies with an 108P5H8-related protein can be established by a number of well known means, including Western blot, immunoprecipitation, ELISA, and FACS analyses using, as appropriate, 108P5H8-related proteins, 108P5H8-expressing cells or extracts thereof A 108P5H8 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 108P5H8 epitopes are generated using methods generally known in the art. Homodimeric antibodies can also be generated by cross-linking techniques known in the art (e.g., Wolff et al., Cancer Res. 53: 2560-2565).

V.) 108P5H8 CELLULAR IMMUNE RESPONSES

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., Cell 47:1071, 1986; Babbitt, B. P. et al., Nature 317: 359, 1985; Townsend, A. and Bodmer, H., Annu. Rev. Immunol. 7:601, 1989; Germain, R. N., Annu. Rev. Immunol. 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., J. Immunol. 160: 3363, 1998; Rammensee, et al., Immunogenetics 41:178, 1995; Rammensee et al., SYFPEITHI, access via World Wide Web at URL syfpeithi.bmi-heidelberg.com/; Sette, A. and Sidney, J. Curr. Opin. Immunol. 10:478, 1998; Engelhard, V. H., Curr. Opin. Immunol. 6:13, 1994; Sette, A. and Grey, H. M., Curr. Opin. Immunol. 4:79, 1992; Sinigaglia, F. and Hammer, J. Curr. Biol. 6:52, 1994; Ruppert et al., Cell 74:929-937, 1993; Kondo et al., J. Immunol. 155:4307-4312, 1995; Sidney et al., J. Immunol. 157:3480-3490, 1996; Sidney et al., Human Immunol. 45:79-93, 1996; Sette, A. and Sidney, J. Immunogenetics 1999 November; 50(3-4):201-12 Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. Annu. Rev. Immunol. 13:587, 1995; Smith, et al., Immunity 4:203, 1996; Fremont et al., Immunity 8:305, 1998; Stem et al., Structure 2:245, 1994; Jones, E. Y. Curr. Opin. Immunol. 9:75, 1997; Brown, J. H. et al., Nature 364:33, 1993; Guo, H. C. et al., Proc. Natl. Acad. Sci. USA 90:8053, 1993; Guo, H. C. et al., Nature 360:364, 1992; Silver, M. L. et al., Nature 360:367, 1992; Matsumura, M. et al., Science 257:927, 1992; Madden et al., Cell 70:1035, 1992; Fremont, D. H. et al., Science 257:919, 1992; Saper, M. A., Bjorkman, P. J. and Wiley, D. C., J. Mol. Biol. 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., Mol. Immunol. 32:603, 1995; Celis, E. et al., Proc. Natl. Acad. Sci. USA 91:2105, 1994; Tsai, V. et al., J. Immunol. 158:1796, 1997; Kawashima, I. et al., Human Immunol. 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., J. Immunol. 26:97, 1996; Wentworth, P. A. et al., Int. Immunol. 8:651, 1996; Alexander, J. et al., J. Immunol. 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/ or from chronically ill patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}Cr$ release involving peptide-sensitized targets, T cell proliferation, or lymphokine release.

VI.) 108P5H8 TRANSGENIC ANIMALS

Nucleic acids that encode a 108P5H8-related protein can also be used to generate either transgenic animals or "knock out" animals that, in turn, are useful in the development and screening of therapeutically useful reagents. In accordance with established techniques, cDNA encoding 108P5H8 can be used to clone genomic DNA that encodes 108P5H8. The cloned genomic sequences can then be used to generate transgenic animals containing cells that express DNA that encode 108P5H8. Methods for generating transgenic animals, particularly animals such as mice or rats, have become conventional in the art and are described, for example, in U.S. Pat. Nos. 4,736,866 issued 12 Apr. 1988, and 4,870,009 issued 26 September 1989. Typically, particular cells would be targeted for 108P5H8 transgene incorporation with tissue-specific enhancers.

Transgenic animals that include a copy of a transgene encoding 108P5H8 can be used to examine the effect of increased expression of DNA that encodes 108P5H8. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 108P5H8 can be used to construct a 108P5H8 "knock out" animal that has a defective or altered gene encoding 108P5H8 as a result of homologous recombination between the endogenous gene encoding 108P5H8 and altered genomic DNA encoding 108P5H8 introduced into an embryonic cell of the animal. For example, cDNA that encodes 108P5H8 can be used to clone genomic DNA encoding 108P5H8 in accordance with established techniques. A portion of the genomic DNA encoding 108P5H8 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al, *Cell*, 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 108P5H8 polypeptide.

VII.) METHODS FOR THE DETECTION OF 108P5H8

Another aspect of the present invention relates to methods for detecting 108P5H8 polynucleotides and 108P5H8-related proteins, as well as methods for identifying a cell that expresses 108P5H8. The expression profile of 108P5H8 makes it a diagnostic marker for metastasized disease. Accordingly, the status of 108P5H8 gene products provides information useful for predicting a variety of factors including susceptibility to advanced stage disease, rate of progression, and/or tumor aggressiveness. As discussed in detail herein, the status of 108P5H8 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 108P5H8 polynucleotides in a biological sample, such as serum, bone, prostate, and other tissues, urine, semen, cell preparations, and the like. Detectable 108P5H8 polynucleotides include, for example, a 108P5H8 gene or fragment thereof, 108P5H8 mRNA, alternative splice variant 108P5H8 mRNAs, and recombinant DNA or RNA molecules that contain a 108P5H8 polynucleotide. A number of methods for amplifying and/or detecting the presence of 108P5H8 polynucleotides are well known in the art and can be employed in the practice of this aspect of the invention.

In one embodiment, a method for detecting an 108P5H8 mRNA in a biological sample comprises producing cDNA from the sample by reverse transcription using at least one primer; amplifying the cDNA so produced using an 108P5H8 polynucleotides as sense and antisense primers to amplify 108P5H8 cDNAs therein; and detecting the presence of the amplified 108P5H8 cDNA. Optionally, the sequence of the amplified 108P5H8 cDNA can be determined.

In another embodiment, a method of detecting a 108P5H8 gene in a biological sample comprises first isolating genomic DNA from the sample; amplifying the isolated genomic DNA using 108P5H8 polynucleotides as sense and antisense primers; and detecting the presence of the amplified 108P5H8 gene. Any number of appropriate sense and antisense probe combinations can be designed from a 192P1E1B nucleotide sequence (see, e.g., FIG. 2) and used for this purpose.

The invention also provides assays for detecting the presence of an 108P5H8 protein in a tissue or other biological sample such as serum, semen, bone, prostate, urine, cell preparations, and the like. Methods for detecting a 108P5H8-related protein are also well known and include, for example, immunoprecipitation, immunohistochemical analysis, Western blot analysis, molecular binding assays, ELISA, ELIFA and the like. For example, a method of detecting the presence of a 108P5H8-related protein in a biological sample comprises first contacting the sample with a 108P5H8 antibody, a 108P5H8-reactive fragment thereof, or a recombinant protein containing an antigen binding region of a 108P5H8 antibody; and then detecting the binding of 108P5H8-related protein in the sample.

Methods for identifying a cell that expresses 108P5H8 are also within the scope of the invention. In one embodiment, an assay for identifying a cell that expresses a 108P5H8 gene comprises detecting the presence of 108P5H8 mRNA in the cell. Methods for the detection of particular mRNAs in cells are well known and include, for example, hybridization assays using complementary DNA probes (such as in situ hybridization using labeled 108P5H8 riboprobes, Northern blot and related techniques) and various nucleic acid amplification assays (such as RT-PCR using complementary primers specific for 108P5H8, and other amplification type detection methods, such as, for example, branched DNA, SISBA, TMA and the like). Alternatively, an assay for identifying a cell that expresses a 108P5H8 gene comprises detecting the presence of 108P5H8-related protein in the cell or secreted by the cell. Various methods for the detection of proteins are well known in the art and are employed for the detection of 108P5H8-related proteins and cells that express 108P5H8-related proteins.

108P5H8 expression analysis is also useful as a tool for identifying and evaluating agents that modulate 108P5H8 gene expression. For example, 108P5H8 expression is significantly upregulated in prostate cancer, and is expressed in cancers of the tissues listed in Table I. Identification of a molecule or biological agent that inhibits 108P5H8 expression or over-expression in cancer cells is of therapeutic value. For example, such an agent can be identified by using a screen that quantifies 108P5H8 expression by RT-PCR, nucleic acid hybridization or antibody binding.

VIII.) METHODS FOR MONITORING THE STATUS OF 108P5H8-RELATED GENES AND THEIR PRODUCTS

Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23:19-32 (1995)). In this context, examining a biological sample for evidence of dysregulated cell growth (such as aberrant 108P5H8 expression in cancers) allows for early detection of such aberrant physiology, before a pathologic state such as cancer has progressed to a stage that therapeutic options are more limited and or the prognosis is worse. In such examinations, the status of 108P5H8 in a biological sample of interest can be compared, for example, to the status of 108P5H8 in a corresponding normal sample (e.g. a sample from that individual or alternatively another individual that is not affected by a pathology). An alteration in the status of 108P5H8 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306-14 and U.S. Pat. No. 5,837,501) to compare 108P5H8 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 108P5H8 expressing cells) as well as the level, and biological activity of expressed gene products (such as 108P5H8 mRNA, polynucleotides and polypeptides). Typically, an alteration in the status of 108P5H8 comprises a change in the location of 108P5H8 and/or 108P5H8 expressing cells and/or an increase in 108P5H8 mRNA and/or protein expression.

108P5H8 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a 108P5H8 gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 108P5H8 in a biological sample is evaluated by various methods utilized by skilled artisans including, but not limited to genomic Southern analysis (to examine, for example perturbations in a 108P5H8 gene), Northern analysis and/or PCR analysis of 108P5H8 mRNA (to examine, for example alterations in the polynucleotide sequences or expression levels of 108P5H8 mRNAs), and, Western and/or immunohistochemical analysis (to examine, for example alterations in polypeptide sequences, alterations in polypeptide localization within a sample, alterations in expression levels of 108P5H8 proteins and/or associations of 108P5H8 proteins with polypeptide binding partners). Detectable 108P5H8 polynucleotides include, for example, a 108P5H8 gene or fragment thereof, 108P5H8 mRNA, alternative splice variants, 108P5H8 mRNAs, and recombinant DNA or RNA molecules containing a 108P5H8 polynucleotide.

The expression profile of 108P5H8 makes it a diagnostic marker for local and/or metastasized disease, and provides information on the growth or oncogenic potential of a biological sample. In particular, the status of 108P5H8 provides information useful for predicting susceptibility to particular disease stages, progression, and/or tumor aggressiveness. The invention provides methods and assays for determining 108P5H8 status and diagnosing cancers that express 108P5H8, such as cancers of the tissues listed in Table I. For example, because 108P5H8 mRNA is so highly expressed in prostate and other cancers relative to normal prostate tissue, assays that evaluate the levels of 108P5H8 mRNA transcripts or proteins in a biological sample can be used to diagnose a disease associated with 108P5H8 dysregulation, and can provide prognostic information useful in defining appropriate therapeutic options.

The expression status of 108P5H8 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 108P5H8 in biological samples such as those from individuals suffering from, or suspected of suffering from a pathology characterized by dysregulated cellular growth, such as cancer.

As described above, the status of 108P5H8 in a biological sample can be examined by a number of well-known procedures in the art. For example, the status of 108P5H8 in a biological sample taken from a specific location in the body can be examined by evaluating the sample for the presence or absence of 108P5H8 expressing cells (e.g. those that express 108P5H8 mRNAs or proteins). This examination can provide evidence of dysregulated cellular growth, for example, when 108P5H8-expressing cells are found in a biological sample that does not normally contain such cells (such as a lymph node), because such alterations in the status of 108P5H8 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000); Su et al., Semin. Surg. Oncol. 18(1): 17-28 (2000) and Freeman et al., J Urol 1995 August 154(2 Pt 1):474-8).

In one aspect, the invention provides methods for monitoring 108P5H8 gene products by determining the status of 108P5H8 gene products expressed by cells from an individual suspected of having a disease associated with dysregulated cell growth (such as hyperplasia or cancer) and then comparing the status so determined to the status of 108P5H8 gene products in a corresponding normal sample. The presence of aberrant 108P5H8 gene products in the test sample relative to the normal sample provides an indication of the presence of dysregulated cell growth within the cells of the individual.

In another aspect, the invention provides assays useful in determining the presence of cancer in an individual, comprising detecting a significant increase in 108P5H8 mRNA or protein expression in a test cell or tissue sample relative to expression levels in the corresponding normal cell or tissue. The presence of 108P5H8 mRNA can, for example, be evaluated in tissue samples including but not limited to those listed in Table I. The presence of significant 108P5H8 expression in any of these tissues is useful to indicate the emergence, presence and/or severity of a cancer, since the corresponding normal tissues do not express 108P5H8 mRNA or express it at lower levels.

In a related embodiment, 108P5H8 status is determined at the protein level rather than at the nucleic acid level. For example, such a method comprises determining the level of 108P5H8 protein expressed by cells in a test tissue sample and comparing the level so determined to the level of 108P5H8 expressed in a corresponding normal sample. In one embodiment, the presence of 108P5H8 protein is evaluated, for example, using immunohistochemical methods. 108P5H8 antibodies or binding partners capable of detecting 108P5H8 protein expression are used in a variety of assay formats well known in the art for this purpose.

In a further embodiment, one can evaluate the status of 108P5H8 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 108P5H8 may be indicative of the presence or promotion of a tumor. Such assays therefore have diagnostic and predictive value where a mutation in 108P5H8 indicates a potential loss of function or increase in tumor growth.

A wide variety of assays for observing perturbations in nucleotide and amino acid sequences are well known in the art. For example, the size and structure of nucleic acid or amino acid sequences of 108P5H8 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued 7 Sep. 1999, and 5,952,170 issued 17 Jan. 1995).

Additionally, one can examine the methylation status of a 108P5H8 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 108P5H8. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 108P5H8 expression. The presence of RT-PCR amplifiable 108P5H8 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 108P5H8 mRNA or 108P5H8 protein in a tissue sample, its presence indicating susceptibility to cancer, wherein the degree of 108P5H8 mRNA expression correlates to the degree of susceptibility. In a specific embodiment, the presence of 108P5H8 in prostate or other tissue is examined, with the presence of 108P5H8 in the sample providing an indication of prostate cancer susceptibility (or the emergence or existence of a prostate tumor). Similarly, one can evaluate the integrity 108P5H8 nucleotide and amino acid sequences in a biological sample, in order to identify perturbations in the structure of these molecules such as insertions, deletions, substitutions and the like. The presence of one or more perturbations in 108P5H8 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 108P5H8 mRNA or 108P5H8 protein expressed by tumor cells, comparing the level so determined to the level of 108P5H8 mRNA or 108P5H8 protein expressed in a corresponding normal tissue taken from the same individual or a normal tissue reference sample, wherein the degree of 108P5H8 mRNA or 108P5H8 protein expression in the tumor sample relative to the normal sample indicates the degree of aggressiveness. In a specific embodiment, aggressiveness of a tumor is evaluated by determining the extent to which 108P5H8 is expressed in the tumor cells, with higher expression levels indicating more aggressive tumors. Another embodiment is the evaluation of the integrity of 108P5H8 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 108P5H8 mRNA or 108P5H8 protein expressed by cells in a sample of the tumor, comparing the level so determined to the level of 108P5H8 mRNA or 108P5H8 protein expressed in an equivalent tissue sample taken from the same individual at a different time, wherein the degree of 108P5H8 mRNA or 108P5H8 protein expression in the tumor sample over time provides information on the progression of the cancer. In a specific embodiment, the progression of a cancer is evaluated by determining 108P5H8 expression in the tumor cells over time, where increased expression over time indicates a progression of the cancer. Also, one can evaluate the integrity 108P5H8 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 108P5H8 gene and 108P5H8 gene products (or perturbations in 108P5H8 gene and 108P5H8 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of 108P5H8 gene and 108P5H8 gene products (or perturbations in 108P5H8 gene and 108P5H8 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 108P5H8 gene and 108P5H8 gene products (or perturbations in 108P5H8 gene and 108P5H8 gene products) and another factor associated with malignancy entails detecting the overexpression of 108P5H8 mRNA or protein in a tissue sample, detecting the overexpression of PSA mRNA or protein in a tissue sample (or PSCA or PSM expression), and observing a coincidence of 108P5H8 mRNA or protein and PSA mRNA or protein overexpression (or PSCA or PSM expression). In a specific embodiment, the expression of 108P5H8 and PSA mRNA in prostate tissue is examined, where the coincidence of 108P5H8 and PSA mRNA overexpression in the sample indicates the existence of prostate cancer, prostate cancer susceptibility or the emergence or status of a prostate tumor.

Methods for detecting and quantifying the expression of 108P5H8 mRNA or protein are described herein, and standard nucleic acid and protein detection and quantification technologies are well known in the art. Standard methods for the detection and quantification of 108P5H8 mRNA include in situ hybridization using labeled 108P5H8 riboprobes, Northern blot and related techniques using 108P5H8 polynucleotide probes, RT-PCR analysis using primers specific for 108P5H8, and other amplification type detection methods, such as, for example, branched DNA, SISBA, TMA and the like. In a specific embodiment, semi-quantitative RT-PCR is used to detect and quantify 108P5H8 mRNA expression. Any number of primers capable of amplifying 108P5H8 can be used for this purpose, including but not limited to the various primer sets specifically described herein. In a specific embodiment, polyclonal or monoclonal antibodies specifically reactive with the wild-type 108P5H8 protein can be used in an immunohistochemical assay of biopsied tissue.

IX.) IDENTIFICATION OF MOLECULES THAT INTERACT WITH 108P5H8

The 108P5H8 protein and nucleic acid sequences disclosed herein allow a skilled artisan to identify proteins, small molecules and other agents that interact with 108P5H8, as well as pathways activated by 108P5H8 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. Nos. 5,955,280 issued 21 Sep. 1999, 5,925,523 issued 20 Jul. 1999, 5,846,722 issued 8 Dec. 1998 and 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 108P5H8 protein sequences. In such methods, peptides that bind to 108P5H8 are identified by screening libraries that encode a random or controlled collection of amino acids. Peptides encoded by the libraries are expressed as fusion proteins of bacteriophage coat proteins, the bacteriophage particles are then screened against the 108P5H8 protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 108P5H8 protein sequences are disclosed for example in U.S. Pat. Nos. 5,723,286 issued 3 Mar. 1998 and 5,733,731 issued 31 Mar. 1998.

Alternatively, cell lines that express 108P5H8 are used to identify protein-protein interactions mediated by 108P5H8. Such interactions can be examined using immunoprecipitation techniques (see, e.g., Hamilton B. J., et al. Biochem. Biophys. Res. Commun. 1999, 261:646-51). 108P5H8 protein can be immunoprecipitated from 108P5H8-expressing cell lines using anti-108P5H8 antibodies. Alternatively, antibodies against His-tag can be used in a cell line engineered to express fusions of 108P5H8 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 108P5H8 can be identified through related embodiments of such screening assays. For example, small molecules can be identified that interfere with protein function, including molecules that interfere with 108P5H8's ability to mediate phosphorylation and de-phosphorylation, interaction with DNA or RNA molecules as an indication of regulation of cell cycles, second messenger signaling or tumorigenesis. Similarly, small molecules that modulate 108P5H8-related ion channel, protein pump, or cell communication functions are identified and used to treat patients that have a cancer that expresses 108P5H8 (see, e.g., Hille, B., Ionic Channels of Excitable Membranes $2^{nd}$ Ed., Sinauer Assoc., Sunderland, Mass., 1992). Moreover, ligands that regulate 108P5H8 function can be identified based on their ability to bind 108P5H8 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 108P5H8 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators which activate or inhibit 108P5H8.

An embodiment of this invention comprises a method of screening for a molecule that interacts with an 108P5H8 amino acid sequence shown in FIG. 2 or FIG. 3, comprising the steps of contacting a population of molecules with a 108P5H8 amino acid sequence, allowing the population of molecules and the 108P5H8 amino acid sequence to interact under conditions that facilitate an interaction, determining the presence of a molecule that interacts with the 108P5H8 amino acid sequence, and then separating molecules that do not interact with the 108P5H8 amino acid sequence from molecules that do. In a specific embodiment, the method further comprises purifying, characterizing and identifying a molecule that interacts with the 108P5H8 amino acid sequence. The identified molecule can be used to modulate a function performed by 108P5H8. In a preferred embodiment, the 108P5H8 amino acid sequence is contacted with a library of peptides.

X.) THERAPEUTIC METHODS AND COMPOSITIONS

The identification of 108P5H8 as a protein that is normally expressed in a restricted set of tissues, but which is also expressed in prostate and other cancers, opens a number of therapeutic approaches to the treatment of such cancers. As contemplated herein, 108P5H8 functions as a transcription factor involved in activating tumor-promoting genes or repressing genes that block tumorigenesis.

Accordingly, therapeutic approaches that inhibit the activity of a 108P5H8 protein are useful for patients suffering from a cancer that expresses 108P5H8. These therapeutic approaches generally fall into two classes. One class comprises various methods for inhibiting the binding or association of a 108P5H8 protein with its binding partner or with other proteins. Another class comprises a variety of methods for inhibiting the transcription of a 108P5H8 gene or translation of 108P5H8 mRNA.

X.A.) Anti-Cancer Vaccines

The invention provides cancer vaccines comprising a 108P5H8-related protein or 108P5H8-related nucleic acid. In view of the expression of 108P5H8, cancer vaccines prevent and/or treat 108P5H8-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al, 1995, Int. J. Cancer 63:231-237; Fong et al., 1997, J. Immunol. 159:3113-3117).

Such methods can be readily practiced by employing a 108P5H8-related protein, or an 108P5H8-encoding nucleic acid molecule and recombinant vectors capable of expressing and presenting the 108P5H8 immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 February 31(1):66-78; Maruyama et al., Cancer Immunol Immunother 2000 June 49(3): 123-32) Briefly, such methods of generating an immune response (e.g. humoral and/or cell-mediated) in a mammal, comprise the steps of: exposing the mammal's immune system to an immunoreactive epitope (e.g. an epitope present in a 108P5H8 protein shown in FIG. 3 or analog or homolog thereof) so that the mammal generates an immune response that is specific for that epitope (e.g. generates antibodies that specifically recognize that epitope). In a preferred method, a 108P5H8 immunogen contains a biological motif, see e.g., Tables V-XVIII, XXII, and XXIII, or a peptide of a size range from 108P5H8 indicated in FIG. 5, FIG. 6, FIG. 7, FIG. 8, and FIG. 9.

The entire 108P5H8 protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 108P5H8-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-112, GM-CSF, and the like.

Cellular Vaccines:

CTL epitopes can be determined using specific algorithms to identify peptides within 108P5H8 protein that bind corresponding HLA alleles (see e.g., Table IV; Epimer™ and Epimatrix™, Brown University; and, BIMAS. In a preferred embodiment, a 108P5H8 immunogen contains one or more amino acid sequences identified using techniques well known in the art, such as the sequences shown in Tables V-XVIII, XXII, and XXIII or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-Based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 108P5H8 protein) so that an immune response is generated. A typical embodiment consists of a method for generating an immune response to 108P5H8 in a host, by contacting the host with a sufficient amount of at least one 108P5H8B cell or cytotoxic T-cell epitope or analog thereof; and at least one periodic interval thereafter re-contacting the host with the 108P5H8B cell or cytotoxic T-cell epitope or analog thereof. A specific embodiment consists of a method of generating an immune response against a 108P5H8-related protein or a man-made multiepitopic peptide comprising: administering 108P5H8 immunogen (e.g. a 108P5H8 protein or a peptide fragment thereof, an 108P5H8 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 108P5H8 immunogen by: administering in vivo to muscle or skin of the individual's body a DNA molecule that comprises a DNA sequence that encodes an 108P5H8 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 108P5H8, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 108P5H8. Constructs comprising DNA encoding a 108P5H8-related protein/immunogen and appropriate regulatory sequences can be injected directly into muscle or skin of an individual, such that the cells of the muscle or skin take-up the construct and express the encoded 108P5H8 protein/immunogen. Alternatively, a vaccine comprises a 108P5H8-related protein. Expression of the 108P5H8-related protein immunogen results in the generation of prophylactic or therapeutic humoral and cellular immunity against cells that bear a 108P5H8 protein. Various prophylactic and therapeutic genetic immunization techniques known in the art can be used. Nucleic acid-based delivery is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. *J. Natl. Cancer Inst.* 87:982-990 (1995)). Non-viral delivery systems can also be employed by introducing naked DNA encoding a 108P5H8-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 108P5H8-related nucleic acid molecule. In one embodiment, the full-length human 108P5H8 cDNA is employed. In another embodiment, 108P5H8 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 108P5H8 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al, 1996, Prostate 29:371-380). Thus, dendritic cells can be used to present 108P5H8 peptides to T cells in the context of MHC class I or II molecules. In one embodiment, autologous dendritic cells are pulsed with 108P5H8 peptides capable of binding to MHC class I and/or class II molecules. In another embodiment, dendritic cells are pulsed with the complete 108P5H8 protein. Yet another embodiment involves engineering the overexpression of a 108P5H8 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186: 1177-1182). Cells that express 108P5H8 can also be engineered to express immune modulators, such as GM-CSF, and used as immunizing agents.

X.B.) 108P5H8 as a Target for Antibody-Based Therapy

108P5H8 is an attractive target for antibody-based therapeutic strategies. A number of antibody strategies are known in the art for targeting both extracellular and intracellular molecules (see, e.g., complement and ADCC mediated killing as well as the use of intrabodies). Because 108P5H8 is expressed by cancer cells of various lineages relative to corresponding normal cells, systemic administration of 108P5H8-immunoreactive compositions are prepared that exhibit excellent sensitivity without toxic, non-specific and/ or non-target effects caused by binding of the immunoreactive composition to non-target organs and tissues. Antibodies specifically reactive with domains of 108P5H8 are useful to treat 108P5H8-expressing cancers systemically, either as conjugates with a toxin or therapeutic agent, or as naked antibodies capable of inhibiting cell proliferation or function.

108P5H8 antibodies can be introduced into a patient such that the antibody binds to 108P5H8 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 108P5H8, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 108P5H8 sequence shown in FIG. 2 or FIG. 3. In addition, skilled artisans understand that it is routine to conjugate antibodies to cytotoxic agents (see, e.g., Slevers et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. 108P5H8), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-108P5H8 antibody) that binds to a marker (e.g. 108P5H8) expressed, accessible to binding or localized on the cell surfaces. A typical embodiment is a method of delivering a cytotoxic and/or therapeutic agent to a cell expressing 108P5H8, comprising conjugating the cytotoxic agent to an antibody that immunospecifically binds to a 108P5H8 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-108P5H8 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11: 117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). The antibodies can be conjugated to a therapeutic agent. To treat prostate cancer, for example, 108P5H8 antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized $IgG_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although 108P5H8 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although 108P5H8 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 108P5H8 expression, preferably using immunohistochemical assessments of tumor tissue, quantitative 108P5H8 imaging, or other techniques that reliably indicate the presence and degree of 108P5H8 expression. Immunohistochemical analysis of tumor biopsies or surgical specimens is preferred for this purpose. Methods for immunohistochemical analysis of tumor tissues are well known in the art.

Anti-108P5H8 monoclonal antibodies that treat prostate and other cancers include those that initiate a potent immune response against the tumor or those that are directly cytotoxic. In this regard, anti-108P5H8 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-108P5H8 mAbs that exert a direct biological effect on tumor growth are useful to treat cancers that express 108P5H8. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-108P5H8 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 108P5H8 antigen with high affinity but exhibit low or no antigenicity in the patient.

Therapeutic methods of the invention contemplate the administration of single anti-108P5H8 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-108P5H8 mAbs can be administered concomitantly with other therapeutic modalities, including but not limited to various chemotherapeutic agents, androgen-blockers, immune modulators (e.g., IL-2, GM-CSF), surgery or radiation. The anti-108P5H8 mAbs are administered in their "naked" or unconjugated form, or can have a therapeutic agent(s) conjugated to them.

Anti-108P5H8 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-108P5H8 antibody preparation, via an acceptable route of administration such as intravenous injection (IV), typically at a dose in the range of about 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg mAb per week are effective and well tolerated.

Based on clinical experience with the Herceptin™ mAb in the treatment of metastatic breast cancer, an initial loading dose of approximately 4 mg/kg patient body weight IV, followed by weekly doses of about 2 mg/kg IV of the anti-108P5H8 mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 108P5H8 expression in the patient, the extent of circulating shed 108P5H8 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 108P5H8 in a given sample (e.g. the levels of circulating 108P5H8 antigen and/or 108P5H8 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-108P5H8 antibodies can also be used in anti-cancer therapy as a vaccine for inducing an immune response to cells expressing a 108P5H8-related protein. In particular, the generation of anti-idiotypic antibodies is well known in the art; this methodology can readily be adapted to generate anti-idiotypic anti-108P5H8 antibodies that mimic an epitope on a 108P5H8-related protein (see, for example, Wagner et al., 1997, Hybridoma 16: 3340; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

X.C.) 108P5H8 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis *J. Immunol.* 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 108P5H8 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 108P5H8, the PADRE® universal helper T cell epitope (or multiple HTL epitopes from 108P5H8), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.).

Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class ii pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}Cr$) labeled and used as target cells for epitope-specific CTL lines; cytolysis, detected by $^{51}Cr$ release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}Cr$-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 (QYIKANSKFIGITE; SEQ ID NO: 2582), *Plasmodium falciparum* circumsporozoite (CS) protein at positions 378-398 (DIEKKIAKMEKASSVFNVVNS; SEQ ID NO: 2583), and *Streptococcus* 18 kD protein at positions 116-131 (GAVDSILGGVATYGAA; SEQ ID NO: 2584). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed to most preferably bind most HLA-DR (human HLA class II) molecules. For instance, a pan-DR-binding epitope peptide having the formula: aKXVAAWTLKAAa (SEQ ID NO: 2585), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinly-seryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to specifically prime an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 108P5H8. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 108P5H8.

X.D. Adoptive Immunotherapy

Antigenic 108P5H8-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 108P5H8. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 108P5H8. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 108P5H8-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 108P5H8, a vaccine comprising 108P5H8-specific CTL may be more efficacious in killing tumor cells in patient with advanced disease than alternative embodiments.

It is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents.

Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., *Remington's Pharmaceutical Sciences*, 17$^{th}$ Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of 5-10$^7$ to 5×10$^9$ pfu.

For antibodies, a treatment generally involves repeated administration of the anti-108P5H8 antibody preparation, via an acceptable route of administration such as intravenous injection (IV), typically at a dose in the range of about 0.1 to about 10 mg/kg body weight. In general, doses in the range of 10-500 mg mAb per week are effective and well tolerated. Moreover, an initial loading dose of approximately 4 mg/kg patient body weight IV, followed by weekly doses of about 2 mg/kg IV of the anti-108P5H8 mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 108P5H8 expression in the patient, the extent of circulating shed 108P5H8 antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg-1 mg, 1 mg-50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg m$^2$ of body area weekly; 1-600 mg m$^2$ of body area weekly; 225400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^5$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) DIAGNOSTIC AND PROGNOSTIC EMBODIMENTS OF 108P5H8

As disclosed herein, 108P5H8 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in Example 4).

108P5H8 can be analogized to a prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August; 162(2):293-306 (1999) and Fortier et al., J. Nat. Cancer Inst. 91(19): 1635-1640 (1999)). A variety of other diagnostic markers are also used in similar contexts including p53 and K-ras (see, e.g., Tulchinsky et al., Int J Mol Med 1999 July 4(1):99-102 and Minimoto et al., Cancer Detect Prev 2000; 24(1):1-12). Therefore, this disclosure of 108P5H8 polynucleotides and polypeptides (as well as 108P5H8 polynucleotide probes and anti-108P5H8 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 108P5H8 polynucleotides, polypeptides, reactive T cells and antibodies are analogous to those methods from well-established diagnostic assays which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74 (1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 108P5H8 polynucleotides described herein can be utilized in the same way to detect 108P5H8 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 108P5H8 polypeptides described herein can be utilized to generate antibodies for use in detecting 108P5H8 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 108P5H8 polynucleotides and/or polypeptides can be used to provide evidence of metastasis. For example, when a biological sample from tissue that does not normally contain 108P5H8-expressing cells (lymph node) is found to contain 108P5H8-expressing cells such as the 108P5H8 expression seen in LAPC4 and LAPC9, xenografts isolated from lymph node and bone metastasis, respectively, this finding is indicative of metastasis.

Alternatively 108P5H8 polynucleotides and/or polypeptides can be used to provide evidence of cancer, for example, when cells in a biological sample that do not normally express 108P5H8 or express 108P5H8 at a different level are found to express 108P5H8 or have an increased expression of 108P5H8 (see, e.g., the 108P5H8 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 108P5H8) such as PSA, PSCA etc. (see, e.g., Alanen et al., Pathol. Res. Pract. 192(3): 233-237 (1996)).

Just as PSA polynucleotide fragments and polynucleotide variants are employed by skilled artisans for use in methods of monitoring PSA, 108P5H8 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mol. Biol. 98:121-154 (1998)). An additional illustration of the use of such fragments is provided in Example 4, where a 108P5H8 polynucleotide fragment is used as a probe to show the expression of 108P5H8 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December 11(6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a 108P5H8 polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. 108P5H8 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 108P5H8 biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a 108P5H8 polypeptide shown in FIG. 3).

As shown herein, the 108P5H8 polynucleotides and polypeptides (as well as the 108P5H8 polynucleotide probes and anti-108P5H8 antibodies or T cells used to identify the presence of these molecules) exhibit specific properties that make them useful in diagnosing cancers such as those listed in Table I. Diagnostic assays that measure the presence of 108P5H8 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as 108P5H8 polynucleotides and polypeptides (as well as the 108P5H8 polynucleotide probes and anti-108P5H8 antibodies used to identify the presence of these molecules) need to be employed to confirm a metastases of prostatic origin.

Finally, in addition to their use in diagnostic assays, the 108P5H8 polynucleotides disclosed herein have a number of other utilities such as their use in the identification of onco-genetic associated chromosomal abnormalities in the chromosomal region to which the 108P5H8 gene maps (see Example 3 below). Moreover, in addition to their use in diagnostic assays, the 108P5H8-related proteins and polynucleotides disclosed herein have other utilities such as their use in the forensic analysis of tissues of unknown origin (see, e.g., Takahama K Forensic Sci Int 1996 Jun. 28; 80(1-2): 63-9).

Additionally, 108P5H8-related proteins or polynucleotides of the invention can be used to treat a pathologic condition characterized by the over-expression of 108P5H8. For example, the amino acid or nucleic acid sequence of FIG. 2 or FIG. 3, or fragments of either, can be used to generate an immune response to a 108P5H8 antigen. Antibodies or other molecules that react with 108P5H8 can be used to modulate the function of this molecule, and thereby provide a therapeutic benefit.

XII.) INHIBITION OF 108P5H8 PROTEIN FUNCTION

The invention includes various methods and compositions for inhibiting the binding of 108P5H8 to its binding partner or its association with other protein(s) as well as methods for inhibiting 108P5H8 function.

XII.A.) Inhibition of 108P5H8 with Intracellular Antibodies

In one approach, a recombinant vector that encodes single chain antibodies that specifically bind to 108P5H8 are introduced into 108P5H8 expressing cells via gene transfer technologies. Accordingly, the encoded single chain anti-108P5H8 antibody is expressed intracellularly, binds to 108P5H8 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to precisely target the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 108P5H8 in the nucleus, thereby preventing its activity within the nucleus. Nuclear targeting signals are engineered into such 108P5H8 intrabodies in order to achieve the desired targeting. Such 108P5H8 intrabodies are designed to bind specifically to a particular 108P5H8 domain. In another embodiment, cytosolic intrabodies that specifically bind to a 108P5H8 protein are used to prevent 108P5H8 from gaining access to the nucleus, thereby preventing it from exerting any biological activity within the nucleus (e.g., preventing 108P5H8 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 108P5H8 with Recombinant Proteins

In another approach, recombinant molecules bind to 108P5H8 and thereby inhibit 108P5H8 function. For example, these recombinant molecules prevent or inhibit 108P5H8 from accessing/binding to its binding partner(s) or associating with other protein(s). Such recombinant molecules can, for example, contain the reactive part(s) of a 108P5H8 specific antibody molecule. In a particular embodiment, the 108P5H8 binding domain of a 108P5H8 binding partner is engineered into a dimeric fusion protein, whereby the fusion protein comprises two 108P5H8 ligand binding domains linked to the Fc portion of a human IgG, such as human IgG1. Such IgG portion can contain, for example, the $C_H2$ and $C_H3$ domains and the hinge region, but not the $CH_1$ domain. Such dimeric fusion proteins are administered in soluble form to patients suffering from a cancer associated with the expression of 108P5H8, whereby the dimeric fusion protein specifically binds to 108P5H8 and blocks 108P5H8 interaction with a binding partner. Such dimeric fusion proteins are further combined into multimeric proteins using known antibody linking technologies.

XII.C.) Inhibition of 108P5H8 Transcription or Translation

The present invention also comprises various methods and compositions for inhibiting the transcription of the 108P5H8 gene. Similarly, the invention also provides methods and compositions for inhibiting the translation of 108P5H8 mRNA into protein.

In one approach, a method of inhibiting the transcription of the 108P5H8 gene comprises contacting the 108P5H8 gene with a 108P5H8 antisense polynucleotide. In another approach, a method of inhibiting 108P5H8 mRNA translation comprises contacting a 108P5H8 mRNA with an antisense polynucleotide. In another approach, a 108P5H8 specific ribozyme is used to cleave a 108P5H8 message, thereby inhibiting translation. Such antisense and ribozyme based methods can also be directed to the regulatory regions of the 108P5H8 gene, such as 108P5H8 promoter and/or enhancer elements. Similarly, proteins capable of inhibiting a 108P5H8 gene transcription factor are used to inhibit 108P5H8 mRNA transcription. The various polynucleotides and compositions useful in the aforementioned methods have been described above. The use of antisense and ribozyme molecules to inhibit transcription and translation is well known in the art.

Other factors that inhibit the transcription of 108P5H8 by interfering with 108P5H8 transcriptional activation are also useful to treat cancers expressing 108P5H8. Similarly, factors that interfere with 108P5H8 processing are useful to treat cancers that express 108P5H8. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 108P5H8 (i.e., antisense, ribozyme, polynucleotides encoding intrabodies and other 108P5H8 inhibitory molecules). A number of gene therapy approaches are known in the art. Recombinant vectors encoding 108P5H8 antisense polynucleotides, ribozymes, factors capable of interfering with 108P5H8 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 108P5H8 to a binding partner, etc.

In vivo, the effect of a 108P5H8 therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) KITS

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a 108P5H8-related protein or a 108P5H8 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequence of FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes, and package inserts with instructions for use.

A label can be present on the container to indicate that the composition is used for a specific therapy or non-therapeutic application, and can also indicate directions for either in vivo or in vitro use, such as those described above. Directions and or other information can also be included on an insert which is included with the kit.

EXAMPLES

Various aspects of the invention are further described and illustrated by way of the several examples that follow, none of which are intended to limit the scope of the invention.

Example 1

SSH-Generated Isolation of a cDNA Fragment of the 108P5H8 Gene

To isolate genes that are androgen regulated, the androgen-dependent prostate cancer cell line LNCaP was grown in media containing charcoal-stripped serum (steroid hormone depleted) for one week. The cells were subsequently stimulated with 10 nM mibolerone (synthetic androgen) for 9 h and were harvested as a source of mRNA. The 108P5H8 SSH cDNA sequence was derived from a subtraction consisting of LNCaP cells grown in presence of mibolerone minus LNCaP cells grown in absence of mibolerone.

The 108P5H8 SSH cDNA sequence of 448 bp (FIG. 1), showed homology only to ESTs in the dbEST database. The full length 108P5H8 cDNAs and ORFs are described in FIG. 2 with the protein sequences listed in FIG. 3.

Materials and Methods

RNA Isolation:

Tumor tissues were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.
DPNCDN (cDNA Synthesis Primer):
5'TTTTGATCAAGCTT$_{30}$3' (SEQ ID NO: 2586)
Adaptor 1:
5'CTAATACGACTCACTATAGGGCTC-GAGCGGCCGCCCGGGCAG3' (SEQ ID NO: 2587)
3'GGCCCGTCCTAG5' (SEQ ID NO: 2588)
Adaptor 2:
5'GTAATACGACTCACTATAGGGCAGCGTG-GTCGCGGCCGAG3' (SEQ ID NO: 2589)
3'CGGCTCCTAG5' (SEQ ID NO: 2590)
PCR Primer 1:
5'CTAATACGACTCACTATAGGGC3' (SEQ ID NO: 2591)
Nested Primer (NP) 1:
5'TCGAGCGGCCGCCCGGGCAGGA3' (SEQ ID NO: 2592)

Nested Primer (NP)$_2$:

5'AGCGTGGTCGCGGCCGAGGA3' (SEQ ID NO: 2593)

Suppression Subtractive Hybridization:

Suppression Subtractive Hybridization (SSH) was used to identify cDNAs corresponding to genes that are androgen regulated. The SSH reaction utilized cDNA from LNCaP prostate cancer cells grown in presence of mibolerone minus LNCaP cells grown in absence of mibolerone.

The cDNA derived from LNCaP prostate cancer cells grown in absence of mibolerone was used as the source of the "driver" cDNA, while the LNCaP prostate cancer cells grown in presence of mibolerone was used as the source of the "tester" cDNA. Double stranded cDNAs corresponding to tester and driver cDNAs were synthesized from 2 μg of poly (A)$^+$ RNA isolated from the relevant tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Tester cDNA was generated by diluting 1 μl of Dpn II digested cDNA from the relevant tissue source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Seguencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen).

Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 μg of mRNA with oligo (dT) 12-18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 μl with water prior to normalization. First strand cDNAs from 16 different normal human tissues can be obtained from Clontech.

Normalization of the first strand cDNAs from multiple tissues was performed by using the primers 5'-atatcgc-cgcgctcgtcgtcgacaa-3' (SEQ ID NO: 2594) and 5'-agccacacg-cagctcattgtagaagg-3' (SEQ ID NO: 2595) to amplify β-actin. First strand cDNA (5 μl) were amplified in a total volume of 50 μl containing 0.4 μM primers, 0.2 μM each dNTPs, 1×PCR buffer (Clontech, 10 mM Tris-HCL, 1.5 mM MgCl$_2$, 50 mM KCl, pH8.3) and 1× Klentaq DNA polymerase (Clontech). Five μl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 108P5H8 gene, 5 μl of normalized first strand cDNA were analyzed by PCR using 26, and 30 cycles of amplification. Semi-quantitative expression analysis can be achieved by comparing the PCR products at cycle numbers that give light band intensities.

A typical RT-PCR expression analysis is shown in FIG. 10. RT-PCR expression analysis was performed on first strand cDNAs generated using pools of tissues from multiple samples. The cDNAs were shown to be normalized using beta-actin PCR. Strong expression of 108P5H8 was observed in prostate cancer xenograft pool, prostate cancer pool and in the 2 different prostate cancer metastasis samples. Lower expression was detected in bladder cancer pool, kidney cancer pool, colon cancer pool, lung cancer pool, ovary cancer pool, breast cancer pool, metastasis pool, pancreas cancer pool, VP1 and VP2.

Example 2

Full Length Cloning of 108P5H8

To isolate genes that are androgen regulated, the androgen-dependent prostate cancer cell line LNCaP was grown in media containing 2% charcoal-stripped serum (steroid hormone depleted) for one week. The cells were then stimulated with 10 nM Mibolerone (synthetic androgen) for 9 hours and were harvested for RNA.

The gene 108P5H8 was derived from an experiment where cDNA derived from LNCaP cells that was androgen-deprived (by growing in the presence of charcoal-stripped serum) was subtracted from cDNA derived from LNCaP cells that were stimulated with mibolerone for 9 hours. The SSH DNA sequence of 448 bp (FIG. 1) is novel and only exhibited homology to human EST sequences in the dbest database.

A full length 108P5H8 cDNA clone (108P5H8 v.1) of 2364 base pairs (bp) was cloned from a prostate library (Lambda ZAP Express, Stratagene) (FIG. 2). The cDNA encodes a putative open reading frame (ORF) of 429 amino acids.

108P5H8 variant 2 and variant 3 were identified. The nucleic acid and protein sequences of all 3 variants are presented in FIG. 3 and FIG. 4. The alignments of all 3 108P5H8 variants are presented in FIG. 4. The nucleic acid sequences of variants 1 and 2 encode identical protein. 108P5H8 v.3 has a base pair variation with a C at position 342 of v.1 converted into G in v.3. This nucleotide change converted amino acid position 30 from aspartic acid in the 108P5H8 v.1 and v.2 protein sequence, to glutamic acid in 108P5H8 v.3.

Analysis of 108P5H8 protein sequence using the PSORT program reveals 6 predicted transmembrane domains. Sequence analysis of 108P5H8 reveals homology to the human zinc transporter protein ZnT4 (Huang and Gitschier, 1997, Nature Genetics 17:292). The 108P5H8 v.1 sequence includes novel 5' UTR and 3' UTR sequences, and the molecule contains 75% GC sequence, indicating possible translational regulatory sites.

To further confirm the parameters of a variant, a variety of techniques are available in the art, such as full-length cloning, proteomic validation, PCR-based validation, and 5' RACE validation, etc. (see e.g., Proteomic Validation Brennan, S. O., et al., Albumin banks peninsula: a new termination variant characterized by electrospray mass spectrometry, Biochem Biophys Acta. 1999 Aug. 17; 1433(1-2):321-6; Ferranti P, et al., Differential splicing of pre-messenger RNA produces multiple forms of mature caprine alpha(s1)-casein, Eur J. Biochem. 1997 Oct. 1; 249(1): 1-7. For PCR-based Validation: Wellmann S, et al., Specific reverse transcription-PCR quantification of vascular endothelial growth factor (VEGF) splice variants by LightCycler technology, Clin Chem. 2001 April; 47(4):654-60; Jia, H. P., et al., Discovery of new human beta-defensins using a genomics-based approach, Gene. 2001 Jan. 24; 263(1-2):211-8. For PCR-based and 5' RACE Validation: Brigle, K. E., et al., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which 108P5H8 maps is modulated in a particular cancer, the variants of 108P5H8 are modulated as well. Disclosed herein is that 108P5H8 has a particular expression profile. Variants of 108P5H8 that are structurally and/or functionally similar to 108P5H8 share this expression pattern, thus serving as tumor-associated markers/ antigens.

Example 3

Chromosomal Localization

Chromosomal localization can implicate genes in disease pathogenesis. Several chromosome mapping approaches are available, including fluorescent in situ hybridization (FISH), human/hamster Genebridge4 radiation hybrid (RH) panels (Walter et al., 1994; Nature Genetics 7:22; Research Genetics, Huntsville Ala.), human-rodent somatic cell hybrid panels such as is available from the Coriell Institute (Camden, N.J.), and genomic viewers utilizing BLAST homologies to sequenced and mapped genomic clones (NCBI, Bethesda, Md.).

The chromosomal localization of 108P5H8 using the GeneBridge4 radiation hybrid panel was performed using the following PCR primers:

108P5H8.1 5' TGCACACTGGACTTCGTAGAGTAA 3' (SEQ. ID. No.: 2596)

108P5H8.2 5' AAAGCTGTGAGAGTGGCTGAGAAA 3' (SEQ. ID. No.: 2597)

The resulting mapping vector for the 93 radiation hybrid panel DNAs was:

1001010011010001010000000000001101000000001201100 0010110001000010111000101000100000201101100121

This mapping vector and the mapping program placed 108P5H8 to chromosome 15q15.2-q21.1.

Example 4

Expression Analysis of 108P5H8 in Normal Tissues and Patient Specimens

Expression of 108P5H8 was analyzed by RT-PCR (FIG. 10). First strand cDNA was prepared from vital pool 1 (VP1: liver, lung and kidney), vital pool 2 (VP2, pancreas, colon and stomach), prostate xenograft pool (LAPC4AD, LAPC4AI, LAPC-9AD, LAPC-9AI), prostate cancer pool, bladder cancer pool, kidney cancer pool, colon cancer pool, lung cancer pool, ovary cancer pool, breast cancer pool, metastasis cancer pool, pancreas cancer pool, and from prostate cancer metastasis to lymph node from two different patients. Normalization was performed by PCR using primers to actin and GAPDH. Semi-quantitative PCR, using primers to 108P5H8, was performed at 26 and 30 cycles of amplification. Strong expression of 108P5H8 was observed in prostate cancer xenograft pool, prostate cancer pool and in the 2 different prostate cancer metastasis samples. Lower expression was detected in bladder cancer pool, kidney cancer pool, colon cancer pool, lung cancer pool, ovary cancer pool, breast cancer pool, metastasis pool, pancreas cancer pool, VP1 and VP2.

Extensive Northern blot analysis of 108P5H8 in 16 human normal tissues confirmed the expression observed by RT-PCR (FIG. 11). An approximately 7 kb 108P5H8 transcript was strongly expressed in prostate. Significantly lower expression was detected in other tissues.

FIG. 11C shows expression of 108P5H8 in prostate cancer xenografts. RNA was extracted from prostate cancer xenografts, LAPC-4AD, LAPC4AI, LAPC-9AD, and LAPC-9AI. Northern blot with 10 μg of total RNA/lane was probed with 108P5H8 SSH sequence. Results showed expression of 108P5H8 in all four xenograft tissues. More detailed analysis of the xenografts shows that 108P5H8 is highly expressed in the xenografts even when grown within the tibia of mice (FIG. 12). The expression is increased when the LAPC-4 xenograft is grown within a human bone implant (LAPC-4 AD2). It is possible that the human bone environment increases and/or induces the expression of 108P5H8. Northern blot analysis also showed that 108P5H8 is expressed in all human cancer cell lines tested such as prostate, bladder, brain, lung, kidney, breast, testis and ovary cancer cell lines (FIG. 13).

Expression of 108P5H8 was assayed in a panel of human cancers (T) and their respective matched normal tissues (N) on RNA dot blots (FIG. 14). 108P5H8 expression was detected in prostate, kidney, uterus and stomach cancers. The expression detected in some normal adjacent tissues (isolated from diseased tissues), but not in normal tissues (isolated from healthy donors), may indicate that these tissues are not fully normal and that 108P5H8 may be expressed in early stage tumors. 108P5H8 was also expressed in all 9 human cancer cell lines tested.

To test expression of 108P5H8 in patient cancer specimens, RNA was extracted from prostate cancer tumors (T) and their matched normal adjacent tissue (NAT). Northern blots with 10 µg of total RNA/lane were probed with 108P5H8 SSH sequence (FIG. 15). Results showed expression of 108P5H8 in all prostate patient specimens tested.

108P5H8 was isolated from an experiment where cDNA derived from LNCaP cells that was androgen-deprived (by growing in the presence of charcoal-stripped serum) was subtracted from cDNA derived from LNCaP cells that were stimulated with mibolerone. To assess whether 108P5H8 is androgen-regulated, LNCaP cells were grown in charcoal-stripped medium and stimulated with the synthetic androgen mibolerone, for either 14 or 24 hours (FIG. 16). Northern blots with 10 µg of total RNA/lane were probed with either the 108P5H8 sequence (FIG. 16A). Results show expression of 108P5H8 is not regulated by androgen. The experimental samples were confirmed by testing for the expression of the androgen-regulated prostate cancer gene PSA (FIG. 16B). This experiment shows that, as expected, PSA levels go down in presence of charcoal-stripped serum, and expression is induced at 14 and 24 hours in presence of the synthetic androgen. A picture of the ethidium-bromide staining of the RNA gel is also presented (FIG. 16C).

FIG. 17 shows expression of 108P5H8 in cancer metastasis patient specimens. RNA was extracted from prostate cancer metastasis to lymph node isolated from 2 different patients, as well as from normal bladder (NB), normal kidney (NK), normal lung (NL), normal breast (NBr), normal ovary (NO), and normal pancreas (NPa). Northern blots with 10 µg of total RNA/lane was probed with 108P5H8 sequence. The results show expression of 108P5H8 in both cancer metastasis samples but not in normal tissues.

108P5H8 expression showed prostate restricted expression. Its strong expression detected in normal prostate and prostate cancer tissues and the low expression detected in other normal tissues indicate that 108P5H8 is therapeutic and prophylactic target and a diagnostic and prognostic marker for human cancers.

Example 5

Production of Recombinant 108P5H8 in Prokaryotic Systems

To express recombinant 108P5H8 in prokaryotic cells, the full or partial length 108P5H8 cDNA sequences can be cloned into any one of a variety of expression vectors known in the art. One or more of the following regions of 108P5H8 are expressed in these constructs, amino acids 1 to 429 of variant 1 or variant 2; or amino acids 1 to 388 of variant 4, or any 8, 9, 10, 11, 12, 13, 14, 15, 16, 17, 18, 19, 20, 21, 22, 23, 24, 25, 26, 27, 28, 29, 30 or more contiguous amino acids from 108P5H8, variants, or analogs thereof. In certain embodiments a region of 108P5H8 is expressed that encodes an amino acid not shared amongst at least one of the variants, such as a construct encoding the D to E mutation at amino acid 30.

A. In Vitro Transcription and Translation Constructs:

pCRII: To generate 108P5H8 sense and anti-sense RNA probes for RNA in situ investigations, pCRII constructs (Invitrogen, Carlsbad Calif.) are generated encoding either all or fragments of a 108P5H8 cDNA. The pCRII vector has Sp6 and T7 promoters flanking the insert to drive the transcription of 108P5H8 RNA for use as probes in RNA in situ hybridization experiments. These probes are used to analyze the cell and tissue expression of 108P5H8 at the RNA level. Transcribed 108P5H8 RNA representing the cDNA amino acid coding region of the 108P5H8 gene is used in in vitro translation systems such as the TnT™ Coupled Reticulolysate System (Promega, Corp., Madison, Wis.) to synthesize 108P5H8 protein.

B. Bacterial Constructs:

pGEX Constructs: To generate recombinant 108P5H8 proteins in bacteria that are fused to the Glutathione S-transferase (GST) protein, all or parts of a 108P5H8 cDNA protein coding sequence are fused to the GST gene by cloning into pGEX-6P-1 or any other GST-fusion vector of the pGEX family (Amersham Pharmacia Biotech, Piscataway, N.J.). These constructs allow controlled expression of recombinant 108P5H8 protein sequences with GST fused at the amino-terminus and a six histidine epitope (6×His) at the carboxyl-terminus. The GST and 6×His tags permit purification of the recombinant fusion protein from induced bacteria with the appropriate affinity matrix and allow recognition of the fusion protein with anti-GST and anti-His antibodies. The 6×His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 108P5H8-related protein. The ampicillin resistance gene and pBR322 origin permits selection and maintenance of the pGEX plasmids in E. coli.

In one embodiment, a GST-fusion protein was constructed and expressed that encoded amino acids 1-112. This protein was used as an immunogen for generation of a 108P5H8 specific polyclonal antibody as described in example 8.

pMAL Constructs: To generate, in bacteria, recombinant 108P5H8 proteins that are fused to maltose-binding protein (MBP), all or parts of a 108P5H8 cDNA protein coding sequence are fused to the MBP gene by cloning into the pMAL-c2X and pMAL-p2X vectors (New England Biolabs, Beverly, Mass.). These constructs allow controlled expression of recombinant 108P5H8 protein sequences with MBP fused at the amino-terminus and a 6×His epitope tag at the carboxyl-terminus. The MBP and 6×His tags permit purification of the recombinant protein from induced bacteria with the appropriate affinity matrix and allow recognition of the fusion protein with anti-MBP and anti-His antibodies. The 6×His epitope tag is generated by adding 6 histidine codons to the 3' cloning primer. A Factor Xa recognition site permits cleavage of the pMAL tag from 108P5H8. The pMAL-c2X and pMAL-p2X vectors are optimized to express the recombinant protein in the cytoplasm or periplasm respectively. Periplasm expression enhances folding of proteins with disulfide bonds.

pET Constructs: To express 108P5H8 in bacterial cells, all or parts of a 108P5H8 cDNA protein coding sequence are cloned into the pET family of vectors (Novagen, Madison, Wis.). These vectors allow tightly controlled expression of recombinant 108P5H8 protein in bacteria with and without fusion to proteins that enhance solubility, such as NusA and thioredoxin (Trx), and epitope tags, such as 6×His and S-Tag™ that aid purification and detection of the recombinant protein. For example, constructs are made utilizing pET NusA fusion system 43.1 such that regions of a 108P5H8 protein are expressed as amino-terminal fusions to NusA.

C. Yeast Constructs:

pESC Constructs: To express 108P5H8 in the yeast species *Saccharomyces cerevisiae* for generation of recombinant protein and functional studies, all or parts of a 108P5H8 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of 108P5H8. In addition, expression in yeast yields similar post-translational modifications, such as glycosylations and phosphorylations, that are found when expressed in eukaryotic cells.

pESP Constructs: To express 108P5H8 in the yeast species *Saccharomyces pombe*, all or parts of a 108P5H8 cDNA protein coding sequence are cloned into the pESP family of vectors. These vectors allow controlled high level of expression of a 108P5H8 protein sequence that is fused at either the amino terminus or at the carboxyl terminus to GST which aids purification of the recombinant protein. A Flag™ epitope tag allows detection of the recombinant protein with anti-Flag™ antibody.

Example 6

Production of Recombinant 108P5H8 in Eukaryotic Systems

A. Mammalian Constructs:

To express recombinant 108P5H8 in eukaryotic cells, the full or partial length 108P5H8 cDNA sequences can be cloned into any one of a variety of expression vectors known in the art. One or more of the following regions of 108P5H8 are expressed in these constructs, amino acids 1 to 429 of variant, variant 2 or variant 3; or any 8, 9, 10, 11, 12, 13, 14, 15, 16, 17, 18, 19, 20, 21, 22, 23, 24, 25, 26, 27, 28, 29, 30 or more contiguous amino acids from 108P5H8, variants, or analogs thereof. In certain embodiments a region of 108P5H8 is expressed that encodes an amino acid not shared amongst at least two variants.

The constructs can be transfected into any one of a wide variety of mammalian cells such as 293T cells. Transfected 293T cell lysates are probed with an anti-His epitope tag antibody or with anti-108P5H8 polyclonal antibodies to verify protein expression.

pcDNA4/HisMax Constructs: To express 108P5H8 in mammalian cells, a 108P5H8 ORF, or portions thereof, of 108P5H8 are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

pcDNA3.1/MycHis Constructs: To express 108P5H8 in mammalian cells, a 108P5H8 ORF, or portions thereof, of 108P5H8 with a consensus Kozak translation initiation site were cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli*. The pcDNA3.1/MycHis construct encoding 108P5H8 was transfected into 293T cells. Expression of 108P5H8 was assayed by flow cytometry and using anti-His antibody as well as polyclonal anti-108P5H8 antibody (FIG. 22). Results show that 108P5H8 protein was expressed and was localized to the cell surface.

pcDNA3.1/CT-GFP-TOPO Construct: To express 108P5H8 in mammalian cells and to allow detection of the recombinant proteins using fluorescence, a 108P5H8 ORF, or portions thereof, with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1 CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in *E. coli*. Additional constructs with an amino-terminal GFP fusion are made in pcDNA3.1/NT-GFP-TOPO spanning the entire length of a 108P5H8 protein.

PAPtag: A 108P5H8 ORF, or portions thereof, is cloned into pAPtag-5 (GenHunter Corp. Nashville, Tenn.). This construct generates an alkaline phosphatase fusion at the carboxyl-terminus of a 108P5H8 protein while fusing the IgGκ signal sequence to the amino-terminus. Constructs are also generated in which alkaline phosphatase with an amino-terminal IgGκ signal sequence is fused to the amino-terminus of a 108P5H8 protein. The resulting recombinant 108P5H8 proteins are optimized for secretion into the media of transfected mammalian cells and can be used to identify proteins such as ligands or receptors that interact with 108P5H8 proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in *E. coli*.

ptag5: A 108P5H8 ORF, or portions thereof, is cloned into pTag-5. This vector is similar to pAPtag but without the alkaline phosphatase fusion. This construct generates 108P5H8 protein with an amino-terminal IgGκ signal sequence and myc and 6×His epitope tags at the carboxyl-terminus that facilitate detection and affinity purification. The resulting recombinant 108P5H8 protein is optimized for secretion into the media of transfected mammalian cells, and is used as immunogen or ligand to identify proteins such as ligands or receptors that interact with the 108P5H8 proteins. Protein expression is driven from the CMV promoter. The Zeocin resistance gene present in the vector allows for selection of mammalian cells expressing the protein, and the ampicillin resistance gene permits selection of the plasmid in *E. coli*.

PsecFc: A 108P5H8 ORF, or portions thereof, is also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 108P5H8 proteins, while fusing the IgGK signal sequence to N-terminus. 108P5H8 fusions utilizing the murine IgG1 Fc region are also used. The resulting recombinant 108P5H8 proteins are optimized for secretion into the media of transfected mammalian cells, and can be used as immunogens or to identify proteins such as ligands or receptors that interact with 108P5H8 protein. Protein expression is driven from the CMV promoter. The hygromycin resistance gene present in the vector allows for selection of mammalian cells that express the recombinant protein, and the ampicillin resistance gene permits selection of the plasmid in *E. coli*.

pSRα Constructs: To generate mammalian cell lines that express 108P5H8 constitutively, 108P5H8 ORF, or portions thereof, of 108P5H8 were cloned into pSRα constructs. Amphotropic and ecotropic retroviruses are generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 108P5H8, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in *E. coli*. The retroviral vectors can thereafter be used for infection and generation of various cell lines using, for example, PC3, NIH3T3, TsuPr1, 293 or rat-1 cells. Results of expression of 108P5H8 protein driven from the pSRα in PC3 and NIH3T3 cells are shown in FIG. 24.

Additional pSRα constructs are made that fuse an epitope tag such as the FLAG™ tag to the carboxyl-terminus of 108P5H8 sequences to allow detection using anti-Flag antibodies. For example, the FLAG™ sequence 5' gat tac aag gat gac gac gat aag 3' (SEQ. ID. No.: 2598) is added to cloning primer at the 3' end of the ORF. Additional pSRα constructs are made to produce both amino-terminal and carboxyl-terminal GFP and myc/6×His fusion proteins of the full-length 108P5H8 proteins.

Additional Viral Vectors: Additional constructs are made for viral-mediated delivery and expression of 108P5H8. High virus titer leading to high level expression of 108P5H8 is achieved in viral delivery systems such as adenoviral vectors and herpes amplicon vectors. A 108P5H8 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 108P5H8 coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 108P5H8 in mammalian cells, coding sequences of 108P5H8, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 108P5H8. These vectors are thereafter used to control expression of 108P5H8 in various cell lines such as PC3, NIH 3T3, 293 or rat-1 cells.

B. Baculovirus Expression Systems

To generate recombinant 108P5H8 proteins in a baculovirus expression system, 108P5H8 ORF, or portions thereof, are cloned into the baculovirus transfer vector pBlueBac 4.5 (Invitrogen), which provides a His-tag at the N-terminus. Specifically, pBlueBac-108P5H8 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 108P5H8 protein is then generated by infection of HighFive insect cells (Invitrogen) with purified baculovirus. Recombinant 108P5H8 protein can be detected using anti-108P5H8 or anti-His-tag antibody. 108P5H8 protein can be purified and used in various cell-based assays or as immunogen to generate polyclonal and monoclonal antibodies specific for 108P5H8.

Example 7

Antigenicity Profiles and Secondary Structure

FIG. 5, FIG. 6, FIG. 7, FIG. 8, and FIG. 9 depict graphically five amino acid profiles of the 108P5H8 amino acid sequence (variant 1), each assessment is available by accessing the ProtScale website on the ExPasy molecular biology server.

These profiles: FIG. 5, Hydrophilicity, (Hopp T. P., Woods K. R., 1981. Proc. Natl. Acad. Sci. U.S.A. 78:3824-3828); FIG. 6, Hydropathicity, (Kyte J., Doolittle R. F., 1982. J. Mol. Biol. 157:105-132); FIG. 7, Percentage Accessible Residues (Janin J., 1979 Nature 277:491-492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of 108P5H8 protein. Each of the above amino acid profiles of 108P5H8 were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profiles, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the full length 108P5H8 protein (variant 1) indicated, e.g., by the profiles set forth in FIG. 5, FIG. 6, FIG. 7, FIG. 8, and/or FIG. 9 are used to prepare immunogens, either peptides or nucleic acids that encode them, to generate therapeutic and diagnostic anti-108P5H8 antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from 108P5H8 protein. In particular, peptide immunogens of the invention can comprise, a peptide region of at least 5 amino acids of FIG. 2 in any whole number increment up to 429 that includes an amino acid position having a value greater than 0.5 in the Hydrophilicity profile of FIG. 5; a peptide region of at least 5 amino acids of FIG. 2 in any whole number increment up to 429 that includes an amino acid position having a value less than 0.5 in the Hydropathicity profile of FIG. 6; a peptide region of at least 5 amino acids of FIG. 2 in any whole number increment up to 429 that includes an amino acid position having a value greater than 0.5 in the Percent Accessible Residues profile of FIG. 7; a peptide region of at least 5 amino acids of FIG. 2 in any whole number increment up to 429 that includes an amino acid position having a value greater than 0.5 in the Average Flexibility profile on FIG. 8; and, a peptide region of at least 5 amino acids of FIG. 2 in any whole number increment up to 429 that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 108P5H8, namely the predicted presence and location of alpha helices, extended strands, and random coils, is predicted from the primary amino acid sequence of 108P5H8 variant 1 using the HNN—Hierarchical Neural Network method (Guermeur, 1997, accessed from the ExPasy molecular biology server. The analysis indicates that 108P5H8 is composed of 49.88% alpha helix, 11.66% extended strand, and 38.46% random coil (FIG. 18).

Analysis for the potential presence of transmembrane domains in 108P5H8 was carried out using a variety of transmembrane prediction algorithms accessed from the ExPasy molecular biology server. The programs predict the presence of 6 transmembrane domains in 108P5H8. Shown graphically in FIGS. 19A and 19B are the results of analysis using the TMpred and TMHMM prediction programs, respectively, depicting the location of the 6 transmembrane domains. The results of each program, namely the amino acids encoding the transmembrane domains are summarized in Table XXI.

Example 8

Generation of 108P5H8 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with the full length 108P5H8 protein, computer algorithms are employed in design of immunogens that, based on amino acid sequence analysis contain characteristics of being antigenic and available for recognition by the immune system of the immunized host (see the Example entitled "Antigenicity Profiles and Secondary Structure"). Such regions would be predicted to be hydrophilic, flexible, in beta-turn conformations, and be exposed on the surface of the protein (see, e.g., FIG. 5, FIG. 6, FIG. 7, FIG. 8, or FIG. 9 for amino acid profiles that indicate such regions of 108P5H8).

For example, 108P5H8 recombinant bacterial fusion proteins or peptides containing hydrophilic, flexible, beta-turn regions of 108P5H8 are used as antigens to generate polyclonal antibodies in New Zealand White rabbits. Such regions often reside in extracellular and intracellular loops between transmembrane domains. For example, such regions include, but are not limited to, amino acids 1-112 (intracellular amino terminus), amino acids 139-152 ($1^{st}$ extracellular loop), amino acids 201-214 (second extracellular loop), amino acids 294-307 (third extracellular loop), or amino acids 336-429 (carboxyl terminus). It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 294-307 of 108P5H8 is conjugated to KLH and used to immunize the rabbit. Alternatively the immunizing agent may include all or portions of a 108P5H8 protein, analogs or fusion proteins thereof. For example, a 108P5H8 amino acid sequence can be fused using recombinant DNA techniques to any one of a variety of fusion protein partners that are well known in the art, such as glutathione-S-transferase (GST) and HIS tagged fusion proteins. Such fusion proteins are purified from induced bacteria using the appropriate affinity matrix.

In one embodiment, a GST-fusion protein encoding amino acids 1-112 of 108P5H8 was produced and purified and used to immunize a rabbit. This polyclonal antibody specifically recognized both recombinant and endogenous 108P5H8 protein in cells and tissues. FIG. 20 shows non-androgen-regulated expression of 108P5H8 in the prostate cancer cell lines LNCaP and LAPC4. The expression of 108P5H8 is cell surface as detected by the polyclonal antibody in LNCaP and LAPC4 cells (FIG. 21) and when overexpressed in 293T cells (FIG. 22). FIG. 23 shows expression in prostate patient cancer samples, including metastatic disease, indicating the protein is a therapeutic target in both androgen-dependent and independent prostate cancer. 108P5H8 is also expressed in ovarian cancer, but not in normal ovary (FIG. 23), indicating the protein is a therapeutic and diagnostic target in this disease as well.

In addition to GST-fusions, other recombinant bacterial fusion proteins that can be employed include maltose binding protein, LacZ, thioredoxin, NusA, or an immunoglobulin constant region (see the section entitled "Production of 108P5H8 in Prokaryotic Systems" and Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L. (1991) J. Exp. Med. 174, 561-566).

In addition to bacterial-derived fusion proteins, mammalian-expressed protein antigens are also used. These antigens are expressed from mammalian expression vectors such as the Tag5 and Fc-fusion vectors (see the section entitled "Production of Recombinant 108P5H8 in Eukaryotic Systems"), and retain post-translational modifications such as glycosylations found in native protein. In one embodiment, the first extracellular loop of 108P5H8 (amino acids 139-152) is cloned into the Tag5 mammalian secretion vector. The recombinant protein is purified by metal chelate chromatography from tissue culture supernatants of 293T cells stably expressing the recombinant vector. The purified Tag5 108P5H8 protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100-200 μg, of fusion protein or peptide conjugated to KLH mixed in complete Freund's adjuvant (CFA). Rabbits are then injected subcutaneously every two weeks with up to 200 μg, typically 100-200 μg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as the rabbit serum derived from immunization with Tag5 108P5H8 protein or KLH-coupled peptide encoding amino acids 294-307, the full-length 108P5H8 cDNA is cloned into pCDNA 3.1 myc-his expression vector (Invitrogen, see the Example entitled "Production of Recombinant 108P5H8 in Eukaryotic Systems"). After transfection of the constructs into 293T cells, cell lysates are probed with the anti-108P5H8 serum and with anti-His antibody (Santa Cruz Biotechnologies, Santa Cruz, Calif.) to determine specific reactivity to denatured 108P5H8 protein using the Western blot technique (FIG. 20). Immunoprecipitation and flow cytometric analyses of 293T and other recombinant 108P5H8-expressing cells determine recognition of native protein by the antiserum (FIG. 22, FIG. 24). In addition, Western blot, immunoprecipitation, fluorescent microscopy, and flow cytometric techniques using cells that endogenously express 108P5H8 are carried out to test specificity (FIG. 20, FIG. 21).

The anti-serum from the Tag5 108P5H8 immunized rabbit is affinity purified by passage over a column composed of the Tag5 antigen covalently coupled to Affigel matrix (BioRad, Hercules, Calif.). The serum is then further purified by protein G affinity chromatography to isolate the IgG fraction. Serum from rabbits immunized with the GST-fusion protein was purified by depletion of antibodies reactive to the fusion partner sequence (GST) by passage over an affinity column containing the GST alone and then by passage back over a GST-108P5H8 column to isolate gene specific antibodies. Sera from other His-tagged antigens and peptide immunized rabbits as well as fusion partner depleted sera are affinity purified by passage over a column matrix composed of the original protein immunogen or free peptide.

Example 9

Generation of 108P5H8 Monoclonal Antibodies (mAbs)

In one embodiment, therapeutic mAbs to 108P5H8 comprise those that react with epitopes of the protein that would disrupt or modulate the biological function of 108P5H8, for example those that would disrupt its interaction with ligands, proteins, or substrates that mediate its biological activity. Immunogens for generation of such mAbs include those designed to encode or contain an entire 108P5H8 protein or its variants or regions of 108P5H8 protein predicted to be exposed on the cell surface and/or antigenic from computer analysis of the amino acid sequence (see, e.g., FIG. 5, FIG. 6, FIG. 7, FIG. 8, or FIG. 9, and the Example entitled "Antigenicity Profiles and Secondary Structure"). Immunogens include peptides, recombinant bacterial proteins, and mammalian expressed Tag 5 proteins and human and murine IgG FC fusion proteins. In addition, cells expressing high levels of 108P5H8, such as 293T-108P5H8 or 300.19-108P5H8 murine Pre-B cells, are used to immunize mice.

To generate mAbs to 108P5H8, mice are first immunized intraperitoneally (IP) with, typically, 10-50 μg of protein immunogen or $10^7$ 108P5H8-expressing cells mixed in complete Freund's adjuvant. Mice are then subsequently immunized IP every 2-4 weeks with, typically, 10-50 μg of protein immunogen or $10^7$ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding 108P5H8 sequence is used to immunize mice by direct injection of the plasmid DNA. For example, the predicted third extracellular loop, amino acids 294-307 of 108P5H8, is cloned into the Tag5 mammalian secretion vector and the recombinant vector is used as immunogen. In another example the amino acids are cloned into an Fc-fusion secretion vector in which a 108P5H8 sequence is fused at the amino-terminus to an IgK leader sequence and at the carboxyl-terminus to the coding sequence of the human or murine IgG Fc region. This recombinant vector is then used as immunogen. The plasmid immunization protocols are used in combination with purified proteins expressed from the same vector and with cells expressing 108P5H8.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment, monoclonal antibodies are derived from immunization of mice with 300.19 cells engineered to express high levels of 108P5H8 (>30,000 molecules per cell). Balb C mice are initially immunized intraperitoneally with $10^7$ cells mixed in complete Freund's adjuvant. Mice are subsequently immunized every two weeks with $10^7$ cells mixed in incomplete Freund's adjuvant for a total of three immunizations. Reactivity and specificity of serum to the full length 108P5H8 protein is monitored by Western blotting, immunoprecipitation and flow cytometry using various cells engineered to overexpress 108P5H8 protein (FIG. 24). Mice showing the strongest reactivity are rested and given a final injection of cells in PBS and then sacrificed four days later. The spleens of the sacrificed mice are harvested and fused to SPO/2 myeloma cells using standard procedures (see, e.g., Harlow and Lane, 1988). Supernatants from HAT selected growth wells are screened by ELISA, Western blot, immunoprecipitation, fluorescent microscopy, and flow cytometry to identify 108P5H8 specific antibody-producing clones.

The binding affinity of a 108P5H8 monoclonal antibody is determined using standard technologies. Affinity measurements quantify the strength of antibody to epitope binding and are used to help define which 108P5H8 monoclonal antibodies preferred, e.g., for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23: 1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 10

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and IC$_{50}$>[HLA], the measured IC$_{50}$ values are reasonable approximations of the true K$_D$ values. Peptide inhibitors are typically tested at concentrations ranging from 120 μg/ml to 1.2 ng/ml, and are tested in two to four completely independent experiments. To allow comparison of the data obtained in different experiments, a relative binding figure is calculated for each peptide by dividing the IC$_{50}$ of a positive control for inhibition by the IC$_{50}$ for each tested peptide (typically unlabeled versions of the radiolabeled probe peptide). For database purposes, and inter-experiment comparisons, relative binding values are compiled. These values can subsequently be converted back into IC$_{50}$ nM values by dividing the IC$_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides.

Example 11

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-Bearing Epitopes The searches performed to identify the motif-bearing peptide sequences in the Example entitled "Antigenicity Profiles" and Tables V-XVIII, XXII, and XXIII employ the protein sequence data from the gene product of 108P5H8 set forth in FIGS. 2 and 3.

Computer searches for epitopes bearing HLA Class I or Class II supermotifs or motifs are performed as follows. All translated 108P5H8 protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or ΔG) of peptide-HLA molecule interactions can be approximated as a linear polynomial function of the type:

$$\text{``}\Delta G\text{''} = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount j$_i$ to the free energy of binding of the peptide irrespective of the sequence of the rest of the peptide.

The method of derivation of specific algorithm coefficients has been described in Gulukota et al., *J. Mol. Biol.* 267:1258-126, 1997; (see also Sidney et al., *Human Immunol.* 45:79-93, 1996; and Southwood et al., *J. Immunol.* 160:3363-3373, 1998). Briefly, for all i positions, anchor and non-anchor alike, the geometric mean of the average relative binding (ARB) of all peptides carrying j is calculated relative to the remainder of the group, and used as the estimate of j$_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-Reactive Peptides

Protein sequences from 108P5H8 are scanned utilizing motif identification software, to identify 8-9-10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-Bearing Epitopes

The 108P5H8 protein sequence(s) scanned above is also examined for the presence of peptides with the HLA-A3- supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of ≦500 nM, often ≦200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 108P5H8 protein(s) scanned above is also analyzed for the presence of 8-, 9-10-, or 11-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of <500 nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-Bearing Epitopes

To further increase population coverage, HLA-A1 and -A24 epitopes can also be incorporated into vaccine compositions. An analysis of the 108P5H8 protein can also be performed to identify HLA-A1- and A24-motif-containing sequences.

High affinity and/or cross-reactive binding epitopes that bear other motif and/or supermotifs are identified using analogous methodology.

Example 12

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening

The 0.221A2.1 cell line, produced by transferring the HLA-A2.1 gene into the HLA-A, -B, —C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 μg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10 \times 10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dynal immunomagnetic beads (Dynabeads® M-450) and the Detacha-Bead® reagent. Typically about $200-250 \times 10^6$ PBMC are processed to obtain $24 \times 10^6$ CD8+ T-cells (enough for a 48-well plate culture). Briefly, the PBMCs are thawed in RPMI with 30 μg/ml DNAse, washed once with PBS containing 1% human AB serum and resuspended in PBS/1% AB serum at a concentration of $20 \times 10^6$ cells/ml. The magnetic beads are washed 3 times with PBS/AB serum, added to the cells (140 μl beads/$20 \times 10^6$ cells) and incubated for 1 hour at 4° C. with continuous mixing. The beads and cells are washed 4× with PBS/AB serum to remove the nonadherent cells and resuspended at $100 \times 10^6$ cells/ml (based on the original cell number) in PBS/AB serum containing 100 μl/ml Detacha-Bead® reagent and 30 μg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 μg/ml of peptide at a cell concentration of $1-2 \times 10^6$/ml in the presence of 3 g/ml $β_2$-microglobulin for 4 hours at 20° C. The DC are then irradiated (4,200 rads), washed 1 time with medium and counted again.

Setting up induction cultures: 0.25 ml cytokine-generated DC (at $1 \times 10^5$ cells/ml) are co-cultured with 0.25 ml of CD8+ T-cells (at $2 \times 10^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at $5 \times 10^6$ cells/ml and irradiated at ~4200 rads. The PBMCs are plated at $2 \times 10^6$ in 0.5 ml complete medium per well and incubated for 2 hours at 37° C. The plates are washed twice with RPMI by tapping the plate gently to remove the nonadherent cells and the adherent cells pulsed with 10 μg/ml of peptide in the presence of 3 μg/ml $β_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2-3 days later at 501 U/ml (Tsai et al., *Critical Reviews in Immunology* 18(1-2):65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labeled with 200 μCi of $^{51}$Cr sodium chromate (Dupont, Wilmington, Del.) for 1 hour at 37° C. Labeled target cells are resuspended at $10^6$ per ml and diluted 1:10 with K562 cells at a concentration of $3.3\times10^6$/ml (an NK-sensitive erythroblastoma cell line used to reduce non-specific lysis). Target cells (100 μl) and effectors (100 μl) are plated in 96 well round-bottom plates and incubated for 5 hours at 37° C. At that time, 100 μl of supernatant are collected from each well and percent lysis is determined according to the formula: [(cpm of the test sample–cpm of the spontaneous $^{51}$Cr release sample)/(cpm of the maximal $^{51}$Cr release sample–cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-Specific and Endogenous Recognition Immulon 2 plates are coated with mouse anti-human IFNγ monoclonal antibody (4 μg/ml 0.1M NaHCO$_3$, pH8.2) overnight at 4° C. The plates are washed with Ca$^{2+}$, Mg$^{2+}$-free PBS/0.05% Tween 20 and blocked with PBS/10% FCS for two hours, after which the CTLs (100 μl/well) and targets (100 μl/well) are added to each well, leaving empty wells for the standards and blanks (which received media only). The target cells, either peptide-pulsed or endogenous targets, are used at a concentration of $1\times10^6$ cells/ml. The plates are incubated for 48 hours at 37° C. with 5% CO$_2$.

Recombinant human IFN-gamma is added to the standard wells starting at 400 pg or 1200 pg/100 microliter/well and the plate incubated for two hours at 37° C. The plates are washed and 100 μl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5-15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, $5\times10^4$ CD8+ cells are added to a T25 flask containing the following: $1\times10^6$ irradiated (4,200 rad) PBMC (autologous or allogeneic) per ml, $2\times10^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 μM 2-mercaptoethanol, L-glutamine and penicillin/streptomycin. Recombinant human IL2 is added 24 hours later at a final concentration of 200 IU/ml and every three days thereafter with fresh media at 50 IU/ml. The cells are split if the cell concentration exceeds $1\times10^6$/ml and the cultures are assayed between days 13 and 15 at E:T ratios of 30, 10, 3 and 1:1 in the $^{51}$Cr release assay or at $1\times10^6$/ml in the in situ IFNγ assay using the same targets as before the expansion.

Cultures are expanded in the absence of anti-CD3$^+$ as follows. Those cultures that demonstrate specific lytic activity against peptide and endogenous targets are selected and $5\times10^4$ CD8$^+$ cells are added to a T25 flask containing the following: $1\times10^6$ autologous PBMC per ml which have been peptide-pulsed with 10 μg/ml peptide for two hours at 37° C. and irradiated (4,200 rad); $2\times10^5$ irradiated (8,000 rad) EBV-transformed cells per ml RPMI-1640 containing 110% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 108P5H8. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology Example 13

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an IC$_{50}$ of 500 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to $3/5$ of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoging at primary anchor residues of other motif and/or supermotif-bearing epitopes is performed in a like manner.

The analog peptides are then be conformed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 108P5H8-expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and I. Chen, John Wiley & Sons, England, 1999).

Thus, by the use of single amino acid substitutions, the binding properties and/or cross-reactivity of peptide ligands for HLA supertype molecules can be modulated.

Example 14

Identification and Confirmation of 108P5H8-Derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 108P5H8-derived, HLA class II HTL epitopes, a 108P5H8 antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160: 3363-3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 108P5H8-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 108P5H8-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 108P5H8 antigens are analyzed for sequences carrying one of the two DR3-specific binding motifs reported by Geluk et al. (*J. Immunol.* 152:5742-5748, 1994). The corresponding peptides are then synthesized and confirmed as having the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 15

Immunogenicity of 108P5H8-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 108P5H8-expressing tumors.

Example 16

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1−(SQRT(1−af)) (see, e.g., Sidney et al., *Human Immunol.* 45:79-93, 1996). To obtain overall phenotypic frequencies, cumulative gene frequencies are calculated, and the cumulative antigen frequencies derived by the use of the inverse formula [af=1−(1−Cgf)$^2$].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1−A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%. An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 17

CTL Recognition of Endogenously Processed Antigens After Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with 108P5H8 expression vectors.

The results demonstrate that CTL lines obtained from animals primed with peptide epitope recognize endogenously synthesized 108P5H8 antigen. The choice of transgenic mouse model to be used for such an analysis depends upon the epitope(s) that are being evaluated. In addition to HLA-A*0201/K$^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 18

Activity of CTL-HTL Conjugated Epitopes in Transgenic Mice

This example illustrates the induction of CTLs and HTLs in transgenic mice, by use of a 108P5H8-derived CTL and HTL peptide vaccine compositions. The vaccine composition used herein comprise peptides to be administered to a patient with a 108P5H8-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures: Immunization of transgenic mice is performed as described (Alexander et al., J. Immunol. 159:4753-4761, 1997). For example, A2/K$^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/K$^b$ chimeric gene (e.g., Vitiello et al., J. Exp. Med. 173:1007, 1991)

In vitro CTL activation: One week after priming, spleen cells ($30\times10^6$ cells/flask) are co-cultured at 37° C. with syngeneic, irradiated (3000 rads), peptide coated lymphoblasts ($10\times10^6$ cells/flask) in 10 ml of culture medium/T25 flask. After six days, effector cells are harvested and assayed for cytotoxic activity.

Assay for cytotoxic activity: Target cells (1.0 to $1.5\times10^6$) are incubated at 37° C. in the presence of 200 µl of $^{51}$Cr. After 60 minutes, cells are washed three times and resuspended in R10 medium. Peptide is added where required at a concentration of 1 µg/ml. For the assay, $10^4$ $^{51}$Cr-labeled target cells are added to different concentrations of effector cells (final volume of 200 µl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a six hour $^{51}$Cr release assay. To obtain specific lytic units/106, the lytic units/$10^6$ obtained in the absence of peptide is subtracted from the lytic units/$10^6$ obtained in the presence of peptide. For example, if 30% $^{51}$Cr release is obtained at the effector (E):target (T) ratio of 50:1 (i.e., $5\times10^5$ effector cells for 10,000 targets) in the absence of peptide and 5:1 (i.e., $5\times10^4$ effector cells for 10,000 targets) in the presence of peptide, the specific lytic units would be: [(1/50,000)−(1/500,000)]×$10^6$=18 LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity". Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 19

Selection of CTL and HTL Epitopes for Inclusion in an 108P5H8-Specific Vaccine This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated, with 108P5H8 clearance. The number of epitopes used depends on observations of patients who spontaneously clear 108P5H8. For example, if it has been observed that patients who spontaneously clear 108P5H8 generate an immune response to at least three (3) from 108P5H8 antigen, then three or four (3-4) epitopes should be included for HLA class I. A similar rationale is used to determine HLA class II epitopes.

Epitopes are often selected that have a binding affinity of an $IC_{50}$ of 500 µM or less for an HLA class I molecule, or for class II, an $IC_{50}$ of 1000 nM or less; or HLA Class I peptides with high binding scores from the BIMAS web site, at URL bimas.dcrt.nih.gov/.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 108P5H8, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 108P5H8.

Example 20

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 108P5H8, are selected such that multiple supermotifs/motifs are represented to ensure broad population coverage. Similarly, HLA class II epitopes are selected from 108P5H8 to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 21

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g. Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751-761, 1994.

For example, to confirm the capacity of a DNA minigene construct containing at least one HLA-A2 supermotif peptide to induce CTLs in vivo, HLA-A2.1/$K^b$ transgenic mice, for example, are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, 1-Ab-restricted mice, for example, are immunized intramuscularly with 100 µg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. Immunity 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci. USA* 95:7648-53, 1998; Hanke and McMichael, *Immunol. Letters* 66:177-181, 1999; and Robinson et al., *Nature Med.* 5:526-34, 1999).

For example, the efficacy of the DNA minigene used in a prime boost protocol is initially evaluated in transgenic mice. In this example, A2.1/K$^b$ transgenic mice are immunized IM with 100 µg of a DNA minigene encoding the immunogenic peptides including at least one HLA-A2 supermotif-bearing peptide. After an incubation period (ranging from 3-9 weeks), the mice are boosted IP with 10$^7$ pfu/mouse of a recombinant vaccinia virus expressing the same sequence encoded by the DNA minigene. Control mice are immunized with 100 µg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7, motif or supermotif epitopes. The use of prime boost protocols in humans is described below in the Example entitled "Induction of CTL Responses Using a Prime Boost Protocol."

Example 22

Peptide Composition for Prophylactic Uses

Vaccine compositions of the present invention can be used to prevent 108P5H8 expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 108P5H8-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 µg, generally 100-5,000 µg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 108P5H8-associated disease.

Alternatively, a composition typically comprising transfecting agents is used for the administration of a nucleic acid-based vaccine in accordance with methodologies known in the art and disclosed herein.

Example 23

Polyepitopic Vaccine Compositions Derived from Native 108P5H8 Sequences

A native 108P5H8 polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes is selected; it can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 108P5H8 antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (excluding an analoged embodiment) directs the immune response to multiple peptide sequences that are actually present in native 108P5H8, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 24

Polyepitopic Vaccine Compositions from Multiple Antigens

The 108P5H8 peptide epitopes of the present invention are used in conjunction with epitopes from other target tumor-associated antigens, to create a vaccine composition that is useful for the prevention or treatment of cancer that expresses 108P5H8 and such other antigens. For example, a vaccine composition can be provided as a single polypeptide that incorporates multiple epitopes from 108P5H8 as well as tumor-associated antigens that are often expressed with a target cancer associated with 108P5H8 expression, or can be administered as a composition comprising a cocktail of one or more discrete epitopes. Alternatively, the vaccine can be administered as a minigene construct or as dendritic cells which have been loaded with the peptide epitopes in vitro.

Example 25

Use of Peptides to Evaluate an Immune Response

Peptides of the invention may be used to analyze an immune response for the presence of specific antibodies, CTL or HTL directed to 108P5H8. Such an analysis can be performed in a manner described by Ogg et al., *Science* 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 108P5H8 HLA-A*0201-specific CTL frequencies from HLA A*0201-positive individuals at different stages of disease or following immunization comprising an 108P5H8 peptide containing an A*0201 motif. Tetrameric complexes are synthesized as described (Musey et al., *N. Engl. J. Med.* 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 108P5H8 epitope, and thus the status of exposure to 108P5H8, or exposure to a vaccine that elicits a protective or therapeutic response.

Example 26

Use of Peptide Epitopes to Evaluate Recall Responses

The peptide epitopes of the invention are used as reagents to evaluate T cell responses, such as acute or recall responses, in patients. Such an analysis may be performed on patients who have recovered from 108P5H8-associated disease or who have been vaccinated with an 108P5H8 vaccine.

For example, the class I restricted CTL response of persons who have been vaccinated may be analyzed. The vaccine may be any 108P5H8 vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI) and plated using microculture formats. A synthetic peptide comprising an epitope of the invention is added at 10 µg/ml to each well and HBV core 128-140 epitope is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 µl of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with non-diseased control subjects as previously described (Rehermann, et al., *Nature Med.* 2:1104, 1108, 1996; Rehermann et. al., *J. Clin. Invest.* 97:1655-1665, 1996; and Rehermann et al. *J. Clin. Invest.* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670-2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 µM, and labeled with 100 µCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release−spontaneous release)/maximum release−spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 108P5H8 or an 108P5H8 vaccine.

Similarly, Class II restricted HTL responses may also be analyzed. Purified PBMC are cultured in a 96-well flat bottom plate at a density of 1.5×10$^5$ cells/well and are stimulated with 10 µg/ml synthetic peptide of the invention, whole 108P5H8 antigen, or PHA. Cells are routinely plated in replicates of 4-6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 27

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 28

Phase II Trials IN Patients Expressing 108P5H8

Phase II trials are performed to study the effect of administering the CTL-HTL peptide compositions to patients having cancer that expresses 108P5H8. The main objectives of the trial are to determine an effective dose and regimen for inducing CTLs in cancer patients that express 108P5H8, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them have a tumor that expresses 108P5H8.

Clinical manifestations or antigen-specific T-cell responses are monitored to assess the effects of administering the peptide compositions. The vaccine composition is found to be both safe and efficacious in the treatment of 108P5H8-associated disease.

Example 29

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of 'Minigene' Multi-Epitope DNA Plasmids" in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5-10^7$ to $5 \times 10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 108P5H8 is generated.

Example 30

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 108P5H8 protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., Nature Med. 4:328, 1998; Nature Med. 2:52, 1996 and Prostate 32:272, 1997). Although $2-50 \times 10^6$ DC per patient are typically administered, larger number of DC, such as $10^7$ or $10^8$ can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5 \times 10^6$ DC, then the patient will be injected with a total of $2.5 \times 10^8$ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to 108P5H8 antigens can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 31

An Alternative Method of Identifying and Confirming M tif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 108P5H8. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., J. Immunol. 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 108P5H8 to isolate peptides corresponding to 108P5H8 that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 32

Complementary Polynucleotides

Sequences complementary to the 108P5H8-encoding sequences, or any parts thereof, are used to detect, decrease, or inhibit expression of naturally occurring 108P5H8. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 108P5H8. To inhibit transcription, a complementary oligonucleotide is designed from the most unique 5' sequence and used to prevent promoter binding to the coding sequence. To inhibit translation, a complementary oligonucleotide is designed to prevent ribosomal binding to a 108P5H8-encoding transcript.

Example 33

Purification of Naturally-Occurring or Recombinant 108P5H8 Using 108P5H8 Specific Antibodies Naturally occurring or recombinant 108P5H8 is substantially purified by immunoaffinity chromatography using antibodies specific for 108P5H8. An immunoaffinity column is constructed by covalently coupling anti-108P5H8 antibody to an activated chromatographic resin, such as CNBr-activated SEPHAROSE (Amersham Pharmacia Biotech). After the coupling, the resin is blocked and washed according to the manufacturer's instructions.

Media containing 108P5H8 are passed over the immunoaffinity column, and the column is washed under conditions that allow the preferential absorbance of 108P5H8 (e.g., high ionic strength buffers in the presence of detergent). The column is eluted under conditions that disrupt antibody/108P5H8 binding (e.g., a buffer of pH 2 to pH 3, or a high concentration of a chaotrope, such as urea or thiocyanate ion), and GCR.P is collected.

Example 34

Identification of Molecules which Interact with 108P5H8

108P5H8, or biologically active fragments thereof, are labeled with 121 1 Bolton-Hunter reagent. (See, e.g., Bolton et al. (1973) Biochem. J. 133:529.) Candidate molecules previously arrayed in the wells of a multi-well plate are incubated with the labeled 108P5H8, washed, and any wells with labeled 108P5H8 complex are assayed. Data obtained using different concentrations of 108P5H8 are used to calculate values for the number, affinity, and association of 108P5H8 with the candidate molecules.

Example 35

In Vivo Assay for 108P5H8 Tumor Growth Promotion

The effect of a 108P5H8 protein on tumor cell growth can be confirmed in vivo by gene overexpression in a variety of cancer cells such as those in Table I, including prostate, kidney, colon and bladder. For example, SCID mice can be injected SQ on each flank with $1 \times 10^6$ prostate, kidney, colon or bladder cancer cells (such as PC3, DU145, SCaBER, UM-UC-3, HT1376, SK-CO, Caco, RT4, T24, Caki, A-498 and SW839 cells) containing tkNeo empty vector or 108P5H8.

At least two strategies can be used:

(1) Constitutive 108P5H8 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems.

(2) Regulated expression under control of an inducible vector system, such as ecdysone, tet, etc., can be used provided such promoters are compatible with the host cell systems. Tumor volume is then monitored at the appearance of palpable tumors or by following serum markers such as PSA. Tumor development is followed over time to validate that 108P5H8-expressing cells grow at a faster rate and/or that tumors produced by 108P5H8-expressing cells demonstrate characteristics of altered aggressiveness (e.g., enhanced metastasis, vascularization, reduced responsiveness to chemotherapeutic drugs). Tumor volume is evaluated by caliper measurements. Additionally, mice can be implanted with the same cells orthotopically in the prostate, bladder, colon or kidney to determine if 108P5H8 has an effect on local growth, e.g., in the prostate, bladder, colon or kidney or on the ability of the cells to metastasize, specifically to lungs or lymph nodes (Saffran et al., Proc Natl Acad Sci USA. 2001, 98: 2658; Fu, X., et al., Int. J. Cancer, 1991. 49: 938-939; Chang, S., et al., Anticancer Res., 1997, 17: 3239-3242; Peralta, E. A., et al., J. Urol., 1999. 162: 1806-1811). For instance, the orthotopic growth of PC3 and PC3-108P5H8 can be compared in the prostate of SCID mice. Such experiments reveal the effect of 108P5H8 on orthotopic tumor growth, metastasis and/or angiogenic potential.

Furthermore, this assay is useful to confirm the inhibitory effect of candidate therapeutic compositions, such as for example, 108P5H8 antibodies or intrabodies, and 108P5H8 antisense molecules or ribozymes, or 108P5H8 directed small molecules, on cells that express a 108P5H8 protein.

Example 36

108P5H8 Monoclonal Antibody-Mediated Inhibition of Human Xenograft Tumors In Vivo The significant expression of 108P5H8, in cancer tissues, together with its restricted expression in normal tissues along with its cell surface expression makes 108P5H8 an excellent target for antibody therapy. Similarly, 108P5H8 is a target for T cell-based immunotherapy. Thus, the therapeutic efficacy of anti-108P5H8 mAbs is evaluated, e.g., in human prostate cancer xenograft mouse models using androgen-independent LAPC-4 and LAPC-9 xenografts (Craft, N., et al., Cancer Res, 1999. 59(19): p. 5030-5036), prostate cancer cell lines transfected with 108P5H8 (such as PC3-108P5H8, DU145-108P5H8), in human kidney cancer xenografts (AGS-K3, AGS-K6), kidney cancer metastases to lymph node (AGS-K6 met) xenografts, and kidney cancer cell lines transfected with 108P5H8 (769P-108P5H8, A498-108P5H8).

Antibody efficacy on tumor growth and metastasis formation is studied, e.g., in mouse subcutaneous or orthotopic prostate cancer xenograft models and mouse kidney xenograft models. The antibodies can be unconjugated, as discussed in this Example, or can be conjugated to a therapeutic modality, as appreciated in the art. Anti-108P5H8 mAbs inhibit formation of both the androgen-dependent LAPC-9 and androgen-independent PC3-108P5H8 tumor xenografts. Anti-108P5H8 mAbs also retard the growth of established orthotopic tumors and prolonged survival of tumor-bearing mice. These results indicate the utility of anti- 108P5H8 mAbs in the treatment of local and advanced stages of, e.g., prostate cancer. (See, e.g., Saffran, D., et al., PNAS 10: 1073-1078). These results indicate the use of anti-108P5H8 mAbs in the treatment of prostate cancer.

Administration of the anti-108P5H8 mAbs leads to retardation of established orthotopic tumor growth and inhibition of metastasis to distant sites, resulting in a significant prolongation in the survival of tumor-bearing mice. These studies indicate that 108P5H8 is an attractive target for immunotherapy and demonstrate the therapeutic use of anti-108P5H8 mAbs for the treatment of local and metastatic cancer. This example demonstrates that unconjugated 108P5H8 monoclonal antibodies are effective to inhibit the growth of human prostate tumor xenografts and human kidney xenografts grown in SCID mice.

Tumor Inhibition Using Multiple Unconjugated 108P5H8 mAbs

Materials and Methods

108P5H8 Monoclonal Antibodies:

Monoclonal antibodies are obtained against 108P5H8, such as described in the Example entitled "Generation of 108P5H8 Monoclonal Antibodies (mAbs)" or may be obtained commercially. The antibodies are characterized by ELISA, Western blot, FACS, and immunoprecipitation for their capacity to bind 108P5H8. Epitope mapping data for the anti-108P5H8 mAbs, as determined by ELISA and Western analysis, recognize epitopes on a 108P5H8 protein. Immunohistochemical analysis of cancer tissues and cells is performed with these antibodies.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of, e.g., LAPC-9 prostate tumor xenografts.

Cancer Xenografts and Cell Lines

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by s.c. trocar implant (Craft, N., et al., 1999, Cancer Res. 59:5030-5036). Single-cell suspensions of tumor cells are prepared as described in Craft, et al. The prostate carcinoma cell lines PC3 and DU145 (American Type Culture Collection) are maintained in RPMI supplemented with L-glutamine and 10% FBS, and the kidney carcinoma line A498 (American Type Culture Collection) is maintained in DMEM supplemented with L-glutamine and 10% FBS.

PC3-108P5H8, DU145-108P5H8 and A498-108P5H8 cell populations are generated by retroviral gene transfer as described in Hubert, R. S., et al., STEAP: A Prostate-specific Cell-surface Antigen Highly Expressed in Human Prostate Tumors, Proc Natl Acad Sci USA, 1999. 96(25): p. 14523-14528. Anti-108P5H8 staining is detected by using, e.g., an FITC-conjugated goat anti-mouse antibody (Southern Biotechnology Associates) followed by analysis on a Coulter Epics-XL flow cytometer.

Xenograft Mouse Models.

Subcutaneous (s.c.) tumors are generated by injection of $1 \times 10^6$ LAPC-9, PC3, PC3-108P5H8, DU145 or DU145-108P5H8 cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by vernier caliper measurements, and the tumor volume is calculated as length×width×height. Mice with s.c. tumors greater than 1.5 cm in diameter are sacrificed. PSA levels are determined by using a PSA ELISA kit (Anogen, Mississauga, Ontario). Circulating levels of anti-108P5H8 mAbs are determined by a capture ELISA kit (Bethyl Laboratories, Montgomery, Tex.). (See, e.g., (Saffran, D., et al., PNAS 10: 1073-1078).

Orthotopic prostate injections are performed under anesthesia by using ketamine/xylazine. For prostate orthotopic studies, an incision is made through the abdominal muscles to expose the bladder and seminal vesicles, which then are delivered through the incision to expose the dorsal prostate. LAPC-9 cells ($5 \times 10^5$) mixed with Matrigel are injected into each dorsal lobe in a 10 μl volume. To monitor tumor growth, mice are bled on a weekly basis for determination of PSA levels. The mice are segregated into groups for appropriate treatments, with anti-108P5H8 or control mAbs being injected i.p.

Anti-108P5H8 mAbs Inhibit Growth of 108P5H8-Expressing Xenograft-Cancer Tumors

The effect of anti-108P5H8 mAbs on tumor formation is tested by using orthotopic models, e.g., LAPC-9 orthotopic models. As compared with the s.c. tumor model, the orthotopic model, which requires injection of tumor cells directly in the mouse prostate or kidney, respectively, results in a local tumor growth, development of metastasis in distal sites, deterioration of mouse health, and subsequent death (Saffran, D., et al., PNAS supra; Fu, X., et al., Int J Cancer, 1992. 52(6): p. 987-90; Kubota, T., J Cell Biochem, 1994. 56(1): p. 4-8). The features make the orthotopic model more representative of human disease progression and allow for tracking of the therapeutic effect of mAbs on clinically relevant end points.

Accordingly, tumor cells are injected into the mouse prostate or kidney, and the mice are segregated into two groups and treated with either: a) 200-500 μg, of anti-108P5H8 Ab, b) PBS or c) control non-specific monoclonal antibody for two to five weeks.

As noted, a major advantage of the orthotopic prostate-cancer model is the ability to study the development of metastases. Formation of metastasis in mice bearing established orthotopic tumors is studied by IHC analysis on lung sections using an antibody against a prostate-specific cell-surface protein STEAP expressed at high levels in LAPC-9 xenografts (Hubert, R. S., et al., Proc Natl Acad Sci USA, 1999. 96(25): p. 14523-14528).

Mice bearing established orthotopic LAPC-9 tumors are administered one to three injections per week of 500-1000 μg of either anti-108P5H8 mAb, control antibody or PBS two-to three times per week over a 4-8 week period. Mice in both groups are allowed to establish a high tumor burden (PSA levels greater than 300 ng/ml), to ensure a high frequency of metastasis formation in mouse lungs. Mice then are killed and their prostate/kidney and lungs are analyzed for the presence of tumor cells by IHC analysis.

These studies demonstrate a broad anti-tumor efficacy of anti-108P5H8 antibodies on initiation and/or progression of prostate and kidney cancer in xenograft mouse models. Anti-108P5H8 antibodies inhibit tumor formation of both androgen-dependent and androgen-independent prostate tumors as well as retarding the growth of already established tumors and prolong the survival of treated mice. Moreover, anti-108P5H8 mAbs demonstrate a dramatic inhibitory effect on the spread of local prostate tumor to distal sites, even in the presence of a large tumor burden. Similar therapeutic effects are seen in the kidney cancer model. Thus, anti-108P5H8 mAbs are efficacious on major clinically relevant end points (tumor growth), prolongation of survival, and health.

Example 37

Therapeutic and Diagnostic use of Anti-108P5H8 Antibodies in Humans

Anti-108P5H8 monoclonal antibodies are safely and effectively used for diagnostic, prophylactic, prognostic and/or therapeutic purposes in humans. Western blot and immunohistochemical analysis of cancer tissues and cancer xenografts with anti-108P5H8 mAb show strong extensive staining in carcinoma but significantly lower or undetectable levels in normal tissues. Detection of 108P5H8 in carcinoma and in metastatic disease demonstrates the usefulness of the mAb as a diagnostic and/or prognostic indicator. Anti-108P5H8 antibodies are therefore used in diagnostic applications such as immunohistochemistry of biopsy specimens to detect cancer from suspect patients.

As determined by immunofluorescence, anti-108P5H8 mAb specifically binds to carcinoma cells. Thus, anti-108P5H8 antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of 108P5H8. Shedding or release of an extracellular domain of 108P5H8 into the extracellular milieu, such as that seen for alkaline phosphodiesterase B10 (Meerson, N. R., Hepatology 27:563-568 (1998)), allows diagnostic detection of 108P5H8 by anti-108P5H8 antibodies in serum and/or urine samples from suspect patients.

Anti-108P5H8 antibodies that specifically bind 108P5H8 are used in therapeutic applications for the treatment of cancers that express 108P5H8. Anti-108P5H8 antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-108P5H8 antibodies are tested for efficacy of tumor prevention and growth inhibition in the SCID mouse cancer xenograft models, e.g., LAPC9 (see, e.g., the Example entitled "Monoclonal Antibody-mediated Inhibition of Prostate and Kidney Tumors In vivo.") Conjugated and unconjugated anti-108P5H8 antibodies are used as a therapeutic modality in human clinical trials either alone or in combination with other treatments as described in following Examples.

Example 38

Human Clinical Trials for the Treatment and Diagnosis of Human Carcinomas Through Use of Human Anti-108P5H8 Antibodies In Vivo Antibodies are used in accordance with the present invention which recognize an epitope on 108P5H8, and are used in the treatment of certain tumors such as those listed in Table I. Based upon a number of factors, including 108P5H8 expression levels, tumors such as those listed in Table I are presently preferred indications. In connection with each of these indications, three clinical approaches are successfully pursued.

I.) Adjunctive therapy: In adjunctive therapy, patients are treated with anti-108P5H8 antibodies in combination with a chemotherapeutic or antineoplastic agent and/or radiation therapy. Primary cancer targets, such as those listed in Table I, are treated under standard protocols by the addition anti-108P5H8 antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-108P5H8 antibodies are utilized in several adjunctive clinical trials in combination with the chemotherapeutic or antineoplastic agents adriamycin (advanced prostate carcinoma), cisplatin (advanced head and neck and lung carcinomas), taxol (breast cancer), and doxorubicin (preclinical).

II.) Monotherapy: In connection with the use of the anti-108P5H8 antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-108P5H8 antibodies, the radiolabeled antibodies are utilized as a diagnostic and/or imaging agent. In such a role, the labeled antibodies localize to both solid tumors, as well as, metastatic lesions of cells expressing 108P5H8. In connection with the use of the anti-108P5H8 antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-108P5H8 antibody is used as an imaging agent in a Phase I human clinical trial in patients having a carcinoma that expresses 108P5H8 (by analogy see, e.g., Divgi et al. *J. Natl Cancer Inst.* 83:97-104 (1991)). Patients are followed with standard anterior and posterior gamma camera. The results indicate that primary lesions and metastatic lesions are identified Dose and Route of Administration As appreciated by those of ordinary skill in the art, dosing considerations can be determined through comparison with the analogous products that are in the clinic. Thus, anti-108P5H8 antibodies can be administered with doses in the range of 5 to 400 mg/m$^2$, with the lower doses used, e.g., in connection with safety studies. The affinity of anti-108P5H8 antibodies relative to the affinity of a known antibody for its target is one parameter used by those of skill in the art for determining analogous dose regimens. Further, anti-108P5H8 antibodies that are fully human antibodies, as compared to the chimeric antibody, have slower clearance; accordingly, dosing in patients with such fully human anti-108P5H8 antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-108P5H8 antibodies.

Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-108P5H8 antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-108P5H8 antibodies. As will be appreciated, one criteria that can be utilized in connection with enrollment of patients is 108P5H8 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 108P5H8. Standard tests and follow-up are utilized to monitor each of these safety concerns. Anti-108P5H8 antibodies are found to be safe upon human administration.

Example 39

Human Clinical Trial Adjunctive Therapy with Human Anti-108P5H8 Antibody and Chemotherapeutic Agent A phase I human clinical trial is initiated to assess the safety of six intravenous doses of a human anti-108P5H8 antibody in connection with the treatment of a solid tumor, e.g., a cancer of a tissue listed in Table I. In the study, the safety of single doses of anti-108P5H8 antibodies when utilized as an adjunctive therapy to an antineoplastic or chemotherapeutic agent, such as cisplatin, topotecan, doxorubicin, adriamycin, taxol, or the like, is assessed. The trial design includes delivery of six single doses of an anti-108P5H8 antibody with dosage of antibody escalating from approximately about 25 mg/m$^2$ to about 275 mg/m$^2$ over the course of the treatment in accordance with the following schedule:

|  | Day 0 | Day 7 | Day 14 | Day 21 | Day 28 | Day 35 |
| --- | --- | --- | --- | --- | --- | --- |
| mAb Dose | 25 mg/m$^2$ | 75 mg/m$^2$ | 125 mg/mg$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express 108P5H8. Standard tests and follow-up are utilized to monitor each of these safety concerns. Patients are also assessed for clinical outcome, and particularly reduction in tumor mass as evidenced by MRI or other imaging.

The anti-108P5H8 antibodies are demonstrated to be safe and efficacious, Phase II trials confirm the efficacy and refine optimum dosing.

Example 40

Human Clinical Trial: Monotherapy with Human Anti-108P5H8 Antibody

Anti-108P5H8 antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-108P5H8 antibodies.

Example 41

Human Clinical Trial: Diagnostic Imaging with Anti-108P5H8 Antibody

Once again, as the adjunctive therapy discussed above is safe within the safety criteria discussed above, a human clinical trial is conducted concerning the use of anti-108P5H8 antibodies as a diagnostic imaging agent. The protocol is designed in a substantially similar manner to those described in the art, such as in Divgi et al. *J. Natl. Cancer Inst.* 83:97-104 (1991). The antibodies are found to be both safe and efficacious when used as a diagnostic modality.

Example 42

Homology Comparison of 108P5H8 to Known Sequences

The 108P5H8 protein is a six-transmembrane type 3 cell surface protein, consisting of 429 amino acids (table XXI). The 108P5H8 protein has 2 variant forms (FIG. 3), with 108P5H8v.3 differing from 108P5H8 v.1 by one amino acid at position 30 (D to E). This alteration in amino acid at position 30 corresponds to a point mutation at nucleic acid position 90, making variant 3 a true SNP. Both 108P5H8 variants, 108P5H8 v.1 and 108P5H8 v.3 have a calculated molecular weight of 47.5 kDa, and pI of 6.11, and contain an ion efflux motif between amino acid 114-417. Proteins carrying the ion efflux motif are found to increase tolerance to divalent metal ions such as cadmium, zinc, and cobalt. These proteins are thought to be efflux pumps that remove these ions from cells (Kunito T et al, Biosci Biotechnol Biochem 1996, 60:699).

The 108P5H8 protein variants show homology to human zinc transporter 4 (gi 11432533); with 108P5H8v.1 sharing 100% identity and 100% homology with that protein over the entire length of the protein (FIG. 25). 108P5H8v.2 share 100% identity and 100% homology with human zinc transporter ZNT4-gi 8134840 over the entire protein. As with the two 108P5H8 variants, ZNT4 (gi 8134840) and ZNT4-gi 11432533 differ by one amino acid at position 30, showing the same D to E change observed in 108P5H8v.3 and 108P5H8v.1. Based on sequence homology, 108P5H8 is conserved in various species, showing high homology to Rat ZNT4 (90% identify shown in FIG. 25) and mouse ZNT4 (91% identity with gi 8134841).

Zinc has been shown to play an important role in the physiology and pathology of prostate epithelial cells. Zinc ions regulate the activity of chromatin and plasmalemma structures in seminal plasma, and participate in spermadhesin function (Holody D and Strzezek J. Acta Biochini Pol 1999, 46:935). In relation to prostate cancer, zinc was found to inhibit the activity of aminopeptidase N in prostate cancer cells (Ishii K et al, Int J Cancer 2001, 92:49). Efflux of $Zn^{++}$ from the prostate by 108P5H8 or ZNT4 enhances the endogenous activity of aminopeptidase N, thereby increasing matrix degradation and tissue invasion by prostate cancer cells. In addition to its role in invasion, ZNT4 regulates apoptosis and proliferation of prostate cells. Accumulation of $Zn^{++}$ within the prostate induces apoptosis of normal epithelial cells (Feng P et al, Mol Urol 2000, 4:31). Enhanced expression of ZNT4 in prostate cancer cells and the resulting efflux of $Zn^{++}$, allow reduced apoptosis, survival and proliferation of prostate cancer cells. Finally, intracellular $Zn^{++}$ concentrations play a direct role in regulating gene transcription by zinc finger proteins.

This information indicates that 108P5H8 plays a role in the growth of cancer cells, supports cell survival, and regulates gene transcription by regulating events in the nucleus.

Accordingly, when 108P5H8 functions as a regulator of cell transformation, tumor formation, or as a modulator of transcription involved in activating genes associated with inflammation, tumorigenesis or proliferation, 108P5H8 is used for therapeutic, diagnostic, prognostic and/or preventative purposes.

Example 43

Identification and Confirmation of Signal Transduction Pathways

Many mammalian proteins have been reported to interact with signaling molecules and to participate in regulating signaling pathways. (see, e.g., J. Neurochem. 2001; 76:217-223). Using immunoprecipitation and Western blotting techniques, proteins are identified that associate with 108P5H8 and mediate signaling events. Several pathways known to play a role in cancer biology can be regulated by 108P5H8, including phospholipid pathways such as PI3K, AKT, etc, adhesion and migration pathways, including FAK, Rho, Rac-1, etc, as well as mitogenic/survival cascades such as ERK, p38, etc. (Cell Growth Differ. 2000, 11:279; J. Biol. Chem. 1999, 274:801; Oncogene. 2000, 19:3003, J. Cell Biol. 1997, 138:913).

To confirm that 108P5H8 directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by 108P5H8 are mapped and used for the identification and validation of therapeutic targets. When 108P5H8 is involved in cell signaling, it is used as target for diagnostic, prognostic, preventative and/or therapeutic purposes.

Example 44

Involvement in Tumor Progression

The 108P5H8 gene contributes to the growth of cancer cells. The role of 108P5H8 in tumor growth is confirmed in a variety of primary and transfected cell lines including prostate cell lines, as well as NIH 3T3 cells engineered to stably express 108P5H8. Parental cells lacking 108P5H8 and cells expressing 108P5H8 are evaluated for cell growth using a well-documented proliferation assay (Fraser, S. P., et al., Prostate 2000; 44:61, Johnson, D. E., et al., Anticancer Drugs 1996, 7:288).

To confirm the role of 108P5H8 in the transformation process, its effect in colony forming assays is investigated. Parental NIH-3T3 cells lacking 108P5H8 are compared to NIH-3T3 cells expressing 108P5H8, using a soft agar assay under stringent and more permissive conditions (Song, Z., et al., Cancer Res. 2000; 60:6730).

To confirm the role of 108P5H8 in invasion and metastasis of cancer cells, a well-established assay is used, e.g., a Transwell Insert System assay (Becton Dickinson) (Cancer Res. 1999; 59:6010). Control cells, including prostate, colon, bladder and kidney cell lines lacking 108P5H8 are compared to corresponding cells expressing 108P5H8. Cells are loaded with the fluorescent dye, calcein, and plated in the top well of the Transwell insert coated with a basement membrane analog. Invasion is determined by fluorescence of cells in the lower chamber relative to the fluorescence of the entire cell population.

108P5H8 can also play a role in cell cycle and apoptosis. Parental cells and cells expressing 108P5H8 are compared for differences in cell cycle regulation using a well-established BrdU assay (Abdel-Malek Z A., J Cell Physiol. 1988, 136: 247). In short, cells are grown under both optimal (full serum) and limiting (low serum) conditions, labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 108P5H8, including normal and tumor prostate, colon and lung cells. Engineered and parental cells are treated with various chemotherapeutic agents, such as etoposide, flutamide, etc., and protein synthesis inhibitors, such as cycloheximide. Cells are stained with annexin V-FITC and cell death is measured by FACS analysis. Modulation of cell death by 108P5H8 plays a critical role in regulating tumor progression and tumor load.

When 108P5H8 plays a role in cell growth, transformation, invasion or apoptosis, it is used as a target for diagnostic, prognostic, preventative and/or therapeutic purposes.

Example 45

Involvement in Angiogenesis

Angiogenesis or new capillary blood vessel formation is necessary for tumor growth (Hanahan, D., Folkman, J., Cell 1996, 86:353; Folkman, J., Endocrinology 1998, 139:441). Several assays have been developed to measure angiogenesis in vitro and in vivo, such as the tissue culture assays endothelial cell tube formation and endothelial cell proliferation. Using these assays as well as in vitro neo-vascularization, the role of 108P5H8 in angiogenesis, enhancement or inhibition, is confirmed.

For example, endothelial cells engineered to express 108P5H8 are evaluated using tube formation and proliferation assays. The effect of 108P5H8 is also confirmed in animal models in vivo. For example, cells either expressing or lacking 108P5H8 are implanted subcutaneously in immuno-compromised mice.

Endothelial cell migration and angiogenesis are evaluated 5-15 days later using immunohistochemistry techniques. 108P5H8 affects angiogenesis, and it is used as a target for diagnostic, prognostic, preventative and/or therapeutic purposes Example 46

Regulation of Transcription

The cellular localization of 108P5H8 (Table XXI) and its ability to regulate intracellular zinc ion concentrations, 108P5H8 is effectively used as a modulator of the transcriptional regulation of eukaryotic genes. Regulation of gene expression is confirmed, e.g., by studying gene expression in cells expressing or lacking 108P5H8. For this purpose, two types of experiments are performed.

In the first set of experiments, RNA from parental and 108P5H8-expressing cells are extracted and hybridized to commercially available gene arrays (Clontech) (Smid-Koopman, E., et al., Br. J. Cancer, 2000, 83:246). Resting cells as well as cells treated with FBS or androgen are compared. Differentially expressed genes are identified in accordance with procedures known in the art. The differentially expressed genes are then mapped to biological pathways (Chen, K., et al. Thyroid 2001, 11:41.).

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation.

Accordingly, it is found that 108P5H8 plays a role in gene regulation, and it is used as a target for diagnostic, prognostic, preventative and/or therapeutic purposes.

Example 47

Involvement in Cell Adhesion

Cell adhesion plays a critical role in tissue colonization and metastasis. 108P5H8 participates in cellular organization, and as a consequence cell adhesion and motility. To confirm the role of 108P5H8 in the regulation of cell adhesion, control cells lacking 108P5H8 are compared to cells expressing 108P5H8, using techniques previously described (see, e.g., Haier et al., Br. J. Cancer, 1999, 80:1867; Lehr and Pienta, J. Natl. Cancer Inst. 1998, 90:118). Briefly, in one embodiment, cells labeled with a fluorescent indicator, such as calcein, are incubated in tissue culture wells coated with media alone or with matrix proteins.

Adherent cells are detected by fluorimetric analysis and percent adhesion is calculated. In another embodiment, cells lacking or expressing 108P5H8 are analyzed for their ability to mediate cell-cell adhesion using similar experimental techniques as described above. Both of these experimental systems are used to identify proteins, antibodies and/or small molecules that modulate cell adhesion to extracellular matrix and cell-cell interaction. Cell adhesion plays a critical role in tumor growth, progression, and, colonization, and 108P5H8 is involved in these processes. Thus, 108P5H8 serves as a diagnostic, prognostic, preventative and/or therapeutic modality.

Example 48

Protein-Protein Association

Several ion transporters have been shown to interact with other proteins, thereby regulating gene transcription, gene sequence, as well as cell growth. Using immunoprecipitation techniques as well as two yeast hybrid systems, proteins are identified that associate with 108P5H8. Immunoprecipitates from cells expressing 108P5H8 and cells lacking 108P5H8 are compared for specific protein-protein associations.

Studies are performed to confirm the extent of association of 108P5H8 with effector molecules, such as nuclear proteins, transcription factors, kinases, phsophates, etc. Studies comparing 108P5H8 positive and 108P5H8 negative cells as well as studies comparing unstimulated/resting cells and cells treated with epithelial cell activators, such as cytokines, growth factors, androgen and anti-integrin Ab reveal unique interactions.

In addition, protein-protein interactions are confirmed using two yeast hybrid methodology (Curr. Opin. Chem. Biol. 1999, 3:64). A vector carrying a library of proteins fused to the activation domain of a transcription factor is introduced into yeast expressing a 108P5H8-DNA-binding domain fusion protein and a reporter construct. Protein-protein interaction is detected by colorimetric reporter activity. Specific association with effector molecules and transcription factors directs one of skill to the mode of action of 108P5H8, and thus identifies therapeutic, prognostic, preventative and/or diagnostic targets for cancer. This and similar assays are also used to identify and screen for small molecules that interact with 108P5H8.

Thus it is found that 108P5H8 associates with proteins and small molecules. Accordingly, 108P5H8 and these proteins and small molecules are used for diagnostic, prognostic, preventative and/or therapeutic purposes.

Example 49

Ion Flux Activity

To confirm that 108P5H8 functions as an ion channel, FACS analysis and electrophysiology techniques are used (Gergely L, Cook L, Agnello V. Clin Diagn Lab Immunol. 1997; 4:70; Skryma R, et al. J Physiol. 2000, 527: 71). Using FACS analysis and commercially available indicators (Molecular Probes), parental cells and cells expressing genes under consideration are compared for their ability to transport calcium, and zinc. Prostate, colon, bladder and kidney normal and tumor cell lines are used in these studies. For example cells loaded with calcium responsive indicators such as Fluo4 and Fura red are incubated in the presence or absence of ions and analyzed by flow cytometry. Information derived from these experiments provides a mechanism by which cancer cells are regulated. This is particularly true in the case of calcium, as calcium channel inhibitors have been reported to induce the death of certain cancer cells, including prostate cancer cell lines (Batra S, Popper L D, Hartley-Asp B. Prostate. 1991, 19: 299). It is possible to determine efflux and influx of zinc using fluoZin 1, a fluorescent $Zn^{++}$ indicator detected by FACS in a manner similar to Fluo4 above, or using $^{65}Zn$. Prostate, kidney, bladder or colon cells, engineered to express or lack 108P5H8, will be incubated in the presence of $^{65}Zn$. Cells will be evaluated over time for uptake and efflux of $^{65}Zn$ (Kim A H et al, Brain Res. 2000, 886:99; Grass G et al, J Bacteriol. 2001, 183:4664).

Using electrophysiology, uninjected oocytes and oocytes injected with gene-specific cRNA are compared for ion channel activity. Patch/voltage clamp assays are performed on oocytes in the presence or absence of selected ions, including calcium, zinc, etc. Ion channel activators (such as cAMP/GMP, forskolin, TPA, etc) and inhibitors (such as calcicludine, conotoxin, TEA, tetrodotoxin, etc) are used to evaluate the function of 108P5H8 as ion channels (Schweitz H. et al. Proc. Natl. Acad. Sci. 1994. 91:878; Skryma R. et al. Prostate. 1997. 33:112).

Using any of the assays listed above, we can evaluate the effect of antibodies directed against 108P5H8 on ion transport. Similarly, these assays can be used to identify and evaluate small molecule that modulate ion and protein transport.

When 108P5H8 functions as an ion channel, it is used as a target for diagnostic, preventative and therapeutic purposes.

Example 50

Figure 26:
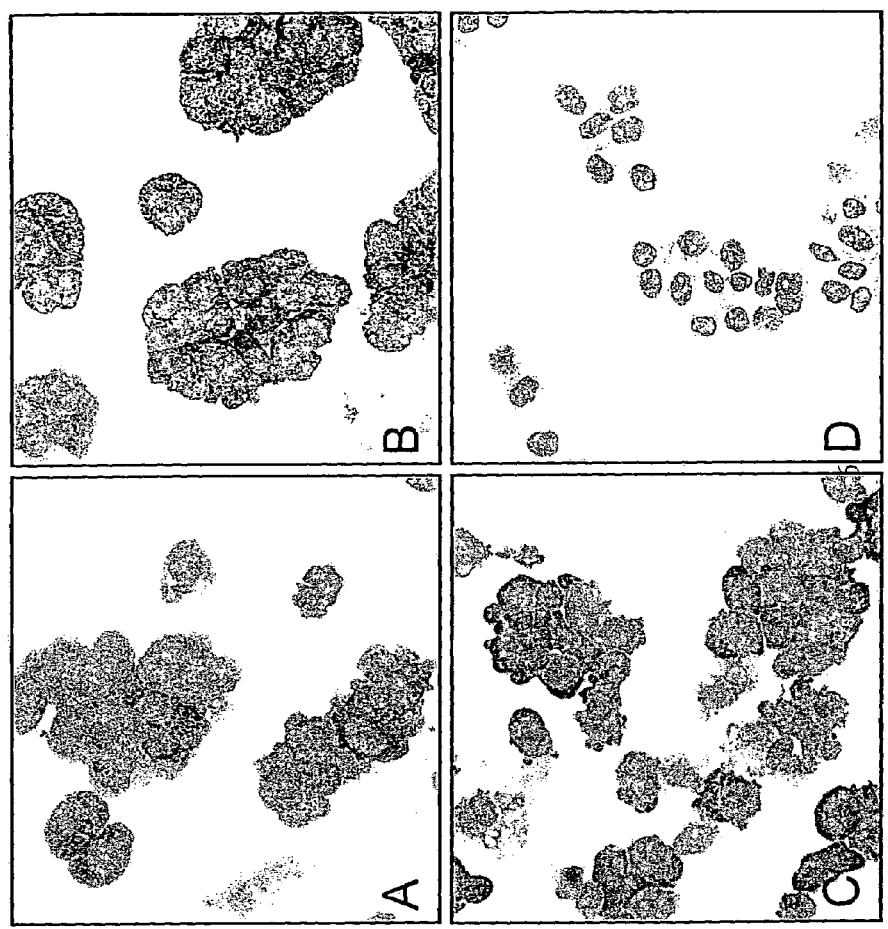
FIG. 26. Detection of 108P5H8 protein by immunocytochemistry in LNCaP cells. Immunocytochemical staining of LNCaP cells (an androgen dependant prostate cancer cell line) showing expression of 108P5H8, which is not androgen regulated. LNCaP cell preparations were made from either cells grown in medium containing 10% fetal bovine serum (Panel A) or from cells grown for 72 hours in androgen free, serum depleted medium (by growing in charcoal dextran stripped medium) (Panel B) or from previously androgen starved cells which were subsequently stimulated with 10 mmol mibolerone, a synthetic androgen, for 48 hours (Panel C). LNCaP cells incubated with Rabbit IgG instead of rabbit antibody to 108P5H8 was included to show no non-specific binding of rabbit immunoglobulin to the cells (Panel D).

Detection of 108P5H8 Protein in LNCaP Cells a Prostate Cancer Cell Line by Immunocytochemistry To assess the expression of 108P5H8 protein in a prostate cancer cell line, preparations of cytocentrifuged LNCaP cells were stained using a rabbit polyclonal antibody to 108P5H8. Preparations of LNCaP cells were made from three differently treated cell populations to assess whether 108P5H8 is androgen regulated. The LNCaP cell preparations were made from cells grown in medium containing 10% fetal bovine serum; from cells grown for 72 hours in androgen free, serum depleted medium (by growing in charcoal dextran stripped medium); or from previously androgen starved cells which were subsequently stimulated with 10 mmol mibolerone (a synthetic androgen) for 48 hours. The cells were spun down, washed twice (in buffer), resuspended (in buffer) and then centrifuged onto slides (1000 rpm for 2 minutes), allowed to dry and then fixed in acetone for 10 minutes. The cells were then incubated with rabbit polyclonal 108P5H8 for 3 hours (FIG. 26 A-C), or rabbit IgG (FIG. 26 D). The slides were washed three times in buffer then incubated in DAKO EnVision+™ peroxidase conjugated goat anti-rabbit secondary antibody (DAKO Corporation, Carpenteria, Calif.) for 1 hour. The cells were then washed in buffer, developed using the DAB kit (SIGMA Chemicals), counterstained using hematoxylin, and analyzed by bright field microscopy. The results showed strong expression of 108P5H8 in all three LNCaP cell preparations demonstrating that expression of 108P5H8 can be detected in this prostate cancer cell line and is not androgen related. This indicates that antibodies to 108P5H8 are useful in detecting non-androgen related cancer of the prostate; the protein is a useful marker.

Example 51

Figure 27:
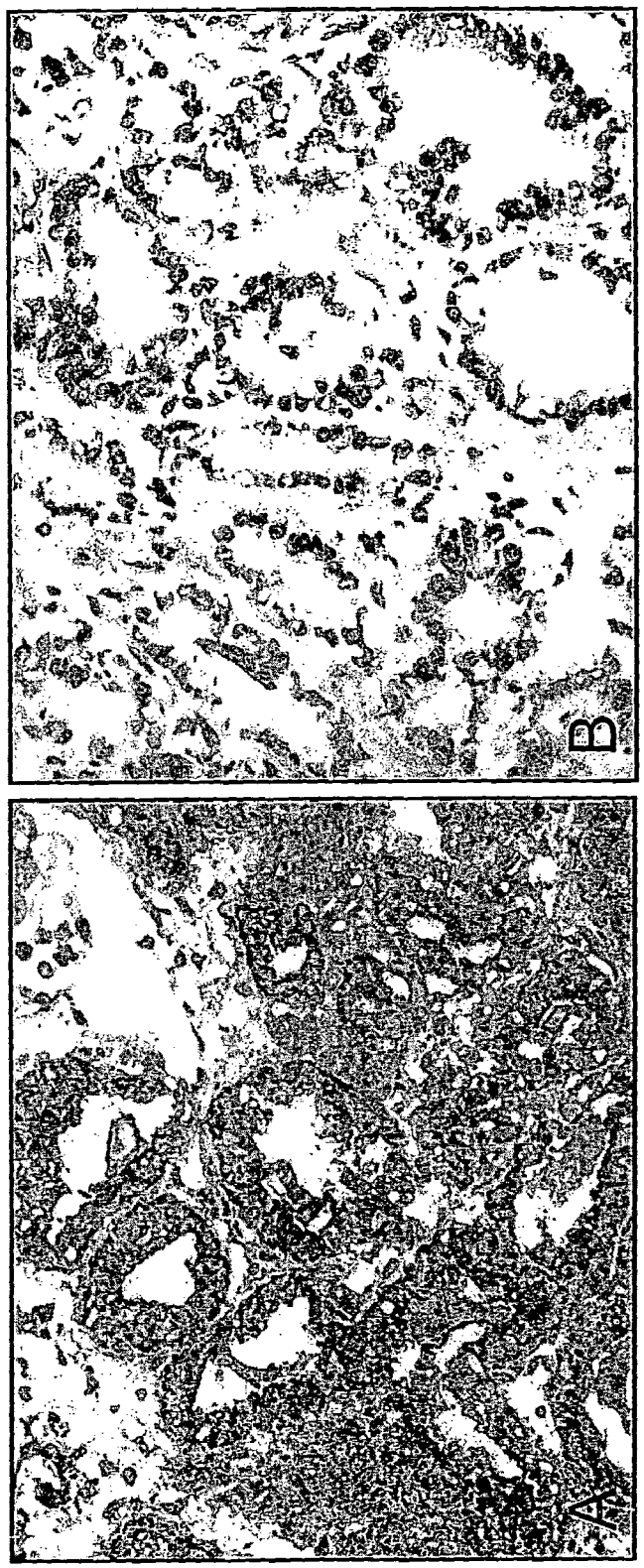
FIG. 27. Detection of 108P5H8 protein by immunohistochemistry in prostate cancer patient specimens. Immunohistochemical staining of frozen sections of a prostate carcinoma specimen (Gleason grade 6) showing expression of 108P5H8 in the neoplastic glands (Panel A) and no non-specific binding of rabbit immunoglobulin in the Rabbit IgG control (Panel B).
Figure 28A:
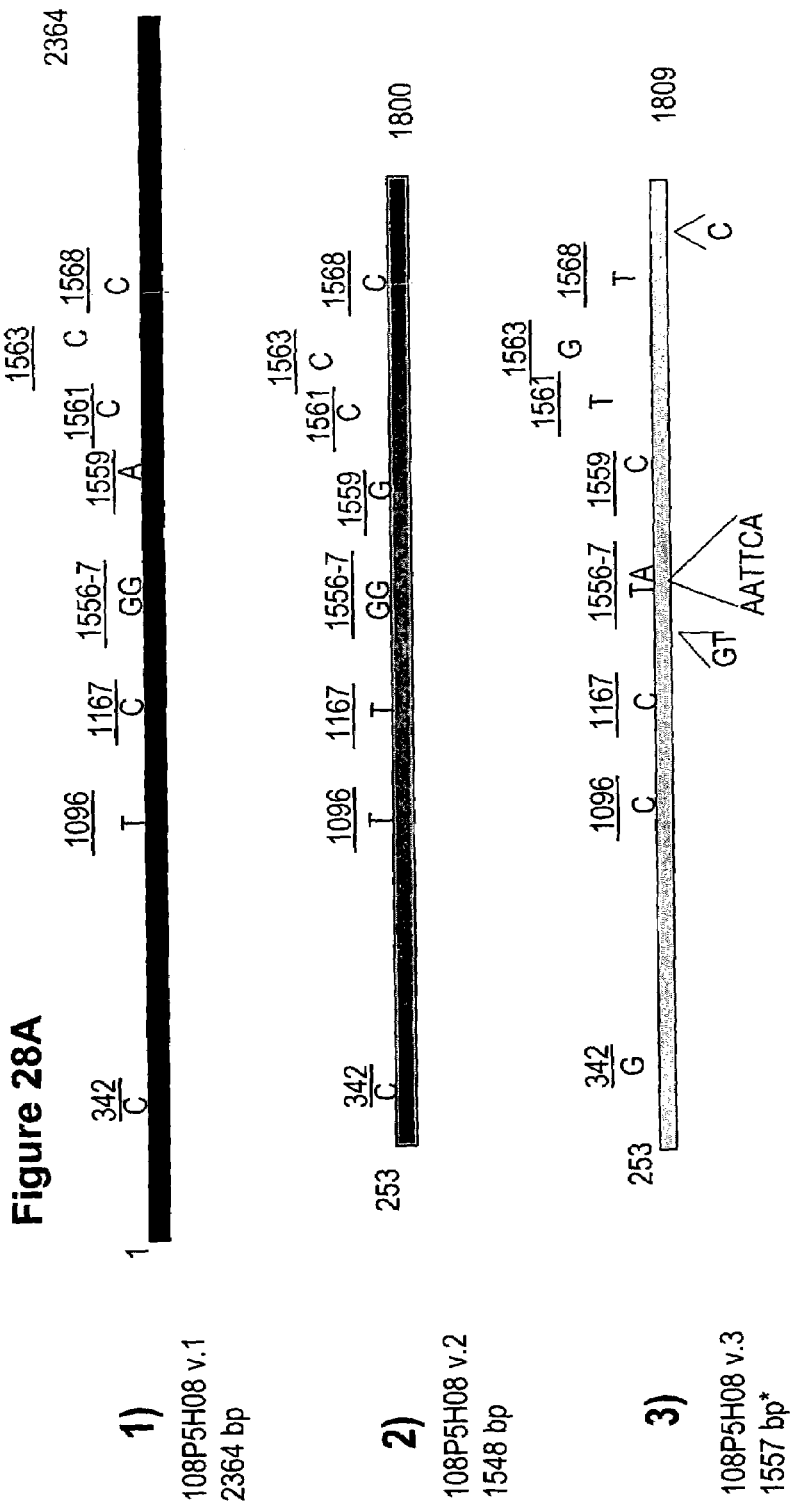
FIGS. 28A & 28B show a vertical alignment comparison between nucleotide and amino acid sequences of the variants.
Figure 28B:
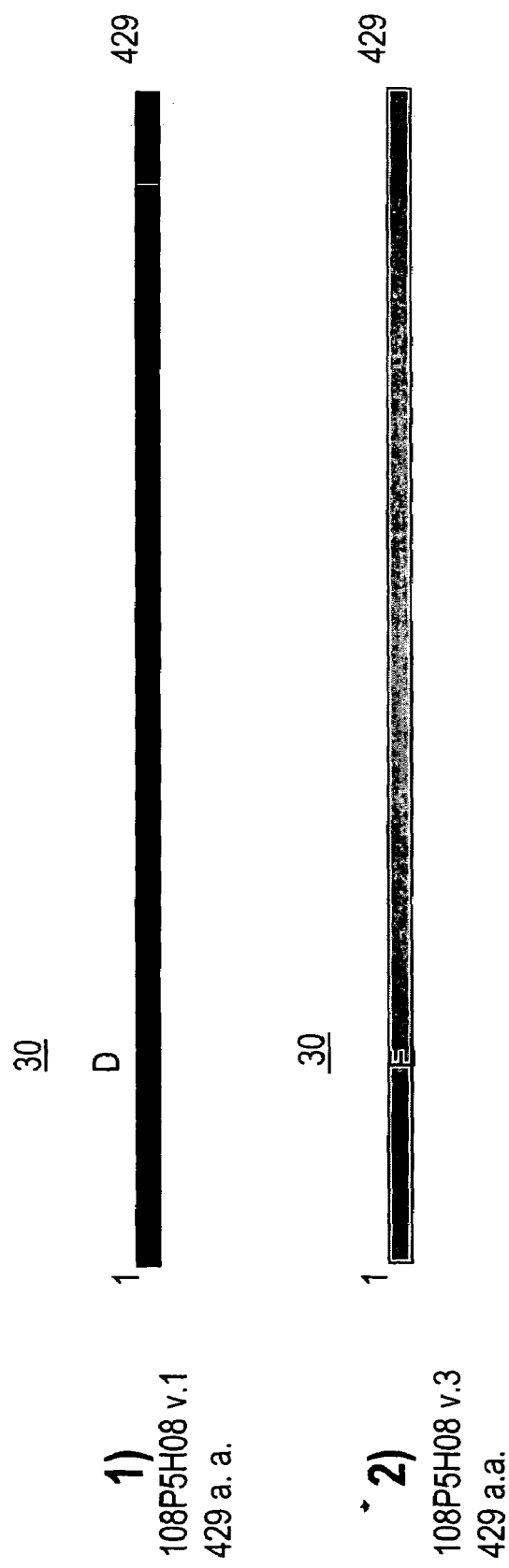

Detection of 108P5H8 Protein in Prostate Cancer Patient Specimens by Immunohistochemistry To assess the expression of 108P5H8 protein, prostate cancer specimens were obtained from prostate cancer patients and stained using a rabbit polyclonal antibody to 108P5H8. Frozen tissues were then cut into 4 micron sections and fixed in acetone for 10 minutes. The sections were then incubated with rabbit polyclonal 108P5H8 for 3 hours (FIG. 27 A), or rabbit IgG (FIG. 27 B). The slides were washed three times in buffer then incubated in DAKO EnVision+™ peroxidase conjugated goat anti-rabbit secondary antibody (DAKO Corporation, Carpenteria, Calif.) for 1 hour. The sections were then washed in buffer, developed using the DAB kit (SIGMA Chemicals), counterstained using hematoxylin, and analyzed by bright field microscopy. The results showed strong expression in the neoplastic glands of the prostate (FIG. 27 A). These results further confirm the utility of 108P5H8 as a prostate tumor marker.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

| Tissues that Express 108P5H8 When Malignant |
|---|
| Prostate |
| Bladder |
| Kidney |
| Colon |
| Lung |
| Ovary |
| Breast |
| Pancreas |
| Uterus |
| Stomach |

TABLE II

AMINO ACID ABBREVIATIONS

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

AMINO ACID SUBSTITUTION MATRIX
Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | -2 | -1 | -2 | 0 | -2 | -1 | -1 | -1 | -1 | -2 | -1 | -1 | -1 | 1 | 0 | 0 | -3 | -2 | A |
| | 9 | -3 | -4 | -2 | -3 | -3 | -1 | -3 | -1 | -1 | -3 | -3 | -3 | -3 | -1 | -1 | -1 | -2 | -2 | C |
| | | 6 | 2 | -3 | -1 | -1 | -3 | -1 | -4 | -3 | 1 | -1 | 0 | -2 | 0 | -1 | -3 | -4 | -3 | D |
| | | | 5 | -3 | -2 | 0 | -3 | 1 | -3 | -2 | 0 | -1 | 2 | 0 | 0 | -1 | -2 | -3 | -2 | E |
| | | | | 6 | -3 | -1 | 0 | -3 | 0 | 0 | -3 | -4 | -3 | -3 | -2 | -2 | -1 | 1 | 3 | F |
| | | | | | 6 | -2 | -4 | -2 | -4 | -3 | 0 | -2 | -2 | -2 | 0 | -2 | -3 | -2 | -3 | G |
| | | | | | | 8 | -3 | -1 | -3 | -2 | 1 | -2 | 0 | 0 | -1 | -2 | -3 | -2 | 2 | H |
| | | | | | | | 4 | -3 | 2 | 1 | -3 | -3 | -3 | -3 | -2 | -1 | 3 | -3 | -1 | I |
| | | | | | | | | 5 | -2 | -1 | 0 | -1 | 1 | 2 | 0 | -1 | -2 | -3 | -2 | K |
| | | | | | | | | | 4 | 2 | -3 | -3 | -2 | -2 | -2 | -1 | 1 | -2 | -1 | L |
| | | | | | | | | | | 5 | -2 | -2 | 0 | -1 | -1 | -1 | 1 | -1 | -1 | M |
| | | | | | | | | | | | 6 | -2 | 0 | 0 | 1 | 0 | -3 | -4 | -2 | N |
| | | | | | | | | | | | | 7 | -1 | -2 | -1 | -1 | -2 | -4 | -3 | P |
| | | | | | | | | | | | | | 5 | 1 | 0 | -1 | -2 | -2 | -1 | Q |
| | | | | | | | | | | | | | | 5 | -1 | -1 | -3 | -3 | -2 | R |
| | | | | | | | | | | | | | | | 4 | 1 | -2 | -3 | -2 | S |
| | | | | | | | | | | | | | | | | 5 | 0 | -2 | -2 | T |
| | | | | | | | | | | | | | | | | | 4 | -3 | -1 | V |
| | | | | | | | | | | | | | | | | | | 11 | 2 | W |
| | | | | | | | | | | | | | | | | | | | 7 | Y |

TABLE IV (A)

| SUPER-MOTIFS | POSITION 2 (Primary Anchor) | POSITION C Terminus (Primary 3 Anchor) | POSITION (Primary Anchor) |
|---|---|---|---|
| A1 | T*ILVMS* | | FWY |
| A2 | LIVM*ATQ* | | IV*MATL* |
| A3 | VSMA*TLI* | | RK |
| A24 | YF*WIVLMT* | | FI*YWLM* |
| B7 | P | | VILF*MWYA* |
| B27 | RHK | | FYL*WMJVA* |
| B44 | E*D* | | FWY*LIMVA* |
| B58 | ATS | | FWY*LIVMA* |
| B62 | QL*IVMP* | | FWY*MIVLA* |

MOTIFS

| | | | |
|---|---|---|---|
| A1 | TSM | | Y |
| A1 | | DE*AS* | Y |
| A2.1 | LM*VQIAT* | | V*LIMAT* |
| A3 | LMVISATF*CGD* | | KYR*HFA* |
| A11 | VTMLISAGN*CDF* | | K*RYH* |
| A24 | YFW*M* | | FLIW |
| A*3101 | MVT*ALIS* | | R*K* |
| A*3301 | MYALF*IST* | | RK |
| A*6801 | AVT*MSLI* | | RK |
| B*0702 | P | | LMF*WYAIV* |
| B*3501 | P | | LMFWY*IVA* |
| B51 | P | | LIVF*WYAM* |
| B*5301 | P | | IMFWY*ALV* |
| B*5401 | P | | ATIVL*MFWY* |

Bolded residues are preferred, italicized residues are less preferred: A peptide is considered motif-bearing if it has primary anchors at each primary anchor position for a motif or supermotif as specified in the above table.

TABLE IV (B)

HLA CLASS II SUPERMOTIF

| 1 | 6 | 9 |
|---|---|---|
| W,F,Y,V,.I,L | A,V,I,L,P,C,S,T | A,V,I,L,C,S,T,M,Y |

TABLE IV (C)

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | T | | I | VST*CPALIM* | MH | | MH |
| | deleterious | | | | W | | | R | | WDE |
| DR1 | preferred | MF*LIVWY* | | | PAMQ | | VM*ATSPLIC* | M | | AVM |
| | deleterious | | C | CH | FD | CWD | | GDE | D | |
| DR7 | preferred | MF*LIVWY* | M | W | A | | IVMSA*CTPL* | M | | IV |
| | deleterious | | C | | G | | | GRD | N | G |
| DR3 | MOTIFS | 1° anchor 1 | 2 | 3 | 1° anchor 4 | 5 | 1° anchor 6 | | | |
| motif a preferred | | LIVMFY | | | D | | | | | |
| motif b preferred | | LIVMFAY | | | DNQEST | | KRH | | | |
| DR Super-motif | | MF*LIVWY* | | | | | VMSTA*CPLI* | | | |

Italicized residues indicate less preferred or "tolerated" residues.

TABLE V(A)

HLA PEPTIDE SCORING RESULTS-108P5H8-A1, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 23 | LNDTSAFDF | 6.250 | 1. |
| 2 | 148 | LTDLSAIIL | 6.250 | 2. |
| 3 | 141 | MTDALHMLT | 6.250 | 3. |
| 4 | 303 | IADPICTYV | 5.000 | 4. |
| 5 | 94 | SCDNCSKQR | 5.000 | 5. |
| 6 | 356 | SVEDLNIWS | 4.500 | 6. |
| 7 | 192 | YILMGFLLY | 2.500 | 7. |
| 8 | 377 | QLIPGSSSK | 2.000 | 8. |
| 9 | 178 | RLEVLSAMI | 1.800 | 9. |
| 10 | 54 | GSEAPERPV | 1.350 | 10. |
| 11 | 184 | AMISVLLVY | 1.250 | 11. |
| 12 | 35 | AGDEGLSRF | 1.250 | 12. |
| 13 | 285 | SVGVLIAAY | 1.000 | 13. |
| 14 | 113 | RLTIAAVLY | 1.000 | 14. |
| 15 | 76 | LLDQDLPLT | 1.000 | 15. |
| 16 | 101 | QREILKQRK | 0.900 | 16. |
| 17 | 331 | ILEGVPSHL | 0.900 | 17. |
| 18 | 166 | KSPTKRFTF | 0.750 | 18. |
| 19 | 31 | FSDEAGDEG | 0.750 | 19. |
| 20 | 214 | NGDIMLITA | 0.625 | 20. |
| 21 | 91 | KVDSCDNCS | 0.500 | 21. |
| 22 | 34 | EAGDEGLSR | 0.500 | 22. |
| 23 | 116 | IAAVLYLLF | 0.500 | 23. |
| 24 | 288 | VLIAAYIIR | 0.500 | 24. |
| 25 | 405 | RCTIQLQSY | 0.500 | 25. |
| 26 | 340 | NVDYIKEAL | 0.500 | 26. |
| 27 | 226 | VAVNVIMGF | 0.500 | 27. |
| 28 | 289 | LIAAYIIRF | 0.500 | 28. |
| 29 | 396 | LLLNTFGMY | 0.500 | 29. |
| 30 | 125 | MIGELVGGY | 0.500 | 30. |
| 31 | 397 | LLNTFGMYR | 0.500 | 31. |
| 32 | 302 | KIADPICTY | 0.500 | 32. |
| 33 | 83 | LTNSQLSLK | 0.500 | 33. |
| 34 | 189 | LLVYILMGF | 0.500 | 34. |
| 35 | 162 | WLSSKSPTK | 0.400 | 35. |
| 36 | 267 | DSLAVRAAF | 0.300 | 36. |
| 37 | 3 | GSGAWKRLK | 0.300 | 37. |
| 38 | 70 | QADDDSLLD | 0.250 | 38. |
| 39 | 406 | CTIQLQSYR | 0.250 | 39. |
| 40 | 335 | VPSHLNVDY | 0.250 | 40. |
| 41 | 126 | IGELVGGYI | 0.225 | 41. |
| 42 | 290 | IAAYIIRFK | 0.200 | 42. |
| 43 | 310 | YVFSLLVAF | 0.200 | 43. |
| 44 | 248 | SLPSNSPTR | 0.200 | 44. |
| 45 | 197 | FLLYEAVQR | 0.200 | 45. |
| 46 | 158 | LLALWLSSK | 0.200 | 46. |
| 47 | 98 | CSKQREILK | 0.150 | 47. |

TABLE V(A)-continued

HLA PEPTIDE SCORING RESULTS-108P5H8-A1, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 48 | 265 | GQDSLAVRA | 0.150 | 48. |
| 49 | 247 | HSLPSNSPT | 0.150 | 49. |
| 50 | 414 | RQEVDRTCA | 0.135 | 50. |

TABLE VI(A)

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 303 | IADPICTYVF | 100.00 | 51. |
| 2 | 91 | KVDSCDNCSK | 10.000 | 52. |
| 3 | 148 | LTDLSAIILT | 6.250 | 53. |
| 4 | 36 | GDEGLSRFNK | 4.500 | 54. |
| 5 | 178 | RLEVLSAMIS | 4.500 | 55. |
| 6 | 247 | HSLPSNSPTR | 3.000 | 56. |
| 7 | 54 | GSEAPERPVN | 2.700 | 57. |
| 8 | 76 | LLDQDLPLTN | 2.500 | 58. |
| 9 | 183 | SAMISVLLVY | 2.500 | 59. |
| 10 | 70 | QADDDSLLDQ | 2.500 | 60. |
| 11 | 284 | QSVGVLIAAY | 1.500 | 61. |
| 12 | 340 | NVDYIKEALM | 1.000 | 62. |
| 13 | 334 | GVPSHLNVDY | 1.000 | 63. |
| 14 | 356 | SVEDLNIWSL | 0.900 | 64. |
| 15 | 331 | ILEGVPSHLN | 0.900 | 65. |
| 16 | 31 | FSDEAGDEGL | 0.750 | 66. |
| 17 | 141 | MTDALHMLTD | 0.625 | 67. |
| 18 | 396 | LLLNTFGMYR | 0.500 | 68. |
| 19 | 225 | GVAVNVIMGF | 0.500 | 69. |
| 20 | 22 | FLNDTSAFDF | 0.500 | 70. |
| 21 | 287 | GVLIAAYIIR | 0.500 | 71. |
| 22 | 346 | EALMKIEDVY | 0.500 | 72. |
| 23 | 51 | ADDGSEAPER | 0.500 | 73. |
| 24 | 188 | VLLVYILMGF | 0.500 | 74. |
| 25 | 395 | HLLLNTFGMY | 0.500 | 75. |
| 26 | 288 | VLIAAYIIRF | 0.500 | 76. |
| 27 | 115 | TIAAVLYLLF | 0.500 | 77. |
| 28 | 126 | IGELVGGYIA | 0.450 | 78. |
| 29 | 165 | SKSPTKRFTF | 0.250 | 79. |
| 30 | 202 | AVQRTIHMNY | 0.250 | 80. |
| 31 | 124 | FMIGELVGGY | 0.250 | 81. |
| 32 | 279 | LGDLVQSVGV | 0.250 | 82. |
| 33 | 298 | KPEYKIADPI | 0.225 | 83. |
| 34 | 210 | NYEINGDIML | 0.225 | 84. |
| 35 | 157 | TLLALWLSSK | 0.200 | 85. |
| 36 | 289 | LIAAYIIRFK | 0.200 | 86. |
| 37 | 350 | KIEDVYSVED | 0.180 | 87. |
| 38 | 93 | DSCDNCSKQR | 0.150 | 88. |
| 39 | 312 | FSLLVAFTTF | 0.150 | 89. |
| 40 | 414 | RQEVDRTCAN | 0.135 | 90. |
| 41 | 15 | RKDDAPLFLN | 0.125 | 91. |
| 42 | 156 | LTLLALWLSS | 0.125 | 92. |
| 43 | 83 | LTNSQLSLKV | 0.125 | 93. |
| 44 | 172 | FTFGFHRLEV | 0.125 | 94. |
| 45 | 214 | NGDIMLITAA | 0.125 | 95. |
| 46 | 308 | CTYVFSLLVA | 0.125 | 96. |
| 47 | 23 | LNDTSAFDFS | 0.125 | 97. |
| 48 | 35 | AGDEGLSRFN | 0.125 | 98. |
| 49 | 191 | VYILMGFLLY | 0.125 | 99. |
| 50 | 97 | NCSKQREILK | 0.100 | 100. |

TABLE VII(A)

HLA PEPTIDE SCORING RESULTS-108P5H8-A2, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 278 | ALGDLVQSV | 655.875 | 101. |
| 2 | 268 | SLAVRAAFV | 382.536 | 102. |
| 3 | 198 | LLYEAVQRT | 382.282 | 103. |
| 4 | 75 | SLLDQDLPL | 324.068 | 104. |
| 5 | 140 | IMTDALHML | 247.333 | 105. |
| 6 | 122 | LLFMIGELV | 214.366 | 106. |
| 7 | 155 | ILTLLALWL | 199.738 | 107. |
| 8 | 218 | MLITAAVGV | 118.238 | 108. |
| 9 | 121 | YLLFMIGEL | 108.713 | 109. |
| 10 | 323 | IIWDTVVII | 78.258 | 110. |
| 11 | 409 | QLQSYRQEV | 69.552 | 111. |
| 12 | 402 | GMYRCTIQL | 49.371 | 112. |
| 13 | 118 | AVLYLLFMI | 45.057 | 113. |
| 14 | 181 | VLSAMISVL | 34.246 | 114. |
| 15 | 185 | MISVLLVYI | 30.849 | 115. |
| 16 | 147 | MLTDLSAII | 29.814 | 116. |
| 17 | 190 | LVYILMGFL | 16.722 | 117. |
| 18 | 69 | LQADDDSLL | 15.096 | 118. |
| 19 | 194 | LMGFLLYEA | 14.029 | 119. |
| 20 | 275 | FVHALGDLV | 13.717 | 120. |
| 21 | 308 | CTYVFSLLV | 11.747 | 121. |
| 22 | 76 | LLDQDLPLT | 11.655 | 122. |
| 23 | 137 | SLAIMTDAL | 10.468 | 123. |
| 24 | 68 | TLQADDDSL | 10.468 | 124. |
| 25 | 315 | LVAFTTFRI | 9.001 | 125. |
| 26 | 183 | SAMISVLLV | 8.221 | 126. |
| 27 | 327 | TVVIILEGV | 6.859 | 127. |
| 28 | 115 | TIAAVLYLL | 6.756 | 128. |
| 29 | 153 | AIILTLLAL | 6.756 | 129. |
| 30 | 319 | TTFRIIWDT | 6.606 | 130. |
| 31 | 114 | LTIAAVLYL | 6.381 | 131. |
| 32 | 87 | QLSLKVDSC | 5.599 | 132. |
| 33 | 364 | SLTSGKSTA | 4.968 | 133. |
| 34 | 357 | VEDLNIWSL | 4.872 | 134. |
| 35 | 312 | FSLLVAFTT | 4.802 | 135. |
| 36 | 193 | ILMGFLLYE | 4.506 | 136. |
| 37 | 180 | EVLSAMISV | 3.884 | 137. |
| 38 | 150 | DLSAIILTL | 3.685 | 138. |
| 39 | 389 | VQSKANHLL | 3.682 | 139. |
| 40 | 395 | HLLLNTFGM | 3.625 | 140. |
| 41 | 303 | IADPICTYV | 3.613 | 141. |
| 42 | 227 | AVNVIMGFL | 3.074 | 142. |
| 43 | 49 | VVADDGSEA | 3.030 | 143. |
| 44 | 133 | YIANSLAIM | 2.963 | 144. |
| 45 | 13 | MLRKDDAPL | 2.760 | 145. |
| 46 | 216 | DIMLITAAV | 2.654 | 146. |
| 47 | 139 | AIMTDALHM | 2.527 | 147. |
| 48 | 187 | SVLLVYILM | 2.413 | 148. |
| 49 | 331 | ILEGVPSHL | 2.324 | 149. |
| 50 | 146 | HMLTDLSAI | 2.180 | 150. |

TABLE VIII (A)

HLA PEPTIDE SCORING RESULTS-108P5H8-A2, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 302 | KIADPICTYV | 754.791 | 151. |
| 2 | 121 | YLLFMIGELV | 580.050 | 152. |
| 3 | 217 | IMLITAAVGV | 315.959 | 153. |
| 4 | 197 | FLLYEAVQRT | 291.716 | 154. |
| 5 | 113 | RLTIAAVLYL | 270.234 | 155. |
| 6 | 75 | SLLDQDLPLT | 260.008 | 156. |
| 7 | 323 | IIWDTVVIIL | 160.242 | 157. |
| 8 | 310 | YVFSLLVAFT | 140.388 | 158. |
| 9 | 314 | LLVAFTTFRI | 102.867 | 159. |
| 10 | 154 | IILTLLALWL | 101.617 | 160. |
| 11 | 184 | AMISVLLVYI | 95.315 | 161. |

TABLE VIII (A)-continued

HLA PEPTIDE SCORING RESULTS-108P5H8-A2, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 12 | 330 | IILEGVPSHL | 75.751 | 162. |
| 13 | 193 | ILMGFLLYEA | 71.872 | 163. |
| 14 | 39 | GLSRFNKLRV | 69.552 | 164. |
| 15 | 194 | LMGFLLYEAV | 62.765 | 165. |
| 16 | 160 | ALWLSSKSPT | 61.852 | 166. |
| 17 | 147 | MLTDLSAIIL | 61.047 | 167. |
| 18 | 189 | LLVYILMGFL | 59.722 | 168. |
| 19 | 190 | LVYILMGFLL | 58.977 | 169. |
| 20 | 12 | SMLRKDDAPL | 57.085 | 170. |
| 21 | 198 | LLYEAVQRTI | 46.539 | 171. |
| 22 | 408 | IQLQSYRQEV | 44.356 | 172. |
| 23 | 140 | IMTDALHMLT | 37.513 | 173. |
| 24 | 181 | VLSAMISVLL | 36.316 | 174. |
| 25 | 139 | AIMTDALHML | 24.997 | 175. |
| 26 | 68 | TLQADDDSLL | 21.362 | 176. |
| 27 | 397 | LLNTFGMYRC | 19.425 | 177. |
| 28 | 172 | FTFGFHRLEV | 16.441 | 178. |
| 29 | 219 | LITAAVGVAV | 16.258 | 179. |
| 30 | 227 | AVNVIMGFLL | 10.841 | 180. |
| 31 | 364 | SLTSGKSTAI | 10.433 | 181. |
| 32 | 356 | SVEDLNIWSL | 8.461 | 182. |
| 33 | 318 | FTTFRIIWDT | 8.213 | 183. |
| 34 | 22 | FLNDTSAFDF | 8.152 | 184. |
| 35 | 125 | MIGELVGGYI | 7.149 | 185. |
| 36 | 348 | LMKIEDVYSV | 6.874 | 186. |
| 37 | 345 | KEALMKIEDV | 5.335 | 187. |
| 38 | 179 | LEVLSAMISV | 5.288 | 188. |
| 39 | 285 | SVGVLIAAYI | 5.021 | 189. |
| 40 | 144 | ALHMLTDLSA | 4.968 | 190. |
| 41 | 133 | YIANSLAIMT | 4.713 | 191. |
| 42 | 185 | MISVLLVYIL | 4.709 | 192. |
| 43 | 150 | DLSAIILTLL | 3.685 | 193. |
| 44 | 389 | VQSKANHLLL | 3.682 | 194. |
| 45 | 129 | LVGGYIANSL | 3.178 | 195. |
| 46 | 319 | TTFRIIWDTV | 2.977 | 196. |
| 47 | 307 | ICTYVFSLLV | 2.933 | 197. |
| 48 | 5 | GAWKRLKSML | 2.463 | 198. |
| 49 | 401 | FGMYRCTIQL | 2.373 | 199. |
| 50 | 332 | LEGVPSHLNV | 2.299 | 200. |

TABLE IX(A)

HLA PEPTIDE SCORING RESULTS-108P5H8-A3, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 158 | LLALWLSSK | 90.000 | 201. |
| 2 | 377 | QLIPGSSSK | 45.000 | 202. |
| 3 | 184 | AMISVLLVY | 27.000 | 203. |
| 4 | 397 | LLNTFGMYR | 24.000 | 204. |
| 5 | 162 | WLSSKSPTK | 20.000 | 205. |
| 6 | 39 | GLSRFNKLR | 18.000 | 206. |
| 7 | 402 | GMYRCTIQL | 18.000 | 207. |
| 8 | 314 | LLVAFTTFR | 18.000 | 208. |
| 9 | 189 | LLVYILMGF | 13.500 | 209. |
| 10 | 288 | VLIAAYIIR | 12.000 | 210. |
| 11 | 361 | NIWSLTSGK | 10.000 | 211. |
| 12 | 347 | ALMKIEDVY | 9.000 | 212. |
| 13 | 313 | SLLVAFTTF | 9.000 | 213. |
| 14 | 197 | FLLYEAVQR | 6.000 | 214. |
| 15 | 396 | LLLNTFGMY | 5.400 | 215. |
| 16 | 113 | RLTIAAVLY | 4.000 | 216. |
| 17 | 248 | SLPSNSPTR | 4.000 | 217. |
| 18 | 192 | YILMGFLLY | 3.600 | 218. |
| 19 | 302 | KIADPICTY | 2.700 | 219. |
| 20 | 198 | LLYEAVQRT | 2.250 | 220. |
| 21 | 294 | IIRFKPEYK | 2.000 | 221. |
| 22 | 289 | LIAAYIIRF | 1.800 | 222. |

TABLE IX(A)-continued

HLA PEPTIDE SCORING RESULTS-108P5H8-A3, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 23 | 293 | YIIRFKPEY | 1.800 | 223. |
| 24 | 234 | FLLNQSGHR | 1.800 | 224. |
| 25 | 75 | SLLDQDLPL | 1.800 | 225. |
| 26 | 122 | LLFMIGELV | 1.500 | 226. |
| 27 | 310 | YVFSLLVAF | 1.500 | 227. |
| 28 | 83 | LTNSQLSLK | 1.500 | 228. |
| 29 | 146 | HMLTDLSAI | 1.350 | 229. |
| 30 | 331 | ILEGVPSHL | 1.350 | 230. |
| 31 | 155 | ILTLLALWL | 1.200 | 231. |
| 32 | 181 | VLSAMISVL | 0.900 | 232. |
| 33 | 395 | HLLLNTFGM | 0.900 | 233. |
| 34 | 194 | LMGFLLYEA | 0.900 | 234. |
| 35 | 323 | IIWDTVVII | 0.900 | 235. |
| 36 | 140 | IMTDALHML | 0.900 | 236. |
| 37 | 150 | DLSAIILTL | 0.810 | 237. |
| 38 | 287 | GVLIAAYII | 0.810 | 238. |
| 39 | 100 | KQREILKQR | 0.608 | 239. |
| 40 | 278 | ALGDLVQSV | 0.600 | 240.. |
| 41 | 409 | QLQSYRQEV | 0.600 | 241. |
| 42 | 137 | SLAIMTDAL | 0.600 | 242. |
| 43 | 68 | TLQADDDSL | 0.600 | 243. |
| 44 | 285 | SVGVLIAAY | 0.600 | 244. |
| 45 | 178 | RLEVLSAMI | 0.600 | 245. |
| 46 | 119 | VLYLLFMIG | 0.600 | 246. |
| 47 | 147 | MLTDLSAII | 0.600 | 247. |
| 48 | 13 | MLRKDDAPL | 0.600 | 248. |
| 49 | 87 | QLSLKVDSC | 0.600 | 249. |
| 50 | 170 | KRFTFGFHR | 0.540 | 250. |

TABLE X(A)

HLA PEPTIDE SCORING RESULTS-108P5H8- A3, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 157 | TLLALWLSSK | 135.000 | 251. |
| 2 | 396 | LLLNTFGMYR | 36.000 | 252. |
| 3 | 288 | VLIAAYIIRF | 27.000 | 253. |
| 4 | 313 | SLLVAFTTFR | 18.000 | 254. |
| 5 | 188 | VLLVYILMGF | 13.500 | 255. |
| 6 | 124 | FMIGELVGGY | 8.100 | 256. |
| 7 | 22 | FLNDTSAFDF | 6.000 | 257. |
| 8 | 91 | KVDSCDNCSK | 6.000 | 258. |
| 9 | 104 | ILKQRKVKAR | 6.000 | 259. |
| 10 | 395 | HLLLNTFGMY | 5.400 | 260. |
| 11 | 162 | WLSSKSPTKR | 4.000 | 261. |
| 12 | 287 | GVLIAAYIIR | 3.600 | 262. |
| 13 | 113 | RLTIAAVLYL | 3.600 | 263. |
| 14 | 293 | YIIRFKPEYK | 3.000 | 264. |
| 15 | 82 | PLTNSQLSLK | 3.000 | 265. |
| 16 | 100 | KQREILKQRK | 2.700 | 266. |
| 17 | 323 | IIWDTVVIIL | 2.700 | 267. |
| 18 | 314 | LLVAFTTFRI | 2.700 | 268. |
| 19 | 225 | GVAVNVIMGF | 2.700 | 269. |
| 20 | 193 | ILMGFLLYEA | 2.025 | 270. |
| 21 | 13 | MLRKDDAPLF | 2.000 | 271. |
| 22 | 348 | LMKIEDVYSV | 1.800 | 272. |
| 23 | 184 | AMISVLLVYI | 1.350 | 273. |
| 24 | 334 | GVPSHLNVDY | 1.200 | 274. |
| 25 | 147 | MLTDLSAIIL | 1.200 | 275. |
| 26 | 39 | GLSRFNKLRV | 1.200 | 276. |
| 27 | 202 | AVQRTIHMNY | 1.200 | 277. |
| 28 | 20 | PLFLNDTSAF | 1.000 | 278. |
| 29 | 376 | IQLIPGSSSK | 0.900 | 279. |
| 30 | 190 | LVYILMGFLL | 0.900 | 280. |
| 31 | 181 | VLSAMISVLL | 0.900 | 281. |
| 32 | 12 | SMLRKDDAPL | 0.900 | 282. |
| 33 | 119 | VLYLLFMIGE | 0.900 | 283. |

TABLE X(A)-continued

HLA PEPTIDE SCORING RESULTS-108P5H8- A3, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 34 | 397 | LLNTFGMYRC | 0.900 | 284. |
| 35 | 146 | HMLTDLSAII | 0.900 | 285. |
| 36 | 198 | LLYEAVQRTI | 0.675 | 286. |
| 37 | 399 | NTFGMYRCTI | 0.675 | 287. |
| 38 | 68 | TLQADDDSLL | 0.600 | 288. |
| 39 | 364 | SLTSGKSTAI | 0.600 | 289. |
| 40 | 268 | SLAVRAAFVH | 0.600 | 290. |
| 41 | 270 | AVRAAFVHAL | 0.540 | 291. |
| 42 | 185 | MISVLLVYIL | 0.540 | 292. |
| 43 | 160 | ALWLSSKSPT | 0.500 | 293. |
| 44 | 402 | GMYRCTIQLQ | 0.450 | 294. |
| 45 | 289 | LIAAYIIRFK | 0.450 | 295. |
| 46 | 338 | HLNVDYIKEA | 0.450 | 296. |
| 47 | 121 | YLLFMIGELV | 0.450 | 297. |
| 48 | 197 | FLLYEAVQRT | 0.450 | 298. |
| 49 | 377 | QLIPGSSSKW | 0.450 | 299. |
| 50 | 150 | DLSAIILTLL | 0.405 | 300. |

TABLE XI (A)

HLA PEPTIDE SCORING RESULTS-108P5H8-A11, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 83 | LTNSQLSLK | 1.000 | 301. |
| 2 | 361 | NIWSLTSGK | 0.800 | 302. |
| 3 | 377 | QLIPGSSSK | 0.600 | 303. |
| 4 | 294 | IIRFKPEYK | 0.400 | 304. |
| 5 | 162 | WLSSKSPTK | 0.400 | 305. |
| 6 | 158 | LLALWLSSK | 0.400 | 306. |
| 7 | 342 | DYIKEALMK | 0.360 | 307. |
| 8 | 406 | CTIQLQSYR | 0.300 | 308. |
| 9 | 288 | VLIAAYIIR | 0.240 | 309. |
| 10 | 8 | KRLKSMLRK | 0.180 | 310. |
| 11 | 287 | GVLIAAYII | 0.180 | 311. |
| 12 | 100 | KQREILKQR | 0.180 | 312. |
| 13 | 397 | LLNTFGMYR | 0.160 | 313. |
| 14 | 39 | GLSRFNKLR | 0.120 | 314. |
| 15 | 197 | FLLYEAVQR | 0.120 | 315. |
| 16 | 234 | FLLNQSGHR | 0.120 | 316. |
| 17 | 314 | LLVAFTTFR | 0.120 | 317. |
| 18 | 205 | RTIHMNYEI | 0.090 | 318. |
| 19 | 118 | AVLYLLFMI | 0.090 | 319. |
| 20 | 103 | EILKQRKVK | 0.090 | 320. |
| 21 | 248 | SLPSNSPTR | 0.080 | 321. |
| 22 | 1 | MAGSGAWKR | 0.080 | 322. |
| 23 | 170 | KRFTFGFHR | 0.072 | 323. |
| 24 | 337 | SHLNVDYIK | 0.060 | 324. |
| 25 | 315 | LVAFTTFRI | 0.060 | 325. |
| 26 | 109 | KVKARLTIA | 0.060 | 326. |
| 27 | 187 | SVLLVYILM | 0.060 | 327. |
| 28 | 37 | DEGLSRFNK | 0.054 | 328. |
| 29 | 402 | GMYRCTIQL | 0.048 | 329. |
| 30 | 190 | LVYILMGFL | 0.040 | 330. |
| 31 | 310 | YVFSLLVAF | 0.040 | 331. |
| 32 | 308 | CTYVFSLLV | 0.040 | 332. |
| 33 | 384 | SKWEEVQSK | 0.040 | 333. |
| 34 | 98 | CSKQREILK | 0.040 | 334. |
| 35 | 132 | GYIANSLAI | 0.036 | 335. |
| 36 | 327 | TVVIILEGV | 0.030 | 336. |
| 37 | 114 | LTIAAVLYL | 0.030 | 337. |
| 38 | 34 | EAGDEGLSR | 0.024 | 338. |
| 39 | 275 | FVHALGDLV | 0.020 | 339. |
| 40 | 94 | SCDNCSKQR | 0.020 | 340. |
| 41 | 49 | VVADDGSEA | 0.020 | 341. |
| 42 | 282 | LVQSVGVLI | 0.020 | 342. |
| 43 | 290 | IAAYIIRFK | 0.020 | 343. |
| 44 | 223 | AVGVAVNVI | 0.020 | 344. |

TABLE XI (A)-continued

HLA PEPTIDE SCORING RESULTS-108P5H8-A11, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 45 | 92 | VDSCDNCSK | 0.020 | 345. |
| 46 | 285 | SVGVLIAAY | 0.020 | 346. |
| 47 | 340 | NVDYIKEAL | 0.020 | 347. |
| 48 | 227 | AVNVIMGFL | 0.020 | 348. |
| 49 | 270 | AVRAAFVHA | 0.020 | 349. |
| 50 | 101 | QREILKQRK | 0.020 | 350. |

TABLE XII (A)

HLA PEPTIDE SCORING RESULTS-108P5H8-A11, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 91 | KVDSCDNCSK | 6.000 | 351. |
| 2 | 287 | GVLIAAYIIR | 3.600 | 352. |
| 3 | 100 | KQREILKQRK | 1.800 | 353. |
| 4 | 376 | IQLIPGSSSK | 0.900 | 354. |
| 5 | 157 | TLLALWLSSK | 0.600 | 355. |
| 6 | 293 | YIIRFKPEYK | 0.600 | 356. |
| 7 | 97 | NCSKQREILK | 0.400 | 357. |
| 8 | 396 | LLLNTFGMYR | 0.240 | 358. |
| 9 | 36 | GDEGLSRFNK | 0.180 | 359. |
| 10 | 196 | GFLLYEAVQR | 0.180 | 360. |
| 11 | 233 | GFLLNQSGHR | 0.180 | 361. |
| 12 | 102 | REILKQRKVK | 0.135 | 362. |
| 13 | 225 | GVAVNVIMGF | 0.120 | 363. |
| 14 | 190 | LVYILMGFLL | 0.120 | 364. |
| 15 | 109 | KVKARLTIAA | 0.120 | 365. |
| 16 | 410 | LQSYRQEVDR | 0.120 | 366. |
| 17 | 405 | RCTIQLQSYR | 0.120 | 367. |
| 18 | 313 | SLLVAFTTFR | 0.120 | 368. |
| 19 | 162 | WLSSKSPTKR | 0.080 | 369. |
| 20 | 341 | VDYIKEALMK | 0.080 | 370. |
| 21 | 360 | LNIWSLTSGK | 0.060 | 371. |
| 22 | 334 | GVPSHLNVDY | 0.060 | 372. |
| 23 | 227 | AVNVIMGFLL | 0.060 | 373. |
| 24 | 253 | SPTRGSGCER | 0.040 | 374. |
| 25 | 7 | WKRLKSMLRK | 0.040 | 375. |
| 26 | 104 | ILKQRKVKAR | 0.040 | 376. |
| 27 | 308 | CTYVFSLLVA | 0.040 | 377. |
| 28 | 282 | LVQSVGVLIA | 0.040 | 378. |
| 29 | 289 | LIAAYIIRFK | 0.040 | 379. |
| 30 | 172 | FTFGFHRLEV | 0.040 | 380. |
| 31 | 356 | SVEDLNIWSL | 0.040 | 381. |
| 32 | 82 | PLTNSQLSLK | 0.040 | 382. |
| 33 | 202 | AVQRTIHMNY | 0.040 | 383. |
| 34 | 161 | LWLSSKSPTK | 0.030 | 384. |
| 35 | 48 | VVVADDGSEA | 0.030 | 385. |
| 36 | 114 | LTIAAVLYLL | 0.030 | 386. |
| 37 | 353 | DVYSVEDLNI | 0.024 | 387. |
| 38 | 39 | GLSRFNKLRV | 0.024 | 388. |
| 39 | 113 | RLTIAAVLYL | 0.024 | 389. |
| 40 | 319 | TTFRIIWDTV | 0.020 | 390. |
| 41 | 223 | AVGVAVNVIM | 0.020 | 391. |
| 42 | 383 | SSKWEEVQSK | 0.020 | 392. |
| 43 | 270 | AVRAAFVHAL | 0.020 | 393. |
| 44 | 399 | NTFGMYRCTI | 0.020 | 394. |
| 45 | 83 | LTNSQLSLKV | 0.020 | 395. |
| 46 | 285 | SVGVLIAAYI | 0.020 | 396. |
| 47 | 129 | LVGGYIANSL | 0.020 | 397. |
| 48 | 340 | NVDYIKEALM | 0.020 | 398. |
| 49 | 314 | LLVAFTTFRI | 0.018 | 399. |
| 50 | 322 | RIIWDTVVII | 0.018 | 400. |

TABLE XIII (A)

HLA PEPTIDE SCORING RESULTS-108P5H8-A24, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 191 | VYILMGFLL | 300.000 | 401. |
| 2 | 199 | LYEAVQRTI | 105.000 | 402. |
| 3 | 132 | GYIANSLAI | 75.000 | 403. |
| 4 | 354 | VYSVEDLNI | 50.000 | 404. |
| 5 | 171 | RFTFGFHRL | 48.000 | 405. |
| 6 | 210 | NYEINGDIM | 37.500 | 406. |
| 7 | 274 | AFVHALGDL | 30.000 | 407. |
| 8 | 21 | LFLNDTSAF | 15.000 | 408. |
| 9 | 106 | KQRKVKARL | 11.200 | 409. |
| 10 | 38 | EGLSRFNKL | 9.504 | 410. |
| 11 | 331 | ILEGVPSHL | 8.400 | 411. |
| 12 | 227 | AVNVIMGFL | 8.400 | 412. |
| 13 | 309 | TYVFSLLVA | 7.500 | 413. |
| 14 | 75 | SLLDQDLPL | 7.200 | 414. |
| 15 | 186 | ISVLLVYIL | 7.200 | 415. |
| 16 | 388 | EVQSKANHL | 7.200 | 416. |
| 17 | 130 | VGGYIANSL | 6.720 | 417. |
| 18 | 307 | ICTYVFSLL | 6.720 | 418. |
| 19 | 121 | YLLFMIGEL | 6.600 | 419. |
| 20 | 153 | AIILTLLAL | 6.000 | 420. |
| 21 | 166 | KSPTKRFTF | 6.000 | 421. |
| 22 | 281 | DLVQSVGVL | 6.000 | 422. |
| 23 | 68 | TLQADDDSL | 6.000 | 423. |
| 24 | 143 | DALHMLTDL | 6.000 | 424. |
| 25 | 228 | VNVIMGFLL | 6.000 | 425. |
| 26 | 80 | DLPLTNSQL | 6.000 | 426. |
| 27 | 114 | LTIAAVLYL | 6.000 | 427. |
| 28 | 150 | DLSAIILTL | 5.600 | 428. |
| 29 | 340 | NVDYIKEAL | 5.600 | 429. |
| 30 | 324 | IWDTVVIIL | 5.600 | 430. |
| 31 | 115 | TIAAVLYLL | 5.600 | 431. |
| 32 | 370 | STAIVHIQL | 5.600 | 432. |
| 33 | 151 | LSAIILTLL | 5.600 | 433. |
| 34 | 182 | LSAMISVLL | 5.600 | 434. |
| 35 | 300 | EYKIADPIC | 5.000 | 435. |
| 36 | 400 | TFGMYRCTI | 5.000 | 436. |
| 37 | 412 | SYRQEVDRT | 5.000 | 437. |
| 38 | 6 | AWKRLKSML | 4.800 | 438. |
| 39 | 190 | LVYILMGFL | 4.800 | 439. |
| 40 | 69 | LQADDDSLL | 4.800 | 440. |
| 41 | 155 | ILTLLALWL | 4.800 | 441. |
| 42 | 140 | IMTDALHML | 4.800 | 442. |
| 43 | 189 | LLVYILMGF | 4.200 | 443. |
| 44 | 226 | VAVNVIMGF | 4.200 | 444. |
| 45 | 267 | DSLAVRAAF | 4.200 | 445. |
| 46 | 13 | MLRKDDAPL | 4.000 | 446. |
| 47 | 402 | GMYRCTIQL | 4.000 | 447. |
| 48 | 2 | AGSGAWKRL | 4.000 | 448. |
| 49 | 97 | NCSKQREIL | 4.000 | 449. |
| 50 | 390 | QSKANHLLL | 4.000 | 450. |

TABLE XIV(A)

HLA PEPTIDE SCORING RESULTS-108P5H8-A24, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 120 | LYLLFMIGEL | 330.000 | 451. |
| 2 | 210 | NYEINGDIML | 300.000 | 452. |
| 3 | 309 | TYVFSLLVAF | 180.000 | 453. |
| 4 | 342 | DYIKEALMKI | 82.500 | 454. |
| 5 | 132 | GYIANSLAIM | 37.500 | 455. |
| 6 | 173 | TFGFHRLEVL | 20.000 | 456. |
| 7 | 60 | RPVNGAHPTL | 12.000 | 457. |
| 8 | 369 | KSTAIVHIQL | 11.200 | 458. |
| 9 | 111 | KARLTIAAVL | 11.200 | 459. |
| 10 | 339 | LNVDYIKEAL | 10.080 | 460. |
| 11 | 330 | IILEGVPSHL | 10.080 | 461. |

TABLE XIV(A)-continued

HLA PEPTIDE SCORING RESULTS-108P5H8-A24, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 12 | 191 | VYILMGFLLY | 9.000 | 462. |
| 13 | 392 | KANHLLLNTF | 8.640 | 463. |
| 14 | 226 | VAVNVIMGFL | 8.400 | 464. |
| 15 | 114 | LTIAAVLYLL | 8.400 | 465. |
| 16 | 292 | AYIIRFKPEY | 8.250 | 466. |
| 17 | 113 | RLTIAAVLYL | 8.000 | 467. |
| 18 | 189 | LLVYILMGFL | 7.200 | 468. |
| 19 | 356 | SVEDLNIWSL | 7.200 | 469. |
| 20 | 154 | IILTLLALWL | 7.200 | 470. |
| 21 | 403 | MYRCTIQLQS | 7.000 | 471. |
| 22 | 412 | SYRQEVDRTC | 7.000 | 472. |
| 23 | 129 | LVGGYIANSL | 6.720 | 473. |
| 24 | 323 | IIWDTVVIIL | 6.720 | 474. |
| 25 | 305 | DPICTYVFSL | 6.000 | 475. |
| 26 | 152 | SAIILTLLAL | 6.000 | 476. |
| 27 | 401 | FGMYRCTIQL | 6.000 | 477. |
| 28 | 12 | SMLRKDDAPL | 6.000 | 478. |
| 29 | 68 | TLQADDDSLL | 6.000 | 479. |
| 30 | 354 | VYSVEDLNIW | 6.000 | 480. |
| 31 | 81 | LPLTNSQLSL | 6.000 | 481. |
| 32 | 227 | AVNVIMGFLL | 6.000 | 482. |
| 33 | 139 | AIMTDALHML | 6.000 | 483. |
| 34 | 136 | NSLAIMTDAL | 6.000 | 484. |
| 35 | 388 | EVQSKANHLL | 6.000 | 485. |
| 36 | 180 | EVLSAMISVL | 6.000 | 486. |
| 37 | 74 | DSLLDQDLPL | 6.000 | 487. |
| 38 | 150 | DLSAIILTLL | 5.600 | 488. |
| 39 | 181 | VLSAMISVLL | 5.600 | 489. |
| 40 | 300 | EYKIADPICT | 5.000 | 490. |
| 41 | 185 | MISVLLVYIL | 4.800 | 491. |
| 42 | 5 | GAWKRLKSML | 4.800 | 492. |
| 43 | 147 | MLTDLSAIIL | 4.800 | 493. |
| 44 | 31 | FSDEAGDEGL | 4.800 | 494. |
| 45 | 298 | KPEYKIADPI | 4.200 | 495. |
| 46 | 188 | VLLVYILMGF | 4.200 | 496. |
| 47 | 273 | AAFVHALGDL | 4.000 | 497. |
| 48 | 270 | AVRAAFVHAL | 4.000 | 498. |
| 49 | 1 | MAGSGAWKRL | 4.000 | 499. |
| 50 | 96 | DNCSKQREIL | 4.000 | 500. |

TABLE XV (A)

HLA PEPTIDE SCORING RESULTS-108P5H8-B7, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 227 | AVNVIMGFL | 60.000 | 501. |
| 2 | 106 | KQRKVKARL | 40.000 | 502. |
| 3 | 13 | MLRKDDAPL | 40.000 | 503. |
| 4 | 190 | LVYILMGFL | 20.000 | 504. |
| 5 | 388 | EVQSKANHL | 20.000 | 505. |
| 6 | 270 | AVRAAFVHA | 15.000 | 506. |
| 7 | 2 | AGSGAWKRL | 12.000 | 507. |
| 8 | 143 | DALHMLTDL | 12.000 | 508. |
| 9 | 153 | AIILTLLAL | 12.000 | 509. |
| 10 | 139 | AIMTDALHM | 9.000 | 510. |
| 11 | 117 | AAVLYLLFM | 9.000 | 511. |
| 12 | 340 | NVDYIKEAL | 6.000 | 512. |
| 13 | 97 | NCSKQREIL | 6.000 | 513. |
| 14 | 111 | KARLTIAAV | 6.000 | 514. |
| 15 | 118 | AVLYLLFMI | 6.000 | 515. |
| 16 | 223 | AVGVAVNVI | 6.000 | 516. |
| 17 | 187 | SVLLVYILM | 5.000 | 517. |
| 18 | 150 | DLSAIILTL | 4.000 | 518. |
| 19 | 307 | ICTYVFSLL | 4.000 | 519. |
| 20 | 186 | ISVLLVYIL | 4.000 | 520. |
| 21 | 130 | VGGYIANSL | 4.000 | 521. |
| 22 | 151 | LSAIILTLL | 4.000 | 522. |

TABLE XV (A)-continued

HLA PEPTIDE SCORING RESULTS-108P5H8-B7, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 23 | 182 | LSAMISVLL | 4.000 | 523. |
| 24 | 390 | QSKANHLLL | 4.000 | 524. |
| 25 | 155 | ILTLLALWL | 4.000 | 525. |
| 26 | 402 | GMYRCTIQL | 4.000 | 526. |
| 27 | 75 | SLLDQDLPL | 4.000 | 527. |
| 28 | 69 | LQADDDSLL | 4.000 | 528. |
| 29 | 181 | VLSAMISVL | 4.000 | 529. |
| 30 | 370 | STAIVHIQL | 4.000 | 530. |
| 31 | 114 | LTIAAVLYL | 4.000 | 531. |
| 32 | 281 | DLVQSVGVL | 4.000 | 532. |
| 33 | 80 | DLPLTNSQL | 4.000 | 533. |
| 34 | 389 | VQSKANHLL | 4.000 | 534. |
| 35 | 38 | EGLSRFNKL | 4.000 | 535. |
| 36 | 115 | TIAAVLYLL | 4.000 | 536. |
| 37 | 140 | IMTDALHML | 4.000 | 537. |
| 38 | 68 | TLQADDDSL | 4.000 | 538. |
| 39 | 174 | FGFHRLEVL | 4.000 | 539. |
| 40 | 228 | VNVIMGFLL | 4.000 | 540. |
| 41 | 121 | YLLFMIGEL | 4.000 | 541. |
| 42 | 137 | SLAIMTDAL | 4.000 | 542. |
| 43 | 5 | GAWKRLKSM | 3.000 | 543. |
| 44 | 201 | EAVQRTIHM | 3.000 | 544. |
| 45 | 57 | APERPVNGA | 2.700 | 545. |
| 46 | 61 | PVNGAHPTL | 2.000 | 546. |
| 47 | 282 | LVQSVGVLI | 2.000 | 547. |
| 48 | 287 | GVLIAAYII | 2.000 | 548. |
| 49 | 315 | LVAFTTFRI | 2.000 | 549. |
| 50 | 40 | LSRFNKLRV | 2.000 | 550. |

TABLE XVI (A)

HLA PEPTIDE SCORING RESULTS-108P5H8-B7, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 270 | AVRAAFVHAL | 600.000 | 551. |
| 2 | 111 | KARLTIAAVL | 120.000 | 552. |
| 3 | 60 | RPVNGAHPTL | 80.000 | 553. |
| 4 | 81 | LPLTNSQLSL | 80.000 | 554. |
| 5 | 305 | DPICTYVFSL | 80.000 | 555. |
| 6 | 227 | AVNVIMGFLL | 60.000 | 556. |
| 7 | 273 | AAFVHALGDL | 36.000 | 557. |
| 8 | 139 | AIMTDALHML | 36.000 | 558. |
| 9 | 388 | EVQSKANHLL | 20.000 | 559. |
| 10 | 180 | EVLSAMISVL | 20.000 | 560. |
| 11 | 190 | LVYILMGFLL | 20.000 | 561. |
| 12 | 129 | LVGGYIANSL | 20.000 | 562. |
| 13 | 223 | AVGVAVNVIM | 15.000 | 563. |
| 14 | 5 | GAWKRLKSML | 12.000 | 564. |
| 15 | 1 | MAGSGAWKRL | 12.000 | 565. |
| 16 | 152 | SAIILTLLAL | 12.000 | 566. |
| 17 | 401 | FGMYRCTIQL | 12.000 | 567. |
| 18 | 226 | VAVNVIMGFL | 12.000 | 568. |
| 19 | 335 | VPSHLNVDYI | 8.000 | 569. |
| 20 | 356 | SVEDLNIWSL | 6.000 | 570. |
| 21 | 19 | APLFLNDTSA | 6.000 | 571. |
| 22 | 96 | DNCSKQREIL | 6.000 | 572. |
| 23 | 294 | IIRFKPEYKI | 6.000 | 573. |
| 24 | 113 | RLTIAAVLYL | 4.000 | 574. |
| 25 | 150 | DLSAIILTLL | 4.000 | 575. |
| 26 | 339 | LNVDYIKEAL | 4.000 | 576. |
| 27 | 240 | GHRHSHSHSL | 4.000 | 577. |
| 28 | 147 | MLTDLSAIIL | 4.000 | 578. |
| 29 | 330 | IILEGVPSHL | 4.000 | 579. |
| 30 | 114 | LTIAAVLYLL | 4.000 | 580. |
| 31 | 189 | LLVYILMGFL | 4.000 | 581. |
| 32 | 12 | SMLRKDDAPL | 4.000 | 582. |
| 33 | 74 | DSLLDQDLPL | 4.000 | 583. |

TABLE XVI (A)-continued

HLA PEPTIDE SCORING RESULTS-108P5H8-B7, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 34 | 185 | MISVLLVYIL | 4.000 | 584. |
| 35 | 260 | CERNHGQDSL | 4.000 | 585. |
| 36 | 181 | VLSAMISVLL | 4.000 | 586. |
| 37 | 323 | IIWDTVVIIL | 4.000 | 587. |
| 38 | 68 | TLQADDDSLL | 4.000 | 588. |
| 39 | 136 | NSLAIMTDAL | 4.000 | 589. |
| 40 | 154 | IILTLLALWL | 4.000 | 590. |
| 41 | 369 | KSTAIVHIQL | 4.000 | 591. |
| 42 | 389 | VQSKANHLLL | 4.000 | 592. |
| 43 | 117 | AAVLYLLFMI | 3.600 | 593. |
| 44 | 222 | AAVGVAVNVI | 3.600 | 594. |
| 45 | 138 | LAIMTDALHM | 3.000 | 595. |
| 46 | 116 | IAAVLYLLFM | 3.000 | 596. |
| 47 | 298 | KPEYKIADPI | 2.400 | 597. |
| 48 | 315 | LVAFTTFRII | 2.000 | 598. |
| 49 | 285 | SVGVLIAAYI | 2.000 | 599. |
| 50 | 40 | LSRFNKLRVV | 2.000 | 600. |

TABLE XVII (A)

HLA PEPTIDE SCORING RESULTS-108P5H8-B35, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 335 | VPSHLNVDY | 40.000 | 601. |
| 2 | 390 | QSKANHLLL | 15.000 | 602. |
| 3 | 164 | SSKSPTKRF | 15.000 | 603. |
| 4 | 166 | KSPTKRFTF | 10.000 | 604. |
| 5 | 302 | KIADPICTY | 8.000 | 605. |
| 6 | 355 | YSVEDLNIW | 7.500 | 606. |
| 7 | 201 | EAVQRTIHM | 6.000 | 607. |
| 8 | 5 | GAWKRLKSM | 6.000 | 608. |
| 9 | 203 | VQRTIHMNY | 6.000 | 609. |
| 10 | 117 | AAVLYLLFM | 6.000 | 610. |
| 11 | 106 | KQRKVKARL | 6.000 | 611. |
| 12 | 267 | DSLAVRAAF | 5.000 | 612. |
| 13 | 151 | LSAIILTLL | 5.000 | 613. |
| 14 | 182 | LSAMISVLL | 5.000 | 614. |
| 15 | 186 | ISVLLVYIL | 5.000 | 615. |
| 16 | 13 | MLRKDDAPL | 4.500 | 616. |
| 17 | 60 | RPVNGAHPT | 4.000 | 617. |
| 18 | 125 | MIGELVGGY | 4.000 | 618. |
| 19 | 113 | RLTIAAVLY | 4.000 | 619. |
| 20 | 405 | RCTIQLQSY | 4.000 | 620. |
| 21 | 111 | KARLTIAAV | 3.600 | 621. |
| 22 | 143 | DALHMLTDL | 3.000 | 622. |
| 23 | 69 | LQADDDSLL | 3.000 | 623. |
| 24 | 116 | IAAVLYLLF | 3.000 | 624. |
| 25 | 40 | LSRFNKLRV | 3.000 | 625. |
| 26 | 226 | VAVNVIMGF | 3.000 | 626. |
| 27 | 139 | AIMTDALHM | 3.000 | 627. |
| 28 | 343 | YIKEALMKI | 2.400 | 628. |
| 29 | 383 | SSKWEEVQS | 2.250 | 629. |
| 30 | 19 | APLFLNDTS | 2.000 | 630. |
| 31 | 192 | YILMGFLLY | 2.000 | 631. |
| 32 | 293 | YIIRFKPEY | 2.000 | 632. |
| 33 | 184 | AMISVLLVY | 2.000 | 633. |
| 34 | 75 | SLLDQDLPL | 2.000 | 634. |
| 35 | 187 | SVLLVYILM | 2.000 | 635. |
| 36 | 224 | VGVAVNVIM | 2.000 | 636. |
| 37 | 81 | LPLTNSQLS | 2.000 | 637. |
| 38 | 133 | YIANSLAIM | 2.000 | 638. |
| 39 | 347 | ALMKIEDVY | 2.000 | 639. |
| 40 | 305 | DPICTYVFS | 2.000 | 640. |
| 41 | 285 | SVGVLIAAY | 2.000 | 641. |
| 42 | 140 | IMTDALHML | 2.000 | 642. |
| 43 | 395 | HLLLNTFGM | 2.000 | 643. |
| 44 | 396 | LLLNTFGMY | 2.000 | 644. |

TABLE XVII (A)-continued

HLA PEPTIDE SCORING RESULTS-108P5H8-B35, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 45 | 68 | TLQADDDSL | 1.500 | 645. |
| 46 | 371 | TAIVHIQLI | 1.200 | 646. |
| 47 | 316 | VAFTTFRII | 1.200 | 647. |
| 48 | 322 | RIIWDTVVI | 1.200 | 648. |
| 49 | 97 | NCSKQREIL | 1.000 | 649. |
| 50 | 181 | VLSAMISVL | 1.000 | 650. |

TABLE XVIII (A)

HLA PEPTIDE SCORING RESULTS-108P5H8-B35, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 60 | RPVNGAHPTL | 40.000 | 651. |
| 2 | 305 | DPICTYVFSL | 20.000 | 652. |
| 3 | 81 | LPLTNSQLSL | 20.000 | 653. |
| 4 | 167 | SPTKRFTFGF | 20.000 | 654. |
| 5 | 111 | KARLTIAAVL | 18.000 | 655. |
| 6 | 369 | KSTAIVHIQL | 10.000 | 656. |
| 7 | 284 | QSVGVLIAAY | 10.000 | 657. |
| 8 | 186 | ISVLLVYILM | 10.000 | 658. |
| 9 | 138 | LAIMTDALHM | 9.000 | 659. |
| 10 | 335 | VPSHLNVDYI | 8.000 | 660. |
| 11 | 392 | KANHLLLNTF | 6.000 | 661. |
| 12 | 34 | EAGDEGLSRF | 6.000 | 662. |
| 13 | 346 | EALMKIEDVY | 6.000 | 663. |
| 14 | 116 | IAAVLYLLFM | 6.000 | 664. |
| 15 | 183 | SAMISVLLVY | 6.000 | 665. |
| 16 | 136 | NSLAIMTDAL | 5.000 | 666. |
| 17 | 74 | DSLLDQDLPL | 5.000 | 667. |
| 18 | 312 | FSLLVAFTTF | 5.000 | 668. |
| 19 | 163 | LSSKSPTKRF | 5.000 | 669. |
| 20 | 298 | KPEYKIADPI | 4.800 | 670. |
| 21 | 13 | MLRKDDAPLF | 4.500 | 671. |
| 22 | 209 | MNYEINGDIM | 4.000 | 672. |
| 23 | 40 | LSRFNKLRVV | 3.000 | 673. |
| 24 | 270 | AVRAAFVHAL | 3.000 | 674. |
| 25 | 273 | AAFVHALGDL | 3.000 | 675. |
| 26 | 226 | VAVNVIMGFL | 3.000 | 676. |
| 27 | 5 | GAWKRLKSML | 3.000 | 677. |
| 28 | 1 | MAGSGAWKRL | 3.000 | 678. |
| 29 | 152 | SAIILTLLAL | 3.000 | 679. |
| 30 | 31 | FSDEAGDEGL | 3.000 | 680. |
| 31 | 19 | APLFLNDTSA | 2.000 | 681. |
| 32 | 4 | SGAWKRLKSM | 2.000 | 682. |
| 33 | 113 | RLTIAAVLYL | 2.000 | 683. |
| 34 | 395 | HLLLNTFGMY | 2.000 | 684. |
| 35 | 147 | MLTDLSAIIL | 2.000 | 685. |
| 36 | 334 | GVPSHLNVDY | 2.000 | 686. |
| 37 | 66 | HPTLQADDDS | 2.000 | 687. |
| 38 | 339 | LNVDYIKEAL | 2.000 | 688. |
| 39 | 249 | LPSNSPTRGS | 2.000 | 689. |
| 40 | 323 | IIWDTVVIIL | 2.000 | 690. |
| 41 | 330 | IILEGVPSHL | 2.000 | 691. |
| 42 | 202 | AVQRTIHMNY | 2.000 | 692. |
| 43 | 124 | FMIGELVGGY | 2.000 | 693. |
| 44 | 22 | FLNDTSAFDF | 2.000 | 694. |
| 45 | 223 | AVGVAVNVIM | 2.000 | 695. |
| 46 | 164 | SSKSPTKRFT | 1.500 | 696. |
| 47 | 390 | QSKANHLLLN | 1.500 | 697. |
| 48 | 12 | SMLRKDDAPL | 1.500 | 698. |
| 49 | 68 | TLQADDDSLL | 1.500 | 699. |
| 50 | 316 | VAFTTFRIIW | 1.500 | 700. |

TABLE V (B)

unique to variant 3 relative to variants 1 and 2
HLA PEPTIDE SCORING RESULTS-108P5H8-A1, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 23 | LNDTSAFEF | 6.250 | 701. |
| 2 | 28 | AFEFSDEAG | 0.045 | 702. |
| 3 | 25 | DTSAFEFSD | 0.013 | 703. |
| 4 | 28 | SAFEFSDEA | 0.010 | 704. |
| 5 | 22 | FLNDTSAFE | 0.002 | 705. |
| 6 | 26 | TSAFEFSDE | 0.002 | 706. |
| 7 | 24 | NDTSAFEFS | 0.001 | 707. |
| 8 | 29 | FEFSDEAGD | 0.000 | 708. |
| 9 | 30 | EFSDEAGDE | 0.000 | 709. |

TABLE VI (B)

unique to variant 3 relative to variants 1 and 2
HLA PEPTIDE SCORING RESULTS-108P5H8-A1, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 22 | FLNDTSAFEF | 0.500 | 710. |
| 2 | 23 | LNDTSAFEFS | 0.125 | 711. |
| 3 | 26 | TSAFEFSDEA | 0.015 | 712. |
| 4 | 27 | SAFEFSDEAG | 0.010 | 713. |
| 5 | 28 | AFEFSDEAGD | 0.009 | 714. |
| 6 | 25 | DTSAFEFSDE | 0.003 | 715. |
| 7 | 30 | EFSDEAGDEG | 0.001 | 716. |
| 8 | 24 | NDTSAFEFSD | 0.000 | 717. |
| 9 | 21 | LFLNDTSAFE | 0.000 | 718. |
| 10 | 29 | FEFSDEAGDE | 0.000 | 719. |

TABLE VII (B)

unique to variant 3 relative to variants 1 and 2
HLA PEPTIDE SCORING RESULTS - 108P5H8 - A2, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 27 | SAFEFSDEA | 1.949 | 720. |
| 2 | 22 | FLNDTSAFE | 1.546 | 721. |
| 3 | 29 | FEFSDEAGD | 0.005 | 722. |
| 4 | 23 | LNDTSAFEF | 0.002 | 723. |
| 5 | 24 | NDTSAFEFS | 0.001 | 724. |
| 6 | 25 | DTSAFEFSD | 0.000 | 725. |
| 7 | 26 | TSAFEFSDE | 0.000 | 726. |
| 8 | 28 | AFEFSDEAG | 0.000 | 727. |
| 9 | 30 | EFSDEAGDE | 0.000 | 728. |

TABLE VIII (B)

unique to variant 3 relative to variants 1 and 2
HLA PEPTIDE SCORING RESULTS - 108P5H8 - A2, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 22 | FLNDTSAFEF | 8.152 | 729. |
| 2 | 26 | TSAFEFSDEA | 0.060 | 730. |
| 3 | 27 | SAFEFSDEAG | 0.008 | 731. |
| 4 | 23 | LNDTSAFEFS | 0.002 | 732. |
| 5 | 29 | FEFSDEAGDE | 0.001 | 733. |
| 6 | 24 | NDTSAFEFSD | 0.000 | 734. |
| 7 | 21 | LFLNDTSAFE | 0.000 | 735. |

TABLE VIII (B)-continued unique to variant 3 relative to variants 1 and 2
HLA PEPTIDE SCORING RESULTS - 108P5H8 - A2, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 8  | 25 | DTSAFEFSDE | 0.000 | 736. |
| 9  | 30 | EFSDEAGDEG | 0.000 | 737. |
| 10 | 28 | AFEFSDEAGD | 0.000 | 738. |

TABLE IX (B)

unique to variant 3 relative to variants 1 and 2
HLA PEPTIDE SCORING RESULTS - 108P5H8 - A3, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 27 | SAFEFSDEA | 0.045 | 739. |
| 2 | 22 | FLNDTSAFE | 0.020 | 740. |
| 3 | 23 | LNDTSAFEF | 0.012 | 741. |
| 4 | 25 | DTSAFEFSD | 0.003 | 742. |
| 5 | 29 | FEFSDEAGD | 0.000 | 743. |
| 6 | 26 | TSAFEFSDE | 0.000 | 744. |
| 7 | 24 | NDTSAFEFS | 0.000 | 745. |
| 8 | 28 | AFEFSDEAG | 0.000 | 746. |
| 9 | 30 | EFSDEAGDE | 0.000 | 747. |

TABLE X (B)

unique to variant 3 relative to variants 1 and 2
HLA PEPTIDE SCORING RESULTS - 108P5H8 - A3, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1  | 22 | FLNDTSAFEF | 6.000 | 748. |
| 2  | 26 | TSAFEFSDEA | 0.003 | 749. |
| 3  | 27 | SAFEFSDEAG | 0.002 | 750. |
| 4  | 25 | DTSAFEFSDE | 0.001 | 751. |
| 5  | 23 | LNDTSAFEFS | 0.000 | 752. |
| 6  | 24 | NDTSAFEFSD | 0.000 | 753. |
| 7  | 29 | FEFSDEAGDE | 0.000 | 754. |
| 8  | 21 | LFLNDTSAFE | 0.000 | 755. |
| 9  | 28 | AFEFSDEAGD | 0.000 | 756. |
| 10 | 30 | EFSDEAGDEG | 0.000 | 757. |

TABLE XI (B)

unique to variant 3 relative to variants 1 and 2
HLA PEPTIDE SCORING RESULTS - 108P5H8 - A11, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 27 | SAFEFSDEA | 0.004 | 758. |
| 2 | 23 | LNDTSAFEF | 0.001 | 759. |
| 3 | 25 | DTSAFEFSD | 0.001 | 760. |
| 4 | 22 | FLNDTSAFE | 0.000 | 761. |
| 5 | 28 | AFEFSDEAG | 0.000 | 762. |
| 6 | 29 | FEFSDEAGD | 0.000 | 763. |
| 7 | 30 | EFSDEAGDE | 0.000 | 764. |
| 8 | 24 | NDTSAFEFS | 0.000 | 765. |
| 9 | 26 | TSAFEFSDE | 0.000 | 766. |

TABLE XII (B)

unique to variant 3 relative to variants 1 and 2
HLA PEPTIDE SCORING RESULTS - 108P5H8 - All, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 22 | FLNDTSAFEF | 0.012 | 767. |
| 2 | 27 | SAFEFSDEAG | 0.000 | 768. |
| 3 | 21 | LFLNDTSAFE | 0.000 | 769. |
| 4 | 25 | DTSAFEFSDE | 0.000 | 770. |
| 5 | 28 | AFEFSDEAGD | 0.000 | 771. |
| 6 | 26 | TSAFEFSDEA | 0.000 | 772. |
| 7 | 29 | FEFSDEAGDE | 0.000 | 773. |
| 8 | 24 | NDTSAFEFSD | 0.000 | 774. |
| 9 | 30 | EFSDEAGDEG | 0.000 | 775. |
| 10 | 23 | LNDTSAFEFS | 0.000 | 776. |

TABLE XIII (B)

unique to variant 3 relative to variants 1 and 2
HLA PEPTIDE SCORING RESULTS - 108P5H8 - A24, 9-MERS

| RANK | STATE POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 23 | LNDTSAFEF | 2.200 | 777. |
| 2 | 27 | SAFEFSDEA | 0.132 | 778. |
| 3 | 28 | AFEFSDEAG | 0.075 | 779. |
| 4 | 30 | EFSDEAGDE | 0.060 | 780. |
| 5 | 22 | FLNDTSAFE | 0.018 | 781. |
| 6 | 24 | NDTSAFEFS | 0.012 | 782. |
| 7 | 26 | TSAFEFSDE | 0.012 | 783. |
| 8 | 25 | DTSAFEFSD | 0.010 | 784. |
| 9 | 29 | FEFSDEAGD | 0.001 | 785. |

TABLE XIV (B)

unique to variant 3 relative to variants 1 and 2
HLA PEPTIDE SCORING RESULTS - 108P5H8 - A24, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 22 | FLNDTSAFEF | 3.960 | 786. |
| 2 | 23 | LNDTSAFEFS | 0.120 | 787. |
| 3 | 26 | TSAFEFSDEA | 0.110 | 788. |
| 4 | 28 | AFEFSDEAGD | 0.075 | 789. |
| 5 | 21 | LFLNDTSAFE | 0.075 | 790. |
| 6 | 30 | EFSDEAGDEG | 0.066 | 791. |
| 7 | 27 | SAFEFSDEAG | 0.012 | 792. |
| 8 | 25 | DTSAFEFSDE | 0.012 | 793. |
| 9 | 24 | NDTSAFEFSD | 0.001 | 794. |
| 10 | 29 | FEFSDEAGDE | 0.001 | 795. |

TABLE XV (B)

unique to variant 3 relative to variants 1 and 2
HLA PEPTIDE SCORING RESULTS - 108P5H8 - B7, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 27 | SAFEFSDEA | 0.300 | 796. |
| 2 | 22 | FLNDTSAFE | 0.010 | 797. |
| 3 | 26 | TSAFEFSDE | 0.010 | 798. |
| 4 | 25 | DTSAFEFSD | 0.010 | 799. |

TABLE XV (B)-continued unique to variant 3 relative to variants 1 and 2
HLA PEPTIDE SCORING RESULTS - 108P5H8 - B7, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 5 | 23 | LNDTSAFEF | 0.006 | 800. |
| 6 | 24 | NDTSAFEFS | 0.002 | 801. |
| 7 | 30 | EFSDEAGDE | 0.001 | 802. |
| 8 | 29 | FEFSDEAGD | 0.001 | 803. |
| 9 | 28 | AFEFSDEAG | 0.001 | 804. |

TABLE XVI (B)

unique to variant 3 relative to variants 1 and 2
HLA PEPTIDE SCORING RESULTS - 108P5H8 - B7, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 26 | TSAFEFSDEA | 0.100 | 805. |
| 2 | 27 | SAFEFSDEAG | 0.030 | 806. |
| 3 | 22 | FLNDTSAFEF | 0.020 | 807. |
| 4 | 25 | DTSAFEFSDE | 0.010 | 808. |
| 5 | 23 | LNDTSAFEFS | 0.006 | 809. |
| 6 | 30 | EFSDEAGDEG | 0.001 | 810. |
| 7 | 24 | NDTSAFEFSD | 0.001 | 811. |
| 8 | 29 | FEFSDEAGDE | 0.001 | 812. |
| 9 | 21 | LFLNDTSAFE | 0.001 | 813. |
| 10 | 28 | AFEFSDEAGD | 0.001 | 814. |

TABLE XVII (B)

unique to variant 3 relative to variants 1 and 2
HLA PEPTIDE SCORING RESULTS - 108P5H8 - B35, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 276 | SAFEFSDEA | 0.600 | 815. |
| 2 | 23 | LNDTSAFEF | 0.300 | 816. |
| 3 | 26 | TSAFEFSDE | 0.075 | 817. |
| 4 | 22 | FLNDTSAFE | 0.020 | 818. |
| 5 | 24 | NDTSAFEFS | 0.010 | 819. |
| 6 | 25 | DTSAFEFSD | 0.010 | 820. |
| 7 | 30 | EFSDEAGDE | 0.003 | 821. |
| 8 | 29 | FEFSDEAGD | 0.002 | 822. |
| 9 | 28 | AFEFSDEAG | 0.000 | 823. |

TABLE XVIII (B)

unique to variant 3 relative to variants 1 and 2
HLA PEPTIDE SCORING RESULTS - 108P5H8 - B35, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID # |
|---|---|---|---|---|
| 1 | 22 | FLNDTSAFEF | 2.000 | 824. |
| 2 | 26 | TSAFEFSDEA | 0.500 | 825. |
| 3 | 27 | SAFEFSDEAG | 0.060 | 826. |
| 4 | 23 | LNDTSAFEFS | 0.030 | 827. |
| 5 | 25 | DTSAFEFSDE | 0.015 | 828. |
| 6 | 30 | EFSDEAGDEG | 0.002 | 829. |
| 7 | 29 | FEFSDEAGDE | 0.002 | 830. |
| 8 | 24 | NDTSAFEFSD | 0.001 | 831. |
| 9 | 21 | LFLNDTSAFE | 0.001 | 832. |
| 10 | 28 | AFEFSDEAGD | 0.000 | 833. |

TABLE XIX

Motifs and Post-translational Modifications of 108P5H8

N-glycosylation site

Number of matches: 3
1  24-27   NDTS   (SEQ. ID. No. 834)
2  97-100  NCSK   (SEQ. ID. No. 835)
3  237-240 NQSG   (SEQ. ID. No. 836)

cAMP- and cGMP-dependent protein kinase phosphorylation site

170-173 KRFT   (SEQ. ID. No. 837)

Protein kinase C phosphorylation site

Number of matches: 7
1  89-91   SLK
2  164-166 SSK
3  383-385 SSK
4  169-171 TKR
5  320-322 TFR
6  367-369 SGK
7  164-166 SSK

Casein kinase II phosphorylation site

Number of matches: 5
1  27-30   SAFD   (SEQ. ID. No. 838)
2  75-78   SLLD   (SEQ. ID. No. 839)
3  258-261 SGCE   (SEQ. ID. No. 840)
4  356-359 SVED   (SEQ. ID. No. 841)
5  384-387 SKWE   (SEQ. ID. No. 842)

N-myristoylation site

Number of matches: 6
1  64-69   GAHPTL   (SEQ. ID. No. 843)
2  131-136 GGYIAN   (SEQ. ID. No. 844)
3  225-230 GVAVNV   (SEQ. ID. No. 845)
4  259-264 GCERNH   (SEQ. ID. No. 846)
5  287-292 GVLIAA   (SEQ. ID. No. 847)
6  402-407 GMYRCT   (SEQ. ID. No. 848)

Leucine zipper pattern

69-90  LQADDDSLLDQDLPLTNSQLSL  (SEQ. ID. No. 849)

TABLE XX

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| rvt | 49% | Reverse transcriptase (RNA-dependent DNA polymerase) | |
| ank | 25% | Ank repeat | Cytoplasmic protein, associates integral membrane proteins to the cytoskeleton |
| oxidored_q1 | 32% | NADH-Ubiquinone/plastoquinone (complex I), various chains | membrane associated. Involved in proton translocation across the membrane |
| efhand | 4% | EF hand | calcium-binding domain, consists of a 12 residue loop flanked on both sides by a 12 residue alpha-helical domain |
| rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |

TABLE XX-continued

Frequently Occurring Motifs

| Name | avrg. % identity | Description | Potential Function |
|---|---|---|---|
| fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE XXI

Properties of 108P5H8
Motifs and localization apply to 108P5H8 variants 1 and 2.

| | Bioinformatic Program | Outcome |
|---|---|---|
| ORF | ORF Finder | 1290 (includes stop) |
| Protein Length | n/a | 429 amino acids |
| Transmembrane region | TM Pred | 6 TM, at amino acids 114-130, 147-163, 181-200, 217-236, 273-295, 306-324 |
| | HMMTop | 6 TM, at amino acid 113-130, 135-164, 179-202, 215-236, 271-296, 306-331 |
| | Sosui | 6 TM, at amino acid 113-135, 141-163, 180-202, 215-237, 272-294, 308-330 |
| | TMHMM | 6 TM, at amino acids 114-136, 146-165, 178-200, 215-237, 273-295, 310-332 |
| Signal Peptide | Signal P | Indicates no signal |
| pI | pI/MW tool | pI6.11 |
| Molecular weight | pI/MW tool | 47.5 kDa |
| Localization | PSORT | Plasma membrane 60% |
| | PSORT II | Plasma membrane 43% |
| | iSORT | No signal motif |
| Motifs | Pfam | Ribosomal protein L34; Cation efflux family |
| | Prints | Rhodopsin |
| | Blocks | No motif |
| | Prosite | No motif |

TABLE XXII

MHC Class 1 nonamer and decamer analysis of 108P5H8 for selected alleles. Listed are scores that fall within the top 50% (rounded up) of all scores for the selected allele.

| Pos | 1 | 2 | 3 | 4 | 5 | 6 | 7 | 8 | 9 | score | SEQ. ID. No. |
|---|---|---|---|---|---|---|---|---|---|---|---|
| HLA-A*0201 nonamers | | | | | | | | | | | |
| 278 | A | L | G | D | L | V | Q | S | V | 30 | 1968 |
| 121 | Y | L | L | F | M | I | G | E | L | 29 | 1969 |
| 153 | A | I | I | L | T | L | L | A | L | 28 | 1970 |
| 137 | S | L | A | I | M | T | D | A | L | 27 | 1971 |
| 75 | S | L | L | D | Q | D | L | P | L | 26 | 1972 |

TABLE XXII-continued

MHC Class 1 nonamer and decamer analysis of 108P5H8 for selected alleles. Listed are scores that fall within the top 50% (rounded up) of all scores for the selected allele.

| Pos | 1 | 2 | 3 | 4 | 5 | 6 | 7 | 8 | 9 | score | SEQ. ID. No. |
|---|---|---|---|---|---|---|---|---|---|---|---|
| 150 | D | L | S | A | I | I | L | T | L | 26 | 1973 |
| 268 | S | L | A | V | R | A | A | F | V | 26 | 1974 |
| 323 | I | I | W | D | T | V | V | I | I | 26 | 1975 |
| 115 | T | I | A | A | V | L | Y | L | L | 25 | 1976 |
| 140 | I | M | T | D | A | L | H | M | L | 25 | 1977 |
| 181 | V | L | S | A | M | I | S | V | L | 25 | 1978 |
| 218 | M | L | I | T | A | A | V | G | V | 25 | 1979 |
| 343 | Y | I | K | E | A | L | M | K | I | 25 | 1980 |
| 114 | L | T | I | A | A | V | L | Y | L | 23 | 1981 |
| 122 | L | L | F | M | I | G | E | L | V | 23 | 1982 |
| 146 | H | M | L | T | D | L | S | A | I | 23 | 1983 |
| 155 | I | L | T | L | L | A | L | W | L | 23 | 1984 |
| 185 | M | I | S | V | L | L | V | Y | I | 23 | 1985 |
| 198 | L | L | Y | E | A | V | Q | R | T | 23 | 1986 |
| 216 | D | I | M | L | I | T | A | A | V | 23 | 1987 |
| 281 | D | L | V | Q | S | V | G | V | L | 23 | 1988 |
| 330 | I | I | L | E | G | V | P | S | H | 23 | 1989 |
| 331 | I | L | E | G | V | P | S | H | L | 23 | 1990 |
| 409 | Q | L | Q | S | Y | R | Q | E | V | 23 | 1991 |
| 13 | M | L | R | K | D | D | A | P | L | 22 | 1992 |
| 68 | T | L | Q | A | D | D | D | S | L | 22 | 1993 |
| 111 | K | A | R | L | T | I | A | A | V | 22 | 1994 |
| 133 | Y | I | A | N | S | L | A | I | M | 22 | 1995 |
| 183 | S | A | M | I | S | V | L | L | V | 22 | 1996 |
| 306 | P | I | C | T | Y | V | F | S | L | 22 | 1997 |
| 322 | R | I | I | W | D | T | V | V | I | 22 | 1998 |
| 402 | G | M | Y | R | C | T | I | Q | L | 22 | 1999 |
| 76 | L | L | D | Q | D | L | P | L | T | 21 | 2000 |
| 147 | M | L | T | D | L | S | A | I | I | 21 | 2001 |
| 193 | I | L | M | G | F | L | L | Y | E | 21 | 2002 |
| 194 | L | M | G | F | L | L | Y | E | A | 21 | 2003 |
| 220 | I | T | A | A | V | G | V | A | V | 21 | 2004 |
| 349 | M | K | I | E | D | V | Y | S | V | 21 | 2005 |
| 118 | A | V | L | Y | L | L | F | M | I | 20 | 2006 |
| 124 | F | M | I | G | E | L | V | G | G | 20 | 2007 |
| 158 | L | L | A | L | W | L | S | S | K | 20 | 2008 |
| 178 | R | L | E | V | L | S | A | M | I | 20 | 2009 |
| 212 | E | I | N | G | D | I | M | L | I | 20 | 2010 |
| 222 | A | A | V | G | V | A | V | N | V | 20 | 2011 |
| 271 | V | R | A | A | F | V | H | A | L | 20 | 2012 |
| 80 | D | L | P | L | T | N | S | Q | L | 19 | 2013 |
| 82 | P | L | T | N | S | Q | L | S | L | 19 | 2014 |
| 104 | I | L | K | Q | R | K | Y | K | A | 19 | 2015 |
| 143 | D | A | L | H | M | L | T | D | L | 19 | 2016 |
| 154 | I | I | L | T | L | L | A | L | W | 19 | 2017 |
| 188 | V | L | L | V | Y | I | L | M | G | 19 | 2018 |
| 223 | A | V | G | V | A | V | N | V | I | 19 | 2019 |
| 302 | K | I | A | D | P | I | C | T | Y | 19 | 2020 |
| 327 | T | V | V | I | I | L | E | G | V | 19 | 2021 |
| 364 | S | L | T | S | G | K | S | T | A | 19 | 2022 |
| 395 | H | L | L | L | N | T | F | G | M | 19 | 2023 |
| 41 | S | R | F | N | K | L | R | V | V | 18 | 2024 |
| 151 | L | S | A | I | I | L | T | L | L | 18 | 2025 |
| 186 | I | S | V | L | L | V | Y | I | L | 18 | 2026 |

TABLE XXII-continued

MHC Class 1 nonamer and decamer analysis of 108P5H8 for selected alleles. Listed are scores that fall within the top 50% (rounded up) of all scores for the selected allele.

| | | | | | | | | | | |
|---|---|---|---|---|---|---|---|---|---|---|
| 190 | L | V | Y | I | L | M | G | F | L | 18 | 2027 |
| 230 | V | I | M | G | F | L | L | N | Q | 18 | 2028 |
| 303 | I | A | D | P | I | C | T | Y | V | 18 | 2029 |
| 346 | E | A | L | M | K | I | E | D | V | 18 | 2030 |
| 365 | L | T | S | G | K | S | T | A | I | 18 | 2031 |
| 370 | S | T | A | I | V | H | I | Q | L | 18 | 2032 |
| 371 | T | A | I | V | H | I | Q | L | I | 18 | 2033 |
| 377 | Q | L | I | P | G | S | S | S | K | 18 | 2034 |
| 45 | K | L | R | V | V | V | A | D | D | 17 | 2035 |
| 61 | P | V | N | G | A | H | P | T | L | 17 | 2036 |
| 87 | Q | L | S | L | K | V | D | S | C | 17 | 2037 |
| 184 | A | M | I | S | V | L | L | V | Y | 17 | 2038 |
| 205 | R | T | I | H | M | N | Y | E | I | 17 | 2039 |
| 219 | L | I | T | A | A | V | G | V | A | 17 | 2040 |
| 227 | A | V | N | V | I | M | G | F | L | 17 | 2041 |
| 289 | L | I | A | A | Y | I | I | R | F | 17 | 2042 |
| 308 | C | T | Y | V | F | S | L | L | V | 17 | 2043 |
| 315 | L | V | A | F | T | T | F | R | I | 17 | 2044 |
| 357 | V | E | D | L | N | I | W | S | L | 17 | 2045 |
| 112 | A | R | L | T | I | A | A | V | L | 16 | 2046 |
| 117 | A | A | V | L | Y | L | L | F | M | 16 | 2047 |
| 125 | M | I | G | E | L | V | G | G | Y | 16 | 2048 |
| 139 | A | I | M | T | D | A | L | H | M | 16 | 2049 |
| 148 | L | T | D | L | S | A | I | I | L | 16 | 2050 |
| 152 | S | A | I | I | L | T | L | L | A | 16 | 2051 |
| 157 | T | L | L | A | L | W | L | S | S | 16 | 2052 |
| 174 | F | G | F | H | R | L | E | V | L | 16 | 2053 |
| 182 | L | S | A | M | I | S | V | L | L | 16 | 2054 |
| 189 | L | L | V | Y | I | L | M | G | F | 16 | 2055 |
| 211 | Y | E | I | N | G | D | I | M | L | 16 | 2056 |
| 274 | A | F | V | H | A | L | G | D | L | 16 | 2057 |
| 275 | F | V | H | A | L | G | D | L | V | 16 | 2058 |
| 280 | G | D | L | V | Q | S | V | G | V | 16 | 2059 |
| 282 | L | V | Q | S | V | G | V | L | I | 16 | 2060 |
| 287 | G | V | L | I | A | A | Y | I | I | 16 | 2061 |
| 293 | Y | I | I | R | F | K | P | E | Y | 16 | 2062 |
| 313 | S | L | L | V | A | F | T | T | F | 16 | 2063 |
| 324 | I | W | D | T | V | V | I | I | L | 16 | 2064 |
| 392 | K | A | N | H | L | L | L | N | T | 16 | 2065 |
| 5 | G | A | W | K | R | L | K | S | M | 15 | 2066 |
| 9 | R | L | K | S | M | L | R | K | D | 15 | 2067 |
| 22 | F | L | N | D | T | S | A | F | D | 15 | 2068 |
| 27 | S | A | F | D | F | S | D | E | A | 15 | 2069 |
| 69 | L | Q | A | D | D | D | S | L | L | 15 | 2070 |
| 102 | R | E | I | L | K | Q | R | K | V | 15 | 2071 |
| 129 | L | V | G | G | Y | I | A | N | S | 15 | 2072 |
| 144 | A | L | H | M | L | T | D | L | S | 15 | 2073 |
| 180 | E | V | L | S | A | M | I | S | V | 15 | 2074 |
| 192 | Y | I | L | M | G | F | L | L | Y | 15 | 2075 |
| 231 | I | M | G | F | L | L | N | Q | S | 15 | 2076 |
| 248 | S | L | P | S | N | S | P | T | R | 15 | 2077 |
| 295 | I | R | F | K | P | E | Y | K | I | 15 | 2078 |
| 310 | Y | V | F | S | L | L | V | A | F | 15 | 2079 |
| 314 | L | L | V | A | F | T | T | F | R | 15 | 2080 |
| 368 | G | K | S | T | A | I | V | H | I | 15 | 2081 |
| HLA-A*0203 nonamers | | | | | | | | | | | |
| 49 | V | V | A | D | D | G | S | E | A | 12 | 850 |
| 63 | N | G | A | H | P | T | L | Q | A | 12 | 851 |
| 110 | V | K | A | R | L | T | I | A | A | 12 | 852 |
| 27 | S | A | F | D | F | S | D | E | A | 11 | 853 |
| 152 | S | A | I | I | L | T | L | L | A | 11 | 854 |
| 57 | A | P | E | R | P | V | N | G | A | 10 | 855 |
| 270 | A | V | R | A | A | F | V | H | A | 10 | 856 |
| 11 | K | S | M | L | R | K | D | D | A | 9 | 857 |
| 20 | P | L | F | L | N | D | T | S | A | 9 | 858 |
| 43 | F | N | K | L | R | V | V | V | A | 9 | 859 |
| 104 | I | L | K | Q | R | K | V | K | A | 9 | 860 |
| 109 | K | V | K | A | R | L | T | I | A | 9 | 861 |
| 127 | G | E | L | V | G | G | Y | I | A | 9 | 862 |
| 131 | G | G | Y | I | A | N | S | L | A | 9 | 863 |
| 136 | N | S | L | A | I | M | T | D | A | 9 | 864 |
| 145 | L | H | M | L | T | D | L | S | A | 9 | 865 |
| 176 | F | H | R | L | E | V | L | S | A | 9 | 866 |
| 194 | L | M | G | F | L | L | Y | E | A | 9 | 867 |
| 214 | N | G | D | I | M | L | I | T | A | 9 | 868 |
| 215 | G | D | I | M | L | I | T | A | A | 9 | 869 |
| 219 | L | I | T | A | A | V | G | V | A | 9 | 870 |
| 262 | R | N | H | G | Q | D | S | L | A | 9 | 871 |
| 265 | G | Q | D | S | L | A | V | R | A | 9 | 872 |
| 266 | Q | D | S | L | A | V | R | A | A | 9 | 873 |
| 283 | V | Q | S | V | G | V | L | I | A | 9 | 874 |
| 284 | Q | S | V | G | V | L | I | A | A | 9 | 875 |
| 296 | R | F | K | P | E | Y | K | I | A | 9 | 876 |
| 309 | T | Y | V | F | S | L | L | V | A | 9 | 877 |
| 339 | L | N | V | D | Y | I | K | E | A | 9 | 878 |
| 364 | S | L | T | S | G | K | S | T | A | 9 | 879 |
| 385 | K | W | E | E | V | Q | S | K | A | 9 | 880 |
| 414 | R | Q | E | V | D | R | T | C | A | 9 | 881 |
| HLA-A1 nonamers | | | | | | | | | | | |
| 192 | Y | I | L | M | G | F | L | L | Y | 30 | 882 |
| 184 | A | M | I | S | V | L | L | V | Y | 25 | 883 |
| 148 | L | T | D | L | S | A | I | I | L | 20 | 884 |
| 396 | L | L | L | N | T | F | G | M | Y | 20 | 885 |
| 70 | Q | A | D | D | D | S | L | L | D | 18 | 886 |
| 113 | R | L | T | I | A | A | V | L | Y | 18 | 887 |
| 141 | M | T | D | A | L | H | M | L | T | 18 | 888 |
| 347 | A | L | M | K | I | E | D | V | Y | 18 | 889 |
| 71 | A | D | D | D | S | L | L | D | Q | 17 | 890 |
| 285 | S | V | G | V | L | I | A | A | Y | 17 | 891 |
| 293 | Y | I | I | R | F | K | P | E | Y | 17 | 892 |
| 324 | I | W | D | T | V | V | I | I | L | 17 | 893 |
| 335 | V | P | S | H | L | N | V | D | Y | 17 | 894 |
| 356 | S | V | E | D | L | N | I | W | S | 17 | 895 |
| 405 | R | C | T | I | Q | L | Q | S | Y | 17 | 896 |
| 15 | R | K | D | D | A | P | L | F | L | 16 | 897 |
| 31 | F | S | D | E | A | G | D | E | G | 16 | 898 |
| 125 | M | I | G | E | L | V | G | G | Y | 16 | 899 |
| 203 | V | Q | R | T | I | H | M | N | Y | 16 | 900 |
| 302 | K | I | A | D | P | I | C | T | Y | 16 | 901 |
| 54 | G | S | E | A | P | E | R | P | V | 15 | 902 |
| HLA-A26 nonamers | | | | | | | | | | | |
| 310 | Y | V | F | S | L | L | V | A | F | 30 | 903 |
| 125 | M | I | G | E | L | V | G | G | Y | 28 | 904 |
| 281 | D | L | V | Q | S | V | G | V | L | 28 | 905 |
| 285 | S | V | G | V | L | I | A | A | Y | 27 | 906 |
| 388 | E | V | Q | S | K | A | N | H | L | 27 | 907 |
| 150 | D | L | S | A | I | I | L | T | L | 26 | 908 |
| 289 | L | I | A | A | Y | I | I | R | F | 26 | 909 |
| 302 | K | I | A | D | P | I | C | T | Y | 26 | 910 |
| 80 | D | L | P | L | T | N | S | Q | L | 25 | 911 |
| 133 | Y | I | A | N | S | L | A | I | M | 25 | 912 |
| 153 | A | I | I | L | T | L | L | A | L | 25 | 913 |
| 114 | L | T | I | A | A | V | L | Y | L | 24 | 914 |
| 189 | L | L | V | Y | I | L | M | G | F | 24 | 915 |
| 192 | Y | I | L | M | G | F | L | L | Y | 24 | 916 |
| 293 | Y | I | I | R | F | K | P | E | Y | 24 | 917 |
| 115 | T | I | A | A | V | L | Y | L | L | 23 | 918 |
| 190 | L | V | Y | I | L | M | G | F | L | 23 | 919 |
| 212 | E | I | N | G | D | I | M | L | I | 23 | 920 |
| 306 | P | I | C | T | Y | V | F | S | L | 23 | 921 |
| 396 | L | L | L | N | T | F | G | M | Y | 23 | 922 |
| 168 | P | T | K | R | F | T | F | G | F | 22 | 923 |
| 180 | E | V | L | S | A | M | I | S | V | 22 | 924 |
| 187 | S | V | L | L | V | Y | I | L | M | 22 | 925 |
| 227 | A | V | N | V | I | M | G | F | L | 22 | 926 |
| 313 | S | L | L | V | A | F | T | T | F | 22 | 927 |
| 61 | P | V | N | G | A | H | P | T | L | 21 | 928 |
| 121 | Y | L | L | F | M | I | G | E | L | 21 | 929 |
| 128 | E | L | V | G | G | Y | I | A | N | 21 | 930 |
| 181 | V | L | S | A | M | I | S | V | L | 21 | 931 |
| 326 | D | T | V | V | I | I | L | E | G | 21 | 932 |
| 38 | E | G | L | S | R | F | N | K | L | 20 | 933 |
| 148 | L | T | D | L | S | A | I | I | L | 20 | 934 |
| 331 | I | L | E | G | V | P | S | H | L | 20 | 935 |
| 340 | N | V | D | Y | I | K | E | A | L | 20 | 936 |
| 370 | S | T | A | I | V | H | I | Q | L | 20 | 937 |
| 35 | A | G | D | E | G | L | S | R | F | 19 | 938 |

TABLE XXII-continued

MHC Class 1 nonamer and decamer analysis of 108P5H8 for selected alleles. Listed are scores that fall within the top 50% (rounded up) of all scores for the selected allele.

| | | | | | | | | | | |
|---|---|---|---|---|---|---|---|---|---|---|
| 113 | R | L | T | I | A | A | V | L | Y | 19 | 939 |
| 139 | A | I | M | T | D | A | L | H | M | 19 | 940 |
| 171 | R | F | T | F | G | F | H | R | L | 19 | 941 |
| 343 | Y | I | K | E | A | L | M | K | I | 19 | 942 |
| 347 | A | L | M | K | I | E | D | V | Y | 19 | 943 |
| 352 | E | D | V | Y | S | V | E | D | L | 19 | 944 |
| 416 | E | V | D | R | T | C | A | N | C | 19 | 945 |
| 13 | M | L | R | K | D | D | A | P | L | 18 | 946 |
| 21 | L | F | L | N | D | T | S | A | F | 18 | 947 |
| 75 | S | L | L | D | Q | D | L | P | L | 18 | 948 |
| 82 | P | L | T | N | S | Q | L | S | L | 18 | 949 |
| 103 | E | I | L | K | Q | R | K | V | K | 18 | 950 |
| 129 | L | V | G | G | Y | I | A | N | S | 18 | 951 |
| 137 | S | L | A | I | M | T | D | A | L | 18 | 952 |
| 143 | D | A | L | H | M | L | T | D | L | 18 | 953 |
| 216 | D | I | M | L | I | T | A | A | V | 18 | 954 |
| 267 | D | S | L | A | V | R | A | A | F | 18 | 955 |
| 274 | A | F | V | H | A | L | G | D | L | 18 | 956 |
| 330 | I | I | L | E | G | V | P | S | H | 18 | 957 |
| 399 | N | T | F | G | M | Y | R | C | T | 18 | 958 |
| 25 | D | T | S | A | F | D | F | S | D | 17 | 959 |
| 68 | T | L | Q | A | D | D | D | S | L | 17 | 960 |
| 83 | L | T | N | S | Q | L | S | L | K | 17 | 961 |
| 155 | I | L | T | L | L | A | L | W | L | 17 | 962 |
| 184 | A | M | I | S | V | L | L | V | Y | 17 | 963 |
| 230 | V | I | M | G | F | L | L | N | Q | 17 | 964 |
| 353 | D | V | Y | S | V | E | D | L | N | 17 | 965 |
| 395 | H | L | L | L | N | T | F | G | M | 17 | 966 |
| 405 | R | C | T | I | Q | L | Q | S | Y | 17 | 967 |
| 73 | D | D | S | L | L | D | Q | D | L | 16 | 968 |
| 116 | I | A | A | V | L | Y | L | L | F | 16 | 969 |
| 118 | A | V | L | Y | L | L | F | M | I | 16 | 970 |
| 154 | I | I | L | T | L | L | A | L | W | 16 | 971 |
| 177 | H | R | L | E | V | L | S | A | M | 16 | 972 |
| 185 | M | I | S | V | L | L | V | Y | I | 16 | 973 |
| 198 | L | L | Y | E | A | V | Q | R | T | 16 | 974 |
| 201 | E | A | V | Q | R | T | I | H | M | 16 | 975 |
| 225 | G | V | A | V | N | V | I | M | G | 16 | 976 |
| 226 | V | A | V | N | V | I | M | G | F | 16 | 977 |
| 229 | N | V | I | M | G | F | L | L | N | 16 | 978 |
| 270 | A | V | R | A | A | F | V | H | A | 16 | 979 |
| 278 | A | L | G | D | L | V | Q | S | V | 16 | 980 |
| 319 | T | T | F | R | I | I | W | D | T | 16 | 981 |
| 323 | I | I | W | D | T | V | V | I | I | 16 | 982 |
| 334 | G | V | P | S | H | L | N | V | D | 16 | 983 |
| 350 | K | I | E | D | V | Y | S | V | E | 16 | 984 |
| 378 | L | I | P | G | S | S | S | K | W | 16 | 985 |
| 9 | R | L | K | S | M | L | R | K | D | 15 | 986 |
| 17 | D | D | A | P | L | F | L | N | D | 15 | 987 |
| 76 | L | L | D | Q | D | L | P | L | T | 15 | 988 |
| 109 | K | V | K | A | R | L | T | I | A | 15 | 989 |
| 158 | L | L | A | L | W | L | S | S | K | 15 | 990 |
| 202 | A | V | Q | R | T | I | H | M | N | 15 | 991 |
| 261 | E | R | N | H | G | Q | D | S | L | 15 | 992 |
| 327 | T | V | V | I | I | L | E | G | V | 15 | 993 |
| 373 | I | V | H | I | Q | L | I | P | G | 15 | 994 |
| 393 | A | N | H | L | L | L | N | T | F | 15 | 995 |
| 406 | C | T | I | Q | L | Q | S | Y | R | 15 | 996 |

HLA-A3 nonamers

| | | | | | | | | | | |
|---|---|---|---|---|---|---|---|---|---|---|
| 377 | Q | L | I | P | G | S | S | S | K | 35 | 997 |
| 113 | R | L | T | I | A | A | V | L | Y | 28 | 998 |
| 158 | L | L | A | L | W | L | S | S | K | 27 | 999 |
| 197 | F | L | L | Y | E | A | V | Q | R | 26 | 1000 |
| 103 | E | I | L | K | Q | R | K | V | K | 25 | 1001 |
| 162 | W | L | S | S | K | S | P | T | K | 25 | 1002 |
| 294 | I | I | R | F | K | P | E | Y | K | 25 | 1003 |
| 302 | K | I | A | D | P | I | C | T | Y | 23 | 1004 |
| 322 | R | I | I | W | D | T | V | V | I | 23 | 1005 |
| 347 | A | L | M | K | I | E | D | V | Y | 23 | 1006 |
| 270 | A | V | R | A | A | F | V | H | A | 22 | 1007 |
| 313 | S | L | L | V | A | F | T | T | F | 22 | 1008 |
| 192 | Y | I | L | M | G | F | L | L | Y | 21 | 1009 |
| 285 | S | V | G | V | L | I | A | A | Y | 21 | 1010 |
| 330 | I | I | L | E | G | V | P | S | H | 21 | 1011 |
| 361 | N | I | W | S | L | T | S | G | K | 21 | 1012 |
| 396 | L | L | L | N | T | F | G | M | Y | 21 | 1013 |
| 45 | K | L | R | V | V | V | A | D | D | 20 | 1014 |
| 155 | I | L | T | L | L | A | L | W | L | 20 | 1015 |
| 184 | A | M | I | S | V | L | L | V | Y | 20 | 1016 |
| 218 | M | L | I | T | A | A | V | G | V | 20 | 1017 |
| 268 | S | L | A | V | R | A | A | F | V | 20 | 1018 |
| 293 | Y | I | I | R | F | K | P | E | Y | 20 | 1019 |
| 342 | D | Y | I | K | E | A | L | M | K | 20 | 1020 |
| 350 | K | I | E | D | V | Y | S | V | E | 20 | 1021 |
| 364 | S | L | T | S | G | K | S | T | A | 20 | 1022 |
| 104 | I | L | K | Q | R | K | V | K | A | 19 | 1023 |
| 109 | K | V | K | A | R | L | T | I | A | 19 | 1024 |
| 150 | D | L | S | A | I | I | L | T | L | 19 | 1025 |
| 153 | A | I | I | L | T | L | L | A | L | 19 | 1026 |
| 157 | T | L | A | L | W | L | S | S | S | 19 | 1027 |
| 181 | V | L | S | A | M | I | S | V | L | 19 | 1028 |
| 248 | S | L | P | S | N | S | P | T | R | 19 | 1029 |
| 288 | V | L | I | A | A | Y | I | I | R | 19 | 1030 |
| 310 | Y | V | F | S | L | L | V | A | F | 19 | 1031 |
| 328 | V | V | I | I | L | E | G | V | P | 19 | 1032 |
| 329 | V | I | I | L | E | G | V | P | S | 19 | 1033 |
| 331 | I | L | E | G | V | P | S | H | L | 19 | 1034 |
| 8 | K | R | L | K | S | M | L | R | K | 18 | 1035 |
| 49 | V | V | A | D | D | G | S | E | A | 18 | 1036 |
| 178 | R | L | E | V | L | S | A | M | I | 18 | 1037 |
| 229 | N | V | I | M | G | F | L | L | N | 18 | 1038 |
| 234 | F | L | L | N | Q | S | G | H | R | 18 | 1039 |
| 282 | L | V | Q | S | V | G | V | L | I | 18 | 1040 |
| 359 | D | N | I | W | S | L | T | S | 18 | 1041 |
| 397 | L | L | N | T | F | G | M | Y | R | 18 | 1042 |
| 39 | G | L | S | R | F | N | K | L | R | 17 | 1043 |
| 75 | S | L | L | D | Q | D | L | P | L | 17 | 1044 |
| 80 | D | L | P | L | T | N | S | Q | L | 17 | 1045 |
| 139 | A | I | M | T | D | A | L | H | M | 17 | 1046 |
| 193 | I | L | M | G | F | L | L | Y | E | 17 | 1047 |
| 202 | A | V | Q | R | T | I | H | M | N | 17 | 1048 |
| 223 | A | V | G | V | A | V | N | V | I | 17 | 1049 |
| 235 | L | L | N | Q | S | G | H | R | H | 17 | 1050 |
| 314 | L | L | V | A | F | T | T | F | R | 17 | 1051 |
| 411 | Q | S | Y | R | Q | E | V | D | R | 17 | 1052 |

HLA-B*0702 nonamers

| | | | | | | | | | | |
|---|---|---|---|---|---|---|---|---|---|---|
| 57 | A | P | E | R | P | V | N | G | A | 22 | 1053 |
| 60 | R | P | V | N | C | A | H | P | T | 18 | 1054 |
| 2 | A | G | S | G | A | W | K | R | L | 16 | 1055 |
| 13 | M | L | R | K | D | D | A | P | L | 15 | 1056 |
| 15 | R | K | D | D | A | P | L | F | L | 15 | 1057 |
| 106 | K | Q | R | K | V | K | A | R | L | 15 | 1058 |
| 150 | D | L | S | A | I | I | L | T | L | 15 | 1059 |
| 153 | A | I | I | L | T | L | L | A | L | 15 | 1060 |
| 97 | N | C | S | K | Q | R | E | I | L | 14 | 1061 |
| 112 | A | R | L | T | I | A | A | V | L | 14 | 1062 |
| 114 | L | T | I | A | A | V | L | Y | L | 14 | 1063 |
| 167 | S | P | T | K | R | F | T | F | G | 14 | 1064 |
| 181 | V | L | S | A | M | I | S | V | L | 14 | 1065 |
| 270 | A | V | R | A | A | F | V | H | A | 14 | 1066 |
| 271 | V | R | A | A | F | V | H | A | L | 14 | 1067 |
| 335 | V | P | S | H | L | N | V | D | Y | 14 | 1068 |
| 61 | P | V | N | G | A | H | P | T | L | 13 | 1069 |
| 63 | N | G | A | H | P | T | L | Q | A | 13 | 1070 |
| 75 | S | L | L | D | Q | D | L | P | L | 13 | 1071 |
| 137 | S | L | A | I | M | T | D | A | L | 13 | 1072 |
| 155 | I | L | T | L | L | A | L | W | L | 13 | 1073 |
| 182 | L | S | A | M | I | S | V | L | L | 13 | 1074 |
| 220 | I | T | A | A | V | G | V | A | V | 13 | 1075 |
| 227 | A | V | N | V | I | M | G | F | L | 13 | 1076 |
| 249 | L | P | S | N | S | P | T | R | G | 13 | 1077 |
| 305 | D | P | I | C | T | Y | V | F | S | 13 | 1078 |
| 324 | I | W | D | T | V | V | I | I | L | 13 | 1079 |
| 331 | I | L | E | G | V | P | S | H | L | 13 | 1080 |
| 389 | V | Q | S | K | A | N | H | L | L | 13 | 1081 |
| 390 | Q | S | K | A | N | H | L | L | L | 13 | 1082 |
| 6 | A | W | K | R | L | K | S | M | L | 12 | 1083 |
| 19 | A | P | L | F | L | N | D | T | S | 12 | 1084 |

TABLE XXII-continued

MHC Class 1 nonamer and decamer analysis of 108P5H8 for selected alleles. Listed are scores that fall within the top 50% (rounded up) of all scores for the selected allele.

| | | | | | | | | | | | |
|---|---|---|---|---|---|---|---|---|---|---|---|
| 38 | E | G | L | S | R | F | N | K | L | 12 | 1085 |
| 42 | R | F | N | K | L | R | V | V | V | 12 | 1086 |
| 73 | D | D | S | L | L | D | Q | D | L | 12 | 1087 |
| 82 | P | L | T | N | S | Q | L | S | L | 12 | 1088 |
| 115 | T | I | A | A | V | L | Y | L | L | 12 | 1089 |
| 151 | L | S | A | I | I | L | T | L | L | 12 | 1090 |
| 171 | R | F | T | F | G | F | H | R | L | 12 | 1091 |
| 186 | I | S | V | L | L | V | Y | I | L | 12 | 1092 |
| 222 | A | A | V | G | V | A | V | N | V | 12 | 1093 |
| 274 | A | F | V | H | A | L | G | D | L | 12 | 1094 |
| 281 | D | L | V | Q | S | V | G | V | L | 12 | 1095 |
| 298 | K | P | E | Y | K | I | A | D | P | 12 | 1096 |
| 307 | I | C | T | Y | V | F | S | L | L | 12 | 1097 |
| 340 | N | V | D | Y | I | K | E | A | L | 12 | 1098 |
| 352 | E | D | V | Y | S | V | E | D | L | 12 | 1099 |
| 365 | L | T | S | G | K | S | T | A | I | 12 | 1100 |
| 379 | I | P | G | S | S | S | K | W | E | 12 | 1101 |
| 32 | S | D | E | A | G | D | E | G | L | 11 | 1102 |
| 54 | G | S | E | A | P | E | R | P | V | 11 | 1103 |
| 68 | T | L | Q | A | D | D | D | S | L | 11 | 1104 |
| 69 | L | Q | A | D | D | D | S | L | L | 11 | 1105 |
| 108 | R | K | V | K | A | R | L | T | I | 11 | 1106 |
| 111 | K | A | R | L | T | I | A | A | V | 11 | 1107 |
| 117 | A | A | V | L | Y | L | L | F | M | 11 | 1108 |
| 130 | V | G | G | Y | I | A | N | S | L | 11 | 1109 |
| 139 | A | I | M | T | D | A | L | H | M | 11 | 1110 |
| 140 | I | M | T | D | A | L | H | M | L | 11 | 1111 |
| 143 | D | A | L | H | M | L | T | D | L | 11 | 1112 |
| 148 | L | T | D | L | S | A | I | I | L | 11 | 1113 |
| 174 | F | G | F | H | R | L | E | V | L | 11 | 1114 |
| 176 | F | H | R | L | E | V | L | S | A | 11 | 1115 |
| 190 | L | V | Y | I | L | M | G | F | L | 11 | 1116 |
| 191 | V | Y | I | L | M | G | F | L | L | 11 | 1117 |
| 223 | A | V | G | V | A | V | N | V | I | 11 | 1118 |
| 228 | V | N | V | I | M | G | F | L | L | 11 | 1119 |
| 261 | E | R | N | H | G | Q | D | S | L | 11 | 1120 |
| 283 | V | Q | S | V | G | V | L | I | A | 11 | 1121 |
| 295 | I | R | F | K | P | E | Y | K | I | 11 | 1122 |
| 306 | P | I | C | T | Y | V | F | S | L | 11 | 1123 |
| 311 | V | F | S | L | L | V | A | F | T | 11 | 1124 |
| 322 | R | I | I | W | D | T | V | V | I | 11 | 1125 |
| 357 | V | E | D | L | N | I | W | S | L | 11 | 1126 |
| 370 | S | T | A | I | V | H | I | Q | L | 11 | 1127 |
| 388 | E | V | Q | S | K | A | N | H | L | 11 | 1128 |
| 402 | G | M | Y | R | C | T | I | Q | L | 11 | 1129 |

HLA-B*08 nonamers

| | | | | | | | | | | | |
|---|---|---|---|---|---|---|---|---|---|---|---|
| 104 | I | L | K | Q | R | K | V | K | A | 26 | 1130 |
| 13 | M | L | R | K | D | D | A | P | L | 22 | 1131 |
| 43 | F | N | K | L | R | V | V | V | A | 22 | 1132 |
| 343 | Y | I | K | E | A | L | M | K | I | 22 | 1133 |
| 388 | E | V | Q | S | K | A | N | H | L | 22 | 1134 |
| 107 | Q | R | K | V | K | A | R | L | T | 21 | 1135 |
| 294 | I | I | R | F | K | P | E | Y | K | 21 | 1136 |
| 6 | A | W | K | R | L | K | S | M | L | 20 | 1137 |
| 38 | E | G | L | S | R | F | N | K | L | 20 | 1138 |
| 390 | Q | S | K | A | N | H | L | L | L | 20 | 1139 |
| 89 | S | L | K | V | D | S | C | D | N | 19 | 1140 |
| 137 | S | L | A | I | M | T | D | A | L | 19 | 1141 |
| 164 | S | S | K | S | P | T | K | R | F | 19 | 1142 |
| 174 | F | G | F | H | R | L | E | V | L | 19 | 1143 |
| 75 | S | L | L | D | Q | D | L | P | L | 18 | 1144 |
| 80 | D | L | P | L | T | N | S | Q | L | 18 | 1145 |
| 87 | Q | L | S | L | K | V | D | S | C | 18 | 1146 |
| 98 | C | S | K | Q | R | E | I | L | K | 18 | 1147 |
| 109 | K | V | K | A | R | L | T | I | A | 18 | 1148 |
| 121 | Y | L | L | F | M | I | G | E | L | 18 | 1149 |
| 155 | I | L | T | L | L | A | L | W | L | 18 | 1150 |
| 181 | V | L | S | A | M | I | S | V | L | 18 | 1151 |
| 298 | K | P | E | Y | K | I | A | D | P | 18 | 1152 |
| 7 | W | K | R | L | K | S | M | L | R | 17 | 1153 |
| 56 | E | A | P | E | R | P | V | N | G | 17 | 1154 |
| 96 | D | N | C | S | K | Q | R | E | I | 17 | 1155 |
| 150 | D | L | S | A | I | I | L | T | L | 17 | 1156 |
| 268 | S | L | A | V | R | A | A | F | V | 17 | 1157 |
| 281 | D | L | V | Q | S | V | G | V | L | 17 | 1158 |
| 331 | I | L | E | G | V | P | S | H | L | 17 | 1159 |
| 346 | E | A | L | M | K | I | E | D | V | 17 | 1160 |
| 365 | L | T | S | G | K | S | T | A | I | 17 | 1161 |
| 9 | R | L | K | S | M | L | R | K | D | 16 | 1162 |
| 14 | L | R | K | D | D | A | P | L | F | 16 | 1163 |
| 68 | T | L | Q | A | D | D | D | S | L | 16 | 1164 |
| 82 | P | L | T | N | S | Q | L | S | L | 16 | 1165 |
| 106 | K | Q | R | K | V | K | A | R | L | 16 | 1166 |
| 153 | A | I | I | L | T | L | L | A | L | 16 | 1167 |
| 162 | W | L | S | S | K | S | P | T | K | 16 | 1168 |
| 166 | K | S | P | T | K | R | F | T | F | 16 | 1169 |
| 167 | S | P | T | K | R | F | T | F | G | 16 | 1170 |
| 168 | P | T | K | R | F | T | F | G | F | 16 | 1171 |
| 306 | P | I | C | T | Y | V | F | S | L | 15 | 1172 |
| 313 | L | S | P | T | L | A | V | F | T | 15 | 1173 |
| 5 | G | A | W | K | R | L | K | S | M | 14 | 1174 |
| 45 | K | L | R | V | V | V | A | D | D | 14 | 1175 |
| 115 | T | I | A | A | V | L | Y | L | L | 14 | 1176 |
| 143 | D | A | L | H | M | L | T | D | L | 14 | 1177 |
| 201 | E | A | V | Q | R | T | I | H | M | 14 | 1178 |
| 352 | E | D | V | Y | S | V | E | D | L | 14 | 1179 |
| 12 | S | M | L | R | K | D | D | A | P | 13 | 1180 |
| 105 | L | K | Q | R | K | V | K | A | R | 13 | 1181 |
| 111 | K | A | R | L | T | I | A | A | V | 13 | 1182 |
| 178 | R | L | E | V | L | S | A | M | I | 13 | 1183 |
| 186 | I | S | V | L | L | V | Y | I | L | 13 | 1184 |
| 189 | L | L | V | Y | I | L | M | G | F | 13 | 1185 |
| 212 | E | I | N | G | D | I | M | L | I | 13 | 1186 |
| 258 | S | G | C | E | R | N | H | G | Q | 13 | 1187 |
| 271 | V | R | A | A | F | V | H | A | L | 13 | 1188 |
| 323 | I | I | W | D | T | V | V | I | I | 13 | 1189 |
| 357 | V | E | D | L | N | I | W | S | L | 13 | 1190 |
| 383 | S | S | K | W | E | E | V | Q | S | 13 | 1191 |

HLA-B*1510 nonamers

| | | | | | | | | | | | |
|---|---|---|---|---|---|---|---|---|---|---|---|
| 331 | I | L | E | G | V | P | S | H | L | 15 | 1192 |
| 2 | A | G | S | G | A | W | K | R | L | 14 | 1193 |
| 106 | K | Q | R | K | V | K | A | R | L | 14 | 1194 |
| 181 | V | L | S | A | M | I | S | V | L | 14 | 1195 |
| 276 | V | H | A | L | G | D | L | V | Q | 14 | 1196 |
| 281 | D | L | V | Q | S | V | G | V | L | 14 | 1197 |
| 61 | P | V | N | G | A | H | P | T | L | 13 | 1198 |
| 97 | N | C | S | K | Q | R | E | I | L | 13 | 1199 |
| 121 | Y | L | L | F | M | I | G | E | L | 13 | 1200 |
| 140 | I | M | T | D | A | L | H | M | L | 13 | 1201 |
| 150 | D | L | S | A | I | I | L | T | L | 13 | 1202 |
| 171 | R | F | T | F | G | F | H | R | L | 13 | 1203 |
| 182 | L | S | A | M | I | S | V | L | L | 13 | 1204 |
| 186 | I | S | V | L | L | V | Y | I | L | 13 | 1205 |
| 271 | V | R | A | A | F | V | H | A | L | 13 | 1206 |
| 324 | I | W | D | T | V | V | I | I | L | 13 | 1207 |
| 374 | V | H | I | Q | L | I | P | G | S | 13 | 1208 |
| 15 | R | K | D | D | A | P | L | F | L | 12 | 1209 |
| 32 | S | D | E | A | G | D | E | G | L | 12 | 1210 |
| 69 | L | Q | A | D | D | D | S | L | L | 12 | 1211 |
| 112 | A | R | L | T | I | A | A | V | L | 12 | 1212 |
| 115 | T | I | A | A | V | L | Y | L | L | 12 | 1213 |
| 137 | S | L | A | I | M | T | D | A | L | 12 | 1214 |
| 155 | I | L | T | L | L | A | L | W | L | 12 | 1215 |
| 174 | F | G | F | H | R | L | E | V | L | 12 | 1216 |
| 207 | I | H | M | N | Y | E | I | N | G | 12 | 1217 |
| 211 | Y | E | I | N | G | D | I | M | L | 12 | 1218 |
| 227 | A | V | N | V | I | M | G | F | L | 12 | 1219 |
| 244 | S | H | S | H | S | L | P | S | N | 12 | 1220 |
| 246 | H | S | L | P | S | N | S | P | P | 12 | 1221 |
| 261 | E | R | N | H | G | Q | D | S | L | 12 | 1222 |
| 263 | N | H | G | Q | D | S | L | A | V | 12 | 1223 |
| 307 | I | C | T | Y | V | F | S | L | L | 12 | 1224 |
| 340 | N | V | D | Y | I | K | E | A | L | 12 | 1225 |
| 352 | E | D | V | Y | S | V | E | D | L | 12 | 1226 |
| 357 | V | E | D | L | N | I | W | S | L | 12 | 1227 |
| 389 | V | Q | S | K | A | N | H | L | L | 12 | 1228 |
| 6 | A | W | K | R | L | K | S | M | L | 11 | 1229 |
| 13 | M | L | R | K | D | D | A | P | L | 11 | 1230 |

TABLE XXII-continued

MHC Class 1 nonamer and decamer analysis of 108P5H8 for selected alleles. Listed are scores that fall within the top 50% (rounded up) of all scores for the selected allele.

| | | | | | | | | | | |
|---|---|---|---|---|---|---|---|---|---|---|
| 38 | E | G | L | S | R | F | N | K | L | 11 | 1231 |
| 68 | T | L | Q | A | D | D | D | S | L | 11 | 1232 |
| 73 | D | D | S | L | L | D | Q | D | L | 11 | 1233 |
| 75 | S | L | L | D | Q | D | L | P | L | 11 | 1234 |
| 114 | L | T | I | A | A | V | L | Y | L | 11 | 1235 |
| 151 | L | S | A | I | I | L | T | L | L | 11 | 1236 |
| 153 | A | I | I | L | T | L | L | A | L | 11 | 1237 |
| 176 | F | H | R | L | E | V | L | S | A | 11 | 1238 |
| 190 | L | V | Y | I | L | M | G | F | L | 11 | 1239 |
| 240 | G | H | R | H | S | H | S | H | S | 11 | 1240 |
| 242 | R | H | S | H | S | H | S | L | P | 11 | 1241 |
| 306 | P | I | C | T | Y | V | F | S | L | 11 | 1242 |
| 370 | S | T | A | I | V | H | I | Q | L | 11 | 1243 |
| 388 | E | V | Q | S | K | A | N | H | L | 11 | 1244 |
| 390 | Q | S | K | A | N | H | L | L | L | 11 | 1245 |
| 402 | G | M | Y | R | C | T | I | Q | L | 11 | 1246 |
| 35 | A | G | D | E | G | L | S | R | F | 10 | 1247 |
| 65 | A | H | P | T | L | Q | A | D | D | 10 | 1248 |
| 80 | D | L | P | L | T | N | S | Q | L | 10 | 1249 |
| 82 | P | L | T | N | S | Q | L | S | L | 10 | 1250 |
| 116 | I | A | A | V | L | Y | L | L | F | 10 | 1251 |
| 130 | V | G | G | Y | I | A | N | S | L | 10 | 1252 |
| 143 | D | A | L | H | M | L | T | D | L | 10 | 1253 |
| 145 | L | H | M | L | T | D | L | S | A | 10 | 1254 |
| 148 | L | T | D | L | S | A | I | I | L | 10 | 1255 |
| 191 | V | Y | I | L | M | G | F | L | L | 10 | 1256 |
| 228 | V | N | V | I | M | G | F | L | L | 10 | 1257 |
| 241 | H | R | H | S | H | S | H | S | L | 10 | 1258 |
| 274 | A | F | V | H | A | L | G | D | L | 10 | 1259 |
| 289 | L | I | A | A | Y | I | I | R | F | 10 | 1260 |
| 310 | Y | V | F | S | L | L | V | A | F | 10 | 1261 |
| 337 | S | H | L | N | V | D | Y | I | K | 10 | 1262 |
| 394 | N | H | L | L | L | N | T | F | G | 10 | 1263 |
| 164 | S | S | K | S | P | T | K | R | F | 9 | 1264 |
| 5 | G | A | W | K | R | L | K | S | M | 8 | 1265 |
| 14 | L | R | K | D | D | A | P | L | F | 8 | 1266 |
| 133 | Y | I | A | N | S | L | A | I | M | 8 | 1267 |
| 166 | K | S | P | T | K | R | F | T | F | 8 | 1268 |
| 177 | H | R | L | E | V | L | S | A | M | 8 | 1269 |
| 201 | E | A | V | Q | R | T | I | H | M | 8 | 1270 |
| 210 | N | Y | E | I | N | G | D | I | M | 8 | 1271 |
| 224 | V | G | V | A | V | N | V | I | M | 8 | 1272 |
| 267 | D | S | L | A | V | R | A | A | F | 8 | 1273 |
| 304 | A | D | P | I | C | T | Y | V | F | 8 | 1274 |
| 313 | S | L | L | V | A | F | T | T | F | 8 | 1275 |
| 21 | L | F | L | N | D | T | S | A | F | 7 | 1276 |
| 55 | S | E | A | P | E | R | P | V | N | 7 | 1277 |
| 221 | T | A | A | V | G | V | A | V | N | 7 | 1278 |
| 226 | V | A | V | N | V | I | M | G | F | 7 | 1279 |
| 393 | A | N | H | L | L | L | N | T | F | 7 | 1280 |
| 395 | H | L | L | L | N | T | F | G | M | 7 | 1281 |

HLA-B*2705 nonamers

| | | | | | | | | | | |
|---|---|---|---|---|---|---|---|---|---|---|
| 8 | K | R | L | K | S | M | L | R | K | 30 | 1282 |
| 112 | A | R | L | T | I | A | A | V | L | 27 | 1283 |
| 295 | I | R | F | K | P | E | Y | K | I | 26 | 1284 |
| 170 | K | R | F | T | F | G | F | H | R | 25 | 1285 |
| 261 | E | R | N | H | G | Q | D | S | L | 25 | 1286 |
| 101 | Q | R | E | I | L | K | Q | R | K | 24 | 1287 |
| 177 | H | R | L | E | V | L | S | A | M | 24 | 1288 |
| 14 | L | R | K | D | D | A | P | L | F | 22 | 1289 |
| 241 | H | R | H | S | H | S | H | S | L | 22 | 1290 |
| 271 | V | R | A | A | F | V | H | A | L | 21 | 1291 |
| 106 | K | Q | R | K | V | K | A | R | L | 19 | 1292 |
| 35 | A | G | D | E | G | L | S | R | F | 18 | 1293 |
| 171 | R | F | T | F | G | F | H | R | L | 18 | 1294 |
| 377 | Q | L | I | P | G | S | S | S | K | 18 | 1295 |
| 406 | C | T | I | Q | L | Q | S | Y | R | 18 | 1296 |
| 163 | L | S | S | K | S | P | T | K | R | 17 | 1297 |
| 233 | G | F | L | L | N | Q | S | G | H | 17 | 1298 |
| 330 | I | I | L | E | G | V | P | S | H | 17 | 1299 |
| 342 | D | Y | I | K | E | A | L | M | K | 17 | 1300 |
| 402 | G | M | Y | R | C | T | I | Q | L | 17 | 1301 |
| 1 | M | A | G | S | G | A | W | K | R | 16 | 1302 |
| 41 | S | R | F | N | K | L | R | V | V | 16 | 1303 |
| 100 | K | Q | R | E | I | L | K | Q | R | 16 | 1304 |
| 121 | Y | L | L | F | M | I | G | E | L | 16 | 1305 |
| 150 | D | L | S | A | I | I | L | T | L | 16 | 1306 |
| 153 | A | I | I | L | T | L | L | A | L | 16 | 1307 |
| 186 | I | S | V | L | L | V | Y | I | L | 16 | 1308 |
| 197 | F | L | L | Y | E | A | V | Q | R | 16 | 1309 |
| 211 | Y | E | I | N | G | D | I | M | L | 16 | 1310 |
| 226 | V | A | V | N | V | I | M | G | F | 16 | 1311 |
| 256 | R | G | S | G | C | E | R | N | H | 16 | 1312 |
| 281 | D | L | V | Q | S | V | G | V | L | 16 | 1313 |
| 289 | L | I | A | A | Y | I | I | R | F | 16 | 1314 |
| 310 | Y | V | F | S | L | L | V | A | F | 16 | 1315 |
| 321 | F | R | I | I | W | D | T | V | V | 16 | 1316 |
| 357 | V | E | D | L | N | I | W | S | L | 16 | 1317 |
| 387 | E | E | V | Q | S | K | A | N | H | 16 | 1318 |
| 393 | A | N | H | L | L | L | N | T | F | 16 | 1319 |
| 2 | A | G | S | G | A | W | K | R | L | 15 | 1320 |
| 5 | G | A | W | K | R | L | K | S | M | 15 | 1321 |
| 15 | R | K | D | D | A | P | L | F | L | 15 | 1322 |
| 38 | E | G | L | S | R | F | N | K | L | 15 | 1323 |
| 82 | P | L | T | N | S | Q | L | S | L | 15 | 1324 |
| 103 | E | I | L | K | Q | R | K | V | K | 15 | 1325 |
| 108 | R | K | V | K | A | R | L | T | I | 15 | 1326 |
| 143 | D | A | L | H | M | L | T | D | L | 15 | 1327 |
| 155 | I | L | T | L | L | A | L | W | L | 15 | 1328 |
| 174 | F | G | F | H | R | L | E | V | L | 15 | 1329 |
| 181 | V | L | S | A | M | I | S | V | L | 15 | 1330 |
| 184 | A | M | I | S | V | L | L | V | Y | 15 | 1331 |
| 205 | R | T | I | H | M | N | Y | E | I | 15 | 1332 |
| 290 | I | A | A | Y | I | I | R | F | K | 15 | 1333 |
| 302 | K | I | A | D | P | I | C | T | Y | 15 | 1334 |
| 313 | S | L | L | V | A | F | T | T | F | 15 | 1335 |
| 331 | I | L | E | G | V | P | S | H | L | 15 | 1336 |
| 337 | S | H | L | N | V | D | Y | I | K | 15 | 1337 |
| 404 | Y | R | C | T | I | Q | L | Q | S | 15 | 1338 |

HLA-B*2709 nonamers

| | | | | | | | | | | |
|---|---|---|---|---|---|---|---|---|---|---|
| 112 | A | R | L | T | I | A | A | V | L | 25 | 1339 |
| 295 | I | R | F | K | P | E | Y | K | I | 22 | 1340 |
| 14 | L | R | K | D | D | A | P | L | F | 21 | 1341 |
| 241 | H | R | H | S | H | S | H | S | L | 21 | 1342 |
| 271 | V | R | A | A | F | V | H | A | L | 21 | 1343 |
| 41 | S | R | F | N | K | L | R | V | V | 20 | 1344 |
| 177 | H | R | L | E | V | L | S | A | M | 20 | 1345 |
| 261 | E | R | N | H | G | Q | D | S | L | 20 | 1346 |
| 321 | F | R | I | I | W | D | T | V | V | 19 | 1347 |
| 8 | K | R | L | K | S | M | L | R | K | 16 | 1348 |
| 171 | R | F | T | F | G | F | H | R | L | 16 | 1349 |
| 402 | G | M | Y | R | C | T | I | Q | L | 16 | 1350 |
| 15 | R | K | D | D | A | P | L | F | L | 15 | 1351 |
| 287 | G | V | L | I | A | A | Y | I | I | 15 | 1352 |
| 322 | R | I | I | W | D | T | V | V | I | 15 | 1353 |
| 108 | R | K | V | K | A | R | L | T | I | 14 | 1354 |
| 155 | I | L | T | L | L | A | L | W | L | 14 | 1355 |
| 170 | K | R | F | T | F | G | F | H | R | 14 | 1356 |
| 186 | I | S | V | L | L | V | Y | I | L | 14 | 1357 |
| 205 | R | T | I | H | M | N | Y | E | I | 14 | 1358 |
| 280 | G | D | L | V | Q | S | V | G | V | 14 | 1359 |
| 38 | E | G | L | S | R | F | N | K | L | 13 | 1360 |
| 42 | R | F | N | K | L | R | V | V | V | 13 | 1361 |
| 75 | S | L | L | D | Q | D | L | P | L | 13 | 1362 |
| 102 | R | E | I | L | K | Q | R | K | V | 13 | 1363 |
| 106 | K | Q | R | K | V | K | A | R | L | 13 | 1364 |
| 114 | L | T | I | A | A | V | L | Y | L | 13 | 1365 |
| 132 | G | Y | I | A | N | S | L | A | I | 13 | 1366 |
| 153 | A | I | I | L | T | L | L | A | L | 13 | 1367 |
| 222 | A | A | V | G | V | A | V | N | V | 13 | 1368 |
| 404 | Y | R | C | T | I | Q | L | Q | S | 13 | 1369 |
| 2 | A | G | S | G | A | W | K | R | L | 12 | 1370 |
| 46 | L | R | V | V | A | D | D | G | L | 12 | 1371 |
| 82 | P | L | T | N | S | Q | L | S | L | 12 | 1372 |
| 121 | Y | L | L | F | M | I | G | E | L | 12 | 1373 |
| 130 | V | G | G | Y | I | A | N | S | L | 12 | 1374 |
| 139 | A | I | M | T | D | A | L | H | M | 12 | 1375 |
| 140 | I | M | T | D | A | L | H | M | L | 12 | 1376 |

TABLE XXII-continued

MHC Class 1 nonamer and decamer analysis of 108P5H8 for selected alleles. Listed are scores that fall within the top 50% (rounded up) of all scores for the selected allele.

| | | | | | | | | | | | |
|---|---|---|---|---|---|---|---|---|---|---|---|
| 143 | D | A | L | H | M | L | T | D | L | 12 | 1377 |
| 150 | D | L | S | A | I | I | L | T | L | 12 | 1378 |
| 174 | F | G | F | H | R | L | E | V | L | 12 | 1379 |
| 178 | R | L | E | V | L | S | A | M | I | 12 | 1380 |
| 182 | L | S | A | M | I | S | V | L | L | 12 | 1381 |
| 190 | L | V | Y | I | L | M | G | F | L | 12 | 1382 |
| 227 | A | V | N | V | I | M | G | F | L | 12 | 1383 |
| 255 | T | R | G | S | G | C | E | R | N | 12 | 1384 |
| 274 | A | F | V | H | A | L | G | D | L | 12 | 1385 |
| 281 | D | L | V | Q | S | V | G | V | L | 12 | 1386 |
| 299 | P | E | Y | K | I | A | D | P | I | 12 | 1387 |
| 307 | I | C | T | Y | V | F | S | L | L | 12 | 1388 |
| 310 | Y | V | F | S | L | L | V | A | F | 12 | 1389 |
| 324 | I | W | D | T | V | V | I | I | L | 12 | 1390 |
| 333 | E | G | V | P | S | H | L | N | V | 12 | 1391 |
| 349 | M | K | I | E | D | V | Y | S | V | 12 | 1392 |
| 352 | E | D | V | Y | S | V | E | D | L | 12 | 1393 |
| 368 | G | K | S | T | A | I | V | H | I | 12 | 1394 |
| 381 | G | S | S | S | K | W | E | E | V | 12 | 1395 |
| 388 | E | V | Q | S | K | A | N | H | L | 12 | 1396 |
| 418 | D | R | T | C | A | N | C | Q | S | 12 | 1397 |

HLA-B*5101 nonamers

| | | | | | | | | | | | |
|---|---|---|---|---|---|---|---|---|---|---|---|
| 316 | V | A | F | T | T | F | R | I | I | 26 | 1398 |
| 143 | D | A | L | H | M | L | T | D | L | 25 | 1399 |
| 222 | A | A | V | G | V | A | V | N | V | 23 | 1400 |
| 183 | S | A | M | I | S | V | L | L | V | 22 | 1401 |
| 346 | E | A | L | M | K | I | E | D | V | 22 | 1402 |
| 371 | T | A | I | V | H | I | Q | L | I | 22 | 1403 |
| 303 | I | A | D | P | I | C | T | Y | V | 21 | 1404 |
| 111 | K | A | R | L | T | I | A | A | V | 20 | 1405 |
| 126 | I | G | E | L | V | G | G | Y | I | 20 | 1406 |
| 38 | E | G | L | S | R | F | N | K | L | 18 | 1407 |
| 174 | F | G | F | H | R | L | E | V | L | 18 | 1408 |
| 199 | L | Y | E | A | V | Q | R | T | I | 18 | 1409 |
| 209 | M | N | Y | E | I | N | G | D | I | 18 | 1410 |
| 286 | V | G | V | L | I | A | A | Y | I | 18 | 1411 |
| 323 | I | I | W | D | T | V | V | I | I | 18 | 1412 |
| 18 | D | A | P | L | F | L | N | D | T | 17 | 1413 |
| 343 | Y | I | K | E | A | L | M | K | I | 17 | 1414 |
| 96 | D | N | C | S | K | Q | R | E | I | 16 | 1415 |
| 159 | L | A | L | W | L | S | S | K | S | 16 | 1416 |
| 195 | M | G | F | L | L | Y | E | A | V | 16 | 1417 |
| 221 | T | A | A | V | G | V | A | V | N | 16 | 1418 |
| 223 | A | V | G | V | A | V | N | V | I | 16 | 1419 |
| 249 | L | P | S | N | S | P | T | R | G | 16 | 1420 |
| 269 | L | A | V | R | A | A | F | V | H | 16 | 1421 |
| 281 | D | L | V | Q | S | V | G | V | L | 16 | 1422 |
| 291 | A | A | Y | I | I | R | F | K | P | 16 | 1423 |
| 295 | I | R | F | K | P | E | Y | K | I | 16 | 1424 |
| 299 | P | E | Y | K | I | A | D | P | I | 16 | 1425 |
| 305 | D | P | I | C | T | Y | V | F | S | 16 | 1426 |
| 333 | E | G | V | P | S | H | L | N | V | 16 | 1427 |
| 2 | A | G | S | G | A | W | K | R | L | 15 | 1428 |
| 19 | A | P | L | F | L | N | D | T | S | 15 | 1429 |
| 41 | S | R | F | N | K | L | R | V | V | 15 | 1430 |
| 56 | E | A | P | E | R | P | V | N | G | 15 | 1431 |
| 81 | L | P | L | T | N | S | Q | L | S | 15 | 1432 |
| 130 | V | G | G | Y | I | A | N | S | L | 15 | 1433 |
| 150 | D | L | S | A | I | I | L | T | L | 15 | 1434 |
| 277 | H | A | L | G | D | L | V | Q | S | 15 | 1435 |
| 282 | L | V | Q | S | V | G | V | L | I | 15 | 1436 |
| 365 | L | T | S | G | K | S | T | A | I | 15 | 1437 |
| 1 | M | A | G | S | G | A | W | K | R | 14 | 1438 |
| 5 | G | A | W | K | R | L | K | S | M | 14 | 1439 |
| 53 | D | G | S | E | A | P | E | R | P | 14 | 1440 |
| 108 | R | K | V | K | A | R | L | T | I | 14 | 1441 |
| 134 | I | A | N | S | L | A | I | M | T | 14 | 1442 |
| 146 | H | M | L | T | D | L | S | A | I | 14 | 1443 |
| 220 | I | T | A | A | V | G | V | A | V | 14 | 1444 |
| 226 | V | A | V | N | V | I | M | G | F | 14 | 1445 |
| 290 | I | A | A | Y | I | I | R | F | K | 14 | 1446 |
| 315 | L | V | A | F | T | T | F | R | I | 14 | 1447 |
| 322 | R | I | I | W | D | T | V | V | I | 14 | 1448 |
| 324 | I | W | D | T | V | V | I | I | L | 14 | 1449 |
| 368 | G | K | S | T | A | I | V | H | I | 14 | 1450 |
| 379 | I | P | G | S | S | S | K | W | E | 14 | 1451 |
| 400 | T | F | G | M | Y | R | C | T | I | 14 | 1452 |
| 42 | R | F | N | K | L | R | V | V | V | 13 | 1453 |
| 57 | A | P | E | R | P | V | N | G | A | 13 | 1454 |
| 80 | D | L | P | L | T | N | S | Q | L | 13 | 1455 |
| 112 | A | R | L | T | I | A | A | V | L | 13 | 1456 |
| 116 | I | A | A | V | L | Y | L | L | F | 13 | 1457 |
| 117 | A | A | V | L | Y | L | L | F | M | 13 | 1458 |
| 118 | A | V | L | Y | L | L | F | M | I | 13 | 1459 |
| 138 | L | A | I | M | T | D | A | L | H | 13 | 1460 |
| 167 | S | P | T | K | R | F | T | F | G | 13 | 1461 |
| 181 | V | L | S | A | M | I | S | V | L | 13 | 1462 |
| 185 | M | I | S | V | L | L | V | Y | I | 13 | 1463 |
| 273 | A | A | F | V | H | A | L | G | D | 13 | 1464 |
| 279 | L | G | D | L | V | Q | S | V | G | 13 | 1465 |
| 287 | G | V | L | I | A | A | Y | I | I | 13 | 1466 |
| 308 | C | T | Y | V | F | S | L | L | V | 13 | 1467 |
| 321 | F | R | I | I | W | D | T | V | V | 13 | 1468 |
| 331 | I | L | E | G | V | P | S | H | L | 13 | 1469 |
| 335 | V | P | S | H | L | N | V | D | Y | 13 | 1470 |
| 349 | M | K | I | E | D | V | Y | S | V | 13 | 1471 |

| Pos | 1 | 2 | 3 | 4 | 5 | 6 | 7 | 8 | 9 | 0 | score | SEQ. ID. No. |
|---|---|---|---|---|---|---|---|---|---|---|---|---|

HLA-A*0201 decamers

| | | | | | | | | | | | | |
|---|---|---|---|---|---|---|---|---|---|---|---|---|
| 139 | A | I | M | T | D | A | L | H | M | L | 26 | 1472 |
| 184 | A | M | I | S | V | L | L | V | Y | I | 26 | 1473 |
| 193 | I | L | M | G | F | L | L | Y | E | A | 26 | 1474 |
| 323 | I | I | W | D | T | V | V | I | I | L | 26 | 1475 |
| 348 | L | M | K | I | E | D | V | Y | S | V | 26 | 1476 |
| 198 | L | L | Y | E | A | V | Q | R | T | I | 25 | 1477 |
| 217 | I | M | L | I | T | A | A | V | G | V | 25 | 1478 |
| 12 | S | M | L | R | K | D | D | A | P | L | 24 | 1479 |
| 75 | S | L | L | D | Q | D | L | P | L | T | 24 | 1480 |
| 113 | R | L | T | I | A | A | V | L | Y | L | 24 | 1481 |
| 152 | S | A | I | I | L | T | L | L | A | L | 24 | 1482 |
| 277 | H | A | L | G | D | L | V | Q | S | V | 24 | 1483 |
| 322 | R | I | I | W | D | T | V | V | I | I | 24 | 1484 |
| 330 | I | I | L | E | G | V | P | S | H | L | 24 | 1485 |
| 114 | L | T | I | A | A | V | L | Y | L | L | 23 | 1486 |
| 121 | Y | L | L | F | M | I | G | E | L | V | 23 | 1487 |
| 150 | D | L | S | A | I | I | L | T | L | L | 23 | 1488 |
| 154 | I | I | L | T | L | L | A | L | W | L | 23 | 1489 |
| 181 | V | L | S | A | M | I | S | V | L | L | 23 | 1490 |
| 185 | M | I | S | V | L | L | V | Y | I | L | 23 | 1491 |
| 39 | G | L | S | R | F | N | K | L | R | V | 22 | 1492 |
| 219 | L | I | T | A | A | V | G | V | A | V | 22 | 1493 |
| 270 | A | V | R | A | A | F | V | H | A | L | 22 | 1494 |
| 302 | K | I | A | D | P | I | C | T | Y | V | 22 | 1495 |
| 356 | S | V | E | D | L | N | I | W | S | L | 22 | 1496 |
| 129 | L | V | G | G | Y | I | A | N | S | L | 21 | 1497 |
| 172 | F | T | F | G | F | H | R | L | E | V | 21 | 1498 |
| 189 | L | L | V | Y | I | L | M | G | F | L | 21 | 1499 |
| 222 | A | A | V | G | V | A | V | N | V | I | 21 | 1500 |
| 273 | A | A | F | V | H | A | L | G | D | L | 21 | 1501 |
| 68 | T | L | Q | A | D | D | S | L | L | L | 20 | 1502 |
| 83 | L | T | N | S | Q | L | S | L | K | V | 20 | 1503 |
| 110 | V | K | A | R | L | T | I | A | A | V | 20 | 1504 |
| 120 | L | Y | L | L | F | M | I | G | E | L | 20 | 1505 |
| 146 | H | M | L | T | D | L | S | A | I | I | 20 | 1506 |
| 147 | M | L | T | D | L | S | A | I | I | L | 20 | 1507 |
| 194 | L | M | G | F | L | L | Y | E | A | V | 20 | 1508 |
| 197 | F | L | L | Y | E | A | V | Q | R | T | 20 | 1509 |
| 218 | M | L | I | T | A | A | V | G | V | A | 20 | 1510 |
| 294 | I | I | R | F | K | P | E | Y | K | I | 20 | 1511 |
| 314 | L | L | V | A | F | T | T | F | R | I | 20 | 1512 |
| 338 | H | L | N | V | D | Y | I | K | E | A | 20 | 1513 |
| 364 | S | L | T | S | G | K | S | T | A | I | 20 | 1514 |
| 365 | L | T | S | G | K | S | T | A | I | V | 20 | 1515 |
| 370 | S | T | A | I | V | H | I | Q | L | I | 20 | 1516 |
| 144 | A | L | H | M | L | T | D | L | S | A | 19 | 1517 |
| 149 | T | D | L | S | A | I | I | L | T | L | 19 | 1518 |

TABLE XXII-continued

MHC Class 1 nonamer and decamer analysis of 108P5H8 for selected alleles. Listed are scores that fall within the top 50% (rounded up) of all scores for the selected allele.

| | | | | | | | | | | | |
|---|---|---|---|---|---|---|---|---|---|---|---|
| 182 | L | S | A | M | I | S | V | L | L | V | 19 | 1519 |
| 281 | D | L | V | Q | S | V | G | V | L | I | 19 | 1520 |
| 117 | A | A | V | L | Y | L | L | F | M | I | 18 | 1521 |
| 124 | F | M | I | G | E | L | V | G | G | Y | 18 | 1522 |
| 125 | M | I | G | E | L | V | G | G | Y | I | 18 | 1523 |
| 153 | A | I | I | L | T | L | L | A | L | W | 18 | 1524 |
| 157 | T | L | L | A | L | W | L | S | S | K | 18 | 1525 |
| 188 | V | L | L | V | Y | I | L | M | G | F | 18 | 1526 |
| 221 | T | A | A | V | G | V | A | V | N | V | 18 | 1527 |
| 326 | D | T | V | V | I | I | L | E | G | V | 18 | 1528 |
| 329 | V | I | I | L | E | G | V | P | S | H | 18 | 1529 |
| 81 | L | P | L | T | N | S | Q | L | S | L | 17 | 1530 |
| 111 | K | A | R | L | T | I | A | A | V | L | 17 | 1531 |
| 116 | I | A | A | V | L | Y | L | L | F | M | 17 | 1532 |
| 160 | A | L | W | L | S | S | K | S | P | T | 17 | 1533 |
| 180 | E | V | L | S | A | M | I | S | V | L | 17 | 1534 |
| 190 | L | V | Y | I | L | M | G | F | L | L | 17 | 1535 |
| 192 | Y | I | L | M | G | F | L | L | Y | E | 17 | 1536 |
| 227 | A | V | N | V | I | M | G | F | L | L | 17 | 1537 |
| 230 | V | I | M | G | F | L | L | N | Q | S | 17 | 1538 |
| 280 | G | D | L | V | Q | S | V | G | V | L | 17 | 1539 |
| 288 | V | L | I | A | A | Y | I | I | R | F | 17 | 1540 |
| 305 | D | P | I | C | T | Y | V | F | S | L | 17 | 1541 |
| 310 | Y | V | F | S | L | L | V | A | F | T | 17 | 1542 |
| 319 | T | T | F | R | I | L | W | D | T | V | 17 | 1543 |
| 345 | K | E | A | L | M | K | I | E | D | V | 17 | 1544 |
| 399 | N | T | F | G | M | Y | R | C | T | I | 17 | 1545 |
| 5 | G | A | W | K | R | L | K | S | M | L | 16 | 1546 |
| 133 | Y | I | A | N | S | L | A | I | M | T | 16 | 1547 |
| 137 | S | L | A | I | M | T | D | A | L | H | 16 | 1548 |
| 142 | T | D | A | L | H | M | L | T | D | L | 16 | 1549 |
| 145 | L | H | M | L | T | D | L | S | A | I | 16 | 1550 |
| 158 | L | L | A | L | W | L | S | S | K | S | 16 | 1551 |
| 208 | H | M | N | Y | E | I | N | G | D | I | 16 | 1552 |
| 211 | Y | E | I | N | G | D | I | M | L | I | 16 | 1553 |
| 215 | G | D | I | M | L | I | T | A | A | V | 16 | 1554 |
| 285 | S | V | G | V | L | I | A | A | Y | I | 16 | 1555 |
| 289 | L | I | A | A | Y | I | I | R | F | K | 16 | 1556 |
| 351 | I | E | D | V | Y | S | V | E | D | L | 16 | 1557 |
| 359 | D | L | N | I | W | S | L | T | S | G | 16 | 1558 |
| 377 | Q | L | I | P | G | S | S | S | K | W | 16 | 1559 |
| 408 | I | Q | L | Q | S | Y | R | Q | E | V | 16 | 1560 |
| 40 | L | S | R | F | N | K | L | R | V | V | 15 | 1561 |
| 41 | S | R | F | N | K | L | R | V | V | V | 15 | 1562 |
| 67 | P | T | L | Q | A | D | D | D | S | L | 15 | 1563 |
| 76 | L | L | D | Q | D | L | P | L | T | N | 15 | 1564 |
| 103 | E | I | L | K | Q | R | K | V | K | A | 15 | 1565 |
| 104 | I | L | K | Q | R | K | V | K | A | R | 15 | 1566 |
| 128 | E | L | V | G | G | Y | I | A | N | S | 15 | 1567 |
| 155 | I | L | T | L | L | A | L | W | L | S | 15 | 1568 |
| 226 | V | A | V | N | V | I | M | G | F | L | 15 | 1569 |
| 279 | L | G | D | L | V | Q | S | V | G | V | 15 | 1570 |
| 282 | L | V | Q | S | V | G | V | L | I | A | 15 | 1571 |
| 306 | P | I | C | T | Y | V | F | S | L | L | 15 | 1572 |
| 315 | L | V | A | F | T | T | F | R | I | I | 15 | 1573 |
| 342 | D | Y | I | K | E | A | L | M | K | I | 15 | 1574 |
| 347 | A | L | M | K | I | E | D | V | Y | S | 15 | 1575 |
| 367 | S | G | K | S | T | A | I | V | H | I | 15 | 1576 |
| 31 | F | S | D | E | A | G | D | E | G | L | 14 | 1577 |
| 79 | Q | D | L | P | L | T | N | S | Q | L | 14 | 1578 |
| 105 | L | K | Q | R | K | V | K | A | R | L | 14 | 1579 |
| 122 | L | L | F | M | I | G | E | L | V | G | 14 | 1580 |
| 140 | I | M | T | D | A | L | H | M | L | T | 14 | 1581 |
| 148 | L | T | D | L | S | A | I | I | L | T | 14 | 1582 |
| 177 | H | R | L | E | V | L | S | A | M | I | 14 | 1583 |
| 179 | L | E | V | L | S | A | M | I | S | V | 14 | 1584 |
| 220 | I | T | A | A | V | G | V | A | V | N | 14 | 1585 |
| 234 | F | L | L | N | Q | S | G | H | R | H | 14 | 1586 |
| 240 | G | H | R | H | S | H | S | H | S | L | 14 | 1587 |
| 262 | R | N | H | G | Q | D | S | L | A | V | 14 | 1588 |
| 268 | S | L | A | V | R | A | A | F | V | H | 14 | 1589 |
| 308 | C | T | Y | V | F | S | L | L | V | A | 14 | 1590 |
| 313 | S | L | L | V | A | F | T | T | F | R | 14 | 1591 |
| 331 | I | L | E | G | V | P | S | H | L | L | 14 | 1592 |
| 339 | L | N | V | D | Y | I | K | E | A | L | 14 | 1593 |
| 372 | A | I | V | H | I | Q | L | I | P | G | 14 | 1594 |
| 396 | L | L | L | N | T | F | G | M | Y | R | 14 | 1595 |
| 397 | L | L | N | T | F | G | M | Y | R | C | 14 | 1596 |
| 402 | G | M | Y | R | C | T | I | Q | L | Q | 14 | 1597 |
| 1 | M | A | G | S | G | A | W | K | R | L | 13 | 1598 |
| 4 | S | G | A | W | K | R | L | K | S | M | 13 | 1599 |
| 14 | L | R | K | D | D | A | P | L | F | L | 13 | 1600 |
| 22 | F | L | N | D | T | S | A | F | D | F | 13 | 1601 |
| 56 | E | A | P | E | R | P | V | N | G | A | 13 | 1602 |
| 60 | R | P | V | N | G | A | H | P | T | L | 13 | 1603 |
| 119 | V | L | Y | L | L | F | M | I | G | E | 13 | 1604 |
| 132 | G | Y | I | A | N | S | L | A | I | M | 13 | 1605 |
| 134 | I | A | N | S | L | A | I | M | T | D | 13 | 1606 |
| 136 | N | S | L | A | I | M | T | D | A | L | 13 | 1607 |
| 138 | L | A | I | M | T | D | A | L | H | M | 13 | 1608 |
| 170 | K | R | F | T | T | G | F | H | R | L | 13 | 1609 |
| 173 | T | F | G | F | H | R | L | E | V | L | 13 | 1610 |
| 187 | S | V | L | L | V | Y | I | L | M | G | 13 | 1611 |
| 212 | E | I | N | G | D | I | M | L | I | T | 13 | 1612 |
| 213 | I | N | G | D | I | M | L | I | T | A | 13 | 1613 |
| 235 | L | L | N | Q | S | G | H | R | H | S | 13 | 1614 |
| 267 | D | S | L | A | V | R | A | A | F | V | 13 | 1615 |
| 278 | A | L | G | D | L | V | Q | S | V | G | 13 | 1616 |
| 321 | F | R | I | I | W | D | T | V | V | I | 13 | 1617 |
| 332 | L | E | G | V | P | S | H | L | N | V | 13 | 1618 |
| 335 | V | P | S | H | L | N | V | D | Y | I | 13 | 1619 |
| 350 | K | I | E | D | V | Y | S | V | E | D | 13 | 1620 |
| 353 | D | V | Y | S | V | E | D | L | N | I | 13 | 1621 |
| 391 | S | K | A | N | H | L | L | L | N | T | 13 | 1622 |
| 392 | K | A | N | H | L | L | L | N | T | F | 13 | 1623 |

HLA-A*0203 decamers

| | | | | | | | | | | | |
|---|---|---|---|---|---|---|---|---|---|---|---|
| 109 | K | V | K | A | R | L | T | I | A | A | 19 | 1624 |
| 214 | N | G | D | I | M | L | I | T | A | A | 19 | 1625 |
| 265 | G | Q | D | S | L | A | V | R | A | A | 19 | 1626 |
| 283 | V | Q | S | V | G | V | L | I | A | A | 19 | 1627 |
| 110 | V | K | A | R | L | T | I | A | A | V | 17 | 1628 |
| 215 | G | D | I | M | L | I | T | A | A | V | 17 | 1629 |
| 266 | Q | D | S | L | A | V | R | A | A | F | 17 | 1630 |
| 284 | Q | S | V | G | V | L | I | A | A | Y | 17 | 1631 |
| 10 | L | K | S | M | L | R | K | D | D | A | 10 | 1632 |
| 19 | A | P | L | F | L | N | D | T | S | A | 10 | 1633 |
| 26 | T | S | A | F | D | F | S | D | E | A | 10 | 1634 |
| 42 | R | F | N | K | L | R | V | V | V | A | 10 | 1635 |
| 48 | V | V | V | A | D | D | G | S | E | A | 10 | 1636 |
| 56 | E | A | P | E | R | P | V | N | G | A | 10 | 1637 |
| 62 | V | N | G | A | H | P | T | L | Q | A | 10 | 1638 |
| 103 | E | I | L | K | Q | R | K | V | K | A | 10 | 1639 |
| 108 | R | K | V | K | A | R | L | T | I | A | 10 | 1640 |
| 126 | I | G | E | L | V | G | G | Y | I | A | 10 | 1641 |
| 130 | V | G | G | Y | I | A | N | S | L | A | 10 | 1642 |
| 135 | A | N | S | L | A | I | M | T | D | A | 10 | 1643 |
| 144 | A | L | H | M | L | T | D | L | S | A | 10 | 1644 |
| 151 | L | S | A | I | I | L | T | L | L | A | 10 | 1645 |
| 175 | G | F | H | R | L | E | V | L | S | A | 10 | 1646 |
| 193 | I | L | M | G | F | L | L | Y | E | A | 10 | 1647 |
| 213 | I | N | G | D | I | M | L | I | T | A | 10 | 1648 |
| 218 | M | L | I | T | A | A | V | G | V | A | 10 | 1649 |
| 261 | E | R | N | H | G | Q | D | S | L | A | 10 | 1650 |
| 264 | H | G | Q | D | S | L | A | V | R | A | 10 | 1651 |
| 269 | L | A | V | R | A | A | F | V | H | A | 10 | 1652 |
| 282 | L | V | Q | S | V | G | V | L | I | A | 10 | 1653 |
| 295 | I | R | F | K | P | E | G | Y | K | I | 10 | 1654 |
| 308 | C | T | Y | V | F | S | L | L | V | A | 10 | 1655 |
| 338 | H | L | N | V | D | Y | I | K | E | A | 10 | 1656 |
| 363 | W | S | L | T | S | G | K | S | T | A | 10 | 1657 |
| 384 | S | K | W | E | E | V | Q | S | K | A | 10 | 1658 |
| 413 | Y | R | Q | E | V | D | R | T | C | A | 10 | 1659 |
| 11 | K | S | M | L | R | K | D | D | A | P | 9 | 1660 |
| 20 | P | L | F | L | N | D | T | S | A | F | 9 | 1661 |
| 27 | S | A | F | D | F | S | D | E | A | G | 9 | 1662 |
| 43 | F | N | K | L | R | V | V | V | A | D | 9 | 1663 |
| 49 | V | V | A | D | D | G | S | E | A | P | 9 | 1664 |
| 57 | A | P | E | R | P | V | N | G | A | H | 9 | 1665 |
| 63 | N | G | A | H | P | T | L | Q | A | D | 9 | 1666 |

TABLE XXII-continued

MHC Class 1 nonamer and decamer analysis of 108P5H8 for selected alleles. Listed are scores that fall within the top 50% (rounded up) of all scores for the selected allele.

| Pos | 1 | 2 | 3 | 4 | 5 | 6 | 7 | 8 | 9 | Score | # |
|---|---|---|---|---|---|---|---|---|---|---|---|
| 104 | I | L | K | Q | R | K | V | K | A | R | 9 | 1667 |
| 127 | G | E | L | V | G | G | Y | I | A | N | 9 | 1668 |
| 131 | G | G | Y | I | A | N | S | L | A | I | 9 | 1669 |
| 136 | N | S | L | A | I | M | T | D | A | L | 9 | 1670 |
| 145 | L | H | M | L | T | D | L | S | A | I | 9 | 1671 |
| 152 | S | A | I | I | L | T | L | L | A | L | 9 | 1672 |
| 176 | F | H | R | L | E | V | L | S | A | M | 9 | 1673 |
| 194 | L | M | G | F | L | L | Y | E | A | V | 9 | 1674 |
| 219 | L | I | T | A | A | V | G | V | A | V | 9 | 1675 |
| 262 | R | N | H | G | Q | D | S | L | A | V | 9 | 1676 |
| 270 | A | V | R | A | A | F | V | H | A | L | 9 | 1677 |
| 296 | R | F | K | P | E | Y | K | I | A | D | 9 | 1678 |
| 309 | T | Y | V | F | S | L | L | V | A | F | 9 | 1679 |
| 339 | L | N | V | D | Y | I | K | E | A | L | 9 | 1680 |
| 364 | S | L | T | S | G | K | S | T | A | I | 9 | 1681 |
| 385 | K | W | E | E | V | Q | S | K | A | N | 9 | 1682 |
| 414 | R | Q | E | V | D | R | T | C | A | N | 9 | 1683 |

HLA-A1 decamers

| 191 | V | Y | I | L | M | G | F | L | L | Y | 27 | 1684 |
| 183 | S | A | M | I | S | V | L | L | V | Y | 24 | 1685 |
| 141 | M | T | D | A | L | H | M | L | T | D | 22 | 1686 |
| 148 | L | T | D | L | S | A | I | I | L | T | 22 | 1687 |
| 284 | Q | S | V | G | V | L | I | A | A | Y | 20 | 1688 |
| 395 | H | L | L | L | N | T | F | G | M | Y | 20 | 1689 |
| 16 | K | D | D | A | P | L | F | L | N | D | 19 | 1690 |
| 112 | A | R | L | T | I | A | A | V | L | Y | 18 | 1691 |
| 124 | F | M | I | G | E | L | V | G | G | Y | 18 | 1692 |
| 76 | L | L | D | Q | D | L | P | L | T | N | 17 | 1693 |
| 301 | Y | K | I | A | D | P | I | C | T | Y | 17 | 1694 |
| 404 | Y | R | C | T | I | Q | L | Q | S | Y | 17 | 1695 |
| 54 | G | S | E | A | P | E | R | P | V | N | 16 | 1696 |
| 70 | Q | A | D | D | D | S | L | L | D | Q | 16 | 1697 |
| 202 | A | V | Q | R | T | I | H | M | N | Y | 16 | 1698 |
| 292 | A | Y | I | I | R | F | K | P | E | Y | 16 | 1699 |
| 324 | I | W | D | T | V | V | I | I | L | E | 16 | 1700 |
| 334 | G | V | P | S | H | L | N | V | D | Y | 16 | 1701 |
| 346 | E | A | L | M | K | I | E | D | V | Y | 16 | 1702 |
| 31 | F | S | D | E | A | G | D | E | G | L | 15 | 1703 |
| 172 | F | T | F | G | F | H | R | L | E | V | 15 | 1704 |
| 210 | N | Y | E | I | N | G | D | I | M | L | 15 | 1705 |
| 303 | I | A | D | P | I | C | T | Y | V | F | 15 | 1706 |
| 32 | S | D | E | A | G | D | E | G | L | S | 14 | 1707 |
| 83 | L | T | N | S | Q | L | S | L | K | V | 14 | 1708 |
| 331 | I | L | E | G | V | P | S | H | L | N | 14 | 1709 |
| 344 | I | K | E | A | L | M | K | I | E | D | 14 | 1710 |
| 3 | G | S | G | A | W | K | R | L | K | S | 13 | 1711 |
| 23 | L | N | D | T | S | A | F | D | F | S | 13 | 1712 |
| 182 | L | S | A | M | I | S | V | L | L | V | 13 | 1713 |
| 308 | C | T | Y | V | F | S | L | L | V | A | 13 | 1714 |
| 357 | V | E | D | L | N | I | W | S | L | T | 13 | 1715 |

HLA-A26 decamers

| 180 | E | V | L | S | A | M | I | S | V | L | 30 | 1716 |
| 225 | G | V | A | V | N | V | I | M | G | F | 27 | 1717 |
| 150 | D | L | S | A | I | I | L | T | L | L | 26 | 1718 |
| 115 | T | I | A | A | V | L | Y | L | L | F | 25 | 1719 |
| 288 | V | L | I | A | A | Y | I | I | R | F | 25 | 1720 |
| 388 | E | V | Q | S | K | A | N | H | L | L | 25 | 1721 |
| 114 | L | T | I | A | A | V | L | Y | L | L | 24 | 1722 |
| 188 | V | L | L | V | Y | I | L | M | G | F | 24 | 1723 |
| 356 | S | V | E | D | L | N | I | W | S | L | 24 | 1724 |
| 34 | E | A | G | D | E | G | L | S | R | F | 23 | 1725 |
| 139 | A | I | M | T | D | A | L | H | M | L | 23 | 1726 |
| 270 | A | V | R | A | A | F | V | H | A | L | 23 | 1727 |
| 306 | P | I | C | T | Y | V | F | S | L | L | 23 | 1728 |
| 323 | I | I | W | D | T | V | V | I | I | L | 23 | 1729 |
| 334 | G | V | P | S | H | L | N | V | D | Y | 23 | 1730 |
| 395 | H | L | L | L | N | T | F | G | M | Y | 23 | 1731 |
| 20 | P | L | F | L | N | D | T | S | A | F | 22 | 1732 |
| 128 | E | L | V | G | G | Y | I | A | N | S | 22 | 1733 |
| 185 | M | I | S | V | L | L | V | Y | I | L | 22 | 1734 |
| 202 | A | V | Q | R | T | I | H | M | N | Y | 22 | 1735 |
| 212 | E | I | N | G | D | I | M | L | I | T | 22 | 1736 |
| 330 | I | I | L | E | G | V | P | S | H | L | 22 | 1737 |
| 25 | D | T | S | A | F | D | F | S | D | E | 21 | 1738 |
| 129 | L | V | G | G | Y | I | A | N | S | L | 21 | 1739 |
| 305 | D | P | I | C | T | Y | V | F | S | L | 21 | 1740 |
| 326 | D | T | V | V | I | I | L | E | G | V | 21 | 1741 |
| 13 | M | L | R | K | D | D | A | P | L | F | 20 | 1742 |
| 67 | P | T | L | Q | A | D | D | D | S | L | 20 | 1743 |
| 113 | R | L | T | I | A | A | V | L | Y | L | 20 | 1744 |
| 189 | L | L | V | Y | I | L | M | G | F | L | 20 | 1745 |
| 340 | N | V | D | Y | I | K | E | A | L | M | 20 | 1746 |
| 22 | F | L | N | D | T | S | A | F | D | F | 19 | 1747 |
| 37 | D | E | G | L | S | R | F | N | K | L | 19 | 1748 |
| 103 | E | I | L | K | Q | R | K | V | K | A | 19 | 1749 |
| 124 | F | M | I | G | E | L | V | G | G | Y | 19 | 1750 |
| 223 | A | V | G | V | A | V | N | V | I | M | 19 | 1751 |
| 359 | D | L | N | I | W | S | L | T | S | G | 19 | 1752 |
| 154 | I | I | L | T | L | L | A | L | W | L | 18 | 1753 |
| 173 | T | F | G | F | H | R | L | E | V | L | 18 | 1754 |
| 190 | L | V | Y | I | L | M | G | F | L | L | 18 | 1755 |
| 227 | A | V | N | V | I | M | G | F | L | L | 18 | 1756 |
| 284 | Q | S | V | G | V | L | I | A | A | Y | 18 | 1757 |
| 310 | Y | V | F | S | L | L | V | A | F | T | 18 | 1758 |
| 329 | V | I | I | L | E | G | V | P | S | H | 18 | 1759 |
| 353 | D | V | Y | S | V | E | D | L | N | I | 18 | 1760 |
| 68 | T | L | Q | A | D | D | D | S | L | L | 17 | 1761 |
| 72 | D | D | D | S | L | L | D | Q | D | L | 17 | 1762 |
| 147 | M | L | T | D | L | S | A | I | I | L | 17 | 1763 |
| 153 | A | I | I | L | T | L | L | A | L | W | 17 | 1764 |
| 181 | V | L | S | A | M | I | S | V | L | L | 17 | 1765 |
| 216 | D | I | M | L | I | T | A | A | V | G | 17 | 1766 |
| 229 | N | V | I | M | G | F | L | L | N | Q | 17 | 1767 |
| 230 | V | I | M | G | F | L | L | N | Q | S | 17 | 1768 |
| 322 | R | I | I | W | D | T | V | V | I | I | 17 | 1769 |
| 343 | Y | I | K | E | A | L | M | K | I | E | 17 | 1770 |
| 416 | E | V | D | R | T | C | A | N | C | Q | 17 | 1771 |
| 80 | D | L | P | L | T | N | S | Q | L | S | 16 | 1772 |
| 191 | V | Y | I | L | M | G | F | L | L | Y | 16 | 1773 |
| 205 | R | T | I | H | M | N | Y | E | I | N | 16 | 1774 |
| 220 | I | T | A | A | V | G | V | A | V | N | 16 | 1775 |
| 281 | D | L | V | Q | S | V | G | V | L | I | 16 | 1776 |
| 301 | Y | K | I | A | D | P | I | C | T | Y | 16 | 1777 |
| 309 | T | Y | V | F | S | L | L | V | A | F | 16 | 1778 |
| 346 | E | A | L | M | K | I | E | D | V | Y | 16 | 1779 |
| 370 | S | T | A | I | V | H | I | Q | L | I | 16 | 1780 |
| 373 | I | V | H | I | Q | L | I | P | G | S | 16 | 1781 |
| 387 | E | E | V | Q | S | K | A | N | H | L | 16 | 1782 |
| 404 | Y | R | C | T | I | Q | L | Q | S | Y | 16 | 1783 |
| 96 | D | N | C | S | K | Q | R | E | I | L | 15 | 1784 |
| 104 | I | L | K | Q | R | K | V | K | A | R | 15 | 1785 |
| 118 | A | V | L | Y | L | L | F | M | I | G | 15 | 1786 |
| 132 | G | Y | I | A | N | S | L | A | I | M | 15 | 1787 |
| 141 | M | T | D | A | L | H | M | L | T | D | 15 | 1788 |
| 148 | L | T | D | L | S | A | I | I | L | T | 15 | 1789 |
| 152 | S | A | I | I | L | T | L | L | A | L | 15 | 1790 |
| 168 | P | T | K | R | F | T | T | F | G | H | 15 | 1791 |
| 170 | K | R | F | T | T | F | G | F | H | R | 15 | 1792 |
| 172 | F | T | F | G | F | H | R | L | E | V | 15 | 1793 |
| 187 | S | V | L | L | V | Y | I | L | M | G | 15 | 1794 |
| 193 | I | L | M | G | F | L | L | Y | E | A | 15 | 1795 |
| 282 | L | V | Q | S | V | G | V | L | I | A | 15 | 1796 |
| 289 | L | I | A | A | Y | I | I | R | F | K | 15 | 1797 |
| 315 | L | V | A | F | T | T | T | F | R | I | I | 15 | 1798 |
| 342 | D | Y | I | K | E | A | L | M | K | I | 15 | 1799 |
| 407 | T | I | Q | L | Q | S | Y | R | Q | E | 15 | 1800 |

HLA-A3 decamers

| 157 | T | L | L | A | L | W | L | S | S | K | 29 | 1801 |
| 91 | K | V | D | S | C | D | N | C | S | K | 25 | 1802 |
| 293 | Y | I | I | R | F | K | P | E | Y | K | 25 | 1803 |
| 82 | P | L | T | N | S | Q | L | S | L | K | 24 | 1804 |
| 102 | R | E | I | L | K | Q | R | K | V | K | 23 | 1805 |
| 202 | A | V | Q | R | T | I | H | M | N | Y | 23 | 1806 |
| 268 | S | L | A | V | R | A | A | F | V | H | 23 | 1807 |
| 341 | V | D | Y | I | K | E | A | L | M | K | 22 | 1808 |
| 278 | A | L | G | D | L | V | Q | S | V | G | 21 | 1809 |
| 289 | L | I | A | A | Y | I | I | R | F | K | 21 | 1810 |

TABLE XXII-continued

MHC Class 1 nonamer and decamer analysis of 108P5H8 for selected alleles. Listed are scores that fall within the top 50% (rounded up) of all scores for the selected allele.

| | | | | | | | | | | | |
|---|---|---|---|---|---|---|---|---|---|---|---|
| 328 | V | V | I | I | L | E | G | V | P | S | 21 | 1811 |
| 377 | Q | L | I | P | G | S | S | S | K | W | 21 | 2812 |
| 395 | H | L | L | L | N | T | F | G | M | Y | 21 | 1813 |
| 396 | L | L | L | N | T | F | G | M | Y | R | 21 | 1814 |
| 13 | M | L | R | K | D | D | A | P | L | F | 20 | 1815 |
| 137 | S | L | A | I | M | T | D | A | L | H | 20 | 1816 |
| 234 | F | L | L | N | Q | S | G | H | R | H | 20 | 1817 |
| 334 | G | V | P | S | H | L | N | V | D | Y | 20 | 1818 |
| 376 | I | Q | L | I | P | G | S | S | S | K | 20 | 1819 |
| 20 | P | L | F | L | N | D | T | S | A | F | 19 | 1820 |
| 45 | K | L | R | V | V | V | A | D | D | G | 19 | 1821 |
| 154 | I | I | L | T | L | L | A | L | W | L | 19 | 1822 |
| 180 | E | V | L | S | A | M | I | S | V | L | 19 | 1823 |
| 198 | L | L | Y | E | A | V | Q | R | T | I | 19 | 1824 |
| 216 | D | I | M | L | I | T | A | A | V | G | 19 | 1825 |
| 270 | A | V | R | A | A | F | V | H | A | L | 19 | 1826 |
| 275 | F | V | H | A | L | G | D | L | V | Q | 19 | 1827 |
| 288 | V | L | I | A | A | Y | I | I | R | F | 19 | 1828 |
| 322 | R | I | I | W | D | T | V | V | I | I | 19 | 1829 |
| 22 | F | L | N | D | T | S | A | F | D | F | 18 | 1830 |
| 48 | V | V | V | A | D | D | G | S | E | A | 18 | 1831 |
| 76 | L | L | D | Q | D | L | P | L | T | N | 18 | 1832 |
| 104 | I | L | K | Q | R | K | V | K | A | R | 18 | 1833 |
| 112 | A | R | L | T | I | A | A | V | L | Y | 18 | 1834 |
| 113 | R | L | T | I | A | V | L | Y | L | F | 18 | 1835 |
| 115 | T | I | A | A | V | L | Y | L | L | F | 18 | 1836 |
| 144 | A | L | H | M | L | T | D | L | S | A | 18 | 1837 |
| 153 | A | I | I | L | T | L | L | A | L | W | 18 | 1838 |
| 178 | R | L | E | V | L | S | A | M | I | S | 18 | 1839 |
| 187 | S | V | L | L | V | Y | I | L | M | G | 18 | 1840 |
| 190 | L | V | Y | I | L | M | G | F | L | L | 18 | 1841 |
| 218 | M | L | I | T | A | A | V | G | V | A | 18 | 1842 |
| 219 | L | I | T | A | A | V | G | V | A | V | 18 | 1843 |
| 313 | S | L | L | V | A | F | T | T | F | R | 18 | 1844 |
| 329 | V | I | I | L | E | G | V | P | S | H | 18 | 1845 |
| 7 | W | K | R | L | K | S | M | L | R | K | 17 | 1846 |
| 47 | R | V | V | V | A | D | D | G | S | E | 17 | 1847 |
| 100 | K | Q | R | E | I | L | K | Q | R | K | 17 | 1848 |
| 109 | K | V | K | A | R | L | T | I | A | A | 17 | 1849 |
| 111 | K | A | R | L | T | I | A | A | V | L | 17 | 1850 |
| 122 | L | L | F | M | I | G | E | L | V | G | 17 | 1851 |
| 129 | L | V | G | G | Y | I | A | N | S | L | 17 | 1852 |
| 160 | A | L | W | L | S | S | K | S | P | T | 17 | 1853 |
| 188 | V | L | L | V | Y | I | L | M | G | F | 17 | 1854 |
| 196 | G | F | L | L | Y | E | A | V | Q | R | 17 | 1855 |
| 223 | A | V | G | V | A | V | N | V | I | M | 17 | 1856 |
| 281 | D | L | V | Q | S | V | G | V | L | I | 17 | 1857 |
| 285 | S | V | G | V | L | I | A | A | Y | I | 17 | 1858 |
| 287 | G | V | L | I | A | A | Y | I | I | R | 17 | 1859 |
| 330 | I | I | L | E | G | V | P | S | H | L | 17 | 1860 |
| 347 | A | L | M | K | I | E | D | V | Y | S | 17 | 1861 |
| 353 | D | V | Y | S | V | E | D | L | N | I | 17 | 1862 |
| 375 | H | I | Q | L | I | P | G | S | S | S | 17 | 1863 |
| 9 | R | L | K | S | M | L | R | K | D | D | 16 | 1864 |
| 39 | G | L | S | R | F | N | K | L | R | V | 16 | 1865 |
| 87 | Q | L | S | L | K | V | D | S | C | D | 16 | 1866 |
| 118 | A | V | L | Y | L | L | F | M | I | G | 16 | 1867 |
| 161 | L | W | L | S | S | K | S | P | T | K | 16 | 1868 |
| 162 | W | L | S | S | K | S | P | T | K | R | 16 | 1869 |
| 181 | V | L | S | A | M | I | S | V | L | L | 16 | 1870 |
| 225 | G | V | A | V | N | V | I | M | G | F | 16 | 1871 |
| 227 | A | V | N | V | I | M | G | F | L | L | 16 | 1872 |
| 229 | N | V | I | M | G | F | L | L | N | Q | 16 | 1873 |
| 327 | T | V | V | I | I | L | E | G | V | P | 16 | 1874 |
| 350 | K | I | E | D | V | Y | S | V | E | D | 16 | 1875 |
| 360 | L | N | I | W | S | L | T | S | G | K | 16 | 1876 |
| 409 | Q | L | Q | S | Y | R | T | Q | E | V | D | 16 | 1877 |
| 416 | E | V | D | R | T | C | A | N | C | Q | 16 | 1878 |
| 2 | A | G | S | G | A | W | K | R | L | K | 15 | 1879 |
| 33 | D | E | A | G | D | E | G | L | S | R | 15 | 1880 |
| 68 | T | L | Q | A | D | D | D | S | L | L | 15 | 1881 |
| 119 | V | L | Y | L | L | F | M | I | G | E | 15 | 1882 |
| 121 | Y | L | L | F | M | I | G | E | L | V | 15 | 1883 |
| 128 | E | L | V | G | G | Y | I | A | N | S | 15 | 1884 |
| 158 | L | L | A | L | W | L | S | S | K | S | 15 | 1885 |
| 183 | S | A | M | I | S | V | L | L | V | Y | 15 | 1886 |
| 301 | Y | K | I | A | D | P | I | C | T | Y | 15 | 1887 |
| 61 | P | V | N | G | A | H | P | T | L | Q | 14 | 1888 |
| 75 | S | L | L | D | Q | D | L | P | L | T | 14 | 1889 |
| 103 | E | I | L | K | Q | R | K | V | K | A | 14 | 1890 |
| 133 | Y | I | A | N | S | L | A | I | M | T | 14 | 1891 |
| 147 | M | L | T | D | L | S | A | I | I | L | 14 | 1892 |
| 193 | I | L | M | G | F | L | L | Y | E | A | 14 | 1893 |
| 284 | Q | S | V | G | V | L | I | A | A | Y | 14 | 1894 |
| 302 | K | I | A | D | P | I | C | T | Y | V | 14 | 1895 |
| 331 | I | L | E | G | V | P | S | H | L | N | 14 | 1896 |
| 356 | S | V | E | D | L | N | I | W | S | L | 14 | 1897 |
| 359 | D | L | N | I | W | S | L | T | S | G | 14 | 1898 |
| 383 | S | S | K | W | E | E | V | Q | S | K | 14 | 1899 |

HLA-B*0702 decamers

| | | | | | | | | | | | |
|---|---|---|---|---|---|---|---|---|---|---|---|
| 60 | R | P | V | N | G | A | H | P | T | L | 22 | 1900 |
| 81 | L | P | L | T | N | S | Q | L | S | L | 22 | 1901 |
| 305 | D | P | I | C | T | Y | V | F | S | L | 21 | 1902 |
| 19 | A | P | L | F | L | N | D | T | S | A | 19 | 1903 |
| 335 | V | P | S | H | L | N | V | D | Y | I | 19 | 1904 |
| 167 | S | P | T | K | R | F | T | F | G | F | 18 | 1905 |
| 298 | K | P | E | Y | K | I | A | D | P | I | 18 | 1906 |
| 270 | A | V | R | A | A | F | V | H | A | L | 17 | 1907 |
| 111 | K | A | R | L | T | I | A | A | V | L | 15 | 1908 |
| 181 | V | L | S | A | M | I | S | V | L | L | 15 | 1909 |
| 389 | V | Q | S | K | A | N | H | L | L | L | 15 | 1910 |
| 113 | R | L | T | I | A | A | V | L | Y | L | 14 | 1911 |
| 150 | D | L | S | A | I | I | L | T | L | L | 14 | 1912 |
| 14 | L | R | K | D | D | A | P | L | F | L | 13 | 1913 |
| 57 | A | P | E | R | P | V | N | G | A | H | 13 | 1914 |
| 74 | D | S | L | L | D | Q | D | L | P | L | 13 | 1915 |
| 129 | L | V | G | G | Y | I | A | N | S | L | 13 | 1916 |
| 136 | N | S | L | A | I | M | T | D | A | L | 13 | 1917 |
| 139 | A | I | M | T | D | A | L | H | M | L | 13 | 1918 |
| 152 | S | A | I | I | L | T | L | L | A | L | 13 | 1919 |
| 154 | I | I | L | T | L | L | A | L | W | L | 13 | 1920 |
| 185 | M | I | S | V | L | L | V | Y | I | L | 13 | 1921 |
| 249 | L | P | S | N | S | P | T | R | G | S | 13 | 1922 |
| 351 | I | E | D | V | Y | S | V | E | D | L | 13 | 1923 |
| 12 | S | M | L | R | K | D | D | A | P | L | 12 | 1924 |
| 37 | D | E | G | L | S | R | F | N | K | L | 12 | 1925 |
| 42 | R | F | N | K | L | R | V | V | V | A | 12 | 1926 |
| 142 | T | D | A | L | H | M | L | T | D | L | 12 | 1927 |
| 149 | T | D | L | S | A | I | I | L | T | L | 12 | 1928 |
| 170 | K | R | F | T | F | G | F | H | R | L | 12 | 1929 |
| 173 | T | F | G | F | H | R | L | E | V | L | 12 | 1930 |
| 180 | E | V | L | S | A | M | I | S | V | L | 12 | 1931 |
| 222 | A | A | V | G | V | A | V | N | V | I | 12 | 1932 |
| 227 | A | V | N | V | I | M | G | F | L | L | 12 | 1933 |
| 240 | G | H | R | H | S | H | S | H | S | L | 12 | 1934 |
| 260 | C | E | R | N | H | G | Q | D | S | L | 12 | 1935 |
| 262 | R | N | H | G | Q | D | S | L | A | V | 12 | 1936 |
| 273 | A | A | F | V | H | A | L | G | D | L | 12 | 1937 |
| 280 | G | D | L | V | Q | S | V | G | V | L | 12 | 1938 |
| 323 | I | I | W | D | T | V | V | I | I | L | 12 | 1939 |
| 365 | L | T | S | G | K | S | T | A | I | V | 12 | 1940 |
| 369 | K | S | T | A | I | V | H | I | Q | L | 12 | 1941 |
| 379 | I | P | G | S | S | S | K | W | E | E | 12 | 1942 |
| 401 | F | G | M | Y | R | C | T | I | Q | L | 12 | 1943 |
| 1 | M | A | G | S | G | A | W | K | R | L | 11 | 1944 |
| 5 | G | A | W | K | R | L | K | S | M | L | 11 | 1945 |
| 31 | F | S | D | E | A | G | D | E | G | L | 11 | 1946 |
| 62 | V | N | G | A | H | P | T | L | Q | A | 11 | 1947 |
| 68 | T | L | Q | A | D | D | D | S | L | L | 11 | 1948 |
| 72 | D | D | D | S | L | L | D | Q | D | L | 11 | 1949 |
| 79 | Q | D | L | P | L | T | N | S | Q | L | 11 | 1950 |
| 96 | D | N | C | S | K | Q | R | E | I | L | 11 | 1951 |
| 105 | L | K | Q | R | K | V | K | A | R | L | 11 | 1952 |
| 114 | L | T | I | A | A | V | L | Y | L | L | 11 | 1953 |
| 116 | I | A | A | V | L | Y | L | L | F | M | 11 | 1954 |
| 135 | A | N | S | L | A | I | M | T | D | A | 11 | 1955 |
| 172 | F | T | F | G | F | H | R | L | E | V | 11 | 1956 |
| 189 | L | L | V | Y | I | L | M | G | F | L | 11 | 1957 |
| 212 | E | I | N | G | D | I | M | L | I | T | 11 | 1958 |

TABLE XXII-continued

MHC Class 1 nonamer and decamer analysis of 108P5H8 for selected alleles. Listed are scores that fall within the top 50% (rounded up) of all scores for the selected allele.

| 223 | A | V | G | V | A | V | N | V | I | M | 11 | 1959 |
|---|---|---|---|---|---|---|---|---|---|---|---|---|
| 226 | V | A | V | N | V | I | M | G | F | L | 11 | 1960 |
| 266 | Q | D | S | L | A | V | R | A | A | F | 11 | 1961 |
| 303 | I | A | D | P | I | C | T | Y | V | F | 11 | 1962 |
| 306 | P | I | C | T | Y | V | F | S | L | L | 11 | 1963 |
| 330 | I | I | L | E | G | V | P | S | H | L | 11 | 1964 |
| 339 | L | N | V | D | Y | I | K | E | A | L | 11 | 1965 |
| 387 | E | E | V | Q | S | K | A | N | H | L | 11 | 1966 |
| 388 | E | V | Q | S | K | A | N | H | L | L | 11 | 1967 |

MHC Class 1 nonamer and decamer analyses of 108P5H8 flanking the D to E mutation at amino acid 30. Listed are scores that fall within the top 50% (rounded up) of all scores for a selected allele of the 108P5H8 variant 1 sequence that does not contain the mutation.

| Pos | 1 | 2 | 3 | 4 | 5 | 6 | 7 | 8 | 9 | score | SEQ. ID. No. |
|---|---|---|---|---|---|---|---|---|---|---|---|
| HLA-A*0201 nonamers | | | | | | | | | | | |
| 27 | S | A | F | E | F | S | D | E | A | 16 | 2082 |
| 22 | F | L | N | D | T | S | A | F | E | 15 | 2083 |
| HLA-A*0203 nonamers | | | | | | | | | | | |
| 27 | S | A | F | E | F | S | D | E | A | 11 | 2084 |
| 12/21 HLA-A26 nonamers | | | | | | | | | | | |
| 25 | D | T | S | A | F | E | F | S | D | 17 | 2085 |
| HLA-B*1510 nonamers | | | | | | | | | | | |
| 23 | L | N | D | T | S | A | F | E | F | 7 | 2086 |
| HLA-B*5101 nonamers | | | | | | | | | | | |
| 27 | S | A | F | E | F | S | D | E | A | 13 | 2087 |

| Pos | 1 | 2 | 3 | 4 | 5 | 6 | 7 | 8 | 9 | 0 | score | SEQ. ID. No. |
|---|---|---|---|---|---|---|---|---|---|---|---|---|
| HLA-A*0201 decamers | | | | | | | | | | | | |
| 22 | F | L | N | D | T | S | A | F | E | F | 15 | 2088 |
| HLA-A1 decamers | | | | | | | | | | | | |
| 23 | L | N | D | T | S | A | F | E | F | S | 13 | 2089 |
| HLA-A26 decamers | | | | | | | | | | | | |
| 25 | D | T | S | A | F | E | F | S | D | E | 21 | 2090 |
| 22 | F | L | N | D | T | S | A | F | E | F | 20 | 2091 |
| HLA-A3 decamers | | | | | | | | | | | | |
| 22 | F | L | N | D | T | S | A | F | E | F | 18 | 2092 |

TABLE XXIII

MHC Class II 15-mer analysis of 108P5H8 for selected alleles. Listed are scores that fall within the top 50% (rounded up) of all scores for the selected allele.

| | HLA-DRB1*0101 15 - mers | | | | | | | | | | | | | | | | SEQ. |
|---|---|---|---|---|---|---|---|---|---|---|---|---|---|---|---|---|---|
| Pos | 1 | 2 | 3 | 4 | 5 | 6 | 7 | 8 | 9 | 0 | 1 | 2 | 3 | 4 | 5 | score | ID No. |
| 326 | D | T | V | V | I | I | L | E | G | V | P | S | H | L | N | 36 | 2093 |
| 188 | V | L | L | V | Y | I | L | M | G | F | L | L | Y | E | A | 35 | 2094 |
| 145 | L | H | M | L | T | D | L | S | A | I | I | L | T | L | L | 33 | 2095 |
| 123 | L | F | M | I | G | E | L | V | G | G | Y | I | A | N | S | 32 | 2096 |
| 152 | S | A | I | I | L | T | L | L | A | L | W | L | S | S | K | 32 | 2097 |
| 176 | F | H | R | L | E | V | L | S | A | M | I | S | V | L | L | 32 | 2098 |
| 283 | V | Q | S | V | G | V | L | I | A | A | Y | I | I | R | F | 32 | 2099 |
| 119 | V | L | Y | L | L | F | M | I | G | E | L | V | G | G | Y | 31 | 2100 |
| 225 | G | V | A | V | N | V | I | M | G | F | L | L | N | Q | S | 31 | 2101 |
| 359 | D | L | N | I | W | S | L | T | S | G | K | S | T | A | I | 31 | 2102 |
| 373 | I | V | H | I | Q | L | I | P | G | S | S | S | K | W | E | 31 | 2103 |
| 318 | F | T | T | F | R | I | I | W | D | T | V | V | I | I | L | 30 | 2104 |
| 40 | L | S | R | F | N | K | L | R | V | V | V | A | D | D | G | 29 | 2105 |
| 215 | G | D | I | M | L | I | T | A | A | V | G | V | A | V | N | 29 | 2106 |
| 11 | K | S | M | L | R | K | D | D | A | P | L | F | L | N | D | 28 | 2107 |
| 179 | L | E | V | L | S | A | M | I | S | V | L | L | V | Y | I | 28 | 2108 |
| 173 | T | F | G | F | H | R | L | E | V | L | S | A | M | I | S | 27 | 2109 |
| 272 | R | A | F | V | H | A | L | G | D | L | V | Q | S | V | 27 | 2110 |
| 309 | T | Y | V | F | S | L | L | V | A | F | T | T | F | R | I | 27 | 2111 |
| 371 | T | A | I | V | H | I | Q | L | I | P | G | S | S | S | K | 27 | 2112 |
| 153 | A | I | I | L | T | L | L | A | L | W | L | S | S | K | S | 26 | 2113 |
| 325 | W | D | T | V | V | I | I | L | E | G | V | P | S | H | L | 26 | 2114 |
| 4 | S | G | A | W | K | R | L | K | S | M | L | R | K | D | 25 | 2115 |
| 20 | P | L | F | L | N | D | T | S | A | F | D | F | S | D | E | 25 | 2116 |
| 46 | L | R | V | V | V | A | D | D | G | S | E | A | P | E | R | 25 | 2117 |
| 101 | Q | R | E | I | L | K | Q | R | K | V | K | A | R | L | T | 25 | 2118 |
| 142 | T | D | A | L | H | M | L | T | D | L | S | A | I | I | L | 25 | 2119 |
| 192 | Y | I | L | M | G | F | L | L | Y | E | A | V | Q | R | T | 25 | 2120 |
| 217 | I | M | L | I | T | A | A | V | G | V | A | V | N | V | I | 25 | 2121 |
| 279 | L | G | D | L | V | Q | S | V | G | V | L | I | A | A | Y | 25 | 2122 |
| 345 | K | E | A | L | M | K | I | E | D | V | Y | S | V | E | D | 25 | 2123 |

TABLE XXIII-continued

| | | | | | | | | | | | | | | | |
|---|---|---|---|---|---|---|---|---|---|---|---|---|---|---|---|
| 392 | K | A | N | H | L | L | L | N | T | F | G | M | Y | R | C | 25 | 2124 |
| 43 | F | N | K | L | R | V | V | V | A | D | D | G | S | E | A | 24 | 2125 |
| 56 | E | A | P | E | R | P | V | N | G | A | H | P | T | L | Q | 24 | 2126 |
| 124 | F | M | I | G | E | L | V | G | G | Y | I | A | N | S | L | 24 | 2127 |
| 127 | G | E | L | V | G | G | Y | I | A | N | S | L | A | I | M | 24 | 2128 |
| 156 | L | T | L | L | A | L | W | L | S | S | K | S | P | T | K | 24 | 2129 |
| 183 | S | A | M | I | S | V | L | L | V | Y | I | L | M | G | F | 24 | 2130 |
| 284 | Q | S | V | G | V | L | I | A | A | Y | Y | I | R | F | K | 24 | 2131 |
| 354 | V | Y | S | V | E | D | L | N | I | W | S | L | T | S | G | 24 | 2132 |
| 362 | I | W | S | L | T | S | G | K | S | T | A | I | V | H | I | 24 | 2133 |
| 18 | D | A | P | L | F | L | N | D | T | S | A | F | D | F | S | 23 | 2134 |
| 47 | R | V | V | V | A | D | D | G | S | E | A | P | E | R | P | 23 | 2135 |
| 78 | D | Q | D | L | P | L | T | N | S | Q | L | S | L | K | V | 23 | 2136 |
| 107 | Q | R | K | V | K | A | R | L | T | I | A | A | V | L | Y | 23 | 2137 |
| 148 | L | T | D | L | S | A | I | I | L | T | L | L | A | L | W | 23 | 2138 |
| 149 | T | D | L | S | A | I | I | L | T | L | L | A | L | W | L | 23 | 2139 |
| 157 | T | L | L | A | L | W | L | S | S | K | S | P | T | K | R | 23 | 2140 |
| 187 | S | V | L | L | V | Y | I | L | M | G | F | L | L | Y | E | 23 | 2141 |
| 213 | I | N | G | D | I | M | L | I | T | A | A | V | G | V | A | 23 | 2142 |
| 214 | N | G | D | I | M | L | I | T | A | A | V | G | V | A | V | 23 | 2143 |
| 277 | H | A | L | G | D | L | V | Q | S | V | G | V | L | I | A | 23 | 2144 |
| 280 | G | D | L | V | Q | S | V | G | V | L | I | A | A | Y | I | 23 | 2145 |
| 312 | F | S | L | L | V | A | F | T | T | F | R | I | I | W | D | 23 | 2146 |
| 351 | I | E | D | V | Y | S | V | E | D | L | N | I | W | S | L | 23 | 2147 |
| 383 | S | S | K | W | E | E | V | Q | S | K | A | N | H | L | L | 23 | 2148 |
| 81 | L | P | L | T | N | S | Q | L | S | L | K | V | D | S | C | 22 | 2149 |
| 113 | R | L | T | I | A | A | V | L | Y | L | L | F | M | I | G | 22 | 2150 |
| 144 | A | L | H | M | L | T | D | L | S | A | I | I | L | T | L | 22 | 2151 |
| 182 | L | S | A | M | I | S | V | L | L | V | Y | I | L | M | G | 22 | 2152 |
| 207 | I | H | M | N | Y | E | I | N | G | D | I | M | L | I | T | 22 | 2153 |
| 208 | H | M | N | Y | E | I | N | G | D | I | M | L | I | T | A | 22 | 2154 |
| 232 | M | G | F | L | L | N | Q | S | G | H | R | H | S | H | S | 22 | 2155 |
| 243 | H | S | H | S | H | S | L | P | S | N | S | P | T | R | G | 22 | 2156 |
| 265 | G | Q | D | S | L | A | V | R | A | A | F | V | H | A | L | 22 | 2157 |
| 328 | V | V | I | I | L | E | G | V | P | S | H | L | N | V | D | 22 | 2158 |
| 338 | H | L | N | V | D | Y | I | K | E | A | L | M | K | I | E | 22 | 2159 |
| 372 | A | I | V | H | I | Q | L | I | P | G | S | S | S | K | W | 22 | 2160 |
| 99 | S | K | Q | R | E | I | L | K | Q | R | K | V | K | A | R | 21 | 2161 |
| 305 | D | P | I | C | T | Y | V | F | S | L | L | V | A | F | T | 21 | 2162 |
| 340 | N | V | D | Y | I | K | E | A | L | M | K | I | E | D | V | 21 | 2163 |
| 111 | K | A | R | L | T | I | A | A | V | L | Y | L | L | F | M | 20 | 2164 |
| 134 | I | A | N | S | L | A | I | M | T | D | A | L | H | M | L | 20 | 2165 |
| 141 | M | T | D | A | L | H | M | L | T | D | L | S | A | I | I | 20 | 2166 |
| 175 | G | F | H | R | L | E | V | L | S | A | M | I | S | V | L | 20 | 2167 |
| 194 | L | M | G | F | L | L | Y | E | A | V | Q | R | T | I | H | 20 | 2168 |
| 198 | L | L | Y | E | A | V | Q | R | T | I | H | M | N | Y | E | 20 | 2169 |
| 260 | C | E | R | N | H | G | Q | D | S | L | A | V | R | A | A | 20 | 2170 |
| 292 | A | Y | I | I | R | F | K | P | E | Y | K | I | A | D | P | 20 | 2171 |
| 298 | K | P | E | Y | K | I | A | D | P | I | C | T | Y | V | F | 20 | 2172 |
| 301 | Y | K | I | A | D | P | I | C | T | Y | V | F | S | L | L | 20 | 2173 |
| 307 | I | C | T | Y | V | F | S | L | L | V | A | F | T | T | F | 20 | 2174 |
| 329 | V | I | I | L | E | G | V | P | S | H | L | N | V | D | Y | 20 | 2175 |
| 346 | E | A | L | M | K | I | E | D | V | Y | S | V | E | D | L | 20 | 2176 |
| 348 | L | M | K | I | E | D | V | Y | S | V | E | D | L | N | I | 20 | 2177 |
| 356 | S | V | E | D | L | N | I | W | S | L | T | S | G | K | S | 20 | 2178 |
| 360 | L | N | I | W | S | L | T | S | G | K | S | T | A | I | V | 20 | 2179 |
| 401 | F | G | M | Y | R | C | T | I | Q | L | Q | S | Y | R | Q | 20 | 2180 |
| 104 | I | L | K | Q | R | K | V | K | A | R | L | T | I | A | A | 19 | 2181 |
| 109 | K | V | K | A | R | L | T | I | A | A | V | L | Y | L | L | 19 | 2182 |
| 117 | A | A | V | L | Y | L | L | F | M | I | G | E | L | V | G | 19 | 2183 |
| 118 | A | V | L | Y | L | L | F | M | I | G | E | L | V | G | G | 19 | 2184 |
| 150 | D | L | S | A | I | I | L | T | L | L | A | L | W | L | S | 19 | 2185 |
| 165 | S | K | S | P | T | K | R | F | T | F | G | F | H | R | L | 19 | 2186 |
| 171 | R | F | T | F | G | F | H | R | L | E | V | L | S | A | M | 19 | 2187 |
| 233 | G | F | L | L | N | Q | S | G | H | R | H | S | H | S | H | 19 | 2188 |
| 17 | D | D | A | P | L | F | L | N | D | T | S | A | F | D | F | 18 | 2189 |
| 28 | A | F | D | F | S | D | E | A | G | D | E | G | L | S | R | 18 | 2190 |
| 130 | V | G | G | Y | I | A | N | S | L | A | I | M | T | D | A | 18 | 2191 |
| 184 | A | M | I | S | V | L | L | V | Y | I | L | M | G | F | L | 18 | 2192 |
| 186 | I | S | V | L | L | V | Y | I | L | M | G | F | L | L | Y | 18 | 2193 |
| 189 | L | L | V | Y | I | L | M | G | F | L | L | Y | E | A | V | 18 | 2194 |
| 212 | E | I | N | G | D | I | M | L | I | T | A | A | V | G | V | 18 | 2195 |
| 223 | A | V | G | V | A | V | N | V | I | M | G | F | L | L | N | 18 | 2196 |
| 268 | S | L | A | V | R | A | A | F | V | H | A | L | G | D | L | 18 | 2197 |
| 313 | S | L | L | V | A | F | T | T | F | R | I | I | W | D | T | 18 | 2198 |
| 336 | P | S | H | L | N | V | D | Y | I | K | E | A | L | M | K | 18 | 2199 |

TABLE XXIII-continued

| | HLA-DRB1*0301 (DR17) 15 - mers | | | | | | | | | | | | | | | SEQ. |
|---|---|---|---|---|---|---|---|---|---|---|---|---|---|---|---|---|
| Pos | 1 | 2 | 3 | 4 | 5 | 6 | 7 | 8 | 9 | 0 | 1 | 2 | 3 | 4 | 5 | score | ID. No. |
| 11 | K | S | M | L | R | K | D | D | A | P | L | F | L | N | D | 30 | 2200 |
| 66 | H | P | T | L | Q | A | D | D | D | S | L | L | D | Q | D | 29 | 2201 |
| 137 | S | L | A | I | M | T | D | A | L | H | M | L | T | D | L | 28 | 2202 |
| 332 | L | E | G | V | P | S | H | L | N | V | D | Y | I | K | E | 27 | 2203 |
| 386 | W | E | E | V | Q | S | K | A | N | H | L | L | L | N | T | 26 | 2204 |
| 144 | A | L | H | M | L | T | D | L | S | A | I | I | L | T | L | 24 | 2205 |
| 87 | Q | L | S | L | K | V | D | S | C | D | N | C | S | K | Q | 23 | 2206 |
| 47 | R | V | V | V | A | D | D | G | S | E | A | P | E | R | P | 22 | 2207 |
| 72 | D | D | D | S | L | L | D | Q | D | L | P | L | T | N | S | 22 | 2208 |
| 74 | D | S | L | L | D | Q | D | L | P | L | T | N | S | Q | L | 22 | 2209 |
| 152 | S | A | I | I | L | T | L | L | A | L | W | L | S | S | K | 22 | 2210 |
| 320 | T | F | R | I | I | W | D | T | V | V | I | I | L | E | G | 22 | 2211 |
| 10 | L | K | S | M | L | R | K | D | D | A | P | L | F | L | N | 21 | 2212 |
| 19 | A | P | L | F | L | N | D | T | S | A | F | D | F | S | D | 21 | 2213 |
| 46 | L | R | V | V | V | A | D | D | G | S | E | A | P | E | R | 21 | 2214 |
| 113 | R | L | T | I | A | A | V | L | Y | L | L | F | M | I | G | 21 | 2215 |
| 178 | R | L | E | V | L | S | A | M | I | S | V | L | L | V | Y | 21 | 2216 |
| 210 | N | Y | E | I | N | G | D | I | M | L | I | T | A | A | V | 21 | 2217 |
| 328 | V | V | I | I | L | E | G | V | P | S | H | L | N | V | D | 21 | 2218 |
| 393 | A | N | H | L | L | L | N | T | F | G | M | Y | R | C | T | 21 | 2219 |
| 12 | S | M | L | R | K | D | D | A | P | L | F | L | N | D | T | 20 | 2220 |
| 18 | D | A | P | L | F | L | N | D | T | S | A | F | D | F | S | 20 | 2221 |
| 101 | Q | R | E | I | L | K | Q | R | K | V | K | A | R | L | T | 20 | 2222 |
| 111 | K | A | R | L | T | I | A | A | V | L | Y | L | L | F | M | 20 | 2223 |
| 122 | L | L | F | M | I | G | E | L | V | G | G | Y | I | A | N | 20 | 2224 |
| 145 | L | H | M | L | T | D | L | S | A | I | I | L | T | L | L | 20 | 2225 |
| 179 | L | E | V | L | S | A | M | I | S | V | L | L | V | Y | I | 20 | 2226 |
| 186 | I | S | V | L | L | V | Y | I | L | M | G | F | L | L | Y | 20 | 2227 |
| 187 | S | V | L | L | V | Y | I | L | M | G | F | L | L | Y | E | 20 | 2228 |
| 268 | S | L | A | V | R | A | A | F | V | H | A | L | G | D | L | 20 | 2229 |
| 299 | P | E | Y | K | I | A | D | P | I | C | T | Y | V | F | S | 20 | 2230 |
| 336 | P | S | H | L | N | V | D | Y | I | K | E | A | L | M | K | 20 | 2231 |
| 7 | W | K | R | L | K | S | M | L | R | K | D | D | A | P | L | 19 | 2232 |
| 20 | P | L | F | L | N | D | T | S | A | F | D | F | S | D | E | 19 | 2233 |
| 120 | L | Y | L | L | F | M | I | G | E | L | V | G | G | Y | I | 19 | 2234 |
| 127 | G | E | L | V | G | G | Y | I | A | N | S | L | A | I | M | 19 | 2235 |
| 148 | L | T | D | L | S | A | I | I | L | T | L | L | A | L | W | 19 | 2236 |
| 183 | S | A | M | I | S | V | L | L | V | Y | I | L | M | G | F | 19 | 2237 |
| 188 | V | L | L | V | Y | I | L | M | G | F | L | L | Y | E | A | 19 | 2238 |
| 200 | Y | E | A | V | Q | R | T | I | H | M | N | Y | E | I | N | 19 | 2239 |
| 225 | G | V | A | V | N | V | I | M | G | F | L | L | N | Q | S | 19 | 2240 |
| 286 | V | G | V | L | I | A | Y | I | I | R | F | K | P | E | 19 | 2241 |
| 292 | A | Y | I | I | R | F | K | P | E | Y | K | I | A | D | P | 19 | 2242 |
| 304 | A | D | P | I | C | T | Y | V | F | S | L | L | V | A | F | 19 | 2243 |
| 338 | H | L | N | V | D | Y | I | K | E | A | L | M | K | I | E | 19 | 2244 |
| 353 | D | V | Y | S | V | E | D | L | N | I | W | S | L | T | S | 19 | 2245 |
| 79 | Q | D | L | P | L | T | N | S | Q | L | S | L | K | V | D | 18 | 2246 |
| 158 | L | L | A | L | W | L | S | S | K | S | P | T | K | R | F | 18 | 2247 |
| 204 | Q | R | T | I | H | M | N | Y | E | I | N | G | D | I | M | 18 | 2248 |
| 223 | A | V | G | V | A | V | N | V | I | M | G | F | L | L | N | 18 | 2249 |
| 229 | N | V | I | M | G | F | L | L | N | Q | S | G | H | R | H | 18 | 2250 |
| 321 | F | R | I | I | W | D | T | V | V | I | I | L | E | G | V | 18 | 2251 |
| 325 | W | D | T | V | V | I | I | L | E | G | V | P | S | H | L | 18 | 2252 |
| 354 | V | Y | S | V | E | D | L | N | I | W | S | L | T | S | G | 18 | 2253 |
| 37 | D | E | G | L | S | R | F | N | K | L | R | V | V | V | A | 17 | 2254 |
| 77 | L | D | Q | D | L | P | L | T | N | S | Q | L | S | L | K | 17 | 2255 |
| 89 | S | L | K | V | D | S | C | D | N | C | S | K | Q | R | E | 17 | 2256 |
| 196 | G | F | L | L | Y | E | A | V | Q | R | T | I | H | M | N | 17 | 2257 |
| 221 | T | A | A | V | G | V | A | V | N | V | I | M | G | F | L | 17 | 2258 |
| 264 | H | G | Q | D | S | L | A | V | R | A | A | F | V | H | A | 17 | 2259 |
| 294 | I | I | R | F | K | P | E | Y | K | I | A | D | P | I | C | 17 | 2260 |
| 344 | I | K | E | A | L | M | K | I | E | D | V | Y | S | V | E | 17 | 2261 |
| 407 | T | I | Q | L | Q | S | Y | R | Q | E | V | D | R | T | C | 17 | 2262 |
| 163 | L | S | S | K | S | P | T | K | R | F | T | F | G | F | H | 16 | 2263 |
| 171 | R | F | T | F | G | F | H | R | L | E | V | L | S | A | M | 16 | 2264 |
| 206 | T | I | H | M | N | Y | E | I | N | G | D | I | M | L | I | 16 | 2265 |
| 258 | S | G | C | E | R | N | H | G | Q | D | S | L | A | V | R | 16 | 2266 |
| 276 | V | H | A | L | G | D | L | V | Q | S | V | G | V | L | I | 16 | 2267 |
| 337 | S | H | L | N | V | D | Y | I | K | E | A | L | M | K | I | 16 | 2268 |
| 3 | G | S | G | A | W | K | R | L | K | S | M | L | R | K | D | 15 | 2269 |
| 26 | T | S | A | F | D | F | S | D | E | A | G | D | S | G | L | 15 | 2270 |
| 94 | S | C | D | N | C | S | K | Q | R | E | I | L | K | Q | R | 15 | 2271 |
| 103 | E | I | L | K | Q | R | K | V | K | A | R | L | T | I | A | 15 | 2272 |

TABLE XXIII-continued

| Pos | 1 | 2 | 3 | 4 | 5 | 6 | 7 | 8 | 9 | 0 | 1 | 2 | 3 | 4 | 5 | score | SEQ. ID. No. |
|---|---|---|---|---|---|---|---|---|---|---|---|---|---|---|---|---|---|
| 151 | L | S | A | I | I | L | T | L | L | A | L | W | L | S | S | 15 | 2273 |
| 290 | I | A | A | Y | I | I | R | F | K | P | E | Y | K | I | A | 15 | 2274 |

| HLA-DRB1*0401 (DR4Dw4) 15 - mers | | | | | | | | | | | | | | | | | SEQ. |
|---|---|---|---|---|---|---|---|---|---|---|---|---|---|---|---|---|---|
| Pos | 1 | 2 | 3 | 4 | 5 | 6 | 7 | 8 | 9 | 0 | 1 | 2 | 3 | 4 | 5 | score | ID. No. |
| 383 | S | S | K | W | E | V | Q | S | K | A | N | H | L | L | | 28 | 2275 |
| 138 | L | A | I | M | T | D | A | L | H | M | L | T | D | L | S | 26 | 2276 |
| 144 | A | L | H | M | L | T | D | L | S | A | I | I | L | T | L | 26 | 2277 |
| 196 | G | F | L | L | Y | E | A | V | Q | R | T | I | H | M | N | 26 | 2278 |
| 206 | T | I | H | M | N | Y | E | I | N | G | D | I | M | L | I | 26 | 2279 |
| 221 | T | A | A | V | G | V | A | V | N | V | I | M | G | F | L | 26 | 2280 |
| 312 | F | S | L | L | V | A | F | T | T | F | R | I | I | W | D | 26 | 2281 |
| 329 | V | I | I | L | E | G | V | P | S | H | L | N | V | D | Y | 26 | 2282 |
| 359 | D | L | N | I | W | S | L | T | S | G | K | S | T | A | I | 26 | 2283 |
| 4 | S | G | A | W | K | R | L | K | S | M | L | R | K | D | D | 22 | 2284 |
| 19 | A | P | L | F | L | N | D | T | S | A | F | D | F | S | D | 22 | 2285 |
| 40 | L | S | R | F | N | K | L | R | V | V | V | A | D | D | G | 22 | 2286 |
| 118 | A | V | L | Y | L | L | F | M | I | G | E | L | V | G | G | 22 | 2287 |
| 159 | L | A | L | W | L | S | S | K | S | P | T | K | R | F | T | 22 | 2288 |
| 173 | T | F | G | F | H | R | L | E | V | L | S | A | M | I | S | 22 | 2289 |
| 197 | F | L | L | Y | E | A | V | Q | R | T | I | H | M | N | Y | 22 | 2290 |
| 272 | R | A | A | F | V | H | A | L | G | D | L | V | Q | S | V | 22 | 2291 |
| 298 | K | P | E | Y | K | I | A | D | P | I | C | T | Y | V | F | 22 | 2292 |
| 309 | T | Y | V | F | S | L | L | V | A | F | T | T | F | R | I | 22 | 2293 |
| 318 | F | T | T | F | R | I | I | W | D | T | V | V | I | I | L | 22 | 2294 |
| 340 | N | V | D | Y | I | K | E | A | L | M | K | I | E | D | V | 22 | 2295 |
| 401 | F | G | M | Y | R | C | T | I | Q | L | Q | S | Y | R | Q | 22 | 2296 |
| 37 | D | E | G | L | S | R | F | N | K | L | R | V | V | V | A | 20 | 2297 |
| 46 | L | R | V | V | V | A | D | D | G | S | E | A | P | E | R | 20 | 2298 |
| 47 | R | V | V | V | A | D | D | G | S | E | A | P | E | R | P | 20 | 2299 |
| 59 | E | R | P | V | N | G | A | H | P | T | L | Q | A | D | D | 20 | 2300 |
| 66 | H | P | T | L | Q | A | D | D | D | S | L | L | D | Q | D | 20 | 2301 |
| 74 | D | S | L | L | D | Q | D | L | P | L | T | N | S | Q | L | 20 | 2302 |
| 78 | D | Q | D | L | P | L | T | N | S | Q | L | S | L | K | V | 20 | 2303 |
| 89 | S | L | K | V | D | S | C | D | N | C | S | K | Q | R | E | 20 | 2304 |
| 111 | K | A | R | L | T | I | A | A | V | L | Y | L | L | F | M | 20 | 2305 |
| 123 | L | F | M | I | G | E | L | V | G | G | Y | I | A | N | S | 20 | 2306 |
| 137 | S | L | A | I | M | T | D | A | L | H | M | L | T | D | L | 20 | 2307 |
| 142 | T | D | A | L | H | M | L | T | D | L | S | A | I | I | L | 20 | 2308 |
| 145 | L | H | M | L | T | D | L | S | A | I | I | L | T | L | L | 20 | 2309 |
| 148 | L | T | D | L | S | A | I | I | L | T | L | L | A | L | W | 20 | 2310 |
| 152 | S | A | I | I | L | T | L | L | A | L | W | L | S | S | K | 20 | 2311 |
| 153 | A | I | I | L | T | L | L | A | L | W | L | S | S | K | S | 20 | 2312 |
| 155 | I | L | T | L | L | A | L | W | L | S | S | K | S | P | T | 20 | 2313 |
| 156 | L | T | L | L | A | L | W | L | S | S | K | S | P | T | K | 20 | 2314 |
| 176 | F | H | R | L | E | V | L | S | A | M | I | S | V | L | L | 20 | 2315 |
| 178 | R | L | E | V | L | S | A | M | I | S | V | L | L | V | Y | 20 | 2316 |
| 179 | L | E | V | L | S | A | M | I | S | V | L | L | V | Y | I | 20 | 2317 |
| 182 | L | S | A | M | I | S | V | L | L | V | Y | I | L | M | G | 20 | 2318 |
| 183 | S | A | M | I | S | V | L | L | V | Y | I | L | M | G | F | 20 | 2319 |
| 187 | S | V | L | L | V | Y | I | L | M | G | F | L | L | Y | E | 20 | 2320 |
| 188 | V | L | L | V | Y | I | L | M | G | F | L | L | Y | E | A | 20 | 2321 |
| 191 | V | Y | I | L | M | G | F | L | L | Y | E | A | V | Q | R | 20 | 2322 |
| 192 | Y | I | L | M | G | F | L | L | Y | E | A | V | Q | R | T | 20 | 2323 |
| 195 | M | G | F | L | L | Y | E | A | V | Q | R | T | I | H | M | 20 | 2324 |
| 210 | N | Y | E | I | N | G | D | I | M | L | I | T | A | A | V | 20 | 2325 |
| 216 | D | I | M | L | I | T | A | A | V | G | V | A | V | N | V | 20 | 2326 |
| 217 | I | M | L | I | T | A | A | V | G | V | A | V | N | V | I | 20 | 2327 |
| 225 | G | V | A | V | N | V | I | M | G | F | L | L | N | Q | S | 20 | 2328 |
| 228 | V | N | V | I | M | G | F | L | L | N | Q | S | G | H | R | 20 | 2329 |
| 229 | N | V | I | M | G | F | L | L | N | Q | S | G | H | R | H | 20 | 2330 |
| 233 | G | F | L | L | N | Q | S | G | H | R | H | S | H | S | H | 20 | 2331 |
| 268 | S | L | A | V | R | A | A | F | V | H | A | L | G | D | L | 20 | 2332 |
| 273 | A | A | F | V | H | A | L | G | D | L | V | Q | S | V | G | 20 | 2333 |
| 276 | V | H | A | L | G | D | L | V | Q | S | V | G | V | L | I | 20 | 2334 |
| 280 | G | D | L | V | Q | S | V | G | V | L | I | A | A | Y | I | 20 | 2335 |
| 283 | V | Q | S | V | G | V | L | I | A | A | Y | I | I | R | F | 20 | 2336 |
| 291 | A | A | Y | I | I | R | F | K | P | E | Y | K | I | A | D | 20 | 2337 |
| 308 | C | T | Y | V | F | S | L | L | V | A | F | T | T | F | R | 20 | 2338 |
| 311 | V | F | S | L | L | V | A | F | T | T | F | R | I | I | W | 20 | 2339 |
| 320 | T | F | R | I | I | W | D | T | V | V | I | I | L | E | G | 20 | 2340 |
| 326 | D | T | V | V | I | I | L | E | G | V | P | S | H | L | N | 20 | 2341 |
| 336 | P | S | H | L | N | V | D | Y | I | K | E | A | L | M | K | 20 | 2342 |
| 338 | H | L | N | V | D | Y | I | K | E | A | L | M | K | I | E | 20 | 2343 |
| 345 | K | E | A | L | M | K | I | E | D | V | Y | S | V | E | D | 20 | 2344 |
| 346 | E | A | L | M | K | I | E | D | V | Y | S | V | E | D | L | 20 | 2345 |
| 348 | L | M | K | I | E | D | V | Y | S | V | E | D | L | N | I | 20 | 2346 |

TABLE XXIII-continued

| | | | | | | | | | | | | | | | |
|---|---|---|---|---|---|---|---|---|---|---|---|---|---|---|---|
| 351 | I | E | D | V | Y | S | V | E | D | L | N | I | W | S | L | 20 | 2347 |
| 354 | V | Y | S | V | E | D | L | N | I | W | S | L | T | S | G | 20 | 2348 |
| 362 | I | W | S | L | T | S | G | K | S | T | A | I | V | H | I | 20 | 2349 |
| 373 | I | V | H | I | Q | L | I | P | G | S | S | S | K | W | E | 20 | 2350 |
| 16 | K | D | D | A | P | L | F | L | N | D | T | S | A | F | D | 18 | 2351 |
| 24 | N | D | T | S | A | F | D | F | S | D | E | A | G | D | E | 18 | 2352 |
| 34 | E | A | G | D | E | G | L | S | R | F | N | K | L | R | V | 18 | 2353 |
| 77 | L | D | Q | D | L | P | L | T | N | S | Q | L | S | L | K | 18 | 2354 |
| 86 | S | Q | L | S | L | K | V | D | S | C | D | N | C | S | K | 18 | 2355 |
| 99 | S | K | Q | R | E | I | L | K | Q | R | K | V | K | A | R | 18 | 2356 |
| 128 | E | L | V | G | G | Y | I | A | N | S | L | A | I | M | T | 18 | 2357 |
| 129 | L | V | G | G | Y | I | A | N | S | L | A | I | M | T | D | 18 | 2358 |
| 134 | I | A | N | S | L | A | I | M | T | D | A | L | H | M | L | 18 | 2359 |
| 149 | T | D | L | S | A | I | I | L | T | L | L | A | L | W | L | 18 | 2360 |
| 170 | K | R | F | T | F | G | F | H | R | L | E | V | L | S | A | 18 | 2361 |
| 175 | G | F | H | R | L | E | V | L | S | A | M | I | S | V | L | 18 | 2362 |
| 213 | I | N | G | D | I | M | L | I | T | A | A | V | G | V | A | 18 | 2363 |
| 255 | T | R | G | S | G | C | E | R | N | H | G | Q | D | S | L | 18 | 2364 |
| 277 | H | A | L | G | D | L | V | Q | S | V | G | V | L | I | A | 18 | 2365 |
| 305 | D | P | I | C | T | Y | V | F | S | L | L | V | A | F | T | 18 | 2366 |
| 353 | D | V | Y | S | V | E | D | L | N | I | W | S | L | T | S | 18 | 2367 |
| 356 | S | V | E | D | L | N | I | W | S | L | T | S | G | K | S | 18 | 2368 |
| 367 | S | G | K | S | T | A | I | V | H | I | Q | L | I | P | G | 18 | 2369 |
| 382 | S | S | S | K | W | E | E | V | Q | S | K | A | N | H | L | 18 | 2370 |
| 387 | E | E | V | Q | S | K | A | N | H | L | L | L | N | T | F | 18 | 2371 |
| 392 | K | A | N | H | L | L | L | N | T | F | G | M | Y | R | C | 18 | 2372 |
| 404 | Y | R | C | T | I | Q | L | Q | S | Y | R | Q | E | V | D | 18 | 2373 |
| 411 | Q | S | Y | R | Q | E | V | D | R | T | C | A | N | C | Q | 18 | 2374 |
| 412 | S | Y | R | Q | E | V | D | R | T | C | A | N | C | Q | S | 18 | 2375 |
| 28 | A | F | D | F | S | D | E | A | G | D | E | G | L | S | R | 16 | 2376 |
| 130 | V | G | G | Y | I | A | N | S | L | A | I | M | T | D | A | 16 | 2377 |
| 169 | T | K | R | F | T | F | G | F | H | R | L | E | V | L | S | 16 | 2378 |
| 171 | R | F | T | F | G | F | H | R | L | E | V | L | S | A | M | 16 | 2379 |
| 208 | H | M | N | Y | E | I | N | G | D | I | M | L | I | T | A | 16 | 2380 |
| 231 | I | M | G | F | L | L | N | Q | S | G | H | R | H | S | H | 16 | 2381 |
| 294 | I | I | R | F | K | P | E | Y | K | I | A | D | P | I | C | 16 | 2382 |
| 315 | L | V | A | F | T | T | F | R | I | I | W | D | T | V | V | 16 | 2383 |
| 322 | R | I | I | W | D | T | V | V | I | I | L | E | G | V | P | 16 | 2384 |
| 352 | E | D | V | Y | S | V | E | D | L | N | I | W | S | L | T | 16 | 2385 |
| 360 | L | N | I | W | S | L | T | S | G | K | S | T | A | I | V | 16 | 2386 |
| 398 | L | N | T | F | G | M | Y | R | C | T | I | Q | L | Q | S | 16 | 2387 |
| 410 | L | Q | S | Y | R | Q | E | V | D | R | T | C | A | N | C | 16 | 2388 |
| 107 | Q | R | K | V | K | A | R | L | T | I | A | A | V | L | Y | 15 | 2389 |
| 386 | W | E | E | V | Q | S | K | A | N | H | L | L | L | N | T | 15 | 2390 |
| 7 | W | K | R | L | K | S | M | L | R | K | D | D | A | P | L | 14 | 2391 |
| 11 | K | S | M | L | R | K | D | D | A | P | L | F | L | N | D | 14 | 2392 |
| 18 | D | A | P | L | F | L | N | D | T | S | A | F | D | F | S | 14 | 2393 |
| 43 | F | N | K | L | R | V | V | V | A | D | D | G | S | E | A | 14 | 2394 |
| 45 | K | L | R | V | V | V | A | D | D | G | S | E | A | P | E | 14 | 2395 |
| 73 | D | D | S | L | L | D | Q | D | L | P | L | T | N | S | Q | 14 | 2396 |
| 80 | D | L | P | L | T | N | S | Q | L | S | L | K | V | D | S | 14 | 2397 |
| 87 | Q | L | S | L | K | V | D | S | C | D | N | C | S | K | Q | 14 | 2398 |
| 101 | Q | R | E | I | L | K | Q | R | K | V | K | A | R | L | T | 14 | 2399 |
| 113 | R | L | T | I | A | A | V | L | Y | L | L | F | M | I | G | 14 | 2400 |
| 116 | I | A | A | V | L | Y | L | L | F | M | I | G | E | L | V | 14 | 2401 |
| 117 | A | A | V | L | Y | L | L | F | M | I | G | E | L | V | G | 14 | 2402 |
| 119 | V | L | Y | L | L | F | M | I | G | E | L | V | G | G | Y | 14 | 2403 |
| 120 | L | Y | L | L | F | M | I | G | E | L | V | G | G | Y | I | 14 | 2404 |
| 122 | L | L | F | M | I | G | E | L | V | G | G | Y | I | A | N | 14 | 2405 |
| 126 | I | G | E | L | V | G | G | Y | I | A | N | S | L | A | I | 14 | 2406 |
| 127 | G | E | L | V | G | G | Y | I | A | N | S | L | A | I | M | 14 | 2407 |
| 131 | G | G | Y | I | A | N | S | L | A | I | M | T | D | A | L | 14 | 2408 |
| 158 | L | L | A | L | W | L | S | S | K | S | P | T | K | R | F | 14 | 2409 |
| 185 | M | I | S | V | L | L | V | Y | I | L | M | G | F | L | L | 14 | 2410 |
| 200 | Y | E | A | V | Q | R | T | I | H | M | N | Y | E | I | N | 14 | 2411 |
| 214 | N | G | D | I | M | L | I | T | A | A | V | G | V | A | V | 14 | 2412 |
| 215 | G | D | I | M | L | I | T | A | A | V | G | V | A | V | N | 14 | 2413 |
| 227 | A | V | N | V | I | M | G | F | L | L | N | Q | S | G | H | 14 | 2414 |
| 279 | L | G | D | L | V | Q | S | V | G | V | L | I | A | A | Y | 14 | 2415 |
| 285 | S | V | G | V | L | I | A | A | Y | I | I | R | F | K | P | 14 | 2416 |
| 286 | V | G | V | L | I | A | A | Y | I | I | R | F | K | P | E | 14 | 2417 |
| 287 | G | V | L | I | A | A | Y | I | I | R | F | K | P | E | Y | 14 | 2418 |
| 300 | E | Y | K | I | A | D | P | I | C | T | Y | V | F | S | L | 14 | 2419 |
| 304 | A | D | P | I | C | T | Y | V | F | S | L | L | V | A | F | 14 | 2420 |
| 313 | S | L | L | V | A | F | T | T | F | R | I | I | W | D | T | 14 | 2421 |
| 321 | F | R | I | I | W | D | T | V | V | I | I | L | E | G | V | 14 | 2422 |
| 325 | W | D | T | V | V | I | I | L | E | G | V | P | S | H | L | 14 | 2423 |
| 327 | T | V | V | I | I | L | E | G | V | P | S | H | L | N | V | 14 | 2424 |
| 328 | V | V | I | I | L | E | G | V | P | S | H | L | N | V | D | 14 | 2425 |

TABLE XXIII-continued

| Pos | 1 | 2 | 3 | 4 | 5 | 6 | 7 | 8 | 9 | 0 | 1 | 2 | 3 | 4 | 5 | score | SEQ. ID. No. |
|---|---|---|---|---|---|---|---|---|---|---|---|---|---|---|---|---|---|
| 332 | L | E | G | V | P | S | H | L | N | V | D | Y | I | K | E | 14 | 2426 |
| 341 | V | D | Y | I | K | E | A | L | M | K | I | E | D | V | Y | 14 | 2427 |
| 370 | S | T | A | I | V | H | I | Q | L | I | P | G | S | S | S | 14 | 2428 |
| 371 | T | A | I | V | H | I | Q | L | I | P | G | S | S | S | K | 14 | 2429 |
| 375 | H | I | Q | L | I | P | G | S | S | S | K | W | E | E | V | 14 | 2430 |
| 376 | I | Q | L | I | P | G | S | S | S | K | W | E | E | V | Q | 14 | 2431 |
| 395 | H | L | L | L | N | T | F | G | M | Y | R | C | T | I | Q | 14 | 2432 |
| 400 | T | F | G | M | Y | R | C | T | I | Q | L | Q | S | Y | R | 14 | 2433 |
| 407 | T | I | Q | L | Q | S | Y | R | Q | E | V | D | R | T | C | 14 | 2434 |
| 414 | R | Q | E | V | D | R | T | C | A | N | C | Q | S | S | S | 14 | 2435 |

HLA-DRB1*1101 15 - mers

| Pos | 1 | 2 | 3 | 4 | 5 | 6 | 7 | 8 | 9 | 0 | 1 | 2 | 3 | 4 | 5 | score | SEQ. ID. No. |
|---|---|---|---|---|---|---|---|---|---|---|---|---|---|---|---|---|---|
| 197 | F | L | L | Y | E | A | V | Q | R | T | I | H | M | N | Y | 25 | 2436 |
| 40 | L | S | R | F | N | K | L | R | V | V | A | D | D | G | 23 | 2437 |
| 169 | T | K | R | F | T | F | G | F | H | R | L | E | V | L | S | 22 | 2438 |
| 173 | T | F | G | F | H | R | L | E | V | L | S | A | M | I | S | 22 | 2439 |
| 43 | F | N | K | L | R | V | V | V | A | D | D | G | S | E | A | 21 | 2440 |
| 101 | Q | R | E | I | L | K | Q | R | K | V | K | A | R | L | T | 21 | 2441 |
| 153 | A | I | I | L | T | L | L | A | L | W | L | S | S | K | S | 21 | 2442 |
| 233 | G | F | L | L | N | Q | S | G | H | R | H | S | H | S | H | 21 | 2443 |
| 276 | V | H | A | L | G | D | L | V | Q | S | V | G | V | L | I | 21 | 2444 |
| 288 | V | L | I | A | A | Y | I | I | R | F | K | P | E | Y | K | 21 | 2445 |
| 7 | W | K | R | L | K | S | M | L | R | K | D | D | A | P | L | 20 | 2446 |
| 8 | K | R | L | K | S | M | L | R | K | D | D | A | P | L | F | 20 | 2447 |
| 120 | L | Y | L | L | F | M | I | G | E | L | V | G | G | Y | I | 20 | 2448 |
| 176 | F | H | R | L | E | V | L | S | A | M | I | S | V | L | L | 20 | 2449 |
| 411 | Q | S | Y | R | Q | E | V | D | R | T | C | A | N | C | Q | 20 | 2450 |
| 116 | I | A | A | V | L | Y | L | L | F | M | I | G | E | L | V | 19 | 2451 |
| 214 | N | G | D | I | M | L | I | T | A | V | G | V | A | V | 19 | 2452 |
| 280 | G | D | L | V | Q | S | V | G | V | L | I | A | A | Y | I | 19 | 2453 |
| 322 | R | I | I | W | D | T | V | V | I | I | L | E | G | V | P | 19 | 2454 |
| 325 | W | D | T | V | V | I | I | L | E | G | V | P | S | H | L | 19 | 2455 |
| 359 | D | L | N | I | W | S | L | T | S | G | K | S | T | A | I | 19 | 2456 |
| 142 | T | D | A | L | H | M | L | T | D | L | S | A | I | I | L | 18 | 2457 |
| 185 | M | I | S | V | L | L | V | Y | I | L | M | G | F | L | L | 18 | 2458 |
| 229 | N | V | I | M | G | F | L | L | N | Q | S | G | H | R | H | 18 | 2459 |
| 290 | I | A | A | Y | I | I | R | F | K | P | E | Y | K | I | A | 18 | 2460 |
| 294 | I | I | R | F | K | P | E | Y | K | I | A | D | P | I | C | 18 | 2461 |
| 309 | T | Y | V | F | S | L | L | V | A | F | T | T | F | R | I | 18 | 2462 |
| 326 | D | T | V | V | I | I | L | E | G | V | P | S | H | L | N | 18 | 2463 |
| 345 | K | E | A | L | M | K | I | E | D | V | Y | S | V | E | D | 18 | 2464 |
| 367 | S | G | K | S | T | A | I | V | H | I | Q | L | I | P | G | 18 | 2465 |
| 370 | S | T | A | I | V | H | I | Q | L | I | P | G | S | S | S | 18 | 2466 |
| 373 | I | V | H | I | Q | L | I | P | G | S | S | S | K | W | E | 18 | 2467 |
| 4 | S | G | A | W | K | R | L | K | S | M | L | R | K | D | D | 17 | 2468 |
| 138 | L | A | I | M | T | D | A | L | H | M | L | T | D | L | S | 17 | 2469 |
| 189 | L | L | V | Y | I | L | M | G | F | L | L | Y | E | A | V | 17 | 2470 |
| 269 | L | A | V | R | A | A | F | V | H | A | L | G | D | L | V | 17 | 2471 |
| 318 | F | T | T | F | R | I | I | W | D | T | V | V | I | I | L | 17 | 2472 |
| 28 | A | F | D | F | S | D | E | A | G | D | E | G | L | S | R | 16 | 2473 |
| 37 | D | E | G | L | S | R | F | N | K | L | R | V | V | V | A | 16 | 2474 |
| 98 | C | S | K | Q | R | E | I | L | K | Q | R | K | V | K | A | 16 | 2475 |
| 121 | Y | L | L | F | M | I | G | E | L | V | G | G | Y | I | A | 16 | 2476 |
| 383 | S | S | K | W | E | E | V | Q | S | K | A | N | H | L | L | 16 | 2477 |
| 401 | F | G | M | Y | R | C | T | I | Q | L | Q | S | Y | R | Q | 16 | 2478 |
| 1 | M | A | G | S | G | A | W | K | R | L | K | S | M | L | R | 15 | 2479 |
| 145 | L | H | M | L | T | D | L | S | A | I | I | L | T | L | L | 15 | 2480 |
| 239 | S | G | H | R | H | S | H | S | H | S | L | P | S | N | S | 15 | 2481 |
| 323 | I | I | W | D | T | V | V | I | I | L | E | G | V | P | S | 15 | 2482 |
| 397 | L | L | N | T | F | G | M | Y | R | C | T | I | Q | L | Q | 15 | 2483 |
| 34 | E | A | G | D | E | G | L | S | R | F | N | K | L | R | V | 14 | 2484 |
| 83 | L | T | N | S | Q | L | S | L | K | V | D | S | C | D | N | 14 | 2485 |
| 123 | L | F | M | I | G | E | L | V | G | G | Y | I | A | N | S | 14 | 2486 |
| 158 | L | L | A | L | W | L | S | S | K | S | P | T | K | R | F | 14 | 2487 |
| 183 | S | A | M | I | S | V | L | L | V | Y | I | L | M | G | F | 14 | 2488 |
| 200 | Y | E | A | V | Q | R | T | I | H | M | N | Y | E | I | N | 14 | 2489 |
| 225 | G | V | A | V | N | V | I | M | G | F | L | L | N | Q | S | 14 | 2490 |
| 235 | L | L | N | Q | S | G | H | R | H | S | H | S | H | S | L | 14 | 2491 |
| 237 | N | Q | S | G | H | R | H | S | H | S | H | S | L | P | S | 14 | 2492 |
| 246 | S | H | S | L | P | S | N | S | P | T | R | G | S | G | C | 14 | 2493 |
| 248 | S | L | P | S | N | S | P | T | R | G | S | G | C | E | R | 14 | 2494 |
| 254 | P | T | R | G | S | G | C | E | R | N | H | G | Q | D | S | 14 | 2495 |
| 342 | D | Y | I | K | E | A | L | M | K | I | E | D | V | Y | S | 14 | 2496 |
| 361 | N | I | W | S | L | T | S | G | K | S | T | A | I | V | H | 14 | 2497 |
| 44 | N | K | L | R | V | V | V | A | D | D | G | S | E | A | P | 13 | 2498 |
| 71 | A | D | D | D | S | L | L | D | Q | D | L | P | L | T | N | 13 | 2499 |

TABLE XXIII-continued

| Pos | 1 | 2 | 3 | 4 | 5 | 6 | 7 | 8 | 9 | 10 | 11 | 12 | 13 | 14 | 15 | score | SEQ. ID. NO. |
|---|---|---|---|---|---|---|---|---|---|---|---|---|---|---|---|---|---|
| 78 | D | Q | D | L | P | L | T | N | S | Q | L | S | L | K | V | 13 | 2500 |
| 113 | R | L | T | I | A | A | V | L | Y | L | L | F | M | I | G | 13 | 2501 |
| 119 | V | L | Y | L | L | F | M | I | G | E | L | V | G | G | Y | 13 | 2502 |
| 124 | F | M | I | G | E | L | V | G | G | Y | I | A | N | S | L | 13 | 2503 |
| 128 | E | L | V | G | G | Y | I | A | N | S | L | A | I | M | T | 13 | 2504 |
| 135 | A | N | S | L | A | I | M | T | D | A | L | H | M | L | T | 13 | 2505 |
| 141 | M | T | D | A | L | H | M | L | T | D | L | S | A | I | I | 13 | 2506 |
| 148 | L | T | D | L | S | A | I | I | L | T | L | L | A | L | W | 13 | 2507 |
| 149 | T | D | L | S | A | I | I | L | T | L | L | A | L | W | L | 13 | 2508 |
| 156 | L | T | L | L | A | L | W | L | S | S | K | S | P | T | K | 13 | 2509 |
| 179 | L | E | V | L | S | A | M | I | S | V | L | L | V | Y | I | 13 | 2510 |
| 188 | V | L | L | V | Y | I | L | M | G | F | L | L | Y | E | A | 13 | 2511 |
| 216 | D | I | M | L | I | T | A | A | V | G | V | A | V | N | V | 13 | 2512 |
| 263 | N | H | G | Q | D | S | L | A | V | R | A | A | F | V | H | 13 | 2513 |
| 273 | A | A | F | V | H | A | L | G | D | L | V | Q | S | V | G | 13 | 2514 |
| 283 | V | Q | S | V | G | V | L | I | A | A | Y | I | I | R | F | 13 | 2515 |
| 308 | C | T | Y | V | F | S | L | L | V | A | F | T | T | F | R | 13 | 2516 |
| 329 | V | I | I | L | E | G | V | P | S | H | L | N | V | D | Y | 13 | 2517 |
| 336 | P | S | H | L | N | V | D | Y | I | K | E | A | L | M | K | 13 | 2518 |
| 338 | H | L | N | V | D | Y | I | K | E | A | L | M | K | I | E | 13 | 2519 |
| 410 | L | Q | S | Y | R | Q | E | V | D | R | T | C | A | N | C | 13 | 2520 |
| 17 | D | D | A | P | L | F | L | N | D | T | S | A | F | D | F | 12 | 2521 |
| 46 | L | R | V | V | V | A | D | D | G | S | E | A | P | E | R | 12 | 2522 |
| 47 | R | V | V | V | A | D | D | G | S | E | A | P | E | R | P | 12 | 2523 |
| 56 | E | A | P | E | R | P | V | N | G | A | H | P | T | L | Q | 12 | 2524 |
| 75 | S | L | L | D | Q | D | L | P | L | T | N | S | Q | L | S | 12 | 2525 |
| 103 | E | I | L | K | Q | R | K | V | K | A | R | L | T | I | A | 12 | 2526 |
| 107 | Q | R | K | V | K | A | R | L | T | I | A | A | V | L | Y | 12 | 2527 |
| 117 | A | A | V | L | Y | L | L | F | M | I | G | E | L | V | G | 12 | 2528 |
| 126 | I | G | E | L | V | G | G | Y | I | A | N | S | L | A | I | 12 | 2529 |
| 152 | S | A | I | I | L | T | L | L | A | L | W | L | S | S | K | 12 | 2530 |
| 155 | I | L | T | L | L | A | L | W | L | S | S | K | S | P | T | 12 | 2531 |
| 157 | T | L | L | A | L | W | L | S | S | K | S | P | T | K | R | 12 | 2532 |
| 182 | L | S | A | M | I | S | V | L | L | V | Y | I | L | M | G | 12 | 2533 |
| 187 | S | V | L | L | V | Y | I | L | M | G | F | L | L | Y | E | 12 | 2534 |
| 191 | V | Y | I | L | M | G | F | L | L | Y | E | A | V | Q | R | 12 | 2535 |
| 192 | Y | I | L | M | G | F | L | L | Y | E | A | V | Q | R | T | 12 | 2536 |
| 204 | Q | R | T | I | H | M | N | Y | E | I | N | G | D | I | M | 12 | 2537 |
| 211 | Y | E | I | N | G | D | I | M | L | I | T | A | A | V | G | 12 | 2538 |
| 212 | E | I | N | G | D | I | M | L | I | T | A | A | V | G | V | 12 | 2539 |
| 222 | A | A | V | G | V | A | V | N | V | I | M | G | F | L | L | 12 | 2540 |
| 228 | V | N | V | I | M | G | F | L | L | N | Q | S | G | H | R | 12 | 2541 |
| 243 | H | S | H | S | H | S | L | P | S | N | S | P | T | R | G | 12 | 2542 |
| 315 | L | V | A | F | T | T | F | R | I | I | W | D | T | V | V | 12 | 2543 |
| 348 | L | M | K | I | E | D | V | Y | S | V | E | D | L | N | I | 12 | 2544 |
| 351 | I | E | D | V | Y | S | V | E | D | L | N | I | W | S | L | 12 | 2545 |
| 352 | E | D | V | Y | S | V | E | D | L | N | I | W | S | L | T | 12 | 2546 |
| 354 | V | Y | S | V | E | D | L | N | I | W | S | L | T | S | G | 12 | 2547 |
| 356 | S | V | E | D | L | N | I | W | S | L | T | S | G | K | S | 12 | 2548 |
| 357 | V | E | D | L | N | I | W | S | L | T | S | G | K | S | T | 12 | 2549 |
| 371 | T | A | I | V | H | I | Q | L | I | P | G | S | S | S | K | 12 | 2550 |
| 372 | A | I | V | H | I | Q | L | I | P | G | S | S | S | K | W | 12 | 2551 |
| 391 | S | K | A | N | H | L | L | N | T | F | G | M | Y | R | | 12 | 2552 |

MHC Class II analysis of 108P5H8 flanking the D to E mutation at amino acid 30. Listed are scores that fall within the top 50% (rounded up) of all scores for a selected allele of the 108P5H8 variant 1 sequence that does not contain the mutation.

| Pos | 1 | 2 | 3 | 4 | 5 | 6 | 7 | 8 | 9 | 0 | 1 | 2 | 3 | 4 | 5 | score | SEQ. ID. NO. |
|---|---|---|---|---|---|---|---|---|---|---|---|---|---|---|---|---|---|
| HLA-DRB1*0101 15 - mers | | | | | | | | | | | | | | | | | |
| 20 | P | L | F | L | N | D | T | S | A | F | E | F | S | D | E | 25 | 2553 |
| 18 | D | A | P | L | F | L | N | D | T | S | A | F | E | F | S | 23 | 2554 |
| 17 | D | D | A | P | L | F | L | N | D | T | S | A | F | E | F | 18 | 2555 |
| 28 | A | F | E | F | S | D | E | A | G | D | E | G | L | S | R | 18 | 2556 |
| HLA-DRB1*0301 (DR17) 15 - mers | | | | | | | | | | | | | | | | | |
| 19 | A | P | L | F | L | N | D | T | S | A | F | E | F | S | D | 21 | 2557 |
| 18 | D | A | P | L | F | L | N | D | T | S | A | F | E | F | S | 20 | 2558 |
| 20 | P | L | F | L | N | D | T | S | A | F | E | F | S | D | E | 19 | 2559 |
| 26 | T | S | A | F | E | F | S | D | E | A | G | D | E | G | L | 15 | 2560 |
| HLA-DRB1*0401 (DR4Dw4) 15 - mers | | | | | | | | | | | | | | | | | |
| 19 | A | P | L | F | L | N | D | T | S | A | F | E | F | S | D | 22 | 2561 |
| 16 | K | D | D | A | P | L | F | L | N | D | T | S | A | F | E | 18 | 2562 |

TABLE XXIII-continued

| 24 | N | D | T | S | A | F | E | F | S | D | E | A | G | D | E | 18 | 2563 |
|---|---|---|---|---|---|---|---|---|---|---|---|---|---|---|---|---|---|
| 28 | A | F | E | F | S | D | E | A | G | D | E | G | L | S | R | 16 | 2564 |
| 18 | D | A | P | L | F | L | N | D | T | S | A | F | E | F | S | 14 | 2565 |
| HLA-DRB1*1101 15 - mers | | | | | | | | | | | | | | | | | |
| 28 | A | F | E | F | S | D | E | A | G | D | E | G | L | S | R | 16 | 2566 |
| 17 | D | D | A | P | L | F | L | N | D | T | S | A | F | E | F | 12 | 2567 |

The invention claimed is:

1. A method for inhibiting growth or survival of a prostate cancer cell expressing a protein having an amino acid sequence of SEQ ID NO: 2570, comprising:
   providing to the cell a composition comprising an antibody or fragment thereof that specifically binds to said protein having an amino acid sequence of SEQ ID NO: 2570;
   whereby the growth, survival, or growth and survival of the cell is inhibited.

2. The method of claim 1, wherein said antibody is a monoclonal antibody.

3. The method of claim 1, wherein the antibody or fragment thereof is selected from the group consisting of Fab, F(ab')$_2$, Fv and sFv.

4. The method of claim 1, wherein the antibody is labeled with an agent.

5. The method of claim 4, wherein the agent is selected from the group consisting of radioisotopes, chemotherapeutic agents, and toxins.

6. The method of claim 5, wherein the radioisotope is selected from the group consisting of $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

7. The method of claim 1, wherein the antibody is a single-chain monoclonal antibody.

* * * * *

SEQUENCE LISTING

<160> NUMBER OF SEQ ID NOS: 2598

<210> SEQ ID NO 1
<211> LENGTH: 9
<212> TYPE: PRT
<213> ORGANISM: homo sapien

<400> SEQUENCE: 1

Leu Asn Asp Thr Ser Ala Phe Asp Phe
 1               5

<210> SEQ ID NO 2
<211> LENGTH: 9
<212> TYPE: PRT
<213> ORGANISM: homo sapien

<400> SEQUENCE: 2

Leu Thr Asp Leu Ser Ala Ile Ile Leu
 1               5

<210> SEQ ID NO 3
<211> LENGTH: 9
<212> TYPE: PRT
<213> ORGANISM: homo sapien

<400> SEQUENCE: 3

Met Thr Asp Ala Leu His Met Leu Thr
 1               5

<210> SEQ ID NO 4
<211> LENGTH: 9
<212> TYPE: PRT
<213> ORGANISM: homo sapien

<400> SEQUENCE: 4

Ile Ala Asp Pro Ile Cys Thr Tyr Val
 1               5

<210> SEQ ID NO 5
<211> LENGTH: 9
<212> TYPE: PRT
<213> ORGANISM: homo sapien

<400> SEQUENCE: 5

Ser Cys Asp Asn Cys Ser Lys Gln Arg
 1               5

<210> SEQ ID NO 6
<211> LENGTH: 9
<212> TYPE: PRT
<213> ORGANISM: homo sapien

<400> SEQUENCE: 6

```
Ser Val Glu Asp Leu Asn Ile Trp Ser
  1               5
```

<210> SEQ ID NO 7
<211> LENGTH: 9
<212> TYPE: PRT
<213> ORGANISM: homo sapien

<400> SEQUENCE: 7

```
Tyr Ile Leu Met Gly Phe Leu Leu Tyr
  1               5
```

<210> SEQ ID NO 8
<211> LENGTH: 9
<212> TYPE: PRT
<213> ORGANISM: homo sapien

<400> SEQUENCE: 8

```
Gln Leu Ile Pro Gly Ser Ser Ser Lys
  1               5
```

<210> SEQ ID NO 9
<211> LENGTH: 9
<212> TYPE: PRT
<213> ORGANISM: homo sapien

<400> SEQUENCE: 9

```
Arg Leu Glu Val Leu Ser Ala Met Ile
  1               5
```

<210> SEQ ID NO 10
<211> LENGTH: 9
<212> TYPE: PRT
<213> ORGANISM: homo sapien

<400> SEQUENCE: 10

```
Gly Ser Glu Ala Pro Glu Arg Pro Val
  1               5
```

<210> SEQ ID NO 11
<211> LENGTH: 9
<212> TYPE: PRT
<213> ORGANISM: homo sapien

<400> SEQUENCE: 11

```
Ala Met Ile Ser Val Leu Leu Val Tyr
  1               5
```

<210> SEQ ID NO 12
<211> LENGTH: 9
<212> TYPE: PRT
<213> ORGANISM: homo sapien

<400> SEQUENCE: 12

```
Ala Gly Asp Glu Gly Leu Ser Arg Phe
  1               5
```

<210> SEQ ID NO 13
<211> LENGTH: 9
<212> TYPE: PRT
<213> ORGANISM: homo sapien

<400> SEQUENCE: 13

```
Ser Val Gly Val Leu Ile Ala Ala Tyr
```

```
<210> SEQ ID NO 14
<211> LENGTH: 9
<212> TYPE: PRT
<213> ORGANISM: homo sapien

<400> SEQUENCE: 14

Arg Leu Thr Ile Ala Ala Val Leu Tyr
1               5

<210> SEQ ID NO 15
<211> LENGTH: 9
<212> TYPE: PRT
<213> ORGANISM: homo sapien

<400> SEQUENCE: 15

Leu Leu Asp Gln Asp Leu Pro Leu Thr
1               5

<210> SEQ ID NO 16
<211> LENGTH: 9
<212> TYPE: PRT
<213> ORGANISM: homo sapien

<400> SEQUENCE: 16

Gln Arg Glu Ile Leu Lys Gln Arg Lys
1               5

<210> SEQ ID NO 17
<211> LENGTH: 9
<212> TYPE: PRT
<213> ORGANISM: homo sapien

<400> SEQUENCE: 17

Ile Leu Glu Gly Val Pro Ser His Leu
1               5

<210> SEQ ID NO 18
<211> LENGTH: 9
<212> TYPE: PRT
<213> ORGANISM: homo sapien

<400> SEQUENCE: 18

Lys Ser Pro Thr Lys Arg Phe Thr Phe
1               5

<210> SEQ ID NO 19
<211> LENGTH: 9
<212> TYPE: PRT
<213> ORGANISM: homo sapien

<400> SEQUENCE: 19

Phe Ser Asp Glu Ala Gly Asp Glu Gly
1               5

<210> SEQ ID NO 20
<211> LENGTH: 9
<212> TYPE: PRT
<213> ORGANISM: homo sapien

<400> SEQUENCE: 20

Asn Gly Asp Ile Met Leu Ile Thr Ala
1               5
```

```
<210> SEQ ID NO 21
<211> LENGTH: 9
<212> TYPE: PRT
<213> ORGANISM: homo sapien

<400> SEQUENCE: 21

Lys Val Asp Ser Cys Asp Asn Cys Ser
1               5

<210> SEQ ID NO 22
<211> LENGTH: 9
<212> TYPE: PRT
<213> ORGANISM: homo sapien

<400> SEQUENCE: 22

Glu Ala Gly Asp Glu Gly Leu Ser Arg
1               5

<210> SEQ ID NO 23
<211> LENGTH: 9
<212> TYPE: PRT
<213> ORGANISM: homo sapien

<400> SEQUENCE: 23

Ile Ala Ala Val Leu Tyr Leu Leu Phe
1               5

<210> SEQ ID NO 24
<211> LENGTH: 9
<212> TYPE: PRT
<213> ORGANISM: homo sapien

<400> SEQUENCE: 24

Val Leu Ile Ala Ala Tyr Ile Ile Arg
1               5

<210> SEQ ID NO 25
<211> LENGTH: 9
<212> TYPE: PRT
<213> ORGANISM: homo sapien

<400> SEQUENCE: 25

Arg Cys Thr Ile Gln Leu Gln Ser Tyr
1               5

<210> SEQ ID NO 26
<211> LENGTH: 9
<212> TYPE: PRT
<213> ORGANISM: homo sapien

<400> SEQUENCE: 26

Asn Val Asp Tyr Ile Lys Glu Ala Leu
1               5

<210> SEQ ID NO 27
<211> LENGTH: 9
<212> TYPE: PRT
<213> ORGANISM: homo sapien

<400> SEQUENCE: 27

Val Ala Val Asn Val Ile Met Gly Phe
1               5

<210> SEQ ID NO 28
```

```
<211> LENGTH: 9
<212> TYPE: PRT
<213> ORGANISM: homo sapien

<400> SEQUENCE: 28

Leu Ile Ala Ala Tyr Ile Ile Arg Phe
1               5

<210> SEQ ID NO 29
<211> LENGTH: 9
<212> TYPE: PRT
<213> ORGANISM: homo sapien

<400> SEQUENCE: 29

Leu Leu Leu Asn Thr Phe Gly Met Tyr
1               5

<210> SEQ ID NO 30
<211> LENGTH: 9
<212> TYPE: PRT
<213> ORGANISM: homo sapien

<400> SEQUENCE: 30

Met Ile Gly Glu Leu Val Gly Gly Tyr
1               5

<210> SEQ ID NO 31
<211> LENGTH: 9
<212> TYPE: PRT
<213> ORGANISM: homo sapien

<400> SEQUENCE: 31

Leu Leu Asn Thr Phe Gly Met Tyr Arg
1               5

<210> SEQ ID NO 32
<211> LENGTH: 9
<212> TYPE: PRT
<213> ORGANISM: homo sapien

<400> SEQUENCE: 32

Lys Ile Ala Asp Pro Ile Cys Thr Tyr
1               5

<210> SEQ ID NO 33
<211> LENGTH: 9
<212> TYPE: PRT
<213> ORGANISM: homo sapien

<400> SEQUENCE: 33

Leu Thr Asn Ser Gln Leu Ser Leu Lys
1               5

<210> SEQ ID NO 34
<211> LENGTH: 9
<212> TYPE: PRT
<213> ORGANISM: homo sapien

<400> SEQUENCE: 34

Leu Leu Val Tyr Ile Leu Met Gly Phe
1               5

<210> SEQ ID NO 35
<211> LENGTH: 9
<212> TYPE: PRT
```

-continued

<213> ORGANISM: homo sapien

<400> SEQUENCE: 35

Trp Leu Ser Ser Lys Ser Pro Thr Lys
1               5

<210> SEQ ID NO 36
<211> LENGTH: 9
<212> TYPE: PRT
<213> ORGANISM: homo sapien

<400> SEQUENCE: 36

Asp Ser Leu Ala Val Arg Ala Ala Phe
1               5

<210> SEQ ID NO 37
<211> LENGTH: 9
<212> TYPE: PRT
<213> ORGANISM: homo sapien

<400> SEQUENCE: 37

Gly Ser Gly Ala Trp Lys Arg Leu Lys
1               5

<210> SEQ ID NO 38
<211> LENGTH: 9
<212> TYPE: PRT
<213> ORGANISM: homo sapien

<400> SEQUENCE: 38

Gln Ala Asp Asp Ser Leu Leu Asp
1               5

<210> SEQ ID NO 39
<211> LENGTH: 9
<212> TYPE: PRT
<213> ORGANISM: homo sapien

<400> SEQUENCE: 39

Cys Thr Ile Gln Leu Gln Ser Tyr Arg
1               5

<210> SEQ ID NO 40
<211> LENGTH: 9
<212> TYPE: PRT
<213> ORGANISM: homo sapien

<400> SEQUENCE: 40

Val Pro Ser His Leu Asn Val Asp Tyr
1               5

<210> SEQ ID NO 41
<211> LENGTH: 9
<212> TYPE: PRT
<213> ORGANISM: homo sapien

<400> SEQUENCE: 41

Ile Gly Glu Leu Val Gly Gly Tyr Ile
1               5

<210> SEQ ID NO 42
<211> LENGTH: 9
<212> TYPE: PRT
<213> ORGANISM: homo sapien

<400> SEQUENCE: 42

Ile Ala Ala Tyr Ile Ile Arg Phe Lys
1               5

<210> SEQ ID NO 43
<211> LENGTH: 9
<212> TYPE: PRT
<213> ORGANISM: homo sapien

<400> SEQUENCE: 43

Tyr Val Phe Ser Leu Leu Val Ala Phe
1               5

<210> SEQ ID NO 44
<211> LENGTH: 9
<212> TYPE: PRT
<213> ORGANISM: homo sapien

<400> SEQUENCE: 44

Ser Leu Pro Ser Asn Ser Pro Thr Arg
1               5

<210> SEQ ID NO 45
<211> LENGTH: 9
<212> TYPE: PRT
<213> ORGANISM: homo sapien

<400> SEQUENCE: 45

Phe Leu Leu Tyr Glu Ala Val Gln Arg
1               5

<210> SEQ ID NO 46
<211> LENGTH: 9
<212> TYPE: PRT
<213> ORGANISM: homo sapien

<400> SEQUENCE: 46

Leu Leu Ala Leu Trp Leu Ser Ser Lys
1               5

<210> SEQ ID NO 47
<211> LENGTH: 9
<212> TYPE: PRT
<213> ORGANISM: homo sapien

<400> SEQUENCE: 47

Cys Ser Lys Gln Arg Glu Ile Leu Lys
1               5

<210> SEQ ID NO 48
<211> LENGTH: 9
<212> TYPE: PRT
<213> ORGANISM: homo sapien

<400> SEQUENCE: 48

Gly Gln Asp Ser Leu Ala Val Arg Ala
1               5

<210> SEQ ID NO 49
<211> LENGTH: 9
<212> TYPE: PRT
<213> ORGANISM: homo sapien

<400> SEQUENCE: 49

His Ser Leu Pro Ser Asn Ser Pro Thr
1               5

```
<210> SEQ ID NO 50
<211> LENGTH: 9
<212> TYPE: PRT
<213> ORGANISM: homo sapien

<400> SEQUENCE: 50

Arg Gln Glu Val Asp Arg Thr Cys Ala
 1               5

<210> SEQ ID NO 51
<211> LENGTH: 10
<212> TYPE: PRT
<213> ORGANISM: homo sapien

<400> SEQUENCE: 51

Ile Ala Asp Pro Ile Cys Thr Tyr Val Phe
 1               5                  10

<210> SEQ ID NO 52
<211> LENGTH: 10
<212> TYPE: PRT
<213> ORGANISM: homo sapien

<400> SEQUENCE: 52

Lys Val Asp Ser Cys Asp Asn Cys Ser Lys
 1               5                  10

<210> SEQ ID NO 53
<211> LENGTH: 10
<212> TYPE: PRT
<213> ORGANISM: homo sapien

<400> SEQUENCE: 53

Leu Thr Asp Leu Ser Ala Ile Ile Leu Thr
 1               5                  10

<210> SEQ ID NO 54
<211> LENGTH: 10
<212> TYPE: PRT
<213> ORGANISM: homo sapien

<400> SEQUENCE: 54

Gly Asp Glu Gly Leu Ser Arg Phe Asn Lys
 1               5                  10

<210> SEQ ID NO 55
<211> LENGTH: 10
<212> TYPE: PRT
<213> ORGANISM: homo sapien

<400> SEQUENCE: 55

Arg Leu Glu Val Leu Ser Ala Met Ile Ser
 1               5                  10

<210> SEQ ID NO 56
<211> LENGTH: 10
<212> TYPE: PRT
<213> ORGANISM: homo sapien

<400> SEQUENCE: 56

His Ser Leu Pro Ser Asn Ser Pro Thr Arg
 1               5                  10

<210> SEQ ID NO 57
<211> LENGTH: 10
```

```
<212> TYPE: PRT
<213> ORGANISM: homo sapien

<400> SEQUENCE: 57

Gly Ser Glu Ala Pro Glu Arg Pro Val Asn
 1               5                  10

<210> SEQ ID NO 58
<211> LENGTH: 10
<212> TYPE: PRT
<213> ORGANISM: homo sapien

<400> SEQUENCE: 58

Leu Leu Asp Gln Asp Leu Pro Leu Thr Asn
 1               5                  10

<210> SEQ ID NO 59
<211> LENGTH: 10
<212> TYPE: PRT
<213> ORGANISM: homo sapien

<400> SEQUENCE: 59

Ser Ala Met Ile Ser Val Leu Leu Val Tyr
 1               5                  10

<210> SEQ ID NO 60
<211> LENGTH: 10
<212> TYPE: PRT
<213> ORGANISM: homo sapien

<400> SEQUENCE: 60

Gln Ala Asp Asp Asp Ser Leu Leu Asp Gln
 1               5                  10

<210> SEQ ID NO 61
<211> LENGTH: 10
<212> TYPE: PRT
<213> ORGANISM: homo sapien

<400> SEQUENCE: 61

Gln Ser Val Gly Val Leu Ile Ala Ala Tyr
 1               5                  10

<210> SEQ ID NO 62
<211> LENGTH: 10
<212> TYPE: PRT
<213> ORGANISM: homo sapien

<400> SEQUENCE: 62

Asn Val Asp Tyr Ile Lys Glu Ala Leu Met
 1               5                  10

<210> SEQ ID NO 63
<211> LENGTH: 10
<212> TYPE: PRT
<213> ORGANISM: homo sapien

<400> SEQUENCE: 63

Gly Val Pro Ser His Leu Asn Val Asp Tyr
 1               5                  10

<210> SEQ ID NO 64
<211> LENGTH: 10
<212> TYPE: PRT
<213> ORGANISM: homo sapien
```

-continued

```
<400> SEQUENCE: 64

Ser Val Glu Asp Leu Asn Ile Trp Ser Leu
1               5                   10

<210> SEQ ID NO 65
<211> LENGTH: 10
<212> TYPE: PRT
<213> ORGANISM: homo sapien

<400> SEQUENCE: 65

Ile Leu Glu Gly Val Pro Ser His Leu Asn
1               5                   10

<210> SEQ ID NO 66
<211> LENGTH: 10
<212> TYPE: PRT
<213> ORGANISM: homo sapien

<400> SEQUENCE: 66

Phe Ser Asp Glu Ala Gly Asp Glu Gly Leu
1               5                   10

<210> SEQ ID NO 67
<211> LENGTH: 10
<212> TYPE: PRT
<213> ORGANISM: homo sapien

<400> SEQUENCE: 67

Met Thr Asp Ala Leu His Met Leu Thr Asp
1               5                   10

<210> SEQ ID NO 68
<211> LENGTH: 10
<212> TYPE: PRT
<213> ORGANISM: homo sapien

<400> SEQUENCE: 68

Leu Leu Leu Asn Thr Phe Gly Met Tyr Arg
1               5                   10

<210> SEQ ID NO 69
<211> LENGTH: 10
<212> TYPE: PRT
<213> ORGANISM: homo sapien

<400> SEQUENCE: 69

Gly Val Ala Val Asn Val Ile Met Gly Phe
1               5                   10

<210> SEQ ID NO 70
<211> LENGTH: 10
<212> TYPE: PRT
<213> ORGANISM: homo sapien

<400> SEQUENCE: 70

Phe Leu Asn Asp Thr Ser Ala Phe Asp Phe
1               5                   10

<210> SEQ ID NO 71
<211> LENGTH: 10
<212> TYPE: PRT
<213> ORGANISM: homo sapien

<400> SEQUENCE: 71
```

```
Gly Val Leu Ile Ala Ala Tyr Ile Ile Arg
1               5                   10

<210> SEQ ID NO 72
<211> LENGTH: 10
<212> TYPE: PRT
<213> ORGANISM: homo sapien

<400> SEQUENCE: 72

Glu Ala Leu Met Lys Ile Glu Asp Val Tyr
1               5                   10

<210> SEQ ID NO 73
<211> LENGTH: 10
<212> TYPE: PRT
<213> ORGANISM: homo sapien

<400> SEQUENCE: 73

Ala Asp Asp Gly Ser Glu Ala Pro Glu Arg
1               5                   10

<210> SEQ ID NO 74
<211> LENGTH: 10
<212> TYPE: PRT
<213> ORGANISM: homo sapien

<400> SEQUENCE: 74

Val Leu Leu Val Tyr Ile Leu Met Gly Phe
1               5                   10

<210> SEQ ID NO 75
<211> LENGTH: 10
<212> TYPE: PRT
<213> ORGANISM: homo sapien

<400> SEQUENCE: 75

His Leu Leu Leu Asn Thr Phe Gly Met Tyr
1               5                   10

<210> SEQ ID NO 76
<211> LENGTH: 10
<212> TYPE: PRT
<213> ORGANISM: homo sapien

<400> SEQUENCE: 76

Val Leu Ile Ala Ala Tyr Ile Ile Arg Phe
1               5                   10

<210> SEQ ID NO 77
<211> LENGTH: 10
<212> TYPE: PRT
<213> ORGANISM: homo sapien

<400> SEQUENCE: 77

Thr Ile Ala Ala Val Leu Tyr Leu Leu Phe
1               5                   10

<210> SEQ ID NO 78
<211> LENGTH: 10
<212> TYPE: PRT
<213> ORGANISM: homo sapien

<400> SEQUENCE: 78

Ile Gly Glu Leu Val Gly Gly Tyr Ile Ala
```

<210> SEQ ID NO 79
<211> LENGTH: 10
<212> TYPE: PRT
<213> ORGANISM: homo sapien

<400> SEQUENCE: 79

Ser Lys Ser Pro Thr Lys Arg Phe Thr Phe
1               5                   10

<210> SEQ ID NO 80
<211> LENGTH: 10
<212> TYPE: PRT
<213> ORGANISM: homo sapien

<400> SEQUENCE: 80

Ala Val Gln Arg Thr Ile His Met Asn Tyr
1               5                   10

<210> SEQ ID NO 81
<211> LENGTH: 10
<212> TYPE: PRT
<213> ORGANISM: homo sapien

<400> SEQUENCE: 81

Phe Met Ile Gly Glu Leu Val Gly Gly Tyr
1               5                   10

<210> SEQ ID NO 82
<211> LENGTH: 10
<212> TYPE: PRT
<213> ORGANISM: homo sapien

<400> SEQUENCE: 82

Leu Gly Asp Leu Val Gln Ser Val Gly Val
1               5                   10

<210> SEQ ID NO 83
<211> LENGTH: 10
<212> TYPE: PRT
<213> ORGANISM: homo sapien

<400> SEQUENCE: 83

Lys Pro Glu Tyr Lys Ile Ala Asp Pro Ile
1               5                   10

<210> SEQ ID NO 84
<211> LENGTH: 10
<212> TYPE: PRT
<213> ORGANISM: homo sapien

<400> SEQUENCE: 84

Asn Tyr Glu Ile Asn Gly Asp Ile Met Leu
1               5                   10

<210> SEQ ID NO 85
<211> LENGTH: 10
<212> TYPE: PRT
<213> ORGANISM: homo sapien

<400> SEQUENCE: 85

Thr Leu Leu Ala Leu Trp Leu Ser Ser Lys
1               5                   10

```
<210> SEQ ID NO 86
<211> LENGTH: 10
<212> TYPE: PRT
<213> ORGANISM: homo sapien

<400> SEQUENCE: 86

Leu Ile Ala Ala Tyr Ile Ile Arg Phe Lys
 1               5                  10

<210> SEQ ID NO 87
<211> LENGTH: 10
<212> TYPE: PRT
<213> ORGANISM: homo sapien

<400> SEQUENCE: 87

Lys Ile Glu Asp Val Tyr Ser Val Glu Asp
 1               5                  10

<210> SEQ ID NO 88
<211> LENGTH: 10
<212> TYPE: PRT
<213> ORGANISM: homo sapien

<400> SEQUENCE: 88

Asp Ser Cys Asp Asn Cys Ser Lys Gln Arg
 1               5                  10

<210> SEQ ID NO 89
<211> LENGTH: 10
<212> TYPE: PRT
<213> ORGANISM: homo sapien

<400> SEQUENCE: 89

Phe Ser Leu Leu Val Ala Phe Thr Thr Phe
 1               5                  10

<210> SEQ ID NO 90
<211> LENGTH: 10
<212> TYPE: PRT
<213> ORGANISM: homo sapien

<400> SEQUENCE: 90

Arg Gln Glu Val Asp Arg Thr Cys Ala Asn
 1               5                  10

<210> SEQ ID NO 91
<211> LENGTH: 10
<212> TYPE: PRT
<213> ORGANISM: homo sapien

<400> SEQUENCE: 91

Arg Lys Asp Asp Ala Pro Leu Phe Leu Asn
 1               5                  10

<210> SEQ ID NO 92
<211> LENGTH: 10
<212> TYPE: PRT
<213> ORGANISM: homo sapien

<400> SEQUENCE: 92

Leu Thr Leu Leu Ala Leu Trp Leu Ser Ser
 1               5                  10

<210> SEQ ID NO 93
```

```
<211> LENGTH: 10
<212> TYPE: PRT
<213> ORGANISM: homo sapien

<400> SEQUENCE: 93

Leu Thr Asn Ser Gln Leu Ser Leu Lys Val
1               5                   10

<210> SEQ ID NO 94
<211> LENGTH: 10
<212> TYPE: PRT
<213> ORGANISM: homo sapien

<400> SEQUENCE: 94

Phe Thr Phe Gly Phe His Arg Leu Glu Val
1               5                   10

<210> SEQ ID NO 95
<211> LENGTH: 10
<212> TYPE: PRT
<213> ORGANISM: homo sapien

<400> SEQUENCE: 95

Asn Gly Asp Ile Met Leu Ile Thr Ala Ala
1               5                   10

<210> SEQ ID NO 96
<211> LENGTH: 10
<212> TYPE: PRT
<213> ORGANISM: homo sapien

<400> SEQUENCE: 96

Cys Thr Tyr Val Phe Ser Leu Leu Val Ala
1               5                   10

<210> SEQ ID NO 97
<211> LENGTH: 10
<212> TYPE: PRT
<213> ORGANISM: homo sapien

<400> SEQUENCE: 97

Leu Asn Asp Thr Ser Ala Phe Asp Phe Ser
1               5                   10

<210> SEQ ID NO 98
<211> LENGTH: 10
<212> TYPE: PRT
<213> ORGANISM: homo sapien

<400> SEQUENCE: 98

Ala Gly Asp Glu Gly Leu Ser Arg Phe Asn
1               5                   10

<210> SEQ ID NO 99
<211> LENGTH: 10
<212> TYPE: PRT
<213> ORGANISM: homo sapien

<400> SEQUENCE: 99

Val Tyr Ile Leu Met Gly Phe Leu Leu Tyr
1               5                   10

<210> SEQ ID NO 100
<211> LENGTH: 10
<212> TYPE: PRT
```

<213> ORGANISM: homo sapien

<400> SEQUENCE: 100

Asn Cys Ser Lys Gln Arg Glu Ile Leu Lys
1               5                   10

<210> SEQ ID NO 101
<211> LENGTH: 9
<212> TYPE: PRT
<213> ORGANISM: homo sapien

<400> SEQUENCE: 101

Ala Leu Gly Asp Leu Val Gln Ser Val
1               5

<210> SEQ ID NO 102
<211> LENGTH: 9
<212> TYPE: PRT
<213> ORGANISM: homo sapien

<400> SEQUENCE: 102

Ser Leu Ala Val Arg Ala Ala Phe Val
1               5

<210> SEQ ID NO 103
<211> LENGTH: 9
<212> TYPE: PRT
<213> ORGANISM: homo sapien

<400> SEQUENCE: 103

Leu Leu Tyr Glu Ala Val Gln Arg Thr
1               5

<210> SEQ ID NO 104
<211> LENGTH: 9
<212> TYPE: PRT
<213> ORGANISM: homo sapien

<400> SEQUENCE: 104

Ser Leu Leu Asp Gln Asp Leu Pro Leu
1               5

<210> SEQ ID NO 105
<211> LENGTH: 9
<212> TYPE: PRT
<213> ORGANISM: homo sapien

<400> SEQUENCE: 105

Ile Met Thr Asp Ala Leu His Met Leu
1               5

<210> SEQ ID NO 106
<211> LENGTH: 9
<212> TYPE: PRT
<213> ORGANISM: homo sapien

<400> SEQUENCE: 106

Leu Leu Phe Met Ile Gly Glu Leu Val
1               5

<210> SEQ ID NO 107
<211> LENGTH: 9
<212> TYPE: PRT
<213> ORGANISM: homo sapien

<400> SEQUENCE: 107

Ile Leu Thr Leu Leu Ala Leu Trp Leu
1               5

-continued

Tyr Leu Leu Phe Met Ile Gly Glu Leu
1               5

<210> SEQ ID NO 110
<211> LENGTH: 9
<212> TYPE: PRT
<213> ORGANISM: homo sapien

<400> SEQUENCE: 110

Ile Ile Trp Asp Thr Val Val Ile Ile
1               5

<210> SEQ ID NO 111
<211> LENGTH: 9
<212> TYPE: PRT
<213> ORGANISM: homo sapien

<400> SEQUENCE: 111

Gln Leu Gln Ser Tyr Arg Gln Glu Val
1               5

<210> SEQ ID NO 112
<211> LENGTH: 9
<212> TYPE: PRT
<213> ORGANISM: homo sapien

<400> SEQUENCE: 112

Gly Met Tyr Arg Cys Thr Ile Gln Leu
1               5

<210> SEQ ID NO 113
<211> LENGTH: 9
<212> TYPE: PRT
<213> ORGANISM: homo sapien

<400> SEQUENCE: 113

Ala Val Leu Tyr Leu Leu Phe Met Ile
1               5

<210> SEQ ID NO 114
<211> LENGTH: 9
<212> TYPE: PRT
<213> ORGANISM: homo sapien

<400> SEQUENCE: 114

Val Leu Ser Ala Met Ile Ser Val Leu
1               5

<210> SEQ ID NO 115
<211> LENGTH: 9
<212> TYPE: PRT
<213> ORGANISM: homo sapien

<400> SEQUENCE: 115

Met Ile Ser Val Leu Leu Val Tyr Ile
1               5

<210> SEQ ID NO 116
<211> LENGTH: 9
<212> TYPE: PRT
<213> ORGANISM: homo sapien

<400> SEQUENCE: 116

Met Leu Thr Asp Leu Ser Ala Ile Ile
1               5

<210> SEQ ID NO 117
<211> LENGTH: 9
<212> TYPE: PRT
<213> ORGANISM: homo sapien

<400> SEQUENCE: 117

Leu Val Tyr Ile Leu Met Gly Phe Leu
1               5

<210> SEQ ID NO 118
<211> LENGTH: 9
<212> TYPE: PRT
<213> ORGANISM: homo sapien

<400> SEQUENCE: 118

Leu Gln Ala Asp Asp Asp Ser Leu Leu
1               5

<210> SEQ ID NO 119
<211> LENGTH: 9
<212> TYPE: PRT
<213> ORGANISM: homo sapien

<400> SEQUENCE: 119

Leu Met Gly Phe Leu Leu Tyr Glu Ala
1               5

<210> SEQ ID NO 120
<211> LENGTH: 9
<212> TYPE: PRT
<213> ORGANISM: homo sapien

<400> SEQUENCE: 120

Phe Val His Ala Leu Gly Asp Leu Val
1               5

<210> SEQ ID NO 121
<211> LENGTH: 9
<212> TYPE: PRT
<213> ORGANISM: homo sapien

<400> SEQUENCE: 121

Cys Thr Tyr Val Phe Ser Leu Leu Val
1               5

<210> SEQ ID NO 122
<211> LENGTH: 9
<212> TYPE: PRT
<213> ORGANISM: homo sapien

<400> SEQUENCE: 122

Leu Leu Asp Gln Asp Leu Pro Leu Thr
1               5

<210> SEQ ID NO 123
<211> LENGTH: 9
<212> TYPE: PRT
<213> ORGANISM: homo sapien

<400> SEQUENCE: 123

Ser Leu Ala Ile Met Thr Asp Ala Leu
1               5

```
<210> SEQ ID NO 124
<211> LENGTH: 9
<212> TYPE: PRT
<213> ORGANISM: homo sapien

<400> SEQUENCE: 124

Thr Leu Gln Ala Asp Asp Asp Ser Leu
 1               5

<210> SEQ ID NO 125
<211> LENGTH: 9
<212> TYPE: PRT
<213> ORGANISM: homo sapien

<400> SEQUENCE: 125

Leu Val Ala Phe Thr Thr Phe Arg Ile
 1               5

<210> SEQ ID NO 126
<211> LENGTH: 9
<212> TYPE: PRT
<213> ORGANISM: homo sapien

<400> SEQUENCE: 126

Ser Ala Met Ile Ser Val Leu Leu Val
 1               5

<210> SEQ ID NO 127
<211> LENGTH: 9
<212> TYPE: PRT
<213> ORGANISM: homo sapien

<400> SEQUENCE: 127

Thr Val Val Ile Ile Leu Glu Gly Val
 1               5

<210> SEQ ID NO 128
<211> LENGTH: 9
<212> TYPE: PRT
<213> ORGANISM: homo sapien

<400> SEQUENCE: 128

Thr Ile Ala Ala Val Leu Tyr Leu Leu
 1               5

<210> SEQ ID NO 129
<211> LENGTH: 9
<212> TYPE: PRT
<213> ORGANISM: homo sapien

<400> SEQUENCE: 129

Ala Ile Ile Leu Thr Leu Leu Ala Leu
 1               5

<210> SEQ ID NO 130
<211> LENGTH: 9
<212> TYPE: PRT
<213> ORGANISM: homo sapien

<400> SEQUENCE: 130

Thr Thr Phe Arg Ile Ile Trp Asp Thr
 1               5

<210> SEQ ID NO 131
<211> LENGTH: 9
```

```
<212> TYPE: PRT
<213> ORGANISM: homo sapien

<400> SEQUENCE: 131

Leu Thr Ile Ala Ala Val Leu Tyr Leu
 1               5

<210> SEQ ID NO 132
<211> LENGTH: 9
<212> TYPE: PRT
<213> ORGANISM: homo sapien

<400> SEQUENCE: 132

Gln Leu Ser Leu Lys Val Asp Ser Cys
 1               5

<210> SEQ ID NO 133
<211> LENGTH: 9
<212> TYPE: PRT
<213> ORGANISM: homo sapien

<400> SEQUENCE: 133

Ser Leu Thr Ser Gly Lys Ser Thr Ala
 1               5

<210> SEQ ID NO 134
<211> LENGTH: 9
<212> TYPE: PRT
<213> ORGANISM: homo sapien

<400> SEQUENCE: 134

Val Glu Asp Leu Asn Ile Trp Ser Leu
 1               5

<210> SEQ ID NO 135
<211> LENGTH: 9
<212> TYPE: PRT
<213> ORGANISM: homo sapien

<400> SEQUENCE: 135

Phe Ser Leu Leu Val Ala Phe Thr Thr
 1               5

<210> SEQ ID NO 136
<211> LENGTH: 9
<212> TYPE: PRT
<213> ORGANISM: homo sapien

<400> SEQUENCE: 136

Ile Leu Met Gly Phe Leu Leu Tyr Glu
 1               5

<210> SEQ ID NO 137
<211> LENGTH: 9
<212> TYPE: PRT
<213> ORGANISM: homo sapien

<400> SEQUENCE: 137

Glu Val Leu Ser Ala Met Ile Ser Val
 1               5

<210> SEQ ID NO 138
<211> LENGTH: 9
<212> TYPE: PRT
<213> ORGANISM: homo sapien
```

<400> SEQUENCE: 138

Asp Leu Ser Ala Ile Ile Leu Thr Leu
1               5

<210> SEQ ID NO 139
<211> LENGTH: 9
<212> TYPE: PRT
<213> ORGANISM: homo sapien

<400> SEQUENCE: 139

Val Gln Ser Lys Ala Asn His Leu Leu
1               5

<210> SEQ ID NO 140
<211> LENGTH: 9
<212> TYPE: PRT
<213> ORGANISM: homo sapien

<400> SEQUENCE: 140

His Leu Leu Leu Asn Thr Phe Gly Met
1               5

<210> SEQ ID NO 141
<211> LENGTH: 9
<212> TYPE: PRT
<213> ORGANISM: homo sapien

<400> SEQUENCE: 141

Ile Ala Asp Pro Ile Cys Thr Tyr Val
1               5

<210> SEQ ID NO 142
<211> LENGTH: 9
<212> TYPE: PRT
<213> ORGANISM: homo sapien

<400> SEQUENCE: 142

Ala Val Asn Val Ile Met Gly Phe Leu
1               5

<210> SEQ ID NO 143
<211> LENGTH: 9
<212> TYPE: PRT
<213> ORGANISM: homo sapien

<400> SEQUENCE: 143

Val Val Ala Asp Asp Gly Ser Glu Ala
1               5

<210> SEQ ID NO 144
<211> LENGTH: 9
<212> TYPE: PRT
<213> ORGANISM: homo sapien

<400> SEQUENCE: 144

Tyr Ile Ala Asn Ser Leu Ala Ile Met
1               5

<210> SEQ ID NO 145
<211> LENGTH: 9
<212> TYPE: PRT
<213> ORGANISM: homo sapien

<400> SEQUENCE: 145

```
Met Leu Arg Lys Asp Asp Ala Pro Leu
 1               5
```

<210> SEQ ID NO 146
<211> LENGTH: 9
<212> TYPE: PRT
<213> ORGANISM: homo sapien

<400> SEQUENCE: 146

```
Asp Ile Met Leu Ile Thr Ala Ala Val
 1               5
```

<210> SEQ ID NO 147
<211> LENGTH: 9
<212> TYPE: PRT
<213> ORGANISM: homo sapien

<400> SEQUENCE: 147

```
Ala Ile Met Thr Asp Ala Leu His Met
 1               5
```

<210> SEQ ID NO 148
<211> LENGTH: 9
<212> TYPE: PRT
<213> ORGANISM: homo sapien

<400> SEQUENCE: 148

```
Ser Val Leu Leu Val Tyr Ile Leu Met
 1               5
```

<210> SEQ ID NO 149
<211> LENGTH: 9
<212> TYPE: PRT
<213> ORGANISM: homo sapien

<400> SEQUENCE: 149

```
Ile Leu Glu Gly Val Pro Ser His Leu
 1               5
```

<210> SEQ ID NO 150
<211> LENGTH: 9
<212> TYPE: PRT
<213> ORGANISM: homo sapien

<400> SEQUENCE: 150

```
His Met Leu Thr Asp Leu Ser Ala Ile
 1               5
```

<210> SEQ ID NO 151
<211> LENGTH: 10
<212> TYPE: PRT
<213> ORGANISM: homo sapien

<400> SEQUENCE: 151

```
Lys Ile Ala Asp Pro Ile Cys Thr Tyr Val
 1               5                  10
```

<210> SEQ ID NO 152
<211> LENGTH: 10
<212> TYPE: PRT
<213> ORGANISM: homo sapien

<400> SEQUENCE: 152

```
Tyr Leu Leu Phe Met Ile Gly Glu Leu Val
```

```
                1               5                    10
```

<210> SEQ ID NO 153
<211> LENGTH: 10
<212> TYPE: PRT
<213> ORGANISM: homo sapien
<400> SEQUENCE: 153

```
Ile Met Leu Ile Thr Ala Ala Val Gly Val
1               5                    10
```

<210> SEQ ID NO 154
<211> LENGTH: 10
<212> TYPE: PRT
<213> ORGANISM: homo sapien
<400> SEQUENCE: 154

```
Phe Leu Leu Tyr Glu Ala Val Gln Arg Thr
1               5                    10
```

<210> SEQ ID NO 155
<211> LENGTH: 10
<212> TYPE: PRT
<213> ORGANISM: homo sapien
<400> SEQUENCE: 155

```
Arg Leu Thr Ile Ala Ala Val Leu Tyr Leu
1               5                    10
```

<210> SEQ ID NO 156
<211> LENGTH: 10
<212> TYPE: PRT
<213> ORGANISM: homo sapien
<400> SEQUENCE: 156

```
Ser Leu Leu Asp Gln Asp Leu Pro Leu Thr
1               5                    10
```

<210> SEQ ID NO 157
<211> LENGTH: 10
<212> TYPE: PRT
<213> ORGANISM: homo sapien
<400> SEQUENCE: 157

```
Ile Ile Trp Asp Thr Val Val Ile Ile Leu
1               5                    10
```

<210> SEQ ID NO 158
<211> LENGTH: 10
<212> TYPE: PRT
<213> ORGANISM: homo sapien
<400> SEQUENCE: 158

```
Tyr Val Phe Ser Leu Leu Val Ala Phe Thr
1               5                    10
```

<210> SEQ ID NO 159
<211> LENGTH: 10
<212> TYPE: PRT
<213> ORGANISM: homo sapien
<400> SEQUENCE: 159

```
Leu Leu Val Ala Phe Thr Thr Phe Arg Ile
1               5                    10
```

```
<210> SEQ ID NO 160
<211> LENGTH: 10
<212> TYPE: PRT
<213> ORGANISM: homo sapien

<400> SEQUENCE: 160

Ile Ile Leu Thr Leu Leu Ala Leu Trp Leu
 1               5                  10

<210> SEQ ID NO 161
<211> LENGTH: 10
<212> TYPE: PRT
<213> ORGANISM: homo sapien

<400> SEQUENCE: 161

Ala Met Ile Ser Val Leu Leu Val Tyr Ile
 1               5                  10

<210> SEQ ID NO 162
<211> LENGTH: 10
<212> TYPE: PRT
<213> ORGANISM: homo sapien

<400> SEQUENCE: 162

Ile Ile Leu Glu Gly Val Pro Ser His Leu
 1               5                  10

<210> SEQ ID NO 163
<211> LENGTH: 10
<212> TYPE: PRT
<213> ORGANISM: homo sapien

<400> SEQUENCE: 163

Ile Leu Met Gly Phe Leu Leu Tyr Glu Ala
 1               5                  10

<210> SEQ ID NO 164
<211> LENGTH: 10
<212> TYPE: PRT
<213> ORGANISM: homo sapien

<400> SEQUENCE: 164

Gly Leu Ser Arg Phe Asn Lys Leu Arg Val
 1               5                  10

<210> SEQ ID NO 165
<211> LENGTH: 10
<212> TYPE: PRT
<213> ORGANISM: homo sapien

<400> SEQUENCE: 165

Leu Met Gly Phe Leu Leu Tyr Glu Ala Val
 1               5                  10

<210> SEQ ID NO 166
<211> LENGTH: 10
<212> TYPE: PRT
<213> ORGANISM: homo sapien

<400> SEQUENCE: 166

Ala Leu Trp Leu Ser Ser Lys Ser Pro Thr
 1               5                  10

<210> SEQ ID NO 167
```

```
<211> LENGTH: 10
<212> TYPE: PRT
<213> ORGANISM: homo sapien

<400> SEQUENCE: 167

Met Leu Thr Asp Leu Ser Ala Ile Ile Leu
 1               5                  10

<210> SEQ ID NO 168
<211> LENGTH: 10
<212> TYPE: PRT
<213> ORGANISM: homo sapien

<400> SEQUENCE: 168

Leu Leu Val Tyr Ile Leu Met Gly Phe Leu
 1               5                  10

<210> SEQ ID NO 169
<211> LENGTH: 10
<212> TYPE: PRT
<213> ORGANISM: homo sapien

<400> SEQUENCE: 169

Leu Val Tyr Ile Leu Met Gly Phe Leu Leu
 1               5                  10

<210> SEQ ID NO 170
<211> LENGTH: 10
<212> TYPE: PRT
<213> ORGANISM: homo sapien

<400> SEQUENCE: 170

Ser Met Leu Arg Lys Asp Asp Ala Pro Leu
 1               5                  10

<210> SEQ ID NO 171
<211> LENGTH: 10
<212> TYPE: PRT
<213> ORGANISM: homo sapien

<400> SEQUENCE: 171

Leu Leu Tyr Glu Ala Val Gln Arg Thr Ile
 1               5                  10

<210> SEQ ID NO 172
<211> LENGTH: 10
<212> TYPE: PRT
<213> ORGANISM: homo sapien

<400> SEQUENCE: 172

Ile Gln Leu Gln Ser Tyr Arg Gln Glu Val
 1               5                  10

<210> SEQ ID NO 173
<211> LENGTH: 10
<212> TYPE: PRT
<213> ORGANISM: homo sapien

<400> SEQUENCE: 173

Ile Met Thr Asp Ala Leu His Met Leu Thr
 1               5                  10

<210> SEQ ID NO 174
<211> LENGTH: 10
<212> TYPE: PRT
```

<213> ORGANISM: homo sapien

<400> SEQUENCE: 174

Val Leu Ser Ala Met Ile Ser Val Leu Leu
1               5                   10

<210> SEQ ID NO 175
<211> LENGTH: 10
<212> TYPE: PRT
<213> ORGANISM: homo sapien

<400> SEQUENCE: 175

Ala Ile Met Thr Asp Ala Leu His Met Leu
1               5                   10

<210> SEQ ID NO 176
<211> LENGTH: 10
<212> TYPE: PRT
<213> ORGANISM: homo sapien

<400> SEQUENCE: 176

Thr Leu Gln Ala Asp Asp Ser Leu Leu
1               5                   10

<210> SEQ ID NO 177
<211> LENGTH: 10
<212> TYPE: PRT
<213> ORGANISM: homo sapien

<400> SEQUENCE: 177

Leu Leu Asn Thr Phe Gly Met Tyr Arg Cys
1               5                   10

<210> SEQ ID NO 178
<211> LENGTH: 10
<212> TYPE: PRT
<213> ORGANISM: homo sapien

<400> SEQUENCE: 178

Phe Thr Phe Gly Phe His Arg Leu Glu Val
1               5                   10

<210> SEQ ID NO 179
<211> LENGTH: 10
<212> TYPE: PRT
<213> ORGANISM: homo sapien

<400> SEQUENCE: 179

Leu Ile Thr Ala Ala Val Gly Val Ala Val
1               5                   10

<210> SEQ ID NO 180
<211> LENGTH: 10
<212> TYPE: PRT
<213> ORGANISM: homo sapien

<400> SEQUENCE: 180

Ala Val Asn Val Ile Met Gly Phe Leu Leu
1               5                   10

<210> SEQ ID NO 181
<211> LENGTH: 10
<212> TYPE: PRT
<213> ORGANISM: homo sapien

```
<400> SEQUENCE: 181

Ser Leu Thr Ser Gly Lys Ser Thr Ala Ile
1               5                   10

<210> SEQ ID NO 182
<211> LENGTH: 10
<212> TYPE: PRT
<213> ORGANISM: homo sapien

<400> SEQUENCE: 182

Ser Val Glu Asp Leu Asn Ile Trp Ser Leu
1               5                   10

<210> SEQ ID NO 183
<211> LENGTH: 10
<212> TYPE: PRT
<213> ORGANISM: homo sapien

<400> SEQUENCE: 183

Phe Thr Thr Phe Arg Ile Ile Trp Asp Thr
1               5                   10

<210> SEQ ID NO 184
<211> LENGTH: 10
<212> TYPE: PRT
<213> ORGANISM: homo sapien

<400> SEQUENCE: 184

Phe Leu Asn Asp Thr Ser Ala Phe Asp Phe
1               5                   10

<210> SEQ ID NO 185
<211> LENGTH: 10
<212> TYPE: PRT
<213> ORGANISM: homo sapien

<400> SEQUENCE: 185

Met Ile Gly Glu Leu Val Gly Gly Tyr Ile
1               5                   10

<210> SEQ ID NO 186
<211> LENGTH: 10
<212> TYPE: PRT
<213> ORGANISM: homo sapien

<400> SEQUENCE: 186

Leu Met Lys Ile Glu Asp Val Tyr Ser Val
1               5                   10

<210> SEQ ID NO 187
<211> LENGTH: 10
<212> TYPE: PRT
<213> ORGANISM: homo sapien

<400> SEQUENCE: 187

Lys Glu Ala Leu Met Lys Ile Glu Asp Val
1               5                   10

<210> SEQ ID NO 188
<211> LENGTH: 10
<212> TYPE: PRT
<213> ORGANISM: homo sapien

<400> SEQUENCE: 188
```

Leu Glu Val Leu Ser Ala Met Ile Ser Val
1               5                   10

<210> SEQ ID NO 189
<211> LENGTH: 10
<212> TYPE: PRT
<213> ORGANISM: homo sapien

<400> SEQUENCE: 189

Ser Val Gly Val Leu Ile Ala Ala Tyr Ile
1               5                   10

<210> SEQ ID NO 190
<211> LENGTH: 10
<212> TYPE: PRT
<213> ORGANISM: homo sapien

<400> SEQUENCE: 190

Ala Leu His Met Leu Thr Asp Leu Ser Ala
1               5                   10

<210> SEQ ID NO 191
<211> LENGTH: 10
<212> TYPE: PRT
<213> ORGANISM: homo sapien

<400> SEQUENCE: 191

Tyr Ile Ala Asn Ser Leu Ala Ile Met Thr
1               5                   10

<210> SEQ ID NO 192
<211> LENGTH: 10
<212> TYPE: PRT
<213> ORGANISM: homo sapien

<400> SEQUENCE: 192

Met Ile Ser Val Leu Leu Val Tyr Ile Leu
1               5                   10

<210> SEQ ID NO 193
<211> LENGTH: 10
<212> TYPE: PRT
<213> ORGANISM: homo sapien

<400> SEQUENCE: 193

Asp Leu Ser Ala Ile Ile Leu Thr Leu Leu
1               5                   10

<210> SEQ ID NO 194
<211> LENGTH: 10
<212> TYPE: PRT
<213> ORGANISM: homo sapien

<400> SEQUENCE: 194

Val Gln Ser Lys Ala Asn His Leu Leu Leu
1               5                   10

<210> SEQ ID NO 195
<211> LENGTH: 10
<212> TYPE: PRT
<213> ORGANISM: homo sapien

<400> SEQUENCE: 195

Leu Val Gly Gly Tyr Ile Ala Asn Ser Leu
1               5                   10

<210> SEQ ID NO 196
<211> LENGTH: 10
<212> TYPE: PRT
<213> ORGANISM: homo sapien

<400> SEQUENCE: 196

Thr Thr Phe Arg Ile Ile Trp Asp Thr Val
1               5                   10

<210> SEQ ID NO 197
<211> LENGTH: 10
<212> TYPE: PRT
<213> ORGANISM: homo sapien

<400> SEQUENCE: 197

Ile Cys Thr Tyr Val Phe Ser Leu Leu Val
1               5                   10

<210> SEQ ID NO 198
<211> LENGTH: 10
<212> TYPE: PRT
<213> ORGANISM: homo sapien

<400> SEQUENCE: 198

Gly Ala Trp Lys Arg Leu Lys Ser Met Leu
1               5                   10

<210> SEQ ID NO 199
<211> LENGTH: 10
<212> TYPE: PRT
<213> ORGANISM: homo sapien

<400> SEQUENCE: 199

Phe Gly Met Tyr Arg Cys Thr Ile Gln Leu
1               5                   10

<210> SEQ ID NO 200
<211> LENGTH: 10
<212> TYPE: PRT
<213> ORGANISM: homo sapien

<400> SEQUENCE: 200

Leu Glu Gly Val Pro Ser His Leu Asn Val
1               5                   10

<210> SEQ ID NO 201
<211> LENGTH: 9
<212> TYPE: PRT
<213> ORGANISM: homo sapien

<400> SEQUENCE: 201

Leu Leu Ala Leu Trp Leu Ser Ser Lys
1               5

<210> SEQ ID NO 202
<211> LENGTH: 9
<212> TYPE: PRT
<213> ORGANISM: homo sapien

<400> SEQUENCE: 202

Gln Leu Ile Pro Gly Ser Ser Ser Lys
1               5

```
<210> SEQ ID NO 203
<211> LENGTH: 9
<212> TYPE: PRT
<213> ORGANISM: homo sapien

<400> SEQUENCE: 203

Ala Met Ile Ser Val Leu Leu Val Tyr
1               5

<210> SEQ ID NO 204
<211> LENGTH: 9
<212> TYPE: PRT
<213> ORGANISM: homo sapien

<400> SEQUENCE: 204

Leu Leu Asn Thr Phe Gly Met Tyr Arg
1               5

<210> SEQ ID NO 205
<211> LENGTH: 9
<212> TYPE: PRT
<213> ORGANISM: homo sapien

<400> SEQUENCE: 205

Trp Leu Ser Ser Lys Ser Pro Thr Lys
1               5

<210> SEQ ID NO 206
<211> LENGTH: 9
<212> TYPE: PRT
<213> ORGANISM: homo sapien

<400> SEQUENCE: 206

Gly Leu Ser Arg Phe Asn Lys Leu Arg
1               5

<210> SEQ ID NO 207
<211> LENGTH: 9
<212> TYPE: PRT
<213> ORGANISM: homo sapien

<400> SEQUENCE: 207

Gly Met Tyr Arg Cys Thr Ile Gln Leu
1               5

<210> SEQ ID NO 208
<211> LENGTH: 9
<212> TYPE: PRT
<213> ORGANISM: homo sapien

<400> SEQUENCE: 208

Leu Leu Val Ala Phe Thr Thr Phe Arg
1               5

<210> SEQ ID NO 209
<211> LENGTH: 9
<212> TYPE: PRT
<213> ORGANISM: homo sapien

<400> SEQUENCE: 209

Leu Leu Val Tyr Ile Leu Met Gly Phe
1               5

<210> SEQ ID NO 210
<211> LENGTH: 9
```

```
<212> TYPE: PRT
<213> ORGANISM: homo sapien

<400> SEQUENCE: 210

Val Leu Ile Ala Ala Tyr Ile Ile Arg
 1               5

<210> SEQ ID NO 211
<211> LENGTH: 9
<212> TYPE: PRT
<213> ORGANISM: homo sapien

<400> SEQUENCE: 211

Asn Ile Trp Ser Leu Thr Ser Gly Lys
 1               5

<210> SEQ ID NO 212
<211> LENGTH: 9
<212> TYPE: PRT
<213> ORGANISM: homo sapien

<400> SEQUENCE: 212

Ala Leu Met Lys Ile Glu Asp Val Tyr
 1               5

<210> SEQ ID NO 213
<211> LENGTH: 9
<212> TYPE: PRT
<213> ORGANISM: homo sapien

<400> SEQUENCE: 213

Ser Leu Leu Val Ala Phe Thr Thr Phe
 1               5

<210> SEQ ID NO 214
<211> LENGTH: 9
<212> TYPE: PRT
<213> ORGANISM: homo sapien

<400> SEQUENCE: 214

Phe Leu Leu Tyr Glu Ala Val Gln Arg
 1               5

<210> SEQ ID NO 215
<211> LENGTH: 9
<212> TYPE: PRT
<213> ORGANISM: homo sapien

<400> SEQUENCE: 215

Leu Leu Leu Asn Thr Phe Gly Met Tyr
 1               5

<210> SEQ ID NO 216
<211> LENGTH: 9
<212> TYPE: PRT
<213> ORGANISM: homo sapien

<400> SEQUENCE: 216

Arg Leu Thr Ile Ala Ala Val Leu Tyr
 1               5

<210> SEQ ID NO 217
<211> LENGTH: 9
<212> TYPE: PRT
<213> ORGANISM: homo sapien
```

```
<400> SEQUENCE: 217

Ser Leu Pro Ser Asn Ser Pro Thr Arg
1               5

<210> SEQ ID NO 218
<211> LENGTH: 9
<212> TYPE: PRT
<213> ORGANISM: homo sapien

<400> SEQUENCE: 218

Tyr Ile Leu Met Gly Phe Leu Leu Tyr
1               5

<210> SEQ ID NO 219
<211> LENGTH: 9
<212> TYPE: PRT
<213> ORGANISM: homo sapien

<400> SEQUENCE: 219

Lys Ile Ala Asp Pro Ile Cys Thr Tyr
1               5

<210> SEQ ID NO 220
<211> LENGTH: 9
<212> TYPE: PRT
<213> ORGANISM: homo sapien

<400> SEQUENCE: 220

Leu Leu Tyr Glu Ala Val Gln Arg Thr
1               5

<210> SEQ ID NO 221
<211> LENGTH: 9
<212> TYPE: PRT
<213> ORGANISM: homo sapien

<400> SEQUENCE: 221

Ile Ile Arg Phe Lys Pro Glu Tyr Lys
1               5

<210> SEQ ID NO 222
<211> LENGTH: 9
<212> TYPE: PRT
<213> ORGANISM: homo sapien

<400> SEQUENCE: 222

Leu Ile Ala Ala Tyr Ile Ile Arg Phe
1               5

<210> SEQ ID NO 223
<211> LENGTH: 9
<212> TYPE: PRT
<213> ORGANISM: homo sapien

<400> SEQUENCE: 223

Tyr Ile Ile Arg Phe Lys Pro Glu Tyr
1               5

<210> SEQ ID NO 224
<211> LENGTH: 9
<212> TYPE: PRT
<213> ORGANISM: homo sapien

<400> SEQUENCE: 224
```

Phe Leu Leu Asn Gln Ser Gly His Arg
1               5

<210> SEQ ID NO 225
<211> LENGTH: 9
<212> TYPE: PRT
<213> ORGANISM: homo sapien

<400> SEQUENCE: 225

Ser Leu Leu Asp Gln Asp Leu Pro Leu
1               5

<210> SEQ ID NO 226
<211> LENGTH: 9
<212> TYPE: PRT
<213> ORGANISM: homo sapien

<400> SEQUENCE: 226

Leu Leu Phe Met Ile Gly Glu Leu Val
1               5

<210> SEQ ID NO 227
<211> LENGTH: 9
<212> TYPE: PRT
<213> ORGANISM: homo sapien

<400> SEQUENCE: 227

Tyr Val Phe Ser Leu Leu Val Ala Phe
1               5

<210> SEQ ID NO 228
<211> LENGTH: 9
<212> TYPE: PRT
<213> ORGANISM: homo sapien

<400> SEQUENCE: 228

Leu Thr Asn Ser Gln Leu Ser Leu Lys
1               5

<210> SEQ ID NO 229
<211> LENGTH: 9
<212> TYPE: PRT
<213> ORGANISM: homo sapien

<400> SEQUENCE: 229

His Met Leu Thr Asp Leu Ser Ala Ile
1               5

<210> SEQ ID NO 230
<211> LENGTH: 9
<212> TYPE: PRT
<213> ORGANISM: homo sapien

<400> SEQUENCE: 230

Ile Leu Glu Gly Val Pro Ser His Leu
1               5

<210> SEQ ID NO 231
<211> LENGTH: 9
<212> TYPE: PRT
<213> ORGANISM: homo sapien

<400> SEQUENCE: 231

Ile Leu Thr Leu Leu Ala Leu Trp Leu

```
                        1               5

<210> SEQ ID NO 232
<211> LENGTH: 9
<212> TYPE: PRT
<213> ORGANISM: homo sapien

<400> SEQUENCE: 232

Val Leu Ser Ala Met Ile Ser Val Leu
 1               5

<210> SEQ ID NO 233
<211> LENGTH: 9
<212> TYPE: PRT
<213> ORGANISM: homo sapien

<400> SEQUENCE: 233

His Leu Leu Leu Asn Thr Phe Gly Met
 1               5

<210> SEQ ID NO 234
<211> LENGTH: 9
<212> TYPE: PRT
<213> ORGANISM: homo sapien

<400> SEQUENCE: 234

Leu Met Gly Phe Leu Leu Tyr Glu Ala
 1               5

<210> SEQ ID NO 235
<211> LENGTH: 9
<212> TYPE: PRT
<213> ORGANISM: homo sapien

<400> SEQUENCE: 235

Ile Ile Trp Asp Thr Val Val Ile Ile
 1               5

<210> SEQ ID NO 236
<211> LENGTH: 9
<212> TYPE: PRT
<213> ORGANISM: homo sapien

<400> SEQUENCE: 236

Ile Met Thr Asp Ala Leu His Met Leu
 1               5

<210> SEQ ID NO 237
<211> LENGTH: 9
<212> TYPE: PRT
<213> ORGANISM: homo sapien

<400> SEQUENCE: 237

Asp Leu Ser Ala Ile Ile Leu Thr Leu
 1               5

<210> SEQ ID NO 238
<211> LENGTH: 9
<212> TYPE: PRT
<213> ORGANISM: homo sapien

<400> SEQUENCE: 238

Gly Val Leu Ile Ala Ala Tyr Ile Ile
 1               5
```

<210> SEQ ID NO 239
<211> LENGTH: 9
<212> TYPE: PRT
<213> ORGANISM: homo sapien

<400> SEQUENCE: 239

Lys Gln Arg Glu Ile Leu Lys Gln Arg
 1               5

<210> SEQ ID NO 240
<211> LENGTH: 9
<212> TYPE: PRT
<213> ORGANISM: homo sapien

<400> SEQUENCE: 240

Ala Leu Gly Asp Leu Val Gln Ser Val
 1               5

<210> SEQ ID NO 241
<211> LENGTH: 9
<212> TYPE: PRT
<213> ORGANISM: homo sapien

<400> SEQUENCE: 241

Gln Leu Gln Ser Tyr Arg Gln Glu Val
 1               5

<210> SEQ ID NO 242
<211> LENGTH: 9
<212> TYPE: PRT
<213> ORGANISM: homo sapien

<400> SEQUENCE: 242

Ser Leu Ala Ile Met Thr Asp Ala Leu
 1               5

<210> SEQ ID NO 243
<211> LENGTH: 9
<212> TYPE: PRT
<213> ORGANISM: homo sapien

<400> SEQUENCE: 243

Thr Leu Gln Ala Asp Asp Asp Ser Leu
 1               5

<210> SEQ ID NO 244
<211> LENGTH: 9
<212> TYPE: PRT
<213> ORGANISM: homo sapien

<400> SEQUENCE: 244

Ser Val Gly Val Leu Ile Ala Ala Tyr
 1               5

<210> SEQ ID NO 245
<211> LENGTH: 9
<212> TYPE: PRT
<213> ORGANISM: homo sapien

<400> SEQUENCE: 245

Arg Leu Glu Val Leu Ser Ala Met Ile
 1               5

<210> SEQ ID NO 246

```
<211> LENGTH: 9
<212> TYPE: PRT
<213> ORGANISM: homo sapien

<400> SEQUENCE: 246

Val Leu Tyr Leu Leu Phe Met Ile Gly
 1               5

<210> SEQ ID NO 247
<211> LENGTH: 9
<212> TYPE: PRT
<213> ORGANISM: homo sapien

<400> SEQUENCE: 247

Met Leu Thr Asp Leu Ser Ala Ile Ile
 1               5

<210> SEQ ID NO 248
<211> LENGTH: 9
<212> TYPE: PRT
<213> ORGANISM: homo sapien

<400> SEQUENCE: 248

Met Leu Arg Lys Asp Asp Ala Pro Leu
 1               5

<210> SEQ ID NO 249
<211> LENGTH: 9
<212> TYPE: PRT
<213> ORGANISM: homo sapien

<400> SEQUENCE: 249

Gln Leu Ser Leu Lys Val Asp Ser Cys
 1               5

<210> SEQ ID NO 250
<211> LENGTH: 9
<212> TYPE: PRT
<213> ORGANISM: homo sapien

<400> SEQUENCE: 250

Lys Arg Phe Thr Phe Gly Phe His Arg
 1               5

<210> SEQ ID NO 251
<211> LENGTH: 10
<212> TYPE: PRT
<213> ORGANISM: homo sapien

<400> SEQUENCE: 251

Thr Leu Leu Ala Leu Trp Leu Ser Ser Lys
 1               5                  10

<210> SEQ ID NO 252
<211> LENGTH: 10
<212> TYPE: PRT
<213> ORGANISM: homo sapien

<400> SEQUENCE: 252

Leu Leu Leu Asn Thr Phe Gly Met Tyr Arg
 1               5                  10

<210> SEQ ID NO 253
<211> LENGTH: 10
<212> TYPE: PRT
```

-continued

<213> ORGANISM: homo sapien

<400> SEQUENCE: 253

Val Leu Ile Ala Ala Tyr Ile Ile Arg Phe
1               5                   10

<210> SEQ ID NO 254
<211> LENGTH: 10
<212> TYPE: PRT
<213> ORGANISM: homo sapien

<400> SEQUENCE: 254

Ser Leu Leu Val Ala Phe Thr Thr Phe Arg
1               5                   10

<210> SEQ ID NO 255
<211> LENGTH: 10
<212> TYPE: PRT
<213> ORGANISM: homo sapien

<400> SEQUENCE: 255

Val Leu Leu Val Tyr Ile Leu Met Gly Phe
1               5                   10

<210> SEQ ID NO 256
<211> LENGTH: 10
<212> TYPE: PRT
<213> ORGANISM: homo sapien

<400> SEQUENCE: 256

Phe Met Ile Gly Glu Leu Val Gly Gly Tyr
1               5                   10

<210> SEQ ID NO 257
<211> LENGTH: 10
<212> TYPE: PRT
<213> ORGANISM: homo sapien

<400> SEQUENCE: 257

Phe Leu Asn Asp Thr Ser Ala Phe Asp Phe
1               5                   10

<210> SEQ ID NO 258
<211> LENGTH: 10
<212> TYPE: PRT
<213> ORGANISM: homo sapien

<400> SEQUENCE: 258

Lys Val Asp Ser Cys Asp Asn Cys Ser Lys
1               5                   10

<210> SEQ ID NO 259
<211> LENGTH: 10
<212> TYPE: PRT
<213> ORGANISM: homo sapien

<400> SEQUENCE: 259

Ile Leu Lys Gln Arg Lys Val Lys Ala Arg
1               5                   10

<210> SEQ ID NO 260
<211> LENGTH: 10
<212> TYPE: PRT
<213> ORGANISM: homo sapien

```
<400> SEQUENCE: 260

His Leu Leu Leu Asn Thr Phe Gly Met Tyr
 1               5                  10

<210> SEQ ID NO 261
<211> LENGTH: 10
<212> TYPE: PRT
<213> ORGANISM: homo sapien

<400> SEQUENCE: 261

Trp Leu Ser Ser Lys Ser Pro Thr Lys Arg
 1               5                  10

<210> SEQ ID NO 262
<211> LENGTH: 10
<212> TYPE: PRT
<213> ORGANISM: homo sapien

<400> SEQUENCE: 262

Gly Val Leu Ile Ala Ala Tyr Ile Ile Arg
 1               5                  10

<210> SEQ ID NO 263
<211> LENGTH: 10
<212> TYPE: PRT
<213> ORGANISM: homo sapien

<400> SEQUENCE: 263

Arg Leu Thr Ile Ala Ala Val Leu Tyr Leu
 1               5                  10

<210> SEQ ID NO 264
<211> LENGTH: 10
<212> TYPE: PRT
<213> ORGANISM: homo sapien

<400> SEQUENCE: 264

Tyr Ile Ile Arg Phe Lys Pro Glu Tyr Lys
 1               5                  10

<210> SEQ ID NO 265
<211> LENGTH: 10
<212> TYPE: PRT
<213> ORGANISM: homo sapien

<400> SEQUENCE: 265

Pro Leu Thr Asn Ser Gln Leu Ser Leu Lys
 1               5                  10

<210> SEQ ID NO 266
<211> LENGTH: 10
<212> TYPE: PRT
<213> ORGANISM: homo sapien

<400> SEQUENCE: 266

Lys Gln Arg Glu Ile Leu Lys Gln Arg Lys
 1               5                  10

<210> SEQ ID NO 267
<211> LENGTH: 10
<212> TYPE: PRT
<213> ORGANISM: homo sapien

<400> SEQUENCE: 267
```

```
Ile Ile Trp Asp Thr Val Val Ile Ile Leu
1               5                   10

<210> SEQ ID NO 268
<211> LENGTH: 10
<212> TYPE: PRT
<213> ORGANISM: homo sapien

<400> SEQUENCE: 268

Leu Leu Val Ala Phe Thr Thr Phe Arg Ile
1               5                   10

<210> SEQ ID NO 269
<211> LENGTH: 10
<212> TYPE: PRT
<213> ORGANISM: homo sapien

<400> SEQUENCE: 269

Gly Val Ala Val Asn Val Ile Met Gly Phe
1               5                   10

<210> SEQ ID NO 270
<211> LENGTH: 10
<212> TYPE: PRT
<213> ORGANISM: homo sapien

<400> SEQUENCE: 270

Ile Leu Met Gly Phe Leu Leu Tyr Glu Ala
1               5                   10

<210> SEQ ID NO 271
<211> LENGTH: 10
<212> TYPE: PRT
<213> ORGANISM: homo sapien

<400> SEQUENCE: 271

Met Leu Arg Lys Asp Asp Ala Pro Leu Phe
1               5                   10

<210> SEQ ID NO 272
<211> LENGTH: 10
<212> TYPE: PRT
<213> ORGANISM: homo sapien

<400> SEQUENCE: 272

Leu Met Lys Ile Glu Asp Val Tyr Ser Val
1               5                   10

<210> SEQ ID NO 273
<211> LENGTH: 10
<212> TYPE: PRT
<213> ORGANISM: homo sapien

<400> SEQUENCE: 273

Ala Met Ile Ser Val Leu Leu Val Tyr Ile
1               5                   10

<210> SEQ ID NO 274
<211> LENGTH: 10
<212> TYPE: PRT
<213> ORGANISM: homo sapien

<400> SEQUENCE: 274

Gly Val Pro Ser His Leu Asn Val Asp Tyr
1               5                   10
```

```
<210> SEQ ID NO 275
<211> LENGTH: 10
<212> TYPE: PRT
<213> ORGANISM: homo sapien

<400> SEQUENCE: 275

Met Leu Thr Asp Leu Ser Ala Ile Ile Leu
 1               5                  10

<210> SEQ ID NO 276
<211> LENGTH: 10
<212> TYPE: PRT
<213> ORGANISM: homo sapien

<400> SEQUENCE: 276

Gly Leu Ser Arg Phe Asn Lys Leu Arg Val
 1               5                  10

<210> SEQ ID NO 277
<211> LENGTH: 10
<212> TYPE: PRT
<213> ORGANISM: homo sapien

<400> SEQUENCE: 277

Ala Val Gln Arg Thr Ile His Met Asn Tyr
 1               5                  10

<210> SEQ ID NO 278
<211> LENGTH: 10
<212> TYPE: PRT
<213> ORGANISM: homo sapien

<400> SEQUENCE: 278

Pro Leu Phe Leu Asn Asp Thr Ser Ala Phe
 1               5                  10

<210> SEQ ID NO 279
<211> LENGTH: 10
<212> TYPE: PRT
<213> ORGANISM: homo sapien

<400> SEQUENCE: 279

Ile Gln Leu Ile Pro Gly Ser Ser Ser Lys
 1               5                  10

<210> SEQ ID NO 280
<211> LENGTH: 10
<212> TYPE: PRT
<213> ORGANISM: homo sapien

<400> SEQUENCE: 280

Leu Val Tyr Ile Leu Met Gly Phe Leu Leu
 1               5                  10

<210> SEQ ID NO 281
<211> LENGTH: 10
<212> TYPE: PRT
<213> ORGANISM: homo sapien

<400> SEQUENCE: 281

Val Leu Ser Ala Met Ile Ser Val Leu Leu
 1               5                  10
```

```
<210> SEQ ID NO 282
<211> LENGTH: 10
<212> TYPE: PRT
<213> ORGANISM: homo sapien

<400> SEQUENCE: 282

Ser Met Leu Arg Lys Asp Asp Ala Pro Leu
1               5                   10

<210> SEQ ID NO 283
<211> LENGTH: 10
<212> TYPE: PRT
<213> ORGANISM: homo sapien

<400> SEQUENCE: 283

Val Leu Tyr Leu Leu Phe Met Ile Gly Glu
1               5                   10

<210> SEQ ID NO 284
<211> LENGTH: 10
<212> TYPE: PRT
<213> ORGANISM: homo sapien

<400> SEQUENCE: 284

Leu Leu Asn Thr Phe Gly Met Tyr Arg Cys
1               5                   10

<210> SEQ ID NO 285
<211> LENGTH: 10
<212> TYPE: PRT
<213> ORGANISM: homo sapien

<400> SEQUENCE: 285

His Met Leu Thr Asp Leu Ser Ala Ile Ile
1               5                   10

<210> SEQ ID NO 286
<211> LENGTH: 10
<212> TYPE: PRT
<213> ORGANISM: homo sapien

<400> SEQUENCE: 286

Leu Leu Tyr Glu Ala Val Gln Arg Thr Ile
1               5                   10

<210> SEQ ID NO 287
<211> LENGTH: 10
<212> TYPE: PRT
<213> ORGANISM: homo sapien

<400> SEQUENCE: 287

Asn Thr Phe Gly Met Tyr Arg Cys Thr Ile
1               5                   10

<210> SEQ ID NO 288
<211> LENGTH: 10
<212> TYPE: PRT
<213> ORGANISM: homo sapien

<400> SEQUENCE: 288

Thr Leu Gln Ala Asp Asp Asp Ser Leu Leu
1               5                   10

<210> SEQ ID NO 289
<211> LENGTH: 10
```

```
<212> TYPE: PRT
<213> ORGANISM: homo sapien

<400> SEQUENCE: 289

Ser Leu Thr Ser Gly Lys Ser Thr Ala Ile
1               5                   10

<210> SEQ ID NO 290
<211> LENGTH: 10
<212> TYPE: PRT
<213> ORGANISM: homo sapien

<400> SEQUENCE: 290

Ser Leu Ala Val Arg Ala Ala Phe Val His
1               5                   10

<210> SEQ ID NO 291
<211> LENGTH: 10
<212> TYPE: PRT
<213> ORGANISM: homo sapien

<400> SEQUENCE: 291

Ala Val Arg Ala Ala Phe Val His Ala Leu
1               5                   10

<210> SEQ ID NO 292
<211> LENGTH: 10
<212> TYPE: PRT
<213> ORGANISM: homo sapien

<400> SEQUENCE: 292

Met Ile Ser Val Leu Leu Val Tyr Ile Leu
1               5                   10

<210> SEQ ID NO 293
<211> LENGTH: 10
<212> TYPE: PRT
<213> ORGANISM: homo sapien

<400> SEQUENCE: 293

Ala Leu Trp Leu Ser Ser Lys Ser Pro Thr
1               5                   10

<210> SEQ ID NO 294
<211> LENGTH: 10
<212> TYPE: PRT
<213> ORGANISM: homo sapien

<400> SEQUENCE: 294

Gly Met Tyr Arg Cys Thr Ile Gln Leu Gln
1               5                   10

<210> SEQ ID NO 295
<211> LENGTH: 10
<212> TYPE: PRT
<213> ORGANISM: homo sapien

<400> SEQUENCE: 295

Leu Ile Ala Ala Tyr Ile Ile Arg Phe Lys
1               5                   10

<210> SEQ ID NO 296
<211> LENGTH: 10
<212> TYPE: PRT
<213> ORGANISM: homo sapien
```

```
<400> SEQUENCE: 296

His Leu Asn Val Asp Tyr Ile Lys Glu Ala
 1               5                  10

<210> SEQ ID NO 297
<211> LENGTH: 10
<212> TYPE: PRT
<213> ORGANISM: homo sapien

<400> SEQUENCE: 297

Tyr Leu Leu Phe Met Ile Gly Glu Leu Val
 1               5                  10

<210> SEQ ID NO 298
<211> LENGTH: 10
<212> TYPE: PRT
<213> ORGANISM: homo sapien

<400> SEQUENCE: 298

Phe Leu Leu Tyr Glu Ala Val Gln Arg Thr
 1               5                  10

<210> SEQ ID NO 299
<211> LENGTH: 10
<212> TYPE: PRT
<213> ORGANISM: homo sapien

<400> SEQUENCE: 299

Gln Leu Ile Pro Gly Ser Ser Ser Lys Trp
 1               5                  10

<210> SEQ ID NO 300
<211> LENGTH: 10
<212> TYPE: PRT
<213> ORGANISM: homo sapien

<400> SEQUENCE: 300

Asp Leu Ser Ala Ile Ile Leu Thr Leu Leu
 1               5                  10

<210> SEQ ID NO 301
<211> LENGTH: 9
<212> TYPE: PRT
<213> ORGANISM: homo sapien

<400> SEQUENCE: 301

Leu Thr Asn Ser Gln Leu Ser Leu Lys
 1               5

<210> SEQ ID NO 302
<211> LENGTH: 9
<212> TYPE: PRT
<213> ORGANISM: homo sapien

<400> SEQUENCE: 302

Asn Ile Trp Ser Leu Thr Ser Gly Lys
 1               5

<210> SEQ ID NO 303
<211> LENGTH: 9
<212> TYPE: PRT
<213> ORGANISM: homo sapien

<400> SEQUENCE: 303
```

Gln Leu Ile Pro Gly Ser Ser Ser Lys
1               5

<210> SEQ ID NO 304
<211> LENGTH: 9
<212> TYPE: PRT
<213> ORGANISM: homo sapien

<400> SEQUENCE: 304

Ile Ile Arg Phe Lys Pro Glu Tyr Lys
1               5

<210> SEQ ID NO 305
<211> LENGTH: 9
<212> TYPE: PRT
<213> ORGANISM: homo sapien

<400> SEQUENCE: 305

Trp Leu Ser Ser Lys Ser Pro Thr Lys
1               5

<210> SEQ ID NO 306
<211> LENGTH: 9
<212> TYPE: PRT
<213> ORGANISM: homo sapien

<400> SEQUENCE: 306

Leu Leu Ala Leu Trp Leu Ser Ser Lys
1               5

<210> SEQ ID NO 307
<211> LENGTH: 9
<212> TYPE: PRT
<213> ORGANISM: homo sapien

<400> SEQUENCE: 307

Asp Tyr Ile Lys Glu Ala Leu Met Lys
1               5

<210> SEQ ID NO 308
<211> LENGTH: 9
<212> TYPE: PRT
<213> ORGANISM: homo sapien

<400> SEQUENCE: 308

Cys Thr Ile Gln Leu Gln Ser Tyr Arg
1               5

<210> SEQ ID NO 309
<211> LENGTH: 9
<212> TYPE: PRT
<213> ORGANISM: homo sapien

<400> SEQUENCE: 309

Val Leu Ile Ala Ala Tyr Ile Ile Arg
1               5

<210> SEQ ID NO 310
<211> LENGTH: 9
<212> TYPE: PRT
<213> ORGANISM: homo sapien

<400> SEQUENCE: 310

Lys Arg Leu Lys Ser Met Leu Arg Lys

```
                           1               5

<210> SEQ ID NO 311
<211> LENGTH: 9
<212> TYPE: PRT
<213> ORGANISM: homo sapien

<400> SEQUENCE: 311

Gly Val Leu Ile Ala Ala Tyr Ile Ile
  1               5

<210> SEQ ID NO 312
<211> LENGTH: 9
<212> TYPE: PRT
<213> ORGANISM: homo sapien

<400> SEQUENCE: 312

Lys Gln Arg Glu Ile Leu Lys Gln Arg
  1               5

<210> SEQ ID NO 313
<211> LENGTH: 9
<212> TYPE: PRT
<213> ORGANISM: homo sapien

<400> SEQUENCE: 313

Leu Leu Asn Thr Phe Gly Met Tyr Arg
  1               5

<210> SEQ ID NO 314
<211> LENGTH: 9
<212> TYPE: PRT
<213> ORGANISM: homo sapien

<400> SEQUENCE: 314

Gly Leu Ser Arg Phe Asn Lys Leu Arg
  1               5

<210> SEQ ID NO 315
<211> LENGTH: 9
<212> TYPE: PRT
<213> ORGANISM: homo sapien

<400> SEQUENCE: 315

Phe Leu Leu Tyr Glu Ala Val Gln Arg
  1               5

<210> SEQ ID NO 316
<211> LENGTH: 9
<212> TYPE: PRT
<213> ORGANISM: homo sapien

<400> SEQUENCE: 316

Phe Leu Leu Asn Gln Ser Gly His Arg
  1               5

<210> SEQ ID NO 317
<211> LENGTH: 9
<212> TYPE: PRT
<213> ORGANISM: homo sapien

<400> SEQUENCE: 317

Leu Leu Val Ala Phe Thr Thr Phe Arg
  1               5
```

<210> SEQ ID NO 318
<211> LENGTH: 9
<212> TYPE: PRT
<213> ORGANISM: homo sapien

<400> SEQUENCE: 318

Arg Thr Ile His Met Asn Tyr Glu Ile
1               5

<210> SEQ ID NO 319
<211> LENGTH: 9
<212> TYPE: PRT
<213> ORGANISM: homo sapien

<400> SEQUENCE: 319

Ala Val Leu Tyr Leu Leu Phe Met Ile
1               5

<210> SEQ ID NO 320
<211> LENGTH: 9
<212> TYPE: PRT
<213> ORGANISM: homo sapien

<400> SEQUENCE: 320

Glu Ile Leu Lys Gln Arg Lys Val Lys
1               5

<210> SEQ ID NO 321
<211> LENGTH: 9
<212> TYPE: PRT
<213> ORGANISM: homo sapien

<400> SEQUENCE: 321

Ser Leu Pro Ser Asn Ser Pro Thr Arg
1               5

<210> SEQ ID NO 322
<211> LENGTH: 9
<212> TYPE: PRT
<213> ORGANISM: homo sapien

<400> SEQUENCE: 322

Met Ala Gly Ser Gly Ala Trp Lys Arg
1               5

<210> SEQ ID NO 323
<211> LENGTH: 9
<212> TYPE: PRT
<213> ORGANISM: homo sapien

<400> SEQUENCE: 323

Lys Arg Phe Thr Phe Gly Phe His Arg
1               5

<210> SEQ ID NO 324
<211> LENGTH: 9
<212> TYPE: PRT
<213> ORGANISM: homo sapien

<400> SEQUENCE: 324

Ser His Leu Asn Val Asp Tyr Ile Lys
1               5

<210> SEQ ID NO 325

```
<211> LENGTH: 9
<212> TYPE: PRT
<213> ORGANISM: homo sapien

<400> SEQUENCE: 325

Leu Val Ala Phe Thr Thr Phe Arg Ile
1               5

<210> SEQ ID NO 326
<211> LENGTH: 9
<212> TYPE: PRT
<213> ORGANISM: homo sapien

<400> SEQUENCE: 326

Lys Val Lys Ala Arg Leu Thr Ile Ala
1               5

<210> SEQ ID NO 327
<211> LENGTH: 9
<212> TYPE: PRT
<213> ORGANISM: homo sapien

<400> SEQUENCE: 327

Ser Val Leu Leu Val Tyr Ile Leu Met
1               5

<210> SEQ ID NO 328
<211> LENGTH: 9
<212> TYPE: PRT
<213> ORGANISM: homo sapien

<400> SEQUENCE: 328

Asp Glu Gly Leu Ser Arg Phe Asn Lys
1               5

<210> SEQ ID NO 329
<211> LENGTH: 9
<212> TYPE: PRT
<213> ORGANISM: homo sapien

<400> SEQUENCE: 329

Gly Met Tyr Arg Cys Thr Ile Gln Leu
1               5

<210> SEQ ID NO 330
<211> LENGTH: 9
<212> TYPE: PRT
<213> ORGANISM: homo sapien

<400> SEQUENCE: 330

Leu Val Tyr Ile Leu Met Gly Phe Leu
1               5

<210> SEQ ID NO 331
<211> LENGTH: 9
<212> TYPE: PRT
<213> ORGANISM: homo sapien

<400> SEQUENCE: 331

Tyr Val Phe Ser Leu Leu Val Ala Phe
1               5

<210> SEQ ID NO 332
<211> LENGTH: 9
<212> TYPE: PRT
```

<213> ORGANISM: homo sapien

<400> SEQUENCE: 332

Cys Thr Tyr Val Phe Ser Leu Leu Val
1               5

<210> SEQ ID NO 333
<211> LENGTH: 9
<212> TYPE: PRT
<213> ORGANISM: homo sapien

<400> SEQUENCE: 333

Ser Lys Trp Glu Glu Val Gln Ser Lys
1               5

<210> SEQ ID NO 334
<211> LENGTH: 9
<212> TYPE: PRT
<213> ORGANISM: homo sapien

<400> SEQUENCE: 334

Cys Ser Lys Gln Arg Glu Ile Leu Lys
1               5

<210> SEQ ID NO 335
<211> LENGTH: 9
<212> TYPE: PRT
<213> ORGANISM: homo sapien

<400> SEQUENCE: 335

Gly Tyr Ile Ala Asn Ser Leu Ala Ile
1               5

<210> SEQ ID NO 336
<211> LENGTH: 9
<212> TYPE: PRT
<213> ORGANISM: homo sapien

<400> SEQUENCE: 336

Thr Val Val Ile Ile Leu Glu Gly Val
1               5

<210> SEQ ID NO 337
<211> LENGTH: 9
<212> TYPE: PRT
<213> ORGANISM: homo sapien

<400> SEQUENCE: 337

Leu Thr Ile Ala Ala Val Leu Tyr Leu
1               5

<210> SEQ ID NO 338
<211> LENGTH: 9
<212> TYPE: PRT
<213> ORGANISM: homo sapien

<400> SEQUENCE: 338

Glu Ala Gly Asp Glu Gly Leu Ser Arg
1               5

<210> SEQ ID NO 339
<211> LENGTH: 9
<212> TYPE: PRT
<213> ORGANISM: homo sapien

<400> SEQUENCE: 339

Phe Val His Ala Leu Gly Asp Leu Val
1               5

<210> SEQ ID NO 340
<211> LENGTH: 9
<212> TYPE: PRT
<213> ORGANISM: homo sapien

<400> SEQUENCE: 340

Ser Cys Asp Asn Cys Ser Lys Gln Arg
1               5

<210> SEQ ID NO 341
<211> LENGTH: 9
<212> TYPE: PRT
<213> ORGANISM: homo sapien

<400> SEQUENCE: 341

Val Val Ala Asp Asp Gly Ser Glu Ala
1               5

<210> SEQ ID NO 342
<211> LENGTH: 9
<212> TYPE: PRT
<213> ORGANISM: homo sapien

<400> SEQUENCE: 342

Leu Val Gln Ser Val Gly Val Leu Ile
1               5

<210> SEQ ID NO 343
<211> LENGTH: 9
<212> TYPE: PRT
<213> ORGANISM: homo sapien

<400> SEQUENCE: 343

Ile Ala Ala Tyr Ile Ile Arg Phe Lys
1               5

<210> SEQ ID NO 344
<211> LENGTH: 9
<212> TYPE: PRT
<213> ORGANISM: homo sapien

<400> SEQUENCE: 344

Ala Val Gly Val Ala Val Asn Val Ile
1               5

<210> SEQ ID NO 345
<211> LENGTH: 9
<212> TYPE: PRT
<213> ORGANISM: homo sapien

<400> SEQUENCE: 345

Val Asp Ser Cys Asp Asn Cys Ser Lys
1               5

<210> SEQ ID NO 346
<211> LENGTH: 9
<212> TYPE: PRT
<213> ORGANISM: homo sapien

<400> SEQUENCE: 346

Ser Val Gly Val Leu Ile Ala Ala Tyr
1               5

<210> SEQ ID NO 347
<211> LENGTH: 9
<212> TYPE: PRT
<213> ORGANISM: homo sapien

<400> SEQUENCE: 347

Asn Val Asp Tyr Ile Lys Glu Ala Leu
1               5

<210> SEQ ID NO 348
<211> LENGTH: 9
<212> TYPE: PRT
<213> ORGANISM: homo sapien

<400> SEQUENCE: 348

Ala Val Asn Val Ile Met Gly Phe Leu
1               5

<210> SEQ ID NO 349
<211> LENGTH: 9
<212> TYPE: PRT
<213> ORGANISM: homo sapien

<400> SEQUENCE: 349

Ala Val Arg Ala Ala Phe Val His Ala
1               5

<210> SEQ ID NO 350
<211> LENGTH: 9
<212> TYPE: PRT
<213> ORGANISM: homo sapien

<400> SEQUENCE: 350

Gln Arg Glu Ile Leu Lys Gln Arg Lys
1               5

<210> SEQ ID NO 351
<211> LENGTH: 10
<212> TYPE: PRT
<213> ORGANISM: homo sapien

<400> SEQUENCE: 351

Lys Val Asp Ser Cys Asp Asn Cys Ser Lys
1               5                   10

<210> SEQ ID NO 352
<211> LENGTH: 10
<212> TYPE: PRT
<213> ORGANISM: homo sapien

<400> SEQUENCE: 352

Gly Val Leu Ile Ala Ala Tyr Ile Ile Arg
1               5                   10

<210> SEQ ID NO 353
<211> LENGTH: 10
<212> TYPE: PRT
<213> ORGANISM: homo sapien

<400> SEQUENCE: 353

Lys Gln Arg Glu Ile Leu Lys Gln Arg Lys
1               5                   10

<210> SEQ ID NO 354
<211> LENGTH: 10
<212> TYPE: PRT
<213> ORGANISM: homo sapien

<400> SEQUENCE: 354

Ile Gln Leu Ile Pro Gly Ser Ser Ser Lys
 1               5                  10

<210> SEQ ID NO 355
<211> LENGTH: 10
<212> TYPE: PRT
<213> ORGANISM: homo sapien

<400> SEQUENCE: 355

Thr Leu Leu Ala Leu Trp Leu Ser Ser Lys
 1               5                  10

<210> SEQ ID NO 356
<211> LENGTH: 10
<212> TYPE: PRT
<213> ORGANISM: homo sapien

<400> SEQUENCE: 356

Tyr Ile Ile Arg Phe Lys Pro Glu Tyr Lys
 1               5                  10

<210> SEQ ID NO 357
<211> LENGTH: 10
<212> TYPE: PRT
<213> ORGANISM: homo sapien

<400> SEQUENCE: 357

Asn Cys Ser Lys Gln Arg Glu Ile Leu Lys
 1               5                  10

<210> SEQ ID NO 358
<211> LENGTH: 10
<212> TYPE: PRT
<213> ORGANISM: homo sapien

<400> SEQUENCE: 358

Leu Leu Leu Asn Thr Phe Gly Met Tyr Arg
 1               5                  10

<210> SEQ ID NO 359
<211> LENGTH: 10
<212> TYPE: PRT
<213> ORGANISM: homo sapien

<400> SEQUENCE: 359

Gly Asp Glu Gly Leu Ser Arg Phe Asn Lys
 1               5                  10

<210> SEQ ID NO 360
<211> LENGTH: 10
<212> TYPE: PRT
<213> ORGANISM: homo sapien

<400> SEQUENCE: 360

Gly Phe Leu Leu Tyr Glu Ala Val Gln Arg
 1               5                  10

```
<210> SEQ ID NO 361
<211> LENGTH: 10
<212> TYPE: PRT
<213> ORGANISM: homo sapien

<400> SEQUENCE: 361

Gly Phe Leu Leu Asn Gln Ser Gly His Arg
1               5                   10

<210> SEQ ID NO 362
<211> LENGTH: 10
<212> TYPE: PRT
<213> ORGANISM: homo sapien

<400> SEQUENCE: 362

Arg Glu Ile Leu Lys Gln Arg Lys Val Lys
1               5                   10

<210> SEQ ID NO 363
<211> LENGTH: 10
<212> TYPE: PRT
<213> ORGANISM: homo sapien

<400> SEQUENCE: 363

Gly Val Ala Val Asn Val Ile Met Gly Phe
1               5                   10

<210> SEQ ID NO 364
<211> LENGTH: 10
<212> TYPE: PRT
<213> ORGANISM: homo sapien

<400> SEQUENCE: 364

Leu Val Tyr Ile Leu Met Gly Phe Leu Leu
1               5                   10

<210> SEQ ID NO 365
<211> LENGTH: 10
<212> TYPE: PRT
<213> ORGANISM: homo sapien

<400> SEQUENCE: 365

Lys Val Lys Ala Arg Leu Thr Ile Ala Ala
1               5                   10

<210> SEQ ID NO 366
<211> LENGTH: 10
<212> TYPE: PRT
<213> ORGANISM: homo sapien

<400> SEQUENCE: 366

Leu Gln Ser Tyr Arg Gln Glu Val Asp Arg
1               5                   10

<210> SEQ ID NO 367
<211> LENGTH: 10
<212> TYPE: PRT
<213> ORGANISM: homo sapien

<400> SEQUENCE: 367

Arg Cys Thr Ile Gln Leu Gln Ser Tyr Arg
1               5                   10

<210> SEQ ID NO 368
<211> LENGTH: 10
```

```
<212> TYPE: PRT
<213> ORGANISM: homo sapien

<400> SEQUENCE: 368

Ser Leu Leu Val Ala Phe Thr Thr Phe Arg
1               5                   10

<210> SEQ ID NO 369
<211> LENGTH: 10
<212> TYPE: PRT
<213> ORGANISM: homo sapien

<400> SEQUENCE: 369

Trp Leu Ser Ser Lys Ser Pro Thr Lys Arg
1               5                   10

<210> SEQ ID NO 370
<211> LENGTH: 10
<212> TYPE: PRT
<213> ORGANISM: homo sapien

<400> SEQUENCE: 370

Val Asp Tyr Ile Lys Glu Ala Leu Met Lys
1               5                   10

<210> SEQ ID NO 371
<211> LENGTH: 10
<212> TYPE: PRT
<213> ORGANISM: homo sapien

<400> SEQUENCE: 371

Leu Asn Ile Trp Ser Leu Thr Ser Gly Lys
1               5                   10

<210> SEQ ID NO 372
<211> LENGTH: 10
<212> TYPE: PRT
<213> ORGANISM: homo sapien

<400> SEQUENCE: 372

Gly Val Pro Ser His Leu Asn Val Asp Tyr
1               5                   10

<210> SEQ ID NO 373
<211> LENGTH: 10
<212> TYPE: PRT
<213> ORGANISM: homo sapien

<400> SEQUENCE: 373

Ala Val Asn Val Ile Met Gly Phe Leu Leu
1               5                   10

<210> SEQ ID NO 374
<211> LENGTH: 10
<212> TYPE: PRT
<213> ORGANISM: homo sapien

<400> SEQUENCE: 374

Ser Pro Thr Arg Gly Ser Gly Cys Glu Arg
1               5                   10

<210> SEQ ID NO 375
<211> LENGTH: 10
<212> TYPE: PRT
<213> ORGANISM: homo sapien
```

```
<400> SEQUENCE: 375

Trp Lys Arg Leu Lys Ser Met Leu Arg Lys
1               5                   10

<210> SEQ ID NO 376
<211> LENGTH: 10
<212> TYPE: PRT
<213> ORGANISM: homo sapien

<400> SEQUENCE: 376

Ile Leu Lys Gln Arg Lys Val Lys Ala Arg
1               5                   10

<210> SEQ ID NO 377
<211> LENGTH: 10
<212> TYPE: PRT
<213> ORGANISM: homo sapien

<400> SEQUENCE: 377

Cys Thr Tyr Val Phe Ser Leu Leu Val Ala
1               5                   10

<210> SEQ ID NO 378
<211> LENGTH: 10
<212> TYPE: PRT
<213> ORGANISM: homo sapien

<400> SEQUENCE: 378

Leu Val Gln Ser Val Gly Val Leu Ile Ala
1               5                   10

<210> SEQ ID NO 379
<211> LENGTH: 10
<212> TYPE: PRT
<213> ORGANISM: homo sapien

<400> SEQUENCE: 379

Leu Ile Ala Ala Tyr Ile Ile Arg Phe Lys
1               5                   10

<210> SEQ ID NO 380
<211> LENGTH: 10
<212> TYPE: PRT
<213> ORGANISM: homo sapien

<400> SEQUENCE: 380

Phe Thr Phe Gly Phe His Arg Leu Glu Val
1               5                   10

<210> SEQ ID NO 381
<211> LENGTH: 10
<212> TYPE: PRT
<213> ORGANISM: homo sapien

<400> SEQUENCE: 381

Ser Val Glu Asp Leu Asn Ile Trp Ser Leu
1               5                   10

<210> SEQ ID NO 382
<211> LENGTH: 10
<212> TYPE: PRT
<213> ORGANISM: homo sapien

<400> SEQUENCE: 382
```

```
Pro Leu Thr Asn Ser Gln Leu Ser Leu Lys
 1               5                  10

<210> SEQ ID NO 383
<211> LENGTH: 10
<212> TYPE: PRT
<213> ORGANISM: homo sapien

<400> SEQUENCE: 383

Ala Val Gln Arg Thr Ile His Met Asn Tyr
 1               5                  10

<210> SEQ ID NO 384
<211> LENGTH: 10
<212> TYPE: PRT
<213> ORGANISM: homo sapien

<400> SEQUENCE: 384

Leu Trp Leu Ser Ser Lys Ser Pro Thr Lys
 1               5                  10

<210> SEQ ID NO 385
<211> LENGTH: 10
<212> TYPE: PRT
<213> ORGANISM: homo sapien

<400> SEQUENCE: 385

Val Val Val Ala Asp Asp Gly Ser Glu Ala
 1               5                  10

<210> SEQ ID NO 386
<211> LENGTH: 10
<212> TYPE: PRT
<213> ORGANISM: homo sapien

<400> SEQUENCE: 386

Leu Thr Ile Ala Ala Val Leu Tyr Leu Leu
 1               5                  10

<210> SEQ ID NO 387
<211> LENGTH: 10
<212> TYPE: PRT
<213> ORGANISM: homo sapien

<400> SEQUENCE: 387

Asp Val Tyr Ser Val Glu Asp Leu Asn Ile
 1               5                  10

<210> SEQ ID NO 388
<211> LENGTH: 10
<212> TYPE: PRT
<213> ORGANISM: homo sapien

<400> SEQUENCE: 388

Gly Leu Ser Arg Phe Asn Lys Leu Arg Val
 1               5                  10

<210> SEQ ID NO 389
<211> LENGTH: 10
<212> TYPE: PRT
<213> ORGANISM: homo sapien

<400> SEQUENCE: 389

Arg Leu Thr Ile Ala Ala Val Leu Tyr Leu
```

-continued

<210> SEQ ID NO 390
<211> LENGTH: 10
<212> TYPE: PRT
<213> ORGANISM: homo sapien

<400> SEQUENCE: 390

Thr Thr Phe Arg Ile Ile Trp Asp Thr Val
1               5                   10

<210> SEQ ID NO 391
<211> LENGTH: 10
<212> TYPE: PRT
<213> ORGANISM: homo sapien

<400> SEQUENCE: 391

Ala Val Gly Val Ala Val Asn Val Ile Met
1               5                   10

<210> SEQ ID NO 392
<211> LENGTH: 10
<212> TYPE: PRT
<213> ORGANISM: homo sapien

<400> SEQUENCE: 392

Ser Ser Lys Trp Glu Glu Val Gln Ser Lys
1               5                   10

<210> SEQ ID NO 393
<211> LENGTH: 10
<212> TYPE: PRT
<213> ORGANISM: homo sapien

<400> SEQUENCE: 393

Ala Val Arg Ala Ala Phe Val His Ala Leu
1               5                   10

<210> SEQ ID NO 394
<211> LENGTH: 10
<212> TYPE: PRT
<213> ORGANISM: homo sapien

<400> SEQUENCE: 394

Asn Thr Phe Gly Met Tyr Arg Cys Thr Ile
1               5                   10

<210> SEQ ID NO 395
<211> LENGTH: 10
<212> TYPE: PRT
<213> ORGANISM: homo sapien

<400> SEQUENCE: 395

Leu Thr Asn Ser Gln Leu Ser Leu Lys Val
1               5                   10

<210> SEQ ID NO 396
<211> LENGTH: 10
<212> TYPE: PRT
<213> ORGANISM: homo sapien

<400> SEQUENCE: 396

Ser Val Gly Val Leu Ile Ala Ala Tyr Ile
1               5                   10

<210> SEQ ID NO 397
<211> LENGTH: 10
<212> TYPE: PRT
<213> ORGANISM: homo sapien

<400> SEQUENCE: 397

Leu Val Gly Gly Tyr Ile Ala Asn Ser Leu
1               5                   10

<210> SEQ ID NO 398
<211> LENGTH: 10
<212> TYPE: PRT
<213> ORGANISM: homo sapien

<400> SEQUENCE: 398

Asn Val Asp Tyr Ile Lys Glu Ala Leu Met
1               5                   10

<210> SEQ ID NO 399
<211> LENGTH: 10
<212> TYPE: PRT
<213> ORGANISM: homo sapien

<400> SEQUENCE: 399

Leu Leu Val Ala Phe Thr Thr Phe Arg Ile
1               5                   10

<210> SEQ ID NO 400
<211> LENGTH: 10
<212> TYPE: PRT
<213> ORGANISM: homo sapien

<400> SEQUENCE: 400

Arg Ile Ile Trp Asp Thr Val Val Ile Ile
1               5                   10

<210> SEQ ID NO 401
<211> LENGTH: 9
<212> TYPE: PRT
<213> ORGANISM: homo sapien

<400> SEQUENCE: 401

Val Tyr Ile Leu Met Gly Phe Leu Leu
1               5

<210> SEQ ID NO 402
<211> LENGTH: 9
<212> TYPE: PRT
<213> ORGANISM: homo sapien

<400> SEQUENCE: 402

Leu Tyr Glu Ala Val Gln Arg Thr Ile
1               5

<210> SEQ ID NO 403
<211> LENGTH: 9
<212> TYPE: PRT
<213> ORGANISM: homo sapien

<400> SEQUENCE: 403

Gly Tyr Ile Ala Asn Ser Leu Ala Ile
1               5

<210> SEQ ID NO 404

```
<211> LENGTH: 9
<212> TYPE: PRT
<213> ORGANISM: homo sapien

<400> SEQUENCE: 404

Val Tyr Ser Val Glu Asp Leu Asn Ile
1               5

<210> SEQ ID NO 405
<211> LENGTH: 9
<212> TYPE: PRT
<213> ORGANISM: homo sapien

<400> SEQUENCE: 405

Arg Phe Thr Phe Gly Phe His Arg Leu
1               5

<210> SEQ ID NO 406
<211> LENGTH: 9
<212> TYPE: PRT
<213> ORGANISM: homo sapien

<400> SEQUENCE: 406

Asn Tyr Glu Ile Asn Gly Asp Ile Met
1               5

<210> SEQ ID NO 407
<211> LENGTH: 9
<212> TYPE: PRT
<213> ORGANISM: homo sapien

<400> SEQUENCE: 407

Ala Phe Val His Ala Leu Gly Asp Leu
1               5

<210> SEQ ID NO 408
<211> LENGTH: 9
<212> TYPE: PRT
<213> ORGANISM: homo sapien

<400> SEQUENCE: 408

Leu Phe Leu Asn Asp Thr Ser Ala Phe
1               5

<210> SEQ ID NO 409
<211> LENGTH: 9
<212> TYPE: PRT
<213> ORGANISM: homo sapien

<400> SEQUENCE: 409

Lys Gln Arg Lys Val Lys Ala Arg Leu
1               5

<210> SEQ ID NO 410
<211> LENGTH: 9
<212> TYPE: PRT
<213> ORGANISM: homo sapien

<400> SEQUENCE: 410

Glu Gly Leu Ser Arg Phe Asn Lys Leu
1               5

<210> SEQ ID NO 411
<211> LENGTH: 9
<212> TYPE: PRT
```

<213> ORGANISM: homo sapien

<400> SEQUENCE: 411

Ile Leu Glu Gly Val Pro Ser His Leu
1               5

<210> SEQ ID NO 412
<211> LENGTH: 9
<212> TYPE: PRT
<213> ORGANISM: homo sapien

<400> SEQUENCE: 412

Ala Val Asn Val Ile Met Gly Phe Leu
1               5

<210> SEQ ID NO 413
<211> LENGTH: 9
<212> TYPE: PRT
<213> ORGANISM: homo sapien

<400> SEQUENCE: 413

Thr Tyr Val Phe Ser Leu Leu Val Ala
1               5

<210> SEQ ID NO 414
<211> LENGTH: 9
<212> TYPE: PRT
<213> ORGANISM: homo sapien

<400> SEQUENCE: 414

Ser Leu Leu Asp Gln Asp Leu Pro Leu
1               5

<210> SEQ ID NO 415
<211> LENGTH: 9
<212> TYPE: PRT
<213> ORGANISM: homo sapien

<400> SEQUENCE: 415

Ile Ser Val Leu Leu Val Tyr Ile Leu
1               5

<210> SEQ ID NO 416
<211> LENGTH: 9
<212> TYPE: PRT
<213> ORGANISM: homo sapien

<400> SEQUENCE: 416

Glu Val Gln Ser Lys Ala Asn His Leu
1               5

<210> SEQ ID NO 417
<211> LENGTH: 9
<212> TYPE: PRT
<213> ORGANISM: homo sapien

<400> SEQUENCE: 417

Val Gly Gly Tyr Ile Ala Asn Ser Leu
1               5

<210> SEQ ID NO 418
<211> LENGTH: 9
<212> TYPE: PRT
<213> ORGANISM: homo sapien

```
<400> SEQUENCE: 418

Ile Cys Thr Tyr Val Phe Ser Leu Leu
1               5

<210> SEQ ID NO 419
<211> LENGTH: 9
<212> TYPE: PRT
<213> ORGANISM: homo sapien

<400> SEQUENCE: 419

Tyr Leu Leu Phe Met Ile Gly Glu Leu
1               5

<210> SEQ ID NO 420
<211> LENGTH: 9
<212> TYPE: PRT
<213> ORGANISM: homo sapien

<400> SEQUENCE: 420

Ala Ile Ile Leu Thr Leu Leu Ala Leu
1               5

<210> SEQ ID NO 421
<211> LENGTH: 9
<212> TYPE: PRT
<213> ORGANISM: homo sapien

<400> SEQUENCE: 421

Lys Ser Pro Thr Lys Arg Phe Thr Phe
1               5

<210> SEQ ID NO 422
<211> LENGTH: 9
<212> TYPE: PRT
<213> ORGANISM: homo sapien

<400> SEQUENCE: 422

Asp Leu Val Gln Ser Val Gly Val Leu
1               5

<210> SEQ ID NO 423
<211> LENGTH: 9
<212> TYPE: PRT
<213> ORGANISM: homo sapien

<400> SEQUENCE: 423

Thr Leu Gln Ala Asp Asp Asp Ser Leu
1               5

<210> SEQ ID NO 424
<211> LENGTH: 9
<212> TYPE: PRT
<213> ORGANISM: homo sapien

<400> SEQUENCE: 424

Asp Ala Leu His Met Leu Thr Asp Leu
1               5

<210> SEQ ID NO 425
<211> LENGTH: 9
<212> TYPE: PRT
<213> ORGANISM: homo sapien

<400> SEQUENCE: 425
```

-continued

Val Asn Val Ile Met Gly Phe Leu Leu
1               5

<210> SEQ ID NO 426
<211> LENGTH: 9
<212> TYPE: PRT
<213> ORGANISM: homo sapien

<400> SEQUENCE: 426

Asp Leu Pro Leu Thr Asn Ser Gln Leu
1               5

<210> SEQ ID NO 427
<211> LENGTH: 9
<212> TYPE: PRT
<213> ORGANISM: homo sapien

<400> SEQUENCE: 427

Leu Thr Ile Ala Ala Val Leu Tyr Leu
1               5

<210> SEQ ID NO 428
<211> LENGTH: 9
<212> TYPE: PRT
<213> ORGANISM: homo sapien

<400> SEQUENCE: 428

Asp Leu Ser Ala Ile Ile Leu Thr Leu
1               5

<210> SEQ ID NO 429
<211> LENGTH: 9
<212> TYPE: PRT
<213> ORGANISM: homo sapien

<400> SEQUENCE: 429

Asn Val Asp Tyr Ile Lys Glu Ala Leu
1               5

<210> SEQ ID NO 430
<211> LENGTH: 9
<212> TYPE: PRT
<213> ORGANISM: homo sapien

<400> SEQUENCE: 430

Ile Trp Asp Thr Val Val Ile Ile Leu
1               5

<210> SEQ ID NO 431
<211> LENGTH: 9
<212> TYPE: PRT
<213> ORGANISM: homo sapien

<400> SEQUENCE: 431

Thr Ile Ala Ala Val Leu Tyr Leu Leu
1               5

<210> SEQ ID NO 432
<211> LENGTH: 9
<212> TYPE: PRT
<213> ORGANISM: homo sapien

<400> SEQUENCE: 432

Ser Thr Ala Ile Val His Ile Gln Leu
1               5

<210> SEQ ID NO 433
<211> LENGTH: 9
<212> TYPE: PRT
<213> ORGANISM: homo sapien

<400> SEQUENCE: 433

Leu Ser Ala Ile Ile Leu Thr Leu Leu
 1               5

<210> SEQ ID NO 434
<211> LENGTH: 9
<212> TYPE: PRT
<213> ORGANISM: homo sapien

<400> SEQUENCE: 434

Leu Ser Ala Met Ile Ser Val Leu Leu
 1               5

<210> SEQ ID NO 435
<211> LENGTH: 9
<212> TYPE: PRT
<213> ORGANISM: homo sapien

<400> SEQUENCE: 435

Glu Tyr Lys Ile Ala Asp Pro Ile Cys
 1               5

<210> SEQ ID NO 436
<211> LENGTH: 9
<212> TYPE: PRT
<213> ORGANISM: homo sapien

<400> SEQUENCE: 436

Thr Phe Gly Met Tyr Arg Cys Thr Ile
 1               5

<210> SEQ ID NO 437
<211> LENGTH: 9
<212> TYPE: PRT
<213> ORGANISM: homo sapien

<400> SEQUENCE: 437

Ser Tyr Arg Gln Glu Val Asp Arg Thr
 1               5

<210> SEQ ID NO 438
<211> LENGTH: 9
<212> TYPE: PRT
<213> ORGANISM: homo sapien

<400> SEQUENCE: 438

Ala Trp Lys Arg Leu Lys Ser Met Leu
 1               5

<210> SEQ ID NO 439
<211> LENGTH: 9
<212> TYPE: PRT
<213> ORGANISM: homo sapien

<400> SEQUENCE: 439

Leu Val Tyr Ile Leu Met Gly Phe Leu
 1               5

```
<210> SEQ ID NO 440
<211> LENGTH: 9
<212> TYPE: PRT
<213> ORGANISM: homo sapien

<400> SEQUENCE: 440

Leu Gln Ala Asp Asp Asp Ser Leu Leu
1               5

<210> SEQ ID NO 441
<211> LENGTH: 9
<212> TYPE: PRT
<213> ORGANISM: homo sapien

<400> SEQUENCE: 441

Ile Leu Thr Leu Leu Ala Leu Trp Leu
1               5

<210> SEQ ID NO 442
<211> LENGTH: 9
<212> TYPE: PRT
<213> ORGANISM: homo sapien

<400> SEQUENCE: 442

Ile Met Thr Asp Ala Leu His Met Leu
1               5

<210> SEQ ID NO 443
<211> LENGTH: 9
<212> TYPE: PRT
<213> ORGANISM: homo sapien

<400> SEQUENCE: 443

Leu Leu Val Tyr Ile Leu Met Gly Phe
1               5

<210> SEQ ID NO 444
<211> LENGTH: 9
<212> TYPE: PRT
<213> ORGANISM: homo sapien

<400> SEQUENCE: 444

Val Ala Val Asn Val Ile Met Gly Phe
1               5

<210> SEQ ID NO 445
<211> LENGTH: 9
<212> TYPE: PRT
<213> ORGANISM: homo sapien

<400> SEQUENCE: 445

Asp Ser Leu Ala Val Arg Ala Ala Phe
1               5

<210> SEQ ID NO 446
<211> LENGTH: 9
<212> TYPE: PRT
<213> ORGANISM: homo sapien

<400> SEQUENCE: 446

Met Leu Arg Lys Asp Asp Ala Pro Leu
1               5

<210> SEQ ID NO 447
<211> LENGTH: 9
```

```
<212> TYPE: PRT
<213> ORGANISM: homo sapien

<400> SEQUENCE: 447

Gly Met Tyr Arg Cys Thr Ile Gln Leu
1               5

<210> SEQ ID NO 448
<211> LENGTH: 9
<212> TYPE: PRT
<213> ORGANISM: homo sapien

<400> SEQUENCE: 448

Ala Gly Ser Gly Ala Trp Lys Arg Leu
1               5

<210> SEQ ID NO 449
<211> LENGTH: 9
<212> TYPE: PRT
<213> ORGANISM: homo sapien

<400> SEQUENCE: 449

Asn Cys Ser Lys Gln Arg Glu Ile Leu
1               5

<210> SEQ ID NO 450
<211> LENGTH: 9
<212> TYPE: PRT
<213> ORGANISM: homo sapien

<400> SEQUENCE: 450

Gln Ser Lys Ala Asn His Leu Leu Leu
1               5

<210> SEQ ID NO 451
<211> LENGTH: 10
<212> TYPE: PRT
<213> ORGANISM: homo sapien

<400> SEQUENCE: 451

Leu Tyr Leu Leu Phe Met Ile Gly Glu Leu
1               5                   10

<210> SEQ ID NO 452
<211> LENGTH: 10
<212> TYPE: PRT
<213> ORGANISM: homo sapien

<400> SEQUENCE: 452

Asn Tyr Glu Ile Asn Gly Asp Ile Met Leu
1               5                   10

<210> SEQ ID NO 453
<211> LENGTH: 10
<212> TYPE: PRT
<213> ORGANISM: homo sapien

<400> SEQUENCE: 453

Thr Tyr Val Phe Ser Leu Leu Val Ala Phe
1               5                   10

<210> SEQ ID NO 454
<211> LENGTH: 10
<212> TYPE: PRT
<213> ORGANISM: homo sapien
```

```
<400> SEQUENCE: 454

Asp Tyr Ile Lys Glu Ala Leu Met Lys Ile
1               5                   10

<210> SEQ ID NO 455
<211> LENGTH: 10
<212> TYPE: PRT
<213> ORGANISM: homo sapien

<400> SEQUENCE: 455

Gly Tyr Ile Ala Asn Ser Leu Ala Ile Met
1               5                   10

<210> SEQ ID NO 456
<211> LENGTH: 10
<212> TYPE: PRT
<213> ORGANISM: homo sapien

<400> SEQUENCE: 456

Thr Phe Gly Phe His Arg Leu Glu Val Leu
1               5                   10

<210> SEQ ID NO 457
<211> LENGTH: 10
<212> TYPE: PRT
<213> ORGANISM: homo sapien

<400> SEQUENCE: 457

Arg Pro Val Asn Gly Ala His Pro Thr Leu
1               5                   10

<210> SEQ ID NO 458
<211> LENGTH: 10
<212> TYPE: PRT
<213> ORGANISM: homo sapien

<400> SEQUENCE: 458

Lys Ser Thr Ala Ile Val His Ile Gln Leu
1               5                   10

<210> SEQ ID NO 459
<211> LENGTH: 10
<212> TYPE: PRT
<213> ORGANISM: homo sapien

<400> SEQUENCE: 459

Lys Ala Arg Leu Thr Ile Ala Ala Val Leu
1               5                   10

<210> SEQ ID NO 460
<211> LENGTH: 10
<212> TYPE: PRT
<213> ORGANISM: homo sapien

<400> SEQUENCE: 460

Leu Asn Val Asp Tyr Ile Lys Glu Ala Leu
1               5                   10

<210> SEQ ID NO 461
<211> LENGTH: 10
<212> TYPE: PRT
<213> ORGANISM: homo sapien

<400> SEQUENCE: 461
```

Ile Ile Leu Glu Gly Val Pro Ser His Leu
1               5                   10

<210> SEQ ID NO 462
<211> LENGTH: 10
<212> TYPE: PRT
<213> ORGANISM: homo sapien

<400> SEQUENCE: 462

Val Tyr Ile Leu Met Gly Phe Leu Leu Tyr
1               5                   10

<210> SEQ ID NO 463
<211> LENGTH: 10
<212> TYPE: PRT
<213> ORGANISM: homo sapien

<400> SEQUENCE: 463

Lys Ala Asn His Leu Leu Leu Asn Thr Phe
1               5                   10

<210> SEQ ID NO 464
<211> LENGTH: 10
<212> TYPE: PRT
<213> ORGANISM: homo sapien

<400> SEQUENCE: 464

Val Ala Val Asn Val Ile Met Gly Phe Leu
1               5                   10

<210> SEQ ID NO 465
<211> LENGTH: 10
<212> TYPE: PRT
<213> ORGANISM: homo sapien

<400> SEQUENCE: 465

Leu Thr Ile Ala Ala Val Leu Tyr Leu Leu
1               5                   10

<210> SEQ ID NO 466
<211> LENGTH: 10
<212> TYPE: PRT
<213> ORGANISM: homo sapien

<400> SEQUENCE: 466

Ala Tyr Ile Ile Arg Phe Lys Pro Glu Tyr
1               5                   10

<210> SEQ ID NO 467
<211> LENGTH: 10
<212> TYPE: PRT
<213> ORGANISM: homo sapien

<400> SEQUENCE: 467

Arg Leu Thr Ile Ala Ala Val Leu Tyr Leu
1               5                   10

<210> SEQ ID NO 468
<211> LENGTH: 10
<212> TYPE: PRT
<213> ORGANISM: homo sapien

<400> SEQUENCE: 468

Leu Leu Val Tyr Ile Leu Met Gly Phe Leu

```
1               5               10
```

<210> SEQ ID NO 469
<211> LENGTH: 10
<212> TYPE: PRT
<213> ORGANISM: homo sapien

<400> SEQUENCE: 469

```
Ser Val Glu Asp Leu Asn Ile Trp Ser Leu
 1               5               10
```

<210> SEQ ID NO 470
<211> LENGTH: 10
<212> TYPE: PRT
<213> ORGANISM: homo sapien

<400> SEQUENCE: 470

```
Ile Ile Leu Thr Leu Leu Ala Leu Trp Leu
 1               5               10
```

<210> SEQ ID NO 471
<211> LENGTH: 10
<212> TYPE: PRT
<213> ORGANISM: homo sapien

<400> SEQUENCE: 471

```
Met Tyr Arg Cys Thr Ile Gln Leu Gln Ser
 1               5               10
```

<210> SEQ ID NO 472
<211> LENGTH: 10
<212> TYPE: PRT
<213> ORGANISM: homo sapien

<400> SEQUENCE: 472

```
Ser Tyr Arg Gln Glu Val Asp Arg Thr Cys
 1               5               10
```

<210> SEQ ID NO 473
<211> LENGTH: 10
<212> TYPE: PRT
<213> ORGANISM: homo sapien

<400> SEQUENCE: 473

```
Leu Val Gly Gly Tyr Ile Ala Asn Ser Leu
 1               5               10
```

<210> SEQ ID NO 474
<211> LENGTH: 10
<212> TYPE: PRT
<213> ORGANISM: homo sapien

<400> SEQUENCE: 474

```
Ile Ile Trp Asp Thr Val Val Ile Ile Leu
 1               5               10
```

<210> SEQ ID NO 475
<211> LENGTH: 10
<212> TYPE: PRT
<213> ORGANISM: homo sapien

<400> SEQUENCE: 475

```
Asp Pro Ile Cys Thr Tyr Val Phe Ser Leu
 1               5               10
```

-continued

```
<210> SEQ ID NO 476
<211> LENGTH: 10
<212> TYPE: PRT
<213> ORGANISM: homo sapien

<400> SEQUENCE: 476

Ser Ala Ile Ile Leu Thr Leu Leu Ala Leu
1               5                   10

<210> SEQ ID NO 477
<211> LENGTH: 10
<212> TYPE: PRT
<213> ORGANISM: homo sapien

<400> SEQUENCE: 477

Phe Gly Met Tyr Arg Cys Thr Ile Gln Leu
1               5                   10

<210> SEQ ID NO 478
<211> LENGTH: 10
<212> TYPE: PRT
<213> ORGANISM: homo sapien

<400> SEQUENCE: 478

Ser Met Leu Arg Lys Asp Asp Ala Pro Leu
1               5                   10

<210> SEQ ID NO 479
<211> LENGTH: 10
<212> TYPE: PRT
<213> ORGANISM: homo sapien

<400> SEQUENCE: 479

Thr Leu Gln Ala Asp Asp Ser Leu Leu
1               5                   10

<210> SEQ ID NO 480
<211> LENGTH: 10
<212> TYPE: PRT
<213> ORGANISM: homo sapien

<400> SEQUENCE: 480

Val Tyr Ser Val Glu Asp Leu Asn Ile Trp
1               5                   10

<210> SEQ ID NO 481
<211> LENGTH: 10
<212> TYPE: PRT
<213> ORGANISM: homo sapien

<400> SEQUENCE: 481

Leu Pro Leu Thr Asn Ser Gln Leu Ser Leu
1               5                   10

<210> SEQ ID NO 482
<211> LENGTH: 10
<212> TYPE: PRT
<213> ORGANISM: homo sapien

<400> SEQUENCE: 482

Ala Val Asn Val Ile Met Gly Phe Leu Leu
1               5                   10

<210> SEQ ID NO 483
```

```
<211> LENGTH: 10
<212> TYPE: PRT
<213> ORGANISM: homo sapien

<400> SEQUENCE: 483

Ala Ile Met Thr Asp Ala Leu His Met Leu
 1               5                  10

<210> SEQ ID NO 484
<211> LENGTH: 10
<212> TYPE: PRT
<213> ORGANISM: homo sapien

<400> SEQUENCE: 484

Asn Ser Leu Ala Ile Met Thr Asp Ala Leu
 1               5                  10

<210> SEQ ID NO 485
<211> LENGTH: 10
<212> TYPE: PRT
<213> ORGANISM: homo sapien

<400> SEQUENCE: 485

Glu Val Gln Ser Lys Ala Asn His Leu Leu
 1               5                  10

<210> SEQ ID NO 486
<211> LENGTH: 10
<212> TYPE: PRT
<213> ORGANISM: homo sapien

<400> SEQUENCE: 486

Glu Val Leu Ser Ala Met Ile Ser Val Leu
 1               5                  10

<210> SEQ ID NO 487
<211> LENGTH: 10
<212> TYPE: PRT
<213> ORGANISM: homo sapien

<400> SEQUENCE: 487

Asp Ser Leu Leu Asp Gln Asp Leu Pro Leu
 1               5                  10

<210> SEQ ID NO 488
<211> LENGTH: 10
<212> TYPE: PRT
<213> ORGANISM: homo sapien

<400> SEQUENCE: 488

Asp Leu Ser Ala Ile Ile Leu Thr Leu Leu
 1               5                  10

<210> SEQ ID NO 489
<211> LENGTH: 10
<212> TYPE: PRT
<213> ORGANISM: homo sapien

<400> SEQUENCE: 489

Val Leu Ser Ala Met Ile Ser Val Leu Leu
 1               5                  10

<210> SEQ ID NO 490
<211> LENGTH: 10
<212> TYPE: PRT
```

-continued

<213> ORGANISM: homo sapien

<400> SEQUENCE: 490

Glu Tyr Lys Ile Ala Asp Pro Ile Cys Thr
1               5                   10

<210> SEQ ID NO 491
<211> LENGTH: 10
<212> TYPE: PRT
<213> ORGANISM: homo sapien

<400> SEQUENCE: 491

Met Ile Ser Val Leu Leu Val Tyr Ile Leu
1               5                   10

<210> SEQ ID NO 492
<211> LENGTH: 10
<212> TYPE: PRT
<213> ORGANISM: homo sapien

<400> SEQUENCE: 492

Gly Ala Trp Lys Arg Leu Lys Ser Met Leu
1               5                   10

<210> SEQ ID NO 493
<211> LENGTH: 10
<212> TYPE: PRT
<213> ORGANISM: homo sapien

<400> SEQUENCE: 493

Met Leu Thr Asp Leu Ser Ala Ile Ile Leu
1               5                   10

<210> SEQ ID NO 494
<211> LENGTH: 10
<212> TYPE: PRT
<213> ORGANISM: homo sapien

<400> SEQUENCE: 494

Phe Ser Asp Glu Ala Gly Asp Glu Gly Leu
1               5                   10

<210> SEQ ID NO 495
<211> LENGTH: 10
<212> TYPE: PRT
<213> ORGANISM: homo sapien

<400> SEQUENCE: 495

Lys Pro Glu Tyr Lys Ile Ala Asp Pro Ile
1               5                   10

<210> SEQ ID NO 496
<211> LENGTH: 10
<212> TYPE: PRT
<213> ORGANISM: homo sapien

<400> SEQUENCE: 496

Val Leu Leu Val Tyr Ile Leu Met Gly Phe
1               5                   10

<210> SEQ ID NO 497
<211> LENGTH: 10
<212> TYPE: PRT
<213> ORGANISM: homo sapien

```
<400> SEQUENCE: 497

Ala Ala Phe Val His Ala Leu Gly Asp Leu
 1               5                  10

<210> SEQ ID NO 498
<211> LENGTH: 10
<212> TYPE: PRT
<213> ORGANISM: homo sapien

<400> SEQUENCE: 498

Ala Val Arg Ala Ala Phe Val His Ala Leu
 1               5                  10

<210> SEQ ID NO 499
<211> LENGTH: 10
<212> TYPE: PRT
<213> ORGANISM: homo sapien

<400> SEQUENCE: 499

Met Ala Gly Ser Gly Ala Trp Lys Arg Leu
 1               5                  10

<210> SEQ ID NO 500
<211> LENGTH: 10
<212> TYPE: PRT
<213> ORGANISM: homo sapien

<400> SEQUENCE: 500

Asp Asn Cys Ser Lys Gln Arg Glu Ile Leu
 1               5                  10

<210> SEQ ID NO 501
<211> LENGTH: 9
<212> TYPE: PRT
<213> ORGANISM: homo sapien

<400> SEQUENCE: 501

Ala Val Asn Val Ile Met Gly Phe Leu
 1               5

<210> SEQ ID NO 502
<211> LENGTH: 9
<212> TYPE: PRT
<213> ORGANISM: homo sapien

<400> SEQUENCE: 502

Lys Gln Arg Lys Val Lys Ala Arg Leu
 1               5

<210> SEQ ID NO 503
<211> LENGTH: 9
<212> TYPE: PRT
<213> ORGANISM: homo sapien

<400> SEQUENCE: 503

Met Leu Arg Lys Asp Asp Ala Pro Leu
 1               5

<210> SEQ ID NO 504
<211> LENGTH: 9
<212> TYPE: PRT
<213> ORGANISM: homo sapien

<400> SEQUENCE: 504
```

```
Leu Val Tyr Ile Leu Met Gly Phe Leu
 1               5
```

<210> SEQ ID NO 505
<211> LENGTH: 9
<212> TYPE: PRT
<213> ORGANISM: homo sapien
<400> SEQUENCE: 505

```
Glu Val Gln Ser Lys Ala Asn His Leu
 1               5
```

<210> SEQ ID NO 506
<211> LENGTH: 9
<212> TYPE: PRT
<213> ORGANISM: homo sapien
<400> SEQUENCE: 506

```
Ala Val Arg Ala Ala Phe Val His Ala
 1               5
```

<210> SEQ ID NO 507
<211> LENGTH: 9
<212> TYPE: PRT
<213> ORGANISM: homo sapien
<400> SEQUENCE: 507

```
Ala Gly Ser Gly Ala Trp Lys Arg Leu
 1               5
```

<210> SEQ ID NO 508
<211> LENGTH: 9
<212> TYPE: PRT
<213> ORGANISM: homo sapien
<400> SEQUENCE: 508

```
Asp Ala Leu His Met Leu Thr Asp Leu
 1               5
```

<210> SEQ ID NO 509
<211> LENGTH: 9
<212> TYPE: PRT
<213> ORGANISM: homo sapien
<400> SEQUENCE: 509

```
Ala Ile Ile Leu Thr Leu Leu Ala Leu
 1               5
```

<210> SEQ ID NO 510
<211> LENGTH: 9
<212> TYPE: PRT
<213> ORGANISM: homo sapien
<400> SEQUENCE: 510

```
Ala Ile Met Thr Asp Ala Leu His Met
 1               5
```

<210> SEQ ID NO 511
<211> LENGTH: 9
<212> TYPE: PRT
<213> ORGANISM: homo sapien
<400> SEQUENCE: 511

```
Ala Ala Val Leu Tyr Leu Leu Phe Met
 1               5
```

```
<210> SEQ ID NO 512
<211> LENGTH: 9
<212> TYPE: PRT
<213> ORGANISM: homo sapien

<400> SEQUENCE: 512

Asn Val Asp Tyr Ile Lys Glu Ala Leu
 1               5

<210> SEQ ID NO 513
<211> LENGTH: 9
<212> TYPE: PRT
<213> ORGANISM: homo sapien

<400> SEQUENCE: 513

Asn Cys Ser Lys Gln Arg Glu Ile Leu
 1               5

<210> SEQ ID NO 514
<211> LENGTH: 9
<212> TYPE: PRT
<213> ORGANISM: homo sapien

<400> SEQUENCE: 514

Lys Ala Arg Leu Thr Ile Ala Ala Val
 1               5

<210> SEQ ID NO 515
<211> LENGTH: 9
<212> TYPE: PRT
<213> ORGANISM: homo sapien

<400> SEQUENCE: 515

Ala Val Leu Tyr Leu Leu Phe Met Ile
 1               5

<210> SEQ ID NO 516
<211> LENGTH: 9
<212> TYPE: PRT
<213> ORGANISM: homo sapien

<400> SEQUENCE: 516

Ala Val Gly Val Ala Val Asn Val Ile
 1               5

<210> SEQ ID NO 517
<211> LENGTH: 9
<212> TYPE: PRT
<213> ORGANISM: homo sapien

<400> SEQUENCE: 517

Ser Val Leu Leu Val Tyr Ile Leu Met
 1               5

<210> SEQ ID NO 518
<211> LENGTH: 9
<212> TYPE: PRT
<213> ORGANISM: homo sapien

<400> SEQUENCE: 518

Asp Leu Ser Ala Ile Ile Leu Thr Leu
 1               5
```

```
<210> SEQ ID NO 519
<211> LENGTH: 9
<212> TYPE: PRT
<213> ORGANISM: homo sapien

<400> SEQUENCE: 519

Ile Cys Thr Tyr Val Phe Ser Leu Leu
1               5

<210> SEQ ID NO 520
<211> LENGTH: 9
<212> TYPE: PRT
<213> ORGANISM: homo sapien

<400> SEQUENCE: 520

Ile Ser Val Leu Leu Val Tyr Ile Leu
1               5

<210> SEQ ID NO 521
<211> LENGTH: 9
<212> TYPE: PRT
<213> ORGANISM: homo sapien

<400> SEQUENCE: 521

Val Gly Gly Tyr Ile Ala Asn Ser Leu
1               5

<210> SEQ ID NO 522
<211> LENGTH: 9
<212> TYPE: PRT
<213> ORGANISM: homo sapien

<400> SEQUENCE: 522

Leu Ser Ala Ile Ile Leu Thr Leu Leu
1               5

<210> SEQ ID NO 523
<211> LENGTH: 9
<212> TYPE: PRT
<213> ORGANISM: homo sapien

<400> SEQUENCE: 523

Leu Ser Ala Met Ile Ser Val Leu Leu
1               5

<210> SEQ ID NO 524
<211> LENGTH: 9
<212> TYPE: PRT
<213> ORGANISM: homo sapien

<400> SEQUENCE: 524

Gln Ser Lys Ala Asn His Leu Leu Leu
1               5

<210> SEQ ID NO 525
<211> LENGTH: 9
<212> TYPE: PRT
<213> ORGANISM: homo sapien

<400> SEQUENCE: 525

Ile Leu Thr Leu Leu Ala Leu Trp Leu
1               5

<210> SEQ ID NO 526
<211> LENGTH: 9
```

```
<212> TYPE: PRT
<213> ORGANISM: homo sapien

<400> SEQUENCE: 526

Gly Met Tyr Arg Cys Thr Ile Gln Leu
 1               5

<210> SEQ ID NO 527
<211> LENGTH: 9
<212> TYPE: PRT
<213> ORGANISM: homo sapien

<400> SEQUENCE: 527

Ser Leu Leu Asp Gln Asp Leu Pro Leu
 1               5

<210> SEQ ID NO 528
<211> LENGTH: 9
<212> TYPE: PRT
<213> ORGANISM: homo sapien

<400> SEQUENCE: 528

Leu Gln Ala Asp Asp Ser Leu Leu
 1               5

<210> SEQ ID NO 529
<211> LENGTH: 9
<212> TYPE: PRT
<213> ORGANISM: homo sapien

<400> SEQUENCE: 529

Val Leu Ser Ala Met Ile Ser Val Leu
 1               5

<210> SEQ ID NO 530
<211> LENGTH: 9
<212> TYPE: PRT
<213> ORGANISM: homo sapien

<400> SEQUENCE: 530

Ser Thr Ala Ile Val His Ile Gln Leu
 1               5

<210> SEQ ID NO 531
<211> LENGTH: 9
<212> TYPE: PRT
<213> ORGANISM: homo sapien

<400> SEQUENCE: 531

Leu Thr Ile Ala Ala Val Leu Tyr Leu
 1               5

<210> SEQ ID NO 532
<211> LENGTH: 9
<212> TYPE: PRT
<213> ORGANISM: homo sapien

<400> SEQUENCE: 532

Asp Leu Val Gln Ser Val Gly Val Leu
 1               5

<210> SEQ ID NO 533
<211> LENGTH: 9
<212> TYPE: PRT
<213> ORGANISM: homo sapien
```

<400> SEQUENCE: 533

Asp Leu Pro Leu Thr Asn Ser Gln Leu
1               5

<210> SEQ ID NO 534
<211> LENGTH: 9
<212> TYPE: PRT
<213> ORGANISM: homo sapien

<400> SEQUENCE: 534

Val Gln Ser Lys Ala Asn His Leu Leu
1               5

<210> SEQ ID NO 535
<211> LENGTH: 9
<212> TYPE: PRT
<213> ORGANISM: homo sapien

<400> SEQUENCE: 535

Glu Gly Leu Ser Arg Phe Asn Lys Leu
1               5

<210> SEQ ID NO 536
<211> LENGTH: 9
<212> TYPE: PRT
<213> ORGANISM: homo sapien

<400> SEQUENCE: 536

Thr Ile Ala Ala Val Leu Tyr Leu Leu
1               5

<210> SEQ ID NO 537
<211> LENGTH: 9
<212> TYPE: PRT
<213> ORGANISM: homo sapien

<400> SEQUENCE: 537

Ile Met Thr Asp Ala Leu His Met Leu
1               5

<210> SEQ ID NO 538
<211> LENGTH: 9
<212> TYPE: PRT
<213> ORGANISM: homo sapien

<400> SEQUENCE: 538

Thr Leu Gln Ala Asp Asp Asp Ser Leu
1               5

<210> SEQ ID NO 539
<211> LENGTH: 9
<212> TYPE: PRT
<213> ORGANISM: homo sapien

<400> SEQUENCE: 539

Phe Gly Phe His Arg Leu Glu Val Leu
1               5

<210> SEQ ID NO 540
<211> LENGTH: 9
<212> TYPE: PRT
<213> ORGANISM: homo sapien

<400> SEQUENCE: 540

Val Asn Val Ile Met Gly Phe Leu Leu
1               5

<210> SEQ ID NO 541
<211> LENGTH: 9
<212> TYPE: PRT
<213> ORGANISM: homo sapien

<400> SEQUENCE: 541

Tyr Leu Leu Phe Met Ile Gly Glu Leu
1               5

<210> SEQ ID NO 542
<211> LENGTH: 9
<212> TYPE: PRT
<213> ORGANISM: homo sapien

<400> SEQUENCE: 542

Ser Leu Ala Ile Met Thr Asp Ala Leu
1               5

<210> SEQ ID NO 543
<211> LENGTH: 9
<212> TYPE: PRT
<213> ORGANISM: homo sapien

<400> SEQUENCE: 543

Gly Ala Trp Lys Arg Leu Lys Ser Met
1               5

<210> SEQ ID NO 544
<211> LENGTH: 9
<212> TYPE: PRT
<213> ORGANISM: homo sapien

<400> SEQUENCE: 544

Glu Ala Val Gln Arg Thr Ile His Met
1               5

<210> SEQ ID NO 545
<211> LENGTH: 9
<212> TYPE: PRT
<213> ORGANISM: homo sapien

<400> SEQUENCE: 545

Ala Pro Glu Arg Pro Val Asn Gly Ala
1               5

<210> SEQ ID NO 546
<211> LENGTH: 9
<212> TYPE: PRT
<213> ORGANISM: homo sapien

<400> SEQUENCE: 546

Pro Val Asn Gly Ala His Pro Thr Leu
1               5

<210> SEQ ID NO 547
<211> LENGTH: 9
<212> TYPE: PRT
<213> ORGANISM: homo sapien

<400> SEQUENCE: 547

Leu Val Gln Ser Val Gly Val Leu Ile

```
1               5
```

<210> SEQ ID NO 548
<211> LENGTH: 9
<212> TYPE: PRT
<213> ORGANISM: homo sapien

<400> SEQUENCE: 548

```
Gly Val Leu Ile Ala Ala Tyr Ile Ile
1               5
```

<210> SEQ ID NO 549
<211> LENGTH: 9
<212> TYPE: PRT
<213> ORGANISM: homo sapien

<400> SEQUENCE: 549

```
Leu Val Ala Phe Thr Thr Phe Arg Ile
1               5
```

<210> SEQ ID NO 550
<211> LENGTH: 9
<212> TYPE: PRT
<213> ORGANISM: homo sapien

<400> SEQUENCE: 550

```
Leu Ser Arg Phe Asn Lys Leu Arg Val
1               5
```

<210> SEQ ID NO 551
<211> LENGTH: 10
<212> TYPE: PRT
<213> ORGANISM: homo sapien

<400> SEQUENCE: 551

```
Ala Val Arg Ala Ala Phe Val His Ala Leu
1               5                   10
```

<210> SEQ ID NO 552
<211> LENGTH: 10
<212> TYPE: PRT
<213> ORGANISM: homo sapien

<400> SEQUENCE: 552

```
Lys Ala Arg Leu Thr Ile Ala Ala Val Leu
1               5                   10
```

<210> SEQ ID NO 553
<211> LENGTH: 10
<212> TYPE: PRT
<213> ORGANISM: homo sapien

<400> SEQUENCE: 553

```
Arg Pro Val Asn Gly Ala His Pro Thr Leu
1               5                   10
```

<210> SEQ ID NO 554
<211> LENGTH: 10
<212> TYPE: PRT
<213> ORGANISM: homo sapien

<400> SEQUENCE: 554

```
Leu Pro Leu Thr Asn Ser Gln Leu Ser Leu
1               5                   10
```

<210> SEQ ID NO 555
<211> LENGTH: 10
<212> TYPE: PRT
<213> ORGANISM: homo sapien

<400> SEQUENCE: 555

Asp Pro Ile Cys Thr Tyr Val Phe Ser Leu
1               5                   10

<210> SEQ ID NO 556
<211> LENGTH: 10
<212> TYPE: PRT
<213> ORGANISM: homo sapien

<400> SEQUENCE: 556

Ala Val Asn Val Ile Met Gly Phe Leu Leu
1               5                   10

<210> SEQ ID NO 557
<211> LENGTH: 10
<212> TYPE: PRT
<213> ORGANISM: homo sapien

<400> SEQUENCE: 557

Ala Ala Phe Val His Ala Leu Gly Asp Leu
1               5                   10

<210> SEQ ID NO 558
<211> LENGTH: 10
<212> TYPE: PRT
<213> ORGANISM: homo sapien

<400> SEQUENCE: 558

Ala Ile Met Thr Asp Ala Leu His Met Leu
1               5                   10

<210> SEQ ID NO 559
<211> LENGTH: 10
<212> TYPE: PRT
<213> ORGANISM: homo sapien

<400> SEQUENCE: 559

Glu Val Gln Ser Lys Ala Asn His Leu Leu
1               5                   10

<210> SEQ ID NO 560
<211> LENGTH: 10
<212> TYPE: PRT
<213> ORGANISM: homo sapien

<400> SEQUENCE: 560

Glu Val Leu Ser Ala Met Ile Ser Val Leu
1               5                   10

<210> SEQ ID NO 561
<211> LENGTH: 10
<212> TYPE: PRT
<213> ORGANISM: homo sapien

<400> SEQUENCE: 561

Leu Val Tyr Ile Leu Met Gly Phe Leu Leu
1               5                   10

<210> SEQ ID NO 562

```
<211> LENGTH: 10
<212> TYPE: PRT
<213> ORGANISM: homo sapien

<400> SEQUENCE: 562

Leu Val Gly Gly Tyr Ile Ala Asn Ser Leu
 1               5                  10

<210> SEQ ID NO 563
<211> LENGTH: 10
<212> TYPE: PRT
<213> ORGANISM: homo sapien

<400> SEQUENCE: 563

Ala Val Gly Val Ala Val Asn Val Ile Met
 1               5                  10

<210> SEQ ID NO 564
<211> LENGTH: 10
<212> TYPE: PRT
<213> ORGANISM: homo sapien

<400> SEQUENCE: 564

Gly Ala Trp Lys Arg Leu Lys Ser Met Leu
 1               5                  10

<210> SEQ ID NO 565
<211> LENGTH: 10
<212> TYPE: PRT
<213> ORGANISM: homo sapien

<400> SEQUENCE: 565

Met Ala Gly Ser Gly Ala Trp Lys Arg Leu
 1               5                  10

<210> SEQ ID NO 566
<211> LENGTH: 10
<212> TYPE: PRT
<213> ORGANISM: homo sapien

<400> SEQUENCE: 566

Ser Ala Ile Ile Leu Thr Leu Leu Ala Leu
 1               5                  10

<210> SEQ ID NO 567
<211> LENGTH: 10
<212> TYPE: PRT
<213> ORGANISM: homo sapien

<400> SEQUENCE: 567

Phe Gly Met Tyr Arg Cys Thr Ile Gln Leu
 1               5                  10

<210> SEQ ID NO 568
<211> LENGTH: 10
<212> TYPE: PRT
<213> ORGANISM: homo sapien

<400> SEQUENCE: 568

Val Ala Val Asn Val Ile Met Gly Phe Leu
 1               5                  10

<210> SEQ ID NO 569
<211> LENGTH: 10
<212> TYPE: PRT
```

<213> ORGANISM: homo sapien

<400> SEQUENCE: 569

Val Pro Ser His Leu Asn Val Asp Tyr Ile
1               5                   10

<210> SEQ ID NO 570
<211> LENGTH: 10
<212> TYPE: PRT
<213> ORGANISM: homo sapien

<400> SEQUENCE: 570

Ser Val Glu Asp Leu Asn Ile Trp Ser Leu
1               5                   10

<210> SEQ ID NO 571
<211> LENGTH: 10
<212> TYPE: PRT
<213> ORGANISM: homo sapien

<400> SEQUENCE: 571

Ala Pro Leu Phe Leu Asn Asp Thr Ser Ala
1               5                   10

<210> SEQ ID NO 572
<211> LENGTH: 10
<212> TYPE: PRT
<213> ORGANISM: homo sapien

<400> SEQUENCE: 572

Asp Asn Cys Ser Lys Gln Arg Glu Ile Leu
1               5                   10

<210> SEQ ID NO 573
<211> LENGTH: 10
<212> TYPE: PRT
<213> ORGANISM: homo sapien

<400> SEQUENCE: 573

Ile Ile Arg Phe Lys Pro Glu Tyr Lys Ile
1               5                   10

<210> SEQ ID NO 574
<211> LENGTH: 10
<212> TYPE: PRT
<213> ORGANISM: homo sapien

<400> SEQUENCE: 574

Arg Leu Thr Ile Ala Ala Val Leu Tyr Leu
1               5                   10

<210> SEQ ID NO 575
<211> LENGTH: 10
<212> TYPE: PRT
<213> ORGANISM: homo sapien

<400> SEQUENCE: 575

Asp Leu Ser Ala Ile Ile Leu Thr Leu Leu
1               5                   10

<210> SEQ ID NO 576
<211> LENGTH: 10
<212> TYPE: PRT
<213> ORGANISM: homo sapien -continued

```
<400> SEQUENCE: 576

Leu Asn Val Asp Tyr Ile Lys Glu Ala Leu
1               5                   10

<210> SEQ ID NO 577
<211> LENGTH: 10
<212> TYPE: PRT
<213> ORGANISM: homo sapien

<400> SEQUENCE: 577

Gly His Arg His Ser His Ser His Ser Leu
1               5                   10

<210> SEQ ID NO 578
<211> LENGTH: 10
<212> TYPE: PRT
<213> ORGANISM: homo sapien

<400> SEQUENCE: 578

Met Leu Thr Asp Leu Ser Ala Ile Ile Leu
1               5                   10

<210> SEQ ID NO 579
<211> LENGTH: 10
<212> TYPE: PRT
<213> ORGANISM: homo sapien

<400> SEQUENCE: 579

Ile Ile Leu Glu Gly Val Pro Ser His Leu
1               5                   10

<210> SEQ ID NO 580
<211> LENGTH: 10
<212> TYPE: PRT
<213> ORGANISM: homo sapien

<400> SEQUENCE: 580

Leu Thr Ile Ala Ala Val Leu Tyr Leu Leu
1               5                   10

<210> SEQ ID NO 581
<211> LENGTH: 10
<212> TYPE: PRT
<213> ORGANISM: homo sapien

<400> SEQUENCE: 581

Leu Leu Val Tyr Ile Leu Met Gly Phe Leu
1               5                   10

<210> SEQ ID NO 582
<211> LENGTH: 10
<212> TYPE: PRT
<213> ORGANISM: homo sapien

<400> SEQUENCE: 582

Ser Met Leu Arg Lys Asp Asp Ala Pro Leu
1               5                   10

<210> SEQ ID NO 583
<211> LENGTH: 10
<212> TYPE: PRT
<213> ORGANISM: homo sapien

<400> SEQUENCE: 583
```

-continued

Asp Ser Leu Leu Asp Gln Asp Leu Pro Leu
1               5                   10

<210> SEQ ID NO 584
<211> LENGTH: 10
<212> TYPE: PRT
<213> ORGANISM: homo sapien

<400> SEQUENCE: 584

Met Ile Ser Val Leu Leu Val Tyr Ile Leu
1               5                   10

<210> SEQ ID NO 585
<211> LENGTH: 10
<212> TYPE: PRT
<213> ORGANISM: homo sapien

<400> SEQUENCE: 585

Cys Glu Arg Asn His Gly Gln Asp Ser Leu
1               5                   10

<210> SEQ ID NO 586
<211> LENGTH: 10
<212> TYPE: PRT
<213> ORGANISM: homo sapien

<400> SEQUENCE: 586

Val Leu Ser Ala Met Ile Ser Val Leu Leu
1               5                   10

<210> SEQ ID NO 587
<211> LENGTH: 10
<212> TYPE: PRT
<213> ORGANISM: homo sapien

<400> SEQUENCE: 587

Ile Ile Trp Asp Thr Val Val Ile Ile Leu
1               5                   10

<210> SEQ ID NO 588
<211> LENGTH: 10
<212> TYPE: PRT
<213> ORGANISM: homo sapien

<400> SEQUENCE: 588

Thr Leu Gln Ala Asp Asp Ser Leu Leu
1               5                   10

<210> SEQ ID NO 589
<211> LENGTH: 10
<212> TYPE: PRT
<213> ORGANISM: homo sapien

<400> SEQUENCE: 589

Asn Ser Leu Ala Ile Met Thr Asp Ala Leu
1               5                   10

<210> SEQ ID NO 590
<211> LENGTH: 10
<212> TYPE: PRT
<213> ORGANISM: homo sapien

<400> SEQUENCE: 590

Ile Ile Leu Thr Leu Leu Ala Leu Trp Leu
1               5                   10

```
<210> SEQ ID NO 591
<211> LENGTH: 10
<212> TYPE: PRT
<213> ORGANISM: homo sapien

<400> SEQUENCE: 591

Lys Ser Thr Ala Ile Val His Ile Gln Leu
1               5                   10

<210> SEQ ID NO 592
<211> LENGTH: 10
<212> TYPE: PRT
<213> ORGANISM: homo sapien

<400> SEQUENCE: 592

Val Gln Ser Lys Ala Asn His Leu Leu Leu
1               5                   10

<210> SEQ ID NO 593
<211> LENGTH: 10
<212> TYPE: PRT
<213> ORGANISM: homo sapien

<400> SEQUENCE: 593

Ala Ala Val Leu Tyr Leu Leu Phe Met Ile
1               5                   10

<210> SEQ ID NO 594
<211> LENGTH: 10
<212> TYPE: PRT
<213> ORGANISM: homo sapien

<400> SEQUENCE: 594

Ala Ala Val Gly Val Ala Val Asn Val Ile
1               5                   10

<210> SEQ ID NO 595
<211> LENGTH: 10
<212> TYPE: PRT
<213> ORGANISM: homo sapien

<400> SEQUENCE: 595

Leu Ala Ile Met Thr Asp Ala Leu His Met
1               5                   10

<210> SEQ ID NO 596
<211> LENGTH: 10
<212> TYPE: PRT
<213> ORGANISM: homo sapien

<400> SEQUENCE: 596

Ile Ala Ala Val Leu Tyr Leu Leu Phe Met
1               5                   10

<210> SEQ ID NO 597
<211> LENGTH: 10
<212> TYPE: PRT
<213> ORGANISM: homo sapien

<400> SEQUENCE: 597

Lys Pro Glu Tyr Lys Ile Ala Asp Pro Ile
1               5                   10
```

```
<210> SEQ ID NO 598
<211> LENGTH: 10
<212> TYPE: PRT
<213> ORGANISM: homo sapien

<400> SEQUENCE: 598

Leu Val Ala Phe Thr Thr Phe Arg Ile Ile
 1               5                  10

<210> SEQ ID NO 599
<211> LENGTH: 10
<212> TYPE: PRT
<213> ORGANISM: homo sapien

<400> SEQUENCE: 599

Ser Val Gly Val Leu Ile Ala Ala Tyr Ile
 1               5                  10

<210> SEQ ID NO 600
<211> LENGTH: 10
<212> TYPE: PRT
<213> ORGANISM: homo sapien

<400> SEQUENCE: 600

Leu Ser Arg Phe Asn Lys Leu Arg Val Val
 1               5                  10

<210> SEQ ID NO 601
<211> LENGTH: 9
<212> TYPE: PRT
<213> ORGANISM: homo sapien

<400> SEQUENCE: 601

Val Pro Ser His Leu Asn Val Asp Tyr
 1               5

<210> SEQ ID NO 602
<211> LENGTH: 9
<212> TYPE: PRT
<213> ORGANISM: homo sapien

<400> SEQUENCE: 602

Gln Ser Lys Ala Asn His Leu Leu Leu
 1               5

<210> SEQ ID NO 603
<211> LENGTH: 9
<212> TYPE: PRT
<213> ORGANISM: homo sapien

<400> SEQUENCE: 603

Ser Ser Lys Ser Pro Thr Lys Arg Phe
 1               5

<210> SEQ ID NO 604
<211> LENGTH: 9
<212> TYPE: PRT
<213> ORGANISM: homo sapien

<400> SEQUENCE: 604

Lys Ser Pro Thr Lys Arg Phe Thr Phe
 1               5

<210> SEQ ID NO 605
<211> LENGTH: 9
```

```
<212> TYPE: PRT
<213> ORGANISM: homo sapien

<400> SEQUENCE: 605

Lys Ile Ala Asp Pro Ile Cys Thr Tyr
1               5

<210> SEQ ID NO 606
<211> LENGTH: 9
<212> TYPE: PRT
<213> ORGANISM: homo sapien

<400> SEQUENCE: 606

Tyr Ser Val Glu Asp Leu Asn Ile Trp
1               5

<210> SEQ ID NO 607
<211> LENGTH: 9
<212> TYPE: PRT
<213> ORGANISM: homo sapien

<400> SEQUENCE: 607

Glu Ala Val Gln Arg Thr Ile His Met
1               5

<210> SEQ ID NO 608
<211> LENGTH: 9
<212> TYPE: PRT
<213> ORGANISM: homo sapien

<400> SEQUENCE: 608

Gly Ala Trp Lys Arg Leu Lys Ser Met
1               5

<210> SEQ ID NO 609
<211> LENGTH: 9
<212> TYPE: PRT
<213> ORGANISM: homo sapien

<400> SEQUENCE: 609

Val Gln Arg Thr Ile His Met Asn Tyr
1               5

<210> SEQ ID NO 610
<211> LENGTH: 9
<212> TYPE: PRT
<213> ORGANISM: homo sapien

<400> SEQUENCE: 610

Ala Ala Val Leu Tyr Leu Leu Phe Met
1               5

<210> SEQ ID NO 611
<211> LENGTH: 9
<212> TYPE: PRT
<213> ORGANISM: homo sapien

<400> SEQUENCE: 611

Lys Gln Arg Lys Val Lys Ala Arg Leu
1               5

<210> SEQ ID NO 612
<211> LENGTH: 9
<212> TYPE: PRT
<213> ORGANISM: homo sapien
```

```
<400> SEQUENCE: 612

Asp Ser Leu Ala Val Arg Ala Ala Phe
1               5

<210> SEQ ID NO 613
<211> LENGTH: 9
<212> TYPE: PRT
<213> ORGANISM: homo sapien

<400> SEQUENCE: 613

Leu Ser Ala Ile Ile Leu Thr Leu Leu
1               5

<210> SEQ ID NO 614
<211> LENGTH: 9
<212> TYPE: PRT
<213> ORGANISM: homo sapien

<400> SEQUENCE: 614

Leu Ser Ala Met Ile Ser Val Leu Leu
1               5

<210> SEQ ID NO 615
<211> LENGTH: 9
<212> TYPE: PRT
<213> ORGANISM: homo sapien

<400> SEQUENCE: 615

Ile Ser Val Leu Leu Val Tyr Ile Leu
1               5

<210> SEQ ID NO 616
<211> LENGTH: 9
<212> TYPE: PRT
<213> ORGANISM: homo sapien

<400> SEQUENCE: 616

Met Leu Arg Lys Asp Asp Ala Pro Leu
1               5

<210> SEQ ID NO 617
<211> LENGTH: 9
<212> TYPE: PRT
<213> ORGANISM: homo sapien

<400> SEQUENCE: 617

Arg Pro Val Asn Gly Ala His Pro Thr
1               5

<210> SEQ ID NO 618
<211> LENGTH: 9
<212> TYPE: PRT
<213> ORGANISM: homo sapien

<400> SEQUENCE: 618

Met Ile Gly Glu Leu Val Gly Gly Tyr
1               5

<210> SEQ ID NO 619
<211> LENGTH: 9
<212> TYPE: PRT
<213> ORGANISM: homo sapien

<400> SEQUENCE: 619
```

-continued

Arg Leu Thr Ile Ala Ala Val Leu Tyr
1               5

<210> SEQ ID NO 620
<211> LENGTH: 9
<212> TYPE: PRT
<213> ORGANISM: homo sapien

<400> SEQUENCE: 620

Arg Cys Thr Ile Gln Leu Gln Ser Tyr
1               5

<210> SEQ ID NO 621
<211> LENGTH: 9
<212> TYPE: PRT
<213> ORGANISM: homo sapien

<400> SEQUENCE: 621

Lys Ala Arg Leu Thr Ile Ala Ala Val
1               5

<210> SEQ ID NO 622
<211> LENGTH: 9
<212> TYPE: PRT
<213> ORGANISM: homo sapien

<400> SEQUENCE: 622

Asp Ala Leu His Met Leu Thr Asp Leu
1               5

<210> SEQ ID NO 623
<211> LENGTH: 9
<212> TYPE: PRT
<213> ORGANISM: homo sapien

<400> SEQUENCE: 623

Leu Gln Ala Asp Asp Ser Leu Leu
1               5

<210> SEQ ID NO 624
<211> LENGTH: 9
<212> TYPE: PRT
<213> ORGANISM: homo sapien

<400> SEQUENCE: 624

Ile Ala Ala Val Leu Tyr Leu Leu Phe
1               5

<210> SEQ ID NO 625
<211> LENGTH: 9
<212> TYPE: PRT
<213> ORGANISM: homo sapien

<400> SEQUENCE: 625

Leu Ser Arg Phe Asn Lys Leu Arg Val
1               5

<210> SEQ ID NO 626
<211> LENGTH: 9
<212> TYPE: PRT
<213> ORGANISM: homo sapien

<400> SEQUENCE: 626

Val Ala Val Asn Val Ile Met Gly Phe

```
                              1               5

<210> SEQ ID NO 627
<211> LENGTH: 9
<212> TYPE: PRT
<213> ORGANISM: homo sapien

<400> SEQUENCE: 627

Ala Ile Met Thr Asp Ala Leu His Met
 1               5

<210> SEQ ID NO 628
<211> LENGTH: 9
<212> TYPE: PRT
<213> ORGANISM: homo sapien

<400> SEQUENCE: 628

Tyr Ile Lys Glu Ala Leu Met Lys Ile
 1               5

<210> SEQ ID NO 629
<211> LENGTH: 9
<212> TYPE: PRT
<213> ORGANISM: homo sapien

<400> SEQUENCE: 629

Ser Ser Lys Trp Glu Glu Val Gln Ser
 1               5

<210> SEQ ID NO 630
<211> LENGTH: 9
<212> TYPE: PRT
<213> ORGANISM: homo sapien

<400> SEQUENCE: 630

Ala Pro Leu Phe Leu Asn Asp Thr Ser
 1               5

<210> SEQ ID NO 631
<211> LENGTH: 9
<212> TYPE: PRT
<213> ORGANISM: homo sapien

<400> SEQUENCE: 631

Tyr Ile Leu Met Gly Phe Leu Leu Tyr
 1               5

<210> SEQ ID NO 632
<211> LENGTH: 9
<212> TYPE: PRT
<213> ORGANISM: homo sapien

<400> SEQUENCE: 632

Tyr Ile Ile Arg Phe Lys Pro Glu Tyr
 1               5

<210> SEQ ID NO 633
<211> LENGTH: 9
<212> TYPE: PRT
<213> ORGANISM: homo sapien

<400> SEQUENCE: 633

Ala Met Ile Ser Val Leu Leu Val Tyr
 1               5
```

<210> SEQ ID NO 634
<211> LENGTH: 9
<212> TYPE: PRT
<213> ORGANISM: homo sapien

<400> SEQUENCE: 634

Ser Leu Leu Asp Gln Asp Leu Pro Leu
1               5

<210> SEQ ID NO 635
<211> LENGTH: 9
<212> TYPE: PRT
<213> ORGANISM: homo sapien

<400> SEQUENCE: 635

Ser Val Leu Leu Val Tyr Ile Leu Met
1               5

<210> SEQ ID NO 636
<211> LENGTH: 9
<212> TYPE: PRT
<213> ORGANISM: homo sapien

<400> SEQUENCE: 636

Val Gly Val Ala Val Asn Val Ile Met
1               5

<210> SEQ ID NO 637
<211> LENGTH: 9
<212> TYPE: PRT
<213> ORGANISM: homo sapien

<400> SEQUENCE: 637

Leu Pro Leu Thr Asn Ser Gln Leu Ser
1               5

<210> SEQ ID NO 638
<211> LENGTH: 9
<212> TYPE: PRT
<213> ORGANISM: homo sapien

<400> SEQUENCE: 638

Tyr Ile Ala Asn Ser Leu Ala Ile Met
1               5

<210> SEQ ID NO 639
<211> LENGTH: 9
<212> TYPE: PRT
<213> ORGANISM: homo sapien

<400> SEQUENCE: 639

Ala Leu Met Lys Ile Glu Asp Val Tyr
1               5

<210> SEQ ID NO 640
<211> LENGTH: 9
<212> TYPE: PRT
<213> ORGANISM: homo sapien

<400> SEQUENCE: 640

Asp Pro Ile Cys Thr Tyr Val Phe Ser
1               5

<210> SEQ ID NO 641

```
<211> LENGTH: 9
<212> TYPE: PRT
<213> ORGANISM: homo sapien

<400> SEQUENCE: 641

Ser Val Gly Val Leu Ile Ala Ala Tyr
1               5

<210> SEQ ID NO 642
<211> LENGTH: 9
<212> TYPE: PRT
<213> ORGANISM: homo sapien

<400> SEQUENCE: 642

Ile Met Thr Asp Ala Leu His Met Leu
1               5

<210> SEQ ID NO 643
<211> LENGTH: 9
<212> TYPE: PRT
<213> ORGANISM: homo sapien

<400> SEQUENCE: 643

His Leu Leu Leu Asn Thr Phe Gly Met
1               5

<210> SEQ ID NO 644
<211> LENGTH: 9
<212> TYPE: PRT
<213> ORGANISM: homo sapien

<400> SEQUENCE: 644

Leu Leu Leu Asn Thr Phe Gly Met Tyr
1               5

<210> SEQ ID NO 645
<211> LENGTH: 9
<212> TYPE: PRT
<213> ORGANISM: homo sapien

<400> SEQUENCE: 645

Thr Leu Gln Ala Asp Asp Asp Ser Leu
1               5

<210> SEQ ID NO 646
<211> LENGTH: 9
<212> TYPE: PRT
<213> ORGANISM: homo sapien

<400> SEQUENCE: 646

Thr Ala Ile Val His Ile Gln Leu Ile
1               5

<210> SEQ ID NO 647
<211> LENGTH: 9
<212> TYPE: PRT
<213> ORGANISM: homo sapien

<400> SEQUENCE: 647

Val Ala Phe Thr Thr Phe Arg Ile Ile
1               5

<210> SEQ ID NO 648
<211> LENGTH: 9
<212> TYPE: PRT
```

<213> ORGANISM: homo sapien

<400> SEQUENCE: 648

Arg Ile Ile Trp Asp Thr Val Val Ile
1               5

<210> SEQ ID NO 649
<211> LENGTH: 9
<212> TYPE: PRT
<213> ORGANISM: homo sapien

<400> SEQUENCE: 649

Asn Cys Ser Lys Gln Arg Glu Ile Leu
1               5

<210> SEQ ID NO 650
<211> LENGTH: 9
<212> TYPE: PRT
<213> ORGANISM: homo sapien

<400> SEQUENCE: 650

Val Leu Ser Ala Met Ile Ser Val Leu
1               5

<210> SEQ ID NO 651
<211> LENGTH: 10
<212> TYPE: PRT
<213> ORGANISM: homo sapien

<400> SEQUENCE: 651

Arg Pro Val Asn Gly Ala His Pro Thr Leu
1               5                   10

<210> SEQ ID NO 652
<211> LENGTH: 10
<212> TYPE: PRT
<213> ORGANISM: homo sapien

<400> SEQUENCE: 652

Asp Pro Ile Cys Thr Tyr Val Phe Ser Leu
1               5                   10

<210> SEQ ID NO 653
<211> LENGTH: 10
<212> TYPE: PRT
<213> ORGANISM: homo sapien

<400> SEQUENCE: 653

Leu Pro Leu Thr Asn Ser Gln Leu Ser Leu
1               5                   10

<210> SEQ ID NO 654
<211> LENGTH: 10
<212> TYPE: PRT
<213> ORGANISM: homo sapien

<400> SEQUENCE: 654

Ser Pro Thr Lys Arg Phe Thr Phe Gly Phe
1               5                   10

<210> SEQ ID NO 655
<211> LENGTH: 10
<212> TYPE: PRT
<213> ORGANISM: homo sapien

```
<400> SEQUENCE: 655

Lys Ala Arg Leu Thr Ile Ala Ala Val Leu
1               5                   10

<210> SEQ ID NO 656
<211> LENGTH: 10
<212> TYPE: PRT
<213> ORGANISM: homo sapien

<400> SEQUENCE: 656

Lys Ser Thr Ala Ile Val His Ile Gln Leu
1               5                   10

<210> SEQ ID NO 657
<211> LENGTH: 10
<212> TYPE: PRT
<213> ORGANISM: homo sapien

<400> SEQUENCE: 657

Gln Ser Val Gly Val Leu Ile Ala Ala Tyr
1               5                   10

<210> SEQ ID NO 658
<211> LENGTH: 10
<212> TYPE: PRT
<213> ORGANISM: homo sapien

<400> SEQUENCE: 658

Ile Ser Val Leu Leu Val Tyr Ile Leu Met
1               5                   10

<210> SEQ ID NO 659
<211> LENGTH: 10
<212> TYPE: PRT
<213> ORGANISM: homo sapien

<400> SEQUENCE: 659

Leu Ala Ile Met Thr Asp Ala Leu His Met
1               5                   10

<210> SEQ ID NO 660
<211> LENGTH: 10
<212> TYPE: PRT
<213> ORGANISM: homo sapien

<400> SEQUENCE: 660

Val Pro Ser His Leu Asn Val Asp Tyr Ile
1               5                   10

<210> SEQ ID NO 661
<211> LENGTH: 10
<212> TYPE: PRT
<213> ORGANISM: homo sapien

<400> SEQUENCE: 661

Lys Ala Asn His Leu Leu Leu Asn Thr Phe
1               5                   10

<210> SEQ ID NO 662
<211> LENGTH: 10
<212> TYPE: PRT
<213> ORGANISM: homo sapien

<400> SEQUENCE: 662
```

-continued

```
Glu Ala Gly Asp Glu Gly Leu Ser Arg Phe
1               5                   10

<210> SEQ ID NO 663
<211> LENGTH: 10
<212> TYPE: PRT
<213> ORGANISM: homo sapien

<400> SEQUENCE: 663

Glu Ala Leu Met Lys Ile Glu Asp Val Tyr
1               5                   10

<210> SEQ ID NO 664
<211> LENGTH: 10
<212> TYPE: PRT
<213> ORGANISM: homo sapien

<400> SEQUENCE: 664

Ile Ala Ala Val Leu Tyr Leu Leu Phe Met
1               5                   10

<210> SEQ ID NO 665
<211> LENGTH: 10
<212> TYPE: PRT
<213> ORGANISM: homo sapien

<400> SEQUENCE: 665

Ser Ala Met Ile Ser Val Leu Leu Val Tyr
1               5                   10

<210> SEQ ID NO 666
<211> LENGTH: 10
<212> TYPE: PRT
<213> ORGANISM: homo sapien

<400> SEQUENCE: 666

Asn Ser Leu Ala Ile Met Thr Asp Ala Leu
1               5                   10

<210> SEQ ID NO 667
<211> LENGTH: 10
<212> TYPE: PRT
<213> ORGANISM: homo sapien

<400> SEQUENCE: 667

Asp Ser Leu Leu Asp Gln Asp Leu Pro Leu
1               5                   10

<210> SEQ ID NO 668
<211> LENGTH: 10
<212> TYPE: PRT
<213> ORGANISM: homo sapien

<400> SEQUENCE: 668

Phe Ser Leu Leu Val Ala Phe Thr Thr Phe
1               5                   10

<210> SEQ ID NO 669
<211> LENGTH: 10
<212> TYPE: PRT
<213> ORGANISM: homo sapien

<400> SEQUENCE: 669

Leu Ser Ser Lys Ser Pro Thr Lys Arg Phe
1               5                   10
```

-continued

<210> SEQ ID NO 670
<211> LENGTH: 10
<212> TYPE: PRT
<213> ORGANISM: homo sapien

<400> SEQUENCE: 670

Lys Pro Glu Tyr Lys Ile Ala Asp Pro Ile
1               5                   10

<210> SEQ ID NO 671
<211> LENGTH: 10
<212> TYPE: PRT
<213> ORGANISM: homo sapien

<400> SEQUENCE: 671

Met Leu Arg Lys Asp Asp Ala Pro Leu Phe
1               5                   10

<210> SEQ ID NO 672
<211> LENGTH: 10
<212> TYPE: PRT
<213> ORGANISM: homo sapien

<400> SEQUENCE: 672

Met Asn Tyr Glu Ile Asn Gly Asp Ile Met
1               5                   10

<210> SEQ ID NO 673
<211> LENGTH: 10
<212> TYPE: PRT
<213> ORGANISM: homo sapien

<400> SEQUENCE: 673

Leu Ser Arg Phe Asn Lys Leu Arg Val Val
1               5                   10

<210> SEQ ID NO 674
<211> LENGTH: 10
<212> TYPE: PRT
<213> ORGANISM: homo sapien

<400> SEQUENCE: 674

Ala Val Arg Ala Ala Phe Val His Ala Leu
1               5                   10

<210> SEQ ID NO 675
<211> LENGTH: 10
<212> TYPE: PRT
<213> ORGANISM: homo sapien

<400> SEQUENCE: 675

Ala Ala Phe Val His Ala Leu Gly Asp Leu
1               5                   10

<210> SEQ ID NO 676
<211> LENGTH: 10
<212> TYPE: PRT
<213> ORGANISM: homo sapien

<400> SEQUENCE: 676

Val Ala Val Asn Val Ile Met Gly Phe Leu
1               5                   10

```
<210> SEQ ID NO 677
<211> LENGTH: 10
<212> TYPE: PRT
<213> ORGANISM: homo sapien

<400> SEQUENCE: 677

Gly Ala Trp Lys Arg Leu Lys Ser Met Leu
 1               5                  10

<210> SEQ ID NO 678
<211> LENGTH: 10
<212> TYPE: PRT
<213> ORGANISM: homo sapien

<400> SEQUENCE: 678

Met Ala Gly Ser Gly Ala Trp Lys Arg Leu
 1               5                  10

<210> SEQ ID NO 679
<211> LENGTH: 10
<212> TYPE: PRT
<213> ORGANISM: homo sapien

<400> SEQUENCE: 679

Ser Ala Ile Ile Leu Thr Leu Leu Ala Leu
 1               5                  10

<210> SEQ ID NO 680
<211> LENGTH: 10
<212> TYPE: PRT
<213> ORGANISM: homo sapien

<400> SEQUENCE: 680

Phe Ser Asp Glu Ala Gly Asp Glu Gly Leu
 1               5                  10

<210> SEQ ID NO 681
<211> LENGTH: 10
<212> TYPE: PRT
<213> ORGANISM: homo sapien

<400> SEQUENCE: 681

Ala Pro Leu Phe Leu Asn Asp Thr Ser Ala
 1               5                  10

<210> SEQ ID NO 682
<211> LENGTH: 10
<212> TYPE: PRT
<213> ORGANISM: homo sapien

<400> SEQUENCE: 682

Ser Gly Ala Trp Lys Arg Leu Lys Ser Met
 1               5                  10

<210> SEQ ID NO 683
<211> LENGTH: 10
<212> TYPE: PRT
<213> ORGANISM: homo sapien

<400> SEQUENCE: 683

Arg Leu Thr Ile Ala Ala Val Leu Tyr Leu
 1               5                  10

<210> SEQ ID NO 684
<211> LENGTH: 10
```

```
<212> TYPE: PRT
<213> ORGANISM: homo sapien

<400> SEQUENCE: 684

His Leu Leu Leu Asn Thr Phe Gly Met Tyr
 1               5                  10

<210> SEQ ID NO 685
<211> LENGTH: 10
<212> TYPE: PRT
<213> ORGANISM: homo sapien

<400> SEQUENCE: 685

Met Leu Thr Asp Leu Ser Ala Ile Ile Leu
 1               5                  10

<210> SEQ ID NO 686
<211> LENGTH: 10
<212> TYPE: PRT
<213> ORGANISM: homo sapien

<400> SEQUENCE: 686

Gly Val Pro Ser His Leu Asn Val Asp Tyr
 1               5                  10

<210> SEQ ID NO 687
<211> LENGTH: 10
<212> TYPE: PRT
<213> ORGANISM: homo sapien

<400> SEQUENCE: 687

His Pro Thr Leu Gln Ala Asp Asp Asp Ser
 1               5                  10

<210> SEQ ID NO 688
<211> LENGTH: 10
<212> TYPE: PRT
<213> ORGANISM: homo sapien

<400> SEQUENCE: 688

Leu Asn Val Asp Tyr Ile Lys Glu Ala Leu
 1               5                  10

<210> SEQ ID NO 689
<211> LENGTH: 10
<212> TYPE: PRT
<213> ORGANISM: homo sapien

<400> SEQUENCE: 689

Leu Pro Ser Asn Ser Pro Thr Arg Gly Ser
 1               5                  10

<210> SEQ ID NO 690
<211> LENGTH: 10
<212> TYPE: PRT
<213> ORGANISM: homo sapien

<400> SEQUENCE: 690

Ile Ile Trp Asp Thr Val Val Ile Ile Leu
 1               5                  10

<210> SEQ ID NO 691
<211> LENGTH: 10
<212> TYPE: PRT
<213> ORGANISM: homo sapien
```

-continued

```
<400> SEQUENCE: 691

Ile Ile Leu Glu Gly Val Pro Ser His Leu
1               5                   10

<210> SEQ ID NO 692
<211> LENGTH: 10
<212> TYPE: PRT
<213> ORGANISM: homo sapien

<400> SEQUENCE: 692

Ala Val Gln Arg Thr Ile His Met Asn Tyr
1               5                   10

<210> SEQ ID NO 693
<211> LENGTH: 10
<212> TYPE: PRT
<213> ORGANISM: homo sapien

<400> SEQUENCE: 693

Phe Met Ile Gly Glu Leu Val Gly Gly Tyr
1               5                   10

<210> SEQ ID NO 694
<211> LENGTH: 10
<212> TYPE: PRT
<213> ORGANISM: homo sapien

<400> SEQUENCE: 694

Phe Leu Asn Asp Thr Ser Ala Phe Asp Phe
1               5                   10

<210> SEQ ID NO 695
<211> LENGTH: 10
<212> TYPE: PRT
<213> ORGANISM: homo sapien

<400> SEQUENCE: 695

Ala Val Gly Val Ala Val Asn Val Ile Met
1               5                   10

<210> SEQ ID NO 696
<211> LENGTH: 10
<212> TYPE: PRT
<213> ORGANISM: homo sapien

<400> SEQUENCE: 696

Ser Ser Lys Ser Pro Thr Lys Arg Phe Thr
1               5                   10

<210> SEQ ID NO 697
<211> LENGTH: 10
<212> TYPE: PRT
<213> ORGANISM: homo sapien

<400> SEQUENCE: 697

Gln Ser Lys Ala Asn His Leu Leu Leu Asn
1               5                   10

<210> SEQ ID NO 698
<211> LENGTH: 10
<212> TYPE: PRT
<213> ORGANISM: homo sapien

<400> SEQUENCE: 698
```

Ser Met Leu Arg Lys Asp Asp Ala Pro Leu
1               5                   10

<210> SEQ ID NO 699
<211> LENGTH: 10
<212> TYPE: PRT
<213> ORGANISM: homo sapien

<400> SEQUENCE: 699

Thr Leu Gln Ala Asp Asp Ser Leu Leu
1               5                   10

<210> SEQ ID NO 700
<211> LENGTH: 10
<212> TYPE: PRT
<213> ORGANISM: homo sapien

<400> SEQUENCE: 700

Val Ala Phe Thr Thr Phe Arg Ile Ile Trp
1               5                   10

<210> SEQ ID NO 701
<211> LENGTH: 9
<212> TYPE: PRT
<213> ORGANISM: homo sapien

<400> SEQUENCE: 701

Leu Asn Asp Thr Ser Ala Phe Glu Phe
1               5

<210> SEQ ID NO 702
<211> LENGTH: 9
<212> TYPE: PRT
<213> ORGANISM: homo sapien

<400> SEQUENCE: 702

Ala Phe Glu Phe Ser Asp Glu Ala Gly
1               5

<210> SEQ ID NO 703
<211> LENGTH: 9
<212> TYPE: PRT
<213> ORGANISM: homo sapien

<400> SEQUENCE: 703

Asp Thr Ser Ala Phe Glu Phe Ser Asp
1               5

<210> SEQ ID NO 704
<211> LENGTH: 9
<212> TYPE: PRT
<213> ORGANISM: homo sapien

<400> SEQUENCE: 704

Ser Ala Phe Glu Phe Ser Asp Glu Ala
1               5

<210> SEQ ID NO 705
<211> LENGTH: 9
<212> TYPE: PRT
<213> ORGANISM: homo sapien

<400> SEQUENCE: 705

Phe Leu Asn Asp Thr Ser Ala Phe Glu

-continued

```
<210> SEQ ID NO 706
<211> LENGTH: 9
<212> TYPE: PRT
<213> ORGANISM: homo sapien

<400> SEQUENCE: 706

Thr Ser Ala Phe Glu Phe Ser Asp Glu
 1               5

<210> SEQ ID NO 707
<211> LENGTH: 9
<212> TYPE: PRT
<213> ORGANISM: homo sapien

<400> SEQUENCE: 707

Asn Asp Thr Ser Ala Phe Glu Phe Ser
 1               5

<210> SEQ ID NO 708
<211> LENGTH: 9
<212> TYPE: PRT
<213> ORGANISM: homo sapien

<400> SEQUENCE: 708

Phe Glu Phe Ser Asp Glu Ala Gly Asp
 1               5

<210> SEQ ID NO 709
<211> LENGTH: 9
<212> TYPE: PRT
<213> ORGANISM: homo sapien

<400> SEQUENCE: 709

Glu Phe Ser Asp Glu Ala Gly Asp Glu
 1               5

<210> SEQ ID NO 710
<211> LENGTH: 10
<212> TYPE: PRT
<213> ORGANISM: homo sapien

<400> SEQUENCE: 710

Phe Leu Asn Asp Thr Ser Ala Phe Glu Phe
 1               5                  10

<210> SEQ ID NO 711
<211> LENGTH: 10
<212> TYPE: PRT
<213> ORGANISM: homo sapien

<400> SEQUENCE: 711

Leu Asn Asp Thr Ser Ala Phe Glu Phe Ser
 1               5                  10

<210> SEQ ID NO 712
<211> LENGTH: 10
<212> TYPE: PRT
<213> ORGANISM: homo sapien

<400> SEQUENCE: 712

Thr Ser Ala Phe Glu Phe Ser Asp Glu Ala
 1               5                  10
```

<210> SEQ ID NO 713
<211> LENGTH: 10
<212> TYPE: PRT
<213> ORGANISM: homo sapien

<400> SEQUENCE: 713

Ser Ala Phe Glu Phe Ser Asp Glu Ala Gly
1               5                   10

<210> SEQ ID NO 714
<211> LENGTH: 10
<212> TYPE: PRT
<213> ORGANISM: homo sapien

<400> SEQUENCE: 714

Ala Phe Glu Phe Ser Asp Glu Ala Gly Asp
1               5                   10

<210> SEQ ID NO 715
<211> LENGTH: 10
<212> TYPE: PRT
<213> ORGANISM: homo sapien

<400> SEQUENCE: 715

Asp Thr Ser Ala Phe Glu Phe Ser Asp Glu
1               5                   10

<210> SEQ ID NO 716
<211> LENGTH: 10
<212> TYPE: PRT
<213> ORGANISM: homo sapien

<400> SEQUENCE: 716

Glu Phe Ser Asp Glu Ala Gly Asp Glu Gly
1               5                   10

<210> SEQ ID NO 717
<211> LENGTH: 10
<212> TYPE: PRT
<213> ORGANISM: homo sapien

<400> SEQUENCE: 717

Asn Asp Thr Ser Ala Phe Glu Phe Ser Asp
1               5                   10

<210> SEQ ID NO 718
<211> LENGTH: 10
<212> TYPE: PRT
<213> ORGANISM: homo sapien

<400> SEQUENCE: 718

Leu Phe Leu Asn Asp Thr Ser Ala Phe Glu
1               5                   10

<210> SEQ ID NO 719
<211> LENGTH: 10
<212> TYPE: PRT
<213> ORGANISM: homo sapien

<400> SEQUENCE: 719

Phe Glu Phe Ser Asp Glu Ala Gly Asp Glu
1               5                   10

<210> SEQ ID NO 720

```
<211> LENGTH: 9
<212> TYPE: PRT
<213> ORGANISM: homo sapien

<400> SEQUENCE: 720

Ser Ala Phe Glu Phe Ser Asp Glu Ala
 1               5

<210> SEQ ID NO 721
<211> LENGTH: 9
<212> TYPE: PRT
<213> ORGANISM: homo sapien

<400> SEQUENCE: 721

Phe Leu Asn Asp Thr Ser Ala Phe Glu
 1               5

<210> SEQ ID NO 722
<211> LENGTH: 9
<212> TYPE: PRT
<213> ORGANISM: homo sapien

<400> SEQUENCE: 722

Phe Glu Phe Ser Asp Glu Ala Gly Asp
 1               5

<210> SEQ ID NO 723
<211> LENGTH: 9
<212> TYPE: PRT
<213> ORGANISM: homo sapien

<400> SEQUENCE: 723

Leu Asn Asp Thr Ser Ala Phe Glu Phe
 1               5

<210> SEQ ID NO 724
<211> LENGTH: 9
<212> TYPE: PRT
<213> ORGANISM: homo sapien

<400> SEQUENCE: 724

Asn Asp Thr Ser Ala Phe Glu Phe Ser
 1               5

<210> SEQ ID NO 725
<211> LENGTH: 9
<212> TYPE: PRT
<213> ORGANISM: homo sapien

<400> SEQUENCE: 725

Asp Thr Ser Ala Phe Glu Phe Ser Asp
 1               5

<210> SEQ ID NO 726
<211> LENGTH: 9
<212> TYPE: PRT
<213> ORGANISM: homo sapien

<400> SEQUENCE: 726

Thr Ser Ala Phe Glu Phe Ser Asp Glu
 1               5

<210> SEQ ID NO 727
<211> LENGTH: 9
<212> TYPE: PRT
```

-continued

<213> ORGANISM: homo sapien

<400> SEQUENCE: 727

Ala Phe Glu Phe Ser Asp Glu Ala Gly
 1               5

<210> SEQ ID NO 728
<211> LENGTH: 9
<212> TYPE: PRT
<213> ORGANISM: homo sapien

<400> SEQUENCE: 728

Glu Phe Ser Asp Glu Ala Gly Asp Glu
 1               5

<210> SEQ ID NO 729
<211> LENGTH: 10
<212> TYPE: PRT
<213> ORGANISM: homo sapien

<400> SEQUENCE: 729

Phe Leu Asn Asp Thr Ser Ala Phe Glu Phe
 1               5                  10

<210> SEQ ID NO 730
<211> LENGTH: 10
<212> TYPE: PRT
<213> ORGANISM: homo sapien

<400> SEQUENCE: 730

Thr Ser Ala Phe Glu Phe Ser Asp Glu Ala
 1               5                  10

<210> SEQ ID NO 731
<211> LENGTH: 10
<212> TYPE: PRT
<213> ORGANISM: homo sapien

<400> SEQUENCE: 731

Ser Ala Phe Glu Phe Ser Asp Glu Ala Gly
 1               5                  10

<210> SEQ ID NO 732
<211> LENGTH: 10
<212> TYPE: PRT
<213> ORGANISM: homo sapien

<400> SEQUENCE: 732

Leu Asn Asp Thr Ser Ala Phe Glu Phe Ser
 1               5                  10

<210> SEQ ID NO 733
<211> LENGTH: 10
<212> TYPE: PRT
<213> ORGANISM: homo sapien

<400> SEQUENCE: 733

Phe Glu Phe Ser Asp Glu Ala Gly Asp Glu
 1               5                  10

<210> SEQ ID NO 734
<211> LENGTH: 10
<212> TYPE: PRT
<213> ORGANISM: homo sapien

```
<400> SEQUENCE: 734

Asn Asp Thr Ser Ala Phe Glu Phe Ser Asp
 1               5                  10

<210> SEQ ID NO 735
<211> LENGTH: 10
<212> TYPE: PRT
<213> ORGANISM: homo sapien

<400> SEQUENCE: 735

Leu Phe Leu Asn Asp Thr Ser Ala Phe Glu
 1               5                  10

<210> SEQ ID NO 736
<211> LENGTH: 10
<212> TYPE: PRT
<213> ORGANISM: homo sapien

<400> SEQUENCE: 736

Asp Thr Ser Ala Phe Glu Phe Ser Asp Glu
 1               5                  10

<210> SEQ ID NO 737
<211> LENGTH: 10
<212> TYPE: PRT
<213> ORGANISM: homo sapien

<400> SEQUENCE: 737

Glu Phe Ser Asp Glu Ala Gly Asp Glu Gly
 1               5                  10

<210> SEQ ID NO 738
<211> LENGTH: 10
<212> TYPE: PRT
<213> ORGANISM: homo sapien

<400> SEQUENCE: 738

Ala Phe Glu Phe Ser Asp Glu Ala Gly Asp
 1               5                  10

<210> SEQ ID NO 739
<211> LENGTH: 9
<212> TYPE: PRT
<213> ORGANISM: homo sapien

<400> SEQUENCE: 739

Ser Ala Phe Glu Phe Ser Asp Glu Ala
 1               5

<210> SEQ ID NO 740
<211> LENGTH: 9
<212> TYPE: PRT
<213> ORGANISM: homo sapien

<400> SEQUENCE: 740

Phe Leu Asn Asp Thr Ser Ala Phe Glu
 1               5

<210> SEQ ID NO 741
<211> LENGTH: 9
<212> TYPE: PRT
<213> ORGANISM: homo sapien

<400> SEQUENCE: 741
```

```
Leu Asn Asp Thr Ser Ala Phe Glu Phe
1               5

<210> SEQ ID NO 742
<211> LENGTH: 9
<212> TYPE: PRT
<213> ORGANISM: homo sapien

<400> SEQUENCE: 742

Asp Thr Ser Ala Phe Glu Phe Ser Asp
1               5

<210> SEQ ID NO 743
<211> LENGTH: 9
<212> TYPE: PRT
<213> ORGANISM: homo sapien

<400> SEQUENCE: 743

Phe Glu Phe Ser Asp Glu Ala Gly Asp
1               5

<210> SEQ ID NO 744
<211> LENGTH: 9
<212> TYPE: PRT
<213> ORGANISM: homo sapien

<400> SEQUENCE: 744

Thr Ser Ala Phe Glu Phe Ser Asp Glu
1               5

<210> SEQ ID NO 745
<211> LENGTH: 9
<212> TYPE: PRT
<213> ORGANISM: homo sapien

<400> SEQUENCE: 745

Asn Asp Thr Ser Ala Phe Glu Phe Ser
1               5

<210> SEQ ID NO 746
<211> LENGTH: 9
<212> TYPE: PRT
<213> ORGANISM: homo sapien

<400> SEQUENCE: 746

Ala Phe Glu Phe Ser Asp Glu Ala Gly
1               5

<210> SEQ ID NO 747
<211> LENGTH: 9
<212> TYPE: PRT
<213> ORGANISM: homo sapien

<400> SEQUENCE: 747

Glu Phe Ser Asp Glu Ala Gly Asp Glu
1               5

<210> SEQ ID NO 748
<211> LENGTH: 10
<212> TYPE: PRT
<213> ORGANISM: homo sapien

<400> SEQUENCE: 748

Phe Leu Asn Asp Thr Ser Ala Phe Glu Phe
1               5                   10
```

<210> SEQ ID NO 749
<211> LENGTH: 10
<212> TYPE: PRT
<213> ORGANISM: homo sapien

<400> SEQUENCE: 749

Thr Ser Ala Phe Glu Phe Ser Asp Glu Ala
1               5                   10

<210> SEQ ID NO 750
<211> LENGTH: 10
<212> TYPE: PRT
<213> ORGANISM: homo sapien

<400> SEQUENCE: 750

Ser Ala Phe Glu Phe Ser Asp Glu Ala Gly
1               5                   10

<210> SEQ ID NO 751
<211> LENGTH: 10
<212> TYPE: PRT
<213> ORGANISM: homo sapien

<400> SEQUENCE: 751

Asp Thr Ser Ala Phe Glu Phe Ser Asp Glu
1               5                   10

<210> SEQ ID NO 752
<211> LENGTH: 10
<212> TYPE: PRT
<213> ORGANISM: homo sapien

<400> SEQUENCE: 752

Leu Asn Asp Thr Ser Ala Phe Glu Phe Ser
1               5                   10

<210> SEQ ID NO 753
<211> LENGTH: 10
<212> TYPE: PRT
<213> ORGANISM: homo sapien

<400> SEQUENCE: 753

Asn Asp Thr Ser Ala Phe Glu Phe Ser Asp
1               5                   10

<210> SEQ ID NO 754
<211> LENGTH: 10
<212> TYPE: PRT
<213> ORGANISM: homo sapien

<400> SEQUENCE: 754

Phe Glu Phe Ser Asp Glu Ala Gly Asp Glu
1               5                   10

<210> SEQ ID NO 755
<211> LENGTH: 10
<212> TYPE: PRT
<213> ORGANISM: homo sapien

<400> SEQUENCE: 755

Leu Phe Leu Asn Asp Thr Ser Ala Phe Glu
1               5                   10

```
<210> SEQ ID NO 756
<211> LENGTH: 10
<212> TYPE: PRT
<213> ORGANISM: homo sapien

<400> SEQUENCE: 756

Ala Phe Glu Phe Ser Asp Glu Ala Gly Asp
 1               5                  10

<210> SEQ ID NO 757
<211> LENGTH: 10
<212> TYPE: PRT
<213> ORGANISM: homo sapien

<400> SEQUENCE: 757

Glu Phe Ser Asp Glu Ala Gly Asp Glu Gly
 1               5                  10

<210> SEQ ID NO 758
<211> LENGTH: 9
<212> TYPE: PRT
<213> ORGANISM: homo sapien

<400> SEQUENCE: 758

Ser Ala Phe Glu Phe Ser Asp Glu Ala
 1               5

<210> SEQ ID NO 759
<211> LENGTH: 9
<212> TYPE: PRT
<213> ORGANISM: homo sapien

<400> SEQUENCE: 759

Leu Asn Asp Thr Ser Ala Phe Glu Phe
 1               5

<210> SEQ ID NO 760
<211> LENGTH: 9
<212> TYPE: PRT
<213> ORGANISM: homo sapien

<400> SEQUENCE: 760

Asp Thr Ser Ala Phe Glu Phe Ser Asp
 1               5

<210> SEQ ID NO 761
<211> LENGTH: 9
<212> TYPE: PRT
<213> ORGANISM: homo sapien

<400> SEQUENCE: 761

Phe Leu Asn Asp Thr Ser Ala Phe Glu
 1               5

<210> SEQ ID NO 762
<211> LENGTH: 9
<212> TYPE: PRT
<213> ORGANISM: homo sapien

<400> SEQUENCE: 762

Ala Phe Glu Phe Ser Asp Glu Ala Gly
 1               5

<210> SEQ ID NO 763
<211> LENGTH: 9
```

```
<212> TYPE: PRT
<213> ORGANISM: homo sapien

<400> SEQUENCE: 763

Phe Glu Phe Ser Asp Glu Ala Gly Asp
 1               5

<210> SEQ ID NO 764
<211> LENGTH: 9
<212> TYPE: PRT
<213> ORGANISM: homo sapien

<400> SEQUENCE: 764

Glu Phe Ser Asp Glu Ala Gly Asp Glu
 1               5

<210> SEQ ID NO 765
<211> LENGTH: 9
<212> TYPE: PRT
<213> ORGANISM: homo sapien

<400> SEQUENCE: 765

Asn Asp Thr Ser Ala Phe Glu Phe Ser
 1               5

<210> SEQ ID NO 766
<211> LENGTH: 9
<212> TYPE: PRT
<213> ORGANISM: homo sapien

<400> SEQUENCE: 766

Thr Ser Ala Phe Glu Phe Ser Asp Glu
 1               5

<210> SEQ ID NO 767
<211> LENGTH: 10
<212> TYPE: PRT
<213> ORGANISM: homo sapien

<400> SEQUENCE: 767

Phe Leu Asn Asp Thr Ser Ala Phe Glu Phe
 1               5                  10

<210> SEQ ID NO 768
<211> LENGTH: 10
<212> TYPE: PRT
<213> ORGANISM: homo sapien

<400> SEQUENCE: 768

Ser Ala Phe Glu Phe Ser Asp Glu Ala Gly
 1               5                  10

<210> SEQ ID NO 769
<211> LENGTH: 10
<212> TYPE: PRT
<213> ORGANISM: homo sapien

<400> SEQUENCE: 769

Leu Phe Leu Asn Asp Thr Ser Ala Phe Glu
 1               5                  10

<210> SEQ ID NO 770
<211> LENGTH: 10
<212> TYPE: PRT
<213> ORGANISM: homo sapien
```

<400> SEQUENCE: 770

Asp Thr Ser Ala Phe Glu Phe Ser Asp Glu
1               5                   10

<210> SEQ ID NO 771
<211> LENGTH: 10
<212> TYPE: PRT
<213> ORGANISM: homo sapien

<400> SEQUENCE: 771

Ala Phe Glu Phe Ser Asp Glu Ala Gly Asp
1               5                   10

<210> SEQ ID NO 772
<211> LENGTH: 10
<212> TYPE: PRT
<213> ORGANISM: homo sapien

<400> SEQUENCE: 772

Thr Ser Ala Phe Glu Phe Ser Asp Glu Ala
1               5                   10

<210> SEQ ID NO 773
<211> LENGTH: 10
<212> TYPE: PRT
<213> ORGANISM: homo sapien

<400> SEQUENCE: 773

Phe Glu Phe Ser Asp Glu Ala Gly Asp Glu
1               5                   10

<210> SEQ ID NO 774
<211> LENGTH: 10
<212> TYPE: PRT
<213> ORGANISM: homo sapien

<400> SEQUENCE: 774

Asn Asp Thr Ser Ala Phe Glu Phe Ser Asp
1               5                   10

<210> SEQ ID NO 775
<211> LENGTH: 10
<212> TYPE: PRT
<213> ORGANISM: homo sapien

<400> SEQUENCE: 775

Glu Phe Ser Asp Glu Ala Gly Asp Glu Gly
1               5                   10

<210> SEQ ID NO 776
<211> LENGTH: 10
<212> TYPE: PRT
<213> ORGANISM: homo sapien

<400> SEQUENCE: 776

Leu Asn Asp Thr Ser Ala Phe Glu Phe Ser
1               5                   10

<210> SEQ ID NO 777
<211> LENGTH: 9
<212> TYPE: PRT
<213> ORGANISM: homo sapien

<400> SEQUENCE: 777

-continued

Leu Asn Asp Thr Ser Ala Phe Glu Phe
1               5

<210> SEQ ID NO 778
<211> LENGTH: 9
<212> TYPE: PRT
<213> ORGANISM: homo sapien

<400> SEQUENCE: 778

Ser Ala Phe Glu Phe Ser Asp Glu Ala
1               5

<210> SEQ ID NO 779
<211> LENGTH: 9
<212> TYPE: PRT
<213> ORGANISM: homo sapien

<400> SEQUENCE: 779

Ala Phe Glu Phe Ser Asp Glu Ala Gly
1               5

<210> SEQ ID NO 780
<211> LENGTH: 9
<212> TYPE: PRT
<213> ORGANISM: homo sapien

<400> SEQUENCE: 780

Glu Phe Ser Asp Glu Ala Gly Asp Glu
1               5

<210> SEQ ID NO 781
<211> LENGTH: 9
<212> TYPE: PRT
<213> ORGANISM: homo sapien

<400> SEQUENCE: 781

Phe Leu Asn Asp Thr Ser Ala Phe Glu
1               5

<210> SEQ ID NO 782
<211> LENGTH: 9
<212> TYPE: PRT
<213> ORGANISM: homo sapien

<400> SEQUENCE: 782

Asn Asp Thr Ser Ala Phe Glu Phe Ser
1               5

<210> SEQ ID NO 783
<211> LENGTH: 9
<212> TYPE: PRT
<213> ORGANISM: homo sapien

<400> SEQUENCE: 783

Thr Ser Ala Phe Glu Phe Ser Asp Glu
1               5

<210> SEQ ID NO 784
<211> LENGTH: 9
<212> TYPE: PRT
<213> ORGANISM: homo sapien

<400> SEQUENCE: 784

Asp Thr Ser Ala Phe Glu Phe Ser Asp

-continued

```
1               5

<210> SEQ ID NO 785
<211> LENGTH: 9
<212> TYPE: PRT
<213> ORGANISM: homo sapien

<400> SEQUENCE: 785

Phe Glu Phe Ser Asp Glu Ala Gly Asp
1               5

<210> SEQ ID NO 786
<211> LENGTH: 10
<212> TYPE: PRT
<213> ORGANISM: homo sapien

<400> SEQUENCE: 786

Phe Leu Asn Asp Thr Ser Ala Phe Glu Phe
1               5                   10

<210> SEQ ID NO 787
<211> LENGTH: 10
<212> TYPE: PRT
<213> ORGANISM: homo sapien

<400> SEQUENCE: 787

Leu Asn Asp Thr Ser Ala Phe Glu Phe Ser
1               5                   10

<210> SEQ ID NO 788
<211> LENGTH: 10
<212> TYPE: PRT
<213> ORGANISM: homo sapien

<400> SEQUENCE: 788

Thr Ser Ala Phe Glu Phe Ser Asp Glu Ala
1               5                   10

<210> SEQ ID NO 789
<211> LENGTH: 10
<212> TYPE: PRT
<213> ORGANISM: homo sapien

<400> SEQUENCE: 789

Ala Phe Glu Phe Ser Asp Glu Ala Gly Asp
1               5                   10

<210> SEQ ID NO 790
<211> LENGTH: 10
<212> TYPE: PRT
<213> ORGANISM: homo sapien

<400> SEQUENCE: 790

Leu Phe Leu Asn Asp Thr Ser Ala Phe Glu
1               5                   10

<210> SEQ ID NO 791
<211> LENGTH: 10
<212> TYPE: PRT
<213> ORGANISM: homo sapien

<400> SEQUENCE: 791

Glu Phe Ser Asp Glu Ala Gly Asp Glu Gly
1               5                   10
```

```
<210> SEQ ID NO 792
<211> LENGTH: 10
<212> TYPE: PRT
<213> ORGANISM: homo sapien

<400> SEQUENCE: 792

Ser Ala Phe Glu Phe Ser Asp Glu Ala Gly
 1               5                  10

<210> SEQ ID NO 793
<211> LENGTH: 10
<212> TYPE: PRT
<213> ORGANISM: homo sapien

<400> SEQUENCE: 793

Asp Thr Ser Ala Phe Glu Phe Ser Asp Glu
 1               5                  10

<210> SEQ ID NO 794
<211> LENGTH: 10
<212> TYPE: PRT
<213> ORGANISM: homo sapien

<400> SEQUENCE: 794

Asn Asp Thr Ser Ala Phe Glu Phe Ser Asp
 1               5                  10

<210> SEQ ID NO 795
<211> LENGTH: 10
<212> TYPE: PRT
<213> ORGANISM: homo sapien

<400> SEQUENCE: 795

Phe Glu Phe Ser Asp Glu Ala Gly Asp Glu
 1               5                  10

<210> SEQ ID NO 796
<211> LENGTH: 9
<212> TYPE: PRT
<213> ORGANISM: homo sapien

<400> SEQUENCE: 796

Ser Ala Phe Glu Phe Ser Asp Glu Ala
 1               5

<210> SEQ ID NO 797
<211> LENGTH: 9
<212> TYPE: PRT
<213> ORGANISM: homo sapien

<400> SEQUENCE: 797

Phe Leu Asn Asp Thr Ser Ala Phe Glu
 1               5

<210> SEQ ID NO 798
<211> LENGTH: 9
<212> TYPE: PRT
<213> ORGANISM: homo sapien

<400> SEQUENCE: 798

Thr Ser Ala Phe Glu Phe Ser Asp Glu
 1               5

<210> SEQ ID NO 799
```

-continued

```
<211> LENGTH: 9
<212> TYPE: PRT
<213> ORGANISM: homo sapien

<400> SEQUENCE: 799

Asp Thr Ser Ala Phe Glu Phe Ser Asp
 1               5

<210> SEQ ID NO 800
<211> LENGTH: 9
<212> TYPE: PRT
<213> ORGANISM: homo sapien

<400> SEQUENCE: 800

Leu Asn Asp Thr Ser Ala Phe Glu Phe
 1               5

<210> SEQ ID NO 801
<211> LENGTH: 9
<212> TYPE: PRT
<213> ORGANISM: homo sapien

<400> SEQUENCE: 801

Asn Asp Thr Ser Ala Phe Glu Phe Ser
 1               5

<210> SEQ ID NO 802
<211> LENGTH: 9
<212> TYPE: PRT
<213> ORGANISM: homo sapien

<400> SEQUENCE: 802

Glu Phe Ser Asp Glu Ala Gly Asp Glu
 1               5

<210> SEQ ID NO 803
<211> LENGTH: 9
<212> TYPE: PRT
<213> ORGANISM: homo sapien

<400> SEQUENCE: 803

Phe Glu Phe Ser Asp Glu Ala Gly Asp
 1               5

<210> SEQ ID NO 804
<211> LENGTH: 9
<212> TYPE: PRT
<213> ORGANISM: homo sapien

<400> SEQUENCE: 804

Ala Phe Glu Phe Ser Asp Glu Ala Gly
 1               5

<210> SEQ ID NO 805
<211> LENGTH: 10
<212> TYPE: PRT
<213> ORGANISM: homo sapien

<400> SEQUENCE: 805

Thr Ser Ala Phe Glu Phe Ser Asp Glu Ala
 1               5                  10

<210> SEQ ID NO 806
<211> LENGTH: 10
<212> TYPE: PRT
```

-continued

<213> ORGANISM: homo sapien

<400> SEQUENCE: 806

Ser Ala Phe Glu Phe Ser Asp Glu Ala Gly
1               5                   10

<210> SEQ ID NO 807
<211> LENGTH: 10
<212> TYPE: PRT
<213> ORGANISM: homo sapien

<400> SEQUENCE: 807

Phe Leu Asn Asp Thr Ser Ala Phe Glu Phe
1               5                   10

<210> SEQ ID NO 808
<211> LENGTH: 10
<212> TYPE: PRT
<213> ORGANISM: homo sapien

<400> SEQUENCE: 808

Asp Thr Ser Ala Phe Glu Phe Ser Asp Glu
1               5                   10

<210> SEQ ID NO 809
<211> LENGTH: 10
<212> TYPE: PRT
<213> ORGANISM: homo sapien

<400> SEQUENCE: 809

Leu Asn Asp Thr Ser Ala Phe Glu Phe Ser
1               5                   10

<210> SEQ ID NO 810
<211> LENGTH: 10
<212> TYPE: PRT
<213> ORGANISM: homo sapien

<400> SEQUENCE: 810

Glu Phe Ser Asp Glu Ala Gly Asp Glu Gly
1               5                   10

<210> SEQ ID NO 811
<211> LENGTH: 10
<212> TYPE: PRT
<213> ORGANISM: homo sapien

<400> SEQUENCE: 811

Asn Asp Thr Ser Ala Phe Glu Phe Ser Asp
1               5                   10

<210> SEQ ID NO 812
<211> LENGTH: 10
<212> TYPE: PRT
<213> ORGANISM: homo sapien

<400> SEQUENCE: 812

Phe Glu Phe Ser Asp Glu Ala Gly Asp Glu
1               5                   10

<210> SEQ ID NO 813
<211> LENGTH: 10
<212> TYPE: PRT
<213> ORGANISM: homo sapien

<400> SEQUENCE: 813

Leu Phe Leu Asn Asp Thr Ser Ala Phe Glu
1               5                   10

<210> SEQ ID NO 814
<211> LENGTH: 10
<212> TYPE: PRT
<213> ORGANISM: homo sapien

<400> SEQUENCE: 814

Ala Phe Glu Phe Ser Asp Glu Ala Gly Asp
1               5                   10

<210> SEQ ID NO 815
<211> LENGTH: 9
<212> TYPE: PRT
<213> ORGANISM: homo sapien

<400> SEQUENCE: 815

Ser Ala Phe Glu Phe Ser Asp Glu Ala
1               5

<210> SEQ ID NO 816
<211> LENGTH: 9
<212> TYPE: PRT
<213> ORGANISM: homo sapien

<400> SEQUENCE: 816

Leu Asn Asp Thr Ser Ala Phe Glu Phe
1               5

<210> SEQ ID NO 817
<211> LENGTH: 9
<212> TYPE: PRT
<213> ORGANISM: homo sapien

<400> SEQUENCE: 817

Thr Ser Ala Phe Glu Phe Ser Asp Glu
1               5

<210> SEQ ID NO 818
<211> LENGTH: 9
<212> TYPE: PRT
<213> ORGANISM: homo sapien

<400> SEQUENCE: 818

Phe Leu Asn Asp Thr Ser Ala Phe Glu
1               5

<210> SEQ ID NO 819
<211> LENGTH: 9
<212> TYPE: PRT
<213> ORGANISM: homo sapien

<400> SEQUENCE: 819

Asn Asp Thr Ser Ala Phe Glu Phe Ser
1               5

<210> SEQ ID NO 820
<211> LENGTH: 9
<212> TYPE: PRT
<213> ORGANISM: homo sapien

<400> SEQUENCE: 820

```
Asp Thr Ser Ala Phe Glu Phe Ser Asp
1               5

<210> SEQ ID NO 821
<211> LENGTH: 9
<212> TYPE: PRT
<213> ORGANISM: homo sapien

<400> SEQUENCE: 821

Glu Phe Ser Asp Glu Ala Gly Asp Glu
1               5

<210> SEQ ID NO 822
<211> LENGTH: 9
<212> TYPE: PRT
<213> ORGANISM: homo sapien

<400> SEQUENCE: 822

Phe Glu Phe Ser Asp Glu Ala Gly Asp
1               5

<210> SEQ ID NO 823
<211> LENGTH: 9
<212> TYPE: PRT
<213> ORGANISM: homo sapien

<400> SEQUENCE: 823

Ala Phe Glu Phe Ser Asp Glu Ala Gly
1               5

<210> SEQ ID NO 824
<211> LENGTH: 10
<212> TYPE: PRT
<213> ORGANISM: homo sapien

<400> SEQUENCE: 824

Phe Leu Asn Asp Thr Ser Ala Phe Glu Phe
1               5                   10

<210> SEQ ID NO 825
<211> LENGTH: 10
<212> TYPE: PRT
<213> ORGANISM: homo sapien

<400> SEQUENCE: 825

Thr Ser Ala Phe Glu Phe Ser Asp Glu Ala
1               5                   10

<210> SEQ ID NO 826
<211> LENGTH: 10
<212> TYPE: PRT
<213> ORGANISM: homo sapien

<400> SEQUENCE: 826

Ser Ala Phe Glu Phe Ser Asp Glu Ala Gly
1               5                   10

<210> SEQ ID NO 827
<211> LENGTH: 10
<212> TYPE: PRT
<213> ORGANISM: homo sapien

<400> SEQUENCE: 827

Leu Asn Asp Thr Ser Ala Phe Glu Phe Ser
1               5                   10
```

<210> SEQ ID NO 828
<211> LENGTH: 10
<212> TYPE: PRT
<213> ORGANISM: homo sapien

<400> SEQUENCE: 828

Asp Thr Ser Ala Phe Glu Phe Ser Asp Glu
 1               5                  10

<210> SEQ ID NO 829
<211> LENGTH: 10
<212> TYPE: PRT
<213> ORGANISM: homo sapien

<400> SEQUENCE: 829

Glu Phe Ser Asp Glu Ala Gly Asp Glu Gly
 1               5                  10

<210> SEQ ID NO 830
<211> LENGTH: 10
<212> TYPE: PRT
<213> ORGANISM: homo sapien

<400> SEQUENCE: 830

Phe Glu Phe Ser Asp Glu Ala Gly Asp Glu
 1               5                  10

<210> SEQ ID NO 831
<211> LENGTH: 10
<212> TYPE: PRT
<213> ORGANISM: homo sapien

<400> SEQUENCE: 831

Asn Asp Thr Ser Ala Phe Glu Phe Ser Asp
 1               5                  10

<210> SEQ ID NO 832
<211> LENGTH: 10
<212> TYPE: PRT
<213> ORGANISM: homo sapien

<400> SEQUENCE: 832

Leu Phe Leu Asn Asp Thr Ser Ala Phe Glu
 1               5                  10

<210> SEQ ID NO 833
<211> LENGTH: 10
<212> TYPE: PRT
<213> ORGANISM: homo sapien

<400> SEQUENCE: 833

Ala Phe Glu Phe Ser Asp Glu Ala Gly Asp
 1               5                  10

<210> SEQ ID NO 834
<211> LENGTH: 4
<212> TYPE: PRT
<213> ORGANISM: homo sapien

<400> SEQUENCE: 834

Asn Asp Thr Ser
 1

```
<210> SEQ ID NO 835
<211> LENGTH: 4
<212> TYPE: PRT
<213> ORGANISM: homo sapien

<400> SEQUENCE: 835

Asn Cys Ser Lys
 1

<210> SEQ ID NO 836
<211> LENGTH: 4
<212> TYPE: PRT
<213> ORGANISM: homo sapien

<400> SEQUENCE: 836

Asn Gln Ser Gly
 1

<210> SEQ ID NO 837
<211> LENGTH: 4
<212> TYPE: PRT
<213> ORGANISM: homo sapien

<400> SEQUENCE: 837

Lys Arg Phe Thr
 1

<210> SEQ ID NO 838
<211> LENGTH: 4
<212> TYPE: PRT
<213> ORGANISM: homo sapien

<400> SEQUENCE: 838

Ser Ala Phe Asp
 1

<210> SEQ ID NO 839
<211> LENGTH: 4
<212> TYPE: PRT
<213> ORGANISM: homo sapien

<400> SEQUENCE: 839

Ser Leu Leu Asp
 1

<210> SEQ ID NO 840
<211> LENGTH: 4
<212> TYPE: PRT
<213> ORGANISM: homo sapien

<400> SEQUENCE: 840

Ser Gly Cys Glu
 1

<210> SEQ ID NO 841
<211> LENGTH: 4
<212> TYPE: PRT
<213> ORGANISM: homo sapien

<400> SEQUENCE: 841

Ser Val Glu Asp
 1

<210> SEQ ID NO 842
<211> LENGTH: 4
```

```
<212> TYPE: PRT
<213> ORGANISM: homo sapien

<400> SEQUENCE: 842

Ser Lys Trp Glu
 1

<210> SEQ ID NO 843
<211> LENGTH: 6
<212> TYPE: PRT
<213> ORGANISM: homo sapien

<400> SEQUENCE: 843

Gly Ala His Pro Thr Leu
 1               5

<210> SEQ ID NO 844
<211> LENGTH: 6
<212> TYPE: PRT
<213> ORGANISM: homo sapien

<400> SEQUENCE: 844

Gly Gly Tyr Ile Ala Asn
 1               5

<210> SEQ ID NO 845
<211> LENGTH: 6
<212> TYPE: PRT
<213> ORGANISM: homo sapien

<400> SEQUENCE: 845

Gly Val Ala Val Asn Val
 1               5

<210> SEQ ID NO 846
<211> LENGTH: 6
<212> TYPE: PRT
<213> ORGANISM: homo sapien

<400> SEQUENCE: 846

Gly Cys Glu Arg Asn His
 1               5

<210> SEQ ID NO 847
<211> LENGTH: 6
<212> TYPE: PRT
<213> ORGANISM: homo sapien

<400> SEQUENCE: 847

Gly Val Leu Ile Ala Ala
 1               5

<210> SEQ ID NO 848
<211> LENGTH: 6
<212> TYPE: PRT
<213> ORGANISM: homo sapien

<400> SEQUENCE: 848

Gly Met Tyr Arg Cys Thr
 1               5

<210> SEQ ID NO 849
<211> LENGTH: 22
<212> TYPE: PRT
<213> ORGANISM: homo sapien
```

-continued

<400> SEQUENCE: 849

Leu Gln Ala Asp Asp Ser Leu Leu Asp Gln Asp Leu Pro Leu Thr
 1               5                  10                  15

Asn Ser Gln Leu Ser Leu
            20

<210> SEQ ID NO 850
<211> LENGTH: 9
<212> TYPE: PRT
<213> ORGANISM: homo sapien

<400> SEQUENCE: 850

Val Val Ala Asp Asp Gly Ser Glu Ala
 1               5

<210> SEQ ID NO 851
<211> LENGTH: 9
<212> TYPE: PRT
<213> ORGANISM: homo sapien

<400> SEQUENCE: 851

Asn Gly Ala His Pro Thr Leu Gln Ala
 1               5

<210> SEQ ID NO 852
<211> LENGTH: 9
<212> TYPE: PRT
<213> ORGANISM: homo sapien

<400> SEQUENCE: 852

Val Lys Ala Arg Leu Thr Ile Ala Ala
 1               5

<210> SEQ ID NO 853
<211> LENGTH: 9
<212> TYPE: PRT
<213> ORGANISM: homo sapien

<400> SEQUENCE: 853

Ser Ala Phe Asp Phe Ser Asp Glu Ala
 1               5

<210> SEQ ID NO 854
<211> LENGTH: 9
<212> TYPE: PRT
<213> ORGANISM: homo sapien

<400> SEQUENCE: 854

Ser Ala Ile Ile Leu Thr Leu Leu Ala
 1               5

<210> SEQ ID NO 855
<211> LENGTH: 9
<212> TYPE: PRT
<213> ORGANISM: homo sapien

<400> SEQUENCE: 855

Ala Pro Glu Arg Pro Val Asn Gly Ala
 1               5

<210> SEQ ID NO 856
<211> LENGTH: 9
<212> TYPE: PRT

-continued

<213> ORGANISM: homo sapien

<400> SEQUENCE: 856

Ala Val Arg Ala Ala Phe Val His Ala
 1               5

<210> SEQ ID NO 857
<211> LENGTH: 9
<212> TYPE: PRT
<213> ORGANISM: homo sapien

<400> SEQUENCE: 857

Lys Ser Met Leu Arg Lys Asp Asp Ala
 1               5

<210> SEQ ID NO 858
<211> LENGTH: 9
<212> TYPE: PRT
<213> ORGANISM: homo sapien

<400> SEQUENCE: 858

Pro Leu Phe Leu Asn Asp Thr Ser Ala
 1               5

<210> SEQ ID NO 859
<211> LENGTH: 9
<212> TYPE: PRT
<213> ORGANISM: homo sapien

<400> SEQUENCE: 859

Phe Asn Lys Leu Arg Val Val Val Ala
 1               5

<210> SEQ ID NO 860
<211> LENGTH: 9
<212> TYPE: PRT
<213> ORGANISM: homo sapien

<400> SEQUENCE: 860

Ile Leu Lys Gln Arg Lys Val Lys Ala
 1               5

<210> SEQ ID NO 861
<211> LENGTH: 9
<212> TYPE: PRT
<213> ORGANISM: homo sapien

<400> SEQUENCE: 861

Lys Val Lys Ala Arg Leu Thr Ile Ala
 1               5

<210> SEQ ID NO 862
<211> LENGTH: 9
<212> TYPE: PRT
<213> ORGANISM: homo sapien

<400> SEQUENCE: 862

Gly Glu Leu Val Gly Gly Tyr Ile Ala
 1               5

<210> SEQ ID NO 863
<211> LENGTH: 9
<212> TYPE: PRT
<213> ORGANISM: homo sapien

-continued

<400> SEQUENCE: 863

Gly Gly Tyr Ile Ala Asn Ser Leu Ala
1               5

<210> SEQ ID NO 864
<211> LENGTH: 9
<212> TYPE: PRT
<213> ORGANISM: homo sapien

<400> SEQUENCE: 864

Asn Ser Leu Ala Ile Met Thr Asp Ala
1               5

<210> SEQ ID NO 865
<211> LENGTH: 9
<212> TYPE: PRT
<213> ORGANISM: homo sapien

<400> SEQUENCE: 865

Leu His Met Leu Thr Asp Leu Ser Ala
1               5

<210> SEQ ID NO 866
<211> LENGTH: 9
<212> TYPE: PRT
<213> ORGANISM: homo sapien

<400> SEQUENCE: 866

Phe His Arg Leu Glu Val Leu Ser Ala
1               5

<210> SEQ ID NO 867
<211> LENGTH: 9
<212> TYPE: PRT
<213> ORGANISM: homo sapien

<400> SEQUENCE: 867

Leu Met Gly Phe Leu Leu Tyr Glu Ala
1               5

<210> SEQ ID NO 868
<211> LENGTH: 9
<212> TYPE: PRT
<213> ORGANISM: homo sapien

<400> SEQUENCE: 868

Asn Gly Asp Ile Met Leu Ile Thr Ala
1               5

<210> SEQ ID NO 869
<211> LENGTH: 9
<212> TYPE: PRT
<213> ORGANISM: homo sapien

<400> SEQUENCE: 869

Gly Asp Ile Met Leu Ile Thr Ala Ala
1               5

<210> SEQ ID NO 870
<211> LENGTH: 9
<212> TYPE: PRT
<213> ORGANISM: homo sapien

<400> SEQUENCE: 870

Leu Ile Thr Ala Ala Val Gly Val Ala
1               5

<210> SEQ ID NO 871
<211> LENGTH: 9
<212> TYPE: PRT
<213> ORGANISM: homo sapien

<400> SEQUENCE: 871

Arg Asn His Gly Gln Asp Ser Leu Ala
1               5

<210> SEQ ID NO 872
<211> LENGTH: 9
<212> TYPE: PRT
<213> ORGANISM: homo sapien

<400> SEQUENCE: 872

Gly Gln Asp Ser Leu Ala Val Arg Ala
1               5

<210> SEQ ID NO 873
<211> LENGTH: 9
<212> TYPE: PRT
<213> ORGANISM: homo sapien

<400> SEQUENCE: 873

Gln Asp Ser Leu Ala Val Arg Ala Ala
1               5

<210> SEQ ID NO 874
<211> LENGTH: 9
<212> TYPE: PRT
<213> ORGANISM: homo sapien

<400> SEQUENCE: 874

Val Gln Ser Val Gly Val Leu Ile Ala
1               5

<210> SEQ ID NO 875
<211> LENGTH: 9
<212> TYPE: PRT
<213> ORGANISM: homo sapien

<400> SEQUENCE: 875

Gln Ser Val Gly Val Leu Ile Ala Ala
1               5

<210> SEQ ID NO 876
<211> LENGTH: 9
<212> TYPE: PRT
<213> ORGANISM: homo sapien

<400> SEQUENCE: 876

Arg Phe Lys Pro Glu Tyr Lys Ile Ala
1               5

<210> SEQ ID NO 877
<211> LENGTH: 9
<212> TYPE: PRT
<213> ORGANISM: homo sapien

<400> SEQUENCE: 877

Thr Tyr Val Phe Ser Leu Leu Val Ala
1               5

<210> SEQ ID NO 878
<211> LENGTH: 9
<212> TYPE: PRT
<213> ORGANISM: homo sapien

<400> SEQUENCE: 878

Leu Asn Val Asp Tyr Ile Lys Glu Ala
1               5

<210> SEQ ID NO 879
<211> LENGTH: 9
<212> TYPE: PRT
<213> ORGANISM: homo sapien

<400> SEQUENCE: 879

Ser Leu Thr Ser Gly Lys Ser Thr Ala
1               5

<210> SEQ ID NO 880
<211> LENGTH: 9
<212> TYPE: PRT
<213> ORGANISM: homo sapien

<400> SEQUENCE: 880

Lys Trp Glu Glu Val Gln Ser Lys Ala
1               5

<210> SEQ ID NO 881
<211> LENGTH: 9
<212> TYPE: PRT
<213> ORGANISM: homo sapien

<400> SEQUENCE: 881

Arg Gln Glu Val Asp Arg Thr Cys Ala
1               5

<210> SEQ ID NO 882
<211> LENGTH: 9
<212> TYPE: PRT
<213> ORGANISM: homo sapien

<400> SEQUENCE: 882

Tyr Ile Leu Met Gly Phe Leu Leu Tyr
1               5

<210> SEQ ID NO 883
<211> LENGTH: 9
<212> TYPE: PRT
<213> ORGANISM: homo sapien

<400> SEQUENCE: 883

Ala Met Ile Ser Val Leu Leu Val Tyr
1               5

<210> SEQ ID NO 884
<211> LENGTH: 9
<212> TYPE: PRT
<213> ORGANISM: homo sapien

<400> SEQUENCE: 884

Leu Thr Asp Leu Ser Ala Ile Ile Leu
1               5

```
<210> SEQ ID NO 885
<211> LENGTH: 9
<212> TYPE: PRT
<213> ORGANISM: homo sapien

<400> SEQUENCE: 885

Leu Leu Leu Asn Thr Phe Gly Met Tyr
1               5

<210> SEQ ID NO 886
<211> LENGTH: 9
<212> TYPE: PRT
<213> ORGANISM: homo sapien

<400> SEQUENCE: 886

Gln Ala Asp Asp Asp Ser Leu Leu Asp
1               5

<210> SEQ ID NO 887
<211> LENGTH: 9
<212> TYPE: PRT
<213> ORGANISM: homo sapien

<400> SEQUENCE: 887

Arg Leu Thr Ile Ala Ala Val Leu Tyr
1               5

<210> SEQ ID NO 888
<211> LENGTH: 9
<212> TYPE: PRT
<213> ORGANISM: homo sapien

<400> SEQUENCE: 888

Met Thr Asp Ala Leu His Met Leu Thr
1               5

<210> SEQ ID NO 889
<211> LENGTH: 9
<212> TYPE: PRT
<213> ORGANISM: homo sapien

<400> SEQUENCE: 889

Ala Leu Met Lys Ile Glu Asp Val Tyr
1               5

<210> SEQ ID NO 890
<211> LENGTH: 9
<212> TYPE: PRT
<213> ORGANISM: homo sapien

<400> SEQUENCE: 890

Ala Asp Asp Asp Ser Leu Leu Asp Gln
1               5

<210> SEQ ID NO 891
<211> LENGTH: 9
<212> TYPE: PRT
<213> ORGANISM: homo sapien

<400> SEQUENCE: 891

Ser Val Gly Val Leu Ile Ala Ala Tyr
1               5

<210> SEQ ID NO 892
<211> LENGTH: 9
```

```
<212> TYPE: PRT
<213> ORGANISM: homo sapien

<400> SEQUENCE: 892

Tyr Ile Ile Arg Phe Lys Pro Glu Tyr
 1               5

<210> SEQ ID NO 893
<211> LENGTH: 9
<212> TYPE: PRT
<213> ORGANISM: homo sapien

<400> SEQUENCE: 893

Ile Trp Asp Thr Val Val Ile Ile Leu
 1               5

<210> SEQ ID NO 894
<211> LENGTH: 9
<212> TYPE: PRT
<213> ORGANISM: homo sapien

<400> SEQUENCE: 894

Val Pro Ser His Leu Asn Val Asp Tyr
 1               5

<210> SEQ ID NO 895
<211> LENGTH: 9
<212> TYPE: PRT
<213> ORGANISM: homo sapien

<400> SEQUENCE: 895

Ser Val Glu Asp Leu Asn Ile Trp Ser
 1               5

<210> SEQ ID NO 896
<211> LENGTH: 9
<212> TYPE: PRT
<213> ORGANISM: homo sapien

<400> SEQUENCE: 896

Arg Cys Thr Ile Gln Leu Gln Ser Tyr
 1               5

<210> SEQ ID NO 897
<211> LENGTH: 9
<212> TYPE: PRT
<213> ORGANISM: homo sapien

<400> SEQUENCE: 897

Arg Lys Asp Asp Ala Pro Leu Phe Leu
 1               5

<210> SEQ ID NO 898
<211> LENGTH: 9
<212> TYPE: PRT
<213> ORGANISM: homo sapien

<400> SEQUENCE: 898

Phe Ser Asp Glu Ala Gly Asp Glu Gly
 1               5

<210> SEQ ID NO 899
<211> LENGTH: 9
<212> TYPE: PRT
<213> ORGANISM: homo sapien
```

-continued

<400> SEQUENCE: 899

Met Ile Gly Glu Leu Val Gly Gly Tyr
1               5

<210> SEQ ID NO 900
<211> LENGTH: 9
<212> TYPE: PRT
<213> ORGANISM: homo sapien

<400> SEQUENCE: 900

Val Gln Arg Thr Ile His Met Asn Tyr
1               5

<210> SEQ ID NO 901
<211> LENGTH: 9
<212> TYPE: PRT
<213> ORGANISM: homo sapien

<400> SEQUENCE: 901

Lys Ile Ala Asp Pro Ile Cys Thr Tyr
1               5

<210> SEQ ID NO 902
<211> LENGTH: 9
<212> TYPE: PRT
<213> ORGANISM: homo sapien

<400> SEQUENCE: 902

Gly Ser Glu Ala Pro Glu Arg Pro Val
1               5

<210> SEQ ID NO 903
<211> LENGTH: 9
<212> TYPE: PRT
<213> ORGANISM: homo sapien

<400> SEQUENCE: 903

Tyr Val Phe Ser Leu Leu Val Ala Phe
1               5

<210> SEQ ID NO 904
<211> LENGTH: 9
<212> TYPE: PRT
<213> ORGANISM: homo sapien

<400> SEQUENCE: 904

Met Ile Gly Glu Leu Val Gly Gly Tyr
1               5

<210> SEQ ID NO 905
<211> LENGTH: 9
<212> TYPE: PRT
<213> ORGANISM: homo sapien

<400> SEQUENCE: 905

Asp Leu Val Gln Ser Val Gly Val Leu
1               5

<210> SEQ ID NO 906
<211> LENGTH: 9
<212> TYPE: PRT
<213> ORGANISM: homo sapien

<400> SEQUENCE: 906

-continued

Ser Val Gly Val Leu Ile Ala Ala Tyr
1               5

<210> SEQ ID NO 907
<211> LENGTH: 9
<212> TYPE: PRT
<213> ORGANISM: homo sapien

<400> SEQUENCE: 907

Glu Val Gln Ser Lys Ala Asn His Leu
1               5

<210> SEQ ID NO 908
<211> LENGTH: 9
<212> TYPE: PRT
<213> ORGANISM: homo sapien

<400> SEQUENCE: 908

Asp Leu Ser Ala Ile Ile Leu Thr Leu
1               5

<210> SEQ ID NO 909
<211> LENGTH: 9
<212> TYPE: PRT
<213> ORGANISM: homo sapien

<400> SEQUENCE: 909

Leu Ile Ala Ala Tyr Ile Ile Arg Phe
1               5

<210> SEQ ID NO 910
<211> LENGTH: 9
<212> TYPE: PRT
<213> ORGANISM: homo sapien

<400> SEQUENCE: 910

Lys Ile Ala Asp Pro Ile Cys Thr Tyr
1               5

<210> SEQ ID NO 911
<211> LENGTH: 9
<212> TYPE: PRT
<213> ORGANISM: homo sapien

<400> SEQUENCE: 911

Asp Leu Pro Leu Thr Asn Ser Gln Leu
1               5

<210> SEQ ID NO 912
<211> LENGTH: 9
<212> TYPE: PRT
<213> ORGANISM: homo sapien

<400> SEQUENCE: 912

Tyr Ile Ala Asn Ser Leu Ala Ile Met
1               5

<210> SEQ ID NO 913
<211> LENGTH: 9
<212> TYPE: PRT
<213> ORGANISM: homo sapien

<400> SEQUENCE: 913

Ala Ile Ile Leu Thr Leu Leu Ala Leu

```
1               5

<210> SEQ ID NO 914
<211> LENGTH: 9
<212> TYPE: PRT
<213> ORGANISM: homo sapien

<400> SEQUENCE: 914

Leu Thr Ile Ala Ala Val Leu Tyr Leu
1               5

<210> SEQ ID NO 915
<211> LENGTH: 9
<212> TYPE: PRT
<213> ORGANISM: homo sapien

<400> SEQUENCE: 915

Leu Leu Val Tyr Ile Leu Met Gly Phe
1               5

<210> SEQ ID NO 916
<211> LENGTH: 9
<212> TYPE: PRT
<213> ORGANISM: homo sapien

<400> SEQUENCE: 916

Tyr Ile Leu Met Gly Phe Leu Leu Tyr
1               5

<210> SEQ ID NO 917
<211> LENGTH: 9
<212> TYPE: PRT
<213> ORGANISM: homo sapien

<400> SEQUENCE: 917

Tyr Ile Ile Arg Phe Lys Pro Glu Tyr
1               5

<210> SEQ ID NO 918
<211> LENGTH: 9
<212> TYPE: PRT
<213> ORGANISM: homo sapien

<400> SEQUENCE: 918

Thr Ile Ala Ala Val Leu Tyr Leu Leu
1               5

<210> SEQ ID NO 919
<211> LENGTH: 9
<212> TYPE: PRT
<213> ORGANISM: homo sapien

<400> SEQUENCE: 919

Leu Val Tyr Ile Leu Met Gly Phe Leu
1               5

<210> SEQ ID NO 920
<211> LENGTH: 9
<212> TYPE: PRT
<213> ORGANISM: homo sapien

<400> SEQUENCE: 920

Glu Ile Asn Gly Asp Ile Met Leu Ile
1               5
```

```
<210> SEQ ID NO 921
<211> LENGTH: 9
<212> TYPE: PRT
<213> ORGANISM: homo sapien

<400> SEQUENCE: 921

Pro Ile Cys Thr Tyr Val Phe Ser Leu
1               5

<210> SEQ ID NO 922
<211> LENGTH: 9
<212> TYPE: PRT
<213> ORGANISM: homo sapien

<400> SEQUENCE: 922

Leu Leu Leu Asn Thr Phe Gly Met Tyr
1               5

<210> SEQ ID NO 923
<211> LENGTH: 9
<212> TYPE: PRT
<213> ORGANISM: homo sapien

<400> SEQUENCE: 923

Pro Thr Lys Arg Phe Thr Phe Gly Phe
1               5

<210> SEQ ID NO 924
<211> LENGTH: 9
<212> TYPE: PRT
<213> ORGANISM: homo sapien

<400> SEQUENCE: 924

Glu Val Leu Ser Ala Met Ile Ser Val
1               5

<210> SEQ ID NO 925
<211> LENGTH: 9
<212> TYPE: PRT
<213> ORGANISM: homo sapien

<400> SEQUENCE: 925

Ser Val Leu Leu Val Tyr Ile Leu Met
1               5

<210> SEQ ID NO 926
<211> LENGTH: 9
<212> TYPE: PRT
<213> ORGANISM: homo sapien

<400> SEQUENCE: 926

Ala Val Asn Val Ile Met Gly Phe Leu
1               5

<210> SEQ ID NO 927
<211> LENGTH: 9
<212> TYPE: PRT
<213> ORGANISM: homo sapien

<400> SEQUENCE: 927

Ser Leu Leu Val Ala Phe Thr Thr Phe
1               5

<210> SEQ ID NO 928
```

```
<211> LENGTH: 9
<212> TYPE: PRT
<213> ORGANISM: homo sapien

<400> SEQUENCE: 928

Pro Val Asn Gly Ala His Pro Thr Leu
 1               5

<210> SEQ ID NO 929
<211> LENGTH: 9
<212> TYPE: PRT
<213> ORGANISM: homo sapien

<400> SEQUENCE: 929

Tyr Leu Leu Phe Met Ile Gly Glu Leu
 1               5

<210> SEQ ID NO 930
<211> LENGTH: 9
<212> TYPE: PRT
<213> ORGANISM: homo sapien

<400> SEQUENCE: 930

Glu Leu Val Gly Gly Tyr Ile Ala Asn
 1               5

<210> SEQ ID NO 931
<211> LENGTH: 9
<212> TYPE: PRT
<213> ORGANISM: homo sapien

<400> SEQUENCE: 931

Val Leu Ser Ala Met Ile Ser Val Leu
 1               5

<210> SEQ ID NO 932
<211> LENGTH: 9
<212> TYPE: PRT
<213> ORGANISM: homo sapien

<400> SEQUENCE: 932

Asp Thr Val Val Ile Ile Leu Glu Gly
 1               5

<210> SEQ ID NO 933
<211> LENGTH: 9
<212> TYPE: PRT
<213> ORGANISM: homo sapien

<400> SEQUENCE: 933

Glu Gly Leu Ser Arg Phe Asn Lys Leu
 1               5

<210> SEQ ID NO 934
<211> LENGTH: 9
<212> TYPE: PRT
<213> ORGANISM: homo sapien

<400> SEQUENCE: 934

Leu Thr Asp Leu Ser Ala Ile Ile Leu
 1               5

<210> SEQ ID NO 935
<211> LENGTH: 9
<212> TYPE: PRT
```

<213> ORGANISM: homo sapien

<400> SEQUENCE: 935

Ile Leu Glu Gly Val Pro Ser His Leu
1               5

<210> SEQ ID NO 936
<211> LENGTH: 9
<212> TYPE: PRT
<213> ORGANISM: homo sapien

<400> SEQUENCE: 936

Asn Val Asp Tyr Ile Lys Glu Ala Leu
1               5

<210> SEQ ID NO 937
<211> LENGTH: 9
<212> TYPE: PRT
<213> ORGANISM: homo sapien

<400> SEQUENCE: 937

Ser Thr Ala Ile Val His Ile Gln Leu
1               5

<210> SEQ ID NO 938
<211> LENGTH: 9
<212> TYPE: PRT
<213> ORGANISM: homo sapien

<400> SEQUENCE: 938

Ala Gly Asp Glu Gly Leu Ser Arg Phe
1               5

<210> SEQ ID NO 939
<211> LENGTH: 9
<212> TYPE: PRT
<213> ORGANISM: homo sapien

<400> SEQUENCE: 939

Arg Leu Thr Ile Ala Ala Val Leu Tyr
1               5

<210> SEQ ID NO 940
<211> LENGTH: 9
<212> TYPE: PRT
<213> ORGANISM: homo sapien

<400> SEQUENCE: 940

Ala Ile Met Thr Asp Ala Leu His Met
1               5

<210> SEQ ID NO 941
<211> LENGTH: 9
<212> TYPE: PRT
<213> ORGANISM: homo sapien

<400> SEQUENCE: 941

Arg Phe Thr Phe Gly Phe His Arg Leu
1               5

<210> SEQ ID NO 942
<211> LENGTH: 9
<212> TYPE: PRT
<213> ORGANISM: homo sapien

-continued

<400> SEQUENCE: 942

Tyr Ile Lys Glu Ala Leu Met Lys Ile
1               5

<210> SEQ ID NO 943
<211> LENGTH: 9
<212> TYPE: PRT
<213> ORGANISM: homo sapien

<400> SEQUENCE: 943

Ala Leu Met Lys Ile Glu Asp Val Tyr
1               5

<210> SEQ ID NO 944
<211> LENGTH: 9
<212> TYPE: PRT
<213> ORGANISM: homo sapien

<400> SEQUENCE: 944

Glu Asp Val Tyr Ser Val Glu Asp Leu
1               5

<210> SEQ ID NO 945
<211> LENGTH: 9
<212> TYPE: PRT
<213> ORGANISM: homo sapien

<400> SEQUENCE: 945

Glu Val Asp Arg Thr Cys Ala Asn Cys
1               5

<210> SEQ ID NO 946
<211> LENGTH: 9
<212> TYPE: PRT
<213> ORGANISM: homo sapien

<400> SEQUENCE: 946

Met Leu Arg Lys Asp Asp Ala Pro Leu
1               5

<210> SEQ ID NO 947
<211> LENGTH: 9
<212> TYPE: PRT
<213> ORGANISM: homo sapien

<400> SEQUENCE: 947

Leu Phe Leu Asn Asp Thr Ser Ala Phe
1               5

<210> SEQ ID NO 948
<211> LENGTH: 9
<212> TYPE: PRT
<213> ORGANISM: homo sapien

<400> SEQUENCE: 948

Ser Leu Leu Asp Gln Asp Leu Pro Leu
1               5

<210> SEQ ID NO 949
<211> LENGTH: 9
<212> TYPE: PRT
<213> ORGANISM: homo sapien

<400> SEQUENCE: 949

```
Pro Leu Thr Asn Ser Gln Leu Ser Leu
1               5
```

<210> SEQ ID NO 950
<211> LENGTH: 9
<212> TYPE: PRT
<213> ORGANISM: homo sapien

<400> SEQUENCE: 950

```
Glu Ile Leu Lys Gln Arg Lys Val Lys
1               5
```

<210> SEQ ID NO 951
<211> LENGTH: 9
<212> TYPE: PRT
<213> ORGANISM: homo sapien

<400> SEQUENCE: 951

```
Leu Val Gly Gly Tyr Ile Ala Asn Ser
1               5
```

<210> SEQ ID NO 952
<211> LENGTH: 9
<212> TYPE: PRT
<213> ORGANISM: homo sapien

<400> SEQUENCE: 952

```
Ser Leu Ala Ile Met Thr Asp Ala Leu
1               5
```

<210> SEQ ID NO 953
<211> LENGTH: 9
<212> TYPE: PRT
<213> ORGANISM: homo sapien

<400> SEQUENCE: 953

```
Asp Ala Leu His Met Leu Thr Asp Leu
1               5
```

<210> SEQ ID NO 954
<211> LENGTH: 9
<212> TYPE: PRT
<213> ORGANISM: homo sapien

<400> SEQUENCE: 954

```
Asp Ile Met Leu Ile Thr Ala Ala Val
1               5
```

<210> SEQ ID NO 955
<211> LENGTH: 9
<212> TYPE: PRT
<213> ORGANISM: homo sapien

<400> SEQUENCE: 955

```
Asp Ser Leu Ala Val Arg Ala Ala Phe
1               5
```

<210> SEQ ID NO 956
<211> LENGTH: 9
<212> TYPE: PRT
<213> ORGANISM: homo sapien

<400> SEQUENCE: 956

```
Ala Phe Val His Ala Leu Gly Asp Leu
1               5
```

<210> SEQ ID NO 957
<211> LENGTH: 9
<212> TYPE: PRT
<213> ORGANISM: homo sapien

<400> SEQUENCE: 957

Ile Ile Leu Glu Gly Val Pro Ser His
 1               5

<210> SEQ ID NO 958
<211> LENGTH: 9
<212> TYPE: PRT
<213> ORGANISM: homo sapien

<400> SEQUENCE: 958

Asn Thr Phe Gly Met Tyr Arg Cys Thr
 1               5

<210> SEQ ID NO 959
<211> LENGTH: 9
<212> TYPE: PRT
<213> ORGANISM: homo sapien

<400> SEQUENCE: 959

Asp Thr Ser Ala Phe Asp Phe Ser Asp
 1               5

<210> SEQ ID NO 960
<211> LENGTH: 9
<212> TYPE: PRT
<213> ORGANISM: homo sapien

<400> SEQUENCE: 960

Thr Leu Gln Ala Asp Asp Asp Ser Leu
 1               5

<210> SEQ ID NO 961
<211> LENGTH: 9
<212> TYPE: PRT
<213> ORGANISM: homo sapien

<400> SEQUENCE: 961

Leu Thr Asn Ser Gln Leu Ser Leu Lys
 1               5

<210> SEQ ID NO 962
<211> LENGTH: 9
<212> TYPE: PRT
<213> ORGANISM: homo sapien

<400> SEQUENCE: 962

Ile Leu Thr Leu Leu Ala Leu Trp Leu
 1               5

<210> SEQ ID NO 963
<211> LENGTH: 9
<212> TYPE: PRT
<213> ORGANISM: homo sapien

<400> SEQUENCE: 963

Ala Met Ile Ser Val Leu Leu Val Tyr
 1               5

```
<210> SEQ ID NO 964
<211> LENGTH: 9
<212> TYPE: PRT
<213> ORGANISM: homo sapien

<400> SEQUENCE: 964

Val Ile Met Gly Phe Leu Leu Asn Gln
1               5

<210> SEQ ID NO 965
<211> LENGTH: 9
<212> TYPE: PRT
<213> ORGANISM: homo sapien

<400> SEQUENCE: 965

Asp Val Tyr Ser Val Glu Asp Leu Asn
1               5

<210> SEQ ID NO 966
<211> LENGTH: 9
<212> TYPE: PRT
<213> ORGANISM: homo sapien

<400> SEQUENCE: 966

His Leu Leu Leu Asn Thr Phe Gly Met
1               5

<210> SEQ ID NO 967
<211> LENGTH: 9
<212> TYPE: PRT
<213> ORGANISM: homo sapien

<400> SEQUENCE: 967

Arg Cys Thr Ile Gln Leu Gln Ser Tyr
1               5

<210> SEQ ID NO 968
<211> LENGTH: 9
<212> TYPE: PRT
<213> ORGANISM: homo sapien

<400> SEQUENCE: 968

Asp Asp Ser Leu Leu Asp Gln Asp Leu
1               5

<210> SEQ ID NO 969
<211> LENGTH: 9
<212> TYPE: PRT
<213> ORGANISM: homo sapien

<400> SEQUENCE: 969

Ile Ala Ala Val Leu Tyr Leu Leu Phe
1               5

<210> SEQ ID NO 970
<211> LENGTH: 9
<212> TYPE: PRT
<213> ORGANISM: homo sapien

<400> SEQUENCE: 970

Ala Val Leu Tyr Leu Leu Phe Met Ile
1               5

<210> SEQ ID NO 971
<211> LENGTH: 9
```

<212> TYPE: PRT
<213> ORGANISM: homo sapien

<400> SEQUENCE: 971

Ile Ile Leu Thr Leu Leu Ala Leu Trp
1               5

<210> SEQ ID NO 972
<211> LENGTH: 9
<212> TYPE: PRT
<213> ORGANISM: homo sapien

<400> SEQUENCE: 972

His Arg Leu Glu Val Leu Ser Ala Met
1               5

<210> SEQ ID NO 973
<211> LENGTH: 9
<212> TYPE: PRT
<213> ORGANISM: homo sapien

<400> SEQUENCE: 973

Met Ile Ser Val Leu Leu Val Tyr Ile
1               5

<210> SEQ ID NO 974
<211> LENGTH: 9
<212> TYPE: PRT
<213> ORGANISM: homo sapien

<400> SEQUENCE: 974

Leu Leu Tyr Glu Ala Val Gln Arg Thr
1               5

<210> SEQ ID NO 975
<211> LENGTH: 9
<212> TYPE: PRT
<213> ORGANISM: homo sapien

<400> SEQUENCE: 975

Glu Ala Val Gln Arg Thr Ile His Met
1               5

<210> SEQ ID NO 976
<211> LENGTH: 9
<212> TYPE: PRT
<213> ORGANISM: homo sapien

<400> SEQUENCE: 976

Gly Val Ala Val Asn Val Ile Met Gly
1               5

<210> SEQ ID NO 977
<211> LENGTH: 9
<212> TYPE: PRT
<213> ORGANISM: homo sapien

<400> SEQUENCE: 977

Val Ala Val Asn Val Ile Met Gly Phe
1               5

<210> SEQ ID NO 978
<211> LENGTH: 9
<212> TYPE: PRT
<213> ORGANISM: homo sapien

<400> SEQUENCE: 978

Asn Val Ile Met Gly Phe Leu Leu Asn
1               5

<210> SEQ ID NO 979
<211> LENGTH: 9
<212> TYPE: PRT
<213> ORGANISM: homo sapien

<400> SEQUENCE: 979

Ala Val Arg Ala Ala Phe Val His Ala
1               5

<210> SEQ ID NO 980
<211> LENGTH: 9
<212> TYPE: PRT
<213> ORGANISM: homo sapien

<400> SEQUENCE: 980

Ala Leu Gly Asp Leu Val Gln Ser Val
1               5

<210> SEQ ID NO 981
<211> LENGTH: 9
<212> TYPE: PRT
<213> ORGANISM: homo sapien

<400> SEQUENCE: 981

Thr Thr Phe Arg Ile Ile Trp Asp Thr
1               5

<210> SEQ ID NO 982
<211> LENGTH: 9
<212> TYPE: PRT
<213> ORGANISM: homo sapien

<400> SEQUENCE: 982

Ile Ile Trp Asp Thr Val Val Ile Ile
1               5

<210> SEQ ID NO 983
<211> LENGTH: 9
<212> TYPE: PRT
<213> ORGANISM: homo sapien

<400> SEQUENCE: 983

Gly Val Pro Ser His Leu Asn Val Asp
1               5

<210> SEQ ID NO 984
<211> LENGTH: 9
<212> TYPE: PRT
<213> ORGANISM: homo sapien

<400> SEQUENCE: 984

Lys Ile Glu Asp Val Tyr Ser Val Glu
1               5

<210> SEQ ID NO 985
<211> LENGTH: 9
<212> TYPE: PRT
<213> ORGANISM: homo sapien

<400> SEQUENCE: 985

Leu Ile Pro Gly Ser Ser Ser Lys Trp
1               5

<210> SEQ ID NO 986
<211> LENGTH: 9
<212> TYPE: PRT
<213> ORGANISM: homo sapien

<400> SEQUENCE: 986

Arg Leu Lys Ser Met Leu Arg Lys Asp
1               5

<210> SEQ ID NO 987
<211> LENGTH: 9
<212> TYPE: PRT
<213> ORGANISM: homo sapien

<400> SEQUENCE: 987

Asp Asp Ala Pro Leu Phe Leu Asn Asp
1               5

<210> SEQ ID NO 988
<211> LENGTH: 9
<212> TYPE: PRT
<213> ORGANISM: homo sapien

<400> SEQUENCE: 988

Leu Leu Asp Gln Asp Leu Pro Leu Thr
1               5

<210> SEQ ID NO 989
<211> LENGTH: 9
<212> TYPE: PRT
<213> ORGANISM: homo sapien

<400> SEQUENCE: 989

Lys Val Lys Ala Arg Leu Thr Ile Ala
1               5

<210> SEQ ID NO 990
<211> LENGTH: 9
<212> TYPE: PRT
<213> ORGANISM: homo sapien

<400> SEQUENCE: 990

Leu Leu Ala Leu Trp Leu Ser Ser Lys
1               5

<210> SEQ ID NO 991
<211> LENGTH: 9
<212> TYPE: PRT
<213> ORGANISM: homo sapien

<400> SEQUENCE: 991

Ala Val Gln Arg Thr Ile His Met Asn
1               5

<210> SEQ ID NO 992
<211> LENGTH: 9
<212> TYPE: PRT
<213> ORGANISM: homo sapien

<400> SEQUENCE: 992

Glu Arg Asn His Gly Gln Asp Ser Leu

-continued

```
<210> SEQ ID NO 993
<211> LENGTH: 9
<212> TYPE: PRT
<213> ORGANISM: homo sapien

<400> SEQUENCE: 993

Thr Val Val Ile Ile Leu Glu Gly Val
1               5

<210> SEQ ID NO 994
<211> LENGTH: 9
<212> TYPE: PRT
<213> ORGANISM: homo sapien

<400> SEQUENCE: 994

Ile Val His Ile Gln Leu Ile Pro Gly
1               5

<210> SEQ ID NO 995
<211> LENGTH: 9
<212> TYPE: PRT
<213> ORGANISM: homo sapien

<400> SEQUENCE: 995

Ala Asn His Leu Leu Leu Asn Thr Phe
1               5

<210> SEQ ID NO 996
<211> LENGTH: 9
<212> TYPE: PRT
<213> ORGANISM: homo sapien

<400> SEQUENCE: 996

Cys Thr Ile Gln Leu Gln Ser Tyr Arg
1               5

<210> SEQ ID NO 997
<211> LENGTH: 9
<212> TYPE: PRT
<213> ORGANISM: homo sapien

<400> SEQUENCE: 997

Gln Leu Ile Pro Gly Ser Ser Ser Lys
1               5

<210> SEQ ID NO 998
<211> LENGTH: 9
<212> TYPE: PRT
<213> ORGANISM: homo sapien

<400> SEQUENCE: 998

Arg Leu Thr Ile Ala Ala Val Leu Tyr
1               5

<210> SEQ ID NO 999
<211> LENGTH: 9
<212> TYPE: PRT
<213> ORGANISM: homo sapien

<400> SEQUENCE: 999

Leu Leu Ala Leu Trp Leu Ser Ser Lys
1               5
```

```
<210> SEQ ID NO 1000
<211> LENGTH: 9
<212> TYPE: PRT
<213> ORGANISM: homo sapien

<400> SEQUENCE: 1000

Phe Leu Leu Tyr Glu Ala Val Gln Arg
1               5

<210> SEQ ID NO 1001
<211> LENGTH: 9
<212> TYPE: PRT
<213> ORGANISM: homo sapien

<400> SEQUENCE: 1001

Glu Ile Leu Lys Gln Arg Lys Val Lys
1               5

<210> SEQ ID NO 1002
<211> LENGTH: 9
<212> TYPE: PRT
<213> ORGANISM: homo sapien

<400> SEQUENCE: 1002

Trp Leu Ser Ser Lys Ser Pro Thr Lys
1               5

<210> SEQ ID NO 1003
<211> LENGTH: 9
<212> TYPE: PRT
<213> ORGANISM: homo sapien

<400> SEQUENCE: 1003

Ile Ile Arg Phe Lys Pro Glu Tyr Lys
1               5

<210> SEQ ID NO 1004
<211> LENGTH: 9
<212> TYPE: PRT
<213> ORGANISM: homo sapien

<400> SEQUENCE: 1004

Lys Ile Ala Asp Pro Ile Cys Thr Tyr
1               5

<210> SEQ ID NO 1005
<211> LENGTH: 9
<212> TYPE: PRT
<213> ORGANISM: homo sapien

<400> SEQUENCE: 1005

Arg Ile Ile Trp Asp Thr Val Val Ile
1               5

<210> SEQ ID NO 1006
<211> LENGTH: 9
<212> TYPE: PRT
<213> ORGANISM: homo sapien

<400> SEQUENCE: 1006

Ala Leu Met Lys Ile Glu Asp Val Tyr
1               5

<210> SEQ ID NO 1007
```

-continued

```
<211> LENGTH: 9
<212> TYPE: PRT
<213> ORGANISM: homo sapien

<400> SEQUENCE: 1007

Ala Val Arg Ala Ala Phe Val His Ala
1               5

<210> SEQ ID NO 1008
<211> LENGTH: 9
<212> TYPE: PRT
<213> ORGANISM: homo sapien

<400> SEQUENCE: 1008

Ser Leu Leu Val Ala Phe Thr Thr Phe
1               5

<210> SEQ ID NO 1009
<211> LENGTH: 9
<212> TYPE: PRT
<213> ORGANISM: homo sapien

<400> SEQUENCE: 1009

Tyr Ile Leu Met Gly Phe Leu Leu Tyr
1               5

<210> SEQ ID NO 1010
<211> LENGTH: 9
<212> TYPE: PRT
<213> ORGANISM: homo sapien

<400> SEQUENCE: 1010

Ser Val Gly Val Leu Ile Ala Ala Tyr
1               5

<210> SEQ ID NO 1011
<211> LENGTH: 9
<212> TYPE: PRT
<213> ORGANISM: homo sapien

<400> SEQUENCE: 1011

Ile Ile Leu Glu Gly Val Pro Ser His
1               5

<210> SEQ ID NO 1012
<211> LENGTH: 9
<212> TYPE: PRT
<213> ORGANISM: homo sapien

<400> SEQUENCE: 1012

Asn Ile Trp Ser Leu Thr Ser Gly Lys
1               5

<210> SEQ ID NO 1013
<211> LENGTH: 9
<212> TYPE: PRT
<213> ORGANISM: homo sapien

<400> SEQUENCE: 1013

Leu Leu Leu Asn Thr Phe Gly Met Tyr
1               5

<210> SEQ ID NO 1014
<211> LENGTH: 9
<212> TYPE: PRT
```

```
<213> ORGANISM: homo sapien

<400> SEQUENCE: 1014

Lys Leu Arg Val Val Ala Asp Asp
1               5

<210> SEQ ID NO 1015
<211> LENGTH: 9
<212> TYPE: PRT
<213> ORGANISM: homo sapien

<400> SEQUENCE: 1015

Ile Leu Thr Leu Leu Ala Leu Trp Leu
1               5

<210> SEQ ID NO 1016
<211> LENGTH: 9
<212> TYPE: PRT
<213> ORGANISM: homo sapien

<400> SEQUENCE: 1016

Ala Met Ile Ser Val Leu Leu Val Tyr
1               5

<210> SEQ ID NO 1017
<211> LENGTH: 9
<212> TYPE: PRT
<213> ORGANISM: homo sapien

<400> SEQUENCE: 1017

Met Leu Ile Thr Ala Ala Val Gly Val
1               5

<210> SEQ ID NO 1018
<211> LENGTH: 9
<212> TYPE: PRT
<213> ORGANISM: homo sapien

<400> SEQUENCE: 1018

Ser Leu Ala Val Arg Ala Ala Phe Val
1               5

<210> SEQ ID NO 1019
<211> LENGTH: 9
<212> TYPE: PRT
<213> ORGANISM: homo sapien

<400> SEQUENCE: 1019

Tyr Ile Ile Arg Phe Lys Pro Glu Tyr
1               5

<210> SEQ ID NO 1020
<211> LENGTH: 9
<212> TYPE: PRT
<213> ORGANISM: homo sapien

<400> SEQUENCE: 1020

Asp Tyr Ile Lys Glu Ala Leu Met Lys
1               5

<210> SEQ ID NO 1021
<211> LENGTH: 9
<212> TYPE: PRT
<213> ORGANISM: homo sapien
```

```
<400> SEQUENCE: 1021

Lys Ile Glu Asp Val Tyr Ser Val Glu
 1               5

<210> SEQ ID NO 1022
<211> LENGTH: 9
<212> TYPE: PRT
<213> ORGANISM: homo sapien

<400> SEQUENCE: 1022

Ser Leu Thr Ser Gly Lys Ser Thr Ala
 1               5

<210> SEQ ID NO 1023
<211> LENGTH: 9
<212> TYPE: PRT
<213> ORGANISM: homo sapien

<400> SEQUENCE: 1023

Ile Leu Lys Gln Arg Lys Val Lys Ala
 1               5

<210> SEQ ID NO 1024
<211> LENGTH: 9
<212> TYPE: PRT
<213> ORGANISM: homo sapien

<400> SEQUENCE: 1024

Lys Val Lys Ala Arg Leu Thr Ile Ala
 1               5

<210> SEQ ID NO 1025
<211> LENGTH: 9
<212> TYPE: PRT
<213> ORGANISM: homo sapien

<400> SEQUENCE: 1025

Asp Leu Ser Ala Ile Ile Leu Thr Leu
 1               5

<210> SEQ ID NO 1026
<211> LENGTH: 9
<212> TYPE: PRT
<213> ORGANISM: homo sapien

<400> SEQUENCE: 1026

Ala Ile Ile Leu Thr Leu Leu Ala Leu
 1               5

<210> SEQ ID NO 1027
<211> LENGTH: 9
<212> TYPE: PRT
<213> ORGANISM: homo sapien

<400> SEQUENCE: 1027

Thr Leu Leu Ala Leu Trp Leu Ser Ser
 1               5

<210> SEQ ID NO 1028
<211> LENGTH: 9
<212> TYPE: PRT
<213> ORGANISM: homo sapien

<400> SEQUENCE: 1028
```

```
Val Leu Ser Ala Met Ile Ser Val Leu
1               5

<210> SEQ ID NO 1029
<211> LENGTH: 9
<212> TYPE: PRT
<213> ORGANISM: homo sapien

<400> SEQUENCE: 1029

Ser Leu Pro Ser Asn Ser Pro Thr Arg
1               5

<210> SEQ ID NO 1030
<211> LENGTH: 9
<212> TYPE: PRT
<213> ORGANISM: homo sapien

<400> SEQUENCE: 1030

Val Leu Ile Ala Ala Tyr Ile Ile Arg
1               5

<210> SEQ ID NO 1031
<211> LENGTH: 9
<212> TYPE: PRT
<213> ORGANISM: homo sapien

<400> SEQUENCE: 1031

Tyr Val Phe Ser Leu Leu Val Ala Phe
1               5

<210> SEQ ID NO 1032
<211> LENGTH: 9
<212> TYPE: PRT
<213> ORGANISM: homo sapien

<400> SEQUENCE: 1032

Val Val Ile Ile Leu Glu Gly Val Pro
1               5

<210> SEQ ID NO 1033
<211> LENGTH: 9
<212> TYPE: PRT
<213> ORGANISM: homo sapien

<400> SEQUENCE: 1033

Val Ile Ile Leu Glu Gly Val Pro Ser
1               5

<210> SEQ ID NO 1034
<211> LENGTH: 9
<212> TYPE: PRT
<213> ORGANISM: homo sapien

<400> SEQUENCE: 1034

Ile Leu Glu Gly Val Pro Ser His Leu
1               5

<210> SEQ ID NO 1035
<211> LENGTH: 9
<212> TYPE: PRT
<213> ORGANISM: homo sapien

<400> SEQUENCE: 1035

Lys Arg Leu Lys Ser Met Leu Arg Lys
1               5
```

<210> SEQ ID NO 1036
<211> LENGTH: 9
<212> TYPE: PRT
<213> ORGANISM: homo sapien

<400> SEQUENCE: 1036

Val Val Ala Asp Asp Gly Ser Glu Ala
1               5

<210> SEQ ID NO 1037
<211> LENGTH: 9
<212> TYPE: PRT
<213> ORGANISM: homo sapien

<400> SEQUENCE: 1037

Arg Leu Glu Val Leu Ser Ala Met Ile
1               5

<210> SEQ ID NO 1038
<211> LENGTH: 9
<212> TYPE: PRT
<213> ORGANISM: homo sapien

<400> SEQUENCE: 1038

Asn Val Ile Met Gly Phe Leu Leu Asn
1               5

<210> SEQ ID NO 1039
<211> LENGTH: 9
<212> TYPE: PRT
<213> ORGANISM: homo sapien

<400> SEQUENCE: 1039

Phe Leu Leu Asn Gln Ser Gly His Arg
1               5

<210> SEQ ID NO 1040
<211> LENGTH: 9
<212> TYPE: PRT
<213> ORGANISM: homo sapien

<400> SEQUENCE: 1040

Leu Val Gln Ser Val Gly Val Leu Ile
1               5

<210> SEQ ID NO 1041
<211> LENGTH: 9
<212> TYPE: PRT
<213> ORGANISM: homo sapien

<400> SEQUENCE: 1041

Asp Leu Asn Ile Trp Ser Leu Thr Ser
1               5

<210> SEQ ID NO 1042
<211> LENGTH: 9
<212> TYPE: PRT
<213> ORGANISM: homo sapien

<400> SEQUENCE: 1042

Leu Leu Asn Thr Phe Gly Met Tyr Arg
1               5

```
<210> SEQ ID NO 1043
<211> LENGTH: 9
<212> TYPE: PRT
<213> ORGANISM: homo sapien

<400> SEQUENCE: 1043

Gly Leu Ser Arg Phe Asn Lys Leu Arg
1               5

<210> SEQ ID NO 1044
<211> LENGTH: 9
<212> TYPE: PRT
<213> ORGANISM: homo sapien

<400> SEQUENCE: 1044

Ser Leu Leu Asp Gln Asp Leu Pro Leu
1               5

<210> SEQ ID NO 1045
<211> LENGTH: 9
<212> TYPE: PRT
<213> ORGANISM: homo sapien

<400> SEQUENCE: 1045

Asp Leu Pro Leu Thr Asn Ser Gln Leu
1               5

<210> SEQ ID NO 1046
<211> LENGTH: 9
<212> TYPE: PRT
<213> ORGANISM: homo sapien

<400> SEQUENCE: 1046

Ala Ile Met Thr Asp Ala Leu His Met
1               5

<210> SEQ ID NO 1047
<211> LENGTH: 9
<212> TYPE: PRT
<213> ORGANISM: homo sapien

<400> SEQUENCE: 1047

Ile Leu Met Gly Phe Leu Leu Tyr Glu
1               5

<210> SEQ ID NO 1048
<211> LENGTH: 9
<212> TYPE: PRT
<213> ORGANISM: homo sapien

<400> SEQUENCE: 1048

Ala Val Gln Arg Thr Ile His Met Asn
1               5

<210> SEQ ID NO 1049
<211> LENGTH: 9
<212> TYPE: PRT
<213> ORGANISM: homo sapien

<400> SEQUENCE: 1049

Ala Val Gly Val Ala Val Asn Val Ile
1               5

<210> SEQ ID NO 1050
<211> LENGTH: 9
```

```
<212> TYPE: PRT
<213> ORGANISM: homo sapien

<400> SEQUENCE: 1050

Leu Leu Asn Gln Ser Gly His Arg His
 1               5

<210> SEQ ID NO 1051
<211> LENGTH: 9
<212> TYPE: PRT
<213> ORGANISM: homo sapien

<400> SEQUENCE: 1051

Leu Leu Val Ala Phe Thr Thr Phe Arg
 1               5

<210> SEQ ID NO 1052
<211> LENGTH: 9
<212> TYPE: PRT
<213> ORGANISM: homo sapien

<400> SEQUENCE: 1052

Gln Ser Tyr Arg Gln Glu Val Asp Arg
 1               5

<210> SEQ ID NO 1053
<211> LENGTH: 9
<212> TYPE: PRT
<213> ORGANISM: homo sapien

<400> SEQUENCE: 1053

Ala Pro Glu Arg Pro Val Asn Gly Ala
 1               5

<210> SEQ ID NO 1054
<211> LENGTH: 9
<212> TYPE: PRT
<213> ORGANISM: homo sapien

<400> SEQUENCE: 1054

Arg Pro Val Asn Gly Ala His Pro Thr
 1               5

<210> SEQ ID NO 1055
<211> LENGTH: 9
<212> TYPE: PRT
<213> ORGANISM: homo sapien

<400> SEQUENCE: 1055

Ala Gly Ser Gly Ala Trp Lys Arg Leu
 1               5

<210> SEQ ID NO 1056
<211> LENGTH: 9
<212> TYPE: PRT
<213> ORGANISM: homo sapien

<400> SEQUENCE: 1056

Met Leu Arg Lys Asp Asp Ala Pro Leu
 1               5

<210> SEQ ID NO 1057
<211> LENGTH: 9
<212> TYPE: PRT
<213> ORGANISM: homo sapien
```

-continued

<400> SEQUENCE: 1057

Arg Lys Asp Asp Ala Pro Leu Phe Leu
1               5

<210> SEQ ID NO 1058
<211> LENGTH: 9
<212> TYPE: PRT
<213> ORGANISM: homo sapien

<400> SEQUENCE: 1058

Lys Gln Arg Lys Val Lys Ala Arg Leu
1               5

<210> SEQ ID NO 1059
<211> LENGTH: 9
<212> TYPE: PRT
<213> ORGANISM: homo sapien

<400> SEQUENCE: 1059

Asp Leu Ser Ala Ile Ile Leu Thr Leu
1               5

<210> SEQ ID NO 1060
<211> LENGTH: 9
<212> TYPE: PRT
<213> ORGANISM: homo sapien

<400> SEQUENCE: 1060

Ala Ile Ile Leu Thr Leu Leu Ala Leu
1               5

<210> SEQ ID NO 1061
<211> LENGTH: 9
<212> TYPE: PRT
<213> ORGANISM: homo sapien

<400> SEQUENCE: 1061

Asn Cys Ser Lys Gln Arg Glu Ile Leu
1               5

<210> SEQ ID NO 1062
<211> LENGTH: 9
<212> TYPE: PRT
<213> ORGANISM: homo sapien

<400> SEQUENCE: 1062

Ala Arg Leu Thr Ile Ala Ala Val Leu
1               5

<210> SEQ ID NO 1063
<211> LENGTH: 9
<212> TYPE: PRT
<213> ORGANISM: homo sapien

<400> SEQUENCE: 1063

Leu Thr Ile Ala Ala Val Leu Tyr Leu
1               5

<210> SEQ ID NO 1064
<211> LENGTH: 9
<212> TYPE: PRT
<213> ORGANISM: homo sapien

<400> SEQUENCE: 1064

```
Ser Pro Thr Lys Arg Phe Thr Phe Gly
 1               5
```

<210> SEQ ID NO 1065
<211> LENGTH: 9
<212> TYPE: PRT
<213> ORGANISM: homo sapien

<400> SEQUENCE: 1065

```
Val Leu Ser Ala Met Ile Ser Val Leu
 1               5
```

<210> SEQ ID NO 1066
<211> LENGTH: 9
<212> TYPE: PRT
<213> ORGANISM: homo sapien

<400> SEQUENCE: 1066

```
Ala Val Arg Ala Ala Phe Val His Ala
 1               5
```

<210> SEQ ID NO 1067
<211> LENGTH: 9
<212> TYPE: PRT
<213> ORGANISM: homo sapien

<400> SEQUENCE: 1067

```
Val Arg Ala Ala Phe Val His Ala Leu
 1               5
```

<210> SEQ ID NO 1068
<211> LENGTH: 9
<212> TYPE: PRT
<213> ORGANISM: homo sapien

<400> SEQUENCE: 1068

```
Val Pro Ser His Leu Asn Val Asp Tyr
 1               5
```

<210> SEQ ID NO 1069
<211> LENGTH: 9
<212> TYPE: PRT
<213> ORGANISM: homo sapien

<400> SEQUENCE: 1069

```
Pro Val Asn Gly Ala His Pro Thr Leu
 1               5
```

<210> SEQ ID NO 1070
<211> LENGTH: 9
<212> TYPE: PRT
<213> ORGANISM: homo sapien

<400> SEQUENCE: 1070

```
Asn Gly Ala His Pro Thr Leu Gln Ala
 1               5
```

<210> SEQ ID NO 1071
<211> LENGTH: 9
<212> TYPE: PRT
<213> ORGANISM: homo sapien

<400> SEQUENCE: 1071

```
Ser Leu Leu Asp Gln Asp Leu Pro Leu
```

```
                                1               5
```

<210> SEQ ID NO 1072
<211> LENGTH: 9
<212> TYPE: PRT
<213> ORGANISM: homo sapien

<400> SEQUENCE: 1072

```
Ser Leu Ala Ile Met Thr Asp Ala Leu
 1               5
```

<210> SEQ ID NO 1073
<211> LENGTH: 9
<212> TYPE: PRT
<213> ORGANISM: homo sapien

<400> SEQUENCE: 1073

```
Ile Leu Thr Leu Leu Ala Leu Trp Leu
 1               5
```

<210> SEQ ID NO 1074
<211> LENGTH: 9
<212> TYPE: PRT
<213> ORGANISM: homo sapien

<400> SEQUENCE: 1074

```
Leu Ser Ala Met Ile Ser Val Leu Leu
 1               5
```

<210> SEQ ID NO 1075
<211> LENGTH: 9
<212> TYPE: PRT
<213> ORGANISM: homo sapien

<400> SEQUENCE: 1075

```
Ile Thr Ala Ala Val Gly Val Ala Val
 1               5
```

<210> SEQ ID NO 1076
<211> LENGTH: 9
<212> TYPE: PRT
<213> ORGANISM: homo sapien

<400> SEQUENCE: 1076

```
Ala Val Asn Val Ile Met Gly Phe Leu
 1               5
```

<210> SEQ ID NO 1077
<211> LENGTH: 9
<212> TYPE: PRT
<213> ORGANISM: homo sapien

<400> SEQUENCE: 1077

```
Leu Pro Ser Asn Ser Pro Thr Arg Gly
 1               5
```

<210> SEQ ID NO 1078
<211> LENGTH: 9
<212> TYPE: PRT
<213> ORGANISM: homo sapien

<400> SEQUENCE: 1078

```
Asp Pro Ile Cys Thr Tyr Val Phe Ser
 1               5
```

```
<210> SEQ ID NO 1079
<211> LENGTH: 9
<212> TYPE: PRT
<213> ORGANISM: homo sapien

<400> SEQUENCE: 1079

Ile Trp Asp Thr Val Val Ile Ile Leu
1               5

<210> SEQ ID NO 1080
<211> LENGTH: 9
<212> TYPE: PRT
<213> ORGANISM: homo sapien

<400> SEQUENCE: 1080

Ile Leu Glu Gly Val Pro Ser His Leu
1               5

<210> SEQ ID NO 1081
<211> LENGTH: 9
<212> TYPE: PRT
<213> ORGANISM: homo sapien

<400> SEQUENCE: 1081

Val Gln Ser Lys Ala Asn His Leu Leu
1               5

<210> SEQ ID NO 1082
<211> LENGTH: 9
<212> TYPE: PRT
<213> ORGANISM: homo sapien

<400> SEQUENCE: 1082

Gln Ser Lys Ala Asn His Leu Leu Leu
1               5

<210> SEQ ID NO 1083
<211> LENGTH: 9
<212> TYPE: PRT
<213> ORGANISM: homo sapien

<400> SEQUENCE: 1083

Ala Trp Lys Arg Leu Lys Ser Met Leu
1               5

<210> SEQ ID NO 1084
<211> LENGTH: 9
<212> TYPE: PRT
<213> ORGANISM: homo sapien

<400> SEQUENCE: 1084

Ala Pro Leu Phe Leu Asn Asp Thr Ser
1               5

<210> SEQ ID NO 1085
<211> LENGTH: 9
<212> TYPE: PRT
<213> ORGANISM: homo sapien

<400> SEQUENCE: 1085

Glu Gly Leu Ser Arg Phe Asn Lys Leu
1               5

<210> SEQ ID NO 1086
```

```
<211> LENGTH: 9
<212> TYPE: PRT
<213> ORGANISM: homo sapien

<400> SEQUENCE: 1086

Arg Phe Asn Lys Leu Arg Val Val Val
 1               5

<210> SEQ ID NO 1087
<211> LENGTH: 9
<212> TYPE: PRT
<213> ORGANISM: homo sapien

<400> SEQUENCE: 1087

Asp Asp Ser Leu Leu Asp Gln Asp Leu
 1               5

<210> SEQ ID NO 1088
<211> LENGTH: 9
<212> TYPE: PRT
<213> ORGANISM: homo sapien

<400> SEQUENCE: 1088

Pro Leu Thr Asn Ser Gln Leu Ser Leu
 1               5

<210> SEQ ID NO 1089
<211> LENGTH: 9
<212> TYPE: PRT
<213> ORGANISM: homo sapien

<400> SEQUENCE: 1089

Thr Ile Ala Ala Val Leu Tyr Leu Leu
 1               5

<210> SEQ ID NO 1090
<211> LENGTH: 9
<212> TYPE: PRT
<213> ORGANISM: homo sapien

<400> SEQUENCE: 1090

Leu Ser Ala Ile Ile Leu Thr Leu Leu
 1               5

<210> SEQ ID NO 1091
<211> LENGTH: 9
<212> TYPE: PRT
<213> ORGANISM: homo sapien

<400> SEQUENCE: 1091

Arg Phe Thr Phe Gly Phe His Arg Leu
 1               5

<210> SEQ ID NO 1092
<211> LENGTH: 9
<212> TYPE: PRT
<213> ORGANISM: homo sapien

<400> SEQUENCE: 1092

Ile Ser Val Leu Leu Val Tyr Ile Leu
 1               5

<210> SEQ ID NO 1093
<211> LENGTH: 9
<212> TYPE: PRT
```

<213> ORGANISM: homo sapien

<400> SEQUENCE: 1093

Ala Ala Val Gly Val Ala Val Asn Val
1               5

<210> SEQ ID NO 1094
<211> LENGTH: 9
<212> TYPE: PRT
<213> ORGANISM: homo sapien

<400> SEQUENCE: 1094

Ala Phe Val His Ala Leu Gly Asp Leu
1               5

<210> SEQ ID NO 1095
<211> LENGTH: 9
<212> TYPE: PRT
<213> ORGANISM: homo sapien

<400> SEQUENCE: 1095

Asp Leu Val Gln Ser Val Gly Val Leu
1               5

<210> SEQ ID NO 1096
<211> LENGTH: 9
<212> TYPE: PRT
<213> ORGANISM: homo sapien

<400> SEQUENCE: 1096

Lys Pro Glu Tyr Lys Ile Ala Asp Pro
1               5

<210> SEQ ID NO 1097
<211> LENGTH: 9
<212> TYPE: PRT
<213> ORGANISM: homo sapien

<400> SEQUENCE: 1097

Ile Cys Thr Tyr Val Phe Ser Leu Leu
1               5

<210> SEQ ID NO 1098
<211> LENGTH: 9
<212> TYPE: PRT
<213> ORGANISM: homo sapien

<400> SEQUENCE: 1098

Asn Val Asp Tyr Ile Lys Glu Ala Leu
1               5

<210> SEQ ID NO 1099
<211> LENGTH: 9
<212> TYPE: PRT
<213> ORGANISM: homo sapien

<400> SEQUENCE: 1099

Glu Asp Val Tyr Ser Val Glu Asp Leu
1               5

<210> SEQ ID NO 1100
<211> LENGTH: 9
<212> TYPE: PRT
<213> ORGANISM: homo sapien

```
<400> SEQUENCE: 1100

Leu Thr Ser Gly Lys Ser Thr Ala Ile
1               5

<210> SEQ ID NO 1101
<211> LENGTH: 9
<212> TYPE: PRT
<213> ORGANISM: homo sapien

<400> SEQUENCE: 1101

Ile Pro Gly Ser Ser Ser Lys Trp Glu
1               5

<210> SEQ ID NO 1102
<211> LENGTH: 9
<212> TYPE: PRT
<213> ORGANISM: homo sapien

<400> SEQUENCE: 1102

Ser Asp Glu Ala Gly Asp Glu Gly Leu
1               5

<210> SEQ ID NO 1103
<211> LENGTH: 9
<212> TYPE: PRT
<213> ORGANISM: homo sapien

<400> SEQUENCE: 1103

Gly Ser Glu Ala Pro Glu Arg Pro Val
1               5

<210> SEQ ID NO 1104
<211> LENGTH: 9
<212> TYPE: PRT
<213> ORGANISM: homo sapien

<400> SEQUENCE: 1104

Thr Leu Gln Ala Asp Asp Asp Ser Leu
1               5

<210> SEQ ID NO 1105
<211> LENGTH: 9
<212> TYPE: PRT
<213> ORGANISM: homo sapien

<400> SEQUENCE: 1105

Leu Gln Ala Asp Asp Asp Ser Leu Leu
1               5

<210> SEQ ID NO 1106
<211> LENGTH: 9
<212> TYPE: PRT
<213> ORGANISM: homo sapien

<400> SEQUENCE: 1106

Arg Lys Val Lys Ala Arg Leu Thr Ile
1               5

<210> SEQ ID NO 1107
<211> LENGTH: 9
<212> TYPE: PRT
<213> ORGANISM: homo sapien

<400> SEQUENCE: 1107
```

-continued

Lys Ala Arg Leu Thr Ile Ala Ala Val
1               5

<210> SEQ ID NO 1108
<211> LENGTH: 9
<212> TYPE: PRT
<213> ORGANISM: homo sapien

<400> SEQUENCE: 1108

Ala Ala Val Leu Tyr Leu Leu Phe Met
1               5

<210> SEQ ID NO 1109
<211> LENGTH: 9
<212> TYPE: PRT
<213> ORGANISM: homo sapien

<400> SEQUENCE: 1109

Val Gly Gly Tyr Ile Ala Asn Ser Leu
1               5

<210> SEQ ID NO 1110
<211> LENGTH: 9
<212> TYPE: PRT
<213> ORGANISM: homo sapien

<400> SEQUENCE: 1110

Ala Ile Met Thr Asp Ala Leu His Met
1               5

<210> SEQ ID NO 1111
<211> LENGTH: 9
<212> TYPE: PRT
<213> ORGANISM: homo sapien

<400> SEQUENCE: 1111

Ile Met Thr Asp Ala Leu His Met Leu
1               5

<210> SEQ ID NO 1112
<211> LENGTH: 9
<212> TYPE: PRT
<213> ORGANISM: homo sapien

<400> SEQUENCE: 1112

Asp Ala Leu His Met Leu Thr Asp Leu
1               5

<210> SEQ ID NO 1113
<211> LENGTH: 9
<212> TYPE: PRT
<213> ORGANISM: homo sapien

<400> SEQUENCE: 1113

Leu Thr Asp Leu Ser Ala Ile Ile Leu
1               5

<210> SEQ ID NO 1114
<211> LENGTH: 9
<212> TYPE: PRT
<213> ORGANISM: homo sapien

<400> SEQUENCE: 1114

Phe Gly Phe His Arg Leu Glu Val Leu
1               5

```
<210> SEQ ID NO 1115
<211> LENGTH: 9
<212> TYPE: PRT
<213> ORGANISM: homo sapien

<400> SEQUENCE: 1115

Phe His Arg Leu Glu Val Leu Ser Ala
 1               5

<210> SEQ ID NO 1116
<211> LENGTH: 9
<212> TYPE: PRT
<213> ORGANISM: homo sapien

<400> SEQUENCE: 1116

Leu Val Tyr Ile Leu Met Gly Phe Leu
 1               5

<210> SEQ ID NO 1117
<211> LENGTH: 9
<212> TYPE: PRT
<213> ORGANISM: homo sapien

<400> SEQUENCE: 1117

Val Tyr Ile Leu Met Gly Phe Leu Leu
 1               5

<210> SEQ ID NO 1118
<211> LENGTH: 9
<212> TYPE: PRT
<213> ORGANISM: homo sapien

<400> SEQUENCE: 1118

Ala Val Gly Val Ala Val Asn Val Ile
 1               5

<210> SEQ ID NO 1119
<211> LENGTH: 9
<212> TYPE: PRT
<213> ORGANISM: homo sapien

<400> SEQUENCE: 1119

Val Asn Val Ile Met Gly Phe Leu Leu
 1               5

<210> SEQ ID NO 1120
<211> LENGTH: 9
<212> TYPE: PRT
<213> ORGANISM: homo sapien

<400> SEQUENCE: 1120

Glu Arg Asn His Gly Gln Asp Ser Leu
 1               5

<210> SEQ ID NO 1121
<211> LENGTH: 9
<212> TYPE: PRT
<213> ORGANISM: homo sapien

<400> SEQUENCE: 1121

Val Gln Ser Val Gly Val Leu Ile Ala
 1               5
```

-continued

```
<210> SEQ ID NO 1122
<211> LENGTH: 9
<212> TYPE: PRT
<213> ORGANISM: homo sapien

<400> SEQUENCE: 1122

Ile Arg Phe Lys Pro Glu Tyr Lys Ile
1               5

<210> SEQ ID NO 1123
<211> LENGTH: 9
<212> TYPE: PRT
<213> ORGANISM: homo sapien

<400> SEQUENCE: 1123

Pro Ile Cys Thr Tyr Val Phe Ser Leu
1               5

<210> SEQ ID NO 1124
<211> LENGTH: 9
<212> TYPE: PRT
<213> ORGANISM: homo sapien

<400> SEQUENCE: 1124

Val Phe Ser Leu Leu Val Ala Phe Thr
1               5

<210> SEQ ID NO 1125
<211> LENGTH: 9
<212> TYPE: PRT
<213> ORGANISM: homo sapien

<400> SEQUENCE: 1125

Arg Ile Ile Trp Asp Thr Val Val Ile
1               5

<210> SEQ ID NO 1126
<211> LENGTH: 9
<212> TYPE: PRT
<213> ORGANISM: homo sapien

<400> SEQUENCE: 1126

Val Glu Asp Leu Asn Ile Trp Ser Leu
1               5

<210> SEQ ID NO 1127
<211> LENGTH: 9
<212> TYPE: PRT
<213> ORGANISM: homo sapien

<400> SEQUENCE: 1127

Ser Thr Ala Ile Val His Ile Gln Leu
1               5

<210> SEQ ID NO 1128
<211> LENGTH: 9
<212> TYPE: PRT
<213> ORGANISM: homo sapien

<400> SEQUENCE: 1128

Glu Val Gln Ser Lys Ala Asn His Leu
1               5

<210> SEQ ID NO 1129
<211> LENGTH: 9
```

```
<212> TYPE: PRT
<213> ORGANISM: homo sapien

<400> SEQUENCE: 1129

Gly Met Tyr Arg Cys Thr Ile Gln Leu
 1               5

<210> SEQ ID NO 1130
<211> LENGTH: 9
<212> TYPE: PRT
<213> ORGANISM: homo sapien

<400> SEQUENCE: 1130

Ile Leu Lys Gln Arg Lys Val Lys Ala
 1               5

<210> SEQ ID NO 1131
<211> LENGTH: 9
<212> TYPE: PRT
<213> ORGANISM: homo sapien

<400> SEQUENCE: 1131

Met Leu Arg Lys Asp Asp Ala Pro Leu
 1               5

<210> SEQ ID NO 1132
<211> LENGTH: 9
<212> TYPE: PRT
<213> ORGANISM: homo sapien

<400> SEQUENCE: 1132

Phe Asn Lys Leu Arg Val Val Val Ala
 1               5

<210> SEQ ID NO 1133
<211> LENGTH: 9
<212> TYPE: PRT
<213> ORGANISM: homo sapien

<400> SEQUENCE: 1133

Tyr Ile Lys Glu Ala Leu Met Lys Ile
 1               5

<210> SEQ ID NO 1134
<211> LENGTH: 9
<212> TYPE: PRT
<213> ORGANISM: homo sapien

<400> SEQUENCE: 1134

Glu Val Gln Ser Lys Ala Asn His Leu
 1               5

<210> SEQ ID NO 1135
<211> LENGTH: 9
<212> TYPE: PRT
<213> ORGANISM: homo sapien

<400> SEQUENCE: 1135

Gln Arg Lys Val Lys Ala Arg Leu Thr
 1               5

<210> SEQ ID NO 1136
<211> LENGTH: 9
<212> TYPE: PRT
<213> ORGANISM: homo sapien
```

```
<400> SEQUENCE: 1136

Ile Ile Arg Phe Lys Pro Glu Tyr Lys
1               5

<210> SEQ ID NO 1137
<211> LENGTH: 9
<212> TYPE: PRT
<213> ORGANISM: homo sapien

<400> SEQUENCE: 1137

Ala Trp Lys Arg Leu Lys Ser Met Leu
1               5

<210> SEQ ID NO 1138
<211> LENGTH: 9
<212> TYPE: PRT
<213> ORGANISM: homo sapien

<400> SEQUENCE: 1138

Glu Gly Leu Ser Arg Phe Asn Lys Leu
1               5

<210> SEQ ID NO 1139
<211> LENGTH: 9
<212> TYPE: PRT
<213> ORGANISM: homo sapien

<400> SEQUENCE: 1139

Gln Ser Lys Ala Asn His Leu Leu Leu
1               5

<210> SEQ ID NO 1140
<211> LENGTH: 9
<212> TYPE: PRT
<213> ORGANISM: homo sapien

<400> SEQUENCE: 1140

Ser Leu Lys Val Asp Ser Cys Asp Asn
1               5

<210> SEQ ID NO 1141
<211> LENGTH: 9
<212> TYPE: PRT
<213> ORGANISM: homo sapien

<400> SEQUENCE: 1141

Ser Leu Ala Ile Met Thr Asp Ala Leu
1               5

<210> SEQ ID NO 1142
<211> LENGTH: 9
<212> TYPE: PRT
<213> ORGANISM: homo sapien

<400> SEQUENCE: 1142

Ser Ser Lys Ser Pro Thr Lys Arg Phe
1               5

<210> SEQ ID NO 1143
<211> LENGTH: 9
<212> TYPE: PRT
<213> ORGANISM: homo sapien

<400> SEQUENCE: 1143
```

-continued

Phe Gly Phe His Arg Leu Glu Val Leu
 1               5

<210> SEQ ID NO 1144
<211> LENGTH: 9
<212> TYPE: PRT
<213> ORGANISM: homo sapien

<400> SEQUENCE: 1144

Ser Leu Leu Asp Gln Asp Leu Pro Leu
 1               5

<210> SEQ ID NO 1145
<211> LENGTH: 9
<212> TYPE: PRT
<213> ORGANISM: homo sapien

<400> SEQUENCE: 1145

Asp Leu Pro Leu Thr Asn Ser Gln Leu
 1               5

<210> SEQ ID NO 1146
<211> LENGTH: 9
<212> TYPE: PRT
<213> ORGANISM: homo sapien

<400> SEQUENCE: 1146

Gln Leu Ser Leu Lys Val Asp Ser Cys
 1               5

<210> SEQ ID NO 1147
<211> LENGTH: 9
<212> TYPE: PRT
<213> ORGANISM: homo sapien

<400> SEQUENCE: 1147

Cys Ser Lys Gln Arg Glu Ile Leu Lys
 1               5

<210> SEQ ID NO 1148
<211> LENGTH: 9
<212> TYPE: PRT
<213> ORGANISM: homo sapien

<400> SEQUENCE: 1148

Lys Val Lys Ala Arg Leu Thr Ile Ala
 1               5

<210> SEQ ID NO 1149
<211> LENGTH: 9
<212> TYPE: PRT
<213> ORGANISM: homo sapien

<400> SEQUENCE: 1149

Tyr Leu Leu Phe Met Ile Gly Glu Leu
 1               5

<210> SEQ ID NO 1150
<211> LENGTH: 9
<212> TYPE: PRT
<213> ORGANISM: homo sapien

<400> SEQUENCE: 1150

Ile Leu Thr Leu Leu Ala Leu Trp Leu

-continued

```
<210> SEQ ID NO 1151
<211> LENGTH: 9
<212> TYPE: PRT
<213> ORGANISM: homo sapien

<400> SEQUENCE: 1151

Val Leu Ser Ala Met Ile Ser Val Leu
1               5

<210> SEQ ID NO 1152
<211> LENGTH: 9
<212> TYPE: PRT
<213> ORGANISM: homo sapien

<400> SEQUENCE: 1152

Lys Pro Glu Tyr Lys Ile Ala Asp Pro
1               5

<210> SEQ ID NO 1153
<211> LENGTH: 9
<212> TYPE: PRT
<213> ORGANISM: homo sapien

<400> SEQUENCE: 1153

Trp Lys Arg Leu Lys Ser Met Leu Arg
1               5

<210> SEQ ID NO 1154
<211> LENGTH: 9
<212> TYPE: PRT
<213> ORGANISM: homo sapien

<400> SEQUENCE: 1154

Glu Ala Pro Glu Arg Pro Val Asn Gly
1               5

<210> SEQ ID NO 1155
<211> LENGTH: 9
<212> TYPE: PRT
<213> ORGANISM: homo sapien

<400> SEQUENCE: 1155

Asp Asn Cys Ser Lys Gln Arg Glu Ile
1               5

<210> SEQ ID NO 1156
<211> LENGTH: 9
<212> TYPE: PRT
<213> ORGANISM: homo sapien

<400> SEQUENCE: 1156

Asp Leu Ser Ala Ile Ile Leu Thr Leu
1               5

<210> SEQ ID NO 1157
<211> LENGTH: 9
<212> TYPE: PRT
<213> ORGANISM: homo sapien

<400> SEQUENCE: 1157

Ser Leu Ala Val Arg Ala Ala Phe Val
1               5
```

```
<210> SEQ ID NO 1158
<211> LENGTH: 9
<212> TYPE: PRT
<213> ORGANISM: homo sapien

<400> SEQUENCE: 1158

Asp Leu Val Gln Ser Val Gly Val Leu
1               5

<210> SEQ ID NO 1159
<211> LENGTH: 9
<212> TYPE: PRT
<213> ORGANISM: homo sapien

<400> SEQUENCE: 1159

Ile Leu Glu Gly Val Pro Ser His Leu
1               5

<210> SEQ ID NO 1160
<211> LENGTH: 9
<212> TYPE: PRT
<213> ORGANISM: homo sapien

<400> SEQUENCE: 1160

Glu Ala Leu Met Lys Ile Glu Asp Val
1               5

<210> SEQ ID NO 1161
<211> LENGTH: 9
<212> TYPE: PRT
<213> ORGANISM: homo sapien

<400> SEQUENCE: 1161

Leu Thr Ser Gly Lys Ser Thr Ala Ile
1               5

<210> SEQ ID NO 1162
<211> LENGTH: 9
<212> TYPE: PRT
<213> ORGANISM: homo sapien

<400> SEQUENCE: 1162

Arg Leu Lys Ser Met Leu Arg Lys Asp
1               5

<210> SEQ ID NO 1163
<211> LENGTH: 9
<212> TYPE: PRT
<213> ORGANISM: homo sapien

<400> SEQUENCE: 1163

Leu Arg Lys Asp Asp Ala Pro Leu Phe
1               5

<210> SEQ ID NO 1164
<211> LENGTH: 9
<212> TYPE: PRT
<213> ORGANISM: homo sapien

<400> SEQUENCE: 1164

Thr Leu Gln Ala Asp Asp Asp Ser Leu
1               5

<210> SEQ ID NO 1165
```

```
<211> LENGTH: 9
<212> TYPE: PRT
<213> ORGANISM: homo sapien

<400> SEQUENCE: 1165

Pro Leu Thr Asn Ser Gln Leu Ser Leu
 1               5

<210> SEQ ID NO 1166
<211> LENGTH: 9
<212> TYPE: PRT
<213> ORGANISM: homo sapien

<400> SEQUENCE: 1166

Lys Gln Arg Lys Val Lys Ala Arg Leu
 1               5

<210> SEQ ID NO 1167
<211> LENGTH: 9
<212> TYPE: PRT
<213> ORGANISM: homo sapien

<400> SEQUENCE: 1167

Ala Ile Ile Leu Thr Leu Leu Ala Leu
 1               5

<210> SEQ ID NO 1168
<211> LENGTH: 9
<212> TYPE: PRT
<213> ORGANISM: homo sapien

<400> SEQUENCE: 1168

Trp Leu Ser Ser Lys Ser Pro Thr Lys
 1               5

<210> SEQ ID NO 1169
<211> LENGTH: 9
<212> TYPE: PRT
<213> ORGANISM: homo sapien

<400> SEQUENCE: 1169

Lys Ser Pro Thr Lys Arg Phe Thr Phe
 1               5

<210> SEQ ID NO 1170
<211> LENGTH: 9
<212> TYPE: PRT
<213> ORGANISM: homo sapien

<400> SEQUENCE: 1170

Ser Pro Thr Lys Arg Phe Thr Phe Gly
 1               5

<210> SEQ ID NO 1171
<211> LENGTH: 9
<212> TYPE: PRT
<213> ORGANISM: homo sapien

<400> SEQUENCE: 1171

Pro Thr Lys Arg Phe Thr Phe Gly Phe
 1               5

<210> SEQ ID NO 1172
<211> LENGTH: 9
<212> TYPE: PRT
```

-continued

<213> ORGANISM: homo sapien

<400> SEQUENCE: 1172

Pro Ile Cys Thr Tyr Val Phe Ser Leu
1               5

<210> SEQ ID NO 1173
<211> LENGTH: 9
<212> TYPE: PRT
<213> ORGANISM: homo sapien

<400> SEQUENCE: 1173

Ser Leu Leu Val Ala Phe Thr Thr Phe
1               5

<210> SEQ ID NO 1174
<211> LENGTH: 9
<212> TYPE: PRT
<213> ORGANISM: homo sapien

<400> SEQUENCE: 1174

Gly Ala Trp Lys Arg Leu Lys Ser Met
1               5

<210> SEQ ID NO 1175
<211> LENGTH: 9
<212> TYPE: PRT
<213> ORGANISM: homo sapien

<400> SEQUENCE: 1175

Lys Leu Arg Val Val Ala Asp Asp
1               5

<210> SEQ ID NO 1176
<211> LENGTH: 9
<212> TYPE: PRT
<213> ORGANISM: homo sapien

<400> SEQUENCE: 1176

Thr Ile Ala Ala Val Leu Tyr Leu Leu
1               5

<210> SEQ ID NO 1177
<211> LENGTH: 9
<212> TYPE: PRT
<213> ORGANISM: homo sapien

<400> SEQUENCE: 1177

Asp Ala Leu His Met Leu Thr Asp Leu
1               5

<210> SEQ ID NO 1178
<211> LENGTH: 9
<212> TYPE: PRT
<213> ORGANISM: homo sapien

<400> SEQUENCE: 1178

Glu Ala Val Gln Arg Thr Ile His Met
1               5

<210> SEQ ID NO 1179
<211> LENGTH: 9
<212> TYPE: PRT
<213> ORGANISM: homo sapien -continued

```
<400> SEQUENCE: 1179

Glu Asp Val Tyr Ser Val Glu Asp Leu
1               5

<210> SEQ ID NO 1180
<211> LENGTH: 9
<212> TYPE: PRT
<213> ORGANISM: homo sapien

<400> SEQUENCE: 1180

Ser Met Leu Arg Lys Asp Asp Ala Pro
1               5

<210> SEQ ID NO 1181
<211> LENGTH: 9
<212> TYPE: PRT
<213> ORGANISM: homo sapien

<400> SEQUENCE: 1181

Leu Lys Gln Arg Lys Val Lys Ala Arg
1               5

<210> SEQ ID NO 1182
<211> LENGTH: 9
<212> TYPE: PRT
<213> ORGANISM: homo sapien

<400> SEQUENCE: 1182

Lys Ala Arg Leu Thr Ile Ala Ala Val
1               5

<210> SEQ ID NO 1183
<211> LENGTH: 9
<212> TYPE: PRT
<213> ORGANISM: homo sapien

<400> SEQUENCE: 1183

Arg Leu Glu Val Leu Ser Ala Met Ile
1               5

<210> SEQ ID NO 1184
<211> LENGTH: 9
<212> TYPE: PRT
<213> ORGANISM: homo sapien

<400> SEQUENCE: 1184

Ile Ser Val Leu Leu Val Tyr Ile Leu
1               5

<210> SEQ ID NO 1185
<211> LENGTH: 9
<212> TYPE: PRT
<213> ORGANISM: homo sapien

<400> SEQUENCE: 1185

Leu Leu Val Tyr Ile Leu Met Gly Phe
1               5

<210> SEQ ID NO 1186
<211> LENGTH: 9
<212> TYPE: PRT
<213> ORGANISM: homo sapien

<400> SEQUENCE: 1186
```

Glu Ile Asn Gly Asp Ile Met Leu Ile
1               5

<210> SEQ ID NO 1187
<211> LENGTH: 9
<212> TYPE: PRT
<213> ORGANISM: homo sapien

<400> SEQUENCE: 1187

Ser Gly Cys Glu Arg Asn His Gly Gln
1               5

<210> SEQ ID NO 1188
<211> LENGTH: 9
<212> TYPE: PRT
<213> ORGANISM: homo sapien

<400> SEQUENCE: 1188

Val Arg Ala Ala Phe Val His Ala Leu
1               5

<210> SEQ ID NO 1189
<211> LENGTH: 9
<212> TYPE: PRT
<213> ORGANISM: homo sapien

<400> SEQUENCE: 1189

Ile Ile Trp Asp Thr Val Val Ile Ile
1               5

<210> SEQ ID NO 1190
<211> LENGTH: 9
<212> TYPE: PRT
<213> ORGANISM: homo sapien

<400> SEQUENCE: 1190

Val Glu Asp Leu Asn Ile Trp Ser Leu
1               5

<210> SEQ ID NO 1191
<211> LENGTH: 9
<212> TYPE: PRT
<213> ORGANISM: homo sapien

<400> SEQUENCE: 1191

Ser Ser Lys Trp Glu Glu Val Gln Ser
1               5

<210> SEQ ID NO 1192
<211> LENGTH: 9
<212> TYPE: PRT
<213> ORGANISM: homo sapien

<400> SEQUENCE: 1192

Ile Leu Glu Gly Val Pro Ser His Leu
1               5

<210> SEQ ID NO 1193
<211> LENGTH: 9
<212> TYPE: PRT
<213> ORGANISM: homo sapien

<400> SEQUENCE: 1193

Ala Gly Ser Gly Ala Trp Lys Arg Leu
1               5

```
<210> SEQ ID NO 1194
<211> LENGTH: 9
<212> TYPE: PRT
<213> ORGANISM: homo sapien

<400> SEQUENCE: 1194

Lys Gln Arg Lys Val Lys Ala Arg Leu
 1               5

<210> SEQ ID NO 1195
<211> LENGTH: 9
<212> TYPE: PRT
<213> ORGANISM: homo sapien

<400> SEQUENCE: 1195

Val Leu Ser Ala Met Ile Ser Val Leu
 1               5

<210> SEQ ID NO 1196
<211> LENGTH: 9
<212> TYPE: PRT
<213> ORGANISM: homo sapien

<400> SEQUENCE: 1196

Val His Ala Leu Gly Asp Leu Val Gln
 1               5

<210> SEQ ID NO 1197
<211> LENGTH: 9
<212> TYPE: PRT
<213> ORGANISM: homo sapien

<400> SEQUENCE: 1197

Asp Leu Val Gln Ser Val Gly Val Leu
 1               5

<210> SEQ ID NO 1198
<211> LENGTH: 9
<212> TYPE: PRT
<213> ORGANISM: homo sapien

<400> SEQUENCE: 1198

Pro Val Asn Gly Ala His Pro Thr Leu
 1               5

<210> SEQ ID NO 1199
<211> LENGTH: 9
<212> TYPE: PRT
<213> ORGANISM: homo sapien

<400> SEQUENCE: 1199

Asn Cys Ser Lys Gln Arg Glu Ile Leu
 1               5

<210> SEQ ID NO 1200
<211> LENGTH: 9
<212> TYPE: PRT
<213> ORGANISM: homo sapien

<400> SEQUENCE: 1200

Tyr Leu Leu Phe Met Ile Gly Glu Leu
 1               5
```

```
<210> SEQ ID NO 1201
<211> LENGTH: 9
<212> TYPE: PRT
<213> ORGANISM: homo sapien

<400> SEQUENCE: 1201

Ile Met Thr Asp Ala Leu His Met Leu
1               5

<210> SEQ ID NO 1202
<211> LENGTH: 9
<212> TYPE: PRT
<213> ORGANISM: homo sapien

<400> SEQUENCE: 1202

Asp Leu Ser Ala Ile Ile Leu Thr Leu
1               5

<210> SEQ ID NO 1203
<211> LENGTH: 9
<212> TYPE: PRT
<213> ORGANISM: homo sapien

<400> SEQUENCE: 1203

Arg Phe Thr Phe Gly Phe His Arg Leu
1               5

<210> SEQ ID NO 1204
<211> LENGTH: 9
<212> TYPE: PRT
<213> ORGANISM: homo sapien

<400> SEQUENCE: 1204

Leu Ser Ala Met Ile Ser Val Leu Leu
1               5

<210> SEQ ID NO 1205
<211> LENGTH: 9
<212> TYPE: PRT
<213> ORGANISM: homo sapien

<400> SEQUENCE: 1205

Ile Ser Val Leu Leu Val Tyr Ile Leu
1               5

<210> SEQ ID NO 1206
<211> LENGTH: 9
<212> TYPE: PRT
<213> ORGANISM: homo sapien

<400> SEQUENCE: 1206

Val Arg Ala Ala Phe Val His Ala Leu
1               5

<210> SEQ ID NO 1207
<211> LENGTH: 9
<212> TYPE: PRT
<213> ORGANISM: homo sapien

<400> SEQUENCE: 1207

Ile Trp Asp Thr Val Val Ile Ile Leu
1               5

<210> SEQ ID NO 1208
<211> LENGTH: 9
```

```
<212> TYPE: PRT
<213> ORGANISM: homo sapien

<400> SEQUENCE: 1208

Val His Ile Gln Leu Ile Pro Gly Ser
 1               5

<210> SEQ ID NO 1209
<211> LENGTH: 9
<212> TYPE: PRT
<213> ORGANISM: homo sapien

<400> SEQUENCE: 1209

Arg Lys Asp Asp Ala Pro Leu Phe Leu
 1               5

<210> SEQ ID NO 1210
<211> LENGTH: 9
<212> TYPE: PRT
<213> ORGANISM: homo sapien

<400> SEQUENCE: 1210

Ser Asp Glu Ala Gly Asp Glu Gly Leu
 1               5

<210> SEQ ID NO 1211
<211> LENGTH: 9
<212> TYPE: PRT
<213> ORGANISM: homo sapien

<400> SEQUENCE: 1211

Leu Gln Ala Asp Asp Ser Leu Leu
 1               5

<210> SEQ ID NO 1212
<211> LENGTH: 9
<212> TYPE: PRT
<213> ORGANISM: homo sapien

<400> SEQUENCE: 1212

Ala Arg Leu Thr Ile Ala Ala Val Leu
 1               5

<210> SEQ ID NO 1213
<211> LENGTH: 9
<212> TYPE: PRT
<213> ORGANISM: homo sapien

<400> SEQUENCE: 1213

Thr Ile Ala Ala Val Leu Tyr Leu Leu
 1               5

<210> SEQ ID NO 1214
<211> LENGTH: 9
<212> TYPE: PRT
<213> ORGANISM: homo sapien

<400> SEQUENCE: 1214

Ser Leu Ala Ile Met Thr Asp Ala Leu
 1               5

<210> SEQ ID NO 1215
<211> LENGTH: 9
<212> TYPE: PRT
<213> ORGANISM: homo sapien
```

```
<400> SEQUENCE: 1215

Ile Leu Thr Leu Leu Ala Leu Trp Leu
1               5

<210> SEQ ID NO 1216
<211> LENGTH: 9
<212> TYPE: PRT
<213> ORGANISM: homo sapien

<400> SEQUENCE: 1216

Phe Gly Phe His Arg Leu Glu Val Leu
1               5

<210> SEQ ID NO 1217
<211> LENGTH: 9
<212> TYPE: PRT
<213> ORGANISM: homo sapien

<400> SEQUENCE: 1217

Ile His Met Asn Tyr Glu Ile Asn Gly
1               5

<210> SEQ ID NO 1218
<211> LENGTH: 9
<212> TYPE: PRT
<213> ORGANISM: homo sapien

<400> SEQUENCE: 1218

Tyr Glu Ile Asn Gly Asp Ile Met Leu
1               5

<210> SEQ ID NO 1219
<211> LENGTH: 9
<212> TYPE: PRT
<213> ORGANISM: homo sapien

<400> SEQUENCE: 1219

Ala Val Asn Val Ile Met Gly Phe Leu
1               5

<210> SEQ ID NO 1220
<211> LENGTH: 9
<212> TYPE: PRT
<213> ORGANISM: homo sapien

<400> SEQUENCE: 1220

Ser His Ser His Ser Leu Pro Ser Asn
1               5

<210> SEQ ID NO 1221
<211> LENGTH: 9
<212> TYPE: PRT
<213> ORGANISM: homo sapien

<400> SEQUENCE: 1221

Ser His Ser Leu Pro Ser Asn Ser Pro
1               5

<210> SEQ ID NO 1222
<211> LENGTH: 9
<212> TYPE: PRT
<213> ORGANISM: homo sapien

<400> SEQUENCE: 1222
```

```
Glu Arg Asn His Gly Gln Asp Ser Leu
  1               5

<210> SEQ ID NO 1223
<211> LENGTH: 9
<212> TYPE: PRT
<213> ORGANISM: homo sapien

<400> SEQUENCE: 1223

Asn His Gly Gln Asp Ser Leu Ala Val
  1               5

<210> SEQ ID NO 1224
<211> LENGTH: 9
<212> TYPE: PRT
<213> ORGANISM: homo sapien

<400> SEQUENCE: 1224

Ile Cys Thr Tyr Val Phe Ser Leu Leu
  1               5

<210> SEQ ID NO 1225
<211> LENGTH: 9
<212> TYPE: PRT
<213> ORGANISM: homo sapien

<400> SEQUENCE: 1225

Asn Val Asp Tyr Ile Lys Glu Ala Leu
  1               5

<210> SEQ ID NO 1226
<211> LENGTH: 9
<212> TYPE: PRT
<213> ORGANISM: homo sapien

<400> SEQUENCE: 1226

Glu Asp Val Tyr Ser Val Glu Asp Leu
  1               5

<210> SEQ ID NO 1227
<211> LENGTH: 9
<212> TYPE: PRT
<213> ORGANISM: homo sapien

<400> SEQUENCE: 1227

Val Glu Asp Leu Asn Ile Trp Ser Leu
  1               5

<210> SEQ ID NO 1228
<211> LENGTH: 9
<212> TYPE: PRT
<213> ORGANISM: homo sapien

<400> SEQUENCE: 1228

Val Gln Ser Lys Ala Asn His Leu Leu
  1               5

<210> SEQ ID NO 1229
<211> LENGTH: 9
<212> TYPE: PRT
<213> ORGANISM: homo sapien

<400> SEQUENCE: 1229

Ala Trp Lys Arg Leu Lys Ser Met Leu
```

```
                1               5

<210> SEQ ID NO 1230
<211> LENGTH: 9
<212> TYPE: PRT
<213> ORGANISM: homo sapien

<400> SEQUENCE: 1230

Met Leu Arg Lys Asp Asp Ala Pro Leu
 1               5

<210> SEQ ID NO 1231
<211> LENGTH: 9
<212> TYPE: PRT
<213> ORGANISM: homo sapien

<400> SEQUENCE: 1231

Glu Gly Leu Ser Arg Phe Asn Lys Leu
 1               5

<210> SEQ ID NO 1232
<211> LENGTH: 9
<212> TYPE: PRT
<213> ORGANISM: homo sapien

<400> SEQUENCE: 1232

Thr Leu Gln Ala Asp Asp Asp Ser Leu
 1               5

<210> SEQ ID NO 1233
<211> LENGTH: 9
<212> TYPE: PRT
<213> ORGANISM: homo sapien

<400> SEQUENCE: 1233

Asp Asp Ser Leu Leu Asp Gln Asp Leu
 1               5

<210> SEQ ID NO 1234
<211> LENGTH: 9
<212> TYPE: PRT
<213> ORGANISM: homo sapien

<400> SEQUENCE: 1234

Ser Leu Leu Asp Gln Asp Leu Pro Leu
 1               5

<210> SEQ ID NO 1235
<211> LENGTH: 9
<212> TYPE: PRT
<213> ORGANISM: homo sapien

<400> SEQUENCE: 1235

Leu Thr Ile Ala Ala Val Leu Tyr Leu
 1               5

<210> SEQ ID NO 1236
<211> LENGTH: 9
<212> TYPE: PRT
<213> ORGANISM: homo sapien

<400> SEQUENCE: 1236

Leu Ser Ala Ile Ile Leu Thr Leu Leu
 1               5
```

```
<210> SEQ ID NO 1237
<211> LENGTH: 9
<212> TYPE: PRT
<213> ORGANISM: homo sapien

<400> SEQUENCE: 1237

Ala Ile Ile Leu Thr Leu Leu Ala Leu
1               5

<210> SEQ ID NO 1238
<211> LENGTH: 9
<212> TYPE: PRT
<213> ORGANISM: homo sapien

<400> SEQUENCE: 1238

Phe His Arg Leu Glu Val Leu Ser Ala
1               5

<210> SEQ ID NO 1239
<211> LENGTH: 9
<212> TYPE: PRT
<213> ORGANISM: homo sapien

<400> SEQUENCE: 1239

Leu Val Tyr Ile Leu Met Gly Phe Leu
1               5

<210> SEQ ID NO 1240
<211> LENGTH: 9
<212> TYPE: PRT
<213> ORGANISM: homo sapien

<400> SEQUENCE: 1240

Gly His Arg His Ser His Ser His Ser
1               5

<210> SEQ ID NO 1241
<211> LENGTH: 9
<212> TYPE: PRT
<213> ORGANISM: homo sapien

<400> SEQUENCE: 1241

Arg His Ser His Ser His Ser Leu Pro
1               5

<210> SEQ ID NO 1242
<211> LENGTH: 9
<212> TYPE: PRT
<213> ORGANISM: homo sapien

<400> SEQUENCE: 1242

Pro Ile Cys Thr Tyr Val Phe Ser Leu
1               5

<210> SEQ ID NO 1243
<211> LENGTH: 9
<212> TYPE: PRT
<213> ORGANISM: homo sapien

<400> SEQUENCE: 1243

Ser Thr Ala Ile Val His Ile Gln Leu
1               5

<210> SEQ ID NO 1244
```

```
<211> LENGTH: 9
<212> TYPE: PRT
<213> ORGANISM: homo sapien

<400> SEQUENCE: 1244

Glu Val Gln Ser Lys Ala Asn His Leu
 1               5

<210> SEQ ID NO 1245
<211> LENGTH: 9
<212> TYPE: PRT
<213> ORGANISM: homo sapien

<400> SEQUENCE: 1245

Gln Ser Lys Ala Asn His Leu Leu Leu
 1               5

<210> SEQ ID NO 1246
<211> LENGTH: 9
<212> TYPE: PRT
<213> ORGANISM: homo sapien

<400> SEQUENCE: 1246

Gly Met Tyr Arg Cys Thr Ile Gln Leu
 1               5

<210> SEQ ID NO 1247
<211> LENGTH: 9
<212> TYPE: PRT
<213> ORGANISM: homo sapien

<400> SEQUENCE: 1247

Ala Gly Asp Glu Gly Leu Ser Arg Phe
 1               5

<210> SEQ ID NO 1248
<211> LENGTH: 9
<212> TYPE: PRT
<213> ORGANISM: homo sapien

<400> SEQUENCE: 1248

Ala His Pro Thr Leu Gln Ala Asp Asp
 1               5

<210> SEQ ID NO 1249
<211> LENGTH: 9
<212> TYPE: PRT
<213> ORGANISM: homo sapien

<400> SEQUENCE: 1249

Asp Leu Pro Leu Thr Asn Ser Gln Leu
 1               5

<210> SEQ ID NO 1250
<211> LENGTH: 9
<212> TYPE: PRT
<213> ORGANISM: homo sapien

<400> SEQUENCE: 1250

Pro Leu Thr Asn Ser Gln Leu Ser Leu
 1               5

<210> SEQ ID NO 1251
<211> LENGTH: 9
<212> TYPE: PRT
```

<213> ORGANISM: homo sapien

<400> SEQUENCE: 1251

Ile Ala Ala Val Leu Tyr Leu Leu Phe
1               5

<210> SEQ ID NO 1252
<211> LENGTH: 9
<212> TYPE: PRT
<213> ORGANISM: homo sapien

<400> SEQUENCE: 1252

Val Gly Gly Tyr Ile Ala Asn Ser Leu
1               5

<210> SEQ ID NO 1253
<211> LENGTH: 9
<212> TYPE: PRT
<213> ORGANISM: homo sapien

<400> SEQUENCE: 1253

Asp Ala Leu His Met Leu Thr Asp Leu
1               5

<210> SEQ ID NO 1254
<211> LENGTH: 9
<212> TYPE: PRT
<213> ORGANISM: homo sapien

<400> SEQUENCE: 1254

Leu His Met Leu Thr Asp Leu Ser Ala
1               5

<210> SEQ ID NO 1255
<211> LENGTH: 9
<212> TYPE: PRT
<213> ORGANISM: homo sapien

<400> SEQUENCE: 1255

Leu Thr Asp Leu Ser Ala Ile Ile Leu
1               5

<210> SEQ ID NO 1256
<211> LENGTH: 9
<212> TYPE: PRT
<213> ORGANISM: homo sapien

<400> SEQUENCE: 1256

Val Tyr Ile Leu Met Gly Phe Leu Leu
1               5

<210> SEQ ID NO 1257
<211> LENGTH: 9
<212> TYPE: PRT
<213> ORGANISM: homo sapien

<400> SEQUENCE: 1257

Val Asn Val Ile Met Gly Phe Leu Leu
1               5

<210> SEQ ID NO 1258
<211> LENGTH: 9
<212> TYPE: PRT
<213> ORGANISM: homo sapien

```
<400> SEQUENCE: 1258

His Arg His Ser His Ser His Ser Leu
 1               5

<210> SEQ ID NO 1259
<211> LENGTH: 9
<212> TYPE: PRT
<213> ORGANISM: homo sapien

<400> SEQUENCE: 1259

Ala Phe Val His Ala Leu Gly Asp Leu
 1               5

<210> SEQ ID NO 1260
<211> LENGTH: 9
<212> TYPE: PRT
<213> ORGANISM: homo sapien

<400> SEQUENCE: 1260

Leu Ile Ala Ala Tyr Ile Ile Arg Phe
 1               5

<210> SEQ ID NO 1261
<211> LENGTH: 9
<212> TYPE: PRT
<213> ORGANISM: homo sapien

<400> SEQUENCE: 1261

Tyr Val Phe Ser Leu Leu Val Ala Phe
 1               5

<210> SEQ ID NO 1262
<211> LENGTH: 9
<212> TYPE: PRT
<213> ORGANISM: homo sapien

<400> SEQUENCE: 1262

Ser His Leu Asn Val Asp Tyr Ile Lys
 1               5

<210> SEQ ID NO 1263
<211> LENGTH: 9
<212> TYPE: PRT
<213> ORGANISM: homo sapien

<400> SEQUENCE: 1263

Asn His Leu Leu Leu Asn Thr Phe Gly
 1               5

<210> SEQ ID NO 1264
<211> LENGTH: 9
<212> TYPE: PRT
<213> ORGANISM: homo sapien

<400> SEQUENCE: 1264

Ser Ser Lys Ser Pro Thr Lys Arg Phe
 1               5

<210> SEQ ID NO 1265
<211> LENGTH: 9
<212> TYPE: PRT
<213> ORGANISM: homo sapien

<400> SEQUENCE: 1265
```

```
Gly Ala Trp Lys Arg Leu Lys Ser Met
1               5
```

<210> SEQ ID NO 1266
<211> LENGTH: 9
<212> TYPE: PRT
<213> ORGANISM: homo sapien

<400> SEQUENCE: 1266

```
Leu Arg Lys Asp Asp Ala Pro Leu Phe
1               5
```

<210> SEQ ID NO 1267
<211> LENGTH: 9
<212> TYPE: PRT
<213> ORGANISM: homo sapien

<400> SEQUENCE: 1267

```
Tyr Ile Ala Asn Ser Leu Ala Ile Met
1               5
```

<210> SEQ ID NO 1268
<211> LENGTH: 9
<212> TYPE: PRT
<213> ORGANISM: homo sapien

<400> SEQUENCE: 1268

```
Lys Ser Pro Thr Lys Arg Phe Thr Phe
1               5
```

<210> SEQ ID NO 1269
<211> LENGTH: 9
<212> TYPE: PRT
<213> ORGANISM: homo sapien

<400> SEQUENCE: 1269

```
His Arg Leu Glu Val Leu Ser Ala Met
1               5
```

<210> SEQ ID NO 1270
<211> LENGTH: 9
<212> TYPE: PRT
<213> ORGANISM: homo sapien

<400> SEQUENCE: 1270

```
Glu Ala Val Gln Arg Thr Ile His Met
1               5
```

<210> SEQ ID NO 1271
<211> LENGTH: 9
<212> TYPE: PRT
<213> ORGANISM: homo sapien

<400> SEQUENCE: 1271

```
Asn Tyr Glu Ile Asn Gly Asp Ile Met
1               5
```

<210> SEQ ID NO 1272
<211> LENGTH: 9
<212> TYPE: PRT
<213> ORGANISM: homo sapien

<400> SEQUENCE: 1272

```
Val Gly Val Ala Val Asn Val Ile Met
1               5
```

<210> SEQ ID NO 1273
<211> LENGTH: 9
<212> TYPE: PRT
<213> ORGANISM: homo sapien

<400> SEQUENCE: 1273

Asp Ser Leu Ala Val Arg Ala Ala Phe
1               5

<210> SEQ ID NO 1274
<211> LENGTH: 9
<212> TYPE: PRT
<213> ORGANISM: homo sapien

<400> SEQUENCE: 1274

Ala Asp Pro Ile Cys Thr Tyr Val Phe
1               5

<210> SEQ ID NO 1275
<211> LENGTH: 9
<212> TYPE: PRT
<213> ORGANISM: homo sapien

<400> SEQUENCE: 1275

Ser Leu Leu Val Ala Phe Thr Thr Phe
1               5

<210> SEQ ID NO 1276
<211> LENGTH: 9
<212> TYPE: PRT
<213> ORGANISM: homo sapien

<400> SEQUENCE: 1276

Leu Phe Leu Asn Asp Thr Ser Ala Phe
1               5

<210> SEQ ID NO 1277
<211> LENGTH: 9
<212> TYPE: PRT
<213> ORGANISM: homo sapien

<400> SEQUENCE: 1277

Ser Glu Ala Pro Glu Arg Pro Val Asn
1               5

<210> SEQ ID NO 1278
<211> LENGTH: 9
<212> TYPE: PRT
<213> ORGANISM: homo sapien

<400> SEQUENCE: 1278

Thr Ala Ala Val Gly Val Ala Val Asn
1               5

<210> SEQ ID NO 1279
<211> LENGTH: 9
<212> TYPE: PRT
<213> ORGANISM: homo sapien

<400> SEQUENCE: 1279

Val Ala Val Asn Val Ile Met Gly Phe
1               5

-continued

```
<210> SEQ ID NO 1280
<211> LENGTH: 9
<212> TYPE: PRT
<213> ORGANISM: homo sapien

<400> SEQUENCE: 1280

Ala Asn His Leu Leu Leu Asn Thr Phe
 1               5

<210> SEQ ID NO 1281
<211> LENGTH: 9
<212> TYPE: PRT
<213> ORGANISM: homo sapien

<400> SEQUENCE: 1281

His Leu Leu Leu Asn Thr Phe Gly Met
 1               5

<210> SEQ ID NO 1282
<211> LENGTH: 9
<212> TYPE: PRT
<213> ORGANISM: homo sapien

<400> SEQUENCE: 1282

Lys Arg Leu Lys Ser Met Leu Arg Lys
 1               5

<210> SEQ ID NO 1283
<211> LENGTH: 9
<212> TYPE: PRT
<213> ORGANISM: homo sapien

<400> SEQUENCE: 1283

Ala Arg Leu Thr Ile Ala Ala Val Leu
 1               5

<210> SEQ ID NO 1284
<211> LENGTH: 9
<212> TYPE: PRT
<213> ORGANISM: homo sapien

<400> SEQUENCE: 1284

Ile Arg Phe Lys Pro Glu Tyr Lys Ile
 1               5

<210> SEQ ID NO 1285
<211> LENGTH: 9
<212> TYPE: PRT
<213> ORGANISM: homo sapien

<400> SEQUENCE: 1285

Lys Arg Phe Thr Phe Gly Phe His Arg
 1               5

<210> SEQ ID NO 1286
<211> LENGTH: 9
<212> TYPE: PRT
<213> ORGANISM: homo sapien

<400> SEQUENCE: 1286

Glu Arg Asn His Gly Gln Asp Ser Leu
 1               5

<210> SEQ ID NO 1287
<211> LENGTH: 9
```

```
<212> TYPE: PRT
<213> ORGANISM: homo sapien

<400> SEQUENCE: 1287

Gln Arg Glu Ile Leu Lys Gln Arg Lys
 1               5

<210> SEQ ID NO 1288
<211> LENGTH: 9
<212> TYPE: PRT
<213> ORGANISM: homo sapien

<400> SEQUENCE: 1288

His Arg Leu Glu Val Leu Ser Ala Met
 1               5

<210> SEQ ID NO 1289
<211> LENGTH: 9
<212> TYPE: PRT
<213> ORGANISM: homo sapien

<400> SEQUENCE: 1289

Leu Arg Lys Asp Asp Ala Pro Leu Phe
 1               5

<210> SEQ ID NO 1290
<211> LENGTH: 9
<212> TYPE: PRT
<213> ORGANISM: homo sapien

<400> SEQUENCE: 1290

His Arg His Ser His Ser His Ser Leu
 1               5

<210> SEQ ID NO 1291
<211> LENGTH: 9
<212> TYPE: PRT
<213> ORGANISM: homo sapien

<400> SEQUENCE: 1291

Val Arg Ala Ala Phe Val His Ala Leu
 1               5

<210> SEQ ID NO 1292
<211> LENGTH: 9
<212> TYPE: PRT
<213> ORGANISM: homo sapien

<400> SEQUENCE: 1292

Lys Gln Arg Lys Val Lys Ala Arg Leu
 1               5

<210> SEQ ID NO 1293
<211> LENGTH: 9
<212> TYPE: PRT
<213> ORGANISM: homo sapien

<400> SEQUENCE: 1293

Ala Gly Asp Glu Gly Leu Ser Arg Phe
 1               5

<210> SEQ ID NO 1294
<211> LENGTH: 9
<212> TYPE: PRT
<213> ORGANISM: homo sapien
```

```
<400> SEQUENCE: 1294

Arg Phe Thr Phe Gly Phe His Arg Leu
 1               5

<210> SEQ ID NO 1295
<211> LENGTH: 9
<212> TYPE: PRT
<213> ORGANISM: homo sapien

<400> SEQUENCE: 1295

Gln Leu Ile Pro Gly Ser Ser Ser Lys
 1               5

<210> SEQ ID NO 1296
<211> LENGTH: 9
<212> TYPE: PRT
<213> ORGANISM: homo sapien

<400> SEQUENCE: 1296

Cys Thr Ile Gln Leu Gln Ser Tyr Arg
 1               5

<210> SEQ ID NO 1297
<211> LENGTH: 9
<212> TYPE: PRT
<213> ORGANISM: homo sapien

<400> SEQUENCE: 1297

Leu Ser Ser Lys Ser Pro Thr Lys Arg
 1               5

<210> SEQ ID NO 1298
<211> LENGTH: 9
<212> TYPE: PRT
<213> ORGANISM: homo sapien

<400> SEQUENCE: 1298

Gly Phe Leu Leu Asn Gln Ser Gly His
 1               5

<210> SEQ ID NO 1299
<211> LENGTH: 9
<212> TYPE: PRT
<213> ORGANISM: homo sapien

<400> SEQUENCE: 1299

Ile Ile Leu Glu Gly Val Pro Ser His
 1               5

<210> SEQ ID NO 1300
<211> LENGTH: 9
<212> TYPE: PRT
<213> ORGANISM: homo sapien

<400> SEQUENCE: 1300

Asp Tyr Ile Lys Glu Ala Leu Met Lys
 1               5

<210> SEQ ID NO 1301
<211> LENGTH: 9
<212> TYPE: PRT
<213> ORGANISM: homo sapien

<400> SEQUENCE: 1301
```

-continued

Gly Met Tyr Arg Cys Thr Ile Gln Leu
1               5

<210> SEQ ID NO 1302
<211> LENGTH: 9
<212> TYPE: PRT
<213> ORGANISM: homo sapien

<400> SEQUENCE: 1302

Met Ala Gly Ser Gly Ala Trp Lys Arg
1               5

<210> SEQ ID NO 1303
<211> LENGTH: 9
<212> TYPE: PRT
<213> ORGANISM: homo sapien

<400> SEQUENCE: 1303

Ser Arg Phe Asn Lys Leu Arg Val Val
1               5

<210> SEQ ID NO 1304
<211> LENGTH: 9
<212> TYPE: PRT
<213> ORGANISM: homo sapien

<400> SEQUENCE: 1304

Lys Gln Arg Glu Ile Leu Lys Gln Arg
1               5

<210> SEQ ID NO 1305
<211> LENGTH: 9
<212> TYPE: PRT
<213> ORGANISM: homo sapien

<400> SEQUENCE: 1305

Tyr Leu Leu Phe Met Ile Gly Glu Leu
1               5

<210> SEQ ID NO 1306
<211> LENGTH: 9
<212> TYPE: PRT
<213> ORGANISM: homo sapien

<400> SEQUENCE: 1306

Asp Leu Ser Ala Ile Ile Leu Thr Leu
1               5

<210> SEQ ID NO 1307
<211> LENGTH: 9
<212> TYPE: PRT
<213> ORGANISM: homo sapien

<400> SEQUENCE: 1307

Ala Ile Ile Leu Thr Leu Leu Ala Leu
1               5

<210> SEQ ID NO 1308
<211> LENGTH: 9
<212> TYPE: PRT
<213> ORGANISM: homo sapien

<400> SEQUENCE: 1308

Ile Ser Val Leu Leu Val Tyr Ile Leu

-continued

```
1               5

<210> SEQ ID NO 1309
<211> LENGTH: 9
<212> TYPE: PRT
<213> ORGANISM: homo sapien

<400> SEQUENCE: 1309

Phe Leu Leu Tyr Glu Ala Val Gln Arg
1               5

<210> SEQ ID NO 1310
<211> LENGTH: 9
<212> TYPE: PRT
<213> ORGANISM: homo sapien

<400> SEQUENCE: 1310

Tyr Glu Ile Asn Gly Asp Ile Met Leu
1               5

<210> SEQ ID NO 1311
<211> LENGTH: 9
<212> TYPE: PRT
<213> ORGANISM: homo sapien

<400> SEQUENCE: 1311

Val Ala Val Asn Val Ile Met Gly Phe
1               5

<210> SEQ ID NO 1312
<211> LENGTH: 9
<212> TYPE: PRT
<213> ORGANISM: homo sapien

<400> SEQUENCE: 1312

Arg Gly Ser Gly Cys Glu Arg Asn His
1               5

<210> SEQ ID NO 1313
<211> LENGTH: 9
<212> TYPE: PRT
<213> ORGANISM: homo sapien

<400> SEQUENCE: 1313

Asp Leu Val Gln Ser Val Gly Val Leu
1               5

<210> SEQ ID NO 1314
<211> LENGTH: 9
<212> TYPE: PRT
<213> ORGANISM: homo sapien

<400> SEQUENCE: 1314

Leu Ile Ala Ala Tyr Ile Ile Arg Phe
1               5

<210> SEQ ID NO 1315
<211> LENGTH: 9
<212> TYPE: PRT
<213> ORGANISM: homo sapien

<400> SEQUENCE: 1315

Tyr Val Phe Ser Leu Leu Val Ala Phe
1               5
```

```
<210> SEQ ID NO 1316
<211> LENGTH: 9
<212> TYPE: PRT
<213> ORGANISM: homo sapien

<400> SEQUENCE: 1316

Phe Arg Ile Ile Trp Asp Thr Val Val
 1               5

<210> SEQ ID NO 1317
<211> LENGTH: 9
<212> TYPE: PRT
<213> ORGANISM: homo sapien

<400> SEQUENCE: 1317

Val Glu Asp Leu Asn Ile Trp Ser Leu
 1               5

<210> SEQ ID NO 1318
<211> LENGTH: 9
<212> TYPE: PRT
<213> ORGANISM: homo sapien

<400> SEQUENCE: 1318

Glu Glu Val Gln Ser Lys Ala Asn His
 1               5

<210> SEQ ID NO 1319
<211> LENGTH: 9
<212> TYPE: PRT
<213> ORGANISM: homo sapien

<400> SEQUENCE: 1319

Ala Asn His Leu Leu Leu Asn Thr Phe
 1               5

<210> SEQ ID NO 1320
<211> LENGTH: 9
<212> TYPE: PRT
<213> ORGANISM: homo sapien

<400> SEQUENCE: 1320

Ala Gly Ser Gly Ala Trp Lys Arg Leu
 1               5

<210> SEQ ID NO 1321
<211> LENGTH: 9
<212> TYPE: PRT
<213> ORGANISM: homo sapien

<400> SEQUENCE: 1321

Gly Ala Trp Lys Arg Leu Lys Ser Met
 1               5

<210> SEQ ID NO 1322
<211> LENGTH: 9
<212> TYPE: PRT
<213> ORGANISM: homo sapien

<400> SEQUENCE: 1322

Arg Lys Asp Asp Ala Pro Leu Phe Leu
 1               5

<210> SEQ ID NO 1323
```

-continued

```
<211> LENGTH: 9
<212> TYPE: PRT
<213> ORGANISM: homo sapien

<400> SEQUENCE: 1323

Glu Gly Leu Ser Arg Phe Asn Lys Leu
1               5

<210> SEQ ID NO 1324
<211> LENGTH: 9
<212> TYPE: PRT
<213> ORGANISM: homo sapien

<400> SEQUENCE: 1324

Pro Leu Thr Asn Ser Gln Leu Ser Leu
1               5

<210> SEQ ID NO 1325
<211> LENGTH: 9
<212> TYPE: PRT
<213> ORGANISM: homo sapien

<400> SEQUENCE: 1325

Glu Ile Leu Lys Gln Arg Lys Val Lys
1               5

<210> SEQ ID NO 1326
<211> LENGTH: 9
<212> TYPE: PRT
<213> ORGANISM: homo sapien

<400> SEQUENCE: 1326

Arg Lys Val Lys Ala Arg Leu Thr Ile
1               5

<210> SEQ ID NO 1327
<211> LENGTH: 9
<212> TYPE: PRT
<213> ORGANISM: homo sapien

<400> SEQUENCE: 1327

Asp Ala Leu His Met Leu Thr Asp Leu
1               5

<210> SEQ ID NO 1328
<211> LENGTH: 9
<212> TYPE: PRT
<213> ORGANISM: homo sapien

<400> SEQUENCE: 1328

Ile Leu Thr Leu Leu Ala Leu Trp Leu
1               5

<210> SEQ ID NO 1329
<211> LENGTH: 9
<212> TYPE: PRT
<213> ORGANISM: homo sapien

<400> SEQUENCE: 1329

Phe Gly Phe His Arg Leu Glu Val Leu
1               5

<210> SEQ ID NO 1330
<211> LENGTH: 9
<212> TYPE: PRT
```

<213> ORGANISM: homo sapien

<400> SEQUENCE: 1330

Val Leu Ser Ala Met Ile Ser Val Leu
1               5

<210> SEQ ID NO 1331
<211> LENGTH: 9
<212> TYPE: PRT
<213> ORGANISM: homo sapien

<400> SEQUENCE: 1331

Ala Met Ile Ser Val Leu Leu Val Tyr
1               5

<210> SEQ ID NO 1332
<211> LENGTH: 9
<212> TYPE: PRT
<213> ORGANISM: homo sapien

<400> SEQUENCE: 1332

Arg Thr Ile His Met Asn Tyr Glu Ile
1               5

<210> SEQ ID NO 1333
<211> LENGTH: 9
<212> TYPE: PRT
<213> ORGANISM: homo sapien

<400> SEQUENCE: 1333

Ile Ala Ala Tyr Ile Ile Arg Phe Lys
1               5

<210> SEQ ID NO 1334
<211> LENGTH: 9
<212> TYPE: PRT
<213> ORGANISM: homo sapien

<400> SEQUENCE: 1334

Lys Ile Ala Asp Pro Ile Cys Thr Tyr
1               5

<210> SEQ ID NO 1335
<211> LENGTH: 9
<212> TYPE: PRT
<213> ORGANISM: homo sapien

<400> SEQUENCE: 1335

Ser Leu Leu Val Ala Phe Thr Thr Phe
1               5

<210> SEQ ID NO 1336
<211> LENGTH: 9
<212> TYPE: PRT
<213> ORGANISM: homo sapien

<400> SEQUENCE: 1336

Ile Leu Glu Gly Val Pro Ser His Leu
1               5

<210> SEQ ID NO 1337
<211> LENGTH: 9
<212> TYPE: PRT
<213> ORGANISM: homo sapien

```
<400> SEQUENCE: 1337

Ser His Leu Asn Val Asp Tyr Ile Lys
1               5

<210> SEQ ID NO 1338
<211> LENGTH: 9
<212> TYPE: PRT
<213> ORGANISM: homo sapien

<400> SEQUENCE: 1338

Tyr Arg Cys Thr Ile Gln Leu Gln Ser
1               5

<210> SEQ ID NO 1339
<211> LENGTH: 9
<212> TYPE: PRT
<213> ORGANISM: homo sapien

<400> SEQUENCE: 1339

Ala Arg Leu Thr Ile Ala Ala Val Leu
1               5

<210> SEQ ID NO 1340
<211> LENGTH: 9
<212> TYPE: PRT
<213> ORGANISM: homo sapien

<400> SEQUENCE: 1340

Ile Arg Phe Lys Pro Glu Tyr Lys Ile
1               5

<210> SEQ ID NO 1341
<211> LENGTH: 9
<212> TYPE: PRT
<213> ORGANISM: homo sapien

<400> SEQUENCE: 1341

Leu Arg Lys Asp Asp Ala Pro Leu Phe
1               5

<210> SEQ ID NO 1342
<211> LENGTH: 9
<212> TYPE: PRT
<213> ORGANISM: homo sapien

<400> SEQUENCE: 1342

His Arg His Ser His Ser His Ser Leu
1               5

<210> SEQ ID NO 1343
<211> LENGTH: 9
<212> TYPE: PRT
<213> ORGANISM: homo sapien

<400> SEQUENCE: 1343

Val Arg Ala Ala Phe Val His Ala Leu
1               5

<210> SEQ ID NO 1344
<211> LENGTH: 9
<212> TYPE: PRT
<213> ORGANISM: homo sapien

<400> SEQUENCE: 1344
```

-continued

```
Ser Arg Phe Asn Lys Leu Arg Val Val
1               5
```

<210> SEQ ID NO 1345
<211> LENGTH: 9
<212> TYPE: PRT
<213> ORGANISM: homo sapien

<400> SEQUENCE: 1345

```
His Arg Leu Glu Val Leu Ser Ala Met
1               5
```

<210> SEQ ID NO 1346
<211> LENGTH: 9
<212> TYPE: PRT
<213> ORGANISM: homo sapien

<400> SEQUENCE: 1346

```
Glu Arg Asn His Gly Gln Asp Ser Leu
1               5
```

<210> SEQ ID NO 1347
<211> LENGTH: 9
<212> TYPE: PRT
<213> ORGANISM: homo sapien

<400> SEQUENCE: 1347

```
Phe Arg Ile Ile Trp Asp Thr Val Val
1               5
```

<210> SEQ ID NO 1348
<211> LENGTH: 9
<212> TYPE: PRT
<213> ORGANISM: homo sapien

<400> SEQUENCE: 1348

```
Lys Arg Leu Lys Ser Met Leu Arg Lys
1               5
```

<210> SEQ ID NO 1349
<211> LENGTH: 9
<212> TYPE: PRT
<213> ORGANISM: homo sapien

<400> SEQUENCE: 1349

```
Arg Phe Thr Phe Gly Phe His Arg Leu
1               5
```

<210> SEQ ID NO 1350
<211> LENGTH: 9
<212> TYPE: PRT
<213> ORGANISM: homo sapien

<400> SEQUENCE: 1350

```
Gly Met Tyr Arg Cys Thr Ile Gln Leu
1               5
```

<210> SEQ ID NO 1351
<211> LENGTH: 9
<212> TYPE: PRT
<213> ORGANISM: homo sapien

<400> SEQUENCE: 1351

```
Arg Lys Asp Asp Ala Pro Leu Phe Leu
1               5
```

<210> SEQ ID NO 1352
<211> LENGTH: 9
<212> TYPE: PRT
<213> ORGANISM: homo sapien

<400> SEQUENCE: 1352

Gly Val Leu Ile Ala Ala Tyr Ile Ile
1               5

<210> SEQ ID NO 1353
<211> LENGTH: 9
<212> TYPE: PRT
<213> ORGANISM: homo sapien

<400> SEQUENCE: 1353

Arg Ile Ile Trp Asp Thr Val Val Ile
1               5

<210> SEQ ID NO 1354
<211> LENGTH: 9
<212> TYPE: PRT
<213> ORGANISM: homo sapien

<400> SEQUENCE: 1354

Arg Lys Val Lys Ala Arg Leu Thr Ile
1               5

<210> SEQ ID NO 1355
<211> LENGTH: 9
<212> TYPE: PRT
<213> ORGANISM: homo sapien

<400> SEQUENCE: 1355

Ile Leu Thr Leu Leu Ala Leu Trp Leu
1               5

<210> SEQ ID NO 1356
<211> LENGTH: 9
<212> TYPE: PRT
<213> ORGANISM: homo sapien

<400> SEQUENCE: 1356

Lys Arg Phe Thr Phe Gly Phe His Arg
1               5

<210> SEQ ID NO 1357
<211> LENGTH: 9
<212> TYPE: PRT
<213> ORGANISM: homo sapien

<400> SEQUENCE: 1357

Ile Ser Val Leu Leu Val Tyr Ile Leu
1               5

<210> SEQ ID NO 1358
<211> LENGTH: 9
<212> TYPE: PRT
<213> ORGANISM: homo sapien

<400> SEQUENCE: 1358

Arg Thr Ile His Met Asn Tyr Glu Ile
1               5

```
<210> SEQ ID NO 1359
<211> LENGTH: 9
<212> TYPE: PRT
<213> ORGANISM: homo sapien

<400> SEQUENCE: 1359

Gly Asp Leu Val Gln Ser Val Gly Val
 1               5

<210> SEQ ID NO 1360
<211> LENGTH: 9
<212> TYPE: PRT
<213> ORGANISM: homo sapien

<400> SEQUENCE: 1360

Glu Gly Leu Ser Arg Phe Asn Lys Leu
 1               5

<210> SEQ ID NO 1361
<211> LENGTH: 9
<212> TYPE: PRT
<213> ORGANISM: homo sapien

<400> SEQUENCE: 1361

Arg Phe Asn Lys Leu Arg Val Val Val
 1               5

<210> SEQ ID NO 1362
<211> LENGTH: 9
<212> TYPE: PRT
<213> ORGANISM: homo sapien

<400> SEQUENCE: 1362

Ser Leu Leu Asp Gln Asp Leu Pro Leu
 1               5

<210> SEQ ID NO 1363
<211> LENGTH: 9
<212> TYPE: PRT
<213> ORGANISM: homo sapien

<400> SEQUENCE: 1363

Arg Glu Ile Leu Lys Gln Arg Lys Val
 1               5

<210> SEQ ID NO 1364
<211> LENGTH: 9
<212> TYPE: PRT
<213> ORGANISM: homo sapien

<400> SEQUENCE: 1364

Lys Gln Arg Lys Val Lys Ala Arg Leu
 1               5

<210> SEQ ID NO 1365
<211> LENGTH: 9
<212> TYPE: PRT
<213> ORGANISM: homo sapien

<400> SEQUENCE: 1365

Leu Thr Ile Ala Ala Val Leu Tyr Leu
 1               5

<210> SEQ ID NO 1366
<211> LENGTH: 9
```

```
<212> TYPE: PRT
<213> ORGANISM: homo sapien

<400> SEQUENCE: 1366

Gly Tyr Ile Ala Asn Ser Leu Ala Ile
1               5

<210> SEQ ID NO 1367
<211> LENGTH: 9
<212> TYPE: PRT
<213> ORGANISM: homo sapien

<400> SEQUENCE: 1367

Ala Ile Ile Leu Thr Leu Leu Ala Leu
1               5

<210> SEQ ID NO 1368
<211> LENGTH: 9
<212> TYPE: PRT
<213> ORGANISM: homo sapien

<400> SEQUENCE: 1368

Ala Ala Val Gly Val Ala Val Asn Val
1               5

<210> SEQ ID NO 1369
<211> LENGTH: 9
<212> TYPE: PRT
<213> ORGANISM: homo sapien

<400> SEQUENCE: 1369

Tyr Arg Cys Thr Ile Gln Leu Gln Ser
1               5

<210> SEQ ID NO 1370
<211> LENGTH: 9
<212> TYPE: PRT
<213> ORGANISM: homo sapien

<400> SEQUENCE: 1370

Ala Gly Ser Gly Ala Trp Lys Arg Leu
1               5

<210> SEQ ID NO 1371
<211> LENGTH: 9
<212> TYPE: PRT
<213> ORGANISM: homo sapien

<400> SEQUENCE: 1371

Leu Arg Val Val Val Ala Asp Asp Gly
1               5

<210> SEQ ID NO 1372
<211> LENGTH: 9
<212> TYPE: PRT
<213> ORGANISM: homo sapien

<400> SEQUENCE: 1372

Pro Leu Thr Asn Ser Gln Leu Ser Leu
1               5

<210> SEQ ID NO 1373
<211> LENGTH: 9
<212> TYPE: PRT
<213> ORGANISM: homo sapien
```

```
<400> SEQUENCE: 1373

Tyr Leu Leu Phe Met Ile Gly Glu Leu
1               5

<210> SEQ ID NO 1374
<211> LENGTH: 9
<212> TYPE: PRT
<213> ORGANISM: homo sapien

<400> SEQUENCE: 1374

Val Gly Gly Tyr Ile Ala Asn Ser Leu
1               5

<210> SEQ ID NO 1375
<211> LENGTH: 9
<212> TYPE: PRT
<213> ORGANISM: homo sapien

<400> SEQUENCE: 1375

Ala Ile Met Thr Asp Ala Leu His Met
1               5

<210> SEQ ID NO 1376
<211> LENGTH: 9
<212> TYPE: PRT
<213> ORGANISM: homo sapien

<400> SEQUENCE: 1376

Ile Met Thr Asp Ala Leu His Met Leu
1               5

<210> SEQ ID NO 1377
<211> LENGTH: 9
<212> TYPE: PRT
<213> ORGANISM: homo sapien

<400> SEQUENCE: 1377

Asp Ala Leu His Met Leu Thr Asp Leu
1               5

<210> SEQ ID NO 1378
<211> LENGTH: 9
<212> TYPE: PRT
<213> ORGANISM: homo sapien

<400> SEQUENCE: 1378

Asp Leu Ser Ala Ile Ile Leu Thr Leu
1               5

<210> SEQ ID NO 1379
<211> LENGTH: 9
<212> TYPE: PRT
<213> ORGANISM: homo sapien

<400> SEQUENCE: 1379

Phe Gly Phe His Arg Leu Glu Val Leu
1               5

<210> SEQ ID NO 1380
<211> LENGTH: 9
<212> TYPE: PRT
<213> ORGANISM: homo sapien

<400> SEQUENCE: 1380
```

Arg Leu Glu Val Leu Ser Ala Met Ile
1               5

<210> SEQ ID NO 1381
<211> LENGTH: 9
<212> TYPE: PRT
<213> ORGANISM: homo sapien

<400> SEQUENCE: 1381

Leu Ser Ala Met Ile Ser Val Leu Leu
1               5

<210> SEQ ID NO 1382
<211> LENGTH: 9
<212> TYPE: PRT
<213> ORGANISM: homo sapien

<400> SEQUENCE: 1382

Leu Val Tyr Ile Leu Met Gly Phe Leu
1               5

<210> SEQ ID NO 1383
<211> LENGTH: 9
<212> TYPE: PRT
<213> ORGANISM: homo sapien

<400> SEQUENCE: 1383

Ala Val Asn Val Ile Met Gly Phe Leu
1               5

<210> SEQ ID NO 1384
<211> LENGTH: 9
<212> TYPE: PRT
<213> ORGANISM: homo sapien

<400> SEQUENCE: 1384

Thr Arg Gly Ser Gly Cys Glu Arg Asn
1               5

<210> SEQ ID NO 1385
<211> LENGTH: 9
<212> TYPE: PRT
<213> ORGANISM: homo sapien

<400> SEQUENCE: 1385

Ala Phe Val His Ala Leu Gly Asp Leu
1               5

<210> SEQ ID NO 1386
<211> LENGTH: 9
<212> TYPE: PRT
<213> ORGANISM: homo sapien

<400> SEQUENCE: 1386

Asp Leu Val Gln Ser Val Gly Val Leu
1               5

<210> SEQ ID NO 1387
<211> LENGTH: 9
<212> TYPE: PRT
<213> ORGANISM: homo sapien

<400> SEQUENCE: 1387

Pro Glu Tyr Lys Ile Ala Asp Pro Ile

```
                      1               5

<210> SEQ ID NO 1388
<211> LENGTH: 9
<212> TYPE: PRT
<213> ORGANISM: homo sapien

<400> SEQUENCE: 1388

Ile Cys Thr Tyr Val Phe Ser Leu Leu
 1               5

<210> SEQ ID NO 1389
<211> LENGTH: 9
<212> TYPE: PRT
<213> ORGANISM: homo sapien

<400> SEQUENCE: 1389

Tyr Val Phe Ser Leu Leu Val Ala Phe
 1               5

<210> SEQ ID NO 1390
<211> LENGTH: 9
<212> TYPE: PRT
<213> ORGANISM: homo sapien

<400> SEQUENCE: 1390

Ile Trp Asp Thr Val Val Ile Ile Leu
 1               5

<210> SEQ ID NO 1391
<211> LENGTH: 9
<212> TYPE: PRT
<213> ORGANISM: homo sapien

<400> SEQUENCE: 1391

Glu Gly Val Pro Ser His Leu Asn Val
 1               5

<210> SEQ ID NO 1392
<211> LENGTH: 9
<212> TYPE: PRT
<213> ORGANISM: homo sapien

<400> SEQUENCE: 1392

Met Lys Ile Glu Asp Val Tyr Ser Val
 1               5

<210> SEQ ID NO 1393
<211> LENGTH: 9
<212> TYPE: PRT
<213> ORGANISM: homo sapien

<400> SEQUENCE: 1393

Glu Asp Val Tyr Ser Val Glu Asp Leu
 1               5

<210> SEQ ID NO 1394
<211> LENGTH: 9
<212> TYPE: PRT
<213> ORGANISM: homo sapien

<400> SEQUENCE: 1394

Gly Lys Ser Thr Ala Ile Val His Ile
 1               5
```

```
<210> SEQ ID NO 1395
<211> LENGTH: 9
<212> TYPE: PRT
<213> ORGANISM: homo sapien

<400> SEQUENCE: 1395

Gly Ser Ser Lys Trp Glu Glu Val
 1               5

<210> SEQ ID NO 1396
<211> LENGTH: 9
<212> TYPE: PRT
<213> ORGANISM: homo sapien

<400> SEQUENCE: 1396

Glu Val Gln Ser Lys Ala Asn His Leu
 1               5

<210> SEQ ID NO 1397
<211> LENGTH: 9
<212> TYPE: PRT
<213> ORGANISM: homo sapien

<400> SEQUENCE: 1397

Asp Arg Thr Cys Ala Asn Cys Gln Ser
 1               5

<210> SEQ ID NO 1398
<211> LENGTH: 9
<212> TYPE: PRT
<213> ORGANISM: homo sapien

<400> SEQUENCE: 1398

Val Ala Phe Thr Thr Phe Arg Ile Ile
 1               5

<210> SEQ ID NO 1399
<211> LENGTH: 9
<212> TYPE: PRT
<213> ORGANISM: homo sapien

<400> SEQUENCE: 1399

Asp Ala Leu His Met Leu Thr Asp Leu
 1               5

<210> SEQ ID NO 1400
<211> LENGTH: 9
<212> TYPE: PRT
<213> ORGANISM: homo sapien

<400> SEQUENCE: 1400

Ala Ala Val Gly Val Ala Val Asn Val
 1               5

<210> SEQ ID NO 1401
<211> LENGTH: 9
<212> TYPE: PRT
<213> ORGANISM: homo sapien

<400> SEQUENCE: 1401

Ser Ala Met Ile Ser Val Leu Leu Val
 1               5

<210> SEQ ID NO 1402
```

```
<211> LENGTH: 9
<212> TYPE: PRT
<213> ORGANISM: homo sapien

<400> SEQUENCE: 1402

Glu Ala Leu Met Lys Ile Glu Asp Val
 1               5

<210> SEQ ID NO 1403
<211> LENGTH: 9
<212> TYPE: PRT
<213> ORGANISM: homo sapien

<400> SEQUENCE: 1403

Thr Ala Ile Val His Ile Gln Leu Ile
 1               5

<210> SEQ ID NO 1404
<211> LENGTH: 9
<212> TYPE: PRT
<213> ORGANISM: homo sapien

<400> SEQUENCE: 1404

Ile Ala Asp Pro Ile Cys Thr Tyr Val
 1               5

<210> SEQ ID NO 1405
<211> LENGTH: 9
<212> TYPE: PRT
<213> ORGANISM: homo sapien

<400> SEQUENCE: 1405

Lys Ala Arg Leu Thr Ile Ala Ala Val
 1               5

<210> SEQ ID NO 1406
<211> LENGTH: 9
<212> TYPE: PRT
<213> ORGANISM: homo sapien

<400> SEQUENCE: 1406

Ile Gly Glu Leu Val Gly Gly Tyr Ile
 1               5

<210> SEQ ID NO 1407
<211> LENGTH: 9
<212> TYPE: PRT
<213> ORGANISM: homo sapien

<400> SEQUENCE: 1407

Glu Gly Leu Ser Arg Phe Asn Lys Leu
 1               5

<210> SEQ ID NO 1408
<211> LENGTH: 9
<212> TYPE: PRT
<213> ORGANISM: homo sapien

<400> SEQUENCE: 1408

Phe Gly Phe His Arg Leu Glu Val Leu
 1               5

<210> SEQ ID NO 1409
<211> LENGTH: 9
<212> TYPE: PRT
```

-continued

<213> ORGANISM: homo sapien

<400> SEQUENCE: 1409

Leu Tyr Glu Ala Val Gln Arg Thr Ile
1               5

<210> SEQ ID NO 1410
<211> LENGTH: 9
<212> TYPE: PRT
<213> ORGANISM: homo sapien

<400> SEQUENCE: 1410

Met Asn Tyr Glu Ile Asn Gly Asp Ile
1               5

<210> SEQ ID NO 1411
<211> LENGTH: 9
<212> TYPE: PRT
<213> ORGANISM: homo sapien

<400> SEQUENCE: 1411

Val Gly Val Leu Ile Ala Ala Tyr Ile
1               5

<210> SEQ ID NO 1412
<211> LENGTH: 9
<212> TYPE: PRT
<213> ORGANISM: homo sapien

<400> SEQUENCE: 1412

Ile Ile Trp Asp Thr Val Val Ile Ile
1               5

<210> SEQ ID NO 1413
<211> LENGTH: 9
<212> TYPE: PRT
<213> ORGANISM: homo sapien

<400> SEQUENCE: 1413

Asp Ala Pro Leu Phe Leu Asn Asp Thr
1               5

<210> SEQ ID NO 1414
<211> LENGTH: 9
<212> TYPE: PRT
<213> ORGANISM: homo sapien

<400> SEQUENCE: 1414

Tyr Ile Lys Glu Ala Leu Met Lys Ile
1               5

<210> SEQ ID NO 1415
<211> LENGTH: 9
<212> TYPE: PRT
<213> ORGANISM: homo sapien

<400> SEQUENCE: 1415

Asp Asn Cys Ser Lys Gln Arg Glu Ile
1               5

<210> SEQ ID NO 1416
<211> LENGTH: 9
<212> TYPE: PRT
<213> ORGANISM: homo sapien

<400> SEQUENCE: 1416

Leu Ala Leu Trp Leu Ser Ser Lys Ser
1               5

<210> SEQ ID NO 1417
<211> LENGTH: 9
<212> TYPE: PRT
<213> ORGANISM: homo sapien

<400> SEQUENCE: 1417

Met Gly Phe Leu Leu Tyr Glu Ala Val
1               5

<210> SEQ ID NO 1418
<211> LENGTH: 9
<212> TYPE: PRT
<213> ORGANISM: homo sapien

<400> SEQUENCE: 1418

Thr Ala Ala Val Gly Val Ala Val Asn
1               5

<210> SEQ ID NO 1419
<211> LENGTH: 9
<212> TYPE: PRT
<213> ORGANISM: homo sapien

<400> SEQUENCE: 1419

Ala Val Gly Val Ala Val Asn Val Ile
1               5

<210> SEQ ID NO 1420
<211> LENGTH: 9
<212> TYPE: PRT
<213> ORGANISM: homo sapien

<400> SEQUENCE: 1420

Leu Pro Ser Asn Ser Pro Thr Arg Gly
1               5

<210> SEQ ID NO 1421
<211> LENGTH: 9
<212> TYPE: PRT
<213> ORGANISM: homo sapien

<400> SEQUENCE: 1421

Leu Ala Val Arg Ala Ala Phe Val His
1               5

<210> SEQ ID NO 1422
<211> LENGTH: 9
<212> TYPE: PRT
<213> ORGANISM: homo sapien

<400> SEQUENCE: 1422

Asp Leu Val Gln Ser Val Gly Val Leu
1               5

<210> SEQ ID NO 1423
<211> LENGTH: 9
<212> TYPE: PRT
<213> ORGANISM: homo sapien

<400> SEQUENCE: 1423

-continued

Ala Ala Tyr Ile Ile Arg Phe Lys Pro
1               5

<210> SEQ ID NO 1424
<211> LENGTH: 9
<212> TYPE: PRT
<213> ORGANISM: homo sapien

<400> SEQUENCE: 1424

Ile Arg Phe Lys Pro Glu Tyr Lys Ile
1               5

<210> SEQ ID NO 1425
<211> LENGTH: 9
<212> TYPE: PRT
<213> ORGANISM: homo sapien

<400> SEQUENCE: 1425

Pro Glu Tyr Lys Ile Ala Asp Pro Ile
1               5

<210> SEQ ID NO 1426
<211> LENGTH: 9
<212> TYPE: PRT
<213> ORGANISM: homo sapien

<400> SEQUENCE: 1426

Asp Pro Ile Cys Thr Tyr Val Phe Ser
1               5

<210> SEQ ID NO 1427
<211> LENGTH: 9
<212> TYPE: PRT
<213> ORGANISM: homo sapien

<400> SEQUENCE: 1427

Glu Gly Val Pro Ser His Leu Asn Val
1               5

<210> SEQ ID NO 1428
<211> LENGTH: 9
<212> TYPE: PRT
<213> ORGANISM: homo sapien

<400> SEQUENCE: 1428

Ala Gly Ser Gly Ala Trp Lys Arg Leu
1               5

<210> SEQ ID NO 1429
<211> LENGTH: 9
<212> TYPE: PRT
<213> ORGANISM: homo sapien

<400> SEQUENCE: 1429

Ala Pro Leu Phe Leu Asn Asp Thr Ser
1               5

<210> SEQ ID NO 1430
<211> LENGTH: 9
<212> TYPE: PRT
<213> ORGANISM: homo sapien

<400> SEQUENCE: 1430

Ser Arg Phe Asn Lys Leu Arg Val Val
1               5

```
<210> SEQ ID NO 1431
<211> LENGTH: 9
<212> TYPE: PRT
<213> ORGANISM: homo sapien

<400> SEQUENCE: 1431

Glu Ala Pro Glu Arg Pro Val Asn Gly
1               5

<210> SEQ ID NO 1432
<211> LENGTH: 9
<212> TYPE: PRT
<213> ORGANISM: homo sapien

<400> SEQUENCE: 1432

Leu Pro Leu Thr Asn Ser Gln Leu Ser
1               5

<210> SEQ ID NO 1433
<211> LENGTH: 9
<212> TYPE: PRT
<213> ORGANISM: homo sapien

<400> SEQUENCE: 1433

Val Gly Gly Tyr Ile Ala Asn Ser Leu
1               5

<210> SEQ ID NO 1434
<211> LENGTH: 9
<212> TYPE: PRT
<213> ORGANISM: homo sapien

<400> SEQUENCE: 1434

Asp Leu Ser Ala Ile Ile Leu Thr Leu
1               5

<210> SEQ ID NO 1435
<211> LENGTH: 9
<212> TYPE: PRT
<213> ORGANISM: homo sapien

<400> SEQUENCE: 1435

His Ala Leu Gly Asp Leu Val Gln Ser
1               5

<210> SEQ ID NO 1436
<211> LENGTH: 9
<212> TYPE: PRT
<213> ORGANISM: homo sapien

<400> SEQUENCE: 1436

Leu Val Gln Ser Val Gly Val Leu Ile
1               5

<210> SEQ ID NO 1437
<211> LENGTH: 9
<212> TYPE: PRT
<213> ORGANISM: homo sapien

<400> SEQUENCE: 1437

Leu Thr Ser Gly Lys Ser Thr Ala Ile
1               5
```

```
<210> SEQ ID NO 1438
<211> LENGTH: 9
<212> TYPE: PRT
<213> ORGANISM: homo sapien

<400> SEQUENCE: 1438

Met Ala Gly Ser Gly Ala Trp Lys Arg
 1               5

<210> SEQ ID NO 1439
<211> LENGTH: 9
<212> TYPE: PRT
<213> ORGANISM: homo sapien

<400> SEQUENCE: 1439

Gly Ala Trp Lys Arg Leu Lys Ser Met
 1               5

<210> SEQ ID NO 1440
<211> LENGTH: 9
<212> TYPE: PRT
<213> ORGANISM: homo sapien

<400> SEQUENCE: 1440

Asp Gly Ser Glu Ala Pro Glu Arg Pro
 1               5

<210> SEQ ID NO 1441
<211> LENGTH: 9
<212> TYPE: PRT
<213> ORGANISM: homo sapien

<400> SEQUENCE: 1441

Arg Lys Val Lys Ala Arg Leu Thr Ile
 1               5

<210> SEQ ID NO 1442
<211> LENGTH: 9
<212> TYPE: PRT
<213> ORGANISM: homo sapien

<400> SEQUENCE: 1442

Ile Ala Asn Ser Leu Ala Ile Met Thr
 1               5

<210> SEQ ID NO 1443
<211> LENGTH: 9
<212> TYPE: PRT
<213> ORGANISM: homo sapien

<400> SEQUENCE: 1443

His Met Leu Thr Asp Leu Ser Ala Ile
 1               5

<210> SEQ ID NO 1444
<211> LENGTH: 9
<212> TYPE: PRT
<213> ORGANISM: homo sapien

<400> SEQUENCE: 1444

Ile Thr Ala Ala Val Gly Val Ala Val
 1               5

<210> SEQ ID NO 1445
<211> LENGTH: 9
```

```
<212> TYPE: PRT
<213> ORGANISM: homo sapien

<400> SEQUENCE: 1445

Val Ala Val Asn Val Ile Met Gly Phe
1               5

<210> SEQ ID NO 1446
<211> LENGTH: 9
<212> TYPE: PRT
<213> ORGANISM: homo sapien

<400> SEQUENCE: 1446

Ile Ala Ala Tyr Ile Ile Arg Phe Lys
1               5

<210> SEQ ID NO 1447
<211> LENGTH: 9
<212> TYPE: PRT
<213> ORGANISM: homo sapien

<400> SEQUENCE: 1447

Leu Val Ala Phe Thr Thr Phe Arg Ile
1               5

<210> SEQ ID NO 1448
<211> LENGTH: 9
<212> TYPE: PRT
<213> ORGANISM: homo sapien

<400> SEQUENCE: 1448

Arg Ile Ile Trp Asp Thr Val Val Ile
1               5

<210> SEQ ID NO 1449
<211> LENGTH: 9
<212> TYPE: PRT
<213> ORGANISM: homo sapien

<400> SEQUENCE: 1449

Ile Trp Asp Thr Val Val Ile Ile Leu
1               5

<210> SEQ ID NO 1450
<211> LENGTH: 9
<212> TYPE: PRT
<213> ORGANISM: homo sapien

<400> SEQUENCE: 1450

Gly Lys Ser Thr Ala Ile Val His Ile
1               5

<210> SEQ ID NO 1451
<211> LENGTH: 9
<212> TYPE: PRT
<213> ORGANISM: homo sapien

<400> SEQUENCE: 1451

Ile Pro Gly Ser Ser Ser Lys Trp Glu
1               5

<210> SEQ ID NO 1452
<211> LENGTH: 9
<212> TYPE: PRT
<213> ORGANISM: homo sapien
```

<400> SEQUENCE: 1452

Thr Phe Gly Met Tyr Arg Cys Thr Ile
1               5

<210> SEQ ID NO 1453
<211> LENGTH: 9
<212> TYPE: PRT
<213> ORGANISM: homo sapien

<400> SEQUENCE: 1453

Arg Phe Asn Lys Leu Arg Val Val Val
1               5

<210> SEQ ID NO 1454
<211> LENGTH: 9
<212> TYPE: PRT
<213> ORGANISM: homo sapien

<400> SEQUENCE: 1454

Ala Pro Glu Arg Pro Val Asn Gly Ala
1               5

<210> SEQ ID NO 1455
<211> LENGTH: 9
<212> TYPE: PRT
<213> ORGANISM: homo sapien

<400> SEQUENCE: 1455

Asp Leu Pro Leu Thr Asn Ser Gln Leu
1               5

<210> SEQ ID NO 1456
<211> LENGTH: 9
<212> TYPE: PRT
<213> ORGANISM: homo sapien

<400> SEQUENCE: 1456

Ala Arg Leu Thr Ile Ala Ala Val Leu
1               5

<210> SEQ ID NO 1457
<211> LENGTH: 9
<212> TYPE: PRT
<213> ORGANISM: homo sapien

<400> SEQUENCE: 1457

Ile Ala Ala Val Leu Tyr Leu Leu Phe
1               5

<210> SEQ ID NO 1458
<211> LENGTH: 9
<212> TYPE: PRT
<213> ORGANISM: homo sapien

<400> SEQUENCE: 1458

Ala Ala Val Leu Tyr Leu Leu Phe Met
1               5

<210> SEQ ID NO 1459
<211> LENGTH: 9
<212> TYPE: PRT
<213> ORGANISM: homo sapien

<400> SEQUENCE: 1459

Ala Val Leu Tyr Leu Leu Phe Met Ile
1               5

<210> SEQ ID NO 1460
<211> LENGTH: 9
<212> TYPE: PRT
<213> ORGANISM: homo sapien

<400> SEQUENCE: 1460

Leu Ala Ile Met Thr Asp Ala Leu His
1               5

<210> SEQ ID NO 1461
<211> LENGTH: 9
<212> TYPE: PRT
<213> ORGANISM: homo sapien

<400> SEQUENCE: 1461

Ser Pro Thr Lys Arg Phe Thr Phe Gly
1               5

<210> SEQ ID NO 1462
<211> LENGTH: 9
<212> TYPE: PRT
<213> ORGANISM: homo sapien

<400> SEQUENCE: 1462

Val Leu Ser Ala Met Ile Ser Val Leu
1               5

<210> SEQ ID NO 1463
<211> LENGTH: 9
<212> TYPE: PRT
<213> ORGANISM: homo sapien

<400> SEQUENCE: 1463

Met Ile Ser Val Leu Leu Val Tyr Ile
1               5

<210> SEQ ID NO 1464
<211> LENGTH: 9
<212> TYPE: PRT
<213> ORGANISM: homo sapien

<400> SEQUENCE: 1464

Ala Ala Phe Val His Ala Leu Gly Asp
1               5

<210> SEQ ID NO 1465
<211> LENGTH: 9
<212> TYPE: PRT
<213> ORGANISM: homo sapien

<400> SEQUENCE: 1465

Leu Gly Asp Leu Val Gln Ser Val Gly
1               5

<210> SEQ ID NO 1466
<211> LENGTH: 9
<212> TYPE: PRT
<213> ORGANISM: homo sapien

<400> SEQUENCE: 1466

Gly Val Leu Ile Ala Ala Tyr Ile Ile

-continued

```
               1               5

<210> SEQ ID NO 1467
<211> LENGTH: 9
<212> TYPE: PRT
<213> ORGANISM: homo sapien

<400> SEQUENCE: 1467

Cys Thr Tyr Val Phe Ser Leu Leu Val
  1               5

<210> SEQ ID NO 1468
<211> LENGTH: 9
<212> TYPE: PRT
<213> ORGANISM: homo sapien

<400> SEQUENCE: 1468

Phe Arg Ile Ile Trp Asp Thr Val Val
  1               5

<210> SEQ ID NO 1469
<211> LENGTH: 9
<212> TYPE: PRT
<213> ORGANISM: homo sapien

<400> SEQUENCE: 1469

Ile Leu Glu Gly Val Pro Ser His Leu
  1               5

<210> SEQ ID NO 1470
<211> LENGTH: 9
<212> TYPE: PRT
<213> ORGANISM: homo sapien

<400> SEQUENCE: 1470

Val Pro Ser His Leu Asn Val Asp Tyr
  1               5

<210> SEQ ID NO 1471
<211> LENGTH: 9
<212> TYPE: PRT
<213> ORGANISM: homo sapien

<400> SEQUENCE: 1471

Met Lys Ile Glu Asp Val Tyr Ser Val
  1               5

<210> SEQ ID NO 1472
<211> LENGTH: 10
<212> TYPE: PRT
<213> ORGANISM: homo sapien

<400> SEQUENCE: 1472

Ala Ile Met Thr Asp Ala Leu His Met Leu
  1               5                  10

<210> SEQ ID NO 1473
<211> LENGTH: 10
<212> TYPE: PRT
<213> ORGANISM: homo sapien

<400> SEQUENCE: 1473

Ala Met Ile Ser Val Leu Leu Val Tyr Ile
  1               5                  10
```

```
<210> SEQ ID NO 1474
<211> LENGTH: 10
<212> TYPE: PRT
<213> ORGANISM: homo sapien

<400> SEQUENCE: 1474

Ile Leu Met Gly Phe Leu Leu Tyr Glu Ala
1               5                   10

<210> SEQ ID NO 1475
<211> LENGTH: 10
<212> TYPE: PRT
<213> ORGANISM: homo sapien

<400> SEQUENCE: 1475

Ile Ile Trp Asp Thr Val Val Ile Ile Leu
1               5                   10

<210> SEQ ID NO 1476
<211> LENGTH: 10
<212> TYPE: PRT
<213> ORGANISM: homo sapien

<400> SEQUENCE: 1476

Leu Met Lys Ile Glu Asp Val Tyr Ser Val
1               5                   10

<210> SEQ ID NO 1477
<211> LENGTH: 10
<212> TYPE: PRT
<213> ORGANISM: homo sapien

<400> SEQUENCE: 1477

Leu Leu Tyr Glu Ala Val Gln Arg Thr Ile
1               5                   10

<210> SEQ ID NO 1478
<211> LENGTH: 10
<212> TYPE: PRT
<213> ORGANISM: homo sapien

<400> SEQUENCE: 1478

Ile Met Leu Ile Thr Ala Ala Val Gly Val
1               5                   10

<210> SEQ ID NO 1479
<211> LENGTH: 10
<212> TYPE: PRT
<213> ORGANISM: homo sapien

<400> SEQUENCE: 1479

Ser Met Leu Arg Lys Asp Asp Ala Pro Leu
1               5                   10

<210> SEQ ID NO 1480
<211> LENGTH: 10
<212> TYPE: PRT
<213> ORGANISM: homo sapien

<400> SEQUENCE: 1480

Ser Leu Leu Asp Gln Asp Leu Pro Leu Thr
1               5                   10

<210> SEQ ID NO 1481
```

-continued

```
<211> LENGTH: 10
<212> TYPE: PRT
<213> ORGANISM: homo sapien

<400> SEQUENCE: 1481

Arg Leu Thr Ile Ala Ala Val Leu Tyr Leu
1               5                   10

<210> SEQ ID NO 1482
<211> LENGTH: 10
<212> TYPE: PRT
<213> ORGANISM: homo sapien

<400> SEQUENCE: 1482

Ser Ala Ile Ile Leu Thr Leu Leu Ala Leu
1               5                   10

<210> SEQ ID NO 1483
<211> LENGTH: 10
<212> TYPE: PRT
<213> ORGANISM: homo sapien

<400> SEQUENCE: 1483

His Ala Leu Gly Asp Leu Val Gln Ser Val
1               5                   10

<210> SEQ ID NO 1484
<211> LENGTH: 10
<212> TYPE: PRT
<213> ORGANISM: homo sapien

<400> SEQUENCE: 1484

Arg Ile Ile Trp Asp Thr Val Val Ile Ile
1               5                   10

<210> SEQ ID NO 1485
<211> LENGTH: 10
<212> TYPE: PRT
<213> ORGANISM: homo sapien

<400> SEQUENCE: 1485

Ile Ile Leu Glu Gly Val Pro Ser His Leu
1               5                   10

<210> SEQ ID NO 1486
<211> LENGTH: 10
<212> TYPE: PRT
<213> ORGANISM: homo sapien

<400> SEQUENCE: 1486

Leu Thr Ile Ala Ala Val Leu Tyr Leu Leu
1               5                   10

<210> SEQ ID NO 1487
<211> LENGTH: 10
<212> TYPE: PRT
<213> ORGANISM: homo sapien

<400> SEQUENCE: 1487

Tyr Leu Leu Phe Met Ile Gly Glu Leu Val
1               5                   10

<210> SEQ ID NO 1488
<211> LENGTH: 10
<212> TYPE: PRT
```

```
<213> ORGANISM: homo sapien

<400> SEQUENCE: 1488

Asp Leu Ser Ala Ile Ile Leu Thr Leu Leu
1               5                   10

<210> SEQ ID NO 1489
<211> LENGTH: 10
<212> TYPE: PRT
<213> ORGANISM: homo sapien

<400> SEQUENCE: 1489

Ile Ile Leu Thr Leu Leu Ala Leu Trp Leu
1               5                   10

<210> SEQ ID NO 1490
<211> LENGTH: 10
<212> TYPE: PRT
<213> ORGANISM: homo sapien

<400> SEQUENCE: 1490

Val Leu Ser Ala Met Ile Ser Val Leu Leu
1               5                   10

<210> SEQ ID NO 1491
<211> LENGTH: 10
<212> TYPE: PRT
<213> ORGANISM: homo sapien

<400> SEQUENCE: 1491

Met Ile Ser Val Leu Leu Val Tyr Ile Leu
1               5                   10

<210> SEQ ID NO 1492
<211> LENGTH: 10
<212> TYPE: PRT
<213> ORGANISM: homo sapien

<400> SEQUENCE: 1492

Gly Leu Ser Arg Phe Asn Lys Leu Arg Val
1               5                   10

<210> SEQ ID NO 1493
<211> LENGTH: 10
<212> TYPE: PRT
<213> ORGANISM: homo sapien

<400> SEQUENCE: 1493

Leu Ile Thr Ala Ala Val Gly Val Ala Val
1               5                   10

<210> SEQ ID NO 1494
<211> LENGTH: 10
<212> TYPE: PRT
<213> ORGANISM: homo sapien

<400> SEQUENCE: 1494

Ala Val Arg Ala Ala Phe Val His Ala Leu
1               5                   10

<210> SEQ ID NO 1495
<211> LENGTH: 10
<212> TYPE: PRT
<213> ORGANISM: homo sapien
```

```
<400> SEQUENCE: 1495

Lys Ile Ala Asp Pro Ile Cys Thr Tyr Val
 1               5                  10

<210> SEQ ID NO 1496
<211> LENGTH: 10
<212> TYPE: PRT
<213> ORGANISM: homo sapien

<400> SEQUENCE: 1496

Ser Val Glu Asp Leu Asn Ile Trp Ser Leu
 1               5                  10

<210> SEQ ID NO 1497
<211> LENGTH: 10
<212> TYPE: PRT
<213> ORGANISM: homo sapien

<400> SEQUENCE: 1497

Leu Val Gly Gly Tyr Ile Ala Asn Ser Leu
 1               5                  10

<210> SEQ ID NO 1498
<211> LENGTH: 10
<212> TYPE: PRT
<213> ORGANISM: homo sapien

<400> SEQUENCE: 1498

Phe Thr Phe Gly Phe His Arg Leu Glu Val
 1               5                  10

<210> SEQ ID NO 1499
<211> LENGTH: 10
<212> TYPE: PRT
<213> ORGANISM: homo sapien

<400> SEQUENCE: 1499

Leu Leu Val Tyr Ile Leu Met Gly Phe Leu
 1               5                  10

<210> SEQ ID NO 1500
<211> LENGTH: 10
<212> TYPE: PRT
<213> ORGANISM: homo sapien

<400> SEQUENCE: 1500

Ala Ala Val Gly Val Ala Val Asn Val Ile
 1               5                  10

<210> SEQ ID NO 1501
<211> LENGTH: 10
<212> TYPE: PRT
<213> ORGANISM: homo sapien

<400> SEQUENCE: 1501

Ala Ala Phe Val His Ala Leu Gly Asp Leu
 1               5                  10

<210> SEQ ID NO 1502
<211> LENGTH: 10
<212> TYPE: PRT
<213> ORGANISM: homo sapien

<400> SEQUENCE: 1502
```

-continued

```
Thr Leu Gln Ala Asp Asp Ser Leu Leu
1               5               10

<210> SEQ ID NO 1503
<211> LENGTH: 10
<212> TYPE: PRT
<213> ORGANISM: homo sapien

<400> SEQUENCE: 1503

Leu Thr Asn Ser Gln Leu Ser Leu Lys Val
1               5               10

<210> SEQ ID NO 1504
<211> LENGTH: 10
<212> TYPE: PRT
<213> ORGANISM: homo sapien

<400> SEQUENCE: 1504

Val Lys Ala Arg Leu Thr Ile Ala Ala Val
1               5               10

<210> SEQ ID NO 1505
<211> LENGTH: 10
<212> TYPE: PRT
<213> ORGANISM: homo sapien

<400> SEQUENCE: 1505

Leu Tyr Leu Leu Phe Met Ile Gly Glu Leu
1               5               10

<210> SEQ ID NO 1506
<211> LENGTH: 10
<212> TYPE: PRT
<213> ORGANISM: homo sapien

<400> SEQUENCE: 1506

His Met Leu Thr Asp Leu Ser Ala Ile Ile
1               5               10

<210> SEQ ID NO 1507
<211> LENGTH: 10
<212> TYPE: PRT
<213> ORGANISM: homo sapien

<400> SEQUENCE: 1507

Met Leu Thr Asp Leu Ser Ala Ile Ile Leu
1               5               10

<210> SEQ ID NO 1508
<211> LENGTH: 10
<212> TYPE: PRT
<213> ORGANISM: homo sapien

<400> SEQUENCE: 1508

Leu Met Gly Phe Leu Leu Tyr Glu Ala Val
1               5               10

<210> SEQ ID NO 1509
<211> LENGTH: 10
<212> TYPE: PRT
<213> ORGANISM: homo sapien

<400> SEQUENCE: 1509

Phe Leu Leu Tyr Glu Ala Val Gln Arg Thr
1               5               10
```

```
<210> SEQ ID NO 1510
<211> LENGTH: 10
<212> TYPE: PRT
<213> ORGANISM: homo sapien

<400> SEQUENCE: 1510

Met Leu Ile Thr Ala Ala Val Gly Val Ala
 1               5                  10

<210> SEQ ID NO 1511
<211> LENGTH: 10
<212> TYPE: PRT
<213> ORGANISM: homo sapien

<400> SEQUENCE: 1511

Ile Ile Arg Phe Lys Pro Glu Tyr Lys Ile
 1               5                  10

<210> SEQ ID NO 1512
<211> LENGTH: 10
<212> TYPE: PRT
<213> ORGANISM: homo sapien

<400> SEQUENCE: 1512

Leu Leu Val Ala Phe Thr Thr Phe Arg Ile
 1               5                  10

<210> SEQ ID NO 1513
<211> LENGTH: 10
<212> TYPE: PRT
<213> ORGANISM: homo sapien

<400> SEQUENCE: 1513

His Leu Asn Val Asp Tyr Ile Lys Glu Ala
 1               5                  10

<210> SEQ ID NO 1514
<211> LENGTH: 10
<212> TYPE: PRT
<213> ORGANISM: homo sapien

<400> SEQUENCE: 1514

Ser Leu Thr Ser Gly Lys Ser Thr Ala Ile
 1               5                  10

<210> SEQ ID NO 1515
<211> LENGTH: 10
<212> TYPE: PRT
<213> ORGANISM: homo sapien

<400> SEQUENCE: 1515

Leu Thr Ser Gly Lys Ser Thr Ala Ile Val
 1               5                  10

<210> SEQ ID NO 1516
<211> LENGTH: 10
<212> TYPE: PRT
<213> ORGANISM: homo sapien

<400> SEQUENCE: 1516

Ser Thr Ala Ile Val His Ile Gln Leu Ile
 1               5                  10
```

```
<210> SEQ ID NO 1517
<211> LENGTH: 10
<212> TYPE: PRT
<213> ORGANISM: homo sapien

<400> SEQUENCE: 1517

Ala Leu His Met Leu Thr Asp Leu Ser Ala
1               5                   10

<210> SEQ ID NO 1518
<211> LENGTH: 10
<212> TYPE: PRT
<213> ORGANISM: homo sapien

<400> SEQUENCE: 1518

Thr Asp Leu Ser Ala Ile Ile Leu Thr Leu
1               5                   10

<210> SEQ ID NO 1519
<211> LENGTH: 10
<212> TYPE: PRT
<213> ORGANISM: homo sapien

<400> SEQUENCE: 1519

Leu Ser Ala Met Ile Ser Val Leu Leu Val
1               5                   10

<210> SEQ ID NO 1520
<211> LENGTH: 10
<212> TYPE: PRT
<213> ORGANISM: homo sapien

<400> SEQUENCE: 1520

Asp Leu Val Gln Ser Val Gly Val Leu Ile
1               5                   10

<210> SEQ ID NO 1521
<211> LENGTH: 10
<212> TYPE: PRT
<213> ORGANISM: homo sapien

<400> SEQUENCE: 1521

Ala Ala Val Leu Tyr Leu Leu Phe Met Ile
1               5                   10

<210> SEQ ID NO 1522
<211> LENGTH: 10
<212> TYPE: PRT
<213> ORGANISM: homo sapien

<400> SEQUENCE: 1522

Phe Met Ile Gly Glu Leu Val Gly Gly Tyr
1               5                   10

<210> SEQ ID NO 1523
<211> LENGTH: 10
<212> TYPE: PRT
<213> ORGANISM: homo sapien

<400> SEQUENCE: 1523

Met Ile Gly Glu Leu Val Gly Gly Tyr Ile
1               5                   10

<210> SEQ ID NO 1524
<211> LENGTH: 10
```

-continued

```
<212> TYPE: PRT
<213> ORGANISM: homo sapien

<400> SEQUENCE: 1524

Ala Ile Ile Leu Thr Leu Leu Ala Leu Trp
 1               5                  10

<210> SEQ ID NO 1525
<211> LENGTH: 10
<212> TYPE: PRT
<213> ORGANISM: homo sapien

<400> SEQUENCE: 1525

Thr Leu Leu Ala Leu Trp Leu Ser Ser Lys
 1               5                  10

<210> SEQ ID NO 1526
<211> LENGTH: 10
<212> TYPE: PRT
<213> ORGANISM: homo sapien

<400> SEQUENCE: 1526

Val Leu Leu Val Tyr Ile Leu Met Gly Phe
 1               5                  10

<210> SEQ ID NO 1527
<211> LENGTH: 10
<212> TYPE: PRT
<213> ORGANISM: homo sapien

<400> SEQUENCE: 1527

Thr Ala Ala Val Gly Val Ala Val Asn Val
 1               5                  10

<210> SEQ ID NO 1528
<211> LENGTH: 10
<212> TYPE: PRT
<213> ORGANISM: homo sapien

<400> SEQUENCE: 1528

Asp Thr Val Val Ile Ile Leu Glu Gly Val
 1               5                  10

<210> SEQ ID NO 1529
<211> LENGTH: 10
<212> TYPE: PRT
<213> ORGANISM: homo sapien

<400> SEQUENCE: 1529

Val Ile Ile Leu Glu Gly Val Pro Ser His
 1               5                  10

<210> SEQ ID NO 1530
<211> LENGTH: 10
<212> TYPE: PRT
<213> ORGANISM: homo sapien

<400> SEQUENCE: 1530

Leu Pro Leu Thr Asn Ser Gln Leu Ser Leu
 1               5                  10

<210> SEQ ID NO 1531
<211> LENGTH: 10
<212> TYPE: PRT
<213> ORGANISM: homo sapien
```

```
<400> SEQUENCE: 1531

Lys Ala Arg Leu Thr Ile Ala Ala Val Leu
1               5                   10

<210> SEQ ID NO 1532
<211> LENGTH: 10
<212> TYPE: PRT
<213> ORGANISM: homo sapien

<400> SEQUENCE: 1532

Ile Ala Ala Val Leu Tyr Leu Leu Phe Met
1               5                   10

<210> SEQ ID NO 1533
<211> LENGTH: 10
<212> TYPE: PRT
<213> ORGANISM: homo sapien

<400> SEQUENCE: 1533

Ala Leu Trp Leu Ser Ser Lys Ser Pro Thr
1               5                   10

<210> SEQ ID NO 1534
<211> LENGTH: 10
<212> TYPE: PRT
<213> ORGANISM: homo sapien

<400> SEQUENCE: 1534

Glu Val Leu Ser Ala Met Ile Ser Val Leu
1               5                   10

<210> SEQ ID NO 1535
<211> LENGTH: 10
<212> TYPE: PRT
<213> ORGANISM: homo sapien

<400> SEQUENCE: 1535

Leu Val Tyr Ile Leu Met Gly Phe Leu Leu
1               5                   10

<210> SEQ ID NO 1536
<211> LENGTH: 10
<212> TYPE: PRT
<213> ORGANISM: homo sapien

<400> SEQUENCE: 1536

Tyr Ile Leu Met Gly Phe Leu Leu Tyr Glu
1               5                   10

<210> SEQ ID NO 1537
<211> LENGTH: 10
<212> TYPE: PRT
<213> ORGANISM: homo sapien

<400> SEQUENCE: 1537

Ala Val Asn Val Ile Met Gly Phe Leu Leu
1               5                   10

<210> SEQ ID NO 1538
<211> LENGTH: 10
<212> TYPE: PRT
<213> ORGANISM: homo sapien

<400> SEQUENCE: 1538
```

Val Ile Met Gly Phe Leu Leu Asn Gln Ser
1               5                   10

<210> SEQ ID NO 1539
<211> LENGTH: 10
<212> TYPE: PRT
<213> ORGANISM: homo sapien

<400> SEQUENCE: 1539

Gly Asp Leu Val Gln Ser Val Gly Val Leu
1               5                   10

<210> SEQ ID NO 1540
<211> LENGTH: 10
<212> TYPE: PRT
<213> ORGANISM: homo sapien

<400> SEQUENCE: 1540

Val Leu Ile Ala Ala Tyr Ile Ile Arg Phe
1               5                   10

<210> SEQ ID NO 1541
<211> LENGTH: 10
<212> TYPE: PRT
<213> ORGANISM: homo sapien

<400> SEQUENCE: 1541

Asp Pro Ile Cys Thr Tyr Val Phe Ser Leu
1               5                   10

<210> SEQ ID NO 1542
<211> LENGTH: 10
<212> TYPE: PRT
<213> ORGANISM: homo sapien

<400> SEQUENCE: 1542

Tyr Val Phe Ser Leu Leu Val Ala Phe Thr
1               5                   10

<210> SEQ ID NO 1543
<211> LENGTH: 10
<212> TYPE: PRT
<213> ORGANISM: homo sapien

<400> SEQUENCE: 1543

Thr Thr Phe Arg Ile Ile Trp Asp Thr Val
1               5                   10

<210> SEQ ID NO 1544
<211> LENGTH: 10
<212> TYPE: PRT
<213> ORGANISM: homo sapien

<400> SEQUENCE: 1544

Lys Glu Ala Leu Met Lys Ile Glu Asp Val
1               5                   10

<210> SEQ ID NO 1545
<211> LENGTH: 10
<212> TYPE: PRT
<213> ORGANISM: homo sapien

<400> SEQUENCE: 1545

Asn Thr Phe Gly Met Tyr Arg Cys Thr Ile

-continued

```
  1               5                  10
```

<210> SEQ ID NO 1546
<211> LENGTH: 10
<212> TYPE: PRT
<213> ORGANISM: homo sapien

<400> SEQUENCE: 1546

```
Gly Ala Trp Lys Arg Leu Lys Ser Met Leu
  1               5                  10
```

<210> SEQ ID NO 1547
<211> LENGTH: 10
<212> TYPE: PRT
<213> ORGANISM: homo sapien

<400> SEQUENCE: 1547

```
Tyr Ile Ala Asn Ser Leu Ala Ile Met Thr
  1               5                  10
```

<210> SEQ ID NO 1548
<211> LENGTH: 10
<212> TYPE: PRT
<213> ORGANISM: homo sapien

<400> SEQUENCE: 1548

```
Ser Leu Ala Ile Met Thr Asp Ala Leu His
  1               5                  10
```

<210> SEQ ID NO 1549
<211> LENGTH: 10
<212> TYPE: PRT
<213> ORGANISM: homo sapien

<400> SEQUENCE: 1549

```
Thr Asp Ala Leu His Met Leu Thr Asp Leu
  1               5                  10
```

<210> SEQ ID NO 1550
<211> LENGTH: 10
<212> TYPE: PRT
<213> ORGANISM: homo sapien

<400> SEQUENCE: 1550

```
Leu His Met Leu Thr Asp Leu Ser Ala Ile
  1               5                  10
```

<210> SEQ ID NO 1551
<211> LENGTH: 10
<212> TYPE: PRT
<213> ORGANISM: homo sapien

<400> SEQUENCE: 1551

```
Leu Leu Ala Leu Trp Leu Ser Ser Lys Ser
  1               5                  10
```

<210> SEQ ID NO 1552
<211> LENGTH: 10
<212> TYPE: PRT
<213> ORGANISM: homo sapien

<400> SEQUENCE: 1552

```
His Met Asn Tyr Glu Ile Asn Gly Asp Ile
  1               5                  10
```

<210> SEQ ID NO 1553
<211> LENGTH: 10
<212> TYPE: PRT
<213> ORGANISM: homo sapien

<400> SEQUENCE: 1553

Tyr Glu Ile Asn Gly Asp Ile Met Leu Ile
1               5                   10

<210> SEQ ID NO 1554
<211> LENGTH: 10
<212> TYPE: PRT
<213> ORGANISM: homo sapien

<400> SEQUENCE: 1554

Gly Asp Ile Met Leu Ile Thr Ala Ala Val
1               5                   10

<210> SEQ ID NO 1555
<211> LENGTH: 10
<212> TYPE: PRT
<213> ORGANISM: homo sapien

<400> SEQUENCE: 1555

Ser Val Gly Val Leu Ile Ala Ala Tyr Ile
1               5                   10

<210> SEQ ID NO 1556
<211> LENGTH: 10
<212> TYPE: PRT
<213> ORGANISM: homo sapien

<400> SEQUENCE: 1556

Leu Ile Ala Ala Tyr Ile Ile Arg Phe Lys
1               5                   10

<210> SEQ ID NO 1557
<211> LENGTH: 10
<212> TYPE: PRT
<213> ORGANISM: homo sapien

<400> SEQUENCE: 1557

Ile Glu Asp Val Tyr Ser Val Glu Asp Leu
1               5                   10

<210> SEQ ID NO 1558
<211> LENGTH: 10
<212> TYPE: PRT
<213> ORGANISM: homo sapien

<400> SEQUENCE: 1558

Asp Leu Asn Ile Trp Ser Leu Thr Ser Gly
1               5                   10

<210> SEQ ID NO 1559
<211> LENGTH: 10
<212> TYPE: PRT
<213> ORGANISM: homo sapien

<400> SEQUENCE: 1559

Gln Leu Ile Pro Gly Ser Ser Ser Lys Trp
1               5                   10

<210> SEQ ID NO 1560

```
<211> LENGTH: 10
<212> TYPE: PRT
<213> ORGANISM: homo sapien

<400> SEQUENCE: 1560

Ile Gln Leu Gln Ser Tyr Arg Gln Glu Val
1               5                   10

<210> SEQ ID NO 1561
<211> LENGTH: 10
<212> TYPE: PRT
<213> ORGANISM: homo sapien

<400> SEQUENCE: 1561

Leu Ser Arg Phe Asn Lys Leu Arg Val Val
1               5                   10

<210> SEQ ID NO 1562
<211> LENGTH: 10
<212> TYPE: PRT
<213> ORGANISM: homo sapien

<400> SEQUENCE: 1562

Ser Arg Phe Asn Lys Leu Arg Val Val Val
1               5                   10

<210> SEQ ID NO 1563
<211> LENGTH: 10
<212> TYPE: PRT
<213> ORGANISM: homo sapien

<400> SEQUENCE: 1563

Pro Thr Leu Gln Ala Asp Asp Asp Ser Leu
1               5                   10

<210> SEQ ID NO 1564
<211> LENGTH: 10
<212> TYPE: PRT
<213> ORGANISM: homo sapien

<400> SEQUENCE: 1564

Leu Leu Asp Gln Asp Leu Pro Leu Thr Asn
1               5                   10

<210> SEQ ID NO 1565
<211> LENGTH: 10
<212> TYPE: PRT
<213> ORGANISM: homo sapien

<400> SEQUENCE: 1565

Glu Ile Leu Lys Gln Arg Lys Val Lys Ala
1               5                   10

<210> SEQ ID NO 1566
<211> LENGTH: 10
<212> TYPE: PRT
<213> ORGANISM: homo sapien

<400> SEQUENCE: 1566

Ile Leu Lys Gln Arg Lys Val Lys Ala Arg
1               5                   10

<210> SEQ ID NO 1567
<211> LENGTH: 10
<212> TYPE: PRT
```

-continued

<213> ORGANISM: homo sapien

<400> SEQUENCE: 1567

Glu Leu Val Gly Gly Tyr Ile Ala Asn Ser
1               5                   10

<210> SEQ ID NO 1568
<211> LENGTH: 10
<212> TYPE: PRT
<213> ORGANISM: homo sapien

<400> SEQUENCE: 1568

Ile Leu Thr Leu Leu Ala Leu Trp Leu Ser
1               5                   10

<210> SEQ ID NO 1569
<211> LENGTH: 10
<212> TYPE: PRT
<213> ORGANISM: homo sapien

<400> SEQUENCE: 1569

Val Ala Val Asn Val Ile Met Gly Phe Leu
1               5                   10

<210> SEQ ID NO 1570
<211> LENGTH: 10
<212> TYPE: PRT
<213> ORGANISM: homo sapien

<400> SEQUENCE: 1570

Leu Gly Asp Leu Val Gln Ser Val Gly Val
1               5                   10

<210> SEQ ID NO 1571
<211> LENGTH: 10
<212> TYPE: PRT
<213> ORGANISM: homo sapien

<400> SEQUENCE: 1571

Leu Val Gln Ser Val Gly Val Leu Ile Ala
1               5                   10

<210> SEQ ID NO 1572
<211> LENGTH: 10
<212> TYPE: PRT
<213> ORGANISM: homo sapien

<400> SEQUENCE: 1572

Pro Ile Cys Thr Tyr Val Phe Ser Leu Leu
1               5                   10

<210> SEQ ID NO 1573
<211> LENGTH: 10
<212> TYPE: PRT
<213> ORGANISM: homo sapien

<400> SEQUENCE: 1573

Leu Val Ala Phe Thr Thr Phe Arg Ile Ile
1               5                   10

<210> SEQ ID NO 1574
<211> LENGTH: 10
<212> TYPE: PRT
<213> ORGANISM: homo sapien -continued

```
<400> SEQUENCE: 1574

Asp Tyr Ile Lys Glu Ala Leu Met Lys Ile
1               5                   10

<210> SEQ ID NO 1575
<211> LENGTH: 10
<212> TYPE: PRT
<213> ORGANISM: homo sapien

<400> SEQUENCE: 1575

Ala Leu Met Lys Ile Glu Asp Val Tyr Ser
1               5                   10

<210> SEQ ID NO 1576
<211> LENGTH: 10
<212> TYPE: PRT
<213> ORGANISM: homo sapien

<400> SEQUENCE: 1576

Ser Gly Lys Ser Thr Ala Ile Val His Ile
1               5                   10

<210> SEQ ID NO 1577
<211> LENGTH: 10
<212> TYPE: PRT
<213> ORGANISM: homo sapien

<400> SEQUENCE: 1577

Phe Ser Asp Glu Ala Gly Asp Glu Gly Leu
1               5                   10

<210> SEQ ID NO 1578
<211> LENGTH: 10
<212> TYPE: PRT
<213> ORGANISM: homo sapien

<400> SEQUENCE: 1578

Gln Asp Leu Pro Leu Thr Asn Ser Gln Leu
1               5                   10

<210> SEQ ID NO 1579
<211> LENGTH: 10
<212> TYPE: PRT
<213> ORGANISM: homo sapien

<400> SEQUENCE: 1579

Leu Lys Gln Arg Lys Val Lys Ala Arg Leu
1               5                   10

<210> SEQ ID NO 1580
<211> LENGTH: 10
<212> TYPE: PRT
<213> ORGANISM: homo sapien

<400> SEQUENCE: 1580

Leu Leu Phe Met Ile Gly Glu Leu Val Gly
1               5                   10

<210> SEQ ID NO 1581
<211> LENGTH: 10
<212> TYPE: PRT
<213> ORGANISM: homo sapien

<400> SEQUENCE: 1581
```

```
Ile Met Thr Asp Ala Leu His Met Leu Thr
1               5                   10
```

<210> SEQ ID NO 1582
<211> LENGTH: 10
<212> TYPE: PRT
<213> ORGANISM: homo sapien

<400> SEQUENCE: 1582

```
Leu Thr Asp Leu Ser Ala Ile Ile Leu Thr
1               5                   10
```

<210> SEQ ID NO 1583
<211> LENGTH: 10
<212> TYPE: PRT
<213> ORGANISM: homo sapien

<400> SEQUENCE: 1583

```
His Arg Leu Glu Val Leu Ser Ala Met Ile
1               5                   10
```

<210> SEQ ID NO 1584
<211> LENGTH: 10
<212> TYPE: PRT
<213> ORGANISM: homo sapien

<400> SEQUENCE: 1584

```
Leu Glu Val Leu Ser Ala Met Ile Ser Val
1               5                   10
```

<210> SEQ ID NO 1585
<211> LENGTH: 10
<212> TYPE: PRT
<213> ORGANISM: homo sapien

<400> SEQUENCE: 1585

```
Ile Thr Ala Ala Val Gly Val Ala Val Asn
1               5                   10
```

<210> SEQ ID NO 1586
<211> LENGTH: 10
<212> TYPE: PRT
<213> ORGANISM: homo sapien

<400> SEQUENCE: 1586

```
Phe Leu Leu Asn Gln Ser Gly His Arg His
1               5                   10
```

<210> SEQ ID NO 1587
<211> LENGTH: 10
<212> TYPE: PRT
<213> ORGANISM: homo sapien

<400> SEQUENCE: 1587

```
Gly His Arg His Ser His Ser His Ser Leu
1               5                   10
```

<210> SEQ ID NO 1588
<211> LENGTH: 10
<212> TYPE: PRT
<213> ORGANISM: homo sapien

<400> SEQUENCE: 1588

```
Arg Asn His Gly Gln Asp Ser Leu Ala Val
1               5                   10
```

<210> SEQ ID NO 1589
<211> LENGTH: 10
<212> TYPE: PRT
<213> ORGANISM: homo sapien

<400> SEQUENCE: 1589

Ser Leu Ala Val Arg Ala Ala Phe Val His
1               5                   10

<210> SEQ ID NO 1590
<211> LENGTH: 10
<212> TYPE: PRT
<213> ORGANISM: homo sapien

<400> SEQUENCE: 1590

Cys Thr Tyr Val Phe Ser Leu Leu Val Ala
1               5                   10

<210> SEQ ID NO 1591
<211> LENGTH: 10
<212> TYPE: PRT
<213> ORGANISM: homo sapien

<400> SEQUENCE: 1591

Ser Leu Leu Val Ala Phe Thr Thr Phe Arg
1               5                   10

<210> SEQ ID NO 1592
<211> LENGTH: 10
<212> TYPE: PRT
<213> ORGANISM: homo sapien

<400> SEQUENCE: 1592

Ile Leu Glu Gly Val Pro Ser His Leu Asn
1               5                   10

<210> SEQ ID NO 1593
<211> LENGTH: 10
<212> TYPE: PRT
<213> ORGANISM: homo sapien

<400> SEQUENCE: 1593

Leu Asn Val Asp Tyr Ile Lys Glu Ala Leu
1               5                   10

<210> SEQ ID NO 1594
<211> LENGTH: 10
<212> TYPE: PRT
<213> ORGANISM: homo sapien

<400> SEQUENCE: 1594

Ala Ile Val His Ile Gln Leu Ile Pro Gly
1               5                   10

<210> SEQ ID NO 1595
<211> LENGTH: 10
<212> TYPE: PRT
<213> ORGANISM: homo sapien

<400> SEQUENCE: 1595

Leu Leu Leu Asn Thr Phe Gly Met Tyr Arg
1               5                   10

```
<210> SEQ ID NO 1596
<211> LENGTH: 10
<212> TYPE: PRT
<213> ORGANISM: homo sapien

<400> SEQUENCE: 1596

Leu Leu Asn Thr Phe Gly Met Tyr Arg Cys
1               5                   10

<210> SEQ ID NO 1597
<211> LENGTH: 10
<212> TYPE: PRT
<213> ORGANISM: homo sapien

<400> SEQUENCE: 1597

Gly Met Tyr Arg Cys Thr Ile Gln Leu Gln
1               5                   10

<210> SEQ ID NO 1598
<211> LENGTH: 10
<212> TYPE: PRT
<213> ORGANISM: homo sapien

<400> SEQUENCE: 1598

Met Ala Gly Ser Gly Ala Trp Lys Arg Leu
1               5                   10

<210> SEQ ID NO 1599
<211> LENGTH: 10
<212> TYPE: PRT
<213> ORGANISM: homo sapien

<400> SEQUENCE: 1599

Ser Gly Ala Trp Lys Arg Leu Lys Ser Met
1               5                   10

<210> SEQ ID NO 1600
<211> LENGTH: 10
<212> TYPE: PRT
<213> ORGANISM: homo sapien

<400> SEQUENCE: 1600

Leu Arg Lys Asp Asp Ala Pro Leu Phe Leu
1               5                   10

<210> SEQ ID NO 1601
<211> LENGTH: 10
<212> TYPE: PRT
<213> ORGANISM: homo sapien

<400> SEQUENCE: 1601

Phe Leu Asn Asp Thr Ser Ala Phe Asp Phe
1               5                   10

<210> SEQ ID NO 1602
<211> LENGTH: 10
<212> TYPE: PRT
<213> ORGANISM: homo sapien

<400> SEQUENCE: 1602

Glu Ala Pro Glu Arg Pro Val Asn Gly Ala
1               5                   10

<210> SEQ ID NO 1603
<211> LENGTH: 10
```

```
<212> TYPE: PRT
<213> ORGANISM: homo sapien

<400> SEQUENCE: 1603

Arg Pro Val Asn Gly Ala His Pro Thr Leu
 1               5                  10

<210> SEQ ID NO 1604
<211> LENGTH: 10
<212> TYPE: PRT
<213> ORGANISM: homo sapien

<400> SEQUENCE: 1604

Val Leu Tyr Leu Leu Phe Met Ile Gly Glu
 1               5                  10

<210> SEQ ID NO 1605
<211> LENGTH: 10
<212> TYPE: PRT
<213> ORGANISM: homo sapien

<400> SEQUENCE: 1605

Gly Tyr Ile Ala Asn Ser Leu Ala Ile Met
 1               5                  10

<210> SEQ ID NO 1606
<211> LENGTH: 10
<212> TYPE: PRT
<213> ORGANISM: homo sapien

<400> SEQUENCE: 1606

Ile Ala Asn Ser Leu Ala Ile Met Thr Asp
 1               5                  10

<210> SEQ ID NO 1607
<211> LENGTH: 10
<212> TYPE: PRT
<213> ORGANISM: homo sapien

<400> SEQUENCE: 1607

Asn Ser Leu Ala Ile Met Thr Asp Ala Leu
 1               5                  10

<210> SEQ ID NO 1608
<211> LENGTH: 10
<212> TYPE: PRT
<213> ORGANISM: homo sapien

<400> SEQUENCE: 1608

Leu Ala Ile Met Thr Asp Ala Leu His Met
 1               5                  10

<210> SEQ ID NO 1609
<211> LENGTH: 10
<212> TYPE: PRT
<213> ORGANISM: homo sapien

<400> SEQUENCE: 1609

Lys Arg Phe Thr Phe Gly Phe His Arg Leu
 1               5                  10

<210> SEQ ID NO 1610
<211> LENGTH: 10
<212> TYPE: PRT
<213> ORGANISM: homo sapien
```

-continued

```
<400> SEQUENCE: 1610

Thr Phe Gly Phe His Arg Leu Glu Val Leu
1               5                   10

<210> SEQ ID NO 1611
<211> LENGTH: 10
<212> TYPE: PRT
<213> ORGANISM: homo sapien

<400> SEQUENCE: 1611

Ser Val Leu Leu Val Tyr Ile Leu Met Gly
1               5                   10

<210> SEQ ID NO 1612
<211> LENGTH: 10
<212> TYPE: PRT
<213> ORGANISM: homo sapien

<400> SEQUENCE: 1612

Glu Ile Asn Gly Asp Ile Met Leu Ile Thr
1               5                   10

<210> SEQ ID NO 1613
<211> LENGTH: 10
<212> TYPE: PRT
<213> ORGANISM: homo sapien

<400> SEQUENCE: 1613

Ile Asn Gly Asp Ile Met Leu Ile Thr Ala
1               5                   10

<210> SEQ ID NO 1614
<211> LENGTH: 10
<212> TYPE: PRT
<213> ORGANISM: homo sapien

<400> SEQUENCE: 1614

Leu Leu Asn Gln Ser Gly His Arg His Ser
1               5                   10

<210> SEQ ID NO 1615
<211> LENGTH: 10
<212> TYPE: PRT
<213> ORGANISM: homo sapien

<400> SEQUENCE: 1615

Asp Ser Leu Ala Val Arg Ala Ala Phe Val
1               5                   10

<210> SEQ ID NO 1616
<211> LENGTH: 10
<212> TYPE: PRT
<213> ORGANISM: homo sapien

<400> SEQUENCE: 1616

Ala Leu Gly Asp Leu Val Gln Ser Val Gly
1               5                   10

<210> SEQ ID NO 1617
<211> LENGTH: 10
<212> TYPE: PRT
<213> ORGANISM: homo sapien

<400> SEQUENCE: 1617
```

-continued

```
Phe Arg Ile Ile Trp Asp Thr Val Val Ile
1               5                   10

<210> SEQ ID NO 1618
<211> LENGTH: 10
<212> TYPE: PRT
<213> ORGANISM: homo sapien

<400> SEQUENCE: 1618

Leu Glu Gly Val Pro Ser His Leu Asn Val
1               5                   10

<210> SEQ ID NO 1619
<211> LENGTH: 10
<212> TYPE: PRT
<213> ORGANISM: homo sapien

<400> SEQUENCE: 1619

Val Pro Ser His Leu Asn Val Asp Tyr Ile
1               5                   10

<210> SEQ ID NO 1620
<211> LENGTH: 10
<212> TYPE: PRT
<213> ORGANISM: homo sapien

<400> SEQUENCE: 1620

Lys Ile Glu Asp Val Tyr Ser Val Glu Asp
1               5                   10

<210> SEQ ID NO 1621
<211> LENGTH: 10
<212> TYPE: PRT
<213> ORGANISM: homo sapien

<400> SEQUENCE: 1621

Asp Val Tyr Ser Val Glu Asp Leu Asn Ile
1               5                   10

<210> SEQ ID NO 1622
<211> LENGTH: 10
<212> TYPE: PRT
<213> ORGANISM: homo sapien

<400> SEQUENCE: 1622

Ser Lys Ala Asn His Leu Leu Leu Asn Thr
1               5                   10

<210> SEQ ID NO 1623
<211> LENGTH: 10
<212> TYPE: PRT
<213> ORGANISM: homo sapien

<400> SEQUENCE: 1623

Lys Ala Asn His Leu Leu Leu Asn Thr Phe
1               5                   10

<210> SEQ ID NO 1624
<211> LENGTH: 10
<212> TYPE: PRT
<213> ORGANISM: homo sapien

<400> SEQUENCE: 1624

Lys Val Lys Ala Arg Leu Thr Ile Ala Ala
```

```
                1               5                   10

<210> SEQ ID NO 1625
<211> LENGTH: 10
<212> TYPE: PRT
<213> ORGANISM: homo sapien

<400> SEQUENCE: 1625

Asn Gly Asp Ile Met Leu Ile Thr Ala Ala
 1               5                   10

<210> SEQ ID NO 1626
<211> LENGTH: 10
<212> TYPE: PRT
<213> ORGANISM: homo sapien

<400> SEQUENCE: 1626

Gly Gln Asp Ser Leu Ala Val Arg Ala Ala
 1               5                   10

<210> SEQ ID NO 1627
<211> LENGTH: 10
<212> TYPE: PRT
<213> ORGANISM: homo sapien

<400> SEQUENCE: 1627

Val Gln Ser Val Gly Val Leu Ile Ala Ala
 1               5                   10

<210> SEQ ID NO 1628
<211> LENGTH: 10
<212> TYPE: PRT
<213> ORGANISM: homo sapien

<400> SEQUENCE: 1628

Val Lys Ala Arg Leu Thr Ile Ala Ala Val
 1               5                   10

<210> SEQ ID NO 1629
<211> LENGTH: 10
<212> TYPE: PRT
<213> ORGANISM: homo sapien

<400> SEQUENCE: 1629

Gly Asp Ile Met Leu Ile Thr Ala Ala Val
 1               5                   10

<210> SEQ ID NO 1630
<211> LENGTH: 10
<212> TYPE: PRT
<213> ORGANISM: homo sapien

<400> SEQUENCE: 1630

Gln Asp Ser Leu Ala Val Arg Ala Ala Phe
 1               5                   10

<210> SEQ ID NO 1631
<211> LENGTH: 10
<212> TYPE: PRT
<213> ORGANISM: homo sapien

<400> SEQUENCE: 1631

Gln Ser Val Gly Val Leu Ile Ala Ala Tyr
 1               5                   10
```

<210> SEQ ID NO 1632
<211> LENGTH: 10
<212> TYPE: PRT
<213> ORGANISM: homo sapien

<400> SEQUENCE: 1632

Leu Lys Ser Met Leu Arg Lys Asp Asp Ala
1               5                   10

<210> SEQ ID NO 1633
<211> LENGTH: 10
<212> TYPE: PRT
<213> ORGANISM: homo sapien

<400> SEQUENCE: 1633

Ala Pro Leu Phe Leu Asn Asp Thr Ser Ala
1               5                   10

<210> SEQ ID NO 1634
<211> LENGTH: 10
<212> TYPE: PRT
<213> ORGANISM: homo sapien

<400> SEQUENCE: 1634

Thr Ser Ala Phe Asp Phe Ser Asp Glu Ala
1               5                   10

<210> SEQ ID NO 1635
<211> LENGTH: 10
<212> TYPE: PRT
<213> ORGANISM: homo sapien

<400> SEQUENCE: 1635

Arg Phe Asn Lys Leu Arg Val Val Val Ala
1               5                   10

<210> SEQ ID NO 1636
<211> LENGTH: 10
<212> TYPE: PRT
<213> ORGANISM: homo sapien

<400> SEQUENCE: 1636

Val Val Val Ala Asp Asp Gly Ser Glu Ala
1               5                   10

<210> SEQ ID NO 1637
<211> LENGTH: 10
<212> TYPE: PRT
<213> ORGANISM: homo sapien

<400> SEQUENCE: 1637

Glu Ala Pro Glu Arg Pro Val Asn Gly Ala
1               5                   10

<210> SEQ ID NO 1638
<211> LENGTH: 10
<212> TYPE: PRT
<213> ORGANISM: homo sapien

<400> SEQUENCE: 1638

Val Asn Gly Ala His Pro Thr Leu Gln Ala
1               5                   10

<210> SEQ ID NO 1639

```
<211> LENGTH: 10
<212> TYPE: PRT
<213> ORGANISM: homo sapien

<400> SEQUENCE: 1639

Glu Ile Leu Lys Gln Arg Lys Val Lys Ala
1               5                   10

<210> SEQ ID NO 1640
<211> LENGTH: 10
<212> TYPE: PRT
<213> ORGANISM: homo sapien

<400> SEQUENCE: 1640

Arg Lys Val Lys Ala Arg Leu Thr Ile Ala
1               5                   10

<210> SEQ ID NO 1641
<211> LENGTH: 10
<212> TYPE: PRT
<213> ORGANISM: homo sapien

<400> SEQUENCE: 1641

Ile Gly Glu Leu Val Gly Gly Tyr Ile Ala
1               5                   10

<210> SEQ ID NO 1642
<211> LENGTH: 10
<212> TYPE: PRT
<213> ORGANISM: homo sapien

<400> SEQUENCE: 1642

Val Gly Gly Tyr Ile Ala Asn Ser Leu Ala
1               5                   10

<210> SEQ ID NO 1643
<211> LENGTH: 10
<212> TYPE: PRT
<213> ORGANISM: homo sapien

<400> SEQUENCE: 1643

Ala Asn Ser Leu Ala Ile Met Thr Asp Ala
1               5                   10

<210> SEQ ID NO 1644
<211> LENGTH: 10
<212> TYPE: PRT
<213> ORGANISM: homo sapien

<400> SEQUENCE: 1644

Ala Leu His Met Leu Thr Asp Leu Ser Ala
1               5                   10

<210> SEQ ID NO 1645
<211> LENGTH: 10
<212> TYPE: PRT
<213> ORGANISM: homo sapien

<400> SEQUENCE: 1645

Leu Ser Ala Ile Ile Leu Thr Leu Leu Ala
1               5                   10

<210> SEQ ID NO 1646
<211> LENGTH: 10
<212> TYPE: PRT
```

<213> ORGANISM: homo sapien

<400> SEQUENCE: 1646

Gly Phe His Arg Leu Glu Val Leu Ser Ala
1               5                   10

<210> SEQ ID NO 1647
<211> LENGTH: 10
<212> TYPE: PRT
<213> ORGANISM: homo sapien

<400> SEQUENCE: 1647

Ile Leu Met Gly Phe Leu Leu Tyr Glu Ala
1               5                   10

<210> SEQ ID NO 1648
<211> LENGTH: 10
<212> TYPE: PRT
<213> ORGANISM: homo sapien

<400> SEQUENCE: 1648

Ile Asn Gly Asp Ile Met Leu Ile Thr Ala
1               5                   10

<210> SEQ ID NO 1649
<211> LENGTH: 10
<212> TYPE: PRT
<213> ORGANISM: homo sapien

<400> SEQUENCE: 1649

Met Leu Ile Thr Ala Ala Val Gly Val Ala
1               5                   10

<210> SEQ ID NO 1650
<211> LENGTH: 10
<212> TYPE: PRT
<213> ORGANISM: homo sapien

<400> SEQUENCE: 1650

Glu Arg Asn His Gly Gln Asp Ser Leu Ala
1               5                   10

<210> SEQ ID NO 1651
<211> LENGTH: 10
<212> TYPE: PRT
<213> ORGANISM: homo sapien

<400> SEQUENCE: 1651

His Gly Gln Asp Ser Leu Ala Val Arg Ala
1               5                   10

<210> SEQ ID NO 1652
<211> LENGTH: 10
<212> TYPE: PRT
<213> ORGANISM: homo sapien

<400> SEQUENCE: 1652

Leu Ala Val Arg Ala Ala Phe Val His Ala
1               5                   10

<210> SEQ ID NO 1653
<211> LENGTH: 10
<212> TYPE: PRT
<213> ORGANISM: homo sapien

```
<400> SEQUENCE: 1653

Leu Val Gln Ser Val Gly Val Leu Ile Ala
 1               5                  10

<210> SEQ ID NO 1654
<211> LENGTH: 10
<212> TYPE: PRT
<213> ORGANISM: homo sapien

<400> SEQUENCE: 1654

Ile Arg Phe Lys Pro Glu Tyr Lys Ile Ala
 1               5                  10

<210> SEQ ID NO 1655
<211> LENGTH: 10
<212> TYPE: PRT
<213> ORGANISM: homo sapien

<400> SEQUENCE: 1655

Cys Thr Tyr Val Phe Ser Leu Leu Val Ala
 1               5                  10

<210> SEQ ID NO 1656
<211> LENGTH: 10
<212> TYPE: PRT
<213> ORGANISM: homo sapien

<400> SEQUENCE: 1656

His Leu Asn Val Asp Tyr Ile Lys Glu Ala
 1               5                  10

<210> SEQ ID NO 1657
<211> LENGTH: 10
<212> TYPE: PRT
<213> ORGANISM: homo sapien

<400> SEQUENCE: 1657

Trp Ser Leu Thr Ser Gly Lys Ser Thr Ala
 1               5                  10

<210> SEQ ID NO 1658
<211> LENGTH: 10
<212> TYPE: PRT
<213> ORGANISM: homo sapien

<400> SEQUENCE: 1658

Ser Lys Trp Glu Glu Val Gln Ser Lys Ala
 1               5                  10

<210> SEQ ID NO 1659
<211> LENGTH: 10
<212> TYPE: PRT
<213> ORGANISM: homo sapien

<400> SEQUENCE: 1659

Tyr Arg Gln Glu Val Asp Arg Thr Cys Ala
 1               5                  10

<210> SEQ ID NO 1660
<211> LENGTH: 10
<212> TYPE: PRT
<213> ORGANISM: homo sapien

<400> SEQUENCE: 1660
```

-continued

Lys Ser Met Leu Arg Lys Asp Asp Ala Pro
1               5                   10

<210> SEQ ID NO 1661
<211> LENGTH: 10
<212> TYPE: PRT
<213> ORGANISM: homo sapien

<400> SEQUENCE: 1661

Pro Leu Phe Leu Asn Asp Thr Ser Ala Phe
1               5                   10

<210> SEQ ID NO 1662
<211> LENGTH: 10
<212> TYPE: PRT
<213> ORGANISM: homo sapien

<400> SEQUENCE: 1662

Ser Ala Phe Asp Phe Ser Asp Glu Ala Gly
1               5                   10

<210> SEQ ID NO 1663
<211> LENGTH: 10
<212> TYPE: PRT
<213> ORGANISM: homo sapien

<400> SEQUENCE: 1663

Phe Asn Lys Leu Arg Val Val Val Ala Asp
1               5                   10

<210> SEQ ID NO 1664
<211> LENGTH: 10
<212> TYPE: PRT
<213> ORGANISM: homo sapien

<400> SEQUENCE: 1664

Val Val Ala Asp Asp Gly Ser Glu Ala Pro
1               5                   10

<210> SEQ ID NO 1665
<211> LENGTH: 10
<212> TYPE: PRT
<213> ORGANISM: homo sapien

<400> SEQUENCE: 1665

Ala Pro Glu Arg Pro Val Asn Gly Ala His
1               5                   10

<210> SEQ ID NO 1666
<211> LENGTH: 10
<212> TYPE: PRT
<213> ORGANISM: homo sapien

<400> SEQUENCE: 1666

Asn Gly Ala His Pro Thr Leu Gln Ala Asp
1               5                   10

<210> SEQ ID NO 1667
<211> LENGTH: 10
<212> TYPE: PRT
<213> ORGANISM: homo sapien

<400> SEQUENCE: 1667

Ile Leu Lys Gln Arg Lys Val Lys Ala Arg
1               5                   10

<210> SEQ ID NO 1668
<211> LENGTH: 10
<212> TYPE: PRT
<213> ORGANISM: homo sapien

<400> SEQUENCE: 1668

Gly Glu Leu Val Gly Gly Tyr Ile Ala Asn
1               5                   10

<210> SEQ ID NO 1669
<211> LENGTH: 10
<212> TYPE: PRT
<213> ORGANISM: homo sapien

<400> SEQUENCE: 1669

Gly Gly Tyr Ile Ala Asn Ser Leu Ala Ile
1               5                   10

<210> SEQ ID NO 1670
<211> LENGTH: 10
<212> TYPE: PRT
<213> ORGANISM: homo sapien

<400> SEQUENCE: 1670

Asn Ser Leu Ala Ile Met Thr Asp Ala Leu
1               5                   10

<210> SEQ ID NO 1671
<211> LENGTH: 10
<212> TYPE: PRT
<213> ORGANISM: homo sapien

<400> SEQUENCE: 1671

Leu His Met Leu Thr Asp Leu Ser Ala Ile
1               5                   10

<210> SEQ ID NO 1672
<211> LENGTH: 10
<212> TYPE: PRT
<213> ORGANISM: homo sapien

<400> SEQUENCE: 1672

Ser Ala Ile Ile Leu Thr Leu Leu Ala Leu
1               5                   10

<210> SEQ ID NO 1673
<211> LENGTH: 10
<212> TYPE: PRT
<213> ORGANISM: homo sapien

<400> SEQUENCE: 1673

Phe His Arg Leu Glu Val Leu Ser Ala Met
1               5                   10

<210> SEQ ID NO 1674
<211> LENGTH: 10
<212> TYPE: PRT
<213> ORGANISM: homo sapien

<400> SEQUENCE: 1674

Leu Met Gly Phe Leu Leu Tyr Glu Ala Val
1               5                   10

```
<210> SEQ ID NO 1675
<211> LENGTH: 10
<212> TYPE: PRT
<213> ORGANISM: homo sapien

<400> SEQUENCE: 1675

Leu Ile Thr Ala Ala Val Gly Val Ala Val
1               5                   10

<210> SEQ ID NO 1676
<211> LENGTH: 10
<212> TYPE: PRT
<213> ORGANISM: homo sapien

<400> SEQUENCE: 1676

Arg Asn His Gly Gln Asp Ser Leu Ala Val
1               5                   10

<210> SEQ ID NO 1677
<211> LENGTH: 10
<212> TYPE: PRT
<213> ORGANISM: homo sapien

<400> SEQUENCE: 1677

Ala Val Arg Ala Ala Phe Val His Ala Leu
1               5                   10

<210> SEQ ID NO 1678
<211> LENGTH: 10
<212> TYPE: PRT
<213> ORGANISM: homo sapien

<400> SEQUENCE: 1678

Arg Phe Lys Pro Glu Tyr Lys Ile Ala Asp
1               5                   10

<210> SEQ ID NO 1679
<211> LENGTH: 10
<212> TYPE: PRT
<213> ORGANISM: homo sapien

<400> SEQUENCE: 1679

Thr Tyr Val Phe Ser Leu Leu Val Ala Phe
1               5                   10

<210> SEQ ID NO 1680
<211> LENGTH: 10
<212> TYPE: PRT
<213> ORGANISM: homo sapien

<400> SEQUENCE: 1680

Leu Asn Val Asp Tyr Ile Lys Glu Ala Leu
1               5                   10

<210> SEQ ID NO 1681
<211> LENGTH: 10
<212> TYPE: PRT
<213> ORGANISM: homo sapien

<400> SEQUENCE: 1681

Ser Leu Thr Ser Gly Lys Ser Thr Ala Ile
1               5                   10

<210> SEQ ID NO 1682
<211> LENGTH: 10
```

```
<212> TYPE: PRT
<213> ORGANISM: homo sapien

<400> SEQUENCE: 1682

Lys Trp Glu Glu Val Gln Ser Lys Ala Asn
 1               5                  10

<210> SEQ ID NO 1683
<211> LENGTH: 10
<212> TYPE: PRT
<213> ORGANISM: homo sapien

<400> SEQUENCE: 1683

Arg Gln Glu Val Asp Arg Thr Cys Ala Asn
 1               5                  10

<210> SEQ ID NO 1684
<211> LENGTH: 10
<212> TYPE: PRT
<213> ORGANISM: homo sapien

<400> SEQUENCE: 1684

Val Tyr Ile Leu Met Gly Phe Leu Leu Tyr
 1               5                  10

<210> SEQ ID NO 1685
<211> LENGTH: 10
<212> TYPE: PRT
<213> ORGANISM: homo sapien

<400> SEQUENCE: 1685

Ser Ala Met Ile Ser Val Leu Leu Val Tyr
 1               5                  10

<210> SEQ ID NO 1686
<211> LENGTH: 10
<212> TYPE: PRT
<213> ORGANISM: homo sapien

<400> SEQUENCE: 1686

Met Thr Asp Ala Leu His Met Leu Thr Asp
 1               5                  10

<210> SEQ ID NO 1687
<211> LENGTH: 10
<212> TYPE: PRT
<213> ORGANISM: homo sapien

<400> SEQUENCE: 1687

Leu Thr Asp Leu Ser Ala Ile Ile Leu Thr
 1               5                  10

<210> SEQ ID NO 1688
<211> LENGTH: 10
<212> TYPE: PRT
<213> ORGANISM: homo sapien

<400> SEQUENCE: 1688

Gln Ser Val Gly Val Leu Ile Ala Ala Tyr
 1               5                  10

<210> SEQ ID NO 1689
<211> LENGTH: 10
<212> TYPE: PRT
<213> ORGANISM: homo sapien
```

<400> SEQUENCE: 1689

His Leu Leu Leu Asn Thr Phe Gly Met Tyr
1               5                   10

<210> SEQ ID NO 1690
<211> LENGTH: 10
<212> TYPE: PRT
<213> ORGANISM: homo sapien

<400> SEQUENCE: 1690

Lys Asp Asp Ala Pro Leu Phe Leu Asn Asp
1               5                   10

<210> SEQ ID NO 1691
<211> LENGTH: 10
<212> TYPE: PRT
<213> ORGANISM: homo sapien

<400> SEQUENCE: 1691

Ala Arg Leu Thr Ile Ala Ala Val Leu Tyr
1               5                   10

<210> SEQ ID NO 1692
<211> LENGTH: 10
<212> TYPE: PRT
<213> ORGANISM: homo sapien

<400> SEQUENCE: 1692

Phe Met Ile Gly Glu Leu Val Gly Gly Tyr
1               5                   10

<210> SEQ ID NO 1693
<211> LENGTH: 10
<212> TYPE: PRT
<213> ORGANISM: homo sapien

<400> SEQUENCE: 1693

Leu Leu Asp Gln Asp Leu Pro Leu Thr Asn
1               5                   10

<210> SEQ ID NO 1694
<211> LENGTH: 10
<212> TYPE: PRT
<213> ORGANISM: homo sapien

<400> SEQUENCE: 1694

Tyr Lys Ile Ala Asp Pro Ile Cys Thr Tyr
1               5                   10

<210> SEQ ID NO 1695
<211> LENGTH: 10
<212> TYPE: PRT
<213> ORGANISM: homo sapien

<400> SEQUENCE: 1695

Tyr Arg Cys Thr Ile Gln Leu Gln Ser Tyr
1               5                   10

<210> SEQ ID NO 1696
<211> LENGTH: 10
<212> TYPE: PRT
<213> ORGANISM: homo sapien

<400> SEQUENCE: 1696

```
Gly Ser Glu Ala Pro Glu Arg Pro Val Asn
 1               5                  10

<210> SEQ ID NO 1697
<211> LENGTH: 10
<212> TYPE: PRT
<213> ORGANISM: homo sapien

<400> SEQUENCE: 1697

Gln Ala Asp Asp Ser Leu Leu Asp Gln
 1               5                  10

<210> SEQ ID NO 1698
<211> LENGTH: 10
<212> TYPE: PRT
<213> ORGANISM: homo sapien

<400> SEQUENCE: 1698

Ala Val Gln Arg Thr Ile His Met Asn Tyr
 1               5                  10

<210> SEQ ID NO 1699
<211> LENGTH: 10
<212> TYPE: PRT
<213> ORGANISM: homo sapien

<400> SEQUENCE: 1699

Ala Tyr Ile Ile Arg Phe Lys Pro Glu Tyr
 1               5                  10

<210> SEQ ID NO 1700
<211> LENGTH: 10
<212> TYPE: PRT
<213> ORGANISM: homo sapien

<400> SEQUENCE: 1700

Ile Trp Asp Thr Val Val Ile Ile Leu Glu
 1               5                  10

<210> SEQ ID NO 1701
<211> LENGTH: 10
<212> TYPE: PRT
<213> ORGANISM: homo sapien

<400> SEQUENCE: 1701

Gly Val Pro Ser His Leu Asn Val Asp Tyr
 1               5                  10

<210> SEQ ID NO 1702
<211> LENGTH: 10
<212> TYPE: PRT
<213> ORGANISM: homo sapien

<400> SEQUENCE: 1702

Glu Ala Leu Met Lys Ile Glu Asp Val Tyr
 1               5                  10

<210> SEQ ID NO 1703
<211> LENGTH: 10
<212> TYPE: PRT
<213> ORGANISM: homo sapien

<400> SEQUENCE: 1703

Phe Ser Asp Glu Ala Gly Asp Glu Gly Leu
```

```
                1               5                   10
```

<210> SEQ ID NO 1704
<211> LENGTH: 10
<212> TYPE: PRT
<213> ORGANISM: homo sapien

<400> SEQUENCE: 1704

```
Phe Thr Phe Gly Phe His Arg Leu Glu Val
  1               5                  10
```

<210> SEQ ID NO 1705
<211> LENGTH: 10
<212> TYPE: PRT
<213> ORGANISM: homo sapien

<400> SEQUENCE: 1705

```
Asn Tyr Glu Ile Asn Gly Asp Ile Met Leu
  1               5                  10
```

<210> SEQ ID NO 1706
<211> LENGTH: 10
<212> TYPE: PRT
<213> ORGANISM: homo sapien

<400> SEQUENCE: 1706

```
Ile Ala Asp Pro Ile Cys Thr Tyr Val Phe
  1               5                  10
```

<210> SEQ ID NO 1707
<211> LENGTH: 10
<212> TYPE: PRT
<213> ORGANISM: homo sapien

<400> SEQUENCE: 1707

```
Ser Asp Glu Ala Gly Asp Glu Gly Leu Ser
  1               5                  10
```

<210> SEQ ID NO 1708
<211> LENGTH: 10
<212> TYPE: PRT
<213> ORGANISM: homo sapien

<400> SEQUENCE: 1708

```
Leu Thr Asn Ser Gln Leu Ser Leu Lys Val
  1               5                  10
```

<210> SEQ ID NO 1709
<211> LENGTH: 10
<212> TYPE: PRT
<213> ORGANISM: homo sapien

<400> SEQUENCE: 1709

```
Ile Leu Glu Gly Val Pro Ser His Leu Asn
  1               5                  10
```

<210> SEQ ID NO 1710
<211> LENGTH: 10
<212> TYPE: PRT
<213> ORGANISM: homo sapien

<400> SEQUENCE: 1710

```
Ile Lys Glu Ala Leu Met Lys Ile Glu Asp
  1               5                  10
```

-continued

<210> SEQ ID NO 1711
<211> LENGTH: 10
<212> TYPE: PRT
<213> ORGANISM: homo sapien

<400> SEQUENCE: 1711

Gly Ser Gly Ala Trp Lys Arg Leu Lys Ser
1               5                   10

<210> SEQ ID NO 1712
<211> LENGTH: 10
<212> TYPE: PRT
<213> ORGANISM: homo sapien

<400> SEQUENCE: 1712

Leu Asn Asp Thr Ser Ala Phe Asp Phe Ser
1               5                   10

<210> SEQ ID NO 1713
<211> LENGTH: 10
<212> TYPE: PRT
<213> ORGANISM: homo sapien

<400> SEQUENCE: 1713

Leu Ser Ala Met Ile Ser Val Leu Leu Val
1               5                   10

<210> SEQ ID NO 1714
<211> LENGTH: 10
<212> TYPE: PRT
<213> ORGANISM: homo sapien

<400> SEQUENCE: 1714

Cys Thr Tyr Val Phe Ser Leu Leu Val Ala
1               5                   10

<210> SEQ ID NO 1715
<211> LENGTH: 10
<212> TYPE: PRT
<213> ORGANISM: homo sapien

<400> SEQUENCE: 1715

Val Glu Asp Leu Asn Ile Trp Ser Leu Thr
1               5                   10

<210> SEQ ID NO 1716
<211> LENGTH: 10
<212> TYPE: PRT
<213> ORGANISM: homo sapien

<400> SEQUENCE: 1716

Glu Val Leu Ser Ala Met Ile Ser Val Leu
1               5                   10

<210> SEQ ID NO 1717
<211> LENGTH: 10
<212> TYPE: PRT
<213> ORGANISM: homo sapien

<400> SEQUENCE: 1717

Gly Val Ala Val Asn Val Ile Met Gly Phe
1               5                   10

<210> SEQ ID NO 1718

```
<211> LENGTH: 10
<212> TYPE: PRT
<213> ORGANISM: homo sapien

<400> SEQUENCE: 1718

Asp Leu Ser Ala Ile Ile Leu Thr Leu Leu
 1               5                  10

<210> SEQ ID NO 1719
<211> LENGTH: 10
<212> TYPE: PRT
<213> ORGANISM: homo sapien

<400> SEQUENCE: 1719

Thr Ile Ala Ala Val Leu Tyr Leu Leu Phe
 1               5                  10

<210> SEQ ID NO 1720
<211> LENGTH: 10
<212> TYPE: PRT
<213> ORGANISM: homo sapien

<400> SEQUENCE: 1720

Val Leu Ile Ala Ala Tyr Ile Ile Arg Phe
 1               5                  10

<210> SEQ ID NO 1721
<211> LENGTH: 10
<212> TYPE: PRT
<213> ORGANISM: homo sapien

<400> SEQUENCE: 1721

Glu Val Gln Ser Lys Ala Asn His Leu Leu
 1               5                  10

<210> SEQ ID NO 1722
<211> LENGTH: 10
<212> TYPE: PRT
<213> ORGANISM: homo sapien

<400> SEQUENCE: 1722

Leu Thr Ile Ala Ala Val Leu Tyr Leu Leu
 1               5                  10

<210> SEQ ID NO 1723
<211> LENGTH: 10
<212> TYPE: PRT
<213> ORGANISM: homo sapien

<400> SEQUENCE: 1723

Val Leu Leu Val Tyr Ile Leu Met Gly Phe
 1               5                  10

<210> SEQ ID NO 1724
<211> LENGTH: 10
<212> TYPE: PRT
<213> ORGANISM: homo sapien

<400> SEQUENCE: 1724

Ser Val Glu Asp Leu Asn Ile Trp Ser Leu
 1               5                  10

<210> SEQ ID NO 1725
<211> LENGTH: 10
<212> TYPE: PRT
```

-continued

<213> ORGANISM: homo sapien

<400> SEQUENCE: 1725

Glu Ala Gly Asp Glu Gly Leu Ser Arg Phe
1               5                   10

<210> SEQ ID NO 1726
<211> LENGTH: 10
<212> TYPE: PRT
<213> ORGANISM: homo sapien

<400> SEQUENCE: 1726

Ala Ile Met Thr Asp Ala Leu His Met Leu
1               5                   10

<210> SEQ ID NO 1727
<211> LENGTH: 10
<212> TYPE: PRT
<213> ORGANISM: homo sapien

<400> SEQUENCE: 1727

Ala Val Arg Ala Ala Phe Val His Ala Leu
1               5                   10

<210> SEQ ID NO 1728
<211> LENGTH: 10
<212> TYPE: PRT
<213> ORGANISM: homo sapien

<400> SEQUENCE: 1728

Pro Ile Cys Thr Tyr Val Phe Ser Leu Leu
1               5                   10

<210> SEQ ID NO 1729
<211> LENGTH: 10
<212> TYPE: PRT
<213> ORGANISM: homo sapien

<400> SEQUENCE: 1729

Ile Ile Trp Asp Thr Val Val Ile Ile Leu
1               5                   10

<210> SEQ ID NO 1730
<211> LENGTH: 10
<212> TYPE: PRT
<213> ORGANISM: homo sapien

<400> SEQUENCE: 1730

Gly Val Pro Ser His Leu Asn Val Asp Tyr
1               5                   10

<210> SEQ ID NO 1731
<211> LENGTH: 10
<212> TYPE: PRT
<213> ORGANISM: homo sapien

<400> SEQUENCE: 1731

His Leu Leu Leu Asn Thr Phe Gly Met Tyr
1               5                   10

<210> SEQ ID NO 1732
<211> LENGTH: 10
<212> TYPE: PRT
<213> ORGANISM: homo sapien

```
<400> SEQUENCE: 1732

Pro Leu Phe Leu Asn Asp Thr Ser Ala Phe
1               5                   10

<210> SEQ ID NO 1733
<211> LENGTH: 10
<212> TYPE: PRT
<213> ORGANISM: homo sapien

<400> SEQUENCE: 1733

Glu Leu Val Gly Gly Tyr Ile Ala Asn Ser
1               5                   10

<210> SEQ ID NO 1734
<211> LENGTH: 10
<212> TYPE: PRT
<213> ORGANISM: homo sapien

<400> SEQUENCE: 1734

Met Ile Ser Val Leu Leu Val Tyr Ile Leu
1               5                   10

<210> SEQ ID NO 1735
<211> LENGTH: 10
<212> TYPE: PRT
<213> ORGANISM: homo sapien

<400> SEQUENCE: 1735

Ala Val Gln Arg Thr Ile His Met Asn Tyr
1               5                   10

<210> SEQ ID NO 1736
<211> LENGTH: 10
<212> TYPE: PRT
<213> ORGANISM: homo sapien

<400> SEQUENCE: 1736

Glu Ile Asn Gly Asp Ile Met Leu Ile Thr
1               5                   10

<210> SEQ ID NO 1737
<211> LENGTH: 10
<212> TYPE: PRT
<213> ORGANISM: homo sapien

<400> SEQUENCE: 1737

Ile Ile Leu Glu Gly Val Pro Ser His Leu
1               5                   10

<210> SEQ ID NO 1738
<211> LENGTH: 10
<212> TYPE: PRT
<213> ORGANISM: homo sapien

<400> SEQUENCE: 1738

Asp Thr Ser Ala Phe Asp Phe Ser Asp Glu
1               5                   10

<210> SEQ ID NO 1739
<211> LENGTH: 10
<212> TYPE: PRT
<213> ORGANISM: homo sapien

<400> SEQUENCE: 1739
```

-continued

Leu Val Gly Gly Tyr Ile Ala Asn Ser Leu
 1               5                  10

<210> SEQ ID NO 1740
<211> LENGTH: 10
<212> TYPE: PRT
<213> ORGANISM: homo sapien

<400> SEQUENCE: 1740

Asp Pro Ile Cys Thr Tyr Val Phe Ser Leu
 1               5                  10

<210> SEQ ID NO 1741
<211> LENGTH: 10
<212> TYPE: PRT
<213> ORGANISM: homo sapien

<400> SEQUENCE: 1741

Asp Thr Val Val Ile Ile Leu Glu Gly Val
 1               5                  10

<210> SEQ ID NO 1742
<211> LENGTH: 10
<212> TYPE: PRT
<213> ORGANISM: homo sapien

<400> SEQUENCE: 1742

Met Leu Arg Lys Asp Asp Ala Pro Leu Phe
 1               5                  10

<210> SEQ ID NO 1743
<211> LENGTH: 10
<212> TYPE: PRT
<213> ORGANISM: homo sapien

<400> SEQUENCE: 1743

Pro Thr Leu Gln Ala Asp Asp Ser Leu
 1               5                  10

<210> SEQ ID NO 1744
<211> LENGTH: 10
<212> TYPE: PRT
<213> ORGANISM: homo sapien

<400> SEQUENCE: 1744

Arg Leu Thr Ile Ala Ala Val Leu Tyr Leu
 1               5                  10

<210> SEQ ID NO 1745
<211> LENGTH: 10
<212> TYPE: PRT
<213> ORGANISM: homo sapien

<400> SEQUENCE: 1745

Leu Leu Val Tyr Ile Leu Met Gly Phe Leu
 1               5                  10

<210> SEQ ID NO 1746
<211> LENGTH: 10
<212> TYPE: PRT
<213> ORGANISM: homo sapien

<400> SEQUENCE: 1746

Asn Val Asp Tyr Ile Lys Glu Ala Leu Met
 1               5                  10

<210> SEQ ID NO 1747
<211> LENGTH: 10
<212> TYPE: PRT
<213> ORGANISM: homo sapien

<400> SEQUENCE: 1747

Phe Leu Asn Asp Thr Ser Ala Phe Asp Phe
1               5                   10

<210> SEQ ID NO 1748
<211> LENGTH: 10
<212> TYPE: PRT
<213> ORGANISM: homo sapien

<400> SEQUENCE: 1748

Asp Glu Gly Leu Ser Arg Phe Asn Lys Leu
1               5                   10

<210> SEQ ID NO 1749
<211> LENGTH: 10
<212> TYPE: PRT
<213> ORGANISM: homo sapien

<400> SEQUENCE: 1749

Glu Ile Leu Lys Gln Arg Lys Val Lys Ala
1               5                   10

<210> SEQ ID NO 1750
<211> LENGTH: 10
<212> TYPE: PRT
<213> ORGANISM: homo sapien

<400> SEQUENCE: 1750

Phe Met Ile Gly Glu Leu Val Gly Gly Tyr
1               5                   10

<210> SEQ ID NO 1751
<211> LENGTH: 10
<212> TYPE: PRT
<213> ORGANISM: homo sapien

<400> SEQUENCE: 1751

Ala Val Gly Val Ala Val Asn Val Ile Met
1               5                   10

<210> SEQ ID NO 1752
<211> LENGTH: 10
<212> TYPE: PRT
<213> ORGANISM: homo sapien

<400> SEQUENCE: 1752

Asp Leu Asn Ile Trp Ser Leu Thr Ser Gly
1               5                   10

<210> SEQ ID NO 1753
<211> LENGTH: 10
<212> TYPE: PRT
<213> ORGANISM: homo sapien

<400> SEQUENCE: 1753

Ile Ile Leu Thr Leu Leu Ala Leu Trp Leu
1               5                   10

```
<210> SEQ ID NO 1754
<211> LENGTH: 10
<212> TYPE: PRT
<213> ORGANISM: homo sapien

<400> SEQUENCE: 1754

Thr Phe Gly Phe His Arg Leu Glu Val Leu
 1               5                  10

<210> SEQ ID NO 1755
<211> LENGTH: 10
<212> TYPE: PRT
<213> ORGANISM: homo sapien

<400> SEQUENCE: 1755

Leu Val Tyr Ile Leu Met Gly Phe Leu Leu
 1               5                  10

<210> SEQ ID NO 1756
<211> LENGTH: 10
<212> TYPE: PRT
<213> ORGANISM: homo sapien

<400> SEQUENCE: 1756

Ala Val Asn Val Ile Met Gly Phe Leu Leu
 1               5                  10

<210> SEQ ID NO 1757
<211> LENGTH: 10
<212> TYPE: PRT
<213> ORGANISM: homo sapien

<400> SEQUENCE: 1757

Gln Ser Val Gly Val Leu Ile Ala Ala Tyr
 1               5                  10

<210> SEQ ID NO 1758
<211> LENGTH: 10
<212> TYPE: PRT
<213> ORGANISM: homo sapien

<400> SEQUENCE: 1758

Tyr Val Phe Ser Leu Leu Val Ala Phe Thr
 1               5                  10

<210> SEQ ID NO 1759
<211> LENGTH: 10
<212> TYPE: PRT
<213> ORGANISM: homo sapien

<400> SEQUENCE: 1759

Val Ile Ile Leu Glu Gly Val Pro Ser His
 1               5                  10

<210> SEQ ID NO 1760
<211> LENGTH: 10
<212> TYPE: PRT
<213> ORGANISM: homo sapien

<400> SEQUENCE: 1760

Asp Val Tyr Ser Val Glu Asp Leu Asn Ile
 1               5                  10

<210> SEQ ID NO 1761
<211> LENGTH: 10
```

-continued

<212> TYPE: PRT
<213> ORGANISM: homo sapien

<400> SEQUENCE: 1761

Thr Leu Gln Ala Asp Asp Ser Leu Leu
1               5               10

<210> SEQ ID NO 1762
<211> LENGTH: 10
<212> TYPE: PRT
<213> ORGANISM: homo sapien

<400> SEQUENCE: 1762

Asp Asp Asp Ser Leu Leu Asp Gln Asp Leu
1               5               10

<210> SEQ ID NO 1763
<211> LENGTH: 10
<212> TYPE: PRT
<213> ORGANISM: homo sapien

<400> SEQUENCE: 1763

Met Leu Thr Asp Leu Ser Ala Ile Ile Leu
1               5               10

<210> SEQ ID NO 1764
<211> LENGTH: 10
<212> TYPE: PRT
<213> ORGANISM: homo sapien

<400> SEQUENCE: 1764

Ala Ile Ile Leu Thr Leu Leu Ala Leu Trp
1               5               10

<210> SEQ ID NO 1765
<211> LENGTH: 10
<212> TYPE: PRT
<213> ORGANISM: homo sapien

<400> SEQUENCE: 1765

Val Leu Ser Ala Met Ile Ser Val Leu Leu
1               5               10

<210> SEQ ID NO 1766
<211> LENGTH: 10
<212> TYPE: PRT
<213> ORGANISM: homo sapien

<400> SEQUENCE: 1766

Asp Ile Met Leu Ile Thr Ala Ala Val Gly
1               5               10

<210> SEQ ID NO 1767
<211> LENGTH: 10
<212> TYPE: PRT
<213> ORGANISM: homo sapien

<400> SEQUENCE: 1767

Asn Val Ile Met Gly Phe Leu Leu Asn Gln
1               5               10

<210> SEQ ID NO 1768
<211> LENGTH: 10
<212> TYPE: PRT
<213> ORGANISM: homo sapien -continued

```
<400> SEQUENCE: 1768

Val Ile Met Gly Phe Leu Leu Asn Gln Ser
1               5                   10

<210> SEQ ID NO 1769
<211> LENGTH: 10
<212> TYPE: PRT
<213> ORGANISM: homo sapien

<400> SEQUENCE: 1769

Arg Ile Ile Trp Asp Thr Val Val Ile Ile
1               5                   10

<210> SEQ ID NO 1770
<211> LENGTH: 10
<212> TYPE: PRT
<213> ORGANISM: homo sapien

<400> SEQUENCE: 1770

Tyr Ile Lys Glu Ala Leu Met Lys Ile Glu
1               5                   10

<210> SEQ ID NO 1771
<211> LENGTH: 10
<212> TYPE: PRT
<213> ORGANISM: homo sapien

<400> SEQUENCE: 1771

Glu Val Asp Arg Thr Cys Ala Asn Cys Gln
1               5                   10

<210> SEQ ID NO 1772
<211> LENGTH: 10
<212> TYPE: PRT
<213> ORGANISM: homo sapien

<400> SEQUENCE: 1772

Asp Leu Pro Leu Thr Asn Ser Gln Leu Ser
1               5                   10

<210> SEQ ID NO 1773
<211> LENGTH: 10
<212> TYPE: PRT
<213> ORGANISM: homo sapien

<400> SEQUENCE: 1773

Val Tyr Ile Leu Met Gly Phe Leu Leu Tyr
1               5                   10

<210> SEQ ID NO 1774
<211> LENGTH: 10
<212> TYPE: PRT
<213> ORGANISM: homo sapien

<400> SEQUENCE: 1774

Arg Thr Ile His Met Asn Tyr Glu Ile Asn
1               5                   10

<210> SEQ ID NO 1775
<211> LENGTH: 10
<212> TYPE: PRT
<213> ORGANISM: homo sapien

<400> SEQUENCE: 1775
```

```
Ile Thr Ala Ala Val Gly Val Ala Val Asn
 1               5                  10
```

<210> SEQ ID NO 1776
<211> LENGTH: 10
<212> TYPE: PRT
<213> ORGANISM: homo sapien

<400> SEQUENCE: 1776

```
Asp Leu Val Gln Ser Val Gly Val Leu Ile
 1               5                  10
```

<210> SEQ ID NO 1777
<211> LENGTH: 10
<212> TYPE: PRT
<213> ORGANISM: homo sapien

<400> SEQUENCE: 1777

```
Tyr Lys Ile Ala Asp Pro Ile Cys Thr Tyr
 1               5                  10
```

<210> SEQ ID NO 1778
<211> LENGTH: 10
<212> TYPE: PRT
<213> ORGANISM: homo sapien

<400> SEQUENCE: 1778

```
Thr Tyr Val Phe Ser Leu Leu Val Ala Phe
 1               5                  10
```

<210> SEQ ID NO 1779
<211> LENGTH: 10
<212> TYPE: PRT
<213> ORGANISM: homo sapien

<400> SEQUENCE: 1779

```
Glu Ala Leu Met Lys Ile Glu Asp Val Tyr
 1               5                  10
```

<210> SEQ ID NO 1780
<211> LENGTH: 10
<212> TYPE: PRT
<213> ORGANISM: homo sapien

<400> SEQUENCE: 1780

```
Ser Thr Ala Ile Val His Ile Gln Leu Ile
 1               5                  10
```

<210> SEQ ID NO 1781
<211> LENGTH: 10
<212> TYPE: PRT
<213> ORGANISM: homo sapien

<400> SEQUENCE: 1781

```
Ile Val His Ile Gln Leu Ile Pro Gly Ser
 1               5                  10
```

<210> SEQ ID NO 1782
<211> LENGTH: 10
<212> TYPE: PRT
<213> ORGANISM: homo sapien

<400> SEQUENCE: 1782

Glu Glu Val Gln Ser Lys Ala Asn His Leu

```
                 1               5                  10
```

<210> SEQ ID NO 1783
<211> LENGTH: 10
<212> TYPE: PRT
<213> ORGANISM: homo sapien

<400> SEQUENCE: 1783

```
Tyr Arg Cys Thr Ile Gln Leu Gln Ser Tyr
 1               5                  10
```

<210> SEQ ID NO 1784
<211> LENGTH: 10
<212> TYPE: PRT
<213> ORGANISM: homo sapien

<400> SEQUENCE: 1784

```
Asp Asn Cys Ser Lys Gln Arg Glu Ile Leu
 1               5                  10
```

<210> SEQ ID NO 1785
<211> LENGTH: 10
<212> TYPE: PRT
<213> ORGANISM: homo sapien

<400> SEQUENCE: 1785

```
Ile Leu Lys Gln Arg Lys Val Lys Ala Arg
 1               5                  10
```

<210> SEQ ID NO 1786
<211> LENGTH: 10
<212> TYPE: PRT
<213> ORGANISM: homo sapien

<400> SEQUENCE: 1786

```
Ala Val Leu Tyr Leu Leu Phe Met Ile Gly
 1               5                  10
```

<210> SEQ ID NO 1787
<211> LENGTH: 10
<212> TYPE: PRT
<213> ORGANISM: homo sapien

<400> SEQUENCE: 1787

```
Gly Tyr Ile Ala Asn Ser Leu Ala Ile Met
 1               5                  10
```

<210> SEQ ID NO 1788
<211> LENGTH: 10
<212> TYPE: PRT
<213> ORGANISM: homo sapien

<400> SEQUENCE: 1788

```
Met Thr Asp Ala Leu His Met Leu Thr Asp
 1               5                  10
```

<210> SEQ ID NO 1789
<211> LENGTH: 10
<212> TYPE: PRT
<213> ORGANISM: homo sapien

<400> SEQUENCE: 1789

```
Leu Thr Asp Leu Ser Ala Ile Ile Leu Thr
 1               5                  10
```

<210> SEQ ID NO 1790
<211> LENGTH: 10
<212> TYPE: PRT
<213> ORGANISM: homo sapien

<400> SEQUENCE: 1790

Ser Ala Ile Ile Leu Thr Leu Leu Ala Leu
1               5                   10

<210> SEQ ID NO 1791
<211> LENGTH: 10
<212> TYPE: PRT
<213> ORGANISM: homo sapien

<400> SEQUENCE: 1791

Pro Thr Lys Arg Phe Thr Phe Gly Phe His
1               5                   10

<210> SEQ ID NO 1792
<211> LENGTH: 10
<212> TYPE: PRT
<213> ORGANISM: homo sapien

<400> SEQUENCE: 1792

Lys Arg Phe Thr Phe Gly Phe His Arg Leu
1               5                   10

<210> SEQ ID NO 1793
<211> LENGTH: 10
<212> TYPE: PRT
<213> ORGANISM: homo sapien

<400> SEQUENCE: 1793

Phe Thr Phe Gly Phe His Arg Leu Glu Val
1               5                   10

<210> SEQ ID NO 1794
<211> LENGTH: 10
<212> TYPE: PRT
<213> ORGANISM: homo sapien

<400> SEQUENCE: 1794

Ser Val Leu Leu Val Tyr Ile Leu Met Gly
1               5                   10

<210> SEQ ID NO 1795
<211> LENGTH: 10
<212> TYPE: PRT
<213> ORGANISM: homo sapien

<400> SEQUENCE: 1795

Ile Leu Met Gly Phe Leu Leu Tyr Glu Ala
1               5                   10

<210> SEQ ID NO 1796
<211> LENGTH: 10
<212> TYPE: PRT
<213> ORGANISM: homo sapien

<400> SEQUENCE: 1796

Leu Val Gln Ser Val Gly Val Leu Ile Ala
1               5                   10

<210> SEQ ID NO 1797

```
<211> LENGTH: 10
<212> TYPE: PRT
<213> ORGANISM: homo sapien

<400> SEQUENCE: 1797

Leu Ile Ala Ala Tyr Ile Ile Arg Phe Lys
1               5                   10

<210> SEQ ID NO 1798
<211> LENGTH: 10
<212> TYPE: PRT
<213> ORGANISM: homo sapien

<400> SEQUENCE: 1798

Leu Val Ala Phe Thr Thr Phe Arg Ile Ile
1               5                   10

<210> SEQ ID NO 1799
<211> LENGTH: 10
<212> TYPE: PRT
<213> ORGANISM: homo sapien

<400> SEQUENCE: 1799

Asp Tyr Ile Lys Glu Ala Leu Met Lys Ile
1               5                   10

<210> SEQ ID NO 1800
<211> LENGTH: 10
<212> TYPE: PRT
<213> ORGANISM: homo sapien

<400> SEQUENCE: 1800

Thr Ile Gln Leu Gln Ser Tyr Arg Gln Glu
1               5                   10

<210> SEQ ID NO 1801
<211> LENGTH: 10
<212> TYPE: PRT
<213> ORGANISM: homo sapien

<400> SEQUENCE: 1801

Thr Leu Leu Ala Leu Trp Leu Ser Ser Lys
1               5                   10

<210> SEQ ID NO 1802
<211> LENGTH: 10
<212> TYPE: PRT
<213> ORGANISM: homo sapien

<400> SEQUENCE: 1802

Lys Val Asp Ser Cys Asp Asn Cys Ser Lys
1               5                   10

<210> SEQ ID NO 1803
<211> LENGTH: 10
<212> TYPE: PRT
<213> ORGANISM: homo sapien

<400> SEQUENCE: 1803

Tyr Ile Ile Arg Phe Lys Pro Glu Tyr Lys
1               5                   10

<210> SEQ ID NO 1804
<211> LENGTH: 10
<212> TYPE: PRT
```

<213> ORGANISM: homo sapien

<400> SEQUENCE: 1804

Pro Leu Thr Asn Ser Gln Leu Ser Leu Lys
1               5                   10

<210> SEQ ID NO 1805
<211> LENGTH: 10
<212> TYPE: PRT
<213> ORGANISM: homo sapien

<400> SEQUENCE: 1805

Arg Glu Ile Leu Lys Gln Arg Lys Val Lys
1               5                   10

<210> SEQ ID NO 1806
<211> LENGTH: 10
<212> TYPE: PRT
<213> ORGANISM: homo sapien

<400> SEQUENCE: 1806

Ala Val Gln Arg Thr Ile His Met Asn Tyr
1               5                   10

<210> SEQ ID NO 1807
<211> LENGTH: 10
<212> TYPE: PRT
<213> ORGANISM: homo sapien

<400> SEQUENCE: 1807

Ser Leu Ala Val Arg Ala Ala Phe Val His
1               5                   10

<210> SEQ ID NO 1808
<211> LENGTH: 10
<212> TYPE: PRT
<213> ORGANISM: homo sapien

<400> SEQUENCE: 1808

Val Asp Tyr Ile Lys Glu Ala Leu Met Lys
1               5                   10

<210> SEQ ID NO 1809
<211> LENGTH: 10
<212> TYPE: PRT
<213> ORGANISM: homo sapien

<400> SEQUENCE: 1809

Ala Leu Gly Asp Leu Val Gln Ser Val Gly
1               5                   10

<210> SEQ ID NO 1810
<211> LENGTH: 10
<212> TYPE: PRT
<213> ORGANISM: homo sapien

<400> SEQUENCE: 1810

Leu Ile Ala Ala Tyr Ile Ile Arg Phe Lys
1               5                   10

<210> SEQ ID NO 1811
<211> LENGTH: 10
<212> TYPE: PRT
<213> ORGANISM: homo sapien

```
<400> SEQUENCE: 1811

Val Val Ile Ile Leu Glu Gly Val Pro Ser
 1               5                  10

<210> SEQ ID NO 1812
<211> LENGTH: 10
<212> TYPE: PRT
<213> ORGANISM: homo sapien

<400> SEQUENCE: 1812

Gln Leu Ile Pro Gly Ser Ser Ser Lys Trp
 1               5                  10

<210> SEQ ID NO 1813
<211> LENGTH: 10
<212> TYPE: PRT
<213> ORGANISM: homo sapien

<400> SEQUENCE: 1813

His Leu Leu Leu Asn Thr Phe Gly Met Tyr
 1               5                  10

<210> SEQ ID NO 1814
<211> LENGTH: 10
<212> TYPE: PRT
<213> ORGANISM: homo sapien

<400> SEQUENCE: 1814

Leu Leu Leu Asn Thr Phe Gly Met Tyr Arg
 1               5                  10

<210> SEQ ID NO 1815
<211> LENGTH: 10
<212> TYPE: PRT
<213> ORGANISM: homo sapien

<400> SEQUENCE: 1815

Met Leu Arg Lys Asp Asp Ala Pro Leu Phe
 1               5                  10

<210> SEQ ID NO 1816
<211> LENGTH: 10
<212> TYPE: PRT
<213> ORGANISM: homo sapien

<400> SEQUENCE: 1816

Ser Leu Ala Ile Met Thr Asp Ala Leu His
 1               5                  10

<210> SEQ ID NO 1817
<211> LENGTH: 10
<212> TYPE: PRT
<213> ORGANISM: homo sapien

<400> SEQUENCE: 1817

Phe Leu Leu Asn Gln Ser Gly His Arg His
 1               5                  10

<210> SEQ ID NO 1818
<211> LENGTH: 10
<212> TYPE: PRT
<213> ORGANISM: homo sapien

<400> SEQUENCE: 1818
```

```
Gly Val Pro Ser His Leu Asn Val Asp Tyr
1               5                   10

<210> SEQ ID NO 1819
<211> LENGTH: 10
<212> TYPE: PRT
<213> ORGANISM: homo sapien

<400> SEQUENCE: 1819

Ile Gln Leu Ile Pro Gly Ser Ser Ser Lys
1               5                   10

<210> SEQ ID NO 1820
<211> LENGTH: 10
<212> TYPE: PRT
<213> ORGANISM: homo sapien

<400> SEQUENCE: 1820

Pro Leu Phe Leu Asn Asp Thr Ser Ala Phe
1               5                   10

<210> SEQ ID NO 1821
<211> LENGTH: 10
<212> TYPE: PRT
<213> ORGANISM: homo sapien

<400> SEQUENCE: 1821

Lys Leu Arg Val Val Val Ala Asp Asp Gly
1               5                   10

<210> SEQ ID NO 1822
<211> LENGTH: 10
<212> TYPE: PRT
<213> ORGANISM: homo sapien

<400> SEQUENCE: 1822

Ile Ile Leu Thr Leu Leu Ala Leu Trp Leu
1               5                   10

<210> SEQ ID NO 1823
<211> LENGTH: 10
<212> TYPE: PRT
<213> ORGANISM: homo sapien

<400> SEQUENCE: 1823

Glu Val Leu Ser Ala Met Ile Ser Val Leu
1               5                   10

<210> SEQ ID NO 1824
<211> LENGTH: 10
<212> TYPE: PRT
<213> ORGANISM: homo sapien

<400> SEQUENCE: 1824

Leu Leu Tyr Glu Ala Val Gln Arg Thr Ile
1               5                   10

<210> SEQ ID NO 1825
<211> LENGTH: 10
<212> TYPE: PRT
<213> ORGANISM: homo sapien

<400> SEQUENCE: 1825

Asp Ile Met Leu Ile Thr Ala Ala Val Gly
1               5                   10
```

<210> SEQ ID NO 1826
<211> LENGTH: 10
<212> TYPE: PRT
<213> ORGANISM: homo sapien

<400> SEQUENCE: 1826

Ala Val Arg Ala Ala Phe Val His Ala Leu
1               5                   10

<210> SEQ ID NO 1827
<211> LENGTH: 10
<212> TYPE: PRT
<213> ORGANISM: homo sapien

<400> SEQUENCE: 1827

Phe Val His Ala Leu Gly Asp Leu Val Gln
1               5                   10

<210> SEQ ID NO 1828
<211> LENGTH: 10
<212> TYPE: PRT
<213> ORGANISM: homo sapien

<400> SEQUENCE: 1828

Val Leu Ile Ala Ala Tyr Ile Ile Arg Phe
1               5                   10

<210> SEQ ID NO 1829
<211> LENGTH: 10
<212> TYPE: PRT
<213> ORGANISM: homo sapien

<400> SEQUENCE: 1829

Arg Ile Ile Trp Asp Thr Val Val Ile Ile
1               5                   10

<210> SEQ ID NO 1830
<211> LENGTH: 10
<212> TYPE: PRT
<213> ORGANISM: homo sapien

<400> SEQUENCE: 1830

Phe Leu Asn Asp Thr Ser Ala Phe Asp Phe
1               5                   10

<210> SEQ ID NO 1831
<211> LENGTH: 10
<212> TYPE: PRT
<213> ORGANISM: homo sapien

<400> SEQUENCE: 1831

Val Val Val Ala Asp Asp Gly Ser Glu Ala
1               5                   10

<210> SEQ ID NO 1832
<211> LENGTH: 10
<212> TYPE: PRT
<213> ORGANISM: homo sapien

<400> SEQUENCE: 1832

Leu Leu Asp Gln Asp Leu Pro Leu Thr Asn
1               5                   10

```
<210> SEQ ID NO 1833
<211> LENGTH: 10
<212> TYPE: PRT
<213> ORGANISM: homo sapien

<400> SEQUENCE: 1833

Ile Leu Lys Gln Arg Lys Val Lys Ala Arg
1               5                   10

<210> SEQ ID NO 1834
<211> LENGTH: 10
<212> TYPE: PRT
<213> ORGANISM: homo sapien

<400> SEQUENCE: 1834

Ala Arg Leu Thr Ile Ala Ala Val Leu Tyr
1               5                   10

<210> SEQ ID NO 1835
<211> LENGTH: 10
<212> TYPE: PRT
<213> ORGANISM: homo sapien

<400> SEQUENCE: 1835

Arg Leu Thr Ile Ala Ala Val Leu Tyr Leu
1               5                   10

<210> SEQ ID NO 1836
<211> LENGTH: 10
<212> TYPE: PRT
<213> ORGANISM: homo sapien

<400> SEQUENCE: 1836

Thr Ile Ala Ala Val Leu Tyr Leu Leu Phe
1               5                   10

<210> SEQ ID NO 1837
<211> LENGTH: 10
<212> TYPE: PRT
<213> ORGANISM: homo sapien

<400> SEQUENCE: 1837

Ala Leu His Met Leu Thr Asp Leu Ser Ala
1               5                   10

<210> SEQ ID NO 1838
<211> LENGTH: 10
<212> TYPE: PRT
<213> ORGANISM: homo sapien

<400> SEQUENCE: 1838

Ala Ile Ile Leu Thr Leu Leu Ala Leu Trp
1               5                   10

<210> SEQ ID NO 1839
<211> LENGTH: 10
<212> TYPE: PRT
<213> ORGANISM: homo sapien

<400> SEQUENCE: 1839

Arg Leu Glu Val Leu Ser Ala Met Ile Ser
1               5                   10

<210> SEQ ID NO 1840
<211> LENGTH: 10
```

```
<212> TYPE: PRT
<213> ORGANISM: homo sapien

<400> SEQUENCE: 1840

Ser Val Leu Leu Val Tyr Ile Leu Met Gly
 1               5                  10

<210> SEQ ID NO 1841
<211> LENGTH: 10
<212> TYPE: PRT
<213> ORGANISM: homo sapien

<400> SEQUENCE: 1841

Leu Val Tyr Ile Leu Met Gly Phe Leu Leu
 1               5                  10

<210> SEQ ID NO 1842
<211> LENGTH: 10
<212> TYPE: PRT
<213> ORGANISM: homo sapien

<400> SEQUENCE: 1842

Met Leu Ile Thr Ala Ala Val Gly Val Ala
 1               5                  10

<210> SEQ ID NO 1843
<211> LENGTH: 10
<212> TYPE: PRT
<213> ORGANISM: homo sapien

<400> SEQUENCE: 1843

Leu Ile Thr Ala Ala Val Gly Val Ala Val
 1               5                  10

<210> SEQ ID NO 1844
<211> LENGTH: 10
<212> TYPE: PRT
<213> ORGANISM: homo sapien

<400> SEQUENCE: 1844

Ser Leu Leu Val Ala Phe Thr Thr Phe Arg
 1               5                  10

<210> SEQ ID NO 1845
<211> LENGTH: 10
<212> TYPE: PRT
<213> ORGANISM: homo sapien

<400> SEQUENCE: 1845

Val Ile Ile Leu Glu Gly Val Pro Ser His
 1               5                  10

<210> SEQ ID NO 1846
<211> LENGTH: 10
<212> TYPE: PRT
<213> ORGANISM: homo sapien

<400> SEQUENCE: 1846

Trp Lys Arg Leu Lys Ser Met Leu Arg Lys
 1               5                  10

<210> SEQ ID NO 1847
<211> LENGTH: 10
<212> TYPE: PRT
<213> ORGANISM: homo sapien
```

```
<400> SEQUENCE: 1847

Arg Val Val Ala Asp Asp Gly Ser Glu
 1               5                  10

<210> SEQ ID NO 1848
<211> LENGTH: 10
<212> TYPE: PRT
<213> ORGANISM: homo sapien

<400> SEQUENCE: 1848

Lys Gln Arg Glu Ile Leu Lys Gln Arg Lys
 1               5                  10

<210> SEQ ID NO 1849
<211> LENGTH: 10
<212> TYPE: PRT
<213> ORGANISM: homo sapien

<400> SEQUENCE: 1849

Lys Val Lys Ala Arg Leu Thr Ile Ala Ala
 1               5                  10

<210> SEQ ID NO 1850
<211> LENGTH: 10
<212> TYPE: PRT
<213> ORGANISM: homo sapien

<400> SEQUENCE: 1850

Lys Ala Arg Leu Thr Ile Ala Ala Val Leu
 1               5                  10

<210> SEQ ID NO 1851
<211> LENGTH: 10
<212> TYPE: PRT
<213> ORGANISM: homo sapien

<400> SEQUENCE: 1851

Leu Leu Phe Met Ile Gly Glu Leu Val Gly
 1               5                  10

<210> SEQ ID NO 1852
<211> LENGTH: 10
<212> TYPE: PRT
<213> ORGANISM: homo sapien

<400> SEQUENCE: 1852

Leu Val Gly Gly Tyr Ile Ala Asn Ser Leu
 1               5                  10

<210> SEQ ID NO 1853
<211> LENGTH: 10
<212> TYPE: PRT
<213> ORGANISM: homo sapien

<400> SEQUENCE: 1853

Ala Leu Trp Leu Ser Ser Lys Ser Pro Thr
 1               5                  10

<210> SEQ ID NO 1854
<211> LENGTH: 10
<212> TYPE: PRT
<213> ORGANISM: homo sapien

<400> SEQUENCE: 1854
```

-continued

Val Leu Leu Val Tyr Ile Leu Met Gly Phe
1               5                   10

<210> SEQ ID NO 1855
<211> LENGTH: 10
<212> TYPE: PRT
<213> ORGANISM: homo sapien

<400> SEQUENCE: 1855

Gly Phe Leu Leu Tyr Glu Ala Val Gln Arg
1               5                   10

<210> SEQ ID NO 1856
<211> LENGTH: 10
<212> TYPE: PRT
<213> ORGANISM: homo sapien

<400> SEQUENCE: 1856

Ala Val Gly Val Ala Val Asn Val Ile Met
1               5                   10

<210> SEQ ID NO 1857
<211> LENGTH: 10
<212> TYPE: PRT
<213> ORGANISM: homo sapien

<400> SEQUENCE: 1857

Asp Leu Val Gln Ser Val Gly Val Leu Ile
1               5                   10

<210> SEQ ID NO 1858
<211> LENGTH: 10
<212> TYPE: PRT
<213> ORGANISM: homo sapien

<400> SEQUENCE: 1858

Ser Val Gly Val Leu Ile Ala Ala Tyr Ile
1               5                   10

<210> SEQ ID NO 1859
<211> LENGTH: 10
<212> TYPE: PRT
<213> ORGANISM: homo sapien

<400> SEQUENCE: 1859

Gly Val Leu Ile Ala Ala Tyr Ile Ile Arg
1               5                   10

<210> SEQ ID NO 1860
<211> LENGTH: 10
<212> TYPE: PRT
<213> ORGANISM: homo sapien

<400> SEQUENCE: 1860

Ile Ile Leu Glu Gly Val Pro Ser His Leu
1               5                   10

<210> SEQ ID NO 1861
<211> LENGTH: 10
<212> TYPE: PRT
<213> ORGANISM: homo sapien

<400> SEQUENCE: 1861

Ala Leu Met Lys Ile Glu Asp Val Tyr Ser

-continued

```
1               5               10

<210> SEQ ID NO 1862
<211> LENGTH: 10
<212> TYPE: PRT
<213> ORGANISM: homo sapien

<400> SEQUENCE: 1862

Asp Val Tyr Ser Val Glu Asp Leu Asn Ile
1               5               10

<210> SEQ ID NO 1863
<211> LENGTH: 10
<212> TYPE: PRT
<213> ORGANISM: homo sapien

<400> SEQUENCE: 1863

His Ile Gln Leu Ile Pro Gly Ser Ser Ser
1               5               10

<210> SEQ ID NO 1864
<211> LENGTH: 10
<212> TYPE: PRT
<213> ORGANISM: homo sapien

<400> SEQUENCE: 1864

Arg Leu Lys Ser Met Leu Arg Lys Asp Asp
1               5               10

<210> SEQ ID NO 1865
<211> LENGTH: 10
<212> TYPE: PRT
<213> ORGANISM: homo sapien

<400> SEQUENCE: 1865

Gly Leu Ser Arg Phe Asn Lys Leu Arg Val
1               5               10

<210> SEQ ID NO 1866
<211> LENGTH: 10
<212> TYPE: PRT
<213> ORGANISM: homo sapien

<400> SEQUENCE: 1866

Gln Leu Ser Leu Lys Val Asp Ser Cys Asp
1               5               10

<210> SEQ ID NO 1867
<211> LENGTH: 10
<212> TYPE: PRT
<213> ORGANISM: homo sapien

<400> SEQUENCE: 1867

Ala Val Leu Tyr Leu Leu Phe Met Ile Gly
1               5               10

<210> SEQ ID NO 1868
<211> LENGTH: 10
<212> TYPE: PRT
<213> ORGANISM: homo sapien

<400> SEQUENCE: 1868

Leu Trp Leu Ser Ser Lys Ser Pro Thr Lys
1               5               10
```

```
<210> SEQ ID NO 1869
<211> LENGTH: 10
<212> TYPE: PRT
<213> ORGANISM: homo sapien

<400> SEQUENCE: 1869

Trp Leu Ser Ser Lys Ser Pro Thr Lys Arg
1               5                   10

<210> SEQ ID NO 1870
<211> LENGTH: 10
<212> TYPE: PRT
<213> ORGANISM: homo sapien

<400> SEQUENCE: 1870

Val Leu Ser Ala Met Ile Ser Val Leu Leu
1               5                   10

<210> SEQ ID NO 1871
<211> LENGTH: 10
<212> TYPE: PRT
<213> ORGANISM: homo sapien

<400> SEQUENCE: 1871

Gly Val Ala Val Asn Val Ile Met Gly Phe
1               5                   10

<210> SEQ ID NO 1872
<211> LENGTH: 10
<212> TYPE: PRT
<213> ORGANISM: homo sapien

<400> SEQUENCE: 1872

Ala Val Asn Val Ile Met Gly Phe Leu Leu
1               5                   10

<210> SEQ ID NO 1873
<211> LENGTH: 10
<212> TYPE: PRT
<213> ORGANISM: homo sapien

<400> SEQUENCE: 1873

Asn Val Ile Met Gly Phe Leu Leu Asn Gln
1               5                   10

<210> SEQ ID NO 1874
<211> LENGTH: 10
<212> TYPE: PRT
<213> ORGANISM: homo sapien

<400> SEQUENCE: 1874

Thr Val Val Ile Ile Leu Glu Gly Val Pro
1               5                   10

<210> SEQ ID NO 1875
<211> LENGTH: 10
<212> TYPE: PRT
<213> ORGANISM: homo sapien

<400> SEQUENCE: 1875

Lys Ile Glu Asp Val Tyr Ser Val Glu Asp
1               5                   10

<210> SEQ ID NO 1876
```

```
<211> LENGTH: 10
<212> TYPE: PRT
<213> ORGANISM: homo sapien

<400> SEQUENCE: 1876

Leu Asn Ile Trp Ser Leu Thr Ser Gly Lys
1               5                   10

<210> SEQ ID NO 1877
<211> LENGTH: 10
<212> TYPE: PRT
<213> ORGANISM: homo sapien

<400> SEQUENCE: 1877

Gln Leu Gln Ser Tyr Arg Gln Glu Val Asp
1               5                   10

<210> SEQ ID NO 1878
<211> LENGTH: 10
<212> TYPE: PRT
<213> ORGANISM: homo sapien

<400> SEQUENCE: 1878

Glu Val Asp Arg Thr Cys Ala Asn Cys Gln
1               5                   10

<210> SEQ ID NO 1879
<211> LENGTH: 10
<212> TYPE: PRT
<213> ORGANISM: homo sapien

<400> SEQUENCE: 1879

Ala Gly Ser Gly Ala Trp Lys Arg Leu Lys
1               5                   10

<210> SEQ ID NO 1880
<211> LENGTH: 10
<212> TYPE: PRT
<213> ORGANISM: homo sapien

<400> SEQUENCE: 1880

Asp Glu Ala Gly Asp Glu Gly Leu Ser Arg
1               5                   10

<210> SEQ ID NO 1881
<211> LENGTH: 10
<212> TYPE: PRT
<213> ORGANISM: homo sapien

<400> SEQUENCE: 1881

Thr Leu Gln Ala Asp Asp Ser Leu Leu
1               5                   10

<210> SEQ ID NO 1882
<211> LENGTH: 10
<212> TYPE: PRT
<213> ORGANISM: homo sapien

<400> SEQUENCE: 1882

Val Leu Tyr Leu Leu Phe Met Ile Gly Glu
1               5                   10

<210> SEQ ID NO 1883
<211> LENGTH: 10
<212> TYPE: PRT
```

-continued

<213> ORGANISM: homo sapien

<400> SEQUENCE: 1883

Tyr Leu Leu Phe Met Ile Gly Glu Leu Val
1               5                   10

<210> SEQ ID NO 1884
<211> LENGTH: 10
<212> TYPE: PRT
<213> ORGANISM: homo sapien

<400> SEQUENCE: 1884

Glu Leu Val Gly Gly Tyr Ile Ala Asn Ser
1               5                   10

<210> SEQ ID NO 1885
<211> LENGTH: 10
<212> TYPE: PRT
<213> ORGANISM: homo sapien

<400> SEQUENCE: 1885

Leu Leu Ala Leu Trp Leu Ser Ser Lys Ser
1               5                   10

<210> SEQ ID NO 1886
<211> LENGTH: 10
<212> TYPE: PRT
<213> ORGANISM: homo sapien

<400> SEQUENCE: 1886

Ser Ala Met Ile Ser Val Leu Leu Val Tyr
1               5                   10

<210> SEQ ID NO 1887
<211> LENGTH: 10
<212> TYPE: PRT
<213> ORGANISM: homo sapien

<400> SEQUENCE: 1887

Tyr Lys Ile Ala Asp Pro Ile Cys Thr Tyr
1               5                   10

<210> SEQ ID NO 1888
<211> LENGTH: 10
<212> TYPE: PRT
<213> ORGANISM: homo sapien

<400> SEQUENCE: 1888

Pro Val Asn Gly Ala His Pro Thr Leu Gln
1               5                   10

<210> SEQ ID NO 1889
<211> LENGTH: 10
<212> TYPE: PRT
<213> ORGANISM: homo sapien

<400> SEQUENCE: 1889

Ser Leu Leu Asp Gln Asp Leu Pro Leu Thr
1               5                   10

<210> SEQ ID NO 1890
<211> LENGTH: 10
<212> TYPE: PRT
<213> ORGANISM: homo sapien

```
<400> SEQUENCE: 1890

Glu Ile Leu Lys Gln Arg Lys Val Lys Ala
1               5                   10

<210> SEQ ID NO 1891
<211> LENGTH: 10
<212> TYPE: PRT
<213> ORGANISM: homo sapien

<400> SEQUENCE: 1891

Tyr Ile Ala Asn Ser Leu Ala Ile Met Thr
1               5                   10

<210> SEQ ID NO 1892
<211> LENGTH: 10
<212> TYPE: PRT
<213> ORGANISM: homo sapien

<400> SEQUENCE: 1892

Met Leu Thr Asp Leu Ser Ala Ile Ile Leu
1               5                   10

<210> SEQ ID NO 1893
<211> LENGTH: 10
<212> TYPE: PRT
<213> ORGANISM: homo sapien

<400> SEQUENCE: 1893

Ile Leu Met Gly Phe Leu Leu Tyr Glu Ala
1               5                   10

<210> SEQ ID NO 1894
<211> LENGTH: 10
<212> TYPE: PRT
<213> ORGANISM: homo sapien

<400> SEQUENCE: 1894

Gln Ser Val Gly Val Leu Ile Ala Ala Tyr
1               5                   10

<210> SEQ ID NO 1895
<211> LENGTH: 10
<212> TYPE: PRT
<213> ORGANISM: homo sapien

<400> SEQUENCE: 1895

Lys Ile Ala Asp Pro Ile Cys Thr Tyr Val
1               5                   10

<210> SEQ ID NO 1896
<211> LENGTH: 10
<212> TYPE: PRT
<213> ORGANISM: homo sapien

<400> SEQUENCE: 1896

Ile Leu Glu Gly Val Pro Ser His Leu Asn
1               5                   10

<210> SEQ ID NO 1897
<211> LENGTH: 10
<212> TYPE: PRT
<213> ORGANISM: homo sapien

<400> SEQUENCE: 1897
```

-continued

Ser Val Glu Asp Leu Asn Ile Trp Ser Leu
1               5                   10

<210> SEQ ID NO 1898
<211> LENGTH: 10
<212> TYPE: PRT
<213> ORGANISM: homo sapien

<400> SEQUENCE: 1898

Asp Leu Asn Ile Trp Ser Leu Thr Ser Gly
1               5                   10

<210> SEQ ID NO 1899
<211> LENGTH: 10
<212> TYPE: PRT
<213> ORGANISM: homo sapien

<400> SEQUENCE: 1899

Ser Ser Lys Trp Glu Glu Val Gln Ser Lys
1               5                   10

<210> SEQ ID NO 1900
<211> LENGTH: 10
<212> TYPE: PRT
<213> ORGANISM: homo sapien

<400> SEQUENCE: 1900

Arg Pro Val Asn Gly Ala His Pro Thr Leu
1               5                   10

<210> SEQ ID NO 1901
<211> LENGTH: 10
<212> TYPE: PRT
<213> ORGANISM: homo sapien

<400> SEQUENCE: 1901

Leu Pro Leu Thr Asn Ser Gln Leu Ser Leu
1               5                   10

<210> SEQ ID NO 1902
<211> LENGTH: 10
<212> TYPE: PRT
<213> ORGANISM: homo sapien

<400> SEQUENCE: 1902

Asp Pro Ile Cys Thr Tyr Val Phe Ser Leu
1               5                   10

<210> SEQ ID NO 1903
<211> LENGTH: 10
<212> TYPE: PRT
<213> ORGANISM: homo sapien

<400> SEQUENCE: 1903

Ala Pro Leu Phe Leu Asn Asp Thr Ser Ala
1               5                   10

<210> SEQ ID NO 1904
<211> LENGTH: 10
<212> TYPE: PRT
<213> ORGANISM: homo sapien

<400> SEQUENCE: 1904

Val Pro Ser His Leu Asn Val Asp Tyr Ile
1               5                   10

<210> SEQ ID NO 1905
<211> LENGTH: 10
<212> TYPE: PRT
<213> ORGANISM: homo sapien

<400> SEQUENCE: 1905

Ser Pro Thr Lys Arg Phe Thr Phe Gly Phe
1               5                   10

<210> SEQ ID NO 1906
<211> LENGTH: 10
<212> TYPE: PRT
<213> ORGANISM: homo sapien

<400> SEQUENCE: 1906

Lys Pro Glu Tyr Lys Ile Ala Asp Pro Ile
1               5                   10

<210> SEQ ID NO 1907
<211> LENGTH: 10
<212> TYPE: PRT
<213> ORGANISM: homo sapien

<400> SEQUENCE: 1907

Ala Val Arg Ala Ala Phe Val His Ala Leu
1               5                   10

<210> SEQ ID NO 1908
<211> LENGTH: 10
<212> TYPE: PRT
<213> ORGANISM: homo sapien

<400> SEQUENCE: 1908

Lys Ala Arg Leu Thr Ile Ala Ala Val Leu
1               5                   10

<210> SEQ ID NO 1909
<211> LENGTH: 10
<212> TYPE: PRT
<213> ORGANISM: homo sapien

<400> SEQUENCE: 1909

Val Leu Ser Ala Met Ile Ser Val Leu Leu
1               5                   10

<210> SEQ ID NO 1910
<211> LENGTH: 10
<212> TYPE: PRT
<213> ORGANISM: homo sapien

<400> SEQUENCE: 1910

Val Gln Ser Lys Ala Asn His Leu Leu Leu
1               5                   10

<210> SEQ ID NO 1911
<211> LENGTH: 10
<212> TYPE: PRT
<213> ORGANISM: homo sapien

<400> SEQUENCE: 1911

Arg Leu Thr Ile Ala Ala Val Leu Tyr Leu
1               5                   10

<210> SEQ ID NO 1912
<211> LENGTH: 10
<212> TYPE: PRT
<213> ORGANISM: homo sapien

<400> SEQUENCE: 1912

Asp Leu Ser Ala Ile Ile Leu Thr Leu Leu
1               5                   10

<210> SEQ ID NO 1913
<211> LENGTH: 10
<212> TYPE: PRT
<213> ORGANISM: homo sapien

<400> SEQUENCE: 1913

Leu Arg Lys Asp Asp Ala Pro Leu Phe Leu
1               5                   10

<210> SEQ ID NO 1914
<211> LENGTH: 10
<212> TYPE: PRT
<213> ORGANISM: homo sapien

<400> SEQUENCE: 1914

Ala Pro Glu Arg Pro Val Asn Gly Ala His
1               5                   10

<210> SEQ ID NO 1915
<211> LENGTH: 10
<212> TYPE: PRT
<213> ORGANISM: homo sapien

<400> SEQUENCE: 1915

Asp Ser Leu Leu Asp Gln Asp Leu Pro Leu
1               5                   10

<210> SEQ ID NO 1916
<211> LENGTH: 10
<212> TYPE: PRT
<213> ORGANISM: homo sapien

<400> SEQUENCE: 1916

Leu Val Gly Gly Tyr Ile Ala Asn Ser Leu
1               5                   10

<210> SEQ ID NO 1917
<211> LENGTH: 10
<212> TYPE: PRT
<213> ORGANISM: homo sapien

<400> SEQUENCE: 1917

Asn Ser Leu Ala Ile Met Thr Asp Ala Leu
1               5                   10

<210> SEQ ID NO 1918
<211> LENGTH: 10
<212> TYPE: PRT
<213> ORGANISM: homo sapien

<400> SEQUENCE: 1918

Ala Ile Met Thr Asp Ala Leu His Met Leu
1               5                   10

<210> SEQ ID NO 1919
<211> LENGTH: 10

-continued

```
<212> TYPE: PRT
<213> ORGANISM: homo sapien

<400> SEQUENCE: 1919

Ser Ala Ile Ile Leu Thr Leu Leu Ala Leu
1               5                   10

<210> SEQ ID NO 1920
<211> LENGTH: 10
<212> TYPE: PRT
<213> ORGANISM: homo sapien

<400> SEQUENCE: 1920

Ile Ile Leu Thr Leu Leu Ala Leu Trp Leu
1               5                   10

<210> SEQ ID NO 1921
<211> LENGTH: 10
<212> TYPE: PRT
<213> ORGANISM: homo sapien

<400> SEQUENCE: 1921

Met Ile Ser Val Leu Leu Val Tyr Ile Leu
1               5                   10

<210> SEQ ID NO 1922
<211> LENGTH: 10
<212> TYPE: PRT
<213> ORGANISM: homo sapien

<400> SEQUENCE: 1922

Leu Pro Ser Asn Ser Pro Thr Arg Gly Ser
1               5                   10

<210> SEQ ID NO 1923
<211> LENGTH: 10
<212> TYPE: PRT
<213> ORGANISM: homo sapien

<400> SEQUENCE: 1923

Ile Glu Asp Val Tyr Ser Val Glu Asp Leu
1               5                   10

<210> SEQ ID NO 1924
<211> LENGTH: 10
<212> TYPE: PRT
<213> ORGANISM: homo sapien

<400> SEQUENCE: 1924

Ser Met Leu Arg Lys Asp Asp Ala Pro Leu
1               5                   10

<210> SEQ ID NO 1925
<211> LENGTH: 10
<212> TYPE: PRT
<213> ORGANISM: homo sapien

<400> SEQUENCE: 1925

Asp Glu Gly Leu Ser Arg Phe Asn Lys Leu
1               5                   10

<210> SEQ ID NO 1926
<211> LENGTH: 10
<212> TYPE: PRT
<213> ORGANISM: homo sapien
```

```
<400> SEQUENCE: 1926

Arg Phe Asn Lys Leu Arg Val Val Val Ala
1               5                   10

<210> SEQ ID NO 1927
<211> LENGTH: 10
<212> TYPE: PRT
<213> ORGANISM: homo sapien

<400> SEQUENCE: 1927

Thr Asp Ala Leu His Met Leu Thr Asp Leu
1               5                   10

<210> SEQ ID NO 1928
<211> LENGTH: 10
<212> TYPE: PRT
<213> ORGANISM: homo sapien

<400> SEQUENCE: 1928

Thr Asp Leu Ser Ala Ile Ile Leu Thr Leu
1               5                   10

<210> SEQ ID NO 1929
<211> LENGTH: 10
<212> TYPE: PRT
<213> ORGANISM: homo sapien

<400> SEQUENCE: 1929

Lys Arg Phe Thr Phe Gly Phe His Arg Leu
1               5                   10

<210> SEQ ID NO 1930
<211> LENGTH: 10
<212> TYPE: PRT
<213> ORGANISM: homo sapien

<400> SEQUENCE: 1930

Thr Phe Gly Phe His Arg Leu Glu Val Leu
1               5                   10

<210> SEQ ID NO 1931
<211> LENGTH: 10
<212> TYPE: PRT
<213> ORGANISM: homo sapien

<400> SEQUENCE: 1931

Glu Val Leu Ser Ala Met Ile Ser Val Leu
1               5                   10

<210> SEQ ID NO 1932
<211> LENGTH: 10
<212> TYPE: PRT
<213> ORGANISM: homo sapien

<400> SEQUENCE: 1932

Ala Ala Val Gly Val Ala Val Asn Val Ile
1               5                   10

<210> SEQ ID NO 1933
<211> LENGTH: 10
<212> TYPE: PRT
<213> ORGANISM: homo sapien

<400> SEQUENCE: 1933
```

-continued

Ala Val Asn Val Ile Met Gly Phe Leu Leu
 1               5                  10

<210> SEQ ID NO 1934
<211> LENGTH: 10
<212> TYPE: PRT
<213> ORGANISM: homo sapien

<400> SEQUENCE: 1934

Gly His Arg His Ser His Ser His Ser Leu
 1               5                  10

<210> SEQ ID NO 1935
<211> LENGTH: 10
<212> TYPE: PRT
<213> ORGANISM: homo sapien

<400> SEQUENCE: 1935

Cys Glu Arg Asn His Gly Gln Asp Ser Leu
 1               5                  10

<210> SEQ ID NO 1936
<211> LENGTH: 10
<212> TYPE: PRT
<213> ORGANISM: homo sapien

<400> SEQUENCE: 1936

Arg Asn His Gly Gln Asp Ser Leu Ala Val
 1               5                  10

<210> SEQ ID NO 1937
<211> LENGTH: 10
<212> TYPE: PRT
<213> ORGANISM: homo sapien

<400> SEQUENCE: 1937

Ala Ala Phe Val His Ala Leu Gly Asp Leu
 1               5                  10

<210> SEQ ID NO 1938
<211> LENGTH: 10
<212> TYPE: PRT
<213> ORGANISM: homo sapien

<400> SEQUENCE: 1938

Gly Asp Leu Val Gln Ser Val Gly Val Leu
 1               5                  10

<210> SEQ ID NO 1939
<211> LENGTH: 10
<212> TYPE: PRT
<213> ORGANISM: homo sapien

<400> SEQUENCE: 1939

Ile Ile Trp Asp Thr Val Val Ile Ile Leu
 1               5                  10

<210> SEQ ID NO 1940
<211> LENGTH: 10
<212> TYPE: PRT
<213> ORGANISM: homo sapien

<400> SEQUENCE: 1940

Leu Thr Ser Gly Lys Ser Thr Ala Ile Val

```
                1               5                   10
```

<210> SEQ ID NO 1941
<211> LENGTH: 10
<212> TYPE: PRT
<213> ORGANISM: homo sapien

<400> SEQUENCE: 1941

```
Lys Ser Thr Ala Ile Val His Ile Gln Leu
 1               5                   10
```

<210> SEQ ID NO 1942
<211> LENGTH: 10
<212> TYPE: PRT
<213> ORGANISM: homo sapien

<400> SEQUENCE: 1942

```
Ile Pro Gly Ser Ser Ser Lys Trp Glu Glu
 1               5                   10
```

<210> SEQ ID NO 1943
<211> LENGTH: 10
<212> TYPE: PRT
<213> ORGANISM: homo sapien

<400> SEQUENCE: 1943

```
Phe Gly Met Tyr Arg Cys Thr Ile Gln Leu
 1               5                   10
```

<210> SEQ ID NO 1944
<211> LENGTH: 10
<212> TYPE: PRT
<213> ORGANISM: homo sapien

<400> SEQUENCE: 1944

```
Met Ala Gly Ser Gly Ala Trp Lys Arg Leu
 1               5                   10
```

<210> SEQ ID NO 1945
<211> LENGTH: 10
<212> TYPE: PRT
<213> ORGANISM: homo sapien

<400> SEQUENCE: 1945

```
Gly Ala Trp Lys Arg Leu Lys Ser Met Leu
 1               5                   10
```

<210> SEQ ID NO 1946
<211> LENGTH: 10
<212> TYPE: PRT
<213> ORGANISM: homo sapien

<400> SEQUENCE: 1946

```
Phe Ser Asp Glu Ala Gly Asp Glu Gly Leu
 1               5                   10
```

<210> SEQ ID NO 1947
<211> LENGTH: 10
<212> TYPE: PRT
<213> ORGANISM: homo sapien

<400> SEQUENCE: 1947

```
Val Asn Gly Ala His Pro Thr Leu Gln Ala
 1               5                   10
```

```
<210> SEQ ID NO 1948
<211> LENGTH: 10
<212> TYPE: PRT
<213> ORGANISM: homo sapien

<400> SEQUENCE: 1948

Thr Leu Gln Ala Asp Asp Ser Leu Leu
 1               5                  10

<210> SEQ ID NO 1949
<211> LENGTH: 10
<212> TYPE: PRT
<213> ORGANISM: homo sapien

<400> SEQUENCE: 1949

Asp Asp Asp Ser Leu Leu Asp Gln Asp Leu
 1               5                  10

<210> SEQ ID NO 1950
<211> LENGTH: 10
<212> TYPE: PRT
<213> ORGANISM: homo sapien

<400> SEQUENCE: 1950

Gln Asp Leu Pro Leu Thr Asn Ser Gln Leu
 1               5                  10

<210> SEQ ID NO 1951
<211> LENGTH: 10
<212> TYPE: PRT
<213> ORGANISM: homo sapien

<400> SEQUENCE: 1951

Asp Asn Cys Ser Lys Gln Arg Glu Ile Leu
 1               5                  10

<210> SEQ ID NO 1952
<211> LENGTH: 10
<212> TYPE: PRT
<213> ORGANISM: homo sapien

<400> SEQUENCE: 1952

Leu Lys Gln Arg Lys Val Lys Ala Arg Leu
 1               5                  10

<210> SEQ ID NO 1953
<211> LENGTH: 10
<212> TYPE: PRT
<213> ORGANISM: homo sapien

<400> SEQUENCE: 1953

Leu Thr Ile Ala Ala Val Leu Tyr Leu Leu
 1               5                  10

<210> SEQ ID NO 1954
<211> LENGTH: 10
<212> TYPE: PRT
<213> ORGANISM: homo sapien

<400> SEQUENCE: 1954

Ile Ala Ala Val Leu Tyr Leu Leu Phe Met
 1               5                  10

<210> SEQ ID NO 1955
```

```
<211> LENGTH: 10
<212> TYPE: PRT
<213> ORGANISM: homo sapien

<400> SEQUENCE: 1955

Ala Asn Ser Leu Ala Ile Met Thr Asp Ala
1               5                   10

<210> SEQ ID NO 1956
<211> LENGTH: 10
<212> TYPE: PRT
<213> ORGANISM: homo sapien

<400> SEQUENCE: 1956

Phe Thr Phe Gly Phe His Arg Leu Glu Val
1               5                   10

<210> SEQ ID NO 1957
<211> LENGTH: 10
<212> TYPE: PRT
<213> ORGANISM: homo sapien

<400> SEQUENCE: 1957

Leu Leu Val Tyr Ile Leu Met Gly Phe Leu
1               5                   10

<210> SEQ ID NO 1958
<211> LENGTH: 10
<212> TYPE: PRT
<213> ORGANISM: homo sapien

<400> SEQUENCE: 1958

Glu Ile Asn Gly Asp Ile Met Leu Ile Thr
1               5                   10

<210> SEQ ID NO 1959
<211> LENGTH: 10
<212> TYPE: PRT
<213> ORGANISM: homo sapien

<400> SEQUENCE: 1959

Ala Val Gly Val Ala Val Asn Val Ile Met
1               5                   10

<210> SEQ ID NO 1960
<211> LENGTH: 10
<212> TYPE: PRT
<213> ORGANISM: homo sapien

<400> SEQUENCE: 1960

Val Ala Val Asn Val Ile Met Gly Phe Leu
1               5                   10

<210> SEQ ID NO 1961
<211> LENGTH: 10
<212> TYPE: PRT
<213> ORGANISM: homo sapien

<400> SEQUENCE: 1961

Gln Asp Ser Leu Ala Val Arg Ala Ala Phe
1               5                   10

<210> SEQ ID NO 1962
<211> LENGTH: 10
<212> TYPE: PRT
```

<213> ORGANISM: homo sapien

<400> SEQUENCE: 1962

Ile Ala Asp Pro Ile Cys Thr Tyr Val Phe
1               5                   10

<210> SEQ ID NO 1963
<211> LENGTH: 10
<212> TYPE: PRT
<213> ORGANISM: homo sapien

<400> SEQUENCE: 1963

Pro Ile Cys Thr Tyr Val Phe Ser Leu Leu
1               5                   10

<210> SEQ ID NO 1964
<211> LENGTH: 10
<212> TYPE: PRT
<213> ORGANISM: homo sapien

<400> SEQUENCE: 1964

Ile Ile Leu Glu Gly Val Pro Ser His Leu
1               5                   10

<210> SEQ ID NO 1965
<211> LENGTH: 10
<212> TYPE: PRT
<213> ORGANISM: homo sapien

<400> SEQUENCE: 1965

Leu Asn Val Asp Tyr Ile Lys Glu Ala Leu
1               5                   10

<210> SEQ ID NO 1966
<211> LENGTH: 10
<212> TYPE: PRT
<213> ORGANISM: homo sapien

<400> SEQUENCE: 1966

Glu Glu Val Gln Ser Lys Ala Asn His Leu
1               5                   10

<210> SEQ ID NO 1967
<211> LENGTH: 10
<212> TYPE: PRT
<213> ORGANISM: homo sapien

<400> SEQUENCE: 1967

Glu Val Gln Ser Lys Ala Asn His Leu Leu
1               5                   10

<210> SEQ ID NO 1968
<211> LENGTH: 9
<212> TYPE: PRT
<213> ORGANISM: homo sapien

<400> SEQUENCE: 1968

Ala Leu Gly Asp Leu Val Gln Ser Val
1               5

<210> SEQ ID NO 1969
<211> LENGTH: 9
<212> TYPE: PRT
<213> ORGANISM: homo sapien

```
<400> SEQUENCE: 1969

Tyr Leu Leu Phe Met Ile Gly Glu Leu
1               5

<210> SEQ ID NO 1970
<211> LENGTH: 9
<212> TYPE: PRT
<213> ORGANISM: homo sapien

<400> SEQUENCE: 1970

Ala Ile Ile Leu Thr Leu Leu Ala Leu
1               5

<210> SEQ ID NO 1971
<211> LENGTH: 9
<212> TYPE: PRT
<213> ORGANISM: homo sapien

<400> SEQUENCE: 1971

Ser Leu Ala Ile Met Thr Asp Ala Leu
1               5

<210> SEQ ID NO 1972
<211> LENGTH: 9
<212> TYPE: PRT
<213> ORGANISM: homo sapien

<400> SEQUENCE: 1972

Ser Leu Leu Asp Gln Asp Leu Pro Leu
1               5

<210> SEQ ID NO 1973
<211> LENGTH: 9
<212> TYPE: PRT
<213> ORGANISM: homo sapien

<400> SEQUENCE: 1973

Asp Leu Ser Ala Ile Ile Leu Thr Leu
1               5

<210> SEQ ID NO 1974
<211> LENGTH: 9
<212> TYPE: PRT
<213> ORGANISM: homo sapien

<400> SEQUENCE: 1974

Ser Leu Ala Val Arg Ala Ala Phe Val
1               5

<210> SEQ ID NO 1975
<211> LENGTH: 9
<212> TYPE: PRT
<213> ORGANISM: homo sapien

<400> SEQUENCE: 1975

Ile Ile Trp Asp Thr Val Val Ile Ile
1               5

<210> SEQ ID NO 1976
<211> LENGTH: 9
<212> TYPE: PRT
<213> ORGANISM: homo sapien

<400> SEQUENCE: 1976
```

```
Thr Ile Ala Ala Val Leu Tyr Leu Leu
 1               5

<210> SEQ ID NO 1977
<211> LENGTH: 9
<212> TYPE: PRT
<213> ORGANISM: homo sapien

<400> SEQUENCE: 1977

Ile Met Thr Asp Ala Leu His Met Leu
 1               5

<210> SEQ ID NO 1978
<211> LENGTH: 9
<212> TYPE: PRT
<213> ORGANISM: homo sapien

<400> SEQUENCE: 1978

Val Leu Ser Ala Met Ile Ser Val Leu
 1               5

<210> SEQ ID NO 1979
<211> LENGTH: 9
<212> TYPE: PRT
<213> ORGANISM: homo sapien

<400> SEQUENCE: 1979

Met Leu Ile Thr Ala Ala Val Gly Val
 1               5

<210> SEQ ID NO 1980
<211> LENGTH: 9
<212> TYPE: PRT
<213> ORGANISM: homo sapien

<400> SEQUENCE: 1980

Tyr Ile Lys Glu Ala Leu Met Lys Ile
 1               5

<210> SEQ ID NO 1981
<211> LENGTH: 9
<212> TYPE: PRT
<213> ORGANISM: homo sapien

<400> SEQUENCE: 1981

Leu Thr Ile Ala Ala Val Leu Tyr Leu
 1               5

<210> SEQ ID NO 1982
<211> LENGTH: 9
<212> TYPE: PRT
<213> ORGANISM: homo sapien

<400> SEQUENCE: 1982

Leu Leu Phe Met Ile Gly Glu Leu Val
 1               5

<210> SEQ ID NO 1983
<211> LENGTH: 9
<212> TYPE: PRT
<213> ORGANISM: homo sapien

<400> SEQUENCE: 1983

His Met Leu Thr Asp Leu Ser Ala Ile
 1               5
```

```
<210> SEQ ID NO 1984
<211> LENGTH: 9
<212> TYPE: PRT
<213> ORGANISM: homo sapien

<400> SEQUENCE: 1984

Ile Leu Thr Leu Leu Ala Leu Trp Leu
 1               5

<210> SEQ ID NO 1985
<211> LENGTH: 9
<212> TYPE: PRT
<213> ORGANISM: homo sapien

<400> SEQUENCE: 1985

Met Ile Ser Val Leu Leu Val Tyr Ile
 1               5

<210> SEQ ID NO 1986
<211> LENGTH: 9
<212> TYPE: PRT
<213> ORGANISM: homo sapien

<400> SEQUENCE: 1986

Leu Leu Tyr Glu Ala Val Gln Arg Thr
 1               5

<210> SEQ ID NO 1987
<211> LENGTH: 9
<212> TYPE: PRT
<213> ORGANISM: homo sapien

<400> SEQUENCE: 1987

Asp Ile Met Leu Ile Thr Ala Ala Val
 1               5

<210> SEQ ID NO 1988
<211> LENGTH: 9
<212> TYPE: PRT
<213> ORGANISM: homo sapien

<400> SEQUENCE: 1988

Asp Leu Val Gln Ser Val Gly Val Leu
 1               5

<210> SEQ ID NO 1989
<211> LENGTH: 9
<212> TYPE: PRT
<213> ORGANISM: homo sapien

<400> SEQUENCE: 1989

Ile Ile Leu Glu Gly Val Pro Ser His
 1               5

<210> SEQ ID NO 1990
<211> LENGTH: 9
<212> TYPE: PRT
<213> ORGANISM: homo sapien

<400> SEQUENCE: 1990

Ile Leu Glu Gly Val Pro Ser His Leu
 1               5
```

```
<210> SEQ ID NO 1991
<211> LENGTH: 9
<212> TYPE: PRT
<213> ORGANISM: homo sapien

<400> SEQUENCE: 1991

Gln Leu Gln Ser Tyr Arg Gln Glu Val
 1               5

<210> SEQ ID NO 1992
<211> LENGTH: 9
<212> TYPE: PRT
<213> ORGANISM: homo sapien

<400> SEQUENCE: 1992

Met Leu Arg Lys Asp Asp Ala Pro Leu
 1               5

<210> SEQ ID NO 1993
<211> LENGTH: 9
<212> TYPE: PRT
<213> ORGANISM: homo sapien

<400> SEQUENCE: 1993

Thr Leu Gln Ala Asp Asp Asp Ser Leu
 1               5

<210> SEQ ID NO 1994
<211> LENGTH: 9
<212> TYPE: PRT
<213> ORGANISM: homo sapien

<400> SEQUENCE: 1994

Lys Ala Arg Leu Thr Ile Ala Ala Val
 1               5

<210> SEQ ID NO 1995
<211> LENGTH: 9
<212> TYPE: PRT
<213> ORGANISM: homo sapien

<400> SEQUENCE: 1995

Tyr Ile Ala Asn Ser Leu Ala Ile Met
 1               5

<210> SEQ ID NO 1996
<211> LENGTH: 9
<212> TYPE: PRT
<213> ORGANISM: homo sapien

<400> SEQUENCE: 1996

Ser Ala Met Ile Ser Val Leu Leu Val
 1               5

<210> SEQ ID NO 1997
<211> LENGTH: 9
<212> TYPE: PRT
<213> ORGANISM: homo sapien

<400> SEQUENCE: 1997

Pro Ile Cys Thr Tyr Val Phe Ser Leu
 1               5

<210> SEQ ID NO 1998
<211> LENGTH: 9
```

```
<212> TYPE: PRT
<213> ORGANISM: homo sapien

<400> SEQUENCE: 1998

Arg Ile Ile Trp Asp Thr Val Val Ile
 1               5

<210> SEQ ID NO 1999
<211> LENGTH: 9
<212> TYPE: PRT
<213> ORGANISM: homo sapien

<400> SEQUENCE: 1999

Gly Met Tyr Arg Cys Thr Ile Gln Leu
 1               5

<210> SEQ ID NO 2000
<211> LENGTH: 9
<212> TYPE: PRT
<213> ORGANISM: homo sapien

<400> SEQUENCE: 2000

Leu Leu Asp Gln Asp Leu Pro Leu Thr
 1               5

<210> SEQ ID NO 2001
<211> LENGTH: 9
<212> TYPE: PRT
<213> ORGANISM: homo sapien

<400> SEQUENCE: 2001

Met Leu Thr Asp Leu Ser Ala Ile Ile
 1               5

<210> SEQ ID NO 2002
<211> LENGTH: 9
<212> TYPE: PRT
<213> ORGANISM: homo sapien

<400> SEQUENCE: 2002

Ile Leu Met Gly Phe Leu Leu Tyr Glu
 1               5

<210> SEQ ID NO 2003
<211> LENGTH: 9
<212> TYPE: PRT
<213> ORGANISM: homo sapien

<400> SEQUENCE: 2003

Leu Met Gly Phe Leu Leu Tyr Glu Ala
 1               5

<210> SEQ ID NO 2004
<211> LENGTH: 9
<212> TYPE: PRT
<213> ORGANISM: homo sapien

<400> SEQUENCE: 2004

Ile Thr Ala Ala Val Gly Val Ala Val
 1               5

<210> SEQ ID NO 2005
<211> LENGTH: 9
<212> TYPE: PRT
<213> ORGANISM: homo sapien
```

```
<400> SEQUENCE: 2005

Met Lys Ile Glu Asp Val Tyr Ser Val
1               5

<210> SEQ ID NO 2006
<211> LENGTH: 9
<212> TYPE: PRT
<213> ORGANISM: homo sapien

<400> SEQUENCE: 2006

Ala Val Leu Tyr Leu Leu Phe Met Ile
1               5

<210> SEQ ID NO 2007
<211> LENGTH: 9
<212> TYPE: PRT
<213> ORGANISM: homo sapien

<400> SEQUENCE: 2007

Phe Met Ile Gly Glu Leu Val Gly Gly
1               5

<210> SEQ ID NO 2008
<211> LENGTH: 9
<212> TYPE: PRT
<213> ORGANISM: homo sapien

<400> SEQUENCE: 2008

Leu Leu Ala Leu Trp Leu Ser Ser Lys
1               5

<210> SEQ ID NO 2009
<211> LENGTH: 9
<212> TYPE: PRT
<213> ORGANISM: homo sapien

<400> SEQUENCE: 2009

Arg Leu Glu Val Leu Ser Ala Met Ile
1               5

<210> SEQ ID NO 2010
<211> LENGTH: 9
<212> TYPE: PRT
<213> ORGANISM: homo sapien

<400> SEQUENCE: 2010

Glu Ile Asn Gly Asp Ile Met Leu Ile
1               5

<210> SEQ ID NO 2011
<211> LENGTH: 9
<212> TYPE: PRT
<213> ORGANISM: homo sapien

<400> SEQUENCE: 2011

Ala Ala Val Gly Val Ala Val Asn Val
1               5

<210> SEQ ID NO 2012
<211> LENGTH: 9
<212> TYPE: PRT
<213> ORGANISM: homo sapien

<400> SEQUENCE: 2012
```

Val Arg Ala Ala Phe Val His Ala Leu
1               5

<210> SEQ ID NO 2013
<211> LENGTH: 9
<212> TYPE: PRT
<213> ORGANISM: homo sapien

<400> SEQUENCE: 2013

Asp Leu Pro Leu Thr Asn Ser Gln Leu
1               5

<210> SEQ ID NO 2014
<211> LENGTH: 9
<212> TYPE: PRT
<213> ORGANISM: homo sapien

<400> SEQUENCE: 2014

Pro Leu Thr Asn Ser Gln Leu Ser Leu
1               5

<210> SEQ ID NO 2015
<211> LENGTH: 9
<212> TYPE: PRT
<213> ORGANISM: homo sapien

<400> SEQUENCE: 2015

Ile Leu Lys Gln Arg Lys Val Lys Ala
1               5

<210> SEQ ID NO 2016
<211> LENGTH: 9
<212> TYPE: PRT
<213> ORGANISM: homo sapien

<400> SEQUENCE: 2016

Asp Ala Leu His Met Leu Thr Asp Leu
1               5

<210> SEQ ID NO 2017
<211> LENGTH: 9
<212> TYPE: PRT
<213> ORGANISM: homo sapien

<400> SEQUENCE: 2017

Ile Ile Leu Thr Leu Leu Ala Leu Trp
1               5

<210> SEQ ID NO 2018
<211> LENGTH: 9
<212> TYPE: PRT
<213> ORGANISM: homo sapien

<400> SEQUENCE: 2018

Val Leu Leu Val Tyr Ile Leu Met Gly
1               5

<210> SEQ ID NO 2019
<211> LENGTH: 9
<212> TYPE: PRT
<213> ORGANISM: homo sapien

<400> SEQUENCE: 2019

Ala Val Gly Val Ala Val Asn Val Ile

-continued

```
<210> SEQ ID NO 2020
<211> LENGTH: 9
<212> TYPE: PRT
<213> ORGANISM: homo sapien

<400> SEQUENCE: 2020

Lys Ile Ala Asp Pro Ile Cys Thr Tyr
 1               5

<210> SEQ ID NO 2021
<211> LENGTH: 9
<212> TYPE: PRT
<213> ORGANISM: homo sapien

<400> SEQUENCE: 2021

Thr Val Val Ile Ile Leu Glu Gly Val
 1               5

<210> SEQ ID NO 2022
<211> LENGTH: 9
<212> TYPE: PRT
<213> ORGANISM: homo sapien

<400> SEQUENCE: 2022

Ser Leu Thr Ser Gly Lys Ser Thr Ala
 1               5

<210> SEQ ID NO 2023
<211> LENGTH: 9
<212> TYPE: PRT
<213> ORGANISM: homo sapien

<400> SEQUENCE: 2023

His Leu Leu Leu Asn Thr Phe Gly Met
 1               5

<210> SEQ ID NO 2024
<211> LENGTH: 9
<212> TYPE: PRT
<213> ORGANISM: homo sapien

<400> SEQUENCE: 2024

Ser Arg Phe Asn Lys Leu Arg Val Val
 1               5

<210> SEQ ID NO 2025
<211> LENGTH: 9
<212> TYPE: PRT
<213> ORGANISM: homo sapien

<400> SEQUENCE: 2025

Leu Ser Ala Ile Ile Leu Thr Leu Leu
 1               5

<210> SEQ ID NO 2026
<211> LENGTH: 9
<212> TYPE: PRT
<213> ORGANISM: homo sapien

<400> SEQUENCE: 2026

Ile Ser Val Leu Leu Val Tyr Ile Leu
 1               5
```

```
<210> SEQ ID NO 2027
<211> LENGTH: 9
<212> TYPE: PRT
<213> ORGANISM: homo sapien

<400> SEQUENCE: 2027

Leu Val Tyr Ile Leu Met Gly Phe Leu
1               5

<210> SEQ ID NO 2028
<211> LENGTH: 9
<212> TYPE: PRT
<213> ORGANISM: homo sapien

<400> SEQUENCE: 2028

Val Ile Met Gly Phe Leu Leu Asn Gln
1               5

<210> SEQ ID NO 2029
<211> LENGTH: 9
<212> TYPE: PRT
<213> ORGANISM: homo sapien

<400> SEQUENCE: 2029

Ile Ala Asp Pro Ile Cys Thr Tyr Val
1               5

<210> SEQ ID NO 2030
<211> LENGTH: 9
<212> TYPE: PRT
<213> ORGANISM: homo sapien

<400> SEQUENCE: 2030

Glu Ala Leu Met Lys Ile Glu Asp Val
1               5

<210> SEQ ID NO 2031
<211> LENGTH: 9
<212> TYPE: PRT
<213> ORGANISM: homo sapien

<400> SEQUENCE: 2031

Leu Thr Ser Gly Lys Ser Thr Ala Ile
1               5

<210> SEQ ID NO 2032
<211> LENGTH: 9
<212> TYPE: PRT
<213> ORGANISM: homo sapien

<400> SEQUENCE: 2032

Ser Thr Ala Ile Val His Ile Gln Leu
1               5

<210> SEQ ID NO 2033
<211> LENGTH: 9
<212> TYPE: PRT
<213> ORGANISM: homo sapien

<400> SEQUENCE: 2033

Thr Ala Ile Val His Ile Gln Leu Ile
1               5

<210> SEQ ID NO 2034
```

```
<211> LENGTH: 9
<212> TYPE: PRT
<213> ORGANISM: homo sapien

<400> SEQUENCE: 2034

Gln Leu Ile Pro Gly Ser Ser Ser Lys
1               5

<210> SEQ ID NO 2035
<211> LENGTH: 9
<212> TYPE: PRT
<213> ORGANISM: homo sapien

<400> SEQUENCE: 2035

Lys Leu Arg Val Val Ala Asp Asp
1               5

<210> SEQ ID NO 2036
<211> LENGTH: 9
<212> TYPE: PRT
<213> ORGANISM: homo sapien

<400> SEQUENCE: 2036

Pro Val Asn Gly Ala His Pro Thr Leu
1               5

<210> SEQ ID NO 2037
<211> LENGTH: 9
<212> TYPE: PRT
<213> ORGANISM: homo sapien

<400> SEQUENCE: 2037

Gln Leu Ser Leu Lys Val Asp Ser Cys
1               5

<210> SEQ ID NO 2038
<211> LENGTH: 9
<212> TYPE: PRT
<213> ORGANISM: homo sapien

<400> SEQUENCE: 2038

Ala Met Ile Ser Val Leu Leu Val Tyr
1               5

<210> SEQ ID NO 2039
<211> LENGTH: 9
<212> TYPE: PRT
<213> ORGANISM: homo sapien

<400> SEQUENCE: 2039

Arg Thr Ile His Met Asn Tyr Glu Ile
1               5

<210> SEQ ID NO 2040
<211> LENGTH: 9
<212> TYPE: PRT
<213> ORGANISM: homo sapien

<400> SEQUENCE: 2040

Leu Ile Thr Ala Ala Val Gly Val Ala
1               5

<210> SEQ ID NO 2041
<211> LENGTH: 9
<212> TYPE: PRT
```

-continued

<213> ORGANISM: homo sapien

<400> SEQUENCE: 2041

Ala Val Asn Val Ile Met Gly Phe Leu
1               5

<210> SEQ ID NO 2042
<211> LENGTH: 9
<212> TYPE: PRT
<213> ORGANISM: homo sapien

<400> SEQUENCE: 2042

Leu Ile Ala Ala Tyr Ile Ile Arg Phe
1               5

<210> SEQ ID NO 2043
<211> LENGTH: 9
<212> TYPE: PRT
<213> ORGANISM: homo sapien

<400> SEQUENCE: 2043

Cys Thr Tyr Val Phe Ser Leu Leu Val
1               5

<210> SEQ ID NO 2044
<211> LENGTH: 9
<212> TYPE: PRT
<213> ORGANISM: homo sapien

<400> SEQUENCE: 2044

Leu Val Ala Phe Thr Thr Phe Arg Ile
1               5

<210> SEQ ID NO 2045
<211> LENGTH: 9
<212> TYPE: PRT
<213> ORGANISM: homo sapien

<400> SEQUENCE: 2045

Val Glu Asp Leu Asn Ile Trp Ser Leu
1               5

<210> SEQ ID NO 2046
<211> LENGTH: 9
<212> TYPE: PRT
<213> ORGANISM: homo sapien

<400> SEQUENCE: 2046

Ala Arg Leu Thr Ile Ala Ala Val Leu
1               5

<210> SEQ ID NO 2047
<211> LENGTH: 9
<212> TYPE: PRT
<213> ORGANISM: homo sapien

<400> SEQUENCE: 2047

Ala Ala Val Leu Tyr Leu Leu Phe Met
1               5

<210> SEQ ID NO 2048
<211> LENGTH: 9
<212> TYPE: PRT
<213> ORGANISM: homo sapien

```
<400> SEQUENCE: 2048

Met Ile Gly Glu Leu Val Gly Gly Tyr
1               5

<210> SEQ ID NO 2049
<211> LENGTH: 9
<212> TYPE: PRT
<213> ORGANISM: homo sapien

<400> SEQUENCE: 2049

Ala Ile Met Thr Asp Ala Leu His Met
1               5

<210> SEQ ID NO 2050
<211> LENGTH: 9
<212> TYPE: PRT
<213> ORGANISM: homo sapien

<400> SEQUENCE: 2050

Leu Thr Asp Leu Ser Ala Ile Ile Leu
1               5

<210> SEQ ID NO 2051
<211> LENGTH: 9
<212> TYPE: PRT
<213> ORGANISM: homo sapien

<400> SEQUENCE: 2051

Ser Ala Ile Ile Leu Thr Leu Leu Ala
1               5

<210> SEQ ID NO 2052
<211> LENGTH: 9
<212> TYPE: PRT
<213> ORGANISM: homo sapien

<400> SEQUENCE: 2052

Thr Leu Leu Ala Leu Trp Leu Ser Ser
1               5

<210> SEQ ID NO 2053
<211> LENGTH: 9
<212> TYPE: PRT
<213> ORGANISM: homo sapien

<400> SEQUENCE: 2053

Phe Gly Phe His Arg Leu Glu Val Leu
1               5

<210> SEQ ID NO 2054
<211> LENGTH: 9
<212> TYPE: PRT
<213> ORGANISM: homo sapien

<400> SEQUENCE: 2054

Leu Ser Ala Met Ile Ser Val Leu Leu
1               5

<210> SEQ ID NO 2055
<211> LENGTH: 9
<212> TYPE: PRT
<213> ORGANISM: homo sapien

<400> SEQUENCE: 2055
```

Leu Leu Val Tyr Ile Leu Met Gly Phe
1               5

<210> SEQ ID NO 2056
<211> LENGTH: 9
<212> TYPE: PRT
<213> ORGANISM: homo sapien

<400> SEQUENCE: 2056

Tyr Glu Ile Asn Gly Asp Ile Met Leu
1               5

<210> SEQ ID NO 2057
<211> LENGTH: 9
<212> TYPE: PRT
<213> ORGANISM: homo sapien

<400> SEQUENCE: 2057

Ala Phe Val His Ala Leu Gly Asp Leu
1               5

<210> SEQ ID NO 2058
<211> LENGTH: 9
<212> TYPE: PRT
<213> ORGANISM: homo sapien

<400> SEQUENCE: 2058

Phe Val His Ala Leu Gly Asp Leu Val
1               5

<210> SEQ ID NO 2059
<211> LENGTH: 9
<212> TYPE: PRT
<213> ORGANISM: homo sapien

<400> SEQUENCE: 2059

Gly Asp Leu Val Gln Ser Val Gly Val
1               5

<210> SEQ ID NO 2060
<211> LENGTH: 9
<212> TYPE: PRT
<213> ORGANISM: homo sapien

<400> SEQUENCE: 2060

Leu Val Gln Ser Val Gly Val Leu Ile
1               5

<210> SEQ ID NO 2061
<211> LENGTH: 9
<212> TYPE: PRT
<213> ORGANISM: homo sapien

<400> SEQUENCE: 2061

Gly Val Leu Ile Ala Ala Tyr Ile Ile
1               5

<210> SEQ ID NO 2062
<211> LENGTH: 9
<212> TYPE: PRT
<213> ORGANISM: homo sapien

<400> SEQUENCE: 2062

Tyr Ile Ile Arg Phe Lys Pro Glu Tyr
1               5

<210> SEQ ID NO 2063
<211> LENGTH: 9
<212> TYPE: PRT
<213> ORGANISM: homo sapien

<400> SEQUENCE: 2063

Ser Leu Leu Val Ala Phe Thr Thr Phe
1               5

<210> SEQ ID NO 2064
<211> LENGTH: 9
<212> TYPE: PRT
<213> ORGANISM: homo sapien

<400> SEQUENCE: 2064

Ile Trp Asp Thr Val Val Ile Ile Leu
1               5

<210> SEQ ID NO 2065
<211> LENGTH: 9
<212> TYPE: PRT
<213> ORGANISM: homo sapien

<400> SEQUENCE: 2065

Lys Ala Asn His Leu Leu Leu Asn Thr
1               5

<210> SEQ ID NO 2066
<211> LENGTH: 9
<212> TYPE: PRT
<213> ORGANISM: homo sapien

<400> SEQUENCE: 2066

Gly Ala Trp Lys Arg Leu Lys Ser Met
1               5

<210> SEQ ID NO 2067
<211> LENGTH: 9
<212> TYPE: PRT
<213> ORGANISM: homo sapien

<400> SEQUENCE: 2067

Arg Leu Lys Ser Met Leu Arg Lys Asp
1               5

<210> SEQ ID NO 2068
<211> LENGTH: 9
<212> TYPE: PRT
<213> ORGANISM: homo sapien

<400> SEQUENCE: 2068

Phe Leu Asn Asp Thr Ser Ala Phe Asp
1               5

<210> SEQ ID NO 2069
<211> LENGTH: 9
<212> TYPE: PRT
<213> ORGANISM: homo sapien

<400> SEQUENCE: 2069

Ser Ala Phe Asp Phe Ser Asp Glu Ala
1               5

```
<210> SEQ ID NO 2070
<211> LENGTH: 9
<212> TYPE: PRT
<213> ORGANISM: homo sapien

<400> SEQUENCE: 2070

Leu Gln Ala Asp Asp Asp Ser Leu Leu
1               5

<210> SEQ ID NO 2071
<211> LENGTH: 9
<212> TYPE: PRT
<213> ORGANISM: homo sapien

<400> SEQUENCE: 2071

Arg Glu Ile Leu Lys Gln Arg Lys Val
1               5

<210> SEQ ID NO 2072
<211> LENGTH: 9
<212> TYPE: PRT
<213> ORGANISM: homo sapien

<400> SEQUENCE: 2072

Leu Val Gly Gly Tyr Ile Ala Asn Ser
1               5

<210> SEQ ID NO 2073
<211> LENGTH: 9
<212> TYPE: PRT
<213> ORGANISM: homo sapien

<400> SEQUENCE: 2073

Ala Leu His Met Leu Thr Asp Leu Ser
1               5

<210> SEQ ID NO 2074
<211> LENGTH: 9
<212> TYPE: PRT
<213> ORGANISM: homo sapien

<400> SEQUENCE: 2074

Glu Val Leu Ser Ala Met Ile Ser Val
1               5

<210> SEQ ID NO 2075
<211> LENGTH: 9
<212> TYPE: PRT
<213> ORGANISM: homo sapien

<400> SEQUENCE: 2075

Tyr Ile Leu Met Gly Phe Leu Leu Tyr
1               5

<210> SEQ ID NO 2076
<211> LENGTH: 9
<212> TYPE: PRT
<213> ORGANISM: homo sapien

<400> SEQUENCE: 2076

Ile Met Gly Phe Leu Leu Asn Gln Ser
1               5

<210> SEQ ID NO 2077
<211> LENGTH: 9
```

```
<212> TYPE: PRT
<213> ORGANISM: homo sapien

<400> SEQUENCE: 2077

Ser Leu Pro Ser Asn Ser Pro Thr Arg
1               5

<210> SEQ ID NO 2078
<211> LENGTH: 9
<212> TYPE: PRT
<213> ORGANISM: homo sapien

<400> SEQUENCE: 2078

Ile Arg Phe Lys Pro Glu Tyr Lys Ile
1               5

<210> SEQ ID NO 2079
<211> LENGTH: 9
<212> TYPE: PRT
<213> ORGANISM: homo sapien

<400> SEQUENCE: 2079

Tyr Val Phe Ser Leu Leu Val Ala Phe
1               5

<210> SEQ ID NO 2080
<211> LENGTH: 9
<212> TYPE: PRT
<213> ORGANISM: homo sapien

<400> SEQUENCE: 2080

Leu Leu Val Ala Phe Thr Thr Phe Arg
1               5

<210> SEQ ID NO 2081
<211> LENGTH: 9
<212> TYPE: PRT
<213> ORGANISM: homo sapien

<400> SEQUENCE: 2081

Gly Lys Ser Thr Ala Ile Val His Ile
1               5

<210> SEQ ID NO 2082
<211> LENGTH: 9
<212> TYPE: PRT
<213> ORGANISM: homo sapien

<400> SEQUENCE: 2082

Ser Ala Phe Glu Phe Ser Asp Glu Ala
1               5

<210> SEQ ID NO 2083
<211> LENGTH: 9
<212> TYPE: PRT
<213> ORGANISM: homo sapien

<400> SEQUENCE: 2083

Phe Leu Asn Asp Thr Ser Ala Phe Glu
1               5

<210> SEQ ID NO 2084
<211> LENGTH: 9
<212> TYPE: PRT
<213> ORGANISM: homo sapien
```

```
<400> SEQUENCE: 2084

Ser Ala Phe Glu Phe Ser Asp Glu Ala
 1               5

<210> SEQ ID NO 2085
<211> LENGTH: 9
<212> TYPE: PRT
<213> ORGANISM: homo sapien

<400> SEQUENCE: 2085

Asp Thr Ser Ala Phe Glu Phe Ser Asp
 1               5

<210> SEQ ID NO 2086
<211> LENGTH: 9
<212> TYPE: PRT
<213> ORGANISM: homo sapien

<400> SEQUENCE: 2086

Leu Asn Asp Thr Ser Ala Phe Glu Phe
 1               5

<210> SEQ ID NO 2087
<211> LENGTH: 9
<212> TYPE: PRT
<213> ORGANISM: homo sapien

<400> SEQUENCE: 2087

Ser Ala Phe Glu Phe Ser Asp Glu Ala
 1               5

<210> SEQ ID NO 2088
<211> LENGTH: 10
<212> TYPE: PRT
<213> ORGANISM: homo sapien

<400> SEQUENCE: 2088

Phe Leu Asn Asp Thr Ser Ala Phe Glu Phe
 1               5                  10

<210> SEQ ID NO 2089
<211> LENGTH: 10
<212> TYPE: PRT
<213> ORGANISM: homo sapien

<400> SEQUENCE: 2089

Leu Asn Asp Thr Ser Ala Phe Glu Phe Ser
 1               5                  10

<210> SEQ ID NO 2090
<211> LENGTH: 10
<212> TYPE: PRT
<213> ORGANISM: homo sapien

<400> SEQUENCE: 2090

Asp Thr Ser Ala Phe Glu Phe Ser Asp Glu
 1               5                  10

<210> SEQ ID NO 2091
<211> LENGTH: 10
<212> TYPE: PRT
<213> ORGANISM: homo sapien

<400> SEQUENCE: 2091
```

-continued

Phe Leu Asn Asp Thr Ser Ala Phe Glu Phe
1               5                   10

<210> SEQ ID NO 2092
<211> LENGTH: 10
<212> TYPE: PRT
<213> ORGANISM: homo sapien

<400> SEQUENCE: 2092

Phe Leu Asn Asp Thr Ser Ala Phe Glu Phe
1               5                   10

<210> SEQ ID NO 2093
<211> LENGTH: 15
<212> TYPE: PRT
<213> ORGANISM: homo sapien

<400> SEQUENCE: 2093

Asp Thr Val Val Ile Ile Leu Glu Gly Val Pro Ser His Leu Asn
1               5                   10                  15

<210> SEQ ID NO 2094
<211> LENGTH: 15
<212> TYPE: PRT
<213> ORGANISM: homo sapien

<400> SEQUENCE: 2094

Val Leu Leu Val Tyr Ile Leu Met Gly Phe Leu Leu Tyr Glu Ala
1               5                   10                  15

<210> SEQ ID NO 2095
<211> LENGTH: 15
<212> TYPE: PRT
<213> ORGANISM: homo sapien

<400> SEQUENCE: 2095

Leu His Met Leu Thr Asp Leu Ser Ala Ile Ile Leu Thr Leu Leu
1               5                   10                  15

<210> SEQ ID NO 2096
<211> LENGTH: 15
<212> TYPE: PRT
<213> ORGANISM: homo sapien

<400> SEQUENCE: 2096

Leu Phe Met Ile Gly Glu Leu Val Gly Gly Tyr Ile Ala Asn Ser
1               5                   10                  15

<210> SEQ ID NO 2097
<211> LENGTH: 15
<212> TYPE: PRT
<213> ORGANISM: homo sapien

<400> SEQUENCE: 2097

Ser Ala Ile Ile Leu Thr Leu Leu Ala Leu Trp Leu Ser Ser Lys
1               5                   10                  15

<210> SEQ ID NO 2098
<211> LENGTH: 15
<212> TYPE: PRT
<213> ORGANISM: homo sapien

<400> SEQUENCE: 2098

Phe His Arg Leu Glu Val Leu Ser Ala Met Ile Ser Val Leu Leu

-continued

<210> SEQ ID NO 2099
<211> LENGTH: 15
<212> TYPE: PRT
<213> ORGANISM: homo sapien

<400> SEQUENCE: 2099

Val Gln Ser Val Gly Val Leu Ile Ala Ala Tyr Ile Ile Arg Phe
1               5                   10                  15

<210> SEQ ID NO 2100
<211> LENGTH: 15
<212> TYPE: PRT
<213> ORGANISM: homo sapien

<400> SEQUENCE: 2100

Val Leu Tyr Leu Leu Phe Met Ile Gly Glu Leu Val Gly Gly Tyr
1               5                   10                  15

<210> SEQ ID NO 2101
<211> LENGTH: 15
<212> TYPE: PRT
<213> ORGANISM: homo sapien

<400> SEQUENCE: 2101

Gly Val Ala Val Asn Val Ile Met Gly Phe Leu Leu Asn Gln Ser
1               5                   10                  15

<210> SEQ ID NO 2102
<211> LENGTH: 15
<212> TYPE: PRT
<213> ORGANISM: homo sapien

<400> SEQUENCE: 2102

Asp Leu Asn Ile Trp Ser Leu Thr Ser Gly Lys Ser Thr Ala Ile
1               5                   10                  15

<210> SEQ ID NO 2103
<211> LENGTH: 15
<212> TYPE: PRT
<213> ORGANISM: homo sapien

<400> SEQUENCE: 2103

Ile Val His Ile Gln Leu Ile Pro Gly Ser Ser Ser Lys Trp Glu
1               5                   10                  15

<210> SEQ ID NO 2104
<211> LENGTH: 15
<212> TYPE: PRT
<213> ORGANISM: homo sapien

<400> SEQUENCE: 2104

Phe Thr Thr Phe Arg Ile Ile Trp Asp Thr Val Ile Ile Leu
1               5                   10                  15

<210> SEQ ID NO 2105
<211> LENGTH: 15
<212> TYPE: PRT
<213> ORGANISM: homo sapien

<400> SEQUENCE: 2105

Leu Ser Arg Phe Asn Lys Leu Arg Val Val Val Ala Asp Asp Gly
1               5                   10                  15

```
<210> SEQ ID NO 2106
<211> LENGTH: 15
<212> TYPE: PRT
<213> ORGANISM: homo sapien

<400> SEQUENCE: 2106

Gly Asp Ile Met Leu Ile Thr Ala Ala Val Gly Val Ala Val Asn
 1               5                  10                  15

<210> SEQ ID NO 2107
<211> LENGTH: 15
<212> TYPE: PRT
<213> ORGANISM: homo sapien

<400> SEQUENCE: 2107

Lys Ser Met Leu Arg Lys Asp Asp Ala Pro Leu Phe Leu Asn Asp
 1               5                  10                  15

<210> SEQ ID NO 2108
<211> LENGTH: 15
<212> TYPE: PRT
<213> ORGANISM: homo sapien

<400> SEQUENCE: 2108

Leu Glu Val Leu Ser Ala Met Ile Ser Val Leu Leu Val Tyr Ile
 1               5                  10                  15

<210> SEQ ID NO 2109
<211> LENGTH: 15
<212> TYPE: PRT
<213> ORGANISM: homo sapien

<400> SEQUENCE: 2109

Thr Phe Gly Phe His Arg Leu Glu Val Leu Ser Ala Met Ile Ser
 1               5                  10                  15

<210> SEQ ID NO 2110
<211> LENGTH: 15
<212> TYPE: PRT
<213> ORGANISM: homo sapien

<400> SEQUENCE: 2110

Arg Ala Ala Phe Val His Ala Leu Gly Asp Leu Val Gln Ser Val
 1               5                  10                  15

<210> SEQ ID NO 2111
<211> LENGTH: 15
<212> TYPE: PRT
<213> ORGANISM: homo sapien

<400> SEQUENCE: 2111

Thr Tyr Val Phe Ser Leu Leu Val Ala Phe Thr Thr Phe Arg Ile
 1               5                  10                  15

<210> SEQ ID NO 2112
<211> LENGTH: 15
<212> TYPE: PRT
<213> ORGANISM: homo sapien

<400> SEQUENCE: 2112

Thr Ala Ile Val His Ile Gln Leu Ile Pro Gly Ser Ser Ser Lys
 1               5                  10                  15

<210> SEQ ID NO 2113
```

```
<211> LENGTH: 15
<212> TYPE: PRT
<213> ORGANISM: homo sapien

<400> SEQUENCE: 2113

Ala Ile Ile Leu Thr Leu Leu Ala Leu Trp Leu Ser Ser Lys Ser
 1               5                  10                  15

<210> SEQ ID NO 2114
<211> LENGTH: 15
<212> TYPE: PRT
<213> ORGANISM: homo sapien

<400> SEQUENCE: 2114

Trp Asp Thr Val Val Ile Ile Leu Glu Gly Val Pro Ser His Leu
 1               5                  10                  15

<210> SEQ ID NO 2115
<211> LENGTH: 15
<212> TYPE: PRT
<213> ORGANISM: homo sapien

<400> SEQUENCE: 2115

Ser Gly Ala Trp Lys Arg Leu Lys Ser Met Leu Arg Lys Asp Asp
 1               5                  10                  15

<210> SEQ ID NO 2116
<211> LENGTH: 15
<212> TYPE: PRT
<213> ORGANISM: homo sapien

<400> SEQUENCE: 2116

Pro Leu Phe Leu Asn Asp Thr Ser Ala Phe Asp Phe Ser Asp Glu
 1               5                  10                  15

<210> SEQ ID NO 2117
<211> LENGTH: 15
<212> TYPE: PRT
<213> ORGANISM: homo sapien

<400> SEQUENCE: 2117

Leu Arg Val Val Val Ala Asp Asp Gly Ser Glu Ala Pro Glu Arg
 1               5                  10                  15

<210> SEQ ID NO 2118
<211> LENGTH: 15
<212> TYPE: PRT
<213> ORGANISM: homo sapien

<400> SEQUENCE: 2118

Gln Arg Glu Ile Leu Lys Gln Arg Lys Val Lys Ala Arg Leu Thr
 1               5                  10                  15

<210> SEQ ID NO 2119
<211> LENGTH: 15
<212> TYPE: PRT
<213> ORGANISM: homo sapien

<400> SEQUENCE: 2119

Thr Asp Ala Leu His Met Leu Thr Asp Leu Ser Ala Ile Ile Leu
 1               5                  10                  15

<210> SEQ ID NO 2120
<211> LENGTH: 15
<212> TYPE: PRT
```

<213> ORGANISM: homo sapien

<400> SEQUENCE: 2120

Tyr Ile Leu Met Gly Phe Leu Leu Tyr Glu Ala Val Gln Arg Thr
1               5                   10                  15

<210> SEQ ID NO 2121
<211> LENGTH: 15
<212> TYPE: PRT
<213> ORGANISM: homo sapien

<400> SEQUENCE: 2121

Ile Met Leu Ile Thr Ala Ala Val Gly Val Ala Val Asn Val Ile
1               5                   10                  15

<210> SEQ ID NO 2122
<211> LENGTH: 15
<212> TYPE: PRT
<213> ORGANISM: homo sapien

<400> SEQUENCE: 2122

Leu Gly Asp Leu Val Gln Ser Val Gly Val Leu Ile Ala Ala Tyr
1               5                   10                  15

<210> SEQ ID NO 2123
<211> LENGTH: 15
<212> TYPE: PRT
<213> ORGANISM: homo sapien

<400> SEQUENCE: 2123

Lys Glu Ala Leu Met Lys Ile Glu Asp Val Tyr Ser Val Glu Asp
1               5                   10                  15

<210> SEQ ID NO 2124
<211> LENGTH: 15
<212> TYPE: PRT
<213> ORGANISM: homo sapien

<400> SEQUENCE: 2124

Lys Ala Asn His Leu Leu Leu Asn Thr Phe Gly Met Tyr Arg Cys
1               5                   10                  15

<210> SEQ ID NO 2125
<211> LENGTH: 15
<212> TYPE: PRT
<213> ORGANISM: homo sapien

<400> SEQUENCE: 2125

Phe Asn Lys Leu Arg Val Val Val Ala Asp Asp Gly Ser Glu Ala
1               5                   10                  15

<210> SEQ ID NO 2126
<211> LENGTH: 15
<212> TYPE: PRT
<213> ORGANISM: homo sapien

<400> SEQUENCE: 2126

Glu Ala Pro Glu Arg Pro Val Asn Gly Ala His Pro Thr Leu Gln
1               5                   10                  15

<210> SEQ ID NO 2127
<211> LENGTH: 15
<212> TYPE: PRT
<213> ORGANISM: homo sapien -continued

```
<400> SEQUENCE: 2127

Phe Met Ile Gly Glu Leu Val Gly Gly Tyr Ile Ala Asn Ser Leu
 1               5                  10                  15

<210> SEQ ID NO 2128
<211> LENGTH: 15
<212> TYPE: PRT
<213> ORGANISM: homo sapien

<400> SEQUENCE: 2128

Gly Glu Leu Val Gly Gly Tyr Ile Ala Asn Ser Leu Ala Ile Met
 1               5                  10                  15

<210> SEQ ID NO 2129
<211> LENGTH: 15
<212> TYPE: PRT
<213> ORGANISM: homo sapien

<400> SEQUENCE: 2129

Leu Thr Leu Leu Ala Leu Trp Leu Ser Ser Lys Ser Pro Thr Lys
 1               5                  10                  15

<210> SEQ ID NO 2130
<211> LENGTH: 15
<212> TYPE: PRT
<213> ORGANISM: homo sapien

<400> SEQUENCE: 2130

Ser Ala Met Ile Ser Val Leu Leu Val Tyr Ile Leu Met Gly Phe
 1               5                  10                  15

<210> SEQ ID NO 2131
<211> LENGTH: 15
<212> TYPE: PRT
<213> ORGANISM: homo sapien

<400> SEQUENCE: 2131

Gln Ser Val Gly Val Leu Ile Ala Ala Tyr Ile Ile Arg Phe Lys
 1               5                  10                  15

<210> SEQ ID NO 2132
<211> LENGTH: 15
<212> TYPE: PRT
<213> ORGANISM: homo sapien

<400> SEQUENCE: 2132

Val Tyr Ser Val Glu Asp Leu Asn Ile Trp Ser Leu Thr Ser Gly
 1               5                  10                  15

<210> SEQ ID NO 2133
<211> LENGTH: 15
<212> TYPE: PRT
<213> ORGANISM: homo sapien

<400> SEQUENCE: 2133

Ile Trp Ser Leu Thr Ser Gly Lys Ser Thr Ala Ile Val His Ile
 1               5                  10                  15

<210> SEQ ID NO 2134
<211> LENGTH: 15
<212> TYPE: PRT
<213> ORGANISM: homo sapien

<400> SEQUENCE: 2134
```

-continued

Asp Ala Pro Leu Phe Leu Asn Asp Thr Ser Ala Phe Asp Phe Ser
1               5                   10                  15

<210> SEQ ID NO 2135
<211> LENGTH: 15
<212> TYPE: PRT
<213> ORGANISM: homo sapien

<400> SEQUENCE: 2135

Arg Val Val Val Ala Asp Asp Gly Ser Glu Ala Pro Glu Arg Pro
1               5                   10                  15

<210> SEQ ID NO 2136
<211> LENGTH: 15
<212> TYPE: PRT
<213> ORGANISM: homo sapien

<400> SEQUENCE: 2136

Asp Gln Asp Leu Pro Leu Thr Asn Ser Gln Leu Ser Leu Lys Val
1               5                   10                  15

<210> SEQ ID NO 2137
<211> LENGTH: 15
<212> TYPE: PRT
<213> ORGANISM: homo sapien

<400> SEQUENCE: 2137

Gln Arg Lys Val Lys Ala Arg Leu Thr Ile Ala Ala Val Leu Tyr
1               5                   10                  15

<210> SEQ ID NO 2138
<211> LENGTH: 15
<212> TYPE: PRT
<213> ORGANISM: homo sapien

<400> SEQUENCE: 2138

Leu Thr Asp Leu Ser Ala Ile Ile Leu Thr Leu Leu Ala Leu Trp
1               5                   10                  15

<210> SEQ ID NO 2139
<211> LENGTH: 15
<212> TYPE: PRT
<213> ORGANISM: homo sapien

<400> SEQUENCE: 2139

Thr Asp Leu Ser Ala Ile Ile Leu Thr Leu Leu Ala Leu Trp Leu
1               5                   10                  15

<210> SEQ ID NO 2140
<211> LENGTH: 15
<212> TYPE: PRT
<213> ORGANISM: homo sapien

<400> SEQUENCE: 2140

Thr Leu Leu Ala Leu Trp Leu Ser Ser Lys Ser Pro Thr Lys Arg
1               5                   10                  15

<210> SEQ ID NO 2141
<211> LENGTH: 15
<212> TYPE: PRT
<213> ORGANISM: homo sapien

<400> SEQUENCE: 2141

Ser Val Leu Leu Val Tyr Ile Leu Met Gly Phe Leu Leu Tyr Glu
1               5                   10                  15

```
<210> SEQ ID NO 2142
<211> LENGTH: 15
<212> TYPE: PRT
<213> ORGANISM: homo sapien

<400> SEQUENCE: 2142

Ile Asn Gly Asp Ile Met Leu Ile Thr Ala Ala Val Gly Val Ala
1               5                   10                  15

<210> SEQ ID NO 2143
<211> LENGTH: 15
<212> TYPE: PRT
<213> ORGANISM: homo sapien

<400> SEQUENCE: 2143

Asn Gly Asp Ile Met Leu Ile Thr Ala Ala Val Gly Val Ala Val
1               5                   10                  15

<210> SEQ ID NO 2144
<211> LENGTH: 15
<212> TYPE: PRT
<213> ORGANISM: homo sapien

<400> SEQUENCE: 2144

His Ala Leu Gly Asp Leu Val Gln Ser Val Gly Val Leu Ile Ala
1               5                   10                  15

<210> SEQ ID NO 2145
<211> LENGTH: 15
<212> TYPE: PRT
<213> ORGANISM: homo sapien

<400> SEQUENCE: 2145

Gly Asp Leu Val Gln Ser Val Gly Val Leu Ile Ala Ala Tyr Ile
1               5                   10                  15

<210> SEQ ID NO 2146
<211> LENGTH: 15
<212> TYPE: PRT
<213> ORGANISM: homo sapien

<400> SEQUENCE: 2146

Phe Ser Leu Leu Val Ala Phe Thr Thr Phe Arg Ile Ile Trp Asp
1               5                   10                  15

<210> SEQ ID NO 2147
<211> LENGTH: 15
<212> TYPE: PRT
<213> ORGANISM: homo sapien

<400> SEQUENCE: 2147

Ile Glu Asp Val Tyr Ser Val Glu Asp Leu Asn Ile Trp Ser Leu
1               5                   10                  15

<210> SEQ ID NO 2148
<211> LENGTH: 15
<212> TYPE: PRT
<213> ORGANISM: homo sapien

<400> SEQUENCE: 2148

Ser Ser Lys Trp Glu Glu Val Gln Ser Lys Ala Asn His Leu Leu
1               5                   10                  15
```

<210> SEQ ID NO 2149
<211> LENGTH: 15
<212> TYPE: PRT
<213> ORGANISM: homo sapien

<400> SEQUENCE: 2149

Leu Pro Leu Thr Asn Ser Gln Leu Ser Leu Lys Val Asp Ser Cys
1               5                   10                  15

<210> SEQ ID NO 2150
<211> LENGTH: 15
<212> TYPE: PRT
<213> ORGANISM: homo sapien

<400> SEQUENCE: 2150

Arg Leu Thr Ile Ala Ala Val Leu Tyr Leu Leu Phe Met Ile Gly
1               5                   10                  15

<210> SEQ ID NO 2151
<211> LENGTH: 15
<212> TYPE: PRT
<213> ORGANISM: homo sapien

<400> SEQUENCE: 2151

Ala Leu His Met Leu Thr Asp Leu Ser Ala Ile Ile Leu Thr Leu
1               5                   10                  15

<210> SEQ ID NO 2152
<211> LENGTH: 15
<212> TYPE: PRT
<213> ORGANISM: homo sapien

<400> SEQUENCE: 2152

Leu Ser Ala Met Ile Ser Val Leu Leu Val Tyr Ile Leu Met Gly
1               5                   10                  15

<210> SEQ ID NO 2153
<211> LENGTH: 15
<212> TYPE: PRT
<213> ORGANISM: homo sapien

<400> SEQUENCE: 2153

Ile His Met Asn Tyr Glu Ile Asn Gly Asp Ile Met Leu Ile Thr
1               5                   10                  15

<210> SEQ ID NO 2154
<211> LENGTH: 15
<212> TYPE: PRT
<213> ORGANISM: homo sapien

<400> SEQUENCE: 2154

His Met Asn Tyr Glu Ile Asn Gly Asp Ile Met Leu Ile Thr Ala
1               5                   10                  15

<210> SEQ ID NO 2155
<211> LENGTH: 15
<212> TYPE: PRT
<213> ORGANISM: homo sapien

<400> SEQUENCE: 2155

Met Gly Phe Leu Leu Asn Gln Ser Gly His Arg His Ser His Ser
1               5                   10                  15

<210> SEQ ID NO 2156
<211> LENGTH: 15

-continued

<212> TYPE: PRT
<213> ORGANISM: homo sapien

<400> SEQUENCE: 2156

His Ser His Ser His Ser Leu Pro Ser Asn Ser Pro Thr Arg Gly
1               5                   10                  15

<210> SEQ ID NO 2157
<211> LENGTH: 15
<212> TYPE: PRT
<213> ORGANISM: homo sapien

<400> SEQUENCE: 2157

Gly Gln Asp Ser Leu Ala Val Arg Ala Ala Phe Val His Ala Leu
1               5                   10                  15

<210> SEQ ID NO 2158
<211> LENGTH: 15
<212> TYPE: PRT
<213> ORGANISM: homo sapien

<400> SEQUENCE: 2158

Val Val Ile Ile Leu Glu Gly Val Pro Ser His Leu Asn Val Asp
1               5                   10                  15

<210> SEQ ID NO 2159
<211> LENGTH: 15
<212> TYPE: PRT
<213> ORGANISM: homo sapien

<400> SEQUENCE: 2159

His Leu Asn Val Asp Tyr Ile Lys Glu Ala Leu Met Lys Ile Glu
1               5                   10                  15

<210> SEQ ID NO 2160
<211> LENGTH: 15
<212> TYPE: PRT
<213> ORGANISM: homo sapien

<400> SEQUENCE: 2160

Ala Ile Val His Ile Gln Leu Ile Pro Gly Ser Ser Ser Lys Trp
1               5                   10                  15

<210> SEQ ID NO 2161
<211> LENGTH: 15
<212> TYPE: PRT
<213> ORGANISM: homo sapien

<400> SEQUENCE: 2161

Ser Lys Gln Arg Glu Ile Leu Lys Gln Arg Lys Val Lys Ala Arg
1               5                   10                  15

<210> SEQ ID NO 2162
<211> LENGTH: 15
<212> TYPE: PRT
<213> ORGANISM: homo sapien

<400> SEQUENCE: 2162

Asp Pro Ile Cys Thr Tyr Val Phe Ser Leu Leu Val Ala Phe Thr
1               5                   10                  15

<210> SEQ ID NO 2163
<211> LENGTH: 15
<212> TYPE: PRT
<213> ORGANISM: homo sapien

```
<400> SEQUENCE: 2163

Asn Val Asp Tyr Ile Lys Glu Ala Leu Met Lys Ile Glu Asp Val
 1               5                  10                  15

<210> SEQ ID NO 2164
<211> LENGTH: 15
<212> TYPE: PRT
<213> ORGANISM: homo sapien

<400> SEQUENCE: 2164

Lys Ala Arg Leu Thr Ile Ala Ala Val Leu Tyr Leu Leu Phe Met
 1               5                  10                  15

<210> SEQ ID NO 2165
<211> LENGTH: 15
<212> TYPE: PRT
<213> ORGANISM: homo sapien

<400> SEQUENCE: 2165

Ile Ala Asn Ser Leu Ala Ile Met Thr Asp Ala Leu His Met Leu
 1               5                  10                  15

<210> SEQ ID NO 2166
<211> LENGTH: 15
<212> TYPE: PRT
<213> ORGANISM: homo sapien

<400> SEQUENCE: 2166

Met Thr Asp Ala Leu His Met Leu Thr Asp Leu Ser Ala Ile Ile
 1               5                  10                  15

<210> SEQ ID NO 2167
<211> LENGTH: 15
<212> TYPE: PRT
<213> ORGANISM: homo sapien

<400> SEQUENCE: 2167

Gly Phe His Arg Leu Glu Val Leu Ser Ala Met Ile Ser Val Leu
 1               5                  10                  15

<210> SEQ ID NO 2168
<211> LENGTH: 15
<212> TYPE: PRT
<213> ORGANISM: homo sapien

<400> SEQUENCE: 2168

Leu Met Gly Phe Leu Leu Tyr Glu Ala Val Gln Arg Thr Ile His
 1               5                  10                  15

<210> SEQ ID NO 2169
<211> LENGTH: 15
<212> TYPE: PRT
<213> ORGANISM: homo sapien

<400> SEQUENCE: 2169

Leu Leu Tyr Glu Ala Val Gln Arg Thr Ile His Met Asn Tyr Glu
 1               5                  10                  15

<210> SEQ ID NO 2170
<211> LENGTH: 15
<212> TYPE: PRT
<213> ORGANISM: homo sapien

<400> SEQUENCE: 2170
```

```
Cys Glu Arg Asn His Gly Gln Asp Ser Leu Ala Val Arg Ala Ala
  1               5                  10                  15
```

<210> SEQ ID NO 2171
<211> LENGTH: 15
<212> TYPE: PRT
<213> ORGANISM: homo sapien

<400> SEQUENCE: 2171

```
Ala Tyr Ile Ile Arg Phe Lys Pro Glu Tyr Lys Ile Ala Asp Pro
  1               5                  10                  15
```

<210> SEQ ID NO 2172
<211> LENGTH: 15
<212> TYPE: PRT
<213> ORGANISM: homo sapien

<400> SEQUENCE: 2172

```
Lys Pro Glu Tyr Lys Ile Ala Asp Pro Ile Cys Thr Tyr Val Phe
  1               5                  10                  15
```

<210> SEQ ID NO 2173
<211> LENGTH: 15
<212> TYPE: PRT
<213> ORGANISM: homo sapien

<400> SEQUENCE: 2173

```
Tyr Lys Ile Ala Asp Pro Ile Cys Thr Tyr Val Phe Ser Leu Leu
  1               5                  10                  15
```

<210> SEQ ID NO 2174
<211> LENGTH: 15
<212> TYPE: PRT
<213> ORGANISM: homo sapien

<400> SEQUENCE: 2174

```
Ile Cys Thr Tyr Val Phe Ser Leu Leu Val Ala Phe Thr Thr Phe
  1               5                  10                  15
```

<210> SEQ ID NO 2175
<211> LENGTH: 15
<212> TYPE: PRT
<213> ORGANISM: homo sapien

<400> SEQUENCE: 2175

```
Val Ile Ile Leu Glu Gly Val Pro Ser His Leu Asn Val Asp Tyr
  1               5                  10                  15
```

<210> SEQ ID NO 2176
<211> LENGTH: 15
<212> TYPE: PRT
<213> ORGANISM: homo sapien

<400> SEQUENCE: 2176

```
Glu Ala Leu Met Lys Ile Glu Asp Val Tyr Ser Val Glu Asp Leu
  1               5                  10                  15
```

<210> SEQ ID NO 2177
<211> LENGTH: 15
<212> TYPE: PRT
<213> ORGANISM: homo sapien

<400> SEQUENCE: 2177

```
Leu Met Lys Ile Glu Asp Val Tyr Ser Val Glu Asp Leu Asn Ile
```

-continued

```
<210> SEQ ID NO 2178
<211> LENGTH: 15
<212> TYPE: PRT
<213> ORGANISM: homo sapien

<400> SEQUENCE: 2178

Ser Val Glu Asp Leu Asn Ile Trp Ser Leu Thr Ser Gly Lys Ser
1               5                   10                  15

<210> SEQ ID NO 2179
<211> LENGTH: 15
<212> TYPE: PRT
<213> ORGANISM: homo sapien

<400> SEQUENCE: 2179

Leu Asn Ile Trp Ser Leu Thr Ser Gly Lys Ser Thr Ala Ile Val
1               5                   10                  15

<210> SEQ ID NO 2180
<211> LENGTH: 15
<212> TYPE: PRT
<213> ORGANISM: homo sapien

<400> SEQUENCE: 2180

Phe Gly Met Tyr Arg Cys Thr Ile Gln Leu Gln Ser Tyr Arg Gln
1               5                   10                  15

<210> SEQ ID NO 2181
<211> LENGTH: 15
<212> TYPE: PRT
<213> ORGANISM: homo sapien

<400> SEQUENCE: 2181

Ile Leu Lys Gln Arg Lys Val Lys Ala Arg Leu Thr Ile Ala Ala
1               5                   10                  15

<210> SEQ ID NO 2182
<211> LENGTH: 15
<212> TYPE: PRT
<213> ORGANISM: homo sapien

<400> SEQUENCE: 2182

Lys Val Lys Ala Arg Leu Thr Ile Ala Ala Val Leu Tyr Leu Leu
1               5                   10                  15

<210> SEQ ID NO 2183
<211> LENGTH: 15
<212> TYPE: PRT
<213> ORGANISM: homo sapien

<400> SEQUENCE: 2183

Ala Ala Val Leu Tyr Leu Leu Phe Met Ile Gly Glu Leu Val Gly
1               5                   10                  15

<210> SEQ ID NO 2184
<211> LENGTH: 15
<212> TYPE: PRT
<213> ORGANISM: homo sapien

<400> SEQUENCE: 2184

Ala Val Leu Tyr Leu Leu Phe Met Ile Gly Glu Leu Val Gly Gly
1               5                   10                  15
```

<210> SEQ ID NO 2185
<211> LENGTH: 15
<212> TYPE: PRT
<213> ORGANISM: homo sapien

<400> SEQUENCE: 2185

Asp Leu Ser Ala Ile Ile Leu Thr Leu Leu Ala Leu Trp Leu Ser
1               5                   10                  15

<210> SEQ ID NO 2186
<211> LENGTH: 15
<212> TYPE: PRT
<213> ORGANISM: homo sapien

<400> SEQUENCE: 2186

Ser Lys Ser Pro Thr Lys Arg Phe Thr Phe Gly Phe His Arg Leu
1               5                   10                  15

<210> SEQ ID NO 2187
<211> LENGTH: 15
<212> TYPE: PRT
<213> ORGANISM: homo sapien

<400> SEQUENCE: 2187

Arg Phe Thr Phe Gly Phe His Arg Leu Glu Val Leu Ser Ala Met
1               5                   10                  15

<210> SEQ ID NO 2188
<211> LENGTH: 15
<212> TYPE: PRT
<213> ORGANISM: homo sapien

<400> SEQUENCE: 2188

Gly Phe Leu Leu Asn Gln Ser Gly His Arg His Ser His Ser His
1               5                   10                  15

<210> SEQ ID NO 2189
<211> LENGTH: 15
<212> TYPE: PRT
<213> ORGANISM: homo sapien

<400> SEQUENCE: 2189

Asp Asp Ala Pro Leu Phe Leu Asn Asp Thr Ser Ala Phe Asp Phe
1               5                   10                  15

<210> SEQ ID NO 2190
<211> LENGTH: 15
<212> TYPE: PRT
<213> ORGANISM: homo sapien

<400> SEQUENCE: 2190

Ala Phe Asp Phe Ser Asp Glu Ala Gly Asp Glu Gly Leu Ser Arg
1               5                   10                  15

<210> SEQ ID NO 2191
<211> LENGTH: 15
<212> TYPE: PRT
<213> ORGANISM: homo sapien

<400> SEQUENCE: 2191

Val Gly Gly Tyr Ile Ala Asn Ser Leu Ala Ile Met Thr Asp Ala
1               5                   10                  15

<210> SEQ ID NO 2192

```
<211> LENGTH: 15
<212> TYPE: PRT
<213> ORGANISM: homo sapien

<400> SEQUENCE: 2192

Ala Met Ile Ser Val Leu Leu Val Tyr Ile Leu Met Gly Phe Leu
 1               5                  10                  15

<210> SEQ ID NO 2193
<211> LENGTH: 15
<212> TYPE: PRT
<213> ORGANISM: homo sapien

<400> SEQUENCE: 2193

Ile Ser Val Leu Leu Val Tyr Ile Leu Met Gly Phe Leu Leu Tyr
 1               5                  10                  15

<210> SEQ ID NO 2194
<211> LENGTH: 15
<212> TYPE: PRT
<213> ORGANISM: homo sapien

<400> SEQUENCE: 2194

Leu Leu Val Tyr Ile Leu Met Gly Phe Leu Leu Tyr Glu Ala Val
 1               5                  10                  15

<210> SEQ ID NO 2195
<211> LENGTH: 15
<212> TYPE: PRT
<213> ORGANISM: homo sapien

<400> SEQUENCE: 2195

Glu Ile Asn Gly Asp Ile Met Leu Ile Thr Ala Ala Val Gly Val
 1               5                  10                  15

<210> SEQ ID NO 2196
<211> LENGTH: 15
<212> TYPE: PRT
<213> ORGANISM: homo sapien

<400> SEQUENCE: 2196

Ala Val Gly Val Ala Val Asn Val Ile Met Gly Phe Leu Leu Asn
 1               5                  10                  15

<210> SEQ ID NO 2197
<211> LENGTH: 15
<212> TYPE: PRT
<213> ORGANISM: homo sapien

<400> SEQUENCE: 2197

Ser Leu Ala Val Arg Ala Ala Phe Val His Ala Leu Gly Asp Leu
 1               5                  10                  15

<210> SEQ ID NO 2198
<211> LENGTH: 15
<212> TYPE: PRT
<213> ORGANISM: homo sapien

<400> SEQUENCE: 2198

Ser Leu Leu Val Ala Phe Thr Thr Phe Arg Ile Ile Trp Asp Thr
 1               5                  10                  15

<210> SEQ ID NO 2199
<211> LENGTH: 15
<212> TYPE: PRT
```

-continued

<213> ORGANISM: homo sapien

<400> SEQUENCE: 2199

Pro Ser His Leu Asn Val Asp Tyr Ile Lys Glu Ala Leu Met Lys
1               5                   10                  15

<210> SEQ ID NO 2200
<211> LENGTH: 15
<212> TYPE: PRT
<213> ORGANISM: homo sapien

<400> SEQUENCE: 2200

Lys Ser Met Leu Arg Lys Asp Asp Ala Pro Leu Phe Leu Asn Asp
1               5                   10                  15

<210> SEQ ID NO 2201
<211> LENGTH: 15
<212> TYPE: PRT
<213> ORGANISM: homo sapien

<400> SEQUENCE: 2201

His Pro Thr Leu Gln Ala Asp Asp Ser Leu Leu Asp Gln Asp
1               5                   10                  15

<210> SEQ ID NO 2202
<211> LENGTH: 15
<212> TYPE: PRT
<213> ORGANISM: homo sapien

<400> SEQUENCE: 2202

Ser Leu Ala Ile Met Thr Asp Ala Leu His Met Leu Thr Asp Leu
1               5                   10                  15

<210> SEQ ID NO 2203
<211> LENGTH: 15
<212> TYPE: PRT
<213> ORGANISM: homo sapien

<400> SEQUENCE: 2203

Leu Glu Gly Val Pro Ser His Leu Asn Val Asp Tyr Ile Lys Glu
1               5                   10                  15

<210> SEQ ID NO 2204
<211> LENGTH: 15
<212> TYPE: PRT
<213> ORGANISM: homo sapien

<400> SEQUENCE: 2204

Trp Glu Glu Val Gln Ser Lys Ala Asn His Leu Leu Leu Asn Thr
1               5                   10                  15

<210> SEQ ID NO 2205
<211> LENGTH: 15
<212> TYPE: PRT
<213> ORGANISM: homo sapien

<400> SEQUENCE: 2205

Ala Leu His Met Leu Thr Asp Leu Ser Ala Ile Ile Leu Thr Leu
1               5                   10                  15

<210> SEQ ID NO 2206
<211> LENGTH: 15
<212> TYPE: PRT
<213> ORGANISM: homo sapien

<400> SEQUENCE: 2206

Gln Leu Ser Leu Lys Val Asp Ser Cys Asp Asn Cys Ser Lys Gln
1               5                   10                  15

<210> SEQ ID NO 2207
<211> LENGTH: 15
<212> TYPE: PRT
<213> ORGANISM: homo sapien

<400> SEQUENCE: 2207

Arg Val Val Val Ala Asp Asp Gly Ser Glu Ala Pro Glu Arg Pro
1               5                   10                  15

<210> SEQ ID NO 2208
<211> LENGTH: 15
<212> TYPE: PRT
<213> ORGANISM: homo sapien

<400> SEQUENCE: 2208

Asp Asp Asp Ser Leu Leu Asp Gln Asp Leu Pro Leu Thr Asn Ser
1               5                   10                  15

<210> SEQ ID NO 2209
<211> LENGTH: 15
<212> TYPE: PRT
<213> ORGANISM: homo sapien

<400> SEQUENCE: 2209

Asp Ser Leu Leu Asp Gln Asp Leu Pro Leu Thr Asn Ser Gln Leu
1               5                   10                  15

<210> SEQ ID NO 2210
<211> LENGTH: 15
<212> TYPE: PRT
<213> ORGANISM: homo sapien

<400> SEQUENCE: 2210

Ser Ala Ile Ile Leu Thr Leu Leu Ala Leu Trp Leu Ser Ser Lys
1               5                   10                  15

<210> SEQ ID NO 2211
<211> LENGTH: 15
<212> TYPE: PRT
<213> ORGANISM: homo sapien

<400> SEQUENCE: 2211

Thr Phe Arg Ile Ile Trp Asp Thr Val Val Ile Ile Leu Glu Gly
1               5                   10                  15

<210> SEQ ID NO 2212
<211> LENGTH: 15
<212> TYPE: PRT
<213> ORGANISM: homo sapien

<400> SEQUENCE: 2212

Leu Lys Ser Met Leu Arg Lys Asp Asp Ala Pro Leu Phe Leu Asn
1               5                   10                  15

<210> SEQ ID NO 2213
<211> LENGTH: 15
<212> TYPE: PRT
<213> ORGANISM: homo sapien

<400> SEQUENCE: 2213

-continued

Ala Pro Leu Phe Leu Asn Asp Thr Ser Ala Phe Asp Phe Ser Asp
1               5                   10                  15

<210> SEQ ID NO 2214
<211> LENGTH: 15
<212> TYPE: PRT
<213> ORGANISM: homo sapien

<400> SEQUENCE: 2214

Leu Arg Val Val Val Ala Asp Gly Ser Glu Ala Pro Glu Arg
1               5                   10                  15

<210> SEQ ID NO 2215
<211> LENGTH: 15
<212> TYPE: PRT
<213> ORGANISM: homo sapien

<400> SEQUENCE: 2215

Arg Leu Thr Ile Ala Ala Val Leu Tyr Leu Leu Phe Met Ile Gly
1               5                   10                  15

<210> SEQ ID NO 2216
<211> LENGTH: 15
<212> TYPE: PRT
<213> ORGANISM: homo sapien

<400> SEQUENCE: 2216

Arg Leu Glu Val Leu Ser Ala Met Ile Ser Val Leu Leu Val Tyr
1               5                   10                  15

<210> SEQ ID NO 2217
<211> LENGTH: 15
<212> TYPE: PRT
<213> ORGANISM: homo sapien

<400> SEQUENCE: 2217

Asn Tyr Glu Ile Asn Gly Asp Ile Met Leu Ile Thr Ala Ala Val
1               5                   10                  15

<210> SEQ ID NO 2218
<211> LENGTH: 15
<212> TYPE: PRT
<213> ORGANISM: homo sapien

<400> SEQUENCE: 2218

Val Val Ile Ile Leu Glu Gly Val Pro Ser His Leu Asn Val Asp
1               5                   10                  15

<210> SEQ ID NO 2219
<211> LENGTH: 15
<212> TYPE: PRT
<213> ORGANISM: homo sapien

<400> SEQUENCE: 2219

Ala Asn His Leu Leu Leu Asn Thr Phe Gly Met Tyr Arg Cys Thr
1               5                   10                  15

<210> SEQ ID NO 2220
<211> LENGTH: 15
<212> TYPE: PRT
<213> ORGANISM: homo sapien

<400> SEQUENCE: 2220

Ser Met Leu Arg Lys Asp Asp Ala Pro Leu Phe Leu Asn Asp Thr
1               5                   10                  15

-continued

```
<210> SEQ ID NO 2221
<211> LENGTH: 15
<212> TYPE: PRT
<213> ORGANISM: homo sapien

<400> SEQUENCE: 2221

Asp Ala Pro Leu Phe Leu Asn Asp Thr Ser Ala Phe Asp Phe Ser
1               5                   10                  15

<210> SEQ ID NO 2222
<211> LENGTH: 15
<212> TYPE: PRT
<213> ORGANISM: homo sapien

<400> SEQUENCE: 2222

Gln Arg Glu Ile Leu Lys Gln Arg Lys Val Lys Ala Arg Leu Thr
1               5                   10                  15

<210> SEQ ID NO 2223
<211> LENGTH: 15
<212> TYPE: PRT
<213> ORGANISM: homo sapien

<400> SEQUENCE: 2223

Lys Ala Arg Leu Thr Ile Ala Ala Val Leu Tyr Leu Leu Phe Met
1               5                   10                  15

<210> SEQ ID NO 2224
<211> LENGTH: 15
<212> TYPE: PRT
<213> ORGANISM: homo sapien

<400> SEQUENCE: 2224

Leu Leu Phe Met Ile Gly Glu Leu Val Gly Gly Tyr Ile Ala Asn
1               5                   10                  15

<210> SEQ ID NO 2225
<211> LENGTH: 15
<212> TYPE: PRT
<213> ORGANISM: homo sapien

<400> SEQUENCE: 2225

Leu His Met Leu Thr Asp Leu Ser Ala Ile Ile Leu Thr Leu Leu
1               5                   10                  15

<210> SEQ ID NO 2226
<211> LENGTH: 15
<212> TYPE: PRT
<213> ORGANISM: homo sapien

<400> SEQUENCE: 2226

Leu Glu Val Leu Ser Ala Met Ile Ser Val Leu Leu Val Tyr Ile
1               5                   10                  15

<210> SEQ ID NO 2227
<211> LENGTH: 15
<212> TYPE: PRT
<213> ORGANISM: homo sapien

<400> SEQUENCE: 2227

Ile Ser Val Leu Leu Val Tyr Ile Leu Met Gly Phe Leu Leu Tyr
1               5                   10                  15
```

```
<210> SEQ ID NO 2228
<211> LENGTH: 15
<212> TYPE: PRT
<213> ORGANISM: homo sapien

<400> SEQUENCE: 2228

Ser Val Leu Leu Val Tyr Ile Leu Met Gly Phe Leu Leu Tyr Glu
1               5                   10                  15

<210> SEQ ID NO 2229
<211> LENGTH: 15
<212> TYPE: PRT
<213> ORGANISM: homo sapien

<400> SEQUENCE: 2229

Ser Leu Ala Val Arg Ala Ala Phe Val His Ala Leu Gly Asp Leu
1               5                   10                  15

<210> SEQ ID NO 2230
<211> LENGTH: 15
<212> TYPE: PRT
<213> ORGANISM: homo sapien

<400> SEQUENCE: 2230

Pro Glu Tyr Lys Ile Ala Asp Pro Ile Cys Thr Tyr Val Phe Ser
1               5                   10                  15

<210> SEQ ID NO 2231
<211> LENGTH: 15
<212> TYPE: PRT
<213> ORGANISM: homo sapien

<400> SEQUENCE: 2231

Pro Ser His Leu Asn Val Asp Tyr Ile Lys Glu Ala Leu Met Lys
1               5                   10                  15

<210> SEQ ID NO 2232
<211> LENGTH: 15
<212> TYPE: PRT
<213> ORGANISM: homo sapien

<400> SEQUENCE: 2232

Trp Lys Arg Leu Lys Ser Met Leu Arg Lys Asp Asp Ala Pro Leu
1               5                   10                  15

<210> SEQ ID NO 2233
<211> LENGTH: 15
<212> TYPE: PRT
<213> ORGANISM: homo sapien

<400> SEQUENCE: 2233

Pro Leu Phe Leu Asn Asp Thr Ser Ala Phe Asp Phe Ser Asp Glu
1               5                   10                  15

<210> SEQ ID NO 2234
<211> LENGTH: 15
<212> TYPE: PRT
<213> ORGANISM: homo sapien

<400> SEQUENCE: 2234

Leu Tyr Leu Leu Phe Met Ile Gly Glu Leu Val Gly Gly Tyr Ile
1               5                   10                  15

<210> SEQ ID NO 2235
<211> LENGTH: 15
```

```
<212> TYPE: PRT
<213> ORGANISM: homo sapien

<400> SEQUENCE: 2235

Gly Glu Leu Val Gly Gly Tyr Ile Ala Asn Ser Leu Ala Ile Met
1               5                   10                  15

<210> SEQ ID NO 2236
<211> LENGTH: 15
<212> TYPE: PRT
<213> ORGANISM: homo sapien

<400> SEQUENCE: 2236

Leu Thr Asp Leu Ser Ala Ile Ile Leu Thr Leu Leu Ala Leu Trp
1               5                   10                  15

<210> SEQ ID NO 2237
<211> LENGTH: 15
<212> TYPE: PRT
<213> ORGANISM: homo sapien

<400> SEQUENCE: 2237

Ser Ala Met Ile Ser Val Leu Leu Val Tyr Ile Leu Met Gly Phe
1               5                   10                  15

<210> SEQ ID NO 2238
<211> LENGTH: 15
<212> TYPE: PRT
<213> ORGANISM: homo sapien

<400> SEQUENCE: 2238

Val Leu Leu Val Tyr Ile Leu Met Gly Phe Leu Leu Tyr Glu Ala
1               5                   10                  15

<210> SEQ ID NO 2239
<211> LENGTH: 15
<212> TYPE: PRT
<213> ORGANISM: homo sapien

<400> SEQUENCE: 2239

Tyr Glu Ala Val Gln Arg Thr Ile His Met Asn Tyr Glu Ile Asn
1               5                   10                  15

<210> SEQ ID NO 2240
<211> LENGTH: 15
<212> TYPE: PRT
<213> ORGANISM: homo sapien

<400> SEQUENCE: 2240

Gly Val Ala Val Asn Val Ile Met Gly Phe Leu Leu Asn Gln Ser
1               5                   10                  15

<210> SEQ ID NO 2241
<211> LENGTH: 15
<212> TYPE: PRT
<213> ORGANISM: homo sapien

<400> SEQUENCE: 2241

Val Gly Val Leu Ile Ala Ala Tyr Ile Ile Arg Phe Lys Pro Glu
1               5                   10                  15

<210> SEQ ID NO 2242
<211> LENGTH: 15
<212> TYPE: PRT
<213> ORGANISM: homo sapien
```

-continued

<400> SEQUENCE: 2242

Ala Tyr Ile Ile Arg Phe Lys Pro Glu Tyr Lys Ile Ala Asp Pro
1               5                   10                  15

<210> SEQ ID NO 2243
<211> LENGTH: 15
<212> TYPE: PRT
<213> ORGANISM: homo sapien

<400> SEQUENCE: 2243

Ala Asp Pro Ile Cys Thr Tyr Val Phe Ser Leu Leu Val Ala Phe
1               5                   10                  15

<210> SEQ ID NO 2244
<211> LENGTH: 15
<212> TYPE: PRT
<213> ORGANISM: homo sapien

<400> SEQUENCE: 2244

His Leu Asn Val Asp Tyr Ile Lys Glu Ala Leu Met Lys Ile Glu
1               5                   10                  15

<210> SEQ ID NO 2245
<211> LENGTH: 15
<212> TYPE: PRT
<213> ORGANISM: homo sapien

<400> SEQUENCE: 2245

Asp Val Tyr Ser Val Glu Asp Leu Asn Ile Trp Ser Leu Thr Ser
1               5                   10                  15

<210> SEQ ID NO 2246
<211> LENGTH: 15
<212> TYPE: PRT
<213> ORGANISM: homo sapien

<400> SEQUENCE: 2246

Gln Asp Leu Pro Leu Thr Asn Ser Gln Leu Ser Leu Lys Val Asp
1               5                   10                  15

<210> SEQ ID NO 2247
<211> LENGTH: 15
<212> TYPE: PRT
<213> ORGANISM: homo sapien

<400> SEQUENCE: 2247

Leu Leu Ala Leu Trp Leu Ser Ser Lys Ser Pro Thr Lys Arg Phe
1               5                   10                  15

<210> SEQ ID NO 2248
<211> LENGTH: 15
<212> TYPE: PRT
<213> ORGANISM: homo sapien

<400> SEQUENCE: 2248

Gln Arg Thr Ile His Met Asn Tyr Glu Ile Asn Gly Asp Ile Met
1               5                   10                  15

<210> SEQ ID NO 2249
<211> LENGTH: 15
<212> TYPE: PRT
<213> ORGANISM: homo sapien

<400> SEQUENCE: 2249

-continued

Ala Val Gly Val Ala Val Asn Val Ile Met Gly Phe Leu Leu Asn
1               5                   10                  15

<210> SEQ ID NO 2250
<211> LENGTH: 15
<212> TYPE: PRT
<213> ORGANISM: homo sapien

<400> SEQUENCE: 2250

Asn Val Ile Met Gly Phe Leu Leu Asn Gln Ser Gly His Arg His
1               5                   10                  15

<210> SEQ ID NO 2251
<211> LENGTH: 15
<212> TYPE: PRT
<213> ORGANISM: homo sapien

<400> SEQUENCE: 2251

Phe Arg Ile Ile Trp Asp Thr Val Val Ile Ile Leu Glu Gly Val
1               5                   10                  15

<210> SEQ ID NO 2252
<211> LENGTH: 15
<212> TYPE: PRT
<213> ORGANISM: homo sapien

<400> SEQUENCE: 2252

Trp Asp Thr Val Val Ile Ile Leu Glu Gly Val Pro Ser His Leu
1               5                   10                  15

<210> SEQ ID NO 2253
<211> LENGTH: 15
<212> TYPE: PRT
<213> ORGANISM: homo sapien

<400> SEQUENCE: 2253

Val Tyr Ser Val Glu Asp Leu Asn Ile Trp Ser Leu Thr Ser Gly
1               5                   10                  15

<210> SEQ ID NO 2254
<211> LENGTH: 15
<212> TYPE: PRT
<213> ORGANISM: homo sapien

<400> SEQUENCE: 2254

Asp Glu Gly Leu Ser Arg Phe Asn Lys Leu Arg Val Val Val Ala
1               5                   10                  15

<210> SEQ ID NO 2255
<211> LENGTH: 15
<212> TYPE: PRT
<213> ORGANISM: homo sapien

<400> SEQUENCE: 2255

Leu Asp Gln Asp Leu Pro Leu Thr Asn Ser Gln Leu Ser Leu Lys
1               5                   10                  15

<210> SEQ ID NO 2256
<211> LENGTH: 15
<212> TYPE: PRT
<213> ORGANISM: homo sapien

<400> SEQUENCE: 2256

Ser Leu Lys Val Asp Ser Cys Asp Asn Cys Ser Lys Gln Arg Glu

-continued

```
  1               5              10              15
```

<210> SEQ ID NO 2257
<211> LENGTH: 15
<212> TYPE: PRT
<213> ORGANISM: homo sapien

<400> SEQUENCE: 2257

```
Gly Phe Leu Leu Tyr Glu Ala Val Gln Arg Thr Ile His Met Asn
  1               5              10              15
```

<210> SEQ ID NO 2258
<211> LENGTH: 15
<212> TYPE: PRT
<213> ORGANISM: homo sapien

<400> SEQUENCE: 2258

```
Thr Ala Ala Val Gly Val Ala Val Asn Val Ile Met Gly Phe Leu
  1               5              10              15
```

<210> SEQ ID NO 2259
<211> LENGTH: 15
<212> TYPE: PRT
<213> ORGANISM: homo sapien

<400> SEQUENCE: 2259

```
His Gly Gln Asp Ser Leu Ala Val Arg Ala Ala Phe Val His Ala
  1               5              10              15
```

<210> SEQ ID NO 2260
<211> LENGTH: 15
<212> TYPE: PRT
<213> ORGANISM: homo sapien

<400> SEQUENCE: 2260

```
Ile Ile Arg Phe Lys Pro Glu Tyr Lys Ile Ala Asp Pro Ile Cys
  1               5              10              15
```

<210> SEQ ID NO 2261
<211> LENGTH: 15
<212> TYPE: PRT
<213> ORGANISM: homo sapien

<400> SEQUENCE: 2261

```
Ile Lys Glu Ala Leu Met Lys Ile Glu Asp Val Tyr Ser Val Glu
  1               5              10              15
```

<210> SEQ ID NO 2262
<211> LENGTH: 15
<212> TYPE: PRT
<213> ORGANISM: homo sapien

<400> SEQUENCE: 2262

```
Thr Ile Gln Leu Gln Ser Tyr Arg Gln Glu Val Asp Arg Thr Cys
  1               5              10              15
```

<210> SEQ ID NO 2263
<211> LENGTH: 15
<212> TYPE: PRT
<213> ORGANISM: homo sapien

<400> SEQUENCE: 2263

```
Leu Ser Ser Lys Ser Pro Thr Lys Arg Phe Thr Phe Gly Phe His
  1               5              10              15
```

```
<210> SEQ ID NO 2264
<211> LENGTH: 15
<212> TYPE: PRT
<213> ORGANISM: homo sapien

<400> SEQUENCE: 2264

Arg Phe Thr Phe Gly Phe His Arg Leu Glu Val Leu Ser Ala Met
1               5                   10                  15

<210> SEQ ID NO 2265
<211> LENGTH: 15
<212> TYPE: PRT
<213> ORGANISM: homo sapien

<400> SEQUENCE: 2265

Thr Ile His Met Asn Tyr Glu Ile Asn Gly Asp Ile Met Leu Ile
1               5                   10                  15

<210> SEQ ID NO 2266
<211> LENGTH: 15
<212> TYPE: PRT
<213> ORGANISM: homo sapien

<400> SEQUENCE: 2266

Ser Gly Cys Glu Arg Asn His Gly Gln Asp Ser Leu Ala Val Arg
1               5                   10                  15

<210> SEQ ID NO 2267
<211> LENGTH: 15
<212> TYPE: PRT
<213> ORGANISM: homo sapien

<400> SEQUENCE: 2267

Val His Ala Leu Gly Asp Leu Val Gln Ser Val Gly Val Leu Ile
1               5                   10                  15

<210> SEQ ID NO 2268
<211> LENGTH: 15
<212> TYPE: PRT
<213> ORGANISM: homo sapien

<400> SEQUENCE: 2268

Ser His Leu Asn Val Asp Tyr Ile Lys Glu Ala Leu Met Lys Ile
1               5                   10                  15

<210> SEQ ID NO 2269
<211> LENGTH: 15
<212> TYPE: PRT
<213> ORGANISM: homo sapien

<400> SEQUENCE: 2269

Gly Ser Gly Ala Trp Lys Arg Leu Lys Ser Met Leu Arg Lys Asp
1               5                   10                  15

<210> SEQ ID NO 2270
<211> LENGTH: 15
<212> TYPE: PRT
<213> ORGANISM: homo sapien

<400> SEQUENCE: 2270

Thr Ser Ala Phe Asp Phe Ser Asp Glu Ala Gly Asp Glu Gly Leu
1               5                   10                  15

<210> SEQ ID NO 2271
```

```
<211> LENGTH: 15
<212> TYPE: PRT
<213> ORGANISM: homo sapien

<400> SEQUENCE: 2271

Ser Cys Asp Asn Cys Ser Lys Gln Arg Glu Ile Leu Lys Gln Arg
1               5                   10                  15

<210> SEQ ID NO 2272
<211> LENGTH: 15
<212> TYPE: PRT
<213> ORGANISM: homo sapien

<400> SEQUENCE: 2272

Glu Ile Leu Lys Gln Arg Lys Val Lys Ala Arg Leu Thr Ile Ala
1               5                   10                  15

<210> SEQ ID NO 2273
<211> LENGTH: 15
<212> TYPE: PRT
<213> ORGANISM: homo sapien

<400> SEQUENCE: 2273

Leu Ser Ala Ile Ile Leu Thr Leu Leu Ala Leu Trp Leu Ser Ser
1               5                   10                  15

<210> SEQ ID NO 2274
<211> LENGTH: 15
<212> TYPE: PRT
<213> ORGANISM: homo sapien

<400> SEQUENCE: 2274

Ile Ala Ala Tyr Ile Ile Arg Phe Lys Pro Glu Tyr Lys Ile Ala
1               5                   10                  15

<210> SEQ ID NO 2275
<211> LENGTH: 15
<212> TYPE: PRT
<213> ORGANISM: homo sapien

<400> SEQUENCE: 2275

Ser Ser Lys Trp Glu Glu Val Gln Ser Lys Ala Asn His Leu Leu
1               5                   10                  15

<210> SEQ ID NO 2276
<211> LENGTH: 15
<212> TYPE: PRT
<213> ORGANISM: homo sapien

<400> SEQUENCE: 2276

Leu Ala Ile Met Thr Asp Ala Leu His Met Leu Thr Asp Leu Ser
1               5                   10                  15

<210> SEQ ID NO 2277
<211> LENGTH: 15
<212> TYPE: PRT
<213> ORGANISM: homo sapien

<400> SEQUENCE: 2277

Ala Leu His Met Leu Thr Asp Leu Ser Ala Ile Ile Leu Thr Leu
1               5                   10                  15

<210> SEQ ID NO 2278
<211> LENGTH: 15
<212> TYPE: PRT
```

-continued

<213> ORGANISM: homo sapien

<400> SEQUENCE: 2278

Gly Phe Leu Leu Tyr Glu Ala Val Gln Arg Thr Ile His Met Asn
1               5                   10                  15

<210> SEQ ID NO 2279
<211> LENGTH: 15
<212> TYPE: PRT
<213> ORGANISM: homo sapien

<400> SEQUENCE: 2279

Thr Ile His Met Asn Tyr Glu Ile Asn Gly Asp Ile Met Leu Ile
1               5                   10                  15

<210> SEQ ID NO 2280
<211> LENGTH: 15
<212> TYPE: PRT
<213> ORGANISM: homo sapien

<400> SEQUENCE: 2280

Thr Ala Ala Val Gly Val Ala Val Asn Val Ile Met Gly Phe Leu
1               5                   10                  15

<210> SEQ ID NO 2281
<211> LENGTH: 15
<212> TYPE: PRT
<213> ORGANISM: homo sapien

<400> SEQUENCE: 2281

Phe Ser Leu Leu Val Ala Phe Thr Thr Phe Arg Ile Ile Trp Asp
1               5                   10                  15

<210> SEQ ID NO 2282
<211> LENGTH: 15
<212> TYPE: PRT
<213> ORGANISM: homo sapien

<400> SEQUENCE: 2282

Val Ile Ile Leu Glu Gly Val Pro Ser His Leu Asn Val Asp Tyr
1               5                   10                  15

<210> SEQ ID NO 2283
<211> LENGTH: 15
<212> TYPE: PRT
<213> ORGANISM: homo sapien

<400> SEQUENCE: 2283

Asp Leu Asn Ile Trp Ser Leu Thr Ser Gly Lys Ser Thr Ala Ile
1               5                   10                  15

<210> SEQ ID NO 2284
<211> LENGTH: 15
<212> TYPE: PRT
<213> ORGANISM: homo sapien

<400> SEQUENCE: 2284

Ser Gly Ala Trp Lys Arg Leu Lys Ser Met Leu Arg Lys Asp Asp
1               5                   10                  15

<210> SEQ ID NO 2285
<211> LENGTH: 15
<212> TYPE: PRT
<213> ORGANISM: homo sapien -continued

```
<400> SEQUENCE: 2285

Ala Pro Leu Phe Leu Asn Asp Thr Ser Ala Phe Asp Phe Ser Asp
 1               5                  10                  15

<210> SEQ ID NO 2286
<211> LENGTH: 15
<212> TYPE: PRT
<213> ORGANISM: homo sapien

<400> SEQUENCE: 2286

Leu Ser Arg Phe Asn Lys Leu Arg Val Val Ala Asp Asp Gly
 1               5                  10                  15

<210> SEQ ID NO 2287
<211> LENGTH: 15
<212> TYPE: PRT
<213> ORGANISM: homo sapien

<400> SEQUENCE: 2287

Ala Val Leu Tyr Leu Leu Phe Met Ile Gly Glu Leu Val Gly Gly
 1               5                  10                  15

<210> SEQ ID NO 2288
<211> LENGTH: 15
<212> TYPE: PRT
<213> ORGANISM: homo sapien

<400> SEQUENCE: 2288

Leu Ala Leu Trp Leu Ser Ser Lys Ser Pro Thr Lys Arg Phe Thr
 1               5                  10                  15

<210> SEQ ID NO 2289
<211> LENGTH: 15
<212> TYPE: PRT
<213> ORGANISM: homo sapien

<400> SEQUENCE: 2289

Thr Phe Gly Phe His Arg Leu Glu Val Leu Ser Ala Met Ile Ser
 1               5                  10                  15

<210> SEQ ID NO 2290
<211> LENGTH: 15
<212> TYPE: PRT
<213> ORGANISM: homo sapien

<400> SEQUENCE: 2290

Phe Leu Leu Tyr Glu Ala Val Gln Arg Thr Ile His Met Asn Tyr
 1               5                  10                  15

<210> SEQ ID NO 2291
<211> LENGTH: 15
<212> TYPE: PRT
<213> ORGANISM: homo sapien

<400> SEQUENCE: 2291

Arg Ala Ala Phe Val His Ala Leu Gly Asp Leu Val Gln Ser Val
 1               5                  10                  15

<210> SEQ ID NO 2292
<211> LENGTH: 15
<212> TYPE: PRT
<213> ORGANISM: homo sapien

<400> SEQUENCE: 2292
```

```
Lys Pro Glu Tyr Lys Ile Ala Asp Pro Ile Cys Thr Tyr Val Phe
1               5                   10                  15

<210> SEQ ID NO 2293
<211> LENGTH: 15
<212> TYPE: PRT
<213> ORGANISM: homo sapien

<400> SEQUENCE: 2293

Thr Tyr Val Phe Ser Leu Leu Val Ala Phe Thr Thr Phe Arg Ile
1               5                   10                  15

<210> SEQ ID NO 2294
<211> LENGTH: 15
<212> TYPE: PRT
<213> ORGANISM: homo sapien

<400> SEQUENCE: 2294

Phe Thr Thr Phe Arg Ile Ile Trp Asp Thr Val Val Ile Ile Leu
1               5                   10                  15

<210> SEQ ID NO 2295
<211> LENGTH: 15
<212> TYPE: PRT
<213> ORGANISM: homo sapien

<400> SEQUENCE: 2295

Asn Val Asp Tyr Ile Lys Glu Ala Leu Met Lys Ile Glu Asp Val
1               5                   10                  15

<210> SEQ ID NO 2296
<211> LENGTH: 15
<212> TYPE: PRT
<213> ORGANISM: homo sapien

<400> SEQUENCE: 2296

Phe Gly Met Tyr Arg Cys Thr Ile Gln Leu Gln Ser Tyr Arg Gln
1               5                   10                  15

<210> SEQ ID NO 2297
<211> LENGTH: 15
<212> TYPE: PRT
<213> ORGANISM: homo sapien

<400> SEQUENCE: 2297

Asp Glu Gly Leu Ser Arg Phe Asn Lys Leu Arg Val Val Val Ala
1               5                   10                  15

<210> SEQ ID NO 2298
<211> LENGTH: 15
<212> TYPE: PRT
<213> ORGANISM: homo sapien

<400> SEQUENCE: 2298

Leu Arg Val Val Val Ala Asp Asp Gly Ser Glu Ala Pro Glu Arg
1               5                   10                  15

<210> SEQ ID NO 2299
<211> LENGTH: 15
<212> TYPE: PRT
<213> ORGANISM: homo sapien

<400> SEQUENCE: 2299

Arg Val Val Val Ala Asp Asp Gly Ser Glu Ala Pro Glu Arg Pro
1               5                   10                  15
```

```
<210> SEQ ID NO 2300
<211> LENGTH: 15
<212> TYPE: PRT
<213> ORGANISM: homo sapien

<400> SEQUENCE: 2300

Glu Arg Pro Val Asn Gly Ala His Pro Thr Leu Gln Ala Asp Asp
1               5                   10                  15

<210> SEQ ID NO 2301
<211> LENGTH: 15
<212> TYPE: PRT
<213> ORGANISM: homo sapien

<400> SEQUENCE: 2301

His Pro Thr Leu Gln Ala Asp Asp Ser Leu Leu Asp Gln Asp
1               5                   10                  15

<210> SEQ ID NO 2302
<211> LENGTH: 15
<212> TYPE: PRT
<213> ORGANISM: homo sapien

<400> SEQUENCE: 2302

Asp Ser Leu Leu Asp Gln Asp Leu Pro Leu Thr Asn Ser Gln Leu
1               5                   10                  15

<210> SEQ ID NO 2303
<211> LENGTH: 15
<212> TYPE: PRT
<213> ORGANISM: homo sapien

<400> SEQUENCE: 2303

Asp Gln Asp Leu Pro Leu Thr Asn Ser Gln Leu Ser Leu Lys Val
1               5                   10                  15

<210> SEQ ID NO 2304
<211> LENGTH: 15
<212> TYPE: PRT
<213> ORGANISM: homo sapien

<400> SEQUENCE: 2304

Ser Leu Lys Val Asp Ser Cys Asp Asn Cys Ser Lys Gln Arg Glu
1               5                   10                  15

<210> SEQ ID NO 2305
<211> LENGTH: 15
<212> TYPE: PRT
<213> ORGANISM: homo sapien

<400> SEQUENCE: 2305

Lys Ala Arg Leu Thr Ile Ala Ala Val Leu Tyr Leu Leu Phe Met
1               5                   10                  15

<210> SEQ ID NO 2306
<211> LENGTH: 15
<212> TYPE: PRT
<213> ORGANISM: homo sapien

<400> SEQUENCE: 2306

Leu Phe Met Ile Gly Glu Leu Val Gly Gly Tyr Ile Ala Asn Ser
1               5                   10                  15
```

<210> SEQ ID NO 2307
<211> LENGTH: 15
<212> TYPE: PRT
<213> ORGANISM: homo sapien

<400> SEQUENCE: 2307

Ser Leu Ala Ile Met Thr Asp Ala Leu His Met Leu Thr Asp Leu
1               5                   10                  15

<210> SEQ ID NO 2308
<211> LENGTH: 15
<212> TYPE: PRT
<213> ORGANISM: homo sapien

<400> SEQUENCE: 2308

Thr Asp Ala Leu His Met Leu Thr Asp Leu Ser Ala Ile Ile Leu
1               5                   10                  15

<210> SEQ ID NO 2309
<211> LENGTH: 15
<212> TYPE: PRT
<213> ORGANISM: homo sapien

<400> SEQUENCE: 2309

Leu His Met Leu Thr Asp Leu Ser Ala Ile Ile Leu Thr Leu Leu
1               5                   10                  15

<210> SEQ ID NO 2310
<211> LENGTH: 15
<212> TYPE: PRT
<213> ORGANISM: homo sapien

<400> SEQUENCE: 2310

Leu Thr Asp Leu Ser Ala Ile Ile Leu Thr Leu Leu Ala Leu Trp
1               5                   10                  15

<210> SEQ ID NO 2311
<211> LENGTH: 15
<212> TYPE: PRT
<213> ORGANISM: homo sapien

<400> SEQUENCE: 2311

Ser Ala Ile Ile Leu Thr Leu Leu Ala Leu Trp Leu Ser Ser Lys
1               5                   10                  15

<210> SEQ ID NO 2312
<211> LENGTH: 15
<212> TYPE: PRT
<213> ORGANISM: homo sapien

<400> SEQUENCE: 2312

Ala Ile Ile Leu Thr Leu Leu Ala Leu Trp Leu Ser Ser Lys Ser
1               5                   10                  15

<210> SEQ ID NO 2313
<211> LENGTH: 15
<212> TYPE: PRT
<213> ORGANISM: homo sapien

<400> SEQUENCE: 2313

Ile Leu Thr Leu Leu Ala Leu Trp Leu Ser Ser Lys Ser Pro Thr
1               5                   10                  15

<210> SEQ ID NO 2314
<211> LENGTH: 15

-continued

<212> TYPE: PRT
<213> ORGANISM: homo sapien

<400> SEQUENCE: 2314

Leu Thr Leu Leu Ala Leu Trp Leu Ser Ser Lys Ser Pro Thr Lys
 1               5                  10                  15

<210> SEQ ID NO 2315
<211> LENGTH: 15
<212> TYPE: PRT
<213> ORGANISM: homo sapien

<400> SEQUENCE: 2315

Phe His Arg Leu Glu Val Leu Ser Ala Met Ile Ser Val Leu Leu
 1               5                  10                  15

<210> SEQ ID NO 2316
<211> LENGTH: 15
<212> TYPE: PRT
<213> ORGANISM: homo sapien

<400> SEQUENCE: 2316

Arg Leu Glu Val Leu Ser Ala Met Ile Ser Val Leu Leu Val Tyr
 1               5                  10                  15

<210> SEQ ID NO 2317
<211> LENGTH: 15
<212> TYPE: PRT
<213> ORGANISM: homo sapien

<400> SEQUENCE: 2317

Leu Glu Val Leu Ser Ala Met Ile Ser Val Leu Leu Val Tyr Ile
 1               5                  10                  15

<210> SEQ ID NO 2318
<211> LENGTH: 15
<212> TYPE: PRT
<213> ORGANISM: homo sapien

<400> SEQUENCE: 2318

Leu Ser Ala Met Ile Ser Val Leu Leu Val Tyr Ile Leu Met Gly
 1               5                  10                  15

<210> SEQ ID NO 2319
<211> LENGTH: 15
<212> TYPE: PRT
<213> ORGANISM: homo sapien

<400> SEQUENCE: 2319

Ser Ala Met Ile Ser Val Leu Leu Val Tyr Ile Leu Met Gly Phe
 1               5                  10                  15

<210> SEQ ID NO 2320
<211> LENGTH: 15
<212> TYPE: PRT
<213> ORGANISM: homo sapien

<400> SEQUENCE: 2320

Ser Val Leu Leu Val Tyr Ile Leu Met Gly Phe Leu Leu Tyr Glu
 1               5                  10                  15

<210> SEQ ID NO 2321
<211> LENGTH: 15
<212> TYPE: PRT
<213> ORGANISM: homo sapien -continued

```
<400> SEQUENCE: 2321

Val Leu Leu Val Tyr Ile Leu Met Gly Phe Leu Leu Tyr Glu Ala
1               5                   10                  15

<210> SEQ ID NO 2322
<211> LENGTH: 15
<212> TYPE: PRT
<213> ORGANISM: homo sapien

<400> SEQUENCE: 2322

Val Tyr Ile Leu Met Gly Phe Leu Leu Tyr Glu Ala Val Gln Arg
1               5                   10                  15

<210> SEQ ID NO 2323
<211> LENGTH: 15
<212> TYPE: PRT
<213> ORGANISM: homo sapien

<400> SEQUENCE: 2323

Tyr Ile Leu Met Gly Phe Leu Leu Tyr Glu Ala Val Gln Arg Thr
1               5                   10                  15

<210> SEQ ID NO 2324
<211> LENGTH: 15
<212> TYPE: PRT
<213> ORGANISM: homo sapien

<400> SEQUENCE: 2324

Met Gly Phe Leu Leu Tyr Glu Ala Val Gln Arg Thr Ile His Met
1               5                   10                  15

<210> SEQ ID NO 2325
<211> LENGTH: 15
<212> TYPE: PRT
<213> ORGANISM: homo sapien

<400> SEQUENCE: 2325

Asn Tyr Glu Ile Asn Gly Asp Ile Met Leu Ile Thr Ala Ala Val
1               5                   10                  15

<210> SEQ ID NO 2326
<211> LENGTH: 15
<212> TYPE: PRT
<213> ORGANISM: homo sapien

<400> SEQUENCE: 2326

Asp Ile Met Leu Ile Thr Ala Ala Val Gly Val Ala Val Asn Val
1               5                   10                  15

<210> SEQ ID NO 2327
<211> LENGTH: 15
<212> TYPE: PRT
<213> ORGANISM: homo sapien

<400> SEQUENCE: 2327

Ile Met Leu Ile Thr Ala Ala Val Gly Val Ala Val Asn Val Ile
1               5                   10                  15

<210> SEQ ID NO 2328
<211> LENGTH: 15
<212> TYPE: PRT
<213> ORGANISM: homo sapien

<400> SEQUENCE: 2328
```

Gly Val Ala Val Asn Val Ile Met Gly Phe Leu Leu Asn Gln Ser
1               5                   10                  15

<210> SEQ ID NO 2329
<211> LENGTH: 15
<212> TYPE: PRT
<213> ORGANISM: homo sapien

<400> SEQUENCE: 2329

Val Asn Val Ile Met Gly Phe Leu Leu Asn Gln Ser Gly His Arg
1               5                   10                  15

<210> SEQ ID NO 2330
<211> LENGTH: 15
<212> TYPE: PRT
<213> ORGANISM: homo sapien

<400> SEQUENCE: 2330

Asn Val Ile Met Gly Phe Leu Leu Asn Gln Ser Gly His Arg His
1               5                   10                  15

<210> SEQ ID NO 2331
<211> LENGTH: 15
<212> TYPE: PRT
<213> ORGANISM: homo sapien

<400> SEQUENCE: 2331

Gly Phe Leu Leu Asn Gln Ser Gly His Arg His Ser His Ser His
1               5                   10                  15

<210> SEQ ID NO 2332
<211> LENGTH: 15
<212> TYPE: PRT
<213> ORGANISM: homo sapien

<400> SEQUENCE: 2332

Ser Leu Ala Val Arg Ala Ala Phe Val His Ala Leu Gly Asp Leu
1               5                   10                  15

<210> SEQ ID NO 2333
<211> LENGTH: 15
<212> TYPE: PRT
<213> ORGANISM: homo sapien

<400> SEQUENCE: 2333

Ala Ala Phe Val His Ala Leu Gly Asp Leu Val Gln Ser Val Gly
1               5                   10                  15

<210> SEQ ID NO 2334
<211> LENGTH: 15
<212> TYPE: PRT
<213> ORGANISM: homo sapien

<400> SEQUENCE: 2334

Val His Ala Leu Gly Asp Leu Val Gln Ser Val Gly Val Leu Ile
1               5                   10                  15

<210> SEQ ID NO 2335
<211> LENGTH: 15
<212> TYPE: PRT
<213> ORGANISM: homo sapien

<400> SEQUENCE: 2335

Gly Asp Leu Val Gln Ser Val Gly Val Leu Ile Ala Ala Tyr Ile

```
                 1               5              10              15
```

<210> SEQ ID NO 2336
<211> LENGTH: 15
<212> TYPE: PRT
<213> ORGANISM: homo sapien

<400> SEQUENCE: 2336

```
Val Gln Ser Val Gly Val Leu Ile Ala Ala Tyr Ile Ile Arg Phe
 1               5                  10                  15
```

<210> SEQ ID NO 2337
<211> LENGTH: 15
<212> TYPE: PRT
<213> ORGANISM: homo sapien

<400> SEQUENCE: 2337

```
Ala Ala Tyr Ile Ile Arg Phe Lys Pro Glu Tyr Lys Ile Ala Asp
 1               5                  10                  15
```

<210> SEQ ID NO 2338
<211> LENGTH: 15
<212> TYPE: PRT
<213> ORGANISM: homo sapien

<400> SEQUENCE: 2338

```
Cys Thr Tyr Val Phe Ser Leu Leu Val Ala Phe Thr Thr Phe Arg
 1               5                  10                  15
```

<210> SEQ ID NO 2339
<211> LENGTH: 15
<212> TYPE: PRT
<213> ORGANISM: homo sapien

<400> SEQUENCE: 2339

```
Val Phe Ser Leu Leu Val Ala Phe Thr Thr Phe Arg Ile Ile Trp
 1               5                  10                  15
```

<210> SEQ ID NO 2340
<211> LENGTH: 15
<212> TYPE: PRT
<213> ORGANISM: homo sapien

<400> SEQUENCE: 2340

```
Thr Phe Arg Ile Ile Trp Asp Thr Val Val Ile Ile Leu Glu Gly
 1               5                  10                  15
```

<210> SEQ ID NO 2341
<211> LENGTH: 15
<212> TYPE: PRT
<213> ORGANISM: homo sapien

<400> SEQUENCE: 2341

```
Asp Thr Val Val Ile Ile Leu Glu Gly Val Pro Ser His Leu Asn
 1               5                  10                  15
```

<210> SEQ ID NO 2342
<211> LENGTH: 15
<212> TYPE: PRT
<213> ORGANISM: homo sapien

<400> SEQUENCE: 2342

```
Pro Ser His Leu Asn Val Asp Tyr Ile Lys Glu Ala Leu Met Lys
 1               5                  10                  15
```

-continued

```
<210> SEQ ID NO 2343
<211> LENGTH: 15
<212> TYPE: PRT
<213> ORGANISM: homo sapien

<400> SEQUENCE: 2343

His Leu Asn Val Asp Tyr Ile Lys Glu Ala Leu Met Lys Ile Glu
 1               5                  10                  15

<210> SEQ ID NO 2344
<211> LENGTH: 15
<212> TYPE: PRT
<213> ORGANISM: homo sapien

<400> SEQUENCE: 2344

Lys Glu Ala Leu Met Lys Ile Glu Asp Val Tyr Ser Val Glu Asp
 1               5                  10                  15

<210> SEQ ID NO 2345
<211> LENGTH: 15
<212> TYPE: PRT
<213> ORGANISM: homo sapien

<400> SEQUENCE: 2345

Glu Ala Leu Met Lys Ile Glu Asp Val Tyr Ser Val Glu Asp Leu
 1               5                  10                  15

<210> SEQ ID NO 2346
<211> LENGTH: 15
<212> TYPE: PRT
<213> ORGANISM: homo sapien

<400> SEQUENCE: 2346

Leu Met Lys Ile Glu Asp Val Tyr Ser Val Glu Asp Leu Asn Ile
 1               5                  10                  15

<210> SEQ ID NO 2347
<211> LENGTH: 15
<212> TYPE: PRT
<213> ORGANISM: homo sapien

<400> SEQUENCE: 2347

Ile Glu Asp Val Tyr Ser Val Glu Asp Leu Asn Ile Trp Ser Leu
 1               5                  10                  15

<210> SEQ ID NO 2348
<211> LENGTH: 15
<212> TYPE: PRT
<213> ORGANISM: homo sapien

<400> SEQUENCE: 2348

Val Tyr Ser Val Glu Asp Leu Asn Ile Trp Ser Leu Thr Ser Gly
 1               5                  10                  15

<210> SEQ ID NO 2349
<211> LENGTH: 15
<212> TYPE: PRT
<213> ORGANISM: homo sapien

<400> SEQUENCE: 2349

Ile Trp Ser Leu Thr Ser Gly Lys Ser Thr Ala Ile Val His Ile
 1               5                  10                  15

<210> SEQ ID NO 2350
```

```
<211> LENGTH: 15
<212> TYPE: PRT
<213> ORGANISM: homo sapien

<400> SEQUENCE: 2350

Ile Val His Ile Gln Leu Ile Pro Gly Ser Ser Ser Lys Trp Glu
1               5                   10                  15

<210> SEQ ID NO 2351
<211> LENGTH: 15
<212> TYPE: PRT
<213> ORGANISM: homo sapien

<400> SEQUENCE: 2351

Lys Asp Asp Ala Pro Leu Phe Leu Asn Asp Thr Ser Ala Phe Asp
1               5                   10                  15

<210> SEQ ID NO 2352
<211> LENGTH: 15
<212> TYPE: PRT
<213> ORGANISM: homo sapien

<400> SEQUENCE: 2352

Asn Asp Thr Ser Ala Phe Asp Phe Ser Asp Glu Ala Gly Asp Glu
1               5                   10                  15

<210> SEQ ID NO 2353
<211> LENGTH: 15
<212> TYPE: PRT
<213> ORGANISM: homo sapien

<400> SEQUENCE: 2353

Glu Ala Gly Asp Glu Gly Leu Ser Arg Phe Asn Lys Leu Arg Val
1               5                   10                  15

<210> SEQ ID NO 2354
<211> LENGTH: 15
<212> TYPE: PRT
<213> ORGANISM: homo sapien

<400> SEQUENCE: 2354

Leu Asp Gln Asp Leu Pro Leu Thr Asn Ser Gln Leu Ser Leu Lys
1               5                   10                  15

<210> SEQ ID NO 2355
<211> LENGTH: 15
<212> TYPE: PRT
<213> ORGANISM: homo sapien

<400> SEQUENCE: 2355

Ser Gln Leu Ser Leu Lys Val Asp Ser Cys Asp Asn Cys Ser Lys
1               5                   10                  15

<210> SEQ ID NO 2356
<211> LENGTH: 15
<212> TYPE: PRT
<213> ORGANISM: homo sapien

<400> SEQUENCE: 2356

Ser Lys Gln Arg Glu Ile Leu Lys Gln Arg Lys Val Lys Ala Arg
1               5                   10                  15

<210> SEQ ID NO 2357
<211> LENGTH: 15
<212> TYPE: PRT
```

-continued

<213> ORGANISM: homo sapien

<400> SEQUENCE: 2357

Glu Leu Val Gly Gly Tyr Ile Ala Asn Ser Leu Ala Ile Met Thr
1               5                   10                  15

<210> SEQ ID NO 2358
<211> LENGTH: 15
<212> TYPE: PRT
<213> ORGANISM: homo sapien

<400> SEQUENCE: 2358

Leu Val Gly Gly Tyr Ile Ala Asn Ser Leu Ala Ile Met Thr Asp
1               5                   10                  15

<210> SEQ ID NO 2359
<211> LENGTH: 15
<212> TYPE: PRT
<213> ORGANISM: homo sapien

<400> SEQUENCE: 2359

Ile Ala Asn Ser Leu Ala Ile Met Thr Asp Ala Leu His Met Leu
1               5                   10                  15

<210> SEQ ID NO 2360
<211> LENGTH: 15
<212> TYPE: PRT
<213> ORGANISM: homo sapien

<400> SEQUENCE: 2360

Thr Asp Leu Ser Ala Ile Ile Leu Thr Leu Leu Ala Leu Trp Leu
1               5                   10                  15

<210> SEQ ID NO 2361
<211> LENGTH: 15
<212> TYPE: PRT
<213> ORGANISM: homo sapien

<400> SEQUENCE: 2361

Lys Arg Phe Thr Phe Gly Phe His Arg Leu Glu Val Leu Ser Ala
1               5                   10                  15

<210> SEQ ID NO 2362
<211> LENGTH: 15
<212> TYPE: PRT
<213> ORGANISM: homo sapien

<400> SEQUENCE: 2362

Gly Phe His Arg Leu Glu Val Leu Ser Ala Met Ile Ser Val Leu
1               5                   10                  15

<210> SEQ ID NO 2363
<211> LENGTH: 15
<212> TYPE: PRT
<213> ORGANISM: homo sapien

<400> SEQUENCE: 2363

Ile Asn Gly Asp Ile Met Leu Ile Thr Ala Ala Val Gly Val Ala
1               5                   10                  15

<210> SEQ ID NO 2364
<211> LENGTH: 15
<212> TYPE: PRT
<213> ORGANISM: homo sapien

```
<400> SEQUENCE: 2364

Thr Arg Gly Ser Gly Cys Glu Arg Asn His Gly Gln Asp Ser Leu
1               5                   10                  15

<210> SEQ ID NO 2365
<211> LENGTH: 15
<212> TYPE: PRT
<213> ORGANISM: homo sapien

<400> SEQUENCE: 2365

His Ala Leu Gly Asp Leu Val Gln Ser Val Gly Val Leu Ile Ala
1               5                   10                  15

<210> SEQ ID NO 2366
<211> LENGTH: 15
<212> TYPE: PRT
<213> ORGANISM: homo sapien

<400> SEQUENCE: 2366

Asp Pro Ile Cys Thr Tyr Val Phe Ser Leu Leu Val Ala Phe Thr
1               5                   10                  15

<210> SEQ ID NO 2367
<211> LENGTH: 15
<212> TYPE: PRT
<213> ORGANISM: homo sapien

<400> SEQUENCE: 2367

Asp Val Tyr Ser Val Glu Asp Leu Asn Ile Trp Ser Leu Thr Ser
1               5                   10                  15

<210> SEQ ID NO 2368
<211> LENGTH: 15
<212> TYPE: PRT
<213> ORGANISM: homo sapien

<400> SEQUENCE: 2368

Ser Val Glu Asp Leu Asn Ile Trp Ser Leu Thr Ser Gly Lys Ser
1               5                   10                  15

<210> SEQ ID NO 2369
<211> LENGTH: 15
<212> TYPE: PRT
<213> ORGANISM: homo sapien

<400> SEQUENCE: 2369

Ser Gly Lys Ser Thr Ala Ile Val His Ile Gln Leu Ile Pro Gly
1               5                   10                  15

<210> SEQ ID NO 2370
<211> LENGTH: 15
<212> TYPE: PRT
<213> ORGANISM: homo sapien

<400> SEQUENCE: 2370

Ser Ser Ser Lys Trp Glu Glu Val Gln Ser Lys Ala Asn His Leu
1               5                   10                  15

<210> SEQ ID NO 2371
<211> LENGTH: 15
<212> TYPE: PRT
<213> ORGANISM: homo sapien

<400> SEQUENCE: 2371
```

```
Glu Glu Val Gln Ser Lys Ala Asn His Leu Leu Asn Thr Phe
1               5                   10                  15
```

<210> SEQ ID NO 2372
<211> LENGTH: 15
<212> TYPE: PRT
<213> ORGANISM: homo sapien

<400> SEQUENCE: 2372

```
Lys Ala Asn His Leu Leu Leu Asn Thr Phe Gly Met Tyr Arg Cys
1               5                   10                  15
```

<210> SEQ ID NO 2373
<211> LENGTH: 15
<212> TYPE: PRT
<213> ORGANISM: homo sapien

<400> SEQUENCE: 2373

```
Tyr Arg Cys Thr Ile Gln Leu Gln Ser Tyr Arg Gln Glu Val Asp
1               5                   10                  15
```

<210> SEQ ID NO 2374
<211> LENGTH: 15
<212> TYPE: PRT
<213> ORGANISM: homo sapien

<400> SEQUENCE: 2374

```
Gln Ser Tyr Arg Gln Glu Val Asp Arg Thr Cys Ala Asn Cys Gln
1               5                   10                  15
```

<210> SEQ ID NO 2375
<211> LENGTH: 15
<212> TYPE: PRT
<213> ORGANISM: homo sapien

<400> SEQUENCE: 2375

```
Ser Tyr Arg Gln Glu Val Asp Arg Thr Cys Ala Asn Cys Gln Ser
1               5                   10                  15
```

<210> SEQ ID NO 2376
<211> LENGTH: 15
<212> TYPE: PRT
<213> ORGANISM: homo sapien

<400> SEQUENCE: 2376

```
Ala Phe Asp Phe Ser Asp Glu Ala Gly Asp Glu Gly Leu Ser Arg
1               5                   10                  15
```

<210> SEQ ID NO 2377
<211> LENGTH: 15
<212> TYPE: PRT
<213> ORGANISM: homo sapien

<400> SEQUENCE: 2377

```
Val Gly Gly Tyr Ile Ala Asn Ser Leu Ala Ile Met Thr Asp Ala
1               5                   10                  15
```

<210> SEQ ID NO 2378
<211> LENGTH: 15
<212> TYPE: PRT
<213> ORGANISM: homo sapien

<400> SEQUENCE: 2378

```
Thr Lys Arg Phe Thr Phe Gly Phe His Arg Leu Glu Val Leu Ser
1               5                   10                  15
```

<210> SEQ ID NO 2379
<211> LENGTH: 15
<212> TYPE: PRT
<213> ORGANISM: homo sapien

<400> SEQUENCE: 2379

Arg Phe Thr Phe Gly Phe His Arg Leu Glu Val Leu Ser Ala Met
1               5                   10                  15

<210> SEQ ID NO 2380
<211> LENGTH: 15
<212> TYPE: PRT
<213> ORGANISM: homo sapien

<400> SEQUENCE: 2380

His Met Asn Tyr Glu Ile Asn Gly Asp Ile Met Leu Ile Thr Ala
1               5                   10                  15

<210> SEQ ID NO 2381
<211> LENGTH: 15
<212> TYPE: PRT
<213> ORGANISM: homo sapien

<400> SEQUENCE: 2381

Ile Met Gly Phe Leu Leu Asn Gln Ser Gly His Arg His Ser His
1               5                   10                  15

<210> SEQ ID NO 2382
<211> LENGTH: 15
<212> TYPE: PRT
<213> ORGANISM: homo sapien

<400> SEQUENCE: 2382

Ile Ile Arg Phe Lys Pro Glu Tyr Lys Ile Ala Asp Pro Ile Cys
1               5                   10                  15

<210> SEQ ID NO 2383
<211> LENGTH: 15
<212> TYPE: PRT
<213> ORGANISM: homo sapien

<400> SEQUENCE: 2383

Leu Val Ala Phe Thr Thr Phe Arg Ile Ile Trp Asp Thr Val Val
1               5                   10                  15

<210> SEQ ID NO 2384
<211> LENGTH: 15
<212> TYPE: PRT
<213> ORGANISM: homo sapien

<400> SEQUENCE: 2384

Arg Ile Ile Trp Asp Thr Val Val Ile Ile Leu Glu Gly Val Pro
1               5                   10                  15

<210> SEQ ID NO 2385
<211> LENGTH: 15
<212> TYPE: PRT
<213> ORGANISM: homo sapien

<400> SEQUENCE: 2385

Glu Asp Val Tyr Ser Val Glu Asp Leu Asn Ile Trp Ser Leu Thr
1               5                   10                  15

-continued

```
<210> SEQ ID NO 2386
<211> LENGTH: 15
<212> TYPE: PRT
<213> ORGANISM: homo sapien

<400> SEQUENCE: 2386

Leu Asn Ile Trp Ser Leu Thr Ser Gly Lys Ser Thr Ala Ile Val
1               5                   10                  15

<210> SEQ ID NO 2387
<211> LENGTH: 15
<212> TYPE: PRT
<213> ORGANISM: homo sapien

<400> SEQUENCE: 2387

Leu Asn Thr Phe Gly Met Tyr Arg Cys Thr Ile Gln Leu Gln Ser
1               5                   10                  15

<210> SEQ ID NO 2388
<211> LENGTH: 15
<212> TYPE: PRT
<213> ORGANISM: homo sapien

<400> SEQUENCE: 2388

Leu Gln Ser Tyr Arg Gln Glu Val Asp Arg Thr Cys Ala Asn Cys
1               5                   10                  15

<210> SEQ ID NO 2389
<211> LENGTH: 15
<212> TYPE: PRT
<213> ORGANISM: homo sapien

<400> SEQUENCE: 2389

Gln Arg Lys Val Lys Ala Arg Leu Thr Ile Ala Ala Val Leu Tyr
1               5                   10                  15

<210> SEQ ID NO 2390
<211> LENGTH: 15
<212> TYPE: PRT
<213> ORGANISM: homo sapien

<400> SEQUENCE: 2390

Trp Glu Glu Val Gln Ser Lys Ala Asn His Leu Leu Leu Asn Thr
1               5                   10                  15

<210> SEQ ID NO 2391
<211> LENGTH: 15
<212> TYPE: PRT
<213> ORGANISM: homo sapien

<400> SEQUENCE: 2391

Trp Lys Arg Leu Lys Ser Met Leu Arg Lys Asp Asp Ala Pro Leu
1               5                   10                  15

<210> SEQ ID NO 2392
<211> LENGTH: 15
<212> TYPE: PRT
<213> ORGANISM: homo sapien

<400> SEQUENCE: 2392

Lys Ser Met Leu Arg Lys Asp Asp Ala Pro Leu Phe Leu Asn Asp
1               5                   10                  15

<210> SEQ ID NO 2393
<211> LENGTH: 15
```

-continued

```
<212> TYPE: PRT
<213> ORGANISM: homo sapien

<400> SEQUENCE: 2393

Asp Ala Pro Leu Phe Leu Asn Asp Thr Ser Ala Phe Asp Phe Ser
 1               5                  10                  15

<210> SEQ ID NO 2394
<211> LENGTH: 15
<212> TYPE: PRT
<213> ORGANISM: homo sapien

<400> SEQUENCE: 2394

Phe Asn Lys Leu Arg Val Val Ala Asp Asp Gly Ser Glu Ala
 1               5                  10                  15

<210> SEQ ID NO 2395
<211> LENGTH: 15
<212> TYPE: PRT
<213> ORGANISM: homo sapien

<400> SEQUENCE: 2395

Lys Leu Arg Val Val Ala Asp Asp Gly Ser Glu Ala Pro Glu
 1               5                  10                  15

<210> SEQ ID NO 2396
<211> LENGTH: 15
<212> TYPE: PRT
<213> ORGANISM: homo sapien

<400> SEQUENCE: 2396

Asp Asp Ser Leu Leu Asp Gln Asp Leu Pro Leu Thr Asn Ser Gln
 1               5                  10                  15

<210> SEQ ID NO 2397
<211> LENGTH: 15
<212> TYPE: PRT
<213> ORGANISM: homo sapien

<400> SEQUENCE: 2397

Asp Leu Pro Leu Thr Asn Ser Gln Leu Ser Leu Lys Val Asp Ser
 1               5                  10                  15

<210> SEQ ID NO 2398
<211> LENGTH: 15
<212> TYPE: PRT
<213> ORGANISM: homo sapien

<400> SEQUENCE: 2398

Gln Leu Ser Leu Lys Val Asp Ser Cys Asp Asn Cys Ser Lys Gln
 1               5                  10                  15

<210> SEQ ID NO 2399
<211> LENGTH: 15
<212> TYPE: PRT
<213> ORGANISM: homo sapien

<400> SEQUENCE: 2399

Gln Arg Glu Ile Leu Lys Gln Arg Lys Val Lys Ala Arg Leu Thr
 1               5                  10                  15

<210> SEQ ID NO 2400
<211> LENGTH: 15
<212> TYPE: PRT
<213> ORGANISM: homo sapien
```

```
<400> SEQUENCE: 2400

Arg Leu Thr Ile Ala Ala Val Leu Tyr Leu Leu Phe Met Ile Gly
 1               5                  10                  15

<210> SEQ ID NO 2401
<211> LENGTH: 15
<212> TYPE: PRT
<213> ORGANISM: homo sapien

<400> SEQUENCE: 2401

Ile Ala Ala Val Leu Tyr Leu Leu Phe Met Ile Gly Glu Leu Val
 1               5                  10                  15

<210> SEQ ID NO 2402
<211> LENGTH: 15
<212> TYPE: PRT
<213> ORGANISM: homo sapien

<400> SEQUENCE: 2402

Ala Ala Val Leu Tyr Leu Leu Phe Met Ile Gly Glu Leu Val Gly
 1               5                  10                  15

<210> SEQ ID NO 2403
<211> LENGTH: 15
<212> TYPE: PRT
<213> ORGANISM: homo sapien

<400> SEQUENCE: 2403

Val Leu Tyr Leu Leu Phe Met Ile Gly Glu Leu Val Gly Gly Tyr
 1               5                  10                  15

<210> SEQ ID NO 2404
<211> LENGTH: 15
<212> TYPE: PRT
<213> ORGANISM: homo sapien

<400> SEQUENCE: 2404

Leu Tyr Leu Leu Phe Met Ile Gly Glu Leu Val Gly Gly Tyr Ile
 1               5                  10                  15

<210> SEQ ID NO 2405
<211> LENGTH: 15
<212> TYPE: PRT
<213> ORGANISM: homo sapien

<400> SEQUENCE: 2405

Leu Leu Phe Met Ile Gly Glu Leu Val Gly Gly Tyr Ile Ala Asn
 1               5                  10                  15

<210> SEQ ID NO 2406
<211> LENGTH: 15
<212> TYPE: PRT
<213> ORGANISM: homo sapien

<400> SEQUENCE: 2406

Ile Gly Glu Leu Val Gly Gly Tyr Ile Ala Asn Ser Leu Ala Ile
 1               5                  10                  15

<210> SEQ ID NO 2407
<211> LENGTH: 15
<212> TYPE: PRT
<213> ORGANISM: homo sapien

<400> SEQUENCE: 2407
```

```
Gly Glu Leu Val Gly Gly Tyr Ile Ala Asn Ser Leu Ala Ile Met
 1               5                  10                  15

<210> SEQ ID NO 2408
<211> LENGTH: 15
<212> TYPE: PRT
<213> ORGANISM: homo sapien

<400> SEQUENCE: 2408

Gly Gly Tyr Ile Ala Asn Ser Leu Ala Ile Met Thr Asp Ala Leu
 1               5                  10                  15

<210> SEQ ID NO 2409
<211> LENGTH: 15
<212> TYPE: PRT
<213> ORGANISM: homo sapien

<400> SEQUENCE: 2409

Leu Leu Ala Leu Trp Leu Ser Ser Lys Ser Pro Thr Lys Arg Phe
 1               5                  10                  15

<210> SEQ ID NO 2410
<211> LENGTH: 15
<212> TYPE: PRT
<213> ORGANISM: homo sapien

<400> SEQUENCE: 2410

Met Ile Ser Val Leu Leu Val Tyr Ile Leu Met Gly Phe Leu Leu
 1               5                  10                  15

<210> SEQ ID NO 2411
<211> LENGTH: 15
<212> TYPE: PRT
<213> ORGANISM: homo sapien

<400> SEQUENCE: 2411

Tyr Glu Ala Val Gln Arg Thr Ile His Met Asn Tyr Glu Ile Asn
 1               5                  10                  15

<210> SEQ ID NO 2412
<211> LENGTH: 15
<212> TYPE: PRT
<213> ORGANISM: homo sapien

<400> SEQUENCE: 2412

Asn Gly Asp Ile Met Leu Ile Thr Ala Ala Val Gly Val Ala Val
 1               5                  10                  15

<210> SEQ ID NO 2413
<211> LENGTH: 15
<212> TYPE: PRT
<213> ORGANISM: homo sapien

<400> SEQUENCE: 2413

Gly Asp Ile Met Leu Ile Thr Ala Ala Val Gly Val Ala Val Asn
 1               5                  10                  15

<210> SEQ ID NO 2414
<211> LENGTH: 15
<212> TYPE: PRT
<213> ORGANISM: homo sapien

<400> SEQUENCE: 2414

Ala Val Asn Val Ile Met Gly Phe Leu Leu Asn Gln Ser Gly His
```

-continued

```
                1               5                  10                  15
```

<210> SEQ ID NO 2415
<211> LENGTH: 15
<212> TYPE: PRT
<213> ORGANISM: homo sapien

<400> SEQUENCE: 2415

```
Leu Gly Asp Leu Val Gln Ser Val Gly Val Leu Ile Ala Ala Tyr
 1               5                  10                  15
```

<210> SEQ ID NO 2416
<211> LENGTH: 15
<212> TYPE: PRT
<213> ORGANISM: homo sapien

<400> SEQUENCE: 2416

```
Ser Val Gly Val Leu Ile Ala Ala Tyr Ile Ile Arg Phe Lys Pro
 1               5                  10                  15
```

<210> SEQ ID NO 2417
<211> LENGTH: 15
<212> TYPE: PRT
<213> ORGANISM: homo sapien

<400> SEQUENCE: 2417

```
Val Gly Val Leu Ile Ala Ala Tyr Ile Ile Arg Phe Lys Pro Glu
 1               5                  10                  15
```

<210> SEQ ID NO 2418
<211> LENGTH: 15
<212> TYPE: PRT
<213> ORGANISM: homo sapien

<400> SEQUENCE: 2418

```
Gly Val Leu Ile Ala Ala Tyr Ile Ile Arg Phe Lys Pro Glu Tyr
 1               5                  10                  15
```

<210> SEQ ID NO 2419
<211> LENGTH: 15
<212> TYPE: PRT
<213> ORGANISM: homo sapien

<400> SEQUENCE: 2419

```
Glu Tyr Lys Ile Ala Asp Pro Ile Cys Thr Tyr Val Phe Ser Leu
 1               5                  10                  15
```

<210> SEQ ID NO 2420
<211> LENGTH: 15
<212> TYPE: PRT
<213> ORGANISM: homo sapien

<400> SEQUENCE: 2420

```
Ala Asp Pro Ile Cys Thr Tyr Val Phe Ser Leu Leu Val Ala Phe
 1               5                  10                  15
```

<210> SEQ ID NO 2421
<211> LENGTH: 15
<212> TYPE: PRT
<213> ORGANISM: homo sapien

<400> SEQUENCE: 2421

```
Ser Leu Leu Val Ala Phe Thr Thr Phe Arg Ile Ile Trp Asp Thr
 1               5                  10                  15
```

-continued

<210> SEQ ID NO 2422
<211> LENGTH: 15
<212> TYPE: PRT
<213> ORGANISM: homo sapien

<400> SEQUENCE: 2422

Phe Arg Ile Ile Trp Asp Thr Val Val Ile Ile Leu Glu Gly Val
1               5                   10                  15

<210> SEQ ID NO 2423
<211> LENGTH: 15
<212> TYPE: PRT
<213> ORGANISM: homo sapien

<400> SEQUENCE: 2423

Trp Asp Thr Val Val Ile Ile Leu Glu Gly Val Pro Ser His Leu
1               5                   10                  15

<210> SEQ ID NO 2424
<211> LENGTH: 15
<212> TYPE: PRT
<213> ORGANISM: homo sapien

<400> SEQUENCE: 2424

Thr Val Val Ile Ile Leu Glu Gly Val Pro Ser His Leu Asn Val
1               5                   10                  15

<210> SEQ ID NO 2425
<211> LENGTH: 15
<212> TYPE: PRT
<213> ORGANISM: homo sapien

<400> SEQUENCE: 2425

Val Val Ile Ile Leu Glu Gly Val Pro Ser His Leu Asn Val Asp
1               5                   10                  15

<210> SEQ ID NO 2426
<211> LENGTH: 15
<212> TYPE: PRT
<213> ORGANISM: homo sapien

<400> SEQUENCE: 2426

Leu Glu Gly Val Pro Ser His Leu Asn Val Asp Tyr Ile Lys Glu
1               5                   10                  15

<210> SEQ ID NO 2427
<211> LENGTH: 15
<212> TYPE: PRT
<213> ORGANISM: homo sapien

<400> SEQUENCE: 2427

Val Asp Tyr Ile Lys Glu Ala Leu Met Lys Ile Glu Asp Val Tyr
1               5                   10                  15

<210> SEQ ID NO 2428
<211> LENGTH: 15
<212> TYPE: PRT
<213> ORGANISM: homo sapien

<400> SEQUENCE: 2428

Ser Thr Ala Ile Val His Ile Gln Leu Ile Pro Gly Ser Ser Ser
1               5                   10                  15

<210> SEQ ID NO 2429

```
<211> LENGTH: 15
<212> TYPE: PRT
<213> ORGANISM: homo sapien

<400> SEQUENCE: 2429

Thr Ala Ile Val His Ile Gln Leu Ile Pro Gly Ser Ser Ser Lys
1               5                   10                  15

<210> SEQ ID NO 2430
<211> LENGTH: 15
<212> TYPE: PRT
<213> ORGANISM: homo sapien

<400> SEQUENCE: 2430

His Ile Gln Leu Ile Pro Gly Ser Ser Ser Lys Trp Glu Glu Val
1               5                   10                  15

<210> SEQ ID NO 2431
<211> LENGTH: 15
<212> TYPE: PRT
<213> ORGANISM: homo sapien

<400> SEQUENCE: 2431

Ile Gln Leu Ile Pro Gly Ser Ser Ser Lys Trp Glu Glu Val Gln
1               5                   10                  15

<210> SEQ ID NO 2432
<211> LENGTH: 15
<212> TYPE: PRT
<213> ORGANISM: homo sapien

<400> SEQUENCE: 2432

His Leu Leu Leu Asn Thr Phe Gly Met Tyr Arg Cys Thr Ile Gln
1               5                   10                  15

<210> SEQ ID NO 2433
<211> LENGTH: 15
<212> TYPE: PRT
<213> ORGANISM: homo sapien

<400> SEQUENCE: 2433

Thr Phe Gly Met Tyr Arg Cys Thr Ile Gln Leu Gln Ser Tyr Arg
1               5                   10                  15

<210> SEQ ID NO 2434
<211> LENGTH: 15
<212> TYPE: PRT
<213> ORGANISM: homo sapien

<400> SEQUENCE: 2434

Thr Ile Gln Leu Gln Ser Tyr Arg Gln Glu Val Asp Arg Thr Cys
1               5                   10                  15

<210> SEQ ID NO 2435
<211> LENGTH: 15
<212> TYPE: PRT
<213> ORGANISM: homo sapien

<400> SEQUENCE: 2435

Arg Gln Glu Val Asp Arg Thr Cys Ala Asn Cys Gln Ser Ser Ser
1               5                   10                  15

<210> SEQ ID NO 2436
<211> LENGTH: 15
<212> TYPE: PRT
```

<213> ORGANISM: homo sapien

<400> SEQUENCE: 2436

Phe Leu Leu Tyr Glu Ala Val Gln Arg Thr Ile His Met Asn Tyr
1               5                   10                  15

<210> SEQ ID NO 2437
<211> LENGTH: 15
<212> TYPE: PRT
<213> ORGANISM: homo sapien

<400> SEQUENCE: 2437

Leu Ser Arg Phe Asn Lys Leu Arg Val Val Ala Asp Asp Gly
1               5                   10                  15

<210> SEQ ID NO 2438
<211> LENGTH: 15
<212> TYPE: PRT
<213> ORGANISM: homo sapien

<400> SEQUENCE: 2438

Thr Lys Arg Phe Thr Phe Gly Phe His Arg Leu Glu Val Leu Ser
1               5                   10                  15

<210> SEQ ID NO 2439
<211> LENGTH: 15
<212> TYPE: PRT
<213> ORGANISM: homo sapien

<400> SEQUENCE: 2439

Thr Phe Gly Phe His Arg Leu Glu Val Leu Ser Ala Met Ile Ser
1               5                   10                  15

<210> SEQ ID NO 2440
<211> LENGTH: 15
<212> TYPE: PRT
<213> ORGANISM: homo sapien

<400> SEQUENCE: 2440

Phe Asn Lys Leu Arg Val Val Val Ala Asp Asp Gly Ser Glu Ala
1               5                   10                  15

<210> SEQ ID NO 2441
<211> LENGTH: 15
<212> TYPE: PRT
<213> ORGANISM: homo sapien

<400> SEQUENCE: 2441

Gln Arg Glu Ile Leu Lys Gln Arg Lys Val Lys Ala Arg Leu Thr
1               5                   10                  15

<210> SEQ ID NO 2442
<211> LENGTH: 15
<212> TYPE: PRT
<213> ORGANISM: homo sapien

<400> SEQUENCE: 2442

Ala Ile Ile Leu Thr Leu Leu Ala Leu Trp Leu Ser Ser Lys Ser
1               5                   10                  15

<210> SEQ ID NO 2443
<211> LENGTH: 15
<212> TYPE: PRT
<213> ORGANISM: homo sapien -continued

```
<400> SEQUENCE: 2443

Gly Phe Leu Leu Asn Gln Ser Gly His Arg His Ser His Ser His
1               5                   10                  15

<210> SEQ ID NO 2444
<211> LENGTH: 15
<212> TYPE: PRT
<213> ORGANISM: homo sapien

<400> SEQUENCE: 2444

Val His Ala Leu Gly Asp Leu Val Gln Ser Val Gly Val Leu Ile
1               5                   10                  15

<210> SEQ ID NO 2445
<211> LENGTH: 15
<212> TYPE: PRT
<213> ORGANISM: homo sapien

<400> SEQUENCE: 2445

Val Leu Ile Ala Ala Tyr Ile Ile Arg Phe Lys Pro Glu Tyr Lys
1               5                   10                  15

<210> SEQ ID NO 2446
<211> LENGTH: 15
<212> TYPE: PRT
<213> ORGANISM: homo sapien

<400> SEQUENCE: 2446

Trp Lys Arg Leu Lys Ser Met Leu Arg Lys Asp Asp Ala Pro Leu
1               5                   10                  15

<210> SEQ ID NO 2447
<211> LENGTH: 15
<212> TYPE: PRT
<213> ORGANISM: homo sapien

<400> SEQUENCE: 2447

Lys Arg Leu Lys Ser Met Leu Arg Lys Asp Asp Ala Pro Leu Phe
1               5                   10                  15

<210> SEQ ID NO 2448
<211> LENGTH: 15
<212> TYPE: PRT
<213> ORGANISM: homo sapien

<400> SEQUENCE: 2448

Leu Tyr Leu Leu Phe Met Ile Gly Glu Leu Val Gly Gly Tyr Ile
1               5                   10                  15

<210> SEQ ID NO 2449
<211> LENGTH: 15
<212> TYPE: PRT
<213> ORGANISM: homo sapien

<400> SEQUENCE: 2449

Phe His Arg Leu Glu Val Leu Ser Ala Met Ile Ser Val Leu Leu
1               5                   10                  15

<210> SEQ ID NO 2450
<211> LENGTH: 15
<212> TYPE: PRT
<213> ORGANISM: homo sapien

<400> SEQUENCE: 2450
```

Gln Ser Tyr Arg Gln Glu Val Asp Arg Thr Cys Ala Asn Cys Gln
1               5                   10                  15

<210> SEQ ID NO 2451
<211> LENGTH: 15
<212> TYPE: PRT
<213> ORGANISM: homo sapien

<400> SEQUENCE: 2451

Ile Ala Ala Val Leu Tyr Leu Leu Phe Met Ile Gly Glu Leu Val
1               5                   10                  15

<210> SEQ ID NO 2452
<211> LENGTH: 15
<212> TYPE: PRT
<213> ORGANISM: homo sapien

<400> SEQUENCE: 2452

Asn Gly Asp Ile Met Leu Ile Thr Ala Ala Val Gly Val Ala Val
1               5                   10                  15

<210> SEQ ID NO 2453
<211> LENGTH: 15
<212> TYPE: PRT
<213> ORGANISM: homo sapien

<400> SEQUENCE: 2453

Gly Asp Leu Val Gln Ser Val Gly Val Leu Ile Ala Ala Tyr Ile
1               5                   10                  15

<210> SEQ ID NO 2454
<211> LENGTH: 15
<212> TYPE: PRT
<213> ORGANISM: homo sapien

<400> SEQUENCE: 2454

Arg Ile Ile Trp Asp Thr Val Val Ile Ile Leu Glu Gly Val Pro
1               5                   10                  15

<210> SEQ ID NO 2455
<211> LENGTH: 15
<212> TYPE: PRT
<213> ORGANISM: homo sapien

<400> SEQUENCE: 2455

Trp Asp Thr Val Val Ile Ile Leu Glu Gly Val Pro Ser His Leu
1               5                   10                  15

<210> SEQ ID NO 2456
<211> LENGTH: 15
<212> TYPE: PRT
<213> ORGANISM: homo sapien

<400> SEQUENCE: 2456

Asp Leu Asn Ile Trp Ser Leu Thr Ser Gly Lys Ser Thr Ala Ile
1               5                   10                  15

<210> SEQ ID NO 2457
<211> LENGTH: 15
<212> TYPE: PRT
<213> ORGANISM: homo sapien

<400> SEQUENCE: 2457

Thr Asp Ala Leu His Met Leu Thr Asp Leu Ser Ala Ile Ile Leu
1               5                   10                  15

-continued

<210> SEQ ID NO 2458
<211> LENGTH: 15
<212> TYPE: PRT
<213> ORGANISM: homo sapien

<400> SEQUENCE: 2458

Met Ile Ser Val Leu Leu Val Tyr Ile Leu Met Gly Phe Leu Leu
 1               5                  10                  15

<210> SEQ ID NO 2459
<211> LENGTH: 15
<212> TYPE: PRT
<213> ORGANISM: homo sapien

<400> SEQUENCE: 2459

Asn Val Ile Met Gly Phe Leu Leu Asn Gln Ser Gly His Arg His
 1               5                  10                  15

<210> SEQ ID NO 2460
<211> LENGTH: 15
<212> TYPE: PRT
<213> ORGANISM: homo sapien

<400> SEQUENCE: 2460

Ile Ala Ala Tyr Ile Ile Arg Phe Lys Pro Glu Tyr Lys Ile Ala
 1               5                  10                  15

<210> SEQ ID NO 2461
<211> LENGTH: 15
<212> TYPE: PRT
<213> ORGANISM: homo sapien

<400> SEQUENCE: 2461

Ile Ile Arg Phe Lys Pro Glu Tyr Lys Ile Ala Asp Pro Ile Cys
 1               5                  10                  15

<210> SEQ ID NO 2462
<211> LENGTH: 15
<212> TYPE: PRT
<213> ORGANISM: homo sapien

<400> SEQUENCE: 2462

Thr Tyr Val Phe Ser Leu Leu Val Ala Phe Thr Thr Phe Arg Ile
 1               5                  10                  15

<210> SEQ ID NO 2463
<211> LENGTH: 15
<212> TYPE: PRT
<213> ORGANISM: homo sapien

<400> SEQUENCE: 2463

Asp Thr Val Val Ile Ile Leu Glu Gly Val Pro Ser His Leu Asn
 1               5                  10                  15

<210> SEQ ID NO 2464
<211> LENGTH: 15
<212> TYPE: PRT
<213> ORGANISM: homo sapien

<400> SEQUENCE: 2464

Lys Glu Ala Leu Met Lys Ile Glu Asp Val Tyr Ser Val Glu Asp
 1               5                  10                  15

-continued

```
<210> SEQ ID NO 2465
<211> LENGTH: 15
<212> TYPE: PRT
<213> ORGANISM: homo sapien

<400> SEQUENCE: 2465

Ser Gly Lys Ser Thr Ala Ile Val His Ile Gln Leu Ile Pro Gly
1               5                   10                  15

<210> SEQ ID NO 2466
<211> LENGTH: 15
<212> TYPE: PRT
<213> ORGANISM: homo sapien

<400> SEQUENCE: 2466

Ser Thr Ala Ile Val His Ile Gln Leu Ile Pro Gly Ser Ser Ser
1               5                   10                  15

<210> SEQ ID NO 2467
<211> LENGTH: 15
<212> TYPE: PRT
<213> ORGANISM: homo sapien

<400> SEQUENCE: 2467

Ile Val His Ile Gln Leu Ile Pro Gly Ser Ser Ser Lys Trp Glu
1               5                   10                  15

<210> SEQ ID NO 2468
<211> LENGTH: 15
<212> TYPE: PRT
<213> ORGANISM: homo sapien

<400> SEQUENCE: 2468

Ser Gly Ala Trp Lys Arg Leu Lys Ser Met Leu Arg Lys Asp Asp
1               5                   10                  15

<210> SEQ ID NO 2469
<211> LENGTH: 15
<212> TYPE: PRT
<213> ORGANISM: homo sapien

<400> SEQUENCE: 2469

Leu Ala Ile Met Thr Asp Ala Leu His Met Leu Thr Asp Leu Ser
1               5                   10                  15

<210> SEQ ID NO 2470
<211> LENGTH: 15
<212> TYPE: PRT
<213> ORGANISM: homo sapien

<400> SEQUENCE: 2470

Leu Leu Val Tyr Ile Leu Met Gly Phe Leu Leu Tyr Glu Ala Val
1               5                   10                  15

<210> SEQ ID NO 2471
<211> LENGTH: 15
<212> TYPE: PRT
<213> ORGANISM: homo sapien

<400> SEQUENCE: 2471

Leu Ala Val Arg Ala Ala Phe Val His Ala Leu Gly Asp Leu Val
1               5                   10                  15

<210> SEQ ID NO 2472
<211> LENGTH: 15
```

```
<212> TYPE: PRT
<213> ORGANISM: homo sapien

<400> SEQUENCE: 2472

Phe Thr Thr Phe Arg Ile Ile Trp Asp Thr Val Val Ile Ile Leu
 1               5                  10                  15

<210> SEQ ID NO 2473
<211> LENGTH: 15
<212> TYPE: PRT
<213> ORGANISM: homo sapien

<400> SEQUENCE: 2473

Ala Phe Asp Phe Ser Asp Glu Ala Gly Asp Glu Gly Leu Ser Arg
 1               5                  10                  15

<210> SEQ ID NO 2474
<211> LENGTH: 15
<212> TYPE: PRT
<213> ORGANISM: homo sapien

<400> SEQUENCE: 2474

Asp Glu Gly Leu Ser Arg Phe Asn Lys Leu Arg Val Val Val Ala
 1               5                  10                  15

<210> SEQ ID NO 2475
<211> LENGTH: 15
<212> TYPE: PRT
<213> ORGANISM: homo sapien

<400> SEQUENCE: 2475

Cys Ser Lys Gln Arg Glu Ile Leu Lys Gln Arg Lys Val Lys Ala
 1               5                  10                  15

<210> SEQ ID NO 2476
<211> LENGTH: 15
<212> TYPE: PRT
<213> ORGANISM: homo sapien

<400> SEQUENCE: 2476

Tyr Leu Leu Phe Met Ile Gly Glu Leu Val Gly Gly Tyr Ile Ala
 1               5                  10                  15

<210> SEQ ID NO 2477
<211> LENGTH: 15
<212> TYPE: PRT
<213> ORGANISM: homo sapien

<400> SEQUENCE: 2477

Ser Ser Lys Trp Glu Glu Val Gln Ser Lys Ala Asn His Leu Leu
 1               5                  10                  15

<210> SEQ ID NO 2478
<211> LENGTH: 15
<212> TYPE: PRT
<213> ORGANISM: homo sapien

<400> SEQUENCE: 2478

Phe Gly Met Tyr Arg Cys Thr Ile Gln Leu Gln Ser Tyr Arg Gln
 1               5                  10                  15

<210> SEQ ID NO 2479
<211> LENGTH: 15
<212> TYPE: PRT
<213> ORGANISM: homo sapien
```

```
<400> SEQUENCE: 2479

Met Ala Gly Ser Gly Ala Trp Lys Arg Leu Lys Ser Met Leu Arg
 1               5                  10                  15

<210> SEQ ID NO 2480
<211> LENGTH: 15
<212> TYPE: PRT
<213> ORGANISM: homo sapien

<400> SEQUENCE: 2480

Leu His Met Leu Thr Asp Leu Ser Ala Ile Ile Leu Thr Leu Leu
 1               5                  10                  15

<210> SEQ ID NO 2481
<211> LENGTH: 15
<212> TYPE: PRT
<213> ORGANISM: homo sapien

<400> SEQUENCE: 2481

Ser Gly His Arg His Ser His Ser His Ser Leu Pro Ser Asn Ser
 1               5                  10                  15

<210> SEQ ID NO 2482
<211> LENGTH: 15
<212> TYPE: PRT
<213> ORGANISM: homo sapien

<400> SEQUENCE: 2482

Ile Ile Trp Asp Thr Val Val Ile Ile Leu Glu Gly Val Pro Ser
 1               5                  10                  15

<210> SEQ ID NO 2483
<211> LENGTH: 15
<212> TYPE: PRT
<213> ORGANISM: homo sapien

<400> SEQUENCE: 2483

Leu Leu Asn Thr Phe Gly Met Tyr Arg Cys Thr Ile Gln Leu Gln
 1               5                  10                  15

<210> SEQ ID NO 2484
<211> LENGTH: 15
<212> TYPE: PRT
<213> ORGANISM: homo sapien

<400> SEQUENCE: 2484

Glu Ala Gly Asp Glu Gly Leu Ser Arg Phe Asn Lys Leu Arg Val
 1               5                  10                  15

<210> SEQ ID NO 2485
<211> LENGTH: 15
<212> TYPE: PRT
<213> ORGANISM: homo sapien

<400> SEQUENCE: 2485

Leu Thr Asn Ser Gln Leu Ser Leu Lys Val Asp Ser Cys Asp Asn
 1               5                  10                  15

<210> SEQ ID NO 2486
<211> LENGTH: 15
<212> TYPE: PRT
<213> ORGANISM: homo sapien

<400> SEQUENCE: 2486
```

```
Leu Phe Met Ile Gly Glu Leu Val Gly Gly Tyr Ile Ala Asn Ser
  1               5                  10                  15

<210> SEQ ID NO 2487
<211> LENGTH: 15
<212> TYPE: PRT
<213> ORGANISM: homo sapien

<400> SEQUENCE: 2487

Leu Leu Ala Leu Trp Leu Ser Ser Lys Ser Pro Thr Lys Arg Phe
  1               5                  10                  15

<210> SEQ ID NO 2488
<211> LENGTH: 15
<212> TYPE: PRT
<213> ORGANISM: homo sapien

<400> SEQUENCE: 2488

Ser Ala Met Ile Ser Val Leu Leu Val Tyr Ile Leu Met Gly Phe
  1               5                  10                  15

<210> SEQ ID NO 2489
<211> LENGTH: 15
<212> TYPE: PRT
<213> ORGANISM: homo sapien

<400> SEQUENCE: 2489

Tyr Glu Ala Val Gln Arg Thr Ile His Met Asn Tyr Glu Ile Asn
  1               5                  10                  15

<210> SEQ ID NO 2490
<211> LENGTH: 15
<212> TYPE: PRT
<213> ORGANISM: homo sapien

<400> SEQUENCE: 2490

Gly Val Ala Val Asn Val Ile Met Gly Phe Leu Leu Asn Gln Ser
  1               5                  10                  15

<210> SEQ ID NO 2491
<211> LENGTH: 15
<212> TYPE: PRT
<213> ORGANISM: homo sapien

<400> SEQUENCE: 2491

Leu Leu Asn Gln Ser Gly His Arg His Ser His Ser His Ser Leu
  1               5                  10                  15

<210> SEQ ID NO 2492
<211> LENGTH: 15
<212> TYPE: PRT
<213> ORGANISM: homo sapien

<400> SEQUENCE: 2492

Asn Gln Ser Gly His Arg His Ser His Ser His Ser Leu Pro Ser
  1               5                  10                  15

<210> SEQ ID NO 2493
<211> LENGTH: 15
<212> TYPE: PRT
<213> ORGANISM: homo sapien

<400> SEQUENCE: 2493

Ser His Ser Leu Pro Ser Asn Ser Pro Thr Arg Gly Ser Gly Cys
```

-continued

```
<210> SEQ ID NO 2494
<211> LENGTH: 15
<212> TYPE: PRT
<213> ORGANISM: homo sapien

<400> SEQUENCE: 2494

Ser Leu Pro Ser Asn Ser Pro Thr Arg Gly Ser Gly Cys Glu Arg
 1               5                  10                  15

<210> SEQ ID NO 2495
<211> LENGTH: 15
<212> TYPE: PRT
<213> ORGANISM: homo sapien

<400> SEQUENCE: 2495

Pro Thr Arg Gly Ser Gly Cys Glu Arg Asn His Gly Gln Asp Ser
 1               5                  10                  15

<210> SEQ ID NO 2496
<211> LENGTH: 15
<212> TYPE: PRT
<213> ORGANISM: homo sapien

<400> SEQUENCE: 2496

Asp Tyr Ile Lys Glu Ala Leu Met Lys Ile Glu Asp Val Tyr Ser
 1               5                  10                  15

<210> SEQ ID NO 2497
<211> LENGTH: 15
<212> TYPE: PRT
<213> ORGANISM: homo sapien

<400> SEQUENCE: 2497

Asn Ile Trp Ser Leu Thr Ser Gly Lys Ser Thr Ala Ile Val His
 1               5                  10                  15

<210> SEQ ID NO 2498
<211> LENGTH: 15
<212> TYPE: PRT
<213> ORGANISM: homo sapien

<400> SEQUENCE: 2498

Asn Lys Leu Arg Val Val Ala Asp Asp Gly Ser Glu Ala Pro
 1               5                  10                  15

<210> SEQ ID NO 2499
<211> LENGTH: 15
<212> TYPE: PRT
<213> ORGANISM: homo sapien

<400> SEQUENCE: 2499

Ala Asp Asp Asp Ser Leu Leu Asp Gln Asp Leu Pro Leu Thr Asn
 1               5                  10                  15

<210> SEQ ID NO 2500
<211> LENGTH: 15
<212> TYPE: PRT
<213> ORGANISM: homo sapien

<400> SEQUENCE: 2500

Asp Gln Asp Leu Pro Leu Thr Asn Ser Gln Leu Ser Leu Lys Val
 1               5                  10                  15
```

-continued

```
<210> SEQ ID NO 2501
<211> LENGTH: 15
<212> TYPE: PRT
<213> ORGANISM: homo sapien

<400> SEQUENCE: 2501

Arg Leu Thr Ile Ala Ala Val Leu Tyr Leu Leu Phe Met Ile Gly
1               5                   10                  15

<210> SEQ ID NO 2502
<211> LENGTH: 15
<212> TYPE: PRT
<213> ORGANISM: homo sapien

<400> SEQUENCE: 2502

Val Leu Tyr Leu Leu Phe Met Ile Gly Glu Leu Val Gly Gly Tyr
1               5                   10                  15

<210> SEQ ID NO 2503
<211> LENGTH: 15
<212> TYPE: PRT
<213> ORGANISM: homo sapien

<400> SEQUENCE: 2503

Phe Met Ile Gly Glu Leu Val Gly Gly Tyr Ile Ala Asn Ser Leu
1               5                   10                  15

<210> SEQ ID NO 2504
<211> LENGTH: 15
<212> TYPE: PRT
<213> ORGANISM: homo sapien

<400> SEQUENCE: 2504

Glu Leu Val Gly Gly Tyr Ile Ala Asn Ser Leu Ala Ile Met Thr
1               5                   10                  15

<210> SEQ ID NO 2505
<211> LENGTH: 15
<212> TYPE: PRT
<213> ORGANISM: homo sapien

<400> SEQUENCE: 2505

Ala Asn Ser Leu Ala Ile Met Thr Asp Ala Leu His Met Leu Thr
1               5                   10                  15

<210> SEQ ID NO 2506
<211> LENGTH: 15
<212> TYPE: PRT
<213> ORGANISM: homo sapien

<400> SEQUENCE: 2506

Met Thr Asp Ala Leu His Met Leu Thr Asp Leu Ser Ala Ile Ile
1               5                   10                  15

<210> SEQ ID NO 2507
<211> LENGTH: 15
<212> TYPE: PRT
<213> ORGANISM: homo sapien

<400> SEQUENCE: 2507

Leu Thr Asp Leu Ser Ala Ile Ile Leu Thr Leu Leu Ala Leu Trp
1               5                   10                  15

<210> SEQ ID NO 2508
```

```
<211> LENGTH: 15
<212> TYPE: PRT
<213> ORGANISM: homo sapien

<400> SEQUENCE: 2508

Thr Asp Leu Ser Ala Ile Ile Leu Thr Leu Leu Ala Leu Trp Leu
1               5                   10                  15

<210> SEQ ID NO 2509
<211> LENGTH: 15
<212> TYPE: PRT
<213> ORGANISM: homo sapien

<400> SEQUENCE: 2509

Leu Thr Leu Leu Ala Leu Trp Leu Ser Ser Lys Ser Pro Thr Lys
1               5                   10                  15

<210> SEQ ID NO 2510
<211> LENGTH: 15
<212> TYPE: PRT
<213> ORGANISM: homo sapien

<400> SEQUENCE: 2510

Leu Glu Val Leu Ser Ala Met Ile Ser Val Leu Leu Val Tyr Ile
1               5                   10                  15

<210> SEQ ID NO 2511
<211> LENGTH: 15
<212> TYPE: PRT
<213> ORGANISM: homo sapien

<400> SEQUENCE: 2511

Val Leu Leu Val Tyr Ile Leu Met Gly Phe Leu Leu Tyr Glu Ala
1               5                   10                  15

<210> SEQ ID NO 2512
<211> LENGTH: 15
<212> TYPE: PRT
<213> ORGANISM: homo sapien

<400> SEQUENCE: 2512

Asp Ile Met Leu Ile Thr Ala Ala Val Gly Val Ala Val Asn Val
1               5                   10                  15

<210> SEQ ID NO 2513
<211> LENGTH: 15
<212> TYPE: PRT
<213> ORGANISM: homo sapien

<400> SEQUENCE: 2513

Asn His Gly Gln Asp Ser Leu Ala Val Arg Ala Ala Phe Val His
1               5                   10                  15

<210> SEQ ID NO 2514
<211> LENGTH: 15
<212> TYPE: PRT
<213> ORGANISM: homo sapien

<400> SEQUENCE: 2514

Ala Ala Phe Val His Ala Leu Gly Asp Leu Val Gln Ser Val Gly
1               5                   10                  15

<210> SEQ ID NO 2515
<211> LENGTH: 15
<212> TYPE: PRT
```

-continued

<213> ORGANISM: homo sapien

<400> SEQUENCE: 2515

Val Gln Ser Val Gly Val Leu Ile Ala Ala Tyr Ile Ile Arg Phe
1               5                   10                  15

<210> SEQ ID NO 2516
<211> LENGTH: 15
<212> TYPE: PRT
<213> ORGANISM: homo sapien

<400> SEQUENCE: 2516

Cys Thr Tyr Val Phe Ser Leu Leu Val Ala Phe Thr Thr Phe Arg
1               5                   10                  15

<210> SEQ ID NO 2517
<211> LENGTH: 15
<212> TYPE: PRT
<213> ORGANISM: homo sapien

<400> SEQUENCE: 2517

Val Ile Ile Leu Glu Gly Val Pro Ser His Leu Asn Val Asp Tyr
1               5                   10                  15

<210> SEQ ID NO 2518
<211> LENGTH: 15
<212> TYPE: PRT
<213> ORGANISM: homo sapien

<400> SEQUENCE: 2518

Pro Ser His Leu Asn Val Asp Tyr Ile Lys Glu Ala Leu Met Lys
1               5                   10                  15

<210> SEQ ID NO 2519
<211> LENGTH: 15
<212> TYPE: PRT
<213> ORGANISM: homo sapien

<400> SEQUENCE: 2519

His Leu Asn Val Asp Tyr Ile Lys Glu Ala Leu Met Lys Ile Glu
1               5                   10                  15

<210> SEQ ID NO 2520
<211> LENGTH: 15
<212> TYPE: PRT
<213> ORGANISM: homo sapien

<400> SEQUENCE: 2520

Leu Gln Ser Tyr Arg Gln Glu Val Asp Arg Thr Cys Ala Asn Cys
1               5                   10                  15

<210> SEQ ID NO 2521
<211> LENGTH: 15
<212> TYPE: PRT
<213> ORGANISM: homo sapien

<400> SEQUENCE: 2521

Asp Asp Ala Pro Leu Phe Leu Asn Asp Thr Ser Ala Phe Asp Phe
1               5                   10                  15

<210> SEQ ID NO 2522
<211> LENGTH: 15
<212> TYPE: PRT
<213> ORGANISM: homo sapien

<400> SEQUENCE: 2522

Leu Arg Val Val Ala Asp Asp Gly Ser Glu Ala Pro Glu Arg
1               5                   10                  15

<210> SEQ ID NO 2523
<211> LENGTH: 15
<212> TYPE: PRT
<213> ORGANISM: homo sapien

<400> SEQUENCE: 2523

Arg Val Val Val Ala Asp Asp Gly Ser Glu Ala Pro Glu Arg Pro
1               5                   10                  15

<210> SEQ ID NO 2524
<211> LENGTH: 15
<212> TYPE: PRT
<213> ORGANISM: homo sapien

<400> SEQUENCE: 2524

Glu Ala Pro Glu Arg Pro Val Asn Gly Ala His Pro Thr Leu Gln
1               5                   10                  15

<210> SEQ ID NO 2525
<211> LENGTH: 15
<212> TYPE: PRT
<213> ORGANISM: homo sapien

<400> SEQUENCE: 2525

Ser Leu Leu Asp Gln Asp Leu Pro Leu Thr Asn Ser Gln Leu Ser
1               5                   10                  15

<210> SEQ ID NO 2526
<211> LENGTH: 15
<212> TYPE: PRT
<213> ORGANISM: homo sapien

<400> SEQUENCE: 2526

Glu Ile Leu Lys Gln Arg Lys Val Lys Ala Arg Leu Thr Ile Ala
1               5                   10                  15

<210> SEQ ID NO 2527
<211> LENGTH: 15
<212> TYPE: PRT
<213> ORGANISM: homo sapien

<400> SEQUENCE: 2527

Gln Arg Lys Val Lys Ala Arg Leu Thr Ile Ala Ala Val Leu Tyr
1               5                   10                  15

<210> SEQ ID NO 2528
<211> LENGTH: 15
<212> TYPE: PRT
<213> ORGANISM: homo sapien

<400> SEQUENCE: 2528

Ala Ala Val Leu Tyr Leu Leu Phe Met Ile Gly Glu Leu Val Gly
1               5                   10                  15

<210> SEQ ID NO 2529
<211> LENGTH: 15
<212> TYPE: PRT
<213> ORGANISM: homo sapien

<400> SEQUENCE: 2529

-continued

Ile Gly Glu Leu Val Gly Gly Tyr Ile Ala Asn Ser Leu Ala Ile
1               5                   10                  15

<210> SEQ ID NO 2530
<211> LENGTH: 15
<212> TYPE: PRT
<213> ORGANISM: homo sapien

<400> SEQUENCE: 2530

Ser Ala Ile Ile Leu Thr Leu Leu Ala Leu Trp Leu Ser Ser Lys
1               5                   10                  15

<210> SEQ ID NO 2531
<211> LENGTH: 15
<212> TYPE: PRT
<213> ORGANISM: homo sapien

<400> SEQUENCE: 2531

Ile Leu Thr Leu Leu Ala Leu Trp Leu Ser Ser Lys Ser Pro Thr
1               5                   10                  15

<210> SEQ ID NO 2532
<211> LENGTH: 15
<212> TYPE: PRT
<213> ORGANISM: homo sapien

<400> SEQUENCE: 2532

Thr Leu Leu Ala Leu Trp Leu Ser Ser Lys Ser Pro Thr Lys Arg
1               5                   10                  15

<210> SEQ ID NO 2533
<211> LENGTH: 15
<212> TYPE: PRT
<213> ORGANISM: homo sapien

<400> SEQUENCE: 2533

Leu Ser Ala Met Ile Ser Val Leu Leu Val Tyr Ile Leu Met Gly
1               5                   10                  15

<210> SEQ ID NO 2534
<211> LENGTH: 15
<212> TYPE: PRT
<213> ORGANISM: homo sapien

<400> SEQUENCE: 2534

Ser Val Leu Leu Val Tyr Ile Leu Met Gly Phe Leu Leu Tyr Glu
1               5                   10                  15

<210> SEQ ID NO 2535
<211> LENGTH: 15
<212> TYPE: PRT
<213> ORGANISM: homo sapien

<400> SEQUENCE: 2535

Val Tyr Ile Leu Met Gly Phe Leu Leu Tyr Glu Ala Val Gln Arg
1               5                   10                  15

<210> SEQ ID NO 2536
<211> LENGTH: 15
<212> TYPE: PRT
<213> ORGANISM: homo sapien

<400> SEQUENCE: 2536

Tyr Ile Leu Met Gly Phe Leu Leu Tyr Glu Ala Val Gln Arg Thr
1               5                   10                  15

```
<210> SEQ ID NO 2537
<211> LENGTH: 15
<212> TYPE: PRT
<213> ORGANISM: homo sapien

<400> SEQUENCE: 2537

Gln Arg Thr Ile His Met Asn Tyr Glu Ile Asn Gly Asp Ile Met
 1               5                  10                  15

<210> SEQ ID NO 2538
<211> LENGTH: 15
<212> TYPE: PRT
<213> ORGANISM: homo sapien

<400> SEQUENCE: 2538

Tyr Glu Ile Asn Gly Asp Ile Met Leu Ile Thr Ala Ala Val Gly
 1               5                  10                  15

<210> SEQ ID NO 2539
<211> LENGTH: 15
<212> TYPE: PRT
<213> ORGANISM: homo sapien

<400> SEQUENCE: 2539

Glu Ile Asn Gly Asp Ile Met Leu Ile Thr Ala Ala Val Gly Val
 1               5                  10                  15

<210> SEQ ID NO 2540
<211> LENGTH: 15
<212> TYPE: PRT
<213> ORGANISM: homo sapien

<400> SEQUENCE: 2540

Ala Ala Val Gly Val Ala Val Asn Val Ile Met Gly Phe Leu Leu
 1               5                  10                  15

<210> SEQ ID NO 2541
<211> LENGTH: 15
<212> TYPE: PRT
<213> ORGANISM: homo sapien

<400> SEQUENCE: 2541

Val Asn Val Ile Met Gly Phe Leu Leu Asn Gln Ser Gly His Arg
 1               5                  10                  15

<210> SEQ ID NO 2542
<211> LENGTH: 15
<212> TYPE: PRT
<213> ORGANISM: homo sapien

<400> SEQUENCE: 2542

His Ser His Ser His Ser Leu Pro Ser Asn Ser Pro Thr Arg Gly
 1               5                  10                  15

<210> SEQ ID NO 2543
<211> LENGTH: 15
<212> TYPE: PRT
<213> ORGANISM: homo sapien

<400> SEQUENCE: 2543

Leu Val Ala Phe Thr Thr Phe Arg Ile Ile Trp Asp Thr Val Val
 1               5                  10                  15
```

```
<210> SEQ ID NO 2544
<211> LENGTH: 15
<212> TYPE: PRT
<213> ORGANISM: homo sapien

<400> SEQUENCE: 2544

Leu Met Lys Ile Glu Asp Val Tyr Ser Val Glu Asp Leu Asn Ile
1               5                   10                  15

<210> SEQ ID NO 2545
<211> LENGTH: 15
<212> TYPE: PRT
<213> ORGANISM: homo sapien

<400> SEQUENCE: 2545

Ile Glu Asp Val Tyr Ser Val Glu Asp Leu Asn Ile Trp Ser Leu
1               5                   10                  15

<210> SEQ ID NO 2546
<211> LENGTH: 15
<212> TYPE: PRT
<213> ORGANISM: homo sapien

<400> SEQUENCE: 2546

Glu Asp Val Tyr Ser Val Glu Asp Leu Asn Ile Trp Ser Leu Thr
1               5                   10                  15

<210> SEQ ID NO 2547
<211> LENGTH: 15
<212> TYPE: PRT
<213> ORGANISM: homo sapien

<400> SEQUENCE: 2547

Val Tyr Ser Val Glu Asp Leu Asn Ile Trp Ser Leu Thr Ser Gly
1               5                   10                  15

<210> SEQ ID NO 2548
<211> LENGTH: 15
<212> TYPE: PRT
<213> ORGANISM: homo sapien

<400> SEQUENCE: 2548

Ser Val Glu Asp Leu Asn Ile Trp Ser Leu Thr Ser Gly Lys Ser
1               5                   10                  15

<210> SEQ ID NO 2549
<211> LENGTH: 15
<212> TYPE: PRT
<213> ORGANISM: homo sapien

<400> SEQUENCE: 2549

Val Glu Asp Leu Asn Ile Trp Ser Leu Thr Ser Gly Lys Ser Thr
1               5                   10                  15

<210> SEQ ID NO 2550
<211> LENGTH: 15
<212> TYPE: PRT
<213> ORGANISM: homo sapien

<400> SEQUENCE: 2550

Thr Ala Ile Val His Ile Gln Leu Ile Pro Gly Ser Ser Ser Lys
1               5                   10                  15

<210> SEQ ID NO 2551
<211> LENGTH: 15
```

-continued

<212> TYPE: PRT
<213> ORGANISM: homo sapien

<400> SEQUENCE: 2551

Ala Ile Val His Ile Gln Leu Ile Pro Gly Ser Ser Ser Lys Trp
 1               5                  10                  15

<210> SEQ ID NO 2552
<211> LENGTH: 15
<212> TYPE: PRT
<213> ORGANISM: homo sapien

<400> SEQUENCE: 2552

Ser Lys Ala Asn His Leu Leu Asn Thr Phe Gly Met Tyr Arg
 1               5                  10                  15

<210> SEQ ID NO 2553
<211> LENGTH: 15
<212> TYPE: PRT
<213> ORGANISM: homo sapien

<400> SEQUENCE: 2553

Pro Leu Phe Leu Asn Asp Thr Ser Ala Phe Glu Phe Ser Asp Glu
 1               5                  10                  15

<210> SEQ ID NO 2554
<211> LENGTH: 15
<212> TYPE: PRT
<213> ORGANISM: homo sapien

<400> SEQUENCE: 2554

Asp Ala Pro Leu Phe Leu Asn Asp Thr Ser Ala Phe Glu Phe Ser
 1               5                  10                  15

<210> SEQ ID NO 2555
<211> LENGTH: 15
<212> TYPE: PRT
<213> ORGANISM: homo sapien

<400> SEQUENCE: 2555

Asp Asp Ala Pro Leu Phe Leu Asn Asp Thr Ser Ala Phe Glu Phe
 1               5                  10                  15

<210> SEQ ID NO 2556
<211> LENGTH: 15
<212> TYPE: PRT
<213> ORGANISM: homo sapien

<400> SEQUENCE: 2556

Ala Phe Glu Phe Ser Asp Glu Ala Gly Asp Glu Gly Leu Ser Arg
 1               5                  10                  15

<210> SEQ ID NO 2557
<211> LENGTH: 15
<212> TYPE: PRT
<213> ORGANISM: homo sapien

<400> SEQUENCE: 2557

Ala Pro Leu Phe Leu Asn Asp Thr Ser Ala Phe Glu Phe Ser Asp
 1               5                  10                  15

<210> SEQ ID NO 2558
<211> LENGTH: 15
<212> TYPE: PRT
<213> ORGANISM: homo sapien -continued

<400> SEQUENCE: 2558

Asp Ala Pro Leu Phe Leu Asn Asp Thr Ser Ala Phe Glu Phe Ser
1               5                   10                  15

<210> SEQ ID NO 2559
<211> LENGTH: 15
<212> TYPE: PRT
<213> ORGANISM: homo sapien

<400> SEQUENCE: 2559

Pro Leu Phe Leu Asn Asp Thr Ser Ala Phe Glu Phe Ser Asp Glu
1               5                   10                  15

<210> SEQ ID NO 2560
<211> LENGTH: 15
<212> TYPE: PRT
<213> ORGANISM: homo sapien

<400> SEQUENCE: 2560

Thr Ser Ala Phe Glu Phe Ser Asp Glu Ala Gly Asp Glu Gly Leu
1               5                   10                  15

<210> SEQ ID NO 2561
<211> LENGTH: 15
<212> TYPE: PRT
<213> ORGANISM: homo sapien

<400> SEQUENCE: 2561

Ala Pro Leu Phe Leu Asn Asp Thr Ser Ala Phe Glu Phe Ser Asp
1               5                   10                  15

<210> SEQ ID NO 2562
<211> LENGTH: 15
<212> TYPE: PRT
<213> ORGANISM: homo sapien

<400> SEQUENCE: 2562

Lys Asp Asp Ala Pro Leu Phe Leu Asn Asp Thr Ser Ala Phe Glu
1               5                   10                  15

<210> SEQ ID NO 2563
<211> LENGTH: 15
<212> TYPE: PRT
<213> ORGANISM: homo sapien

<400> SEQUENCE: 2563

Asn Asp Thr Ser Ala Phe Glu Phe Ser Asp Glu Ala Gly Asp Glu
1               5                   10                  15

<210> SEQ ID NO 2564
<211> LENGTH: 15
<212> TYPE: PRT
<213> ORGANISM: homo sapien

<400> SEQUENCE: 2564

Ala Phe Glu Phe Ser Asp Glu Ala Gly Asp Glu Gly Leu Ser Arg
1               5                   10                  15

<210> SEQ ID NO 2565
<211> LENGTH: 15
<212> TYPE: PRT
<213> ORGANISM: homo sapien

<400> SEQUENCE: 2565

Asp Ala Pro Leu Phe Leu Asn Asp Thr Ser Ala Phe Glu Phe Ser
 1               5                  10                  15

<210> SEQ ID NO 2566
<211> LENGTH: 15
<212> TYPE: PRT
<213> ORGANISM: homo sapien

<400> SEQUENCE: 2566

Ala Phe Glu Phe Ser Asp Glu Ala Gly Asp Glu Gly Leu Ser Arg
 1               5                  10                  15

<210> SEQ ID NO 2567
<211> LENGTH: 15
<212> TYPE: PRT
<213> ORGANISM: homo sapien

<400> SEQUENCE: 2567

Asp Asp Ala Pro Leu Phe Leu Asn Asp Thr Ser Ala Phe Glu Phe
 1               5                  10                  15

<210> SEQ ID NO 2568
<211> LENGTH: 446
<212> TYPE: DNA
<213> ORGANISM: homo sapien

<400> SEQUENCE: 2568

| | | | | | |
|---|---|---|---|---|---|
| gatccagatt | tctctgcaca | ctggacttcg | taagtaagtg | tggtagacaa | agagactaca | 60 |
| ctgcacaacc | accagtgaat | atcattgcta | agagactttg | ggtcgtgttt | ctcagccact | 120 |
| ctcacagctt | ttgtagactt | atttgatttt | gaaacaagca | gttagctaaa | tctatttttcc | 180 |
| ttttatgcat | atatgttaat | tggctcaact | taatatggtg | ttcttacaga | atatgagccc | 240 |
| atttgaaata | aggttttagg | caatttttgct | gttggctctg | atttgtatat | agcaaattta | 300 |
| aaggtacaga | gtgtttccta | gatagaagat | tagttcattt | ggttcatttt | gtctttgaag | 360 |
| caagccaagc | tcatgagcca | gttggttatt | tgtcataaat | gaacacccat | cactatatgc | 420 |
| tatgttgagg | ggaggcaagg | ctgatc | | | | 446 |

<210> SEQ ID NO 2569
<211> LENGTH: 2364
<212> TYPE: DNA
<213> ORGANISM: homo sapien

<400> SEQUENCE: 2569

| | | | | | |
|---|---|---|---|---|---|
| gccggcctcc | agcagcgggc | gcggcgggcg | cgagcacgac | cccactctcc | tgcggccgcg | 60 |
| ggtggagcag | cgcgagcccg | cctcgctgag | ccggccgggg | gcggggagat | gagttgcggc | 120 |
| cccgcggcag | cgccccagga | tggggaggga | cgcgcggcac | tgccctcgag | aactggcgct | 180 |
| ccggtgaagt | aggcgccgcc | ggccgtccgc | ctccccccaag | ccgttccgca | ccgcggccgc | 240 |
| tcagcctctg | ccatggccgg | ctctggcgcg | tggaagcgcc | tcaaatctat | gctaaggaag | 300 |
| gatgatgcgc | cgctgttttt | aaatgacacc | agcgcctttg | acttctcgga | tgaggcgggg | 360 |
| gacgaggggc | tttctcggtt | caacaaactt | cgagttgtgg | tggccgatga | cggttccgaa | 420 |
| gccccggaaa | ggcctgttaa | cggggcgcac | ccgaccctcc | aggccgacga | tgattcctta | 480 |
| ctggaccaag | acttaccttt | gaccaacagt | cagctgagtt | tgaaggtgga | ctcctgtgac | 540 |
| aactgcagca | acagagaga | gatactgaag | cagagaaagg | tgaaagccag | gttgaccatt | 600 |
| gctgccgttc | tgtacttgct | tttcatgatt | ggagaacttg | taggtggata | cattgcaaat | 660 |

-continued

```
agcctagcaa tcatgacaga tgcacttcat atgttaactg acctaagcgc catcatactc       720
accctgcttg ctttgtggct atcatcaaaa tcaccaacca aaagattcac ctttggattt       780
catcgcttag aggttttgtc agctatgatt agtgtgctgt tggtgtatat acttatggga       840
ttcctcttat atgaagctgt gcaaagaact atccatatga actatgaaat aaatggagat       900
ataatgctca tcaccgcagc tgttggagtt gcagttaatg taataatggg gtttctgttg       960
aaccagtctg gtcaccgtca ctcccattcc cactccctgc cttcaaattc ccctaccaga      1020
ggttctgggt gtgaacgtaa ccatgggcag gatagcctgg cagtgagagc tgcatttgta      1080
catgctttgg gagatttggt acagagtgtt ggtgtgctaa tagctgcata catcatacga      1140
ttcaagccag aatacaagat tgctgacccc atctgtacat acgtattttc attacttgtg      1200
gcttttacaa catttcgaat catatgggat acagtagtta taatactaga aggtgtgcca      1260
agccatttga atgtagacta tatcaaagaa gccttgatga aaatagaaga tgtatattca      1320
gtcgaagatt taaatatctg gtctctcact tcaggaaaat ctactgccat agttcacata      1380
cagctaattc ctggaagttc atctaaatgg gaggaagtac agtccaaagc aaaccattta      1440
ttattgaaca catttggcat gtatagatgt actattcagc ttcagagtta caggcaagaa      1500
gtggacagaa cttgtgcaaa ttgtcagagt tctagtccct aattttatgt attttgggaa      1560
ctcctgcctt atttatcctg cagtcacaga cttgagagca ataaatgcaa acctaaatga      1620
gaaaatggaa tccctgacag ctgtgtccgt atcaagcatc agtctctcaa acagttgccc      1680
cagcctgaca gtgctagtct ctgtttaatg gtaaaaggag actttgccat aattttcaga      1740
tgaagatgtt tcccaaacac tgtttacaga atgagatgtg actctacaga tacctcatag      1800
aagacaatcc aagatcatac ttcattaact tgacagagta cgtgtcttaa aggaagcatc      1860
aagaattcaa tatttgcatt taaaaatact ttttaaggcc atttttatatt aagccagtgc      1920
tggaaaactg aatttttttt attatgtata ataatctcga cacccagctt ctggaattgc      1980
tgctttcttt ttacagaaat tactacccaa cagatttcag gaagtactag tagttatccc      2040
aaaagtggaa taagcatgta ttcctaagtg tttcagaaat gttttatttc acacataagt      2100
cttaatgtta ttgttatgat tatactttat aaacaacctt ttccagatgc tacagggttt      2160
tgaatctcaa agttaacatt tttcattatt tgtaatctta gaaccaaatc tttatttatt      2220
gtggtcactg ttattaaatg atttaggaaa tactttcaat attattctga atggctgaag      2280
ttagtcttaa actcaaatta ctatatgatg atttaaaaca aataaaagaa gcgaggatgg      2340
ggaaaaaaaa aaaaaaaaa aaaa                                              2364
```

<210> SEQ ID NO 2570
<211> LENGTH: 429
<212> TYPE: PRT
<213> ORGANISM: homo sapien

<400> SEQUENCE: 2570

```
Met Ala Gly Ser Gly Ala Trp Lys Arg Leu Lys Ser Met Leu Arg Lys
 1               5                  10                  15

Asp Asp Ala Pro Leu Phe Leu Asn Asp Thr Ser Ala Phe Asp Phe Ser
                20                  25                  30

Asp Glu Ala Gly Asp Glu Gly Leu Ser Arg Phe Asn Lys Leu Arg Val
            35                  40                  45

Val Val Ala Asp Asp Gly Ser Glu Ala Pro Glu Arg Pro Val Asn Gly
        50                  55                  60
```

```
Ala His Pro Thr Leu Gln Ala Asp Asp Ser Leu Leu Asp Gln Asp
 65                  70                  75                  80

Leu Pro Leu Thr Asn Ser Gln Leu Ser Leu Lys Val Asp Ser Cys Asp
                 85                  90                  95

Asn Cys Ser Lys Gln Arg Glu Ile Leu Lys Gln Arg Lys Val Lys Ala
            100                 105                 110

Arg Leu Thr Ile Ala Ala Val Leu Tyr Leu Phe Met Ile Gly Glu
        115                 120                 125

Leu Val Gly Gly Tyr Ile Ala Asn Ser Leu Ala Ile Met Thr Asp Ala
    130                 135                 140

Leu His Met Leu Thr Asp Leu Ser Ala Ile Ile Leu Thr Leu Leu Ala
145                 150                 155                 160

Leu Trp Leu Ser Ser Lys Ser Pro Thr Lys Arg Phe Thr Phe Gly Phe
                165                 170                 175

His Arg Leu Glu Val Leu Ser Ala Met Ile Ser Val Leu Leu Val Tyr
            180                 185                 190

Ile Leu Met Gly Phe Leu Leu Tyr Glu Ala Val Gln Arg Thr Ile His
        195                 200                 205

Met Asn Tyr Glu Ile Asn Gly Asp Ile Met Leu Ile Thr Ala Ala Val
    210                 215                 220

Gly Val Ala Val Asn Val Ile Met Gly Phe Leu Leu Asn Gln Ser Gly
225                 230                 235                 240

His Arg His Ser His Ser His Ser Leu Pro Ser Asn Ser Pro Thr Arg
                245                 250                 255

Gly Ser Gly Cys Glu Arg Asn His Gly Gln Asp Ser Leu Ala Val Arg
            260                 265                 270

Ala Ala Phe Val His Ala Leu Gly Asp Leu Val Gln Ser Val Gly Val
        275                 280                 285

Leu Ile Ala Ala Tyr Ile Ile Arg Phe Lys Pro Glu Tyr Lys Ile Ala
    290                 295                 300

Asp Pro Ile Cys Thr Tyr Val Phe Ser Leu Leu Val Ala Phe Thr Thr
305                 310                 315                 320

Phe Arg Ile Ile Trp Asp Thr Val Val Ile Ile Leu Glu Gly Val Pro
                325                 330                 335

Ser His Leu Asn Val Asp Tyr Ile Lys Glu Ala Leu Met Lys Ile Glu
            340                 345                 350

Asp Val Tyr Ser Val Glu Asp Leu Asn Ile Trp Ser Leu Thr Ser Gly
        355                 360                 365

Lys Ser Thr Ala Ile Val His Ile Gln Leu Ile Pro Gly Ser Ser Ser
    370                 375                 380

Lys Trp Glu Glu Val Gln Ser Lys Ala Asn His Leu Leu Leu Asn Thr
385                 390                 395                 400

Phe Gly Met Tyr Arg Cys Thr Ile Gln Leu Gln Ser Tyr Arg Gln Glu
                405                 410                 415

Val Asp Arg Thr Cys Ala Asn Cys Gln Ser Ser Pro
            420                 425

<210> SEQ ID NO 2571
<211> LENGTH: 1548
<212> TYPE: DNA
<213> ORGANISM: homo sapien

<400> SEQUENCE: 2571
atggccggct ctggcgcgtg gaagcgcctc aaatctatgc taaggaagga tgatgcgccg    60
```

-continued

```
ctgtttttaa atgacaccag cgcctttgac ttctcggatg aggcggggga cgagggcgtt    120
tctcggttca acaaacttcg agttgtggtg gccgatgacg gttccgaagc cccggaaagg    180
cctgttaacg gggcgcaccc gaccctccag gccgacgatg attccttact ggaccaagac    240
ttacctttga ccaacagtca gctgagtttg aaggtggact cctgtgacaa ctgcagcaaa    300
cagagagaga tactgaagca gagaaaggtg aaagccaggt tgaccattgc tgccgttctg    360
tacttgcttt tcatgattgg agaacttgta ggtggataca ttgcaaatag cctagcaatc    420
atgacagatg cacttcatat gttaactgac ctaagcgcca tcatactcac cctgcttgct    480
ttgtggctat catcaaaatc accaaccaaa agattcacct tggatttca tcgcttagag    540
gttttgtcag ctatgattag tgtgctgttg gtgtatatac ttatgggatt cctcttatat    600
gaagctgtgc aaagaactat ccatatgaac tatgaaataa atggagatat aatgctcatc    660
accgcagctg ttggagttgc agttaatgta ataatggggt ttctgttgaa ccagtctggt    720
caccgtcact cccattccca ctccctgcct tcaaattccc ctaccagagg ttctgggtgt    780
gaacgtaacc atgggcagga tagcctggca gtgagagctg catttgtaca tgctttggga    840
gatttggtac agagtgttgg tgtgctaata gctgcataca tcatacgatt caagccagaa    900
tacaagattg ctgatcccat ctgtacatac gtattttcat tacttgtggc ttttacaaca    960
tttcgaatca tatgggatac agtagttata atactagaag gtgtgccaag ccatttgaat   1020
gtagactata tcaaagaagc cttgatgaaa atagaagatg tatattcagt cgaagattta   1080
aatatctggt ctctcacttc aggaaaatct actgccatag ttcacataca gctaattcct   1140
ggaagttcat ctaaatggga ggaagtacag tccaaagcaa accatttatt attgaacaca   1200
tttggcatgt atagatgtac tattcagctt cagagttaca ggcaagaagt ggacagaact   1260
tgtgcaaatt gtcagagttc tagtccctaa ttttatgtat tttggggact cctgccttat   1320
ttatcctgca gtcacagact tgagagcaat aaatgcaaac ctaaatgaga aaatggaatc   1380
cctgacagct gtgtccgtat caagcatcag tctctcaaac agttgcccca gcctgacagt   1440
gctagtctct gtttaatggt aaaaggagac tttgccataa ttttcagatg aagatgtttc   1500
ccaaacactg tttacagaat gagatgtgac tctacagata cctcatag              1548
```

<210> SEQ ID NO 2572
<211> LENGTH: 429
<212> TYPE: PRT
<213> ORGANISM: homo sapien

<400> SEQUENCE: 2572

```
Met Ala Gly Ser Gly Ala Trp Lys Arg Leu Lys Ser Met Leu Arg Lys
  1               5                  10                  15

Asp Asp Ala Pro Leu Phe Leu Asn Asp Thr Ser Ala Phe Asp Phe Ser
             20                  25                  30

Asp Glu Ala Gly Asp Glu Gly Leu Ser Arg Phe Asn Lys Leu Arg Val
         35                  40                  45

Val Val Ala Asp Asp Gly Ser Glu Ala Pro Glu Arg Pro Val Asn Gly
     50                  55                  60

Ala His Pro Thr Leu Gln Ala Asp Asp Ser Leu Leu Asp Gln Asp
 65                  70                  75                  80

Leu Pro Leu Thr Asn Ser Gln Leu Ser Leu Lys Val Asp Ser Cys Asp
                 85                  90                  95

Asn Cys Ser Lys Gln Arg Glu Ile Leu Lys Gln Arg Lys Val Lys Ala
            100                 105                 110
```

```
Arg Leu Thr Ile Ala Ala Val Leu Tyr Leu Leu Phe Met Ile Gly Glu
        115                 120                 125

Leu Val Gly Gly Tyr Ile Ala Asn Ser Leu Ala Ile Met Thr Asp Ala
130                 135                 140

Leu His Met Leu Thr Asp Leu Ser Ala Ile Ile Leu Thr Leu Leu Ala
145                 150                 155                 160

Leu Trp Leu Ser Ser Lys Ser Pro Thr Lys Arg Phe Thr Phe Gly Phe
                165                 170                 175

His Arg Leu Glu Val Leu Ser Ala Met Ile Ser Val Leu Leu Val Tyr
            180                 185                 190

Ile Leu Met Gly Phe Leu Leu Tyr Glu Ala Val Gln Arg Thr Ile His
        195                 200                 205

Met Asn Tyr Glu Ile Asn Gly Asp Ile Met Leu Ile Thr Ala Ala Val
210                 215                 220

Gly Val Ala Val Asn Val Ile Met Gly Phe Leu Leu Asn Gln Ser Gly
225                 230                 235                 240

His Arg His Ser His Ser His Ser Leu Pro Ser Asn Ser Pro Thr Arg
                245                 250                 255

Gly Ser Gly Cys Glu Arg Asn His Gly Gln Asp Ser Leu Ala Val Arg
            260                 265                 270

Ala Ala Phe Val His Ala Leu Gly Asp Leu Val Gln Ser Val Gly Val
        275                 280                 285

Leu Ile Ala Ala Tyr Ile Ile Arg Phe Lys Pro Glu Tyr Lys Ile Ala
    290                 295                 300

Asp Pro Ile Cys Thr Tyr Val Phe Ser Leu Leu Val Ala Phe Thr Thr
305                 310                 315                 320

Phe Arg Ile Ile Trp Asp Thr Val Val Ile Leu Glu Gly Val Pro
                325                 330                 335

Ser His Leu Asn Val Asp Tyr Ile Lys Glu Ala Leu Met Lys Ile Glu
            340                 345                 350

Asp Val Tyr Ser Val Glu Asp Leu Asn Ile Trp Ser Leu Thr Ser Gly
        355                 360                 365

Lys Ser Thr Ala Ile Val His Ile Gln Leu Ile Pro Gly Ser Ser Ser
370                 375                 380

Lys Trp Glu Glu Val Gln Ser Lys Ala Asn His Leu Leu Leu Asn Thr
385                 390                 395                 400

Phe Gly Met Tyr Arg Cys Thr Ile Gln Leu Gln Ser Tyr Arg Gln Glu
                405                 410                 415

Val Asp Arg Thr Cys Ala Asn Cys Gln Ser Ser Pro
            420                 425

<210> SEQ ID NO 2573
<211> LENGTH: 1557
<212> TYPE: DNA
<213> ORGANISM: homo sapien

<400> SEQUENCE: 2573
atggccggct ctggcgcgtg gaagcgcctc aaatctatgc taaggaagga tgatgcgccg      60 ctgttttaa atgacaccag cgcctttgag ttctcggatg aggcggggga cgagggctt      120 tctcggttca acaaacttcg agttgtggtg gccgatgacg ttccgaagc ccgaaagg      180 cctgttaacg gggcgcaccc gaccctccag gccgacgatg attccttact ggaccaagac    240
ttacctttga ccaacagtca gctgagtttg aaggtggact cctgtgacaa ctgcagcaaa    300
cagagagaga tactgaagca gagaaaggtg aaagccaggt tgaccattgc tgccgttctg    360
```

```
tacttgcttt tcatgattgg agaacttgta ggtggataca ttgcaaatag cctagcaatc    420
atgacagatg cacttcatat gttaactgac ctaagcgcca tcatactcac cctgcttgct    480
ttgtggctat catcaaaatc accaaccaaa agattcacct tggatttca tcgcttagag    540 gttttgtcag ctatgattag tgtgctgttg gtgtatatac ttatgggatt cctcttatat    600
gaagctgtgc aaagaactat ccatatgaac tatgaaataa atggagatat aatgctcatc    660
accgcagctg ttggagttgc agttaatgta ataatggggt ttctgttgaa ccagtctggt    720
caccgtcact cccattccca ctccctgcct tcaaattccc ctaccagagg ttctgggtgt    780
gaacgtaacc atgggcagga tagcctggca gtgagagctg catttgtaca tgctttggga    840
gatctggtac agagtgttgg tgtgctaata gctgcataca tcatacgatt caagccagaa    900
tacaagattg ctgaccccat ctgtacatac gtattttcat tacttgtggc ttttacaaca    960
tttcgaatca tatgggatac agtagttata atactagaag gtgtgccaag ccatttgaat   1020
gtagactata tcaaagaagc cttgatgaaa atagaagatg tatattcagt cgaagattta   1080
aatatctggt ctctcacttc aggaaaatct actgccatag ttcacataca gctaattcct   1140
ggaagttcat ctaaatggga ggaagtacag tccaaagcaa accatttatt attgaacaca   1200
tttggcatgt atagatgtac tattcagctt cagagttaca ggcaagaagt ggacagaact   1260
tgtgcaaatt gtcagagttc tagtccctaa ttttatgtat tgttttagca ttgctgaatt   1320
cactttattt atcctgcagt cacagacttg agacaataa atgcaaacct aaatgagaaa   1380
atggaatccc tgacagctgt gtccgtatca agcatcagtc tctcaaacag ttgccccagc   1440
ctgacagtgc tagtctctgt ttaatggtaa aaggagactt tgccataatt ttcagatgaa   1500
gatgtttccc aaacactgtt tacagaatga gatgtgactc tacagatac ctcatag       1557
```

<210> SEQ ID NO 2574
<211> LENGTH: 429
<212> TYPE: PRT
<213> ORGANISM: homo sapien

<400> SEQUENCE: 2574

```
Met Ala Gly Ser Gly Ala Trp Lys Arg Leu Lys Ser Met Leu Arg Lys
 1               5                  10                  15

Asp Asp Ala Pro Leu Phe Leu Asn Asp Thr Ser Ala Phe Glu Phe Ser
            20                  25                  30

Asp Glu Ala Gly Asp Glu Gly Leu Ser Arg Phe Asn Lys Leu Arg Val
        35                  40                  45

Val Val Ala Asp Asp Gly Ser Glu Ala Pro Glu Arg Pro Val Asn Gly
    50                  55                  60

Ala His Pro Thr Leu Gln Ala Asp Asp Ser Leu Leu Asp Gln Asp
65                  70                  75                  80

Leu Pro Leu Thr Asn Ser Gln Leu Ser Leu Lys Val Asp Ser Cys Asp
                85                  90                  95

Asn Cys Ser Lys Gln Arg Glu Ile Leu Lys Gln Arg Lys Val Lys Ala
            100                 105                 110

Arg Leu Thr Ile Ala Ala Val Leu Tyr Leu Leu Phe Met Ile Gly Glu
        115                 120                 125

Leu Val Gly Gly Tyr Ile Ala Asn Ser Leu Ala Ile Met Thr Asp Ala
    130                 135                 140

Leu His Met Leu Thr Asp Leu Ser Ala Ile Ile Leu Thr Leu Leu Ala
145                 150                 155                 160
```

-continued

Leu Trp Leu Ser Ser Lys Ser Pro Thr Lys Arg Phe Thr Phe Gly Phe
                165                 170                 175

His Arg Leu Glu Val Leu Ser Ala Met Ile Ser Val Leu Leu Val Tyr
            180                 185                 190

Ile Leu Met Gly Phe Leu Leu Tyr Glu Ala Val Gln Arg Thr Ile His
        195                 200                 205

Met Asn Tyr Glu Ile Asn Gly Asp Ile Met Leu Ile Thr Ala Ala Val
    210                 215                 220

Gly Val Ala Val Asn Val Ile Met Gly Phe Leu Leu Asn Gln Ser Gly
225                 230                 235                 240

His Arg His Ser His Ser His Ser Leu Pro Ser Asn Ser Pro Thr Arg
                245                 250                 255

Gly Ser Gly Cys Glu Arg Asn His Gly Gln Asp Ser Leu Ala Val Arg
            260                 265                 270

Ala Ala Phe Val His Ala Leu Gly Asp Leu Val Gln Ser Val Gly Val
        275                 280                 285

Leu Ile Ala Ala Tyr Ile Ile Arg Phe Lys Pro Glu Tyr Lys Ile Ala
    290                 295                 300

Asp Pro Ile Cys Thr Tyr Val Phe Ser Leu Leu Val Ala Phe Thr Thr
305                 310                 315                 320

Phe Arg Ile Ile Trp Asp Thr Val Val Ile Ile Leu Glu Gly Val Pro
                325                 330                 335

Ser His Leu Asn Val Asp Tyr Ile Lys Glu Ala Leu Met Lys Ile Glu
            340                 345                 350

Asp Val Tyr Ser Val Glu Asp Leu Asn Ile Trp Ser Leu Thr Ser Gly
        355                 360                 365

Lys Ser Thr Ala Ile Val His Ile Gln Leu Ile Pro Gly Ser Ser Ser
    370                 375                 380

Lys Trp Glu Glu Val Gln Ser Lys Ala Asn His Leu Leu Asn Thr
385                 390                 395                 400

Phe Gly Met Tyr Arg Cys Thr Ile Gln Leu Gln Ser Tyr Arg Gln Glu
                405                 410                 415

Val Asp Arg Thr Cys Ala Asn Cys Gln Ser Ser Pro
            420                 425

<210> SEQ ID NO 2575
<211> LENGTH: 429
<212> TYPE: PRT
<213> ORGANISM: homo sapien

<400> SEQUENCE: 2575

Met Ala Gly Ser Gly Ala Trp Lys Arg Leu Lys Ser Met Leu Arg Lys
1               5                   10                  15

Asp Asp Ala Pro Leu Phe Leu Asn Asp Thr Ser Ala Phe Asp Phe Ser
            20                  25                  30

Asp Glu Ala Gly Asp Glu Gly Leu Ser Arg Phe Asn Lys Leu Arg Val
        35                  40                  45

Val Val Ala Asp Asp Gly Ser Glu Ala Pro Glu Arg Pro Val Asn Gly
    50                  55                  60

Ala His Pro Thr Leu Gln Ala Asp Asp Ser Leu Leu Asp Gln Asp
65                  70                  75                  80

Leu Pro Leu Thr Asn Ser Gln Leu Ser Leu Lys Val Asp Ser Cys Asp
                85                  90                  95

Asn Cys Ser Lys Gln Arg Glu Ile Leu Lys Gln Arg Lys Val Lys Ala
            100                 105                 110

-continued

```
Arg Leu Thr Ile Ala Ala Val Leu Tyr Leu Leu Phe Met Ile Gly Glu
            115                 120                 125

Leu Val Gly Gly Tyr Ile Ala Asn Ser Leu Ala Ile Met Thr Asp Ala
        130                 135                 140

Leu His Met Leu Thr Asp Leu Ser Ala Ile Ile Leu Thr Leu Leu Ala
145                 150                 155                 160

Leu Trp Leu Ser Ser Lys Ser Pro Thr Lys Arg Phe Thr Phe Gly Phe
                165                 170                 175

His Arg Leu Glu Val Leu Ser Ala Met Ile Ser Val Leu Leu Val Tyr
            180                 185                 190

Ile Leu Met Gly Phe Leu Leu Tyr Glu Ala Val Gln Arg Thr Ile His
        195                 200                 205

Met Asn Tyr Glu Ile Asn Gly Asp Ile Met Leu Ile Thr Ala Ala Val
    210                 215                 220

Gly Val Ala Val Asn Val Ile Met Gly Phe Leu Leu Asn Gln Ser Gly
225                 230                 235                 240

His Arg His Ser His Ser His Ser Leu Pro Ser Asn Ser Pro Thr Arg
                245                 250                 255

Gly Ser Gly Cys Glu Arg Asn His Gly Gln Asp Ser Leu Ala Val Arg
            260                 265                 270

Ala Ala Phe Val His Ala Leu Gly Asp Leu Val Gln Ser Val Gly Val
        275                 280                 285

Leu Ile Ala Ala Tyr Ile Ile Arg Phe Lys Pro Glu Tyr Lys Ile Ala
    290                 295                 300

Asp Pro Ile Cys Thr Tyr Val Phe Ser Leu Leu Val Ala Phe Thr Thr
305                 310                 315                 320

Phe Arg Ile Ile Trp Asp Thr Val Val Ile Leu Glu Gly Val Pro
                325                 330                 335

Ser His Leu Asn Val Asp Tyr Ile Lys Glu Ala Leu Met Lys Ile Glu
            340                 345                 350

Asp Val Tyr Ser Val Glu Asp Leu Asn Ile Trp Ser Leu Thr Ser Gly
        355                 360                 365

Lys Ser Thr Ala Ile Val His Ile Gln Leu Ile Pro Gly Ser Ser Ser
    370                 375                 380

Lys Trp Glu Glu Val Gln Ser Lys Ala Asn His Leu Leu Leu Asn Thr
385                 390                 395                 400

Phe Gly Met Tyr Arg Cys Thr Ile Gln Leu Gln Ser Tyr Arg Gln Glu
                405                 410                 415

Val Asp Arg Thr Cys Ala Asn Cys Gln Ser Ser Pro
            420                 425

<210> SEQ ID NO 2576
<211> LENGTH: 429
<212> TYPE: PRT
<213> ORGANISM: homo sapien

<400> SEQUENCE: 2576

Met Ala Gly Ser Gly Ala Trp Lys Arg Leu Lys Ser Met Leu Arg Lys
  1               5                  10                  15

Asp Asp Ala Pro Leu Phe Leu Asn Asp Thr Ser Ala Phe Asp Phe Ser
            20                  25                  30

Asp Glu Ala Gly Asp Glu Gly Leu Ser Arg Phe Asn Lys Leu Arg Val
        35                  40                  45

Val Val Ala Asp Asp Gly Ser Glu Ala Pro Glu Arg Pro Val Asn Gly
```

-continued

```
                50                  55                  60
Ala His Pro Thr Leu Gln Ala Asp Asp Asp Ser Leu Leu Asp Gln Asp
 65                  70                  75                  80

Leu Pro Leu Thr Asn Ser Gln Leu Ser Leu Lys Val Asp Ser Cys Asp
                 85                  90                  95

Asn Cys Ser Lys Gln Arg Glu Ile Leu Lys Gln Arg Lys Val Lys Ala
                100                 105                 110

Arg Leu Thr Ile Ala Ala Val Leu Tyr Leu Phe Met Ile Gly Glu
                115                 120                 125

Leu Val Gly Gly Tyr Ile Ala Asn Ser Leu Ala Ile Met Thr Asp Ala
130                 135                 140

Leu His Met Leu Thr Asp Leu Ser Ala Ile Ile Leu Thr Leu Leu Ala
145                 150                 155                 160

Leu Trp Leu Ser Ser Lys Ser Pro Thr Lys Arg Phe Thr Phe Gly Phe
                165                 170                 175

His Arg Leu Glu Val Leu Ser Ala Met Ile Ser Val Leu Val Tyr
                180                 185                 190

Ile Leu Met Gly Phe Leu Leu Tyr Glu Ala Val Gln Arg Thr Ile His
                195                 200                 205

Met Asn Tyr Glu Ile Asn Gly Asp Ile Met Leu Ile Thr Ala Ala Val
210                 215                 220

Gly Val Ala Val Asn Val Ile Met Gly Phe Leu Leu Asn Gln Ser Gly
225                 230                 235                 240

His Arg His Ser His Ser His Ser Leu Pro Ser Asn Ser Pro Thr Arg
                245                 250                 255

Gly Ser Gly Cys Glu Arg Asn His Gly Gln Asp Ser Leu Ala Val Arg
                260                 265                 270

Ala Ala Phe Val His Ala Leu Gly Asp Leu Val Gln Ser Val Gly Val
                275                 280                 285

Leu Ile Ala Ala Tyr Ile Ile Arg Phe Lys Pro Glu Tyr Lys Ile Ala
290                 295                 300

Asp Pro Ile Cys Thr Tyr Val Phe Ser Leu Leu Val Ala Phe Thr Thr
305                 310                 315                 320

Phe Arg Ile Ile Trp Asp Thr Val Val Ile Ile Leu Glu Gly Val Pro
                325                 330                 335

Ser His Leu Asn Val Asp Tyr Ile Lys Glu Ala Leu Met Lys Ile Glu
                340                 345                 350

Asp Val Tyr Ser Val Glu Asp Leu Asn Ile Trp Ser Leu Thr Ser Gly
                355                 360                 365

Lys Ser Thr Ala Ile Val His Ile Gln Leu Ile Pro Gly Ser Ser Ser
                370                 375                 380

Lys Trp Glu Glu Val Gln Ser Lys Ala Asn His Leu Leu Asn Thr
385                 390                 395                 400

Phe Gly Met Tyr Arg Cys Thr Ile Gln Leu Gln Ser Tyr Arg Gln Glu
                405                 410                 415

Val Asp Arg Thr Cys Ala Asn Cys Gln Ser Ser Ser Pro
                420                 425
```

<210> SEQ ID NO 2577
<211> LENGTH: 429
<212> TYPE: PRT
<213> ORGANISM: homo sapien

<400> SEQUENCE: 2577

-continued

```
Met Ala Gly Ser Gly Ala Trp Lys Arg Leu Lys Ser Met Leu Arg Lys
 1               5                  10                  15

Asp Asp Ala Pro Leu Phe Leu Asn Asp Thr Ser Ala Phe Asp Phe Ser
            20                  25                  30

Asp Glu Ala Gly Asp Glu Gly Leu Ser Arg Phe Asn Lys Leu Arg Val
        35                  40                  45

Val Val Ala Asp Asp Gly Ser Glu Ala Pro Glu Arg Pro Val Asn Gly
    50                  55                  60

Ala His Pro Thr Leu Gln Ala Asp Asp Ser Leu Leu Asp Gln Asp
65              70                  75                  80

Leu Pro Leu Thr Asn Ser Gln Leu Ser Leu Lys Val Asp Ser Cys Asp
                85                  90                  95

Asn Cys Ser Lys Gln Arg Glu Ile Leu Lys Gln Arg Lys Val Lys Ala
            100                 105                 110

Arg Leu Thr Ile Ala Ala Val Leu Tyr Leu Leu Phe Met Ile Gly Glu
        115                 120                 125

Leu Val Gly Gly Tyr Ile Ala Asn Ser Leu Ala Ile Met Thr Asp Ala
    130                 135                 140

Leu His Met Leu Thr Asp Leu Ser Ala Ile Ile Leu Thr Leu Leu Ala
145                 150                 155                 160

Leu Trp Leu Ser Ser Lys Ser Pro Thr Lys Arg Phe Thr Phe Gly Phe
                165                 170                 175

His Arg Leu Glu Val Leu Ser Ala Met Ile Ser Val Leu Leu Val Tyr
            180                 185                 190

Ile Leu Met Gly Phe Leu Leu Tyr Glu Ala Val Gln Arg Thr Ile His
        195                 200                 205

Met Asn Tyr Glu Ile Asn Gly Asp Ile Met Leu Ile Thr Ala Ala Val
    210                 215                 220

Gly Val Ala Val Asn Val Ile Met Gly Phe Leu Leu Asn Gln Ser Gly
225                 230                 235                 240

His Arg His Ser His Ser His Ser Leu Pro Ser Asn Ser Pro Thr Arg
                245                 250                 255

Gly Ser Gly Cys Glu Arg Asn His Gly Gln Asp Ser Leu Ala Val Arg
            260                 265                 270

Ala Ala Phe Val His Ala Leu Gly Asp Leu Val Gln Ser Val Gly Val
        275                 280                 285

Leu Ile Ala Ala Tyr Ile Ile Arg Phe Lys Pro Glu Tyr Lys Ile Ala
    290                 295                 300

Asp Pro Ile Cys Thr Tyr Val Phe Ser Leu Leu Val Ala Phe Thr Thr
305                 310                 315                 320

Phe Arg Ile Ile Trp Asp Thr Val Val Ile Leu Glu Gly Val Pro
                325                 330                 335

Ser His Leu Asn Val Asp Tyr Ile Lys Glu Ala Leu Met Lys Ile Glu
            340                 345                 350

Asp Val Tyr Ser Val Glu Asp Leu Asn Ile Trp Ser Leu Thr Ser Gly
        355                 360                 365

Lys Ser Thr Ala Ile Val His Ile Gln Leu Ile Pro Gly Ser Ser Ser
    370                 375                 380

Lys Trp Glu Glu Val Gln Ser Lys Ala Asn His Leu Leu Leu Asn Thr
385                 390                 395                 400

Phe Gly Met Tyr Arg Cys Thr Ile Gln Leu Gln Ser Tyr Arg Gln Glu
                405                 410                 415

Val Asp Arg Thr Cys Ala Asn Cys Gln Ser Ser Ser Pro
```

-continued

```
              420             425
```

<210> SEQ ID NO 2578
<211> LENGTH: 429
<212> TYPE: PRT
<213> ORGANISM: homo sapien

<400> SEQUENCE: 2578

```
Met Ala Gly Ser Gly Ala Trp Lys Arg Leu Lys Ser Met Leu Arg Lys
  1               5                  10                  15

Asp Asp Ala Pro Leu Phe Leu Asn Asp Thr Ser Ala Phe Asp Phe Ser
             20                  25                  30

Asp Glu Ala Gly Asp Glu Gly Leu Ser Arg Phe Asn Lys Leu Arg Val
         35                  40                  45

Val Val Ala Asp Asp Gly Ser Glu Ala Pro Glu Arg Pro Val Asn Gly
     50                  55                  60

Ala His Pro Thr Leu Gln Ala Asp Asp Ser Leu Leu Asp Gln Asp
 65                  70                  75                  80

Leu Pro Leu Thr Asn Ser Gln Leu Ser Leu Lys Val Asp Ser Cys Asp
                 85                  90                  95

Asn Cys Ser Lys Gln Arg Glu Ile Leu Lys Gln Arg Lys Val Lys Ala
            100                 105                 110

Arg Leu Thr Ile Ala Ala Val Leu Tyr Leu Leu Phe Met Ile Gly Glu
        115                 120                 125

Leu Val Gly Gly Tyr Ile Ala Asn Ser Leu Ala Ile Met Thr Asp Ala
    130                 135                 140

Leu His Met Leu Thr Asp Leu Ser Ala Ile Ile Leu Thr Leu Leu Ala
145                 150                 155                 160

Leu Trp Leu Ser Ser Lys Ser Pro Thr Lys Arg Phe Thr Phe Gly Phe
                165                 170                 175

His Arg Leu Glu Val Leu Ser Ala Met Ile Ser Val Leu Leu Val Tyr
            180                 185                 190

Ile Leu Met Gly Phe Leu Leu Tyr Glu Ala Val Gln Arg Thr Ile His
        195                 200                 205

Met Asn Tyr Glu Ile Asn Gly Asp Ile Met Leu Ile Thr Ala Ala Val
    210                 215                 220

Gly Val Ala Val Asn Val Ile Met Gly Phe Leu Leu Asn Gln Ser Gly
225                 230                 235                 240

His Arg His Ser His Ser His Ser Leu Pro Ser Asn Ser Pro Thr Arg
                245                 250                 255

Gly Ser Gly Cys Glu Arg Asn His Gly Gln Asp Ser Leu Ala Val Arg
            260                 265                 270

Ala Ala Phe Val His Ala Leu Gly Asp Leu Val Gln Ser Val Gly Val
        275                 280                 285

Leu Ile Ala Ala Tyr Ile Ile Arg Phe Lys Pro Glu Tyr Lys Ile Ala
    290                 295                 300

Asp Pro Ile Cys Thr Tyr Val Phe Ser Leu Leu Val Ala Phe Thr Thr
305                 310                 315                 320

Phe Arg Ile Ile Trp Asp Thr Val Val Ile Leu Glu Gly Val Pro
                325                 330                 335

Ser His Leu Asn Val Asp Tyr Ile Lys Glu Ala Leu Met Lys Ile Glu
            340                 345                 350

Asp Val Tyr Ser Val Glu Asp Leu Asn Ile Trp Ser Leu Thr Ser Gly
        355                 360                 365
```

-continued

```
Lys Ser Thr Ala Ile Val His Ile Gln Leu Ile Pro Gly Ser Ser Ser
    370                 375                 380

Lys Trp Glu Glu Val Gln Ser Lys Ala Asn His Leu Leu Asn Thr
385                 390                 395                 400

Phe Gly Met Tyr Arg Cys Thr Ile Gln Leu Gln Ser Tyr Arg Gln Glu
                405                 410                 415

Val Asp Arg Thr Cys Ala Asn Cys Gln Ser Ser Ser Pro
            420                 425

<210> SEQ ID NO 2579
<211> LENGTH: 429
<212> TYPE: PRT
<213> ORGANISM: homo sapien

<400> SEQUENCE: 2579

Met Ala Gly Ser Gly Ala Trp Lys Arg Leu Lys Ser Met Leu Arg Lys
 1               5                  10                  15

Asp Asp Ala Pro Leu Phe Leu Asn Asp Thr Ser Ala Phe Glu Phe Ser
                20                  25                  30

Asp Glu Ala Gly Asp Glu Gly Leu Ser Arg Phe Asn Lys Leu Arg Val
            35                  40                  45

Val Val Ala Asp Asp Gly Ser Glu Ala Pro Glu Arg Pro Val Asn Gly
 50                  55                  60

Ala His Pro Thr Leu Gln Ala Asp Asp Ser Leu Leu Asp Gln Asp
 65                  70                  75                  80

Leu Pro Leu Thr Asn Ser Gln Leu Ser Leu Lys Val Asp Ser Cys Asp
                85                  90                  95

Asn Cys Ser Lys Gln Arg Glu Ile Leu Lys Gln Arg Lys Val Lys Ala
                100                 105                 110

Arg Leu Thr Ile Ala Ala Val Leu Tyr Leu Leu Phe Met Ile Gly Glu
            115                 120                 125

Leu Val Gly Gly Tyr Ile Ala Asn Ser Leu Ala Ile Met Thr Asp Ala
130                 135                 140

Leu His Met Leu Thr Asp Leu Ser Ala Ile Ile Leu Thr Leu Leu Ala
145                 150                 155                 160

Leu Trp Leu Ser Ser Lys Ser Pro Thr Lys Arg Phe Thr Phe Gly Phe
                165                 170                 175

His Arg Leu Glu Val Leu Ser Ala Met Ile Ser Val Leu Leu Val Tyr
            180                 185                 190

Ile Leu Met Gly Phe Leu Leu Tyr Glu Ala Val Gln Arg Thr Ile His
            195                 200                 205

Met Asn Tyr Glu Ile Asn Gly Asp Ile Met Leu Ile Thr Ala Ala Val
            210                 215                 220

Gly Val Ala Val Asn Val Ile Met Gly Phe Leu Leu Asn Gln Ser Gly
225                 230                 235                 240

His Arg His Ser His Ser His Ser Leu Pro Ser Asn Ser Pro Thr Arg
                245                 250                 255

Gly Ser Gly Cys Glu Arg Asn His Gly Gln Asp Ser Leu Ala Val Arg
            260                 265                 270

Ala Ala Phe Val His Ala Leu Gly Asp Leu Val Gln Ser Val Gly Val
            275                 280                 285

Leu Ile Ala Ala Tyr Ile Ile Arg Phe Lys Pro Glu Tyr Lys Ile Ala
            290                 295                 300

Asp Pro Ile Cys Thr Tyr Val Phe Ser Leu Leu Val Ala Phe Thr Thr
305                 310                 315                 320
```

```
Phe Arg Ile Ile Trp Asp Thr Val Ile Ile Leu Glu Gly Val Pro
                325                 330                 335

Ser His Leu Asn Val Asp Tyr Ile Lys Glu Ala Leu Met Lys Ile Glu
                340                 345                 350

Asp Val Tyr Ser Val Glu Asp Leu Asn Ile Trp Ser Leu Thr Ser Gly
                355                 360                 365

Lys Ser Thr Ala Ile Val His Ile Gln Leu Ile Pro Gly Ser Ser Ser
            370                 375                 380

Lys Trp Glu Glu Val Gln Ser Lys Ala Asn His Leu Leu Leu Asn Thr
385                 390                 395                 400

Phe Gly Met Tyr Arg Cys Thr Ile Gln Leu Gln Ser Tyr Arg Gln Glu
                405                 410                 415

Val Asp Arg Thr Cys Ala Asn Cys Gln Ser Ser Ser Pro
                420                 425

<210> SEQ ID NO 2580
<211> LENGTH: 428
<212> TYPE: PRT
<213> ORGANISM: homo sapien

<400> SEQUENCE: 2580

Met Ala Gly Ser Gly Ala Trp Lys Arg Leu Lys Ser Met Leu Arg Lys
1                   5                   10                  15

Asp Asp Ala Pro Leu Phe Leu Asn Asp Thr Ser Ala Phe Asp Phe Ser
                20                  25                  30

Asp Glu Ala Gly Asp Glu Gly Leu Ser Arg Phe Asn Lys Leu Arg Val
            35                  40                  45

Val Val Ala Asp Asp Gly Ser Glu Ala Pro Glu Arg Pro Val Asn Gly
        50                  55                  60

Ala His Pro Thr Leu Gln Ala Asp Asp Ser Leu Leu Asp Gln Asp
65                  70                  75                  80

Leu Pro Leu Thr Asn Ser Gln Leu Ser Leu Lys Val Asp Ser Cys Asp
                85                  90                  95

Asn Cys Ser Lys Gln Arg Glu Ile Leu Lys Gln Arg Lys Val Lys Ala
                100                 105                 110

Arg Leu Thr Ile Ala Ala Val Leu Tyr Leu Leu Phe Met Ile Gly Glu
            115                 120                 125

Leu Val Gly Gly Tyr Ile Ala Asn Ser Leu Ala Ile Met Thr Asp Ala
        130                 135                 140

Leu His Met Leu Thr Asp Leu Ser Ala Ile Ile Leu Thr Leu Leu Ala
145                 150                 155                 160

Leu Trp Leu Ser Ser Lys Ser Pro Thr Lys Arg Phe Thr Phe Gly Phe
                165                 170                 175

His Arg Leu Glu Val Leu Ser Ala Met Ile Ser Val Leu Leu Val Tyr
                180                 185                 190

Ile Leu Met Gly Phe Leu Leu Tyr Glu Ala Val Gln Arg Thr Ile His
            195                 200                 205

Met Asn Tyr Glu Ile Asn Gly Asp Ile Met Leu Ile Thr Ala Ala Val
        210                 215                 220

Gly Val Ala Val Asn Val Ile Met Gly Phe Leu Leu Asn Gln Ser Gly
225                 230                 235                 240

His Arg His Ser His Ser His Ser Leu Pro Ser Asn Ser Pro Thr Arg
                245                 250                 255

Gly Ser Gly Cys Glu Arg Asn His Gly Gln Asp Ser Leu Ala Val Arg
```

-continued

```
              260                 265                 270
Ala Ala Phe Val His Ala Leu Gly Asp Leu Val Gln Ser Val Gly Val
        275                 280                 285
Leu Ile Ala Ala Tyr Ile Ile Arg Phe Lys Pro Glu Tyr Lys Ile Ala
    290                 295                 300
Asp Pro Ile Cys Thr Tyr Val Phe Ser Leu Leu Val Ala Phe Thr Thr
305                 310                 315                 320
Phe Arg Ile Ile Trp Asp Thr Val Val Ile Leu Glu Gly Val Pro
                325                 330                 335
Ser His Leu Asn Val Asp Tyr Ile Lys Glu Ala Leu Met Lys Ile Glu
            340                 345                 350
Asp Val Tyr Ser Val Glu Asp Leu Asn Ile Trp Ser Leu Thr Ser Gly
        355                 360                 365
Lys Ser Thr Ala Ile Val His Ile Gln Leu Ile Pro Gly Ser Ser Ser
    370                 375                 380
Lys Trp Glu Glu Val Gln Ser Lys Ala Asn His Leu Leu Leu Asn Thr
385                 390                 395                 400
Phe Gly Met Tyr Arg Cys Thr Ile Gln Leu Gln Ser Tyr Arg Gln Glu
                405                 410                 415
Val Asp Arg Thr Cys Ala Asn Cys Gln Ser Ser Ser
            420                 425

<210> SEQ ID NO 2581
<211> LENGTH: 429
<212> TYPE: PRT
<213> ORGANISM: homo sapien

<400> SEQUENCE: 2581

Met Ala Gly Pro Gly Ala Trp Lys Arg Leu Lys Ser Leu Leu Arg Lys
1               5                   10                  15
Asp Asp Ala Pro Leu Phe Leu Asn Asp Thr Ser Ala Phe Asp Phe Leu
            20                  25                  30
Asp Glu Val Ser Asp Glu Gly Leu Ser Arg Phe Asn Lys Leu Arg Val
        35                  40                  45
Val Val Ala Asp Asp Ser Glu Ala Pro Glu Arg Pro Val Asn Gly
    50                  55                  60
Ala His Pro Ala Leu Gln Ala Asp Asp Ser Leu Leu Asp Gln Glu
65                  70                  75                  80
Leu Pro Leu Thr Asn Ser Gln Leu Ser Leu Lys Met Asp Pro Cys Asp
                85                  90                  95
Asn Cys Ser Lys Arg Arg Glu Leu Leu Lys Gln Arg Lys Val Lys Thr
            100                 105                 110
Arg Leu Thr Ile Ala Ala Val Leu Tyr Leu Leu Phe Met Ile Gly Glu
        115                 120                 125
Leu Val Gly Gly Tyr Met Ala Asn Ser Leu Ala Ile Met Thr Asp Ala
    130                 135                 140
Leu His Met Leu Thr Asp Leu Ser Ala Ile Ile Leu Thr Leu Leu Ala
145                 150                 155                 160
Leu Trp Leu Ser Ser Lys Ser Pro Thr Arg Arg Phe Thr Phe Gly Phe
                165                 170                 175
His Arg Leu Glu Val Leu Ser Ala Met Ile Ser Val Met Leu Val Tyr
            180                 185                 190
Val Leu Met Gly Phe Leu Leu Tyr Glu Ala Met Gln Arg Thr Ile His
        195                 200                 205
```

```
Met Asn Tyr Glu Ile Asn Gly Asp Val Met Leu Ile Thr Ala Ala Val
    210                 215                 220

Gly Val Ala Val Asn Val Ile Met Gly Phe Leu Leu Asn Gln Ser Gly
225                 230                 235                 240

His His His Ser His Ala His Ser His Ser Leu Pro Ser Asn Ser Pro
                245                 250                 255

Ser Met Val Ser Ser Gly His Ser His Gly Gln Asp Ser Leu Ala Val
            260                 265                 270

Arg Ala Ala Phe Val His Ala Leu Gly Asp Leu Val Gln Ser Val Gly
            275                 280                 285

Val Leu Ile Ala Ala Tyr Ile Ile Arg Phe Lys Pro Glu Tyr Lys Ile
    290                 295                 300

Ala Asp Pro Ile Cys Thr Tyr Ile Phe Ser Leu Leu Val Ala Phe Thr
305                 310                 315                 320

Thr Leu Arg Ile Ile Trp Asp Thr Val Ile Ile Leu Glu Gly Val
                325                 330                 335

Pro Ser His Leu Asn Val Asp Tyr Ile Lys Glu Ser Leu Met Lys Ile
                340                 345                 350

Glu Asp Val Tyr Ser Val Glu Asp Leu Asn Ile Trp Ser Leu Thr Ser
            355                 360                 365

Gly Lys Ala Thr Ala Ile Val His Met Gln Leu Ile Pro Gly Ser Ser
370                 375                 380

Ser Lys Trp Glu Glu Val Gln Ser Lys Ala Lys His Leu Leu Leu Asn
385                 390                 395                 400

Thr Phe Gly Met Tyr Lys Cys Thr Val Gln Leu Gln Ser Tyr Arg Gln
                405                 410                 415

Glu Ala Thr Arg Thr Cys Ala Asn Cys Gln Ser Ser Ser
            420                 425

<210> SEQ ID NO 2582
<211> LENGTH: 14
<212> TYPE: PRT
<213> ORGANISM: tetanus toxoid

<400> SEQUENCE: 2582

Gln Tyr Ile Lys Ala Asn Ser Lys Phe Ile Gly Ile Thr Glu
1               5                   10

<210> SEQ ID NO 2583
<211> LENGTH: 21
<212> TYPE: PRT
<213> ORGANISM: Plasmodium Falciparum

<400> SEQUENCE: 2583

Asp Ile Glu Lys Lys Ile Ala Lys Met Glu Lys Ala Ser Ser Val Phe
1               5                   10                  15

Asn Val Val Asn Ser
            20

<210> SEQ ID NO 2584
<211> LENGTH: 16
<212> TYPE: PRT
<213> ORGANISM: Streptococcus

<400> SEQUENCE: 2584

Gly Ala Val Asp Ser Ile Leu Gly Gly Val Ala Thr Tyr Gly Ala Ala
1               5                   10                  15
```

```
<210> SEQ ID NO 2585
<211> LENGTH: 11
<212> TYPE: PRT
<213> ORGANISM: homo sapien
<220> FEATURE:
<221> NAME/KEY: VARIANT
<222> LOCATION: 2
<223> OTHER INFORMATION: Xaa = cyclohexylalanine
<220> FEATURE:
<221> NAME/KEY: VARIANT
<222> LOCATION: 2
<223> OTHER INFORMATION: Xaa = phenylalanine
<220> FEATURE:
<221> NAME/KEY: VARIANT
<222> LOCATION: 2
<223> OTHER INFORMATION: Xaa = tyrosine
<220> FEATURE:
<221> NAME/KEY: VARIANT
<222> LOCATION: 2
<223> OTHER INFORMATION: Xaa = D-alanine
<220> FEATURE:
<221> NAME/KEY: VARIANT
<222> LOCATION: 2
<223> OTHER INFORMATION: Xaa = L-alanine

<400> SEQUENCE: 2585

Lys Xaa Val Ala Ala Trp Thr Leu Lys Ala Ala
 1               5                   10

<210> SEQ ID NO 2586
<211> LENGTH: 14
<212> TYPE: DNA
<213> ORGANISM: homo sapien

<400> SEQUENCE: 2586
ttttgatcaa gctt                                                        14

<210> SEQ ID NO 2587
<211> LENGTH: 42
<212> TYPE: DNA
<213> ORGANISM: homo sapien

<400> SEQUENCE: 2587
ctaatacgac tcactatagg gctcgagcgg ccgcccgggc ag                         42

<210> SEQ ID NO 2588
<211> LENGTH: 12
<212> TYPE: DNA
<213> ORGANISM: homo sapien

<400> SEQUENCE: 2588
gatcctgccc gg                                                          12

<210> SEQ ID NO 2589
<211> LENGTH: 40
<212> TYPE: DNA
<213> ORGANISM: homo sapien

<400> SEQUENCE: 2589
gtaatacgac tcactatagg gcagcgtggt cgcggccgag                            40

<210> SEQ ID NO 2590
<211> LENGTH: 10
<212> TYPE: DNA
<213> ORGANISM: homo sapien

<400> SEQUENCE: 2590
gatcctcggc                                                             10
```

```
<210> SEQ ID NO 2591
<211> LENGTH: 22
<212> TYPE: DNA
<213> ORGANISM: homo sapien

<400> SEQUENCE: 2591
ctaatacgac tcactatagg gc                                              22

<210> SEQ ID NO 2592
<211> LENGTH: 22
<212> TYPE: DNA
<213> ORGANISM: homo sapien

<400> SEQUENCE: 2592
tcgagcggcc gcccgggcag ga                                              22

<210> SEQ ID NO 2593
<211> LENGTH: 20
<212> TYPE: DNA
<213> ORGANISM: homo sapien

<400> SEQUENCE: 2593
agcgtggtcg cggccgagga                                                 20

<210> SEQ ID NO 2594
<211> LENGTH: 25
<212> TYPE: DNA
<213> ORGANISM: homo sapien

<400> SEQUENCE: 2594
atatcgccgc gctcgtcgtc gacaa                                           25

<210> SEQ ID NO 2595
<211> LENGTH: 26
<212> TYPE: DNA
<213> ORGANISM: homo sapien

<400> SEQUENCE: 2595
agccacacgc agctcattgt agaagg                                          26

<210> SEQ ID NO 2596
<211> LENGTH: 24
<212> TYPE: DNA
<213> ORGANISM: homo sapien

<400> SEQUENCE: 2596
tgcacactgg acttcgtaga gtaa                                            24

<210> SEQ ID NO 2597
<211> LENGTH: 24
<212> TYPE: DNA
<213> ORGANISM: homo sapien

<400> SEQUENCE: 2597
aaagctgtga gagtggctga gaaa                                            24

<210> SEQ ID NO 2598
<211> LENGTH: 24
```

```
<212> TYPE: DNA
<213> ORGANISM: homo sapien

<400> SEQUENCE: 2598
gattacaagg atgacgacga taag                                    24
```